United States Patent
Cha et al.

(10) Patent No.: US 10,957,857 B2
(45) Date of Patent: Mar. 23, 2021

(54) MULTICYCLIC COMPOUND AND ORGANIC LIGHT EMITTING DEVICE INCLUDING THE SAME

(71) Applicant: LG CHEM LTD., Seoul (KR)

(72) Inventors: Yongbum Cha, Daejeon (KR); Sang Young Jeon, Daejeon (KR); Sung Jae Lee, Daejeon (KR); Sung Kil Hong, Daejeon (KR)

(73) Assignee: LG CHEM LTD., Seoul (KR)

(*) Notice: Subject to any disclaimer, the term of this patent is extended or adjusted under 35 U.S.C. 154(b) by 0 days.

(21) Appl. No.: 16/316,591

(22) PCT Filed: Jul. 27, 2017

(86) PCT No.: PCT/KR2017/008120
§ 371 (c)(1),
(2) Date: Jan. 9, 2019

(87) PCT Pub. No.: WO2018/021854
PCT Pub. Date: Feb. 1, 2018

(65) Prior Publication Data
US 2019/0237674 A1    Aug. 1, 2019

(30) Foreign Application Priority Data
Jul. 27, 2016 (KR) .................. 10-2016-0095564

(51) Int. Cl.
*H01L 51/00* (2006.01)
*C07D 403/10* (2006.01)
(Continued)

(52) U.S. Cl.
CPC ........ *H01L 51/0054* (2013.01); *C07D 213/06* (2013.01); *C07D 213/16* (2013.01);
(Continued)

(58) Field of Classification Search
CPC ............... H01L 51/0032; H01L 51/005; H01L 51/0052; H01L 51/0054; H01L 51/0058; H01L 51/0059; H01L 51/006; H01L 51/0062; H01L 51/0067; H01L 51/0071; H01L 51/0072; H01L 51/0073;
(Continued)

(56) References Cited

U.S. PATENT DOCUMENTS

2011/0266526 A1    11/2011 Ma et al.
2013/0200359 A1*   8/2013 Stoessel .................. C07C 13/62
                                                                257/40
(Continued)

FOREIGN PATENT DOCUMENTS

JP    2007230974 A  *  9/2007
JP    2013-525446 A    6/2013
(Continued)

*Primary Examiner* — Ermias T Woldegeorgis
(74) *Attorney, Agent, or Firm* — Dentons US LLP

(57) ABSTRACT

The present specification relates to a multicyclic compound and an organic light-emitting device including the same. The multicyclic compound of Chemical Formula 1 used in one or more organic material layers of the organic light emitting device provides enhanced efficiency, decreased driving voltage and enhanced lifespan property of the organic light emitting device.

13 Claims, 1 Drawing Sheet

(51) Int. Cl.
  *C07D 405/10* (2006.01)
  *C07D 409/10* (2006.01)
  *C09K 11/06* (2006.01)
  *C07D 213/06* (2006.01)
  *C07D 401/10* (2006.01)
  *H01L 51/50* (2006.01)
  *C07D 213/16* (2006.01)
  *C07D 251/24* (2006.01)
  *C07D 405/14* (2006.01)

(52) U.S. Cl.
  CPC ......... *C07D 251/24* (2013.01); *C07D 401/10* (2013.01); *C07D 403/10* (2013.01); *C07D 405/10* (2013.01); *C07D 405/14* (2013.01); *C07D 409/10* (2013.01); *C09K 11/06* (2013.01); *H01L 51/00* (2013.01); *H01L 51/0056* (2013.01); *H01L 51/0058* (2013.01); *H01L 51/0067* (2013.01); *H01L 51/0072* (2013.01); *H01L 51/0073* (2013.01); *H01L 51/0074* (2013.01); *H01L 51/50* (2013.01); *C09K 2211/1018* (2013.01); *H01L 51/5012* (2013.01); *H01L 51/5016* (2013.01); *H01L 51/5056* (2013.01); *H01L 51/5072* (2013.01); *H01L 51/5088* (2013.01); *H01L 51/5092* (2013.01); *H01L 51/5096* (2013.01)

(58) Field of Classification Search
  CPC ............... H01L 51/0074; H01L 51/50; H01L 51/5012; H01L 51/5016; H01L 51/5072
  See application file for complete search history.

(56) References Cited

U.S. PATENT DOCUMENTS

| | | | |
|---|---|---|---|
| 2014/0275530 | A1 | 9/2014 | Jatsch et al. |
| 2015/0318487 | A1* | 11/2015 | Ito ..................... H01L 51/5096 257/40 |
| 2016/0204352 | A1 | 7/2016 | Adachi et al. |
| 2017/0271595 | A1 | 9/2017 | Adachi et al. |
| 2017/0338417 | A1 | 11/2017 | Adachi et al. |

FOREIGN PATENT DOCUMENTS

| | | |
|---|---|---|
| JP | 2014-504257 A | 2/2014 |
| JP | 2014088399 A | 5/2014 |
| JP | 2015214490 A | 12/2015 |
| KR | 20110043270 A | 4/2011 |
| KR | 20110130904 A | 12/2011 |
| KR | 10-2013-0040133 A | 4/2013 |
| KR | 20140009981 A | 1/2014 |
| KR | 20140080322 A | 6/2014 |
| KR | 20150033074 A | 4/2015 |
| KR | 20150041196 A | 4/2015 |
| KR | 20150126756 A | 11/2015 |
| KR | 20150129928 A | 11/2015 |
| WO | 2009/037155 | 3/2009 |
| WO | 2012/048781 | 4/2012 |
| WO | 2015029354 A1 | 3/2015 |

\* cited by examiner

【FIG. 1】
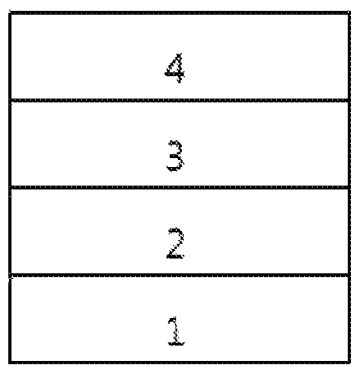
【FIG. 2】
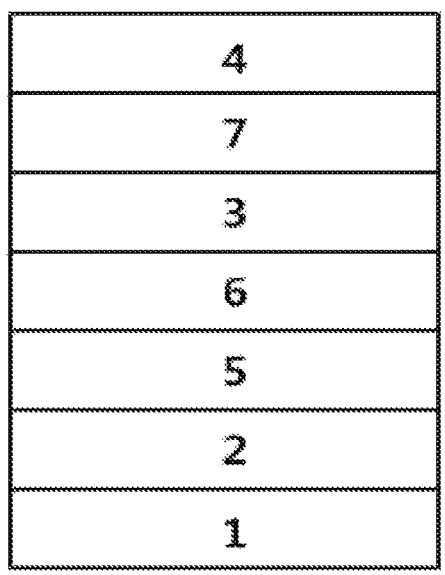

MULTICYCLIC COMPOUND AND ORGANIC LIGHT EMITTING DEVICE INCLUDING THE SAME

This application is a National Stage Application of International Application No. PCT/KR2017/008120, filed Jul. 27, 2017, and claims the benefit of Korean Patent Application No. 10-2016-0095564 filed on Jul. 27, 2016, the entire contents of which are incorporated herein by reference.

TECHNICAL FIELD

The present specification claims priority to and the benefits of Korean Patent Application No. 10-2016-0095564, filed with the Korean Intellectual Property Office on Jul. 27, 2016, the entire contents of which are incorporated herein by reference.

The present specification relates to a multicyclic compound and an organic light emitting device including the same.

BACKGROUND ART

An organic light emission phenomenon generally refers to a phenomenon converting electrical energy to light energy using an organic material. An organic light emitting device using an organic light emission phenomenon normally has a structure including an anode, a cathode, and an organic material layer therebetween. Herein, the organic material layer is often formed in a multilayer structure formed with different materials in order to increase efficiency and stability of the organic light emitting device, and for example, may be formed with a hole injection layer, a hole transfer layer, a light emitting layer, an electron transfer layer, an electron injection layer and the like. When a voltage is applied between the two electrodes in such an organic light emitting device structure, holes and electrons are injected to the organic material layer from the anode and the cathode, respectively, and when the injected holes and electrons meet, excitons are formed, and light emits when these excitons fall back to the ground state.

Development of new materials for such an organic light emitting device has been continuously required.

DISCLOSURE

Technical Problem

The present specification is directed to providing a multicyclic compound and an organic light emitting device including the same.

Technical Solution

One embodiment of the present specification provides a compound represented by the following Chemical Formula 1.

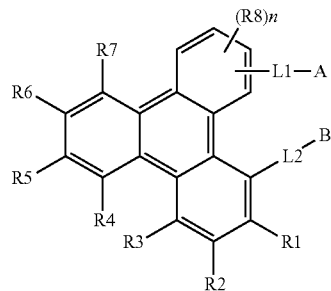

[Chemical Formula 1]

In Chemical Formula 1,

A and B are the same as or different from each other, and each independently represented by one of the following Chemical Formulae 2 and 3, L1 and L2 are the same as or different from each other, and each independently a direct bond; a substituted or unsubstituted arylene group; or a substituted or unsubstituted heteroarylene group, R1 to R8 are the same as or different from each other, and each independently hydrogen; deuterium; a nitrile group; a substituted or unsubstituted alkyl group; a substituted or unsubstituted cycloalkyl group; a substituted or unsubstituted alkoxy group; a substituted or unsubstituted aryloxy group; a substituted or unsubstituted alkenyl group; a substituted or unsubstituted silyl group; a substituted or unsubstituted amine group; a substituted or unsubstituted aryl group; or a substituted or unsubstituted heteroaryl group, n is an integer of 0 to 3, and when n is 2 or greater, R8s are the same as or different from each other,

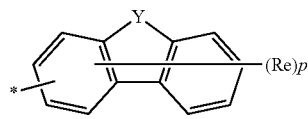

[Chemical Formula 2]

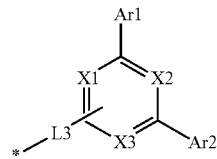

[Chemical Formula 3]

Y is S, O, NRa or CRbRc,

Ar1 and Ar2 are the same as or different from each other, and each independently a substituted or unsubstituted aryl group; or a substituted or unsubstituted heteroaryl group, X1 to X3 are the same as or different from each other, and each independently N or CRd, L3 is a direct bond; a substituted or unsubstituted arylene group; or a substituted or unsubstituted heteroarylene group, Ra to Re are the same as or different from each other, and each independently hydrogen; deuterium; a nitrile group; a substituted or unsubstituted alkyl group; a substituted or unsubstituted aryl group; or a substituted or unsubstituted heteroaryl group, Rb and Rc may bond to each other to form a ring structure, adjacent groups among Res may bond to each other to form a ring, p is an integer of 0 to 7, and when p is 2 or greater, Res are the same as or different from each other, and

*is a site bonding to L1 or L2.

Another embodiment of the present specification provides an organic light emitting device including a first electrode; a second electrode provided opposite to the first electrode; and one or more organic material layers provided between the first electrode and the second electrode, wherein one or more layers of the organic material layers include the compound represented by Chemical Formula 1.

Advantageous Effects

A multicyclic compound according to one embodiment of the present specification can be used as a material of an organic material layer of an organic light emitting device, and by using the same, it is capable of enhancing efficiency, obtaining a low driving voltage and/or enhancing a lifespan property in the organic light emitting device.

DESCRIPTION OF DRAWINGS

FIG. 1 illustrates an example of an organic light emitting device composed of a substrate 1, a positive electrode 2, a light emitting layer 3, and a negative electrode 4.

FIG. 2 illustrates an example of an organic light emitting device composed of a substrate 1, a positive electrode 2, a hole injection layer 5, a hole transporting layer 6, a light emitting layer 3, an electron transporting layer 7, and a negative electrode 4.

MODE FOR DISCLOSURE

Hereinafter, the present specification will be described in more detail.

One embodiment of the present specification provides a compound represented by Chemical Formula 1.

In the present specification, a description of a certain part "including" certain constituents means capable of further including other constituents, and does not exclude other constituents unless particularly stated on the contrary.

In the present specification, a description of one member being placed "on" another member includes not only a case of the one member adjoining the another member but a case of still another member being present between the two members.

Examples of the substituents are described below, however, the substituents are not limited thereto.

The term "substitution" means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents may be the same as or different from each other.

The term "substituted or unsubstituted" in the present specification means being substituted with one, two or more substituents selected from the group consisting of deuterium; a nitrile group; a substituted or unsubstituted alkyl group; a substituted or unsubstituted cycloalkyl group; a substituted or unsubstituted alkoxy group; a substituted or unsubstituted aryloxy group; a substituted or unsubstituted alkenyl group; a substituted or unsubstituted silyl group; a substituted or unsubstituted boron group; a substituted or unsubstituted amine group; a substituted or unsubstituted aryl group; and a substituted or unsubstituted heteroaryl group, or being substituted with a substituent linking two or more substituents among the substituents illustrated above, or having no substituents. For example, "a substituent linking two or more substituents" may include an aryl group substituted with an aryl group, an aryl group substituted with a heteroaryl group, a heteroaryl group substituted with an aryl group, an aryl group substituted with an alkyl group, and the like.

In the present specification, the alkyl group may be linear or branched, and although not particularly limited thereto, the number of carbon atoms is preferably from 1 to 30. Specific examples thereof may include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl and the like, but are not limited thereto.

In the present specification, the cycloalkyl group is not particularly limited, but preferably has 3 to 30 carbon atoms, and specific examples thereof may include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl and the like, but are not limited thereto.

In the present specification, the alkoxy group may be linear, branched or cyclic. The number of carbon atoms of the alkoxy group is not particularly limited, but is preferably from 1 to 30. Specific examples thereof may include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy and the like, but are not limited thereto.

In the present specification, the amine group may be selected from the group consisting of —$NH_2$; an alkylamine group; an N-alkylarylamine group; an arylamine group; an N-arylheteroarylamine group; an N-alkylheteroarylamine group and a heteroarylamine group, and although not particularly limited thereto, the number of carbon atoms is preferably from 1 to 30. Specific examples of the amine group may include a methylamine group, a dimethylamine group, an ethylamine group, a diethylamine group, a phenylamine group, a naphthylamine group, a biphenylamine group, an anthracenylamine group, a 9-methyl-anthracenylamine group, a diphenylamine group, an N-phenylnaphthylamine group, a ditolylamine group, an N-phenyltolylamine group, a triphenylamine group, an N-phenylbiphenylamine group; an N-phenylnaphthylamine group; an N-biphenylnaphthylamine group; an N-naphthylfluorenylamine group; an N-phenylphenanthrenylamine group; an N-biphenylphenanthrenylamine group; an N-phenylfluorenylamine group; an N-phenylterphenylamine group; an N-phenanthrenylfluorenylamine group; an N-biphenylfluorenylamine group and the like, but are not limited thereto.

In the present specification, the N-alkylarylamine group means an amine group in which N of the amine group is substituted with an alkyl group and an aryl group.

In the present specification, the N-arylheteroarylamine group means an amine group in which N of the amine group is substituted with an aryl group and a heteroaryl group.

In the present specification, the N-alkylheteroarylamine group means an amine group in which N of the amine group is substituted with an alkyl group and a heteroaryl group.

In the present specification, the alkyl group in the alkylamine group, the N-arylalkylamine group, the alkylthioxy group, the alkylsulfoxy group and the N-alkylheteroarylamine group is the same as the examples of the alkyl group described above.

In the present specification, the alkenyl group may be linear or branched, and although not particularly limited thereto, the number of carbon atoms is preferably from 2 to 30. Specific examples thereof may include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group and the like, but are not limited thereto.

In the present specification, specific examples of the silyl group may include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, the aryl group is not particularly limited, but preferably has 6 to 30 carbon atoms, and the aryl group may be monocyclic or multicyclic.

When the aryl group is a monocyclic aryl group, the number of carbon atoms is not particularly limited, but is preferably from 6 to 30. Specific examples of the monocyclic aryl group may include a phenyl group, a biphenyl group, a terphenyl group, a quaterphenyl and the like, but are not limited thereto.

When the aryl group is a multicyclic aryl group, the number of carbon atoms is not particularly limited, but is preferably from 10 to 30. Specific examples of the multicyclic aryl group may include a naphthyl group, an anthracenyl group, a phenanthryl group, a triphenyl group, a pyrenyl group, a phenalenyl group, a perylenyl group, a chrysenyl group, a fluorenyl group and the like, but are not limited thereto.

In the present specification, the fluorenyl group may be substituted, and adjacent groups may bond to each other to form a ring.

When the fluorenyl group is substituted,

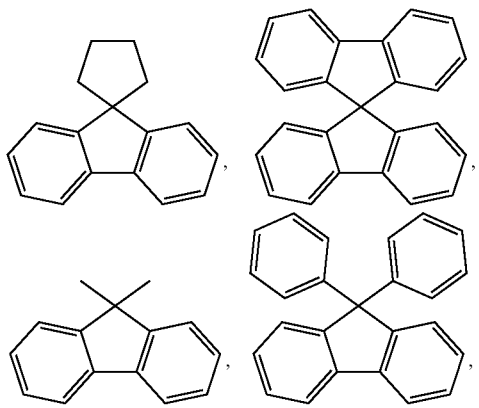

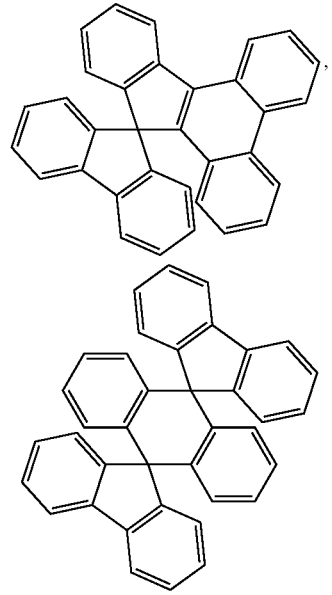

and the like may be included. However, the structure is not limited thereto.

In the present specification, the aryl group in the aryloxy group, the N-arylalkylamine group, and the N-arylheteroarylamine group is the same as the examples of the aryl group described above. Specific examples of the aryloxy group may include a phenoxy group, a p-tolyloxy group, an m-tolyloxy group, a 3,5-dimethyl-phenoxy group, a 2,4,6-trimethylphenoxy group, a p-tert-butylphenoxy group, a 3-biphenyloxy group, a 4-biphenyloxy group, a 1-naphthyloxy group, a 2-naphthyloxy group, a 4-methyl-1-naphthyloxy group, a 5-methyl-2-naphthyloxy group, a 1-anthryloxy group, a 2-anthryloxy group, a 9-anthryloxy group, a 1-phenanthryloxy group, a 3-phenanthryloxy group, a 9-phenanthryloxy group and the like.

In the present specification, the heteroaryl group is a group including one or more atoms that are not carbon, that is, heteroatoms, and specifically, the heteroatom may include one or more atoms selected from the group consisting of O, N, Se, S and the like. The number of carbon atoms is not particularly limited, but is preferably from 2 to 30, and the heteroaryl group may be monocyclic or multicyclic. Examples of the heteroaryl group may include a thiophene group, a furanyl group, a pyrrole group, an imidazolyl group, an oxazolyl group, an a pyridyl group, a bipyridyl group, a pyrimidyl group, a triazinyl group, a triazolyl group, an acridyl group, a pyridazinyl group, a pyrazinyl group, a quinolinyl group, a quinazolinyl group, a quinoxalinyl group, a phthalazinyl group, a pyridopyrimidyl group, a pyridopyrazinyl group, a pyrazinopyrazinyl group, an isoquinolinyl group, an indolyl group, a carbozolyl group, a benzoxazolyl group, a benzimidazolyl group, a benzothiazolyl group, a benzocarbazolyl group, a benzothiophene group, a dibenzothiophene group, a benzofuranyl group, a phenanthroline group, a thiazolyl group, an isoxazolyl group, an oxadiazolyl group, a thiadiazolyl group, a benzothiazolyl group, a phenothiazinyl group, a dibenzopyrrolyl group, a dibenzofuranyl group and the like, but are not limited thereto.

In the present specification, examples of the heteroarylamine group include a substituted or unsubstituted monoheteroarylamine group, a substituted or unsubstituted diheteroarylamine group, or a substituted or unsubstituted triheteroarylamine group. The heteroarylamine group including two or more heteroaryl groups may include monocyclic heteroaryl groups, multicyclic heteroaryl groups, or both monocyclic heteroaryl groups and multicyclic heteroaryl groups. For example, the heteroaryl group in the heteroarylamine group may be selected from among the examples of the heteroaryl group described above.

In the present specification, descriptions on the aryl group provided above may be applied to the arylene except for being a divalent.

In the present specification, descriptions on the heteroaryl group provided above may be applied to the heteroarylene except for being a divalent.

According to one embodiment of the present specification, the compound of Chemical Formula 1 may be represented by the following Chemical Formula 4, 5 or 6.

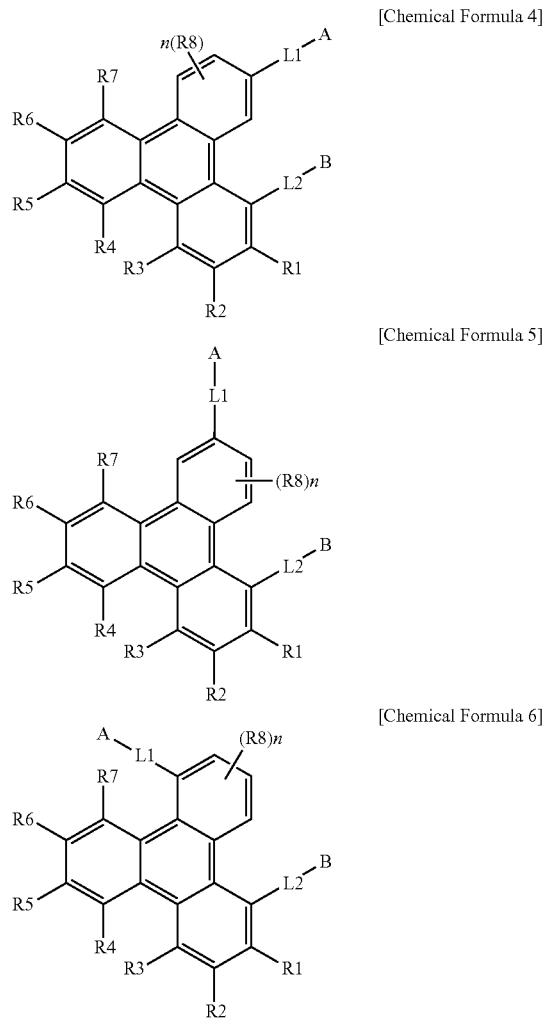

[Chemical Formula 4]

[Chemical Formula 5]

[Chemical Formula 6]

In Chemical Formulae 4 to 6, R1 to R8, n, A, B, L1 and L2 are the same as in Chemical Formula 1.

As in Chemical Formulae 4 to 6, both position 1 and any one of positions 9 to 11 of triphenylene have specific substituents in the core structure, and as a result, light emission efficiency and lifespan of an organic light emitting device may all be enhanced.

According to another embodiment of the present specification, in any one compound of Chemical Formula 1 or Chemical Formulae 4 to 6, A may be represented by Chemical Formula 2 and B may be represented by Chemical Formula 3.

According to another embodiment of the present specification, B may be represented by Chemical Formula 2 and A may be represented by Chemical Formula 3.

According to another embodiment of the present specification, A and B are represented by Chemical Formulae 2 and 3, Y is S, O or NRa, and Ar1, Ar2, X1 to X3 and L3 have the same definitions as above.

According to another embodiment of the present specification, R1 to R8 are the same as or different from each other, and each independently hydrogen, deuterium, a substituted or unsubstituted alkyl group, a substituted or unsubstituted aryl group, or a substituted or unsubstituted heteroaryl group.

According to another embodiment of the present specification, R1 to R8 are each hydrogen.

According to another embodiment of the present specification, L1 to L3 are the same as or different from each other, and each independently a direct bond, a substituted or unsubstituted arylene group, or a substituted or unsubstituted heteroarylene group.

According to another embodiment of the present specification, L1 to L3 are the same as or different from each other, and each independently a direct bond, a phenylene group, a biphenylene group, a fluorenylene group, a naphthalenylene group or a carbazolylene group.

According to another embodiment of the present specification, at least one of L1 and L2 is a direct bond.

According to one embodiment of the present specification, Chemical Formula 2 may be selected from among substituted or unsubstituted fluorene, substituted or unsubstituted dibenzothiophene, substituted or unsubstituted benzonaphthothiophene, substituted or unsubstituted dibenzofuran, substituted or unsubstituted benzonaphthofuran, substituted or unsubstituted carbazole, and substituted or unsubstituted benzocarbazole.

According to one embodiment of the present specification, Chemical Formula 2 may be selected from among the following substituents.

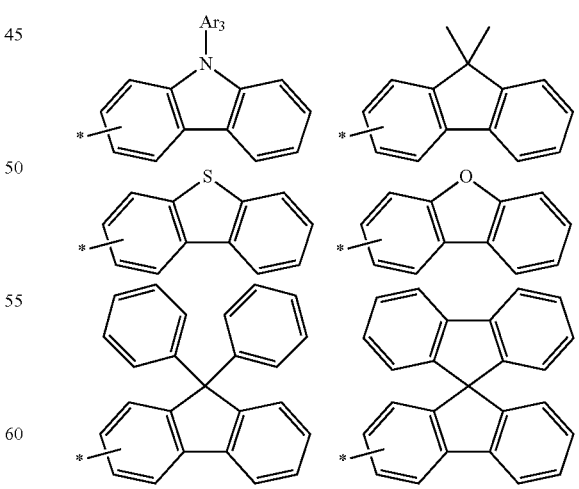

According to one embodiment of the present specification, Ar3 is a substituted or unsubstituted alkyl group, a substituted or unsubstituted aryl group, or a substituted or unsubstituted heteroaryl group.

According to one embodiment of the present specification, Ar3 is a methyl group, a phenyl group, a biphenyl group or a naphthalene group.
According to one embodiment of the present specification, Chemical Formula 2 may be selected from among the following substituents.
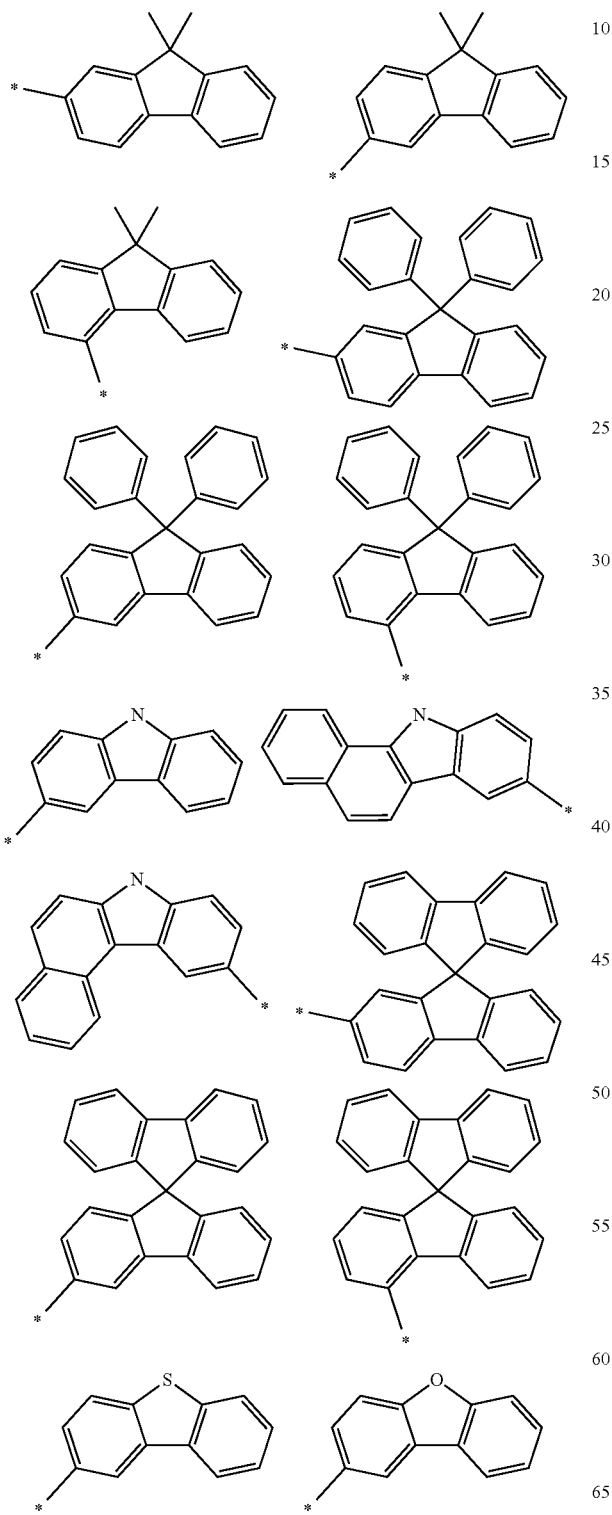
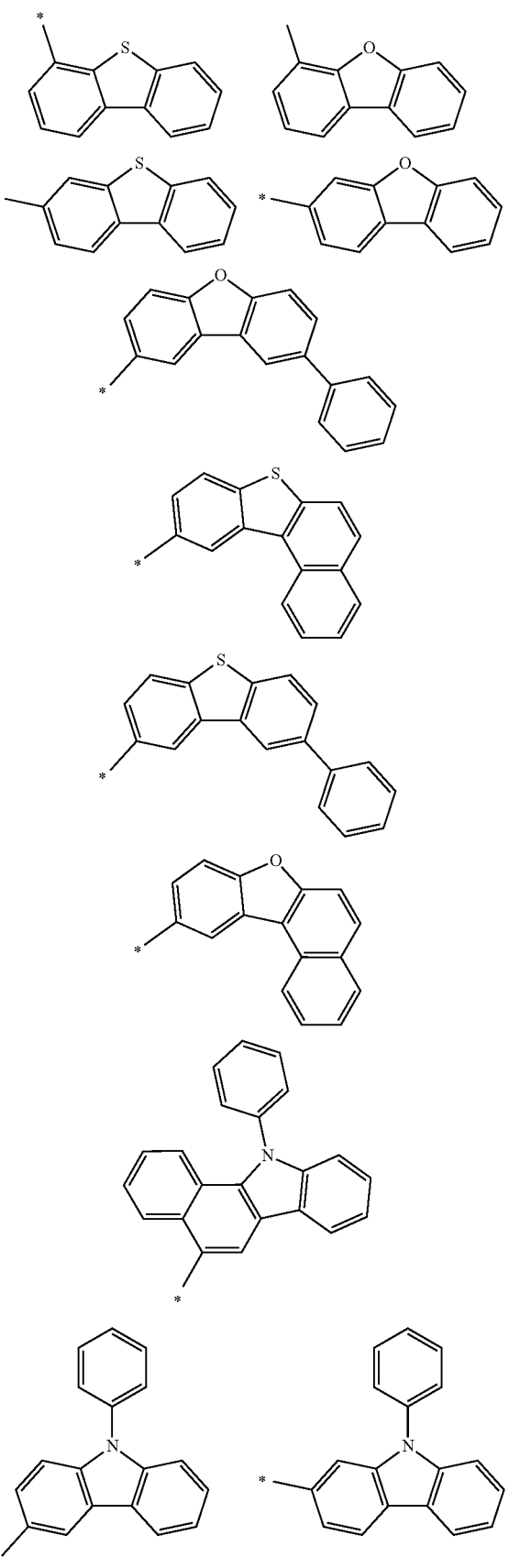

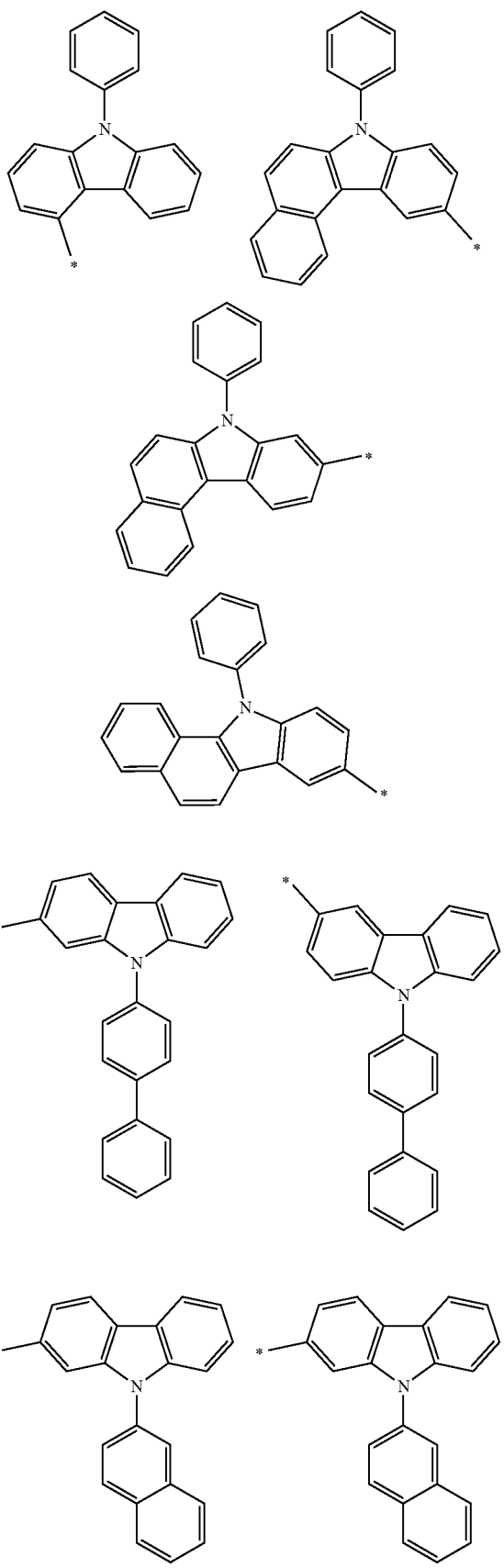

According to one embodiment of the present specification, Chemical Formula 3 is a substituted or unsubstituted aryl group, or a substituted or unsubstituted heteroaryl group.

According to one embodiment of the present specification, Chemical Formula 3 is a substituted or unsubstituted monocyclic N-containing heteroaryl group.

According to one embodiment of the present specification, Chemical Formula 3 may be selected from among a substituted or unsubstituted phenyl group, a substituted or unsubstituted pyridine group, a substituted or unsubstituted pyrimidine group, or a substituted or unsubstituted triazine group.

According to one embodiment of the present specification, Chemical Formula 3 is an N-containing heteroaryl group unsubstituted or substituted with an aryl group.

According to one embodiment of the present specification, Chemical Formula 3 is an N-containing heteroaryl group unsubstituted or substituted with a heteroaryl group.

According to one embodiment of the present specification, Chemical Formula 3 is an N-containing heteroaryl group unsubstituted or substituted with a heteroaryl group containing N, O or S.

According to one embodiment of the present specification, Chemical Formula 3 is an N-containing heteroaryl group unsubstituted or substituted with furan, thiophene, dibenzofuran, dibenzothiophene, carbazole, triazine, pyrimidine, pyridine, quinazol, quinazoline, quinoxaline or phenanthroline.

According to one embodiment of the present specification, Chemical Formula 3 is triazine, pyrimidine or pyridine unsubstituted or substituted with furan, thiophene, dibenzofuran, dibenzothiophene, carbazole, triazine, pyrimidine, pyridine, quinazol, quinazoline, quinoxaline or phenanthroline.

According to one embodiment of the present specification, Chemical Formula 3 is an aryl group unsubstituted or substituted with an N-containing heteroring.

According to one embodiment of the present specification, Chemical Formula 3 is an aryl group unsubstituted or substituted with triazine, pyrimidine, pyridinequinazol, quinazoline, quinoxaline or phenanthroline.

According to one embodiment of the present specification, Chemical Formula 3 is a phenyl group or a fluorene group unsubstituted or substituted with triazine, pyrimidine, pyridinequinazol, quinazoline, quinoxaline or phenanthroline.

According to one embodiment of the present specification, Chemical Formula 3 is an N-containing heteroaryl group unsubstituted or substituted with phenyl, biphenyl, naphthalene, triphenylene or fluorene.

According to one embodiment of the present specification, Chemical Formula 3 is triazine, pyrimidine or pyridine unsubstituted or substituted with phenyl, biphenyl, naphthalene, triphenylene or fluorene.

According to one embodiment of the present specification, Chemical Formula 3 may be selected from among the following substituents.

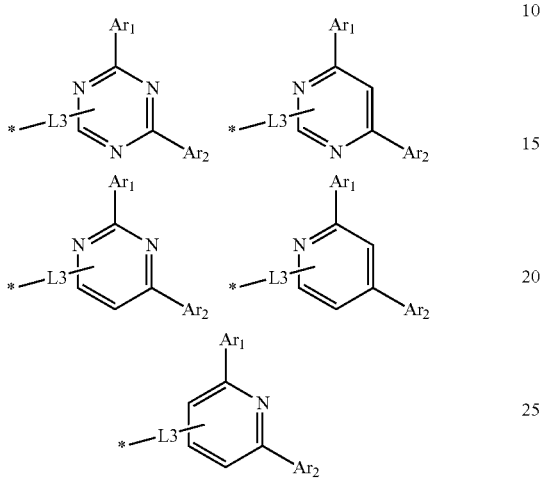

According to one embodiment of the present specification, Ar1 and Ar2 are the same as or different from each other, and each independently a substituted or unsubstituted aryl group; or a substituted or unsubstituted heteroaryl group.

According to one embodiment of the present specification, Ar1 and Ar2 are the same as or different from each other, and each independently a substituted or unsubstituted monocyclic or multicyclic aryl group, or a substituted or unsubstituted monocyclic or multicyclic heteroaryl group.

According to one embodiment of the present specification, Ar1 and Ar2 are the same as or different from each other, and each independently a substituted or unsubstituted phenyl group, a substituted or unsubstituted biphenyl group, a substituted or unsubstituted naphthalene group, a substituted or unsubstituted anthracene group, a substituted or unsubstituted phenanthrene group, a substituted or unsubstituted triphenylene group, a substituted or unsubstituted fluorene group, a substituted or unsubstituted pyridine group, a substituted or unsubstituted pyrimidine group, a substituted or unsubstituted dibenzofuran group, a substituted or unsubstituted dibenzothiophene group, a substituted or unsubstituted triazine group, a substituted or unsubstituted quinoline group, a substituted or unsubstituted quinazoline group, or a substituted or unsubstituted quinoxaline group.

According to one embodiment of the present specification, Ar1 and Ar2 are the same as or different from each other, and each independently a phenyl group, a biphenyl group, a naphthalene group, an anthracene group, a triphenylene group, a dimethylfluorene group, a pyridine group or a pyrimidine group.

According to one embodiment of the present specification, Chemical Formula 3 may be selected from among the following substituents.

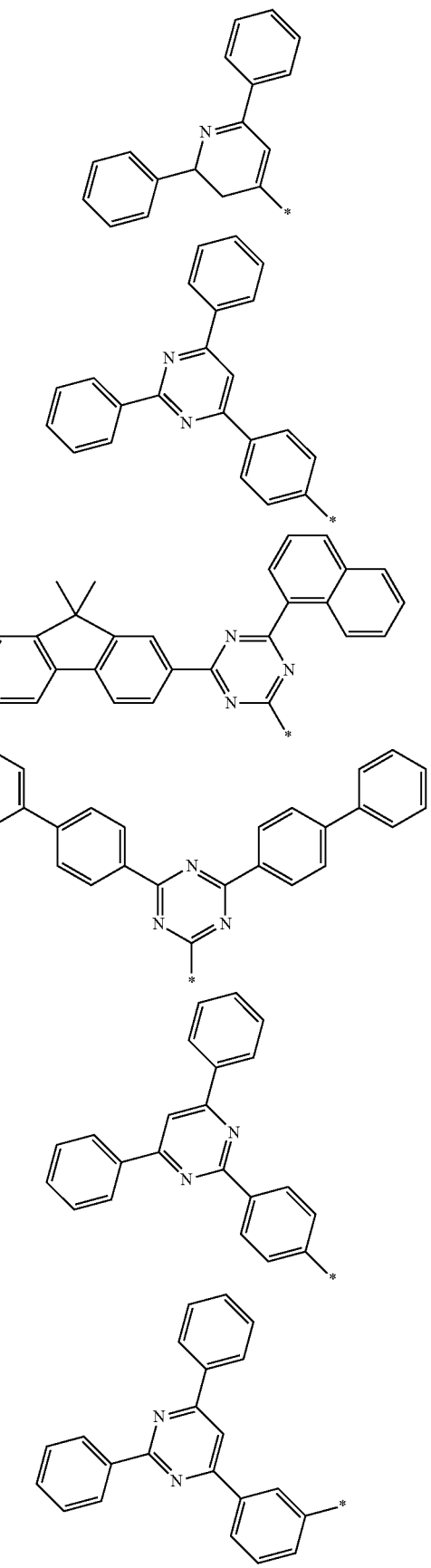

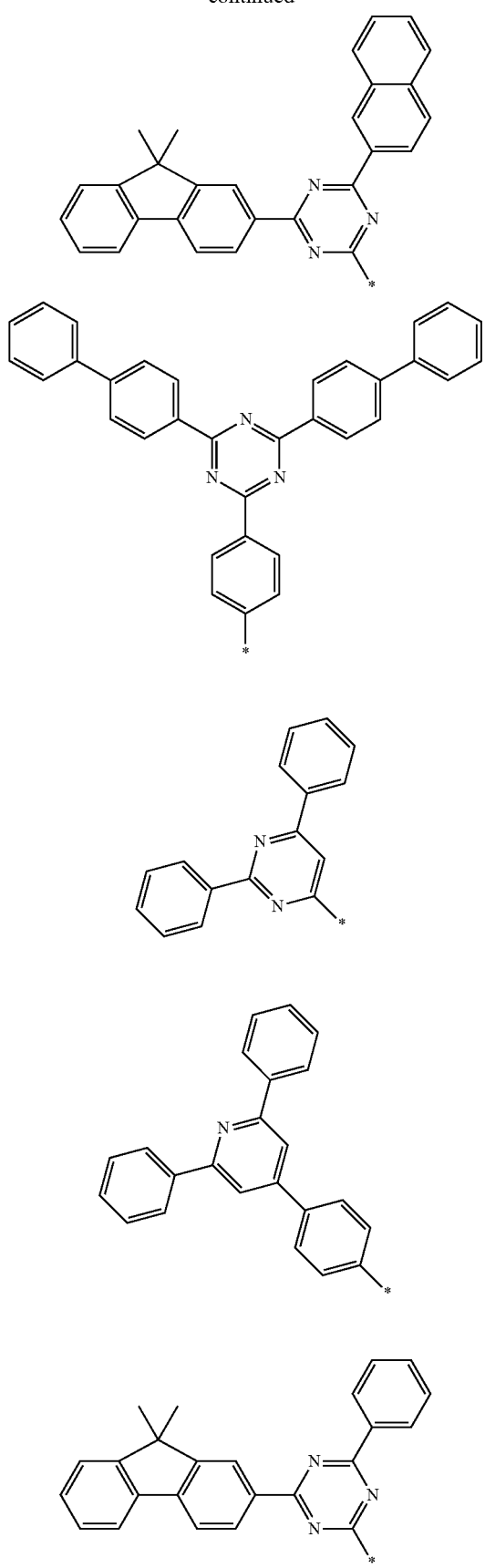
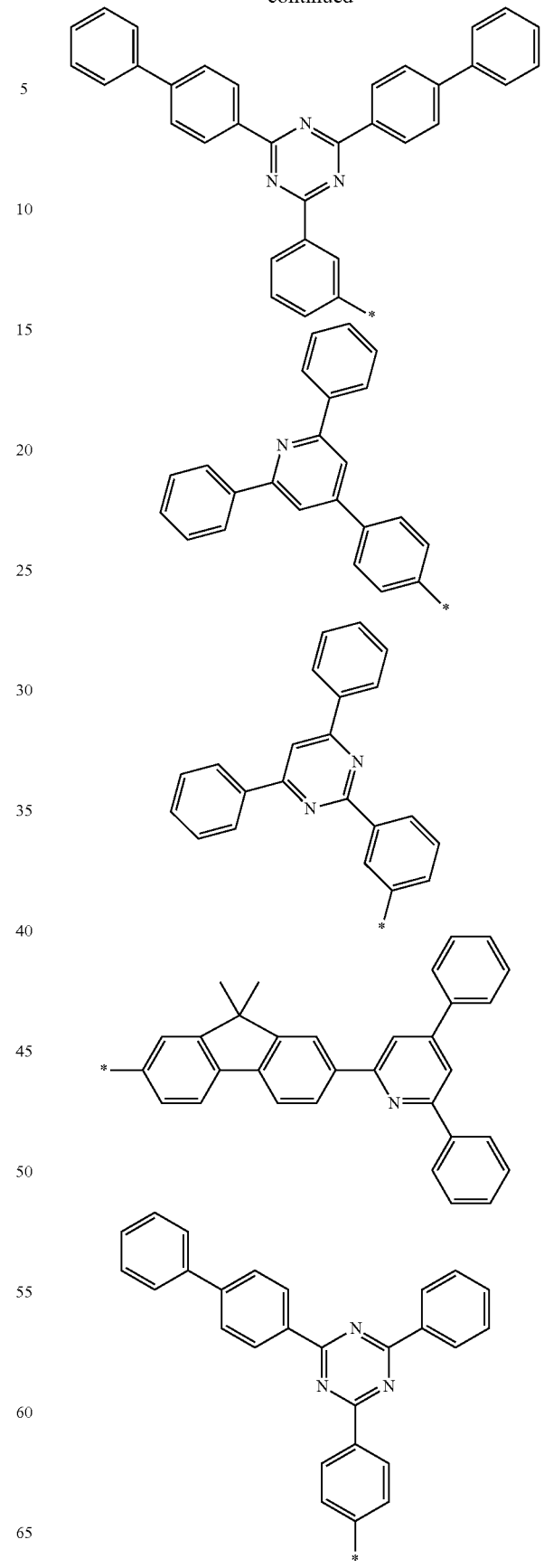

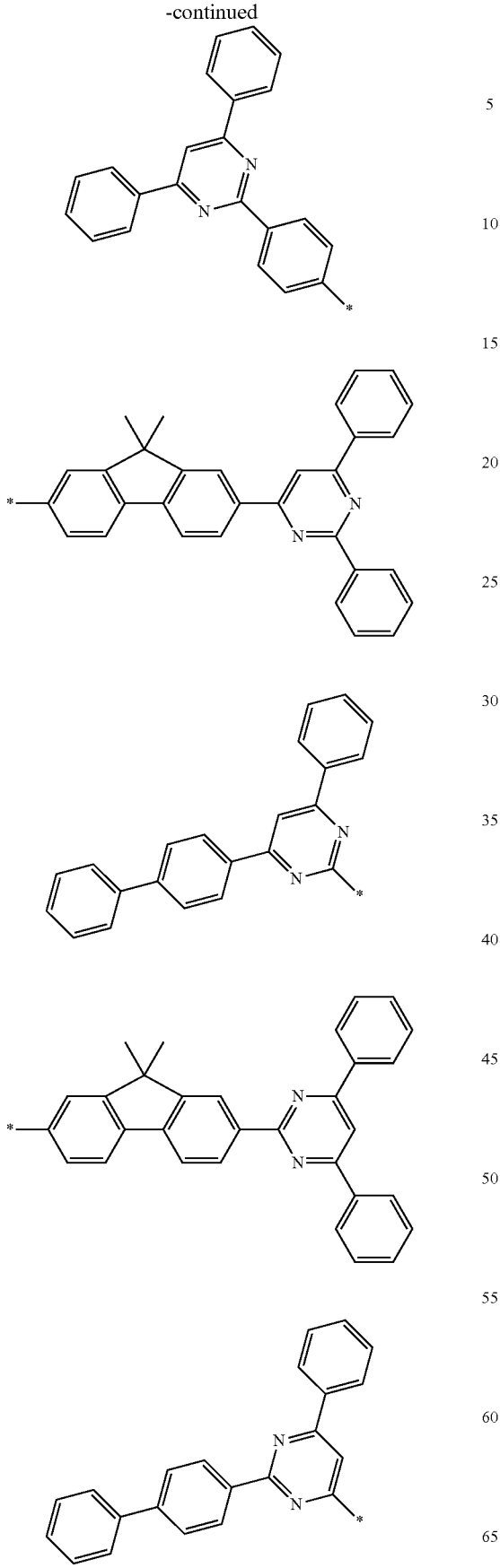
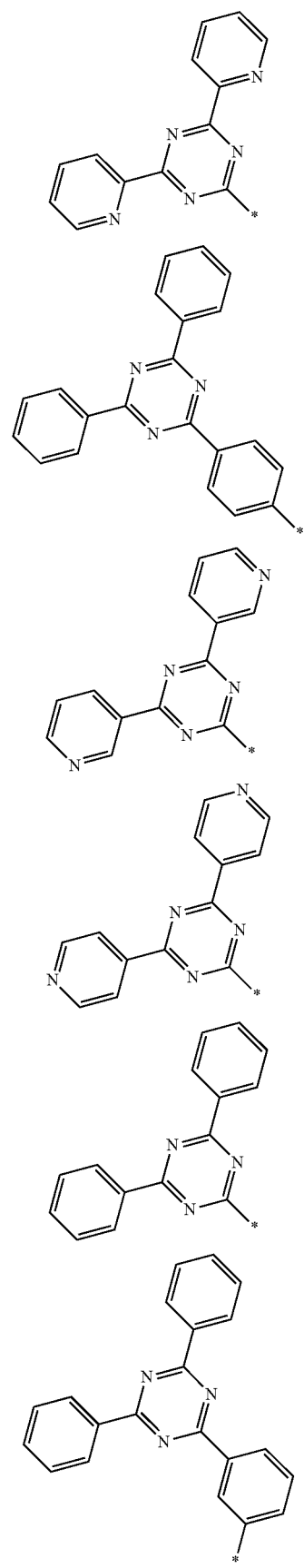

-continued
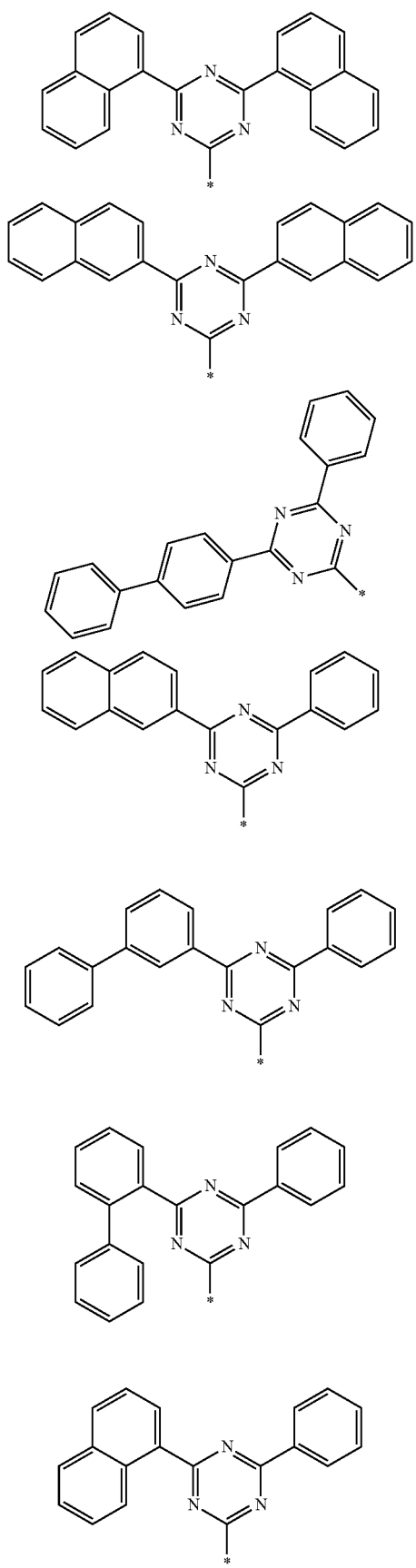
-continued
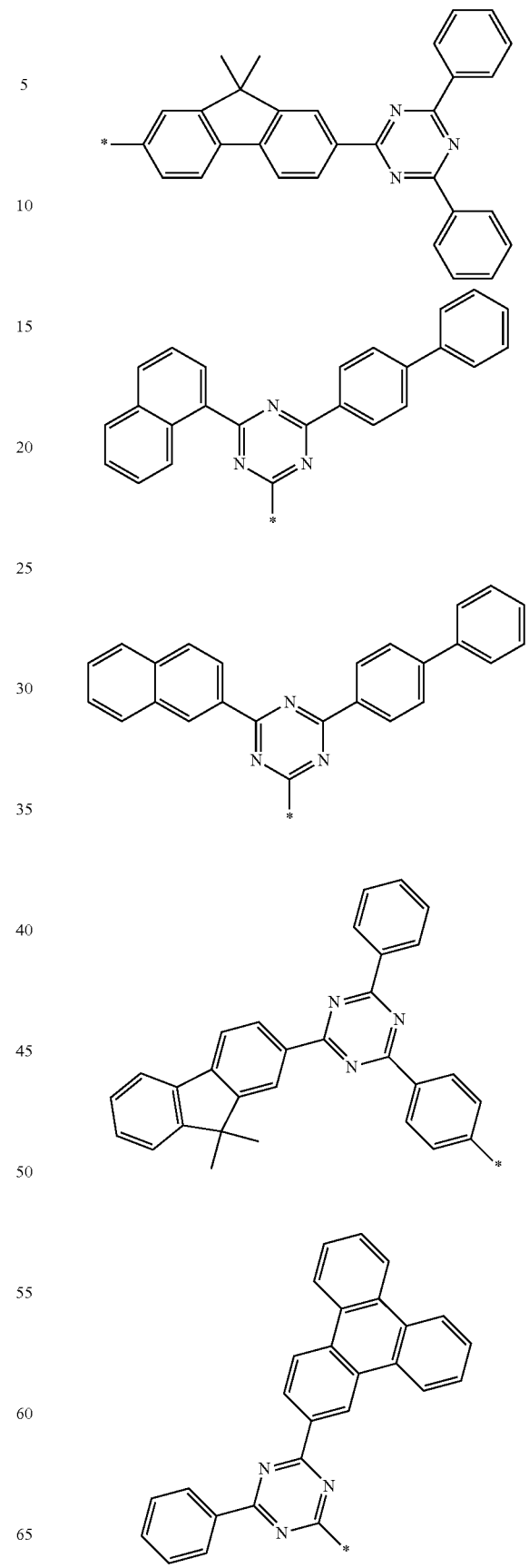

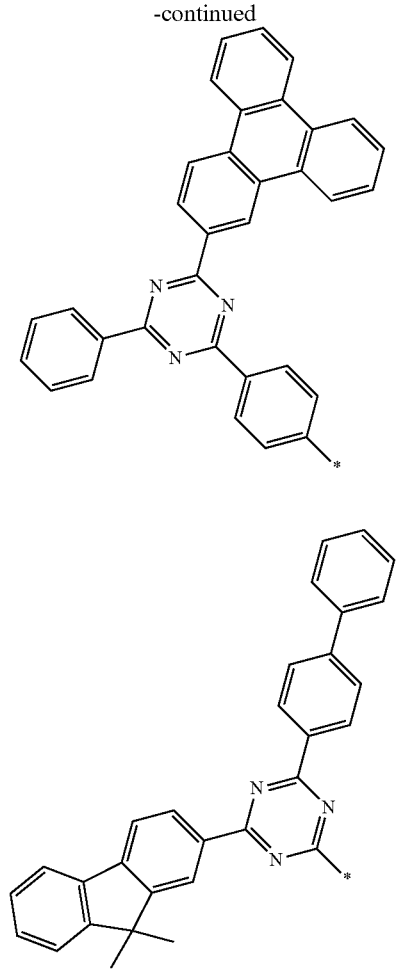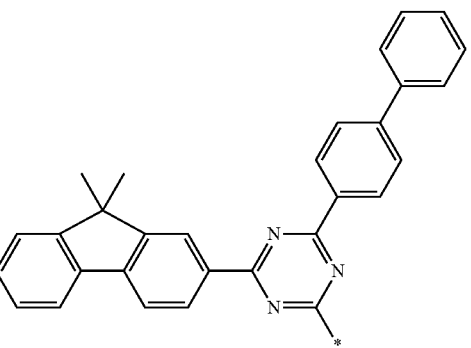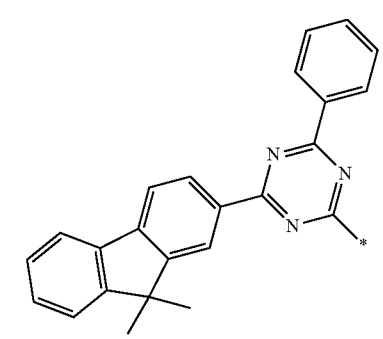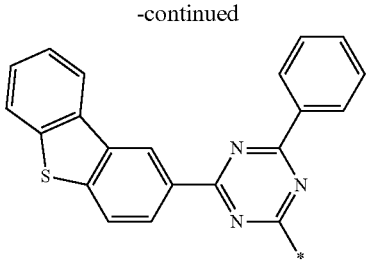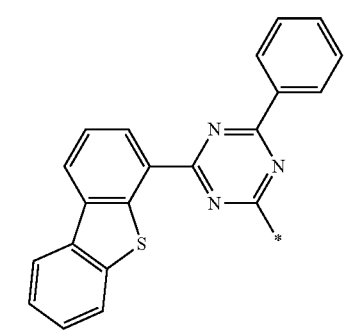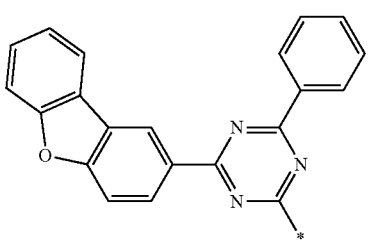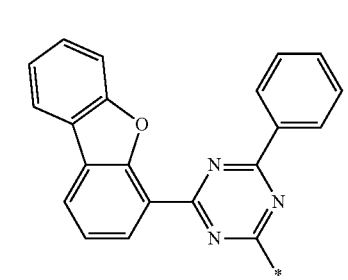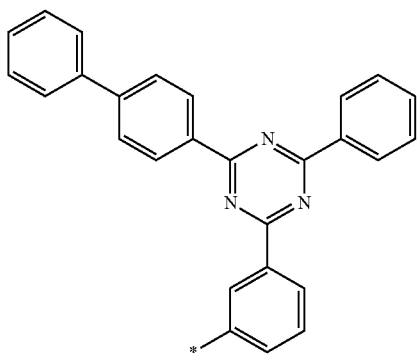

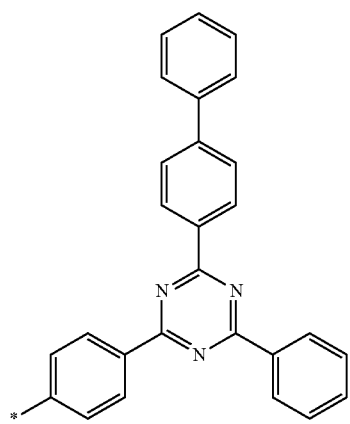
According to one embodiment of the present specification, Ar1 and Ar2 may be selected from among the following compounds.
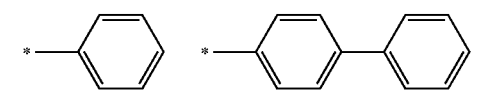
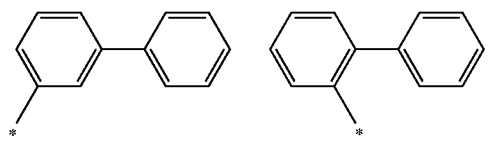
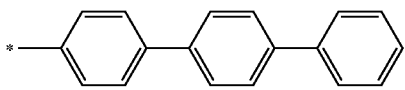
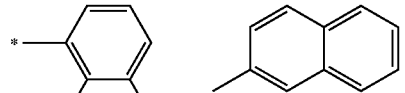
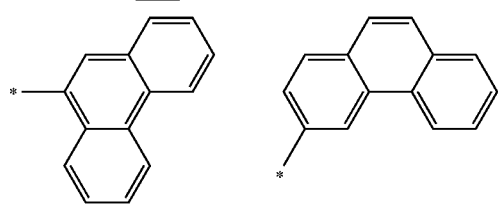
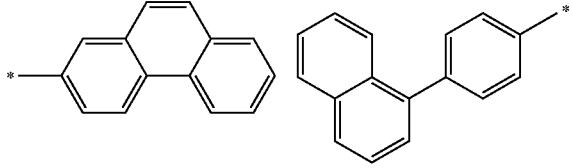
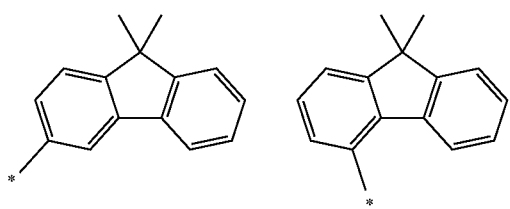
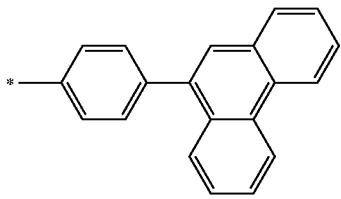
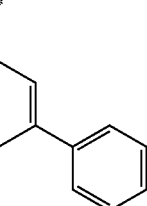
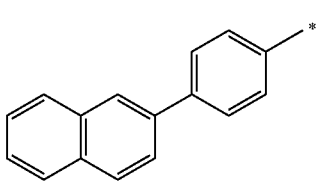
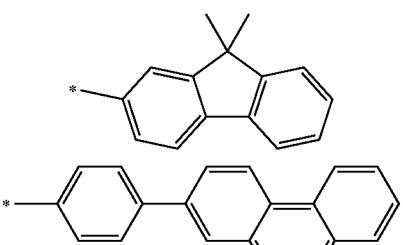
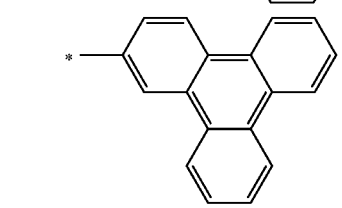
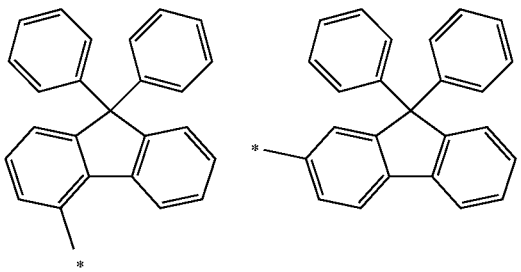
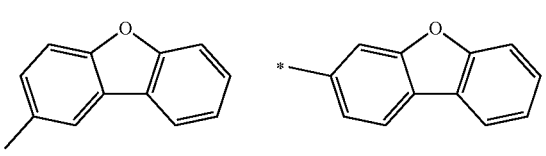

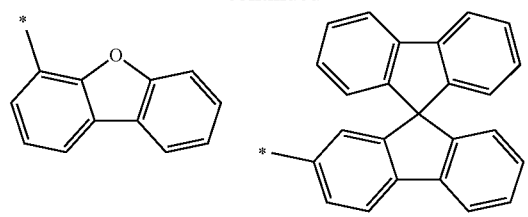
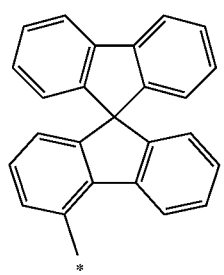
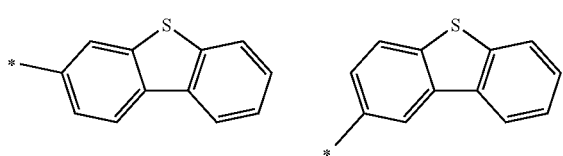
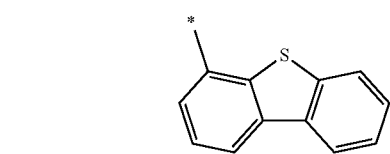
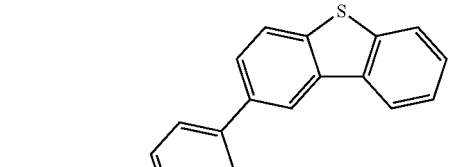
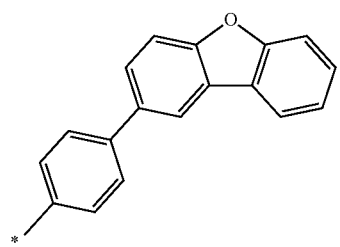
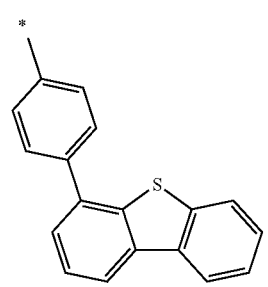

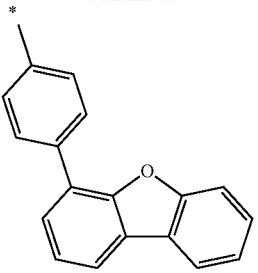

According to one embodiment of the present specification, the compound of Chemical Formula 1 may be represented by the following Chemical Formula 4, 5 or 6.

[Chemical Formula 4]

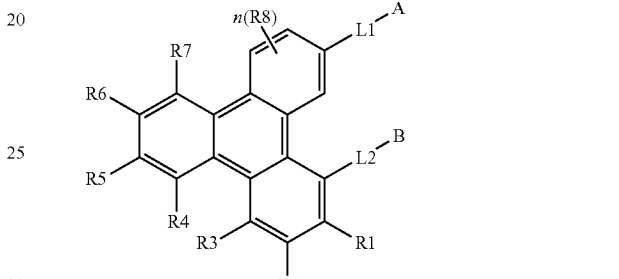

[Chemical Formula 5]

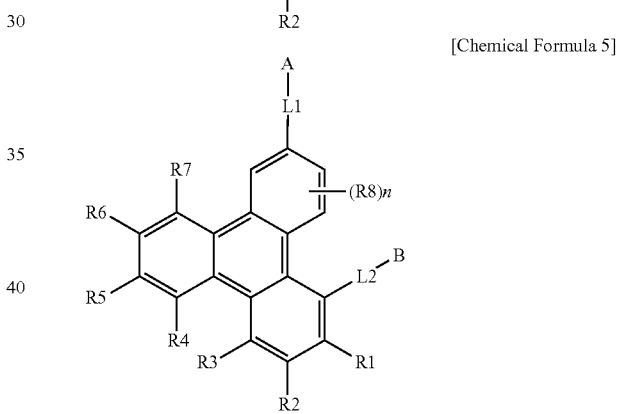

[Chemical Formula 6]

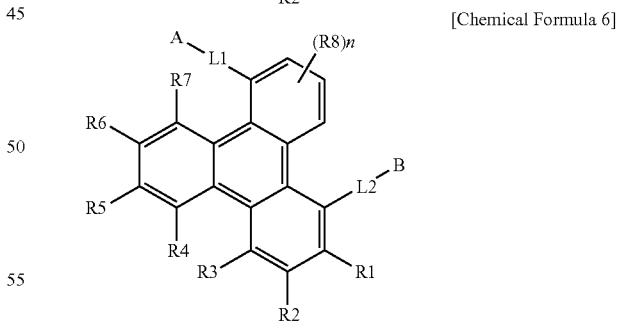

In Chemical Formulae 4, 5, and 6, n, A, B. L1 and L2 are the same as in Chemical Formula 1.

As in Chemical Formulae 4 to 6, both position 1 and any one of positions 9 to 11 of triphenylene have specific substituents in the core structure, and as a result, light emission efficiency and lifespan of an organic light emitting device may all be enhanced.

According to another embodiment of the present specification, in any one compound of Chemical Formula 1 or Chemical Formulae 4 to 6, A may be represented by Chemical Formula 2 and B may be represented by Chemical Formula 3.

According to another embodiment of the present specification, B may be represented by Chemical Formula 2 and A may be represented by Chemical Formula 3.

According to another embodiment of the present specification, A and B are represented by Chemical Formulae 2 and 3, Y is S, O or NRa, and Ar1, Ar2, X1 to X3 and L3 have the same definitions as above.

According to another embodiment of the present specification, R1 to R8 are the same as or different from each other, and each independently hydrogen, deuterium, a substituted or unsubstituted alkyl group, a substituted or unsubstituted aryl group, or a substituted or unsubstituted heteroaryl group.

According to another embodiment of the present specification, R1 to R8 are each hydrogen.

According to another embodiment of the present specification, L1 to L3 are the same as or different from each other, and each independently a direct bond, a substituted or unsubstituted alkyl group, a substituted or unsubstituted aryl group, or a substituted or unsubstituted heteroaryl group.

According to another embodiment of the present specification, L1 to L3 are the same as or different from each other, and each independently a direct bond, a phenyl group, a biphenyl group, a fluorene group, a naphthalene group or a carbazole group.

According to one embodiment of the present specification, Chemical Formula 2 may be selected from among substituted or unsubstituted fluorene, substituted or unsubstituted dibenzothiophene, substituted or unsubstituted benzonaphthothiophene, substituted or unsubstituted dibenzofuran, substituted or unsubstituted benzonaphthofuran, substituted or unsubstituted carbazole, and substituted or unsubstituted benzocarbazole.

According to one embodiment of the present specification, Chemical Formula 2 may be selected from among the following substituents.

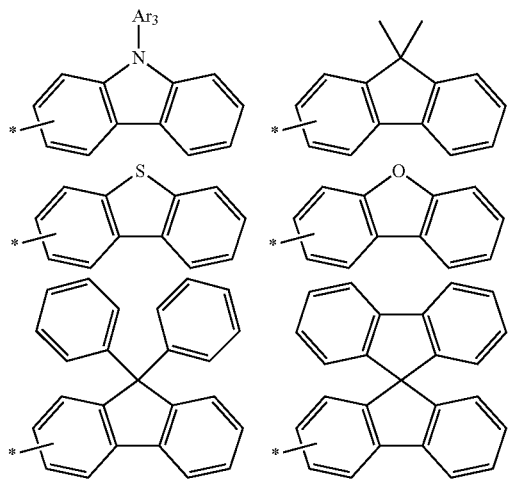

According to one embodiment of the present specification, Ar3 is a substituted or unsubstituted alkyl group, a substituted or unsubstituted aryl group, or a substituted or unsubstituted heteroaryl group.

According to one embodiment of the present specification, Ar3 is a methyl group, a phenyl group, a biphenyl group or a naphthalene group.

According to one embodiment of the present specification, Chemical Formula 2 may be selected from among the following substituents.

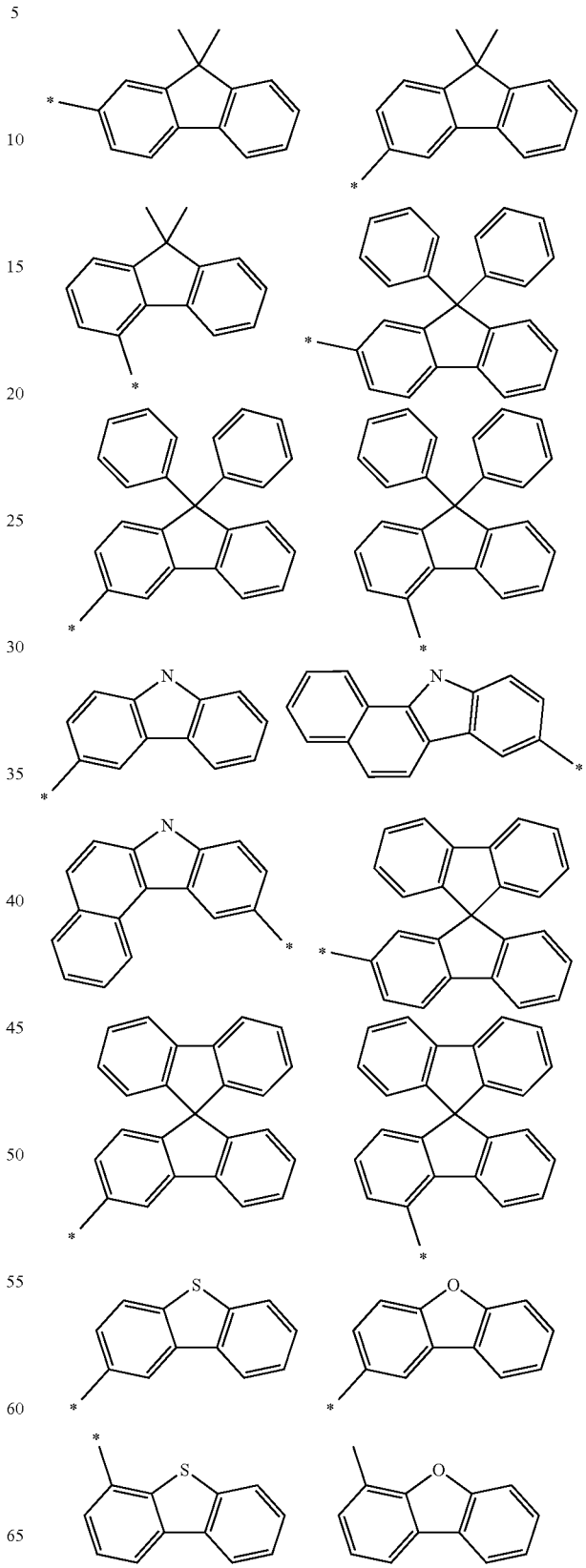

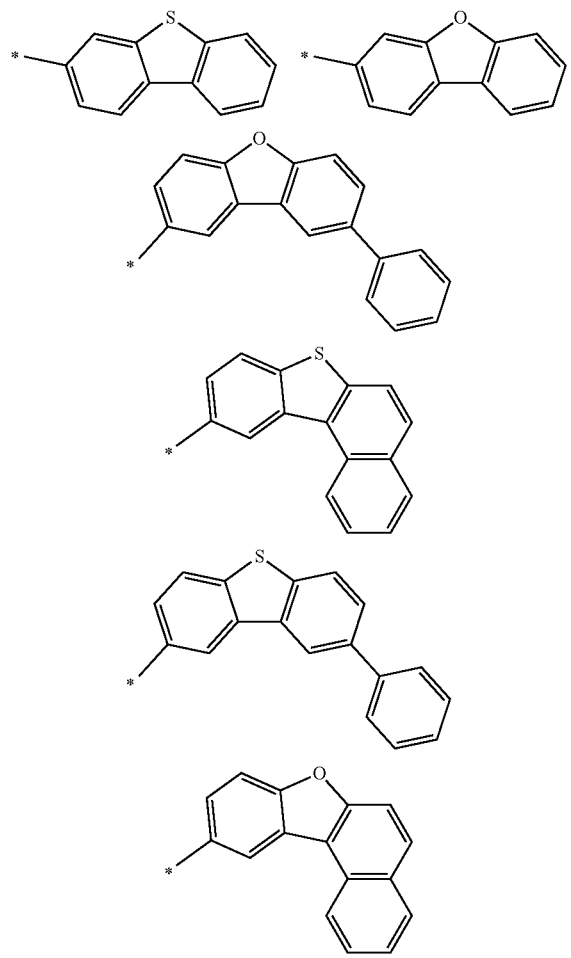
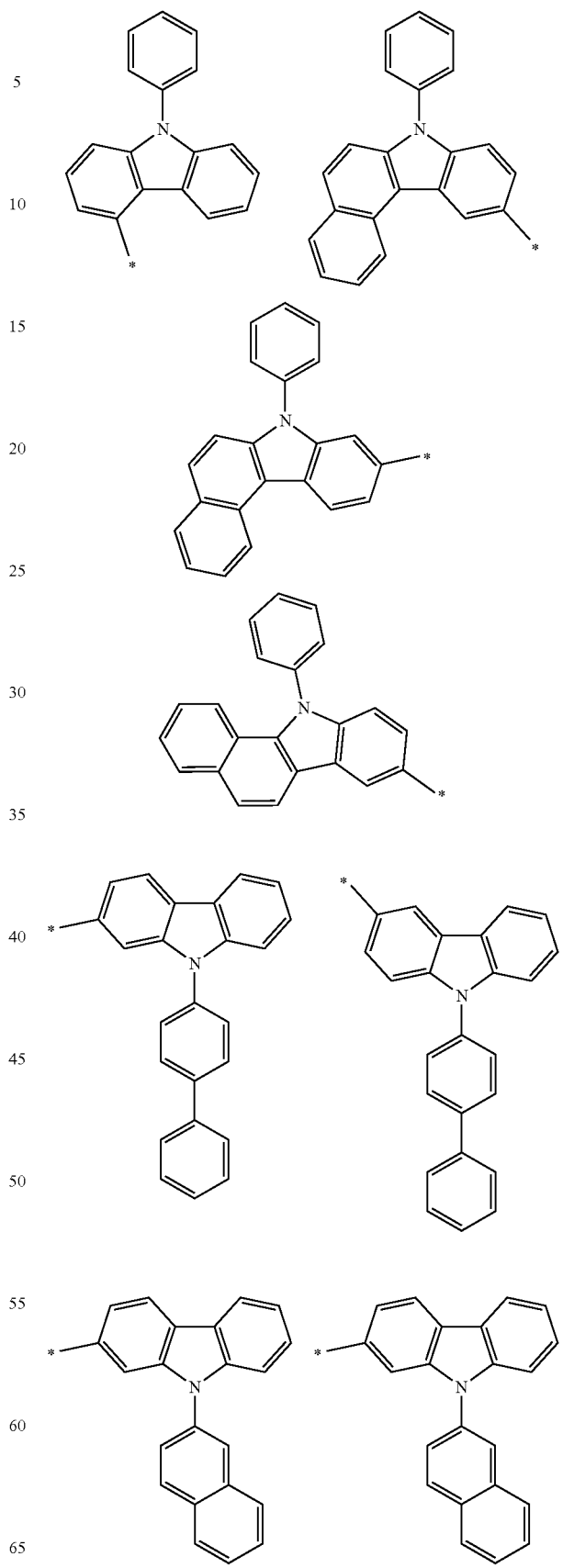

-continued

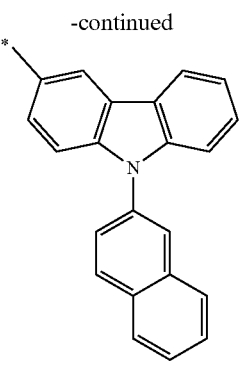

According to one embodiment of the present specification, Chemical Formula 3 is a substituted or unsubstituted aryl group, or a substituted or unsubstituted heteroaryl group.

According to one embodiment of the present specification, Chemical Formula 3 is a substituted or unsubstituted monocyclic N-containing heteroaryl group.

According to one embodiment of the present specification, Chemical Formula 3 may be selected from among a substituted or unsubstituted phenyl group, a substituted or unsubstituted pyridine group, a substituted or unsubstituted pyrimidine group, or a substituted or unsubstituted triazine group.

According to one embodiment of the present specification, Chemical Formula 3 is an N-containing heteroaryl group unsubstituted or substituted with a heteroaryl group.

According to one embodiment of the present specification, Chemical Formula 3 is an N-containing heteroaryl group unsubstituted or substituted with a heteroaryl group containing N, O or S.

According to one embodiment of the present specification, Chemical Formula 3 is an N-containing heteroaryl group unsubstituted or substituted with furan, thiophene, dibenzofuran, dibenzothiophene, carbazole, triazine, pyrimidine, pyridine, quinazol, quinazoline, quinoxaline or phenanthroline.

According to one embodiment of the present specification, Chemical Formula 3 is triazine, pyrimidine or pyridine unsubstituted or substituted with furan, thiophene, dibenzofuran, dibenzothiophene, carbazole, triazine, pyrimidine, pyridine, quinazol, quinazoline, quinoxaline or phenanthroline.

According to one embodiment of the present specification, Chemical Formula 3 is triazine, pyrimidine or pyridine unsubstituted or substituted with dibenzofuran or dibenzothiophene.

According to one embodiment of the present specification, Chemical Formula 3 is an aryl group unsubstituted or substituted with an N-containing heteroring.

According to one embodiment of the present specification, Chemical Formula 3 is an aryl group unsubstituted or substituted with triazine, pyrimidine, pyridinequinazol, quinazoline, quinoxaline or phenanthroline.

According to one embodiment of the present specification, Chemical Formula 3 is a phenyl group or a fluorene group unsubstituted or substituted with triazine, pyrimidine, pyridinequinazol, quinazoline, quinoxaline or phenanthroline.

According to one embodiment of the present specification, Chemical Formula 3 is an N-containing heteroaryl group unsubstituted or substituted with an aryl group.

According to one embodiment of the present specification, Chemical Formula 3 is an N-containing heteroaryl group unsubstituted or substituted with phenyl, biphenyl, naphthalene, triphenylene or fluorene.

According to one embodiment of the present specification, Chemical Formula 3 is triazine, pyrimidine or pyridine unsubstituted or substituted with phenyl, biphenyl, naphthalene, triphenylene or fluorene.

According to one embodiment of the present specification, Chemical Formula 3 may be selected from among the following substituents.

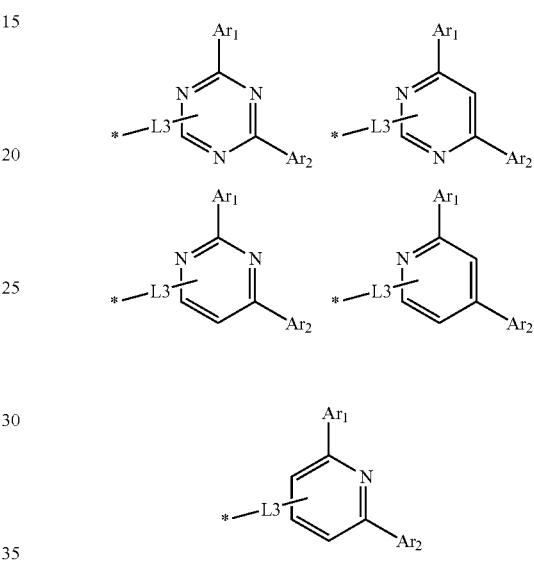

According to one embodiment of the present specification, Chemical Formula 3 may be selected from among the following substituents.

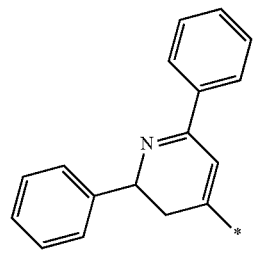

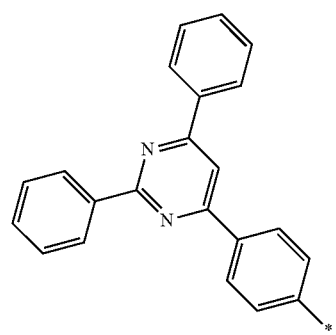

-continued
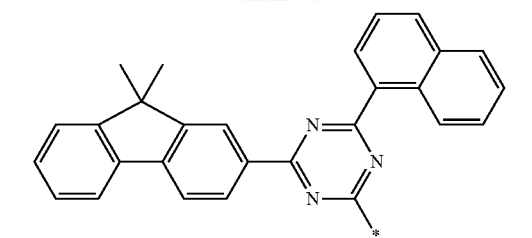
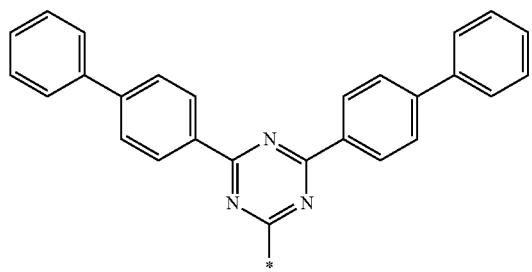
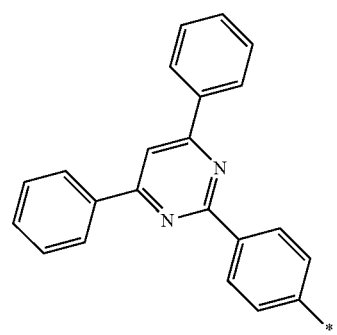
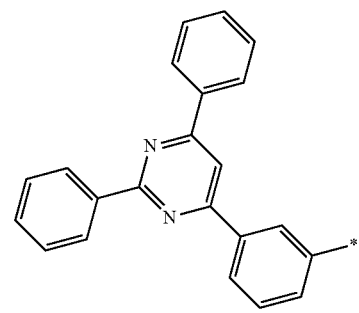
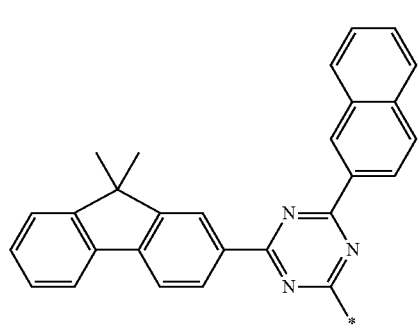
-continued
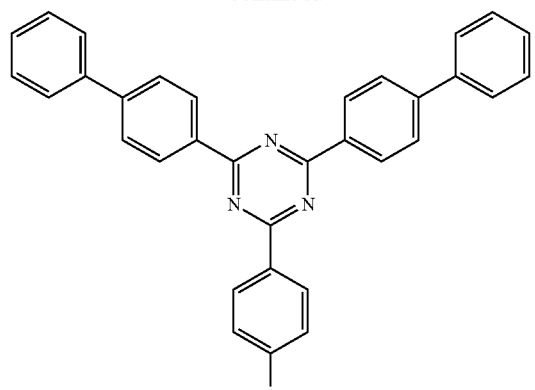
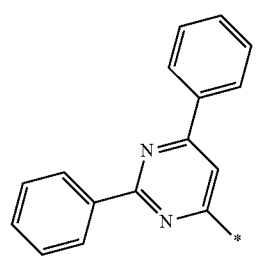
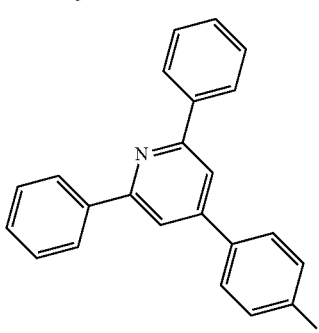
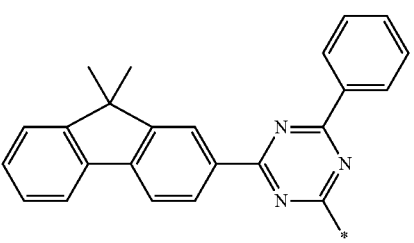
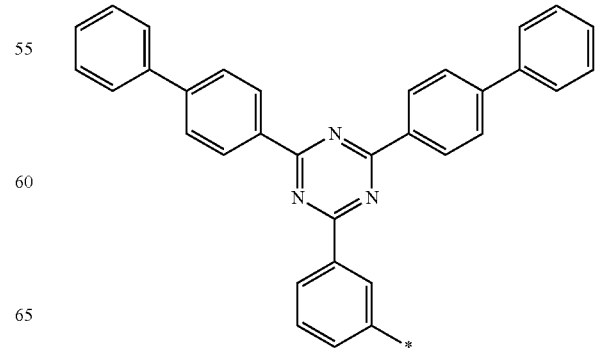

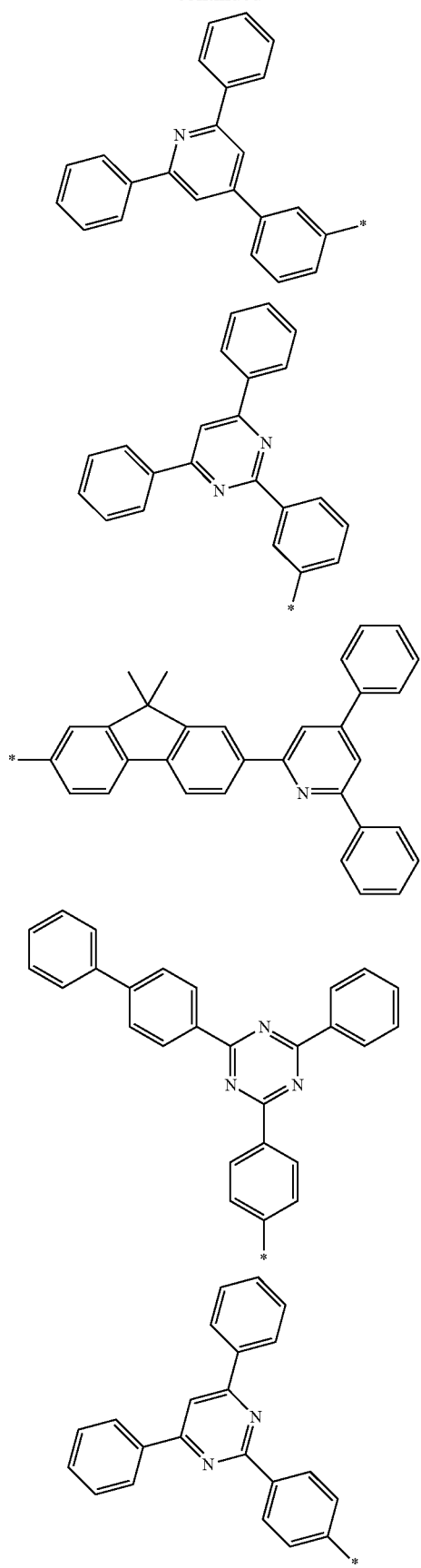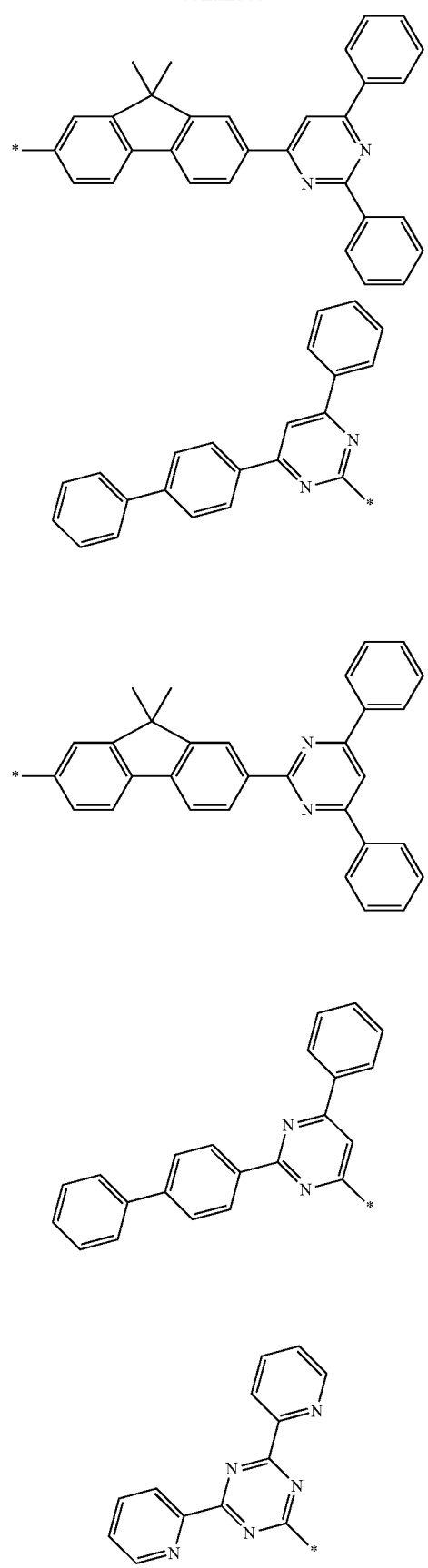

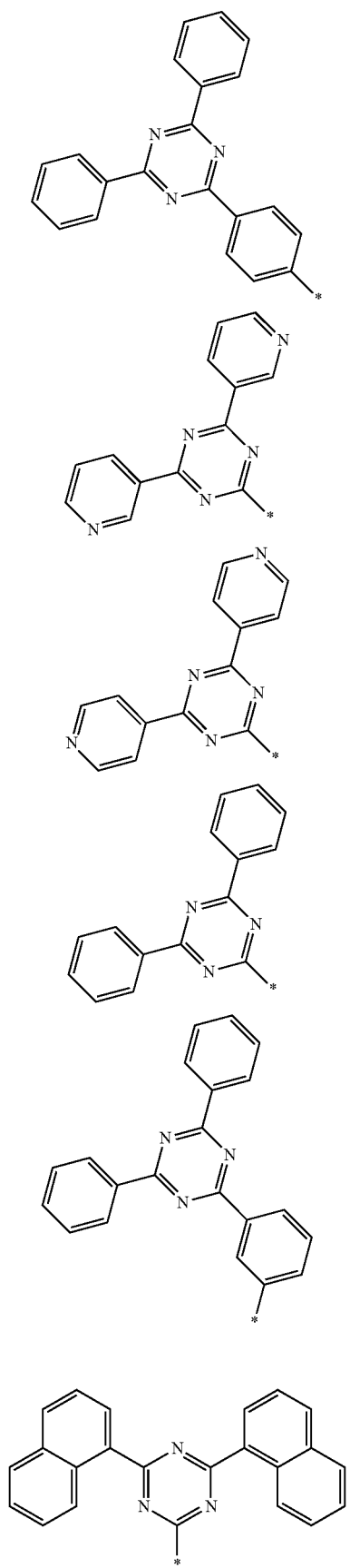
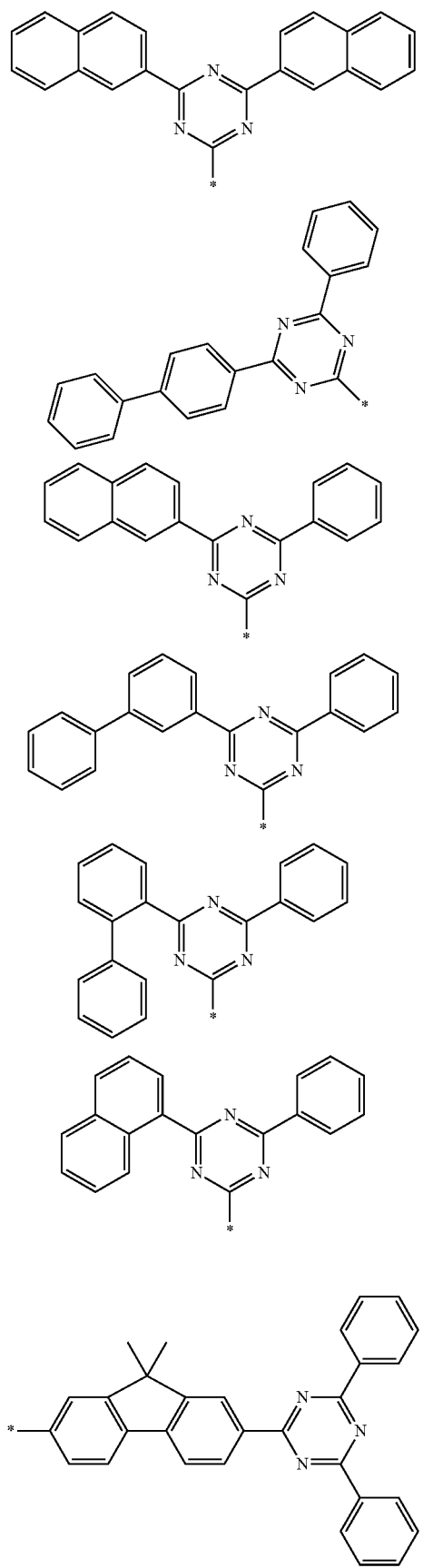

-continued
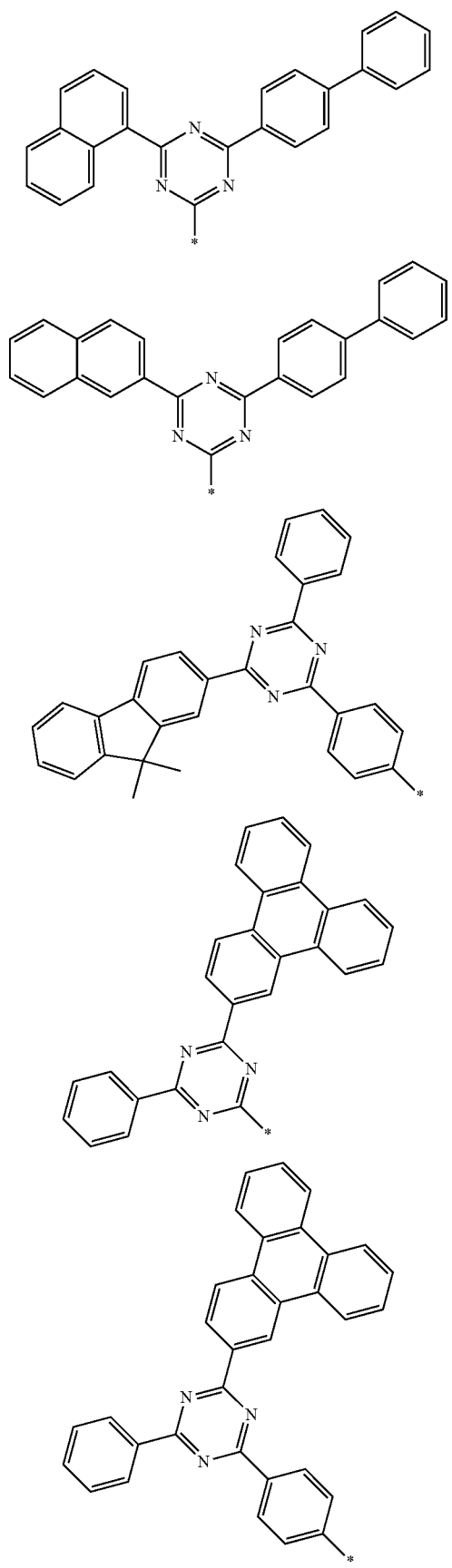
-continued
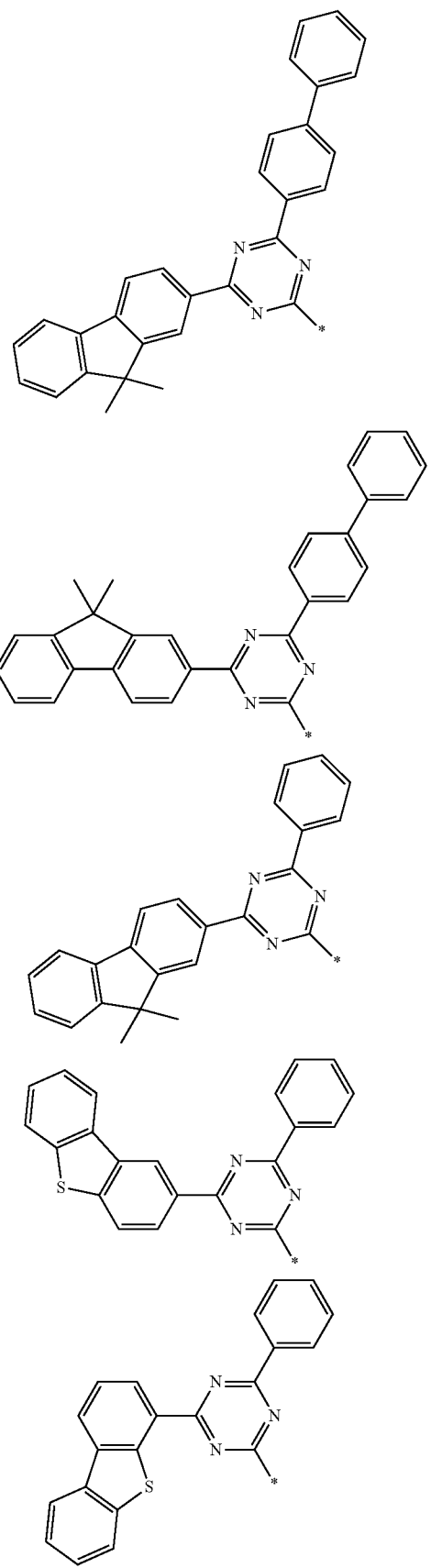

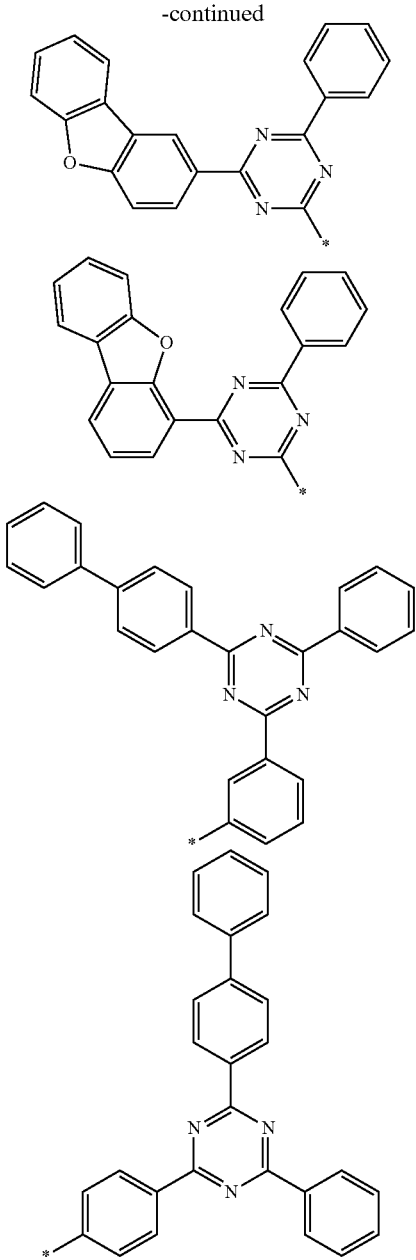

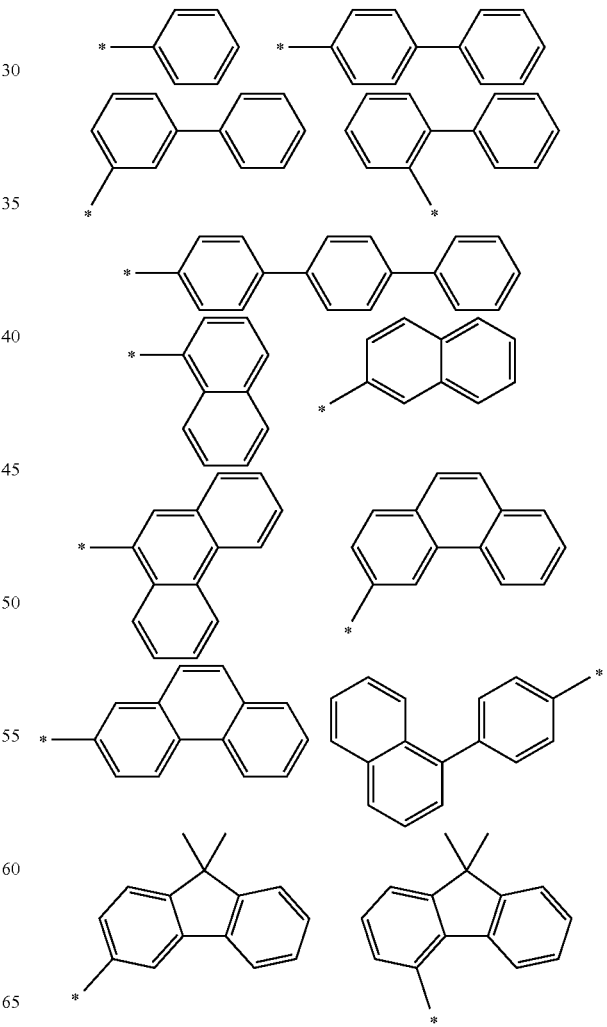

fluorene group, a substituted or unsubstituted pyridine group, a substituted or unsubstituted pyrimidine group, a substituted or unsubstituted dibenzofuran group, a substituted or unsubstituted dibenzothiophene group, a substituted or unsubstituted triazine group, a substituted or unsubstituted quinoline group, a substituted or unsubstituted quinazoline group, or a substituted or unsubstituted quinoxaline group.

According to one embodiment of the present specification, Ar1 and Ar2 are the same as or different from each other, and each independently a phenyl group, a biphenyl group, a naphthalene group, an anthracene group, a triphenylene group, a dimethylfluorene group, a dibenzofuran group, a dibenzothiophene group, a pyridine group or a pyrimidine group.

According to one embodiment of the present specification, Ar1 and Ar2 are the same as or different from each other, and each independently a phenyl group, a biphenyl group, a naphthalene group, an anthracene group, a triphenylene group, a dimethylfluorene group, a pyridine group or a pyrimidine group.

According to one embodiment of the present specification, Ar1 and Ar2 may be selected from among the following substituents.

According to one embodiment of the present specification, Ar1 and Ar2 are the same as or different from each other, and each independently a substituted or unsubstituted aryl group, or a substituted or unsubstituted heteroaryl group.

According to one embodiment of the present specification, Ar1 and Ar2 are the same as or different from each other, and each independently a substituted or unsubstituted monocyclic or multicyclic aryl group, or a substituted or unsubstituted monocyclic or multicyclic heteroaryl group.

According to one embodiment of the present specification, Ar1 and Ar2 are the same as or different from each other, and each independently a substituted or unsubstituted phenyl group, a substituted or unsubstituted biphenyl group, a substituted or unsubstituted naphthalene group, a substituted or unsubstituted anthracene group, a substituted or unsubstituted phenanthrene group, a substituted or unsubstituted triphenylene group, a substituted or unsubstituted

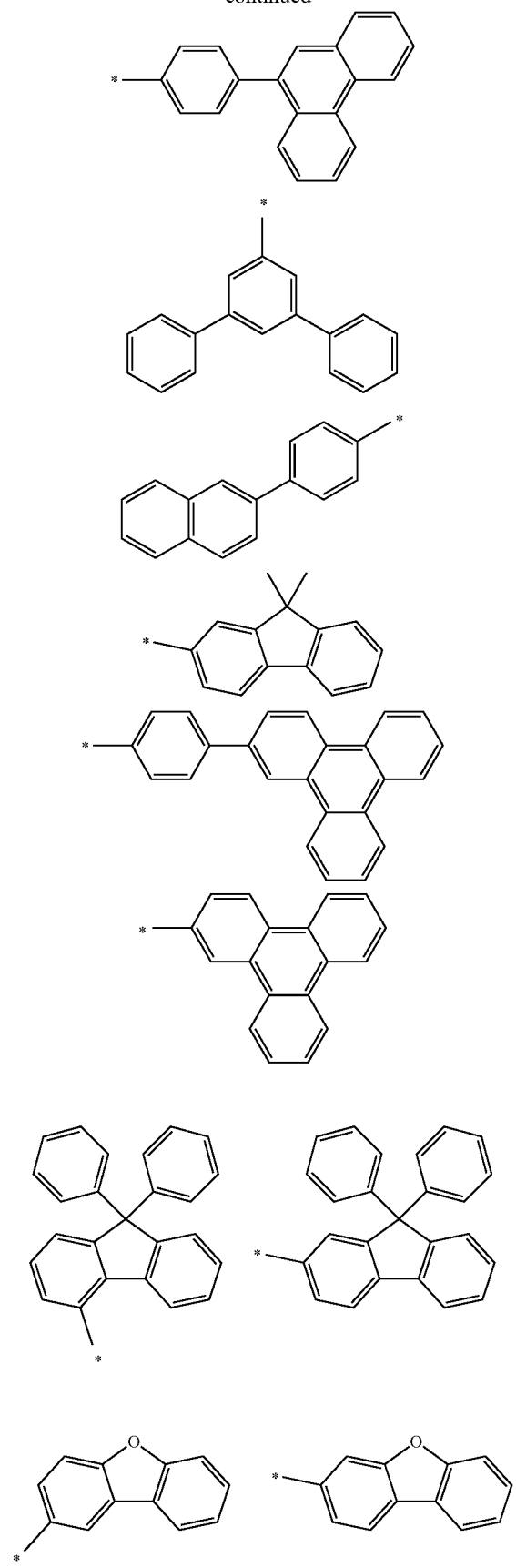
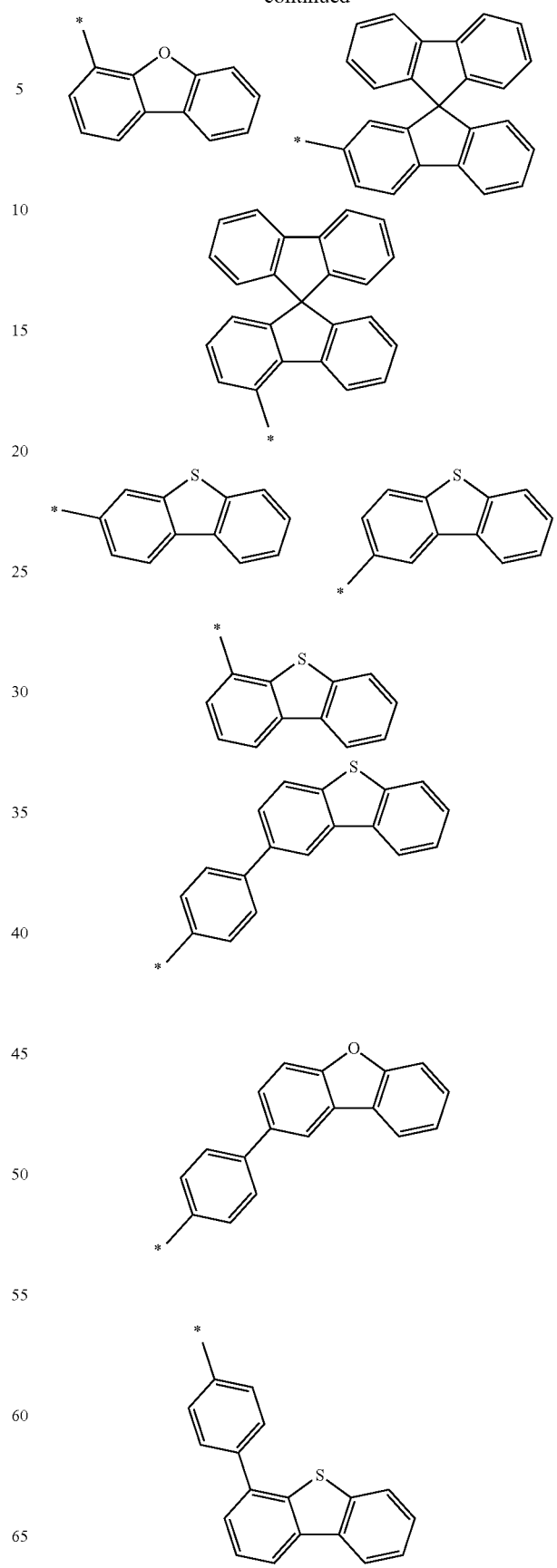

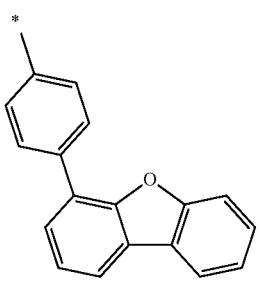
According to another embodiment of the present specification, the compounds of Chemical Formula 1 or Chemical Formulae 4 to 6 may be represented by the following structural formulae.
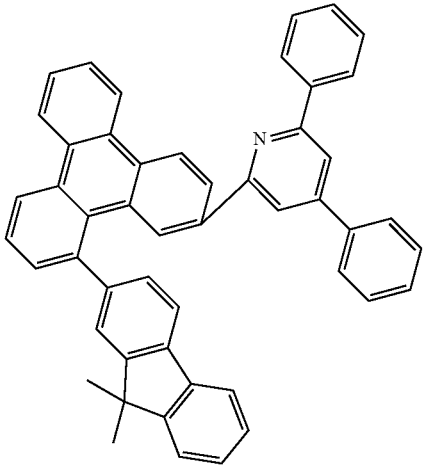
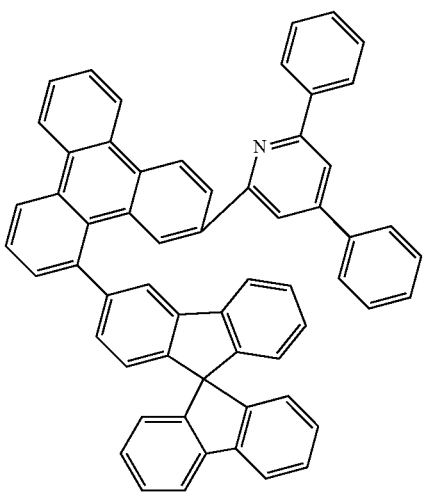
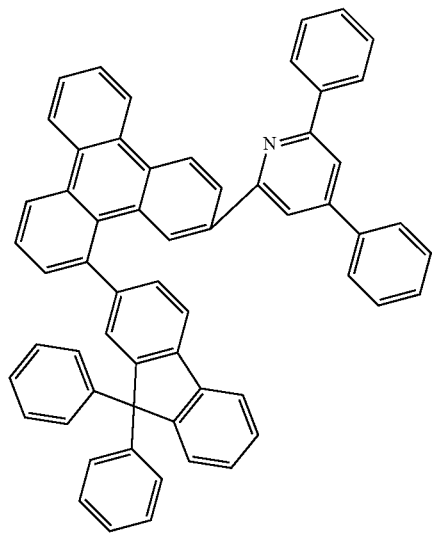
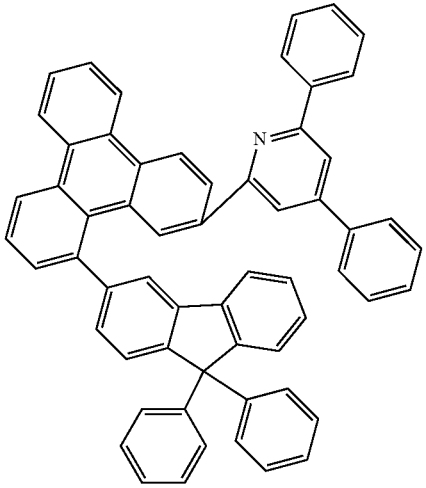

1-6
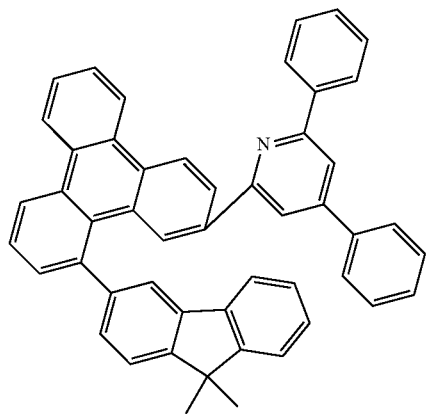
1-7
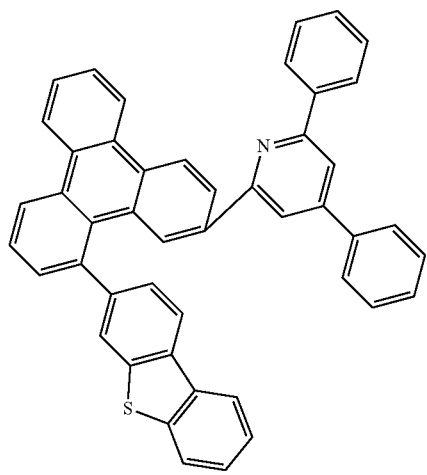
1-8
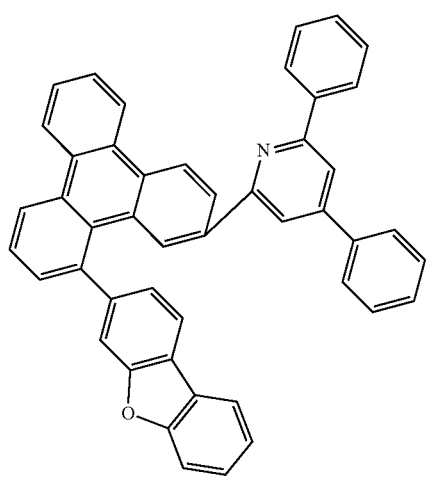
1-9
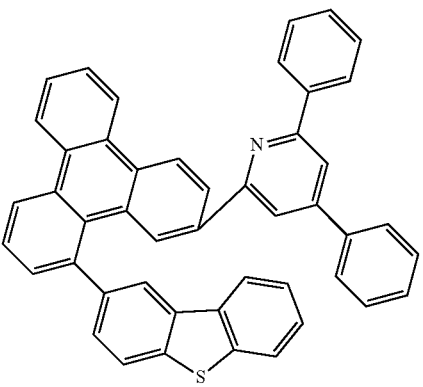
1-10
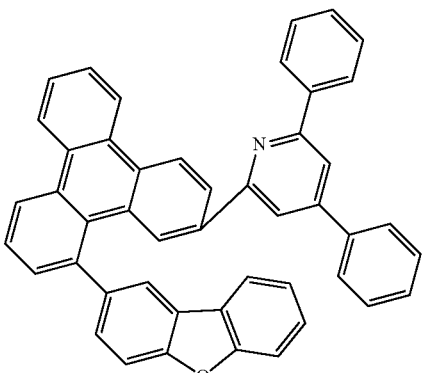
1-11
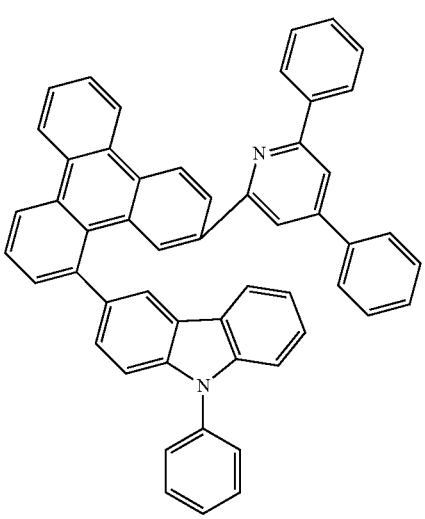

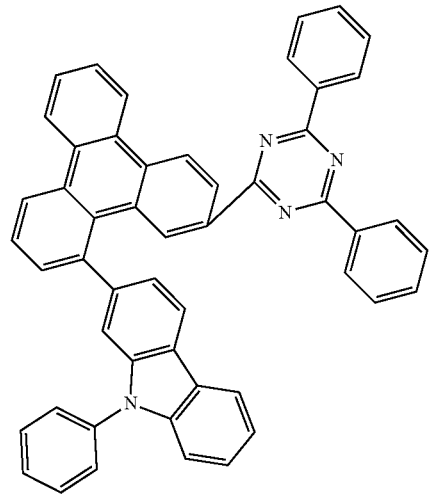
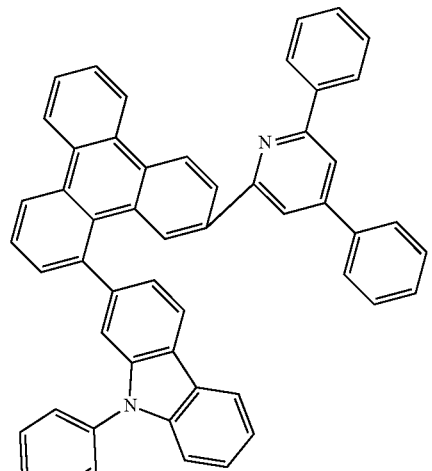
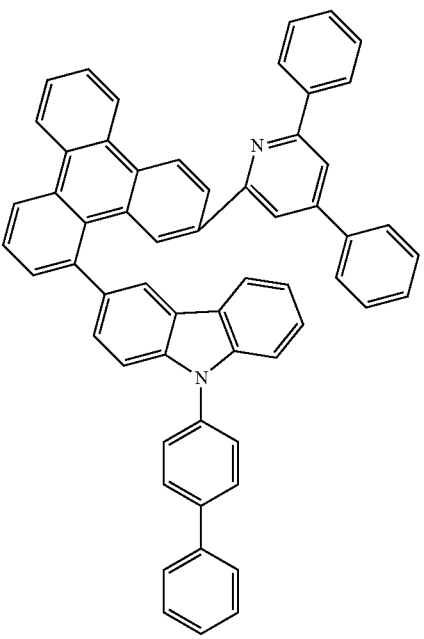

-continued
1-17
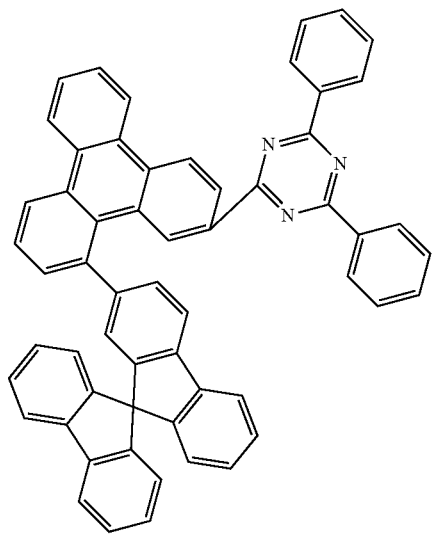
1-18
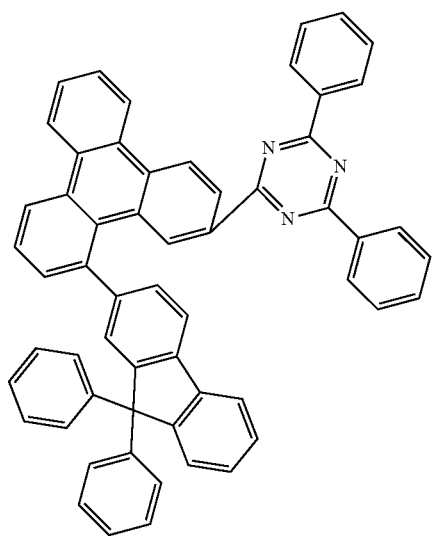
1-19
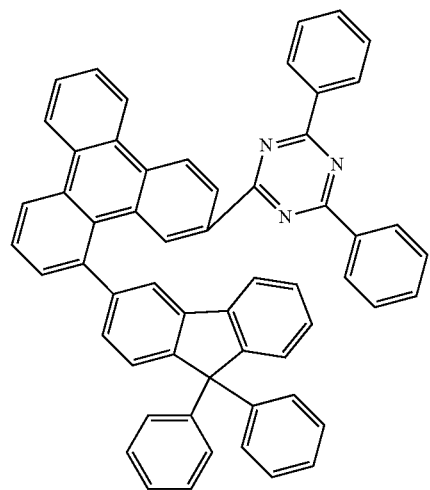
-continued
1-20
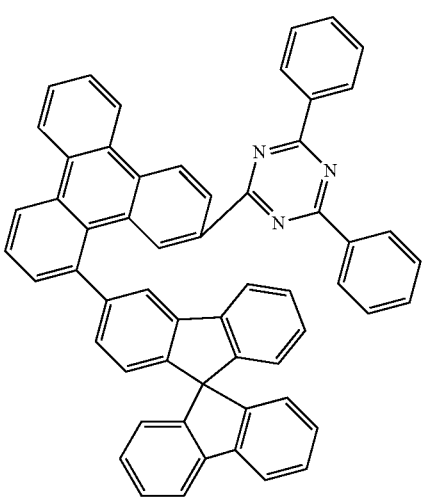
1-21
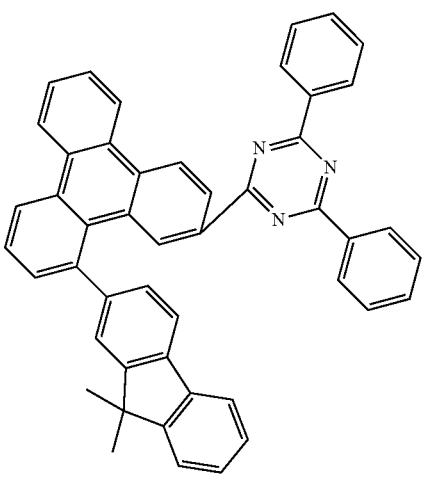
1-22
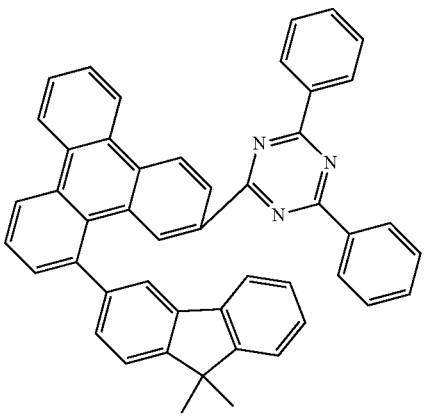

1-23
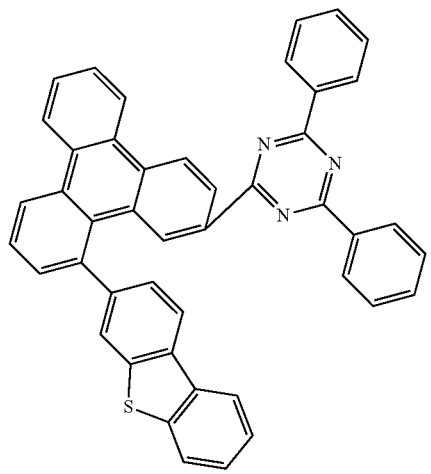
1-26
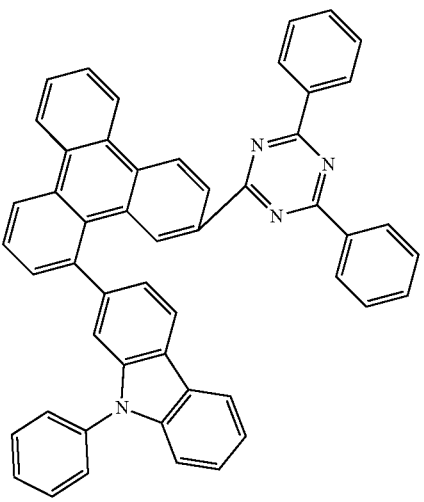
1-24
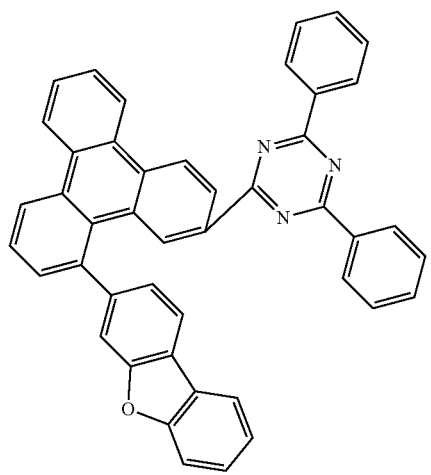
1-27
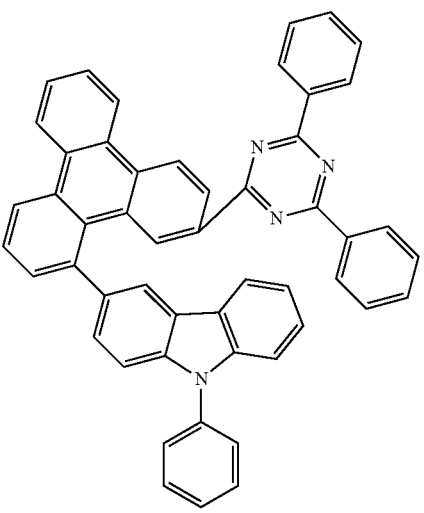
1-25
1-28
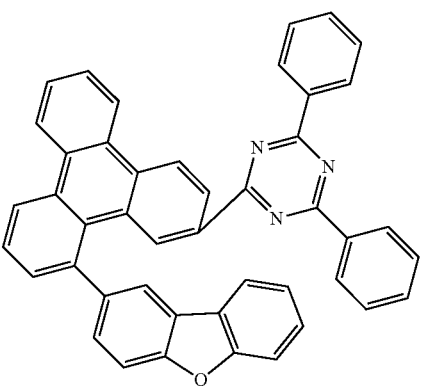

1-29
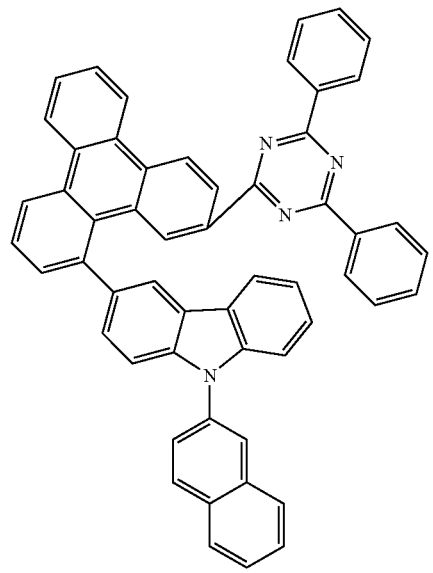
1-31
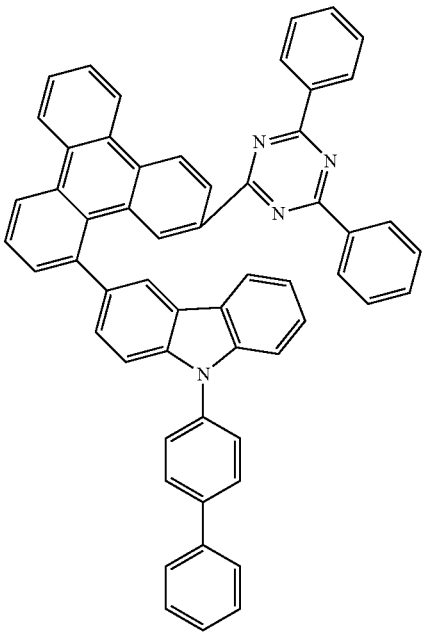
1-30
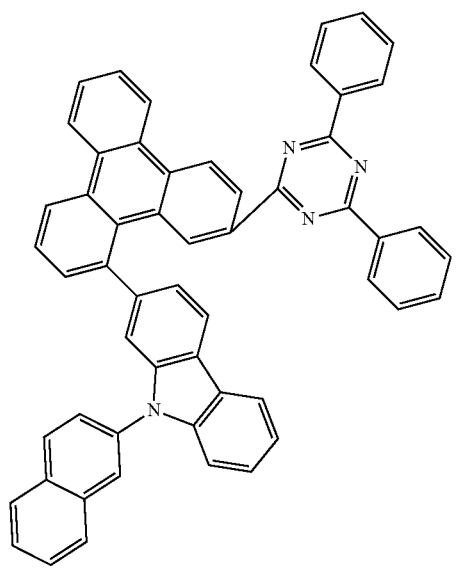
1-32
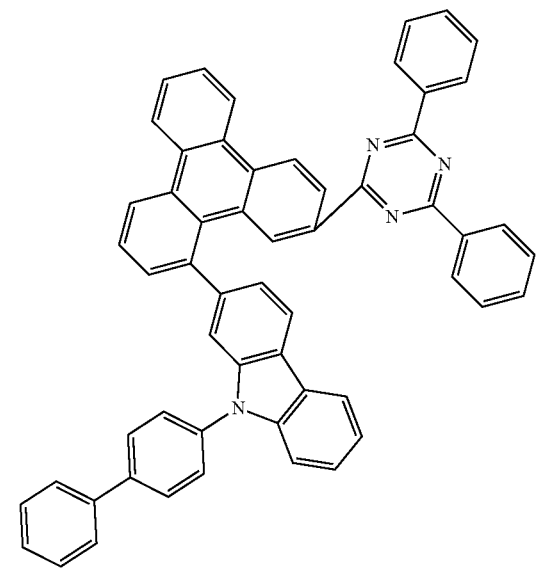

1-33
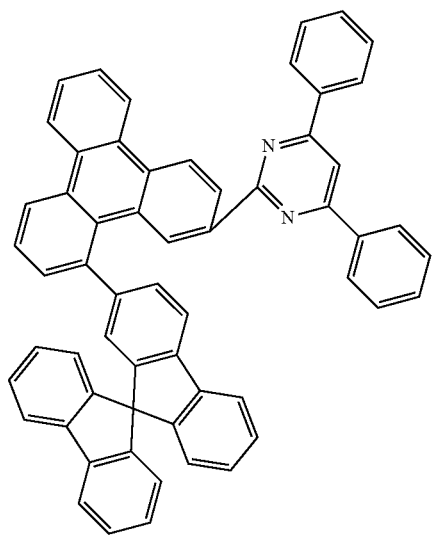
1-34
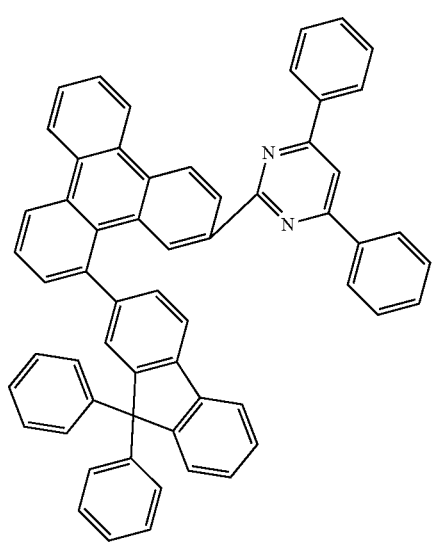
1-35
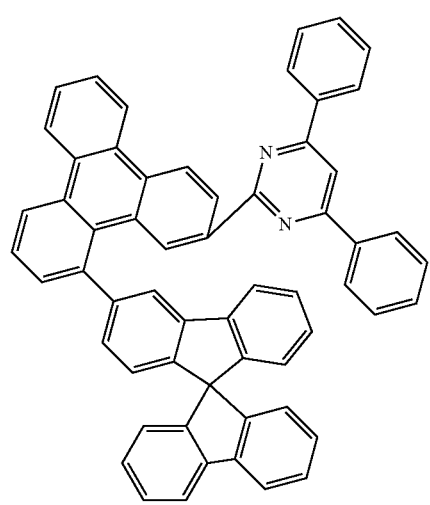
1-36
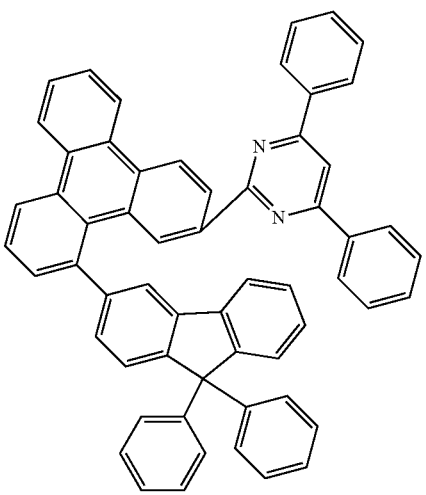
1-37
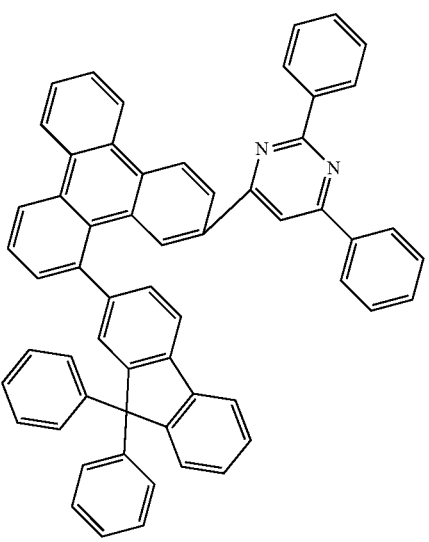
1-38

1-39
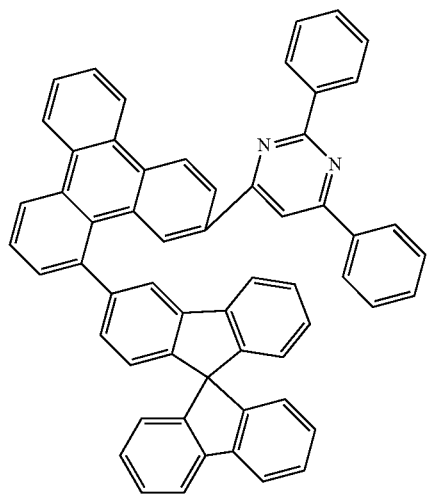
1-40
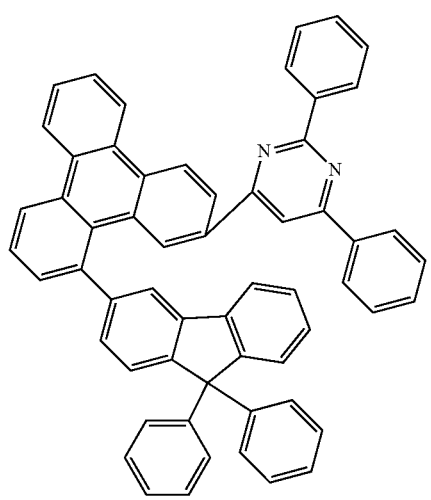
1-41
1-42
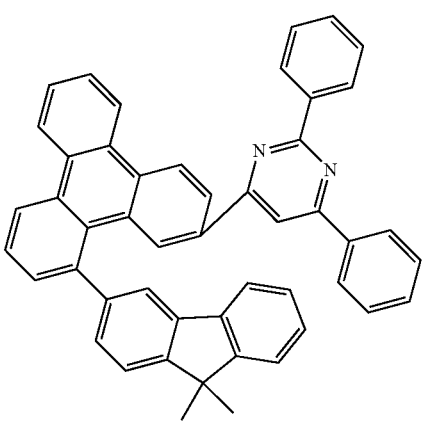
1-43
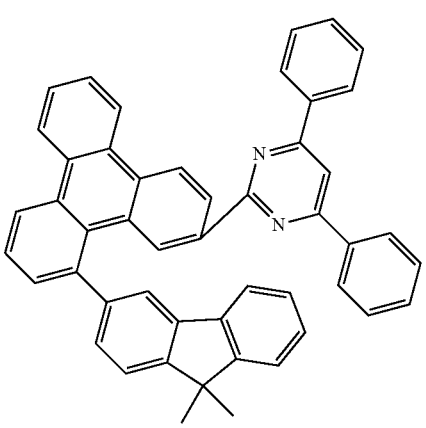
1-44
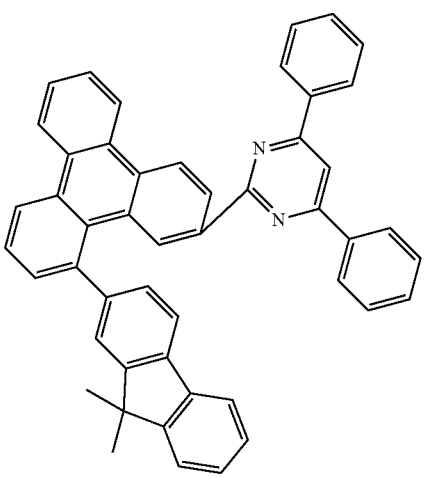

-continued
1-45
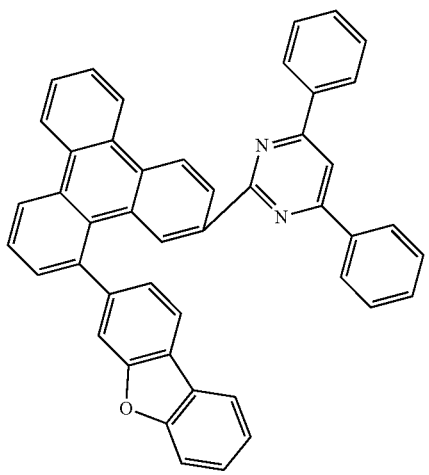
1-46
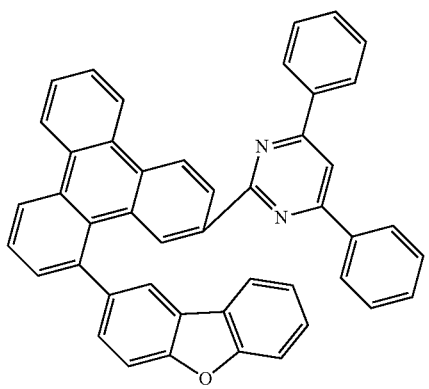
1-47
-continued
1-48
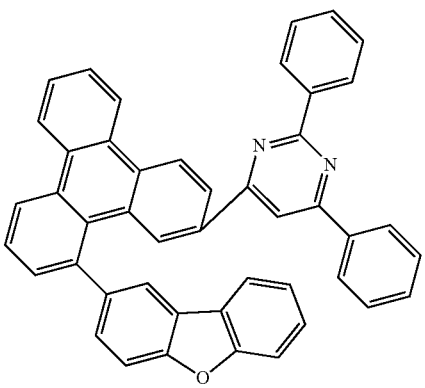
1-49
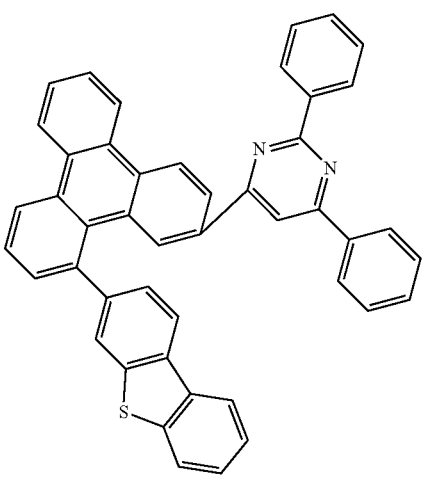
1-50
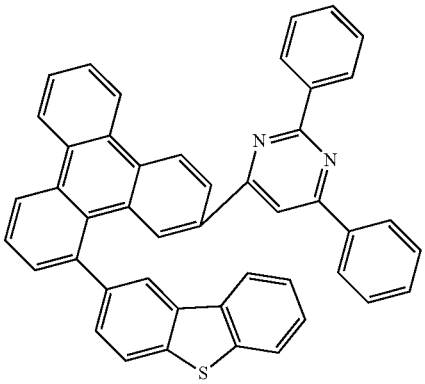

-continued
1-51
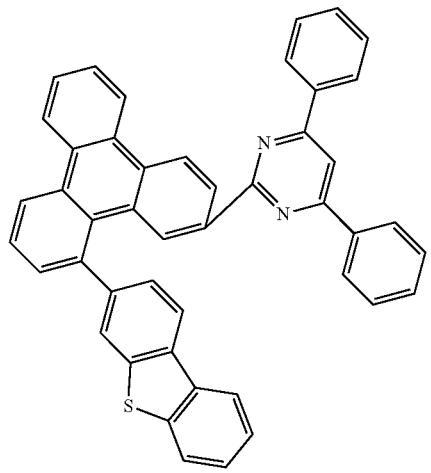
1-52
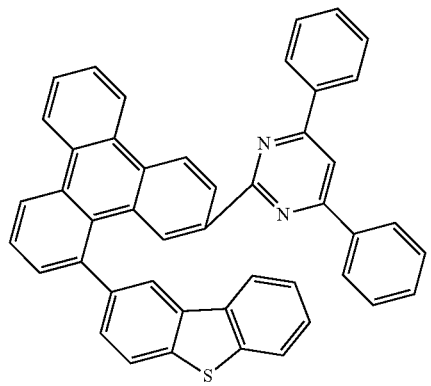
1-53
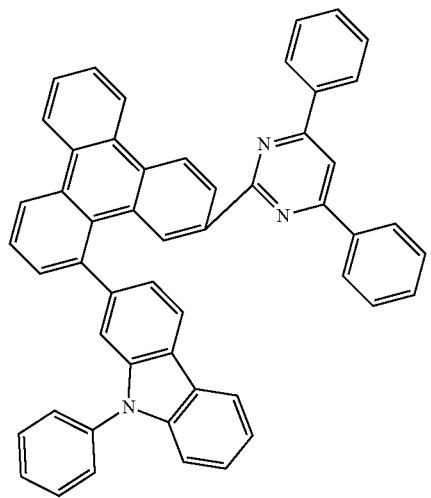
-continued
1-54
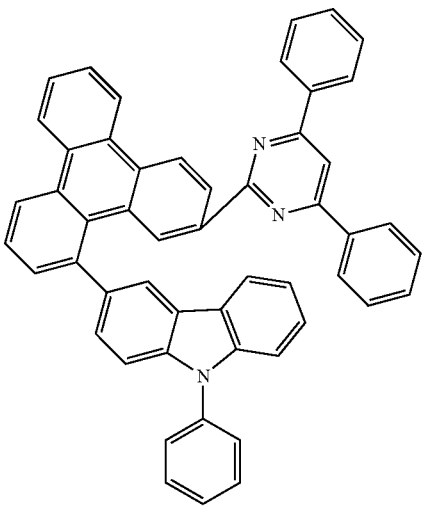
1-55
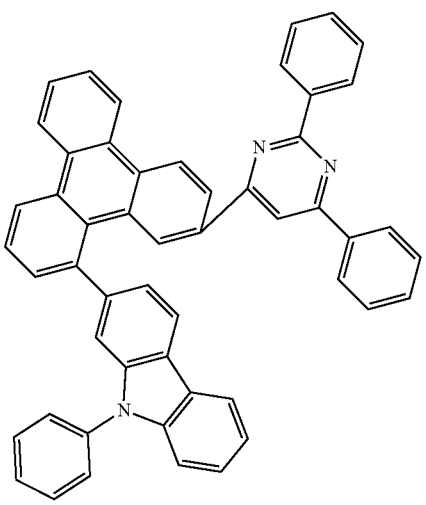
1-56
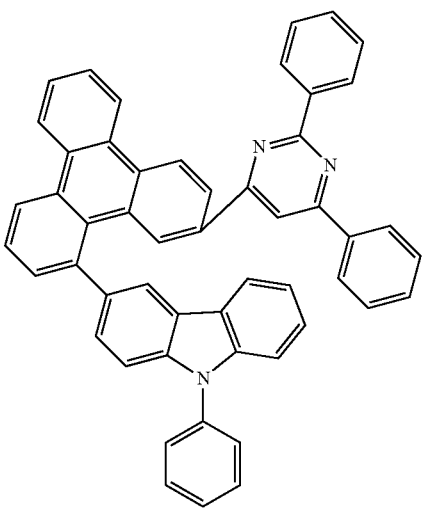

1-57
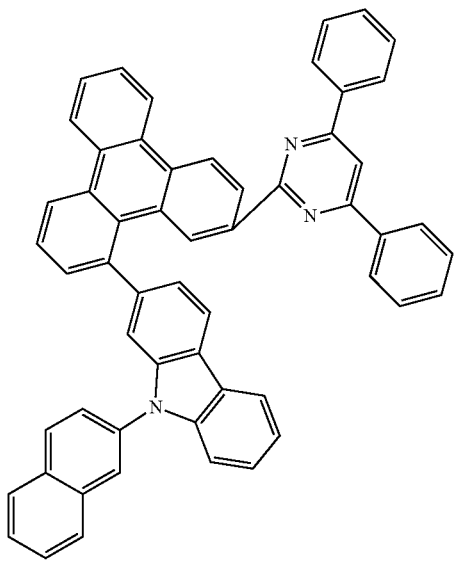
1-58
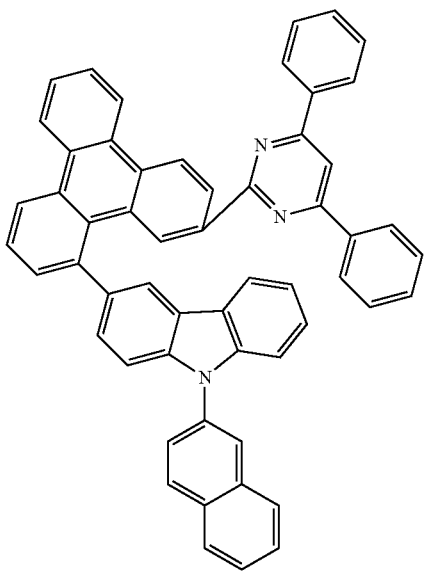
1-59
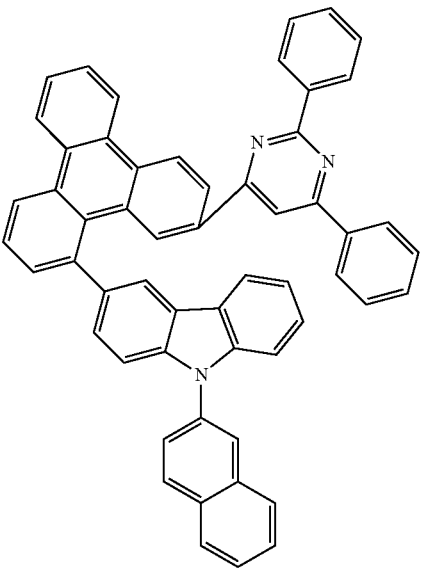
1-60
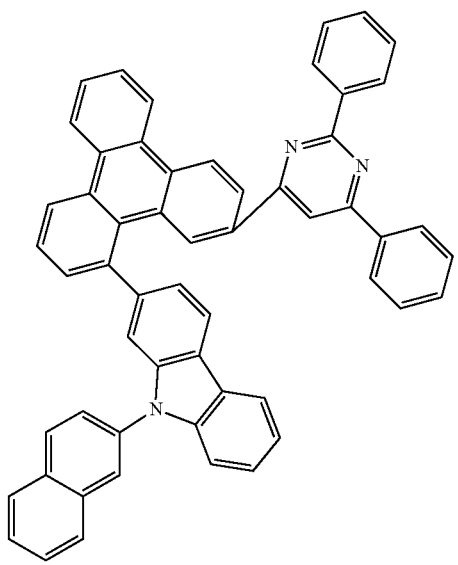

1-61
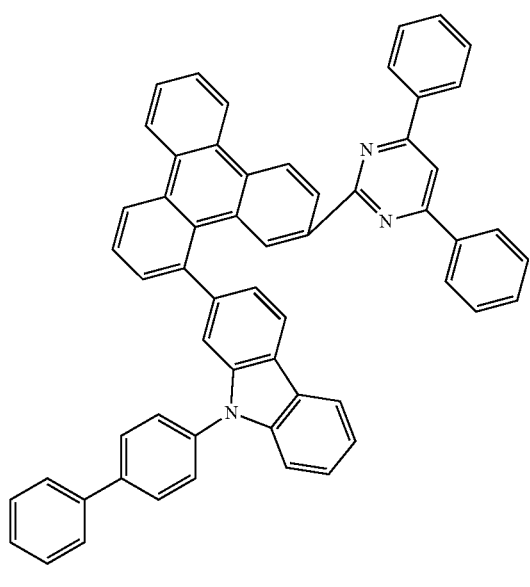
1-63
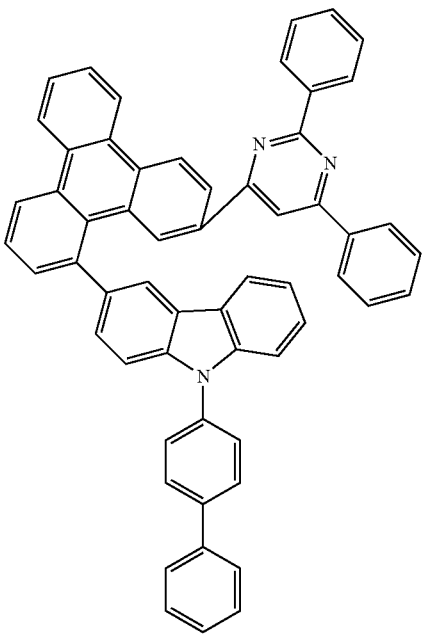
1-62
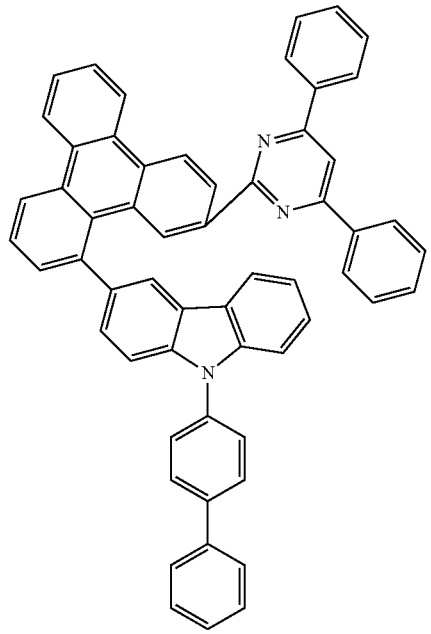
1-64
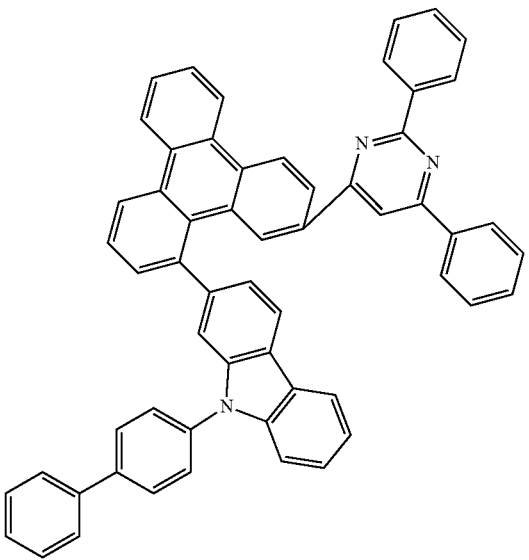

-continued
1-65
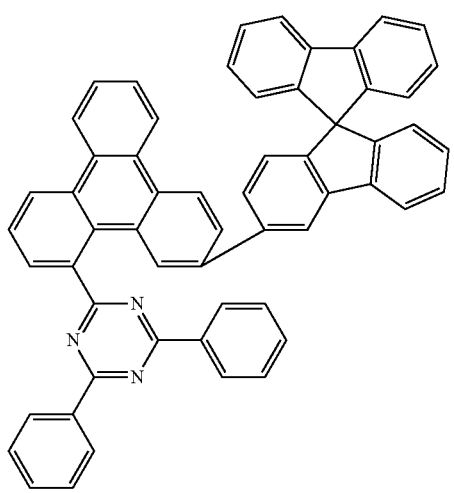
1-68
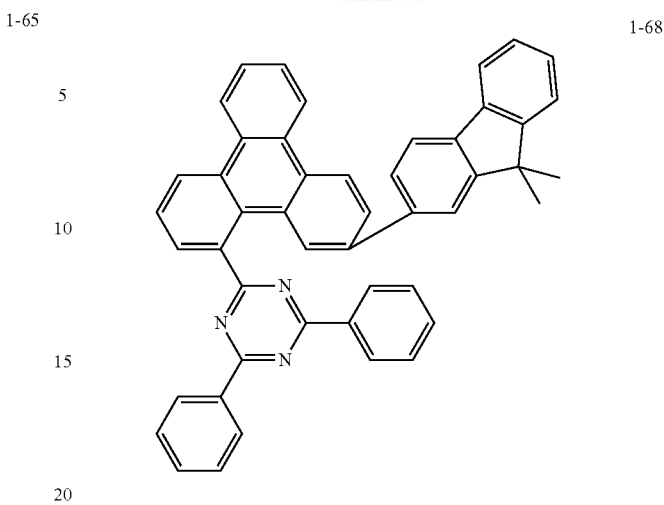
1-66
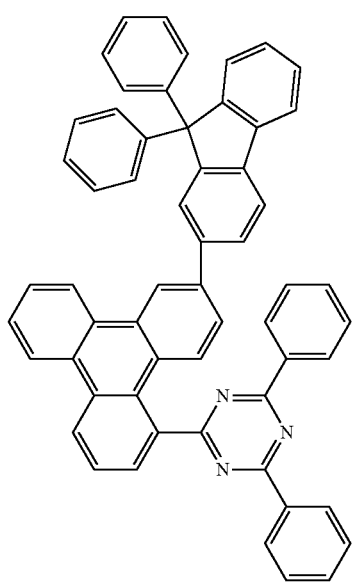
1-69
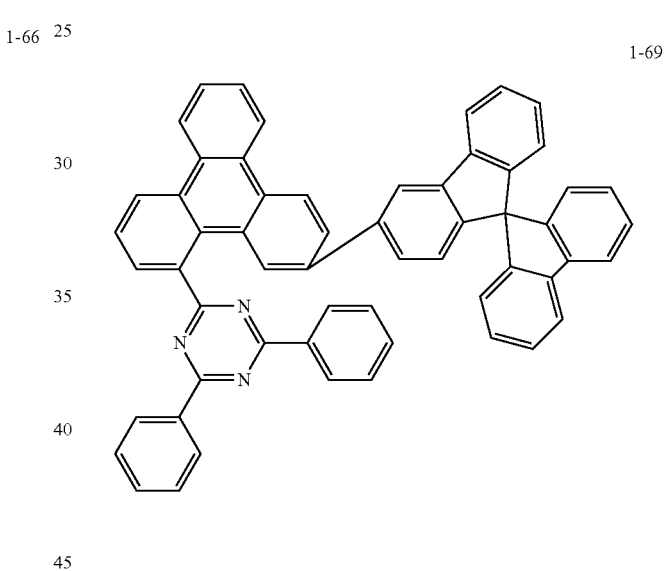
1-67
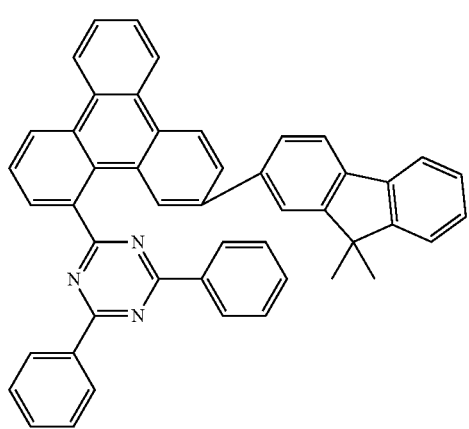
1-70
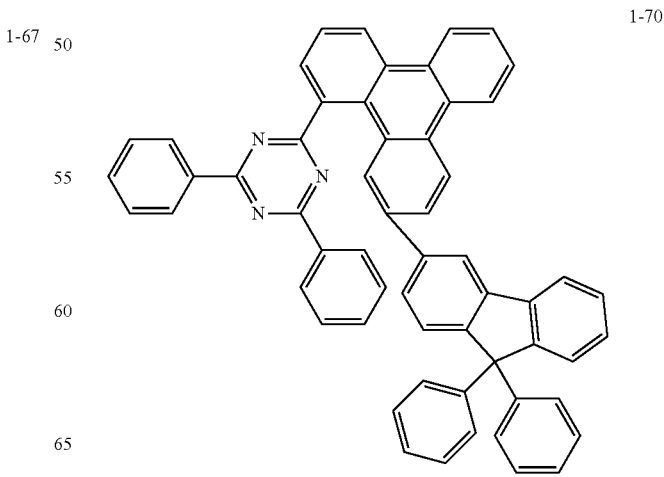

1-71
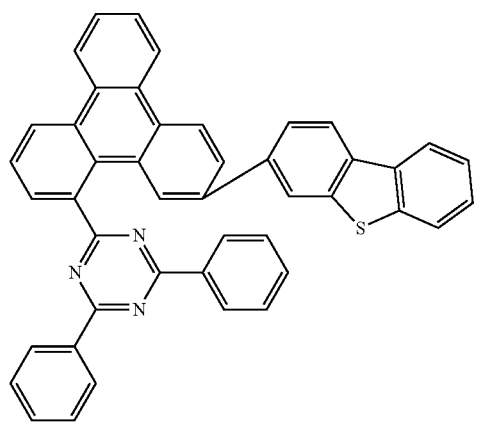
1-74
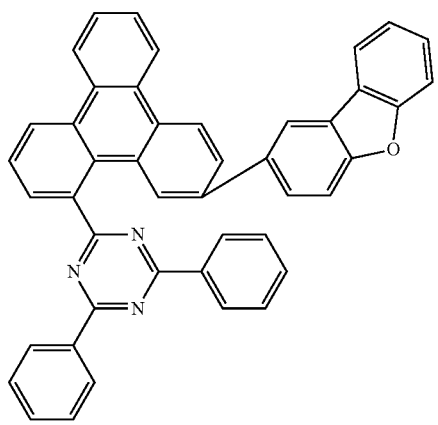
1-72
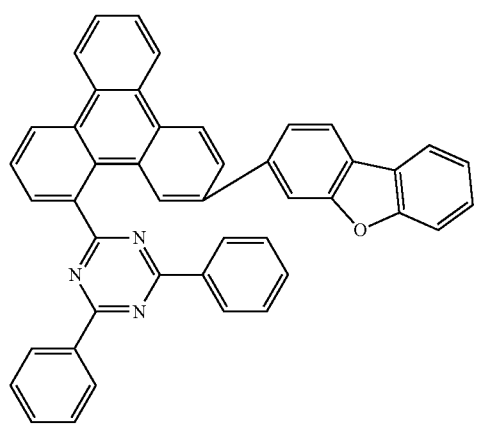
1-75
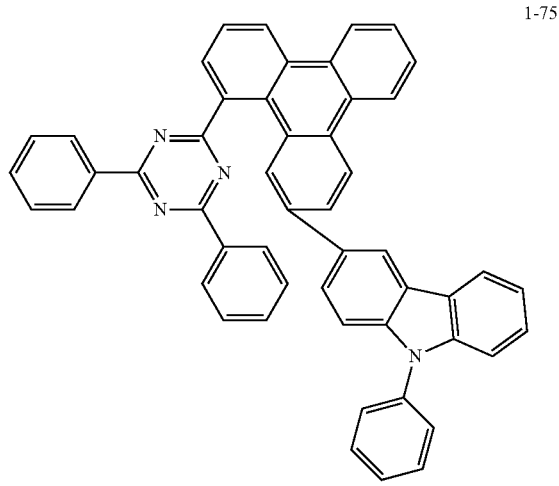
1-73
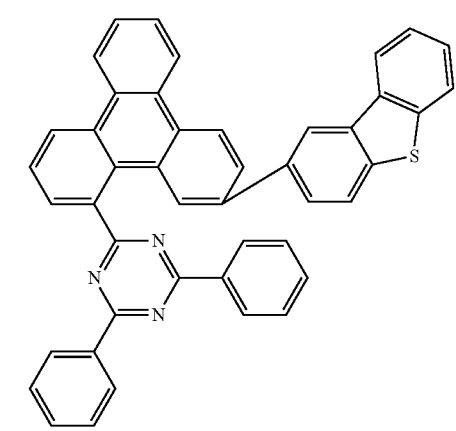
1-76
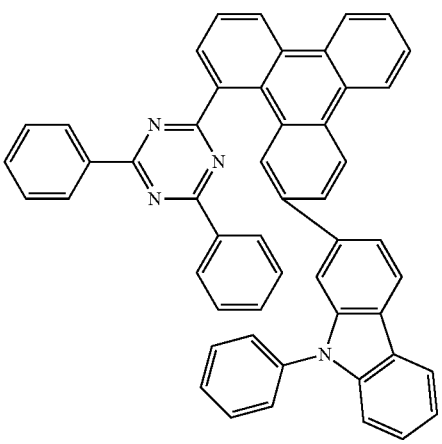

1-77
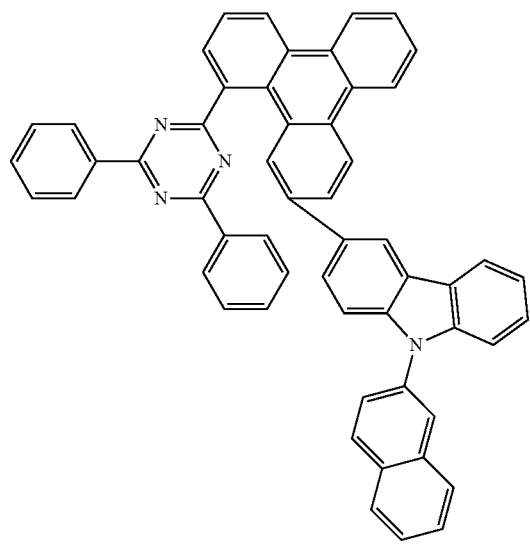
1-78
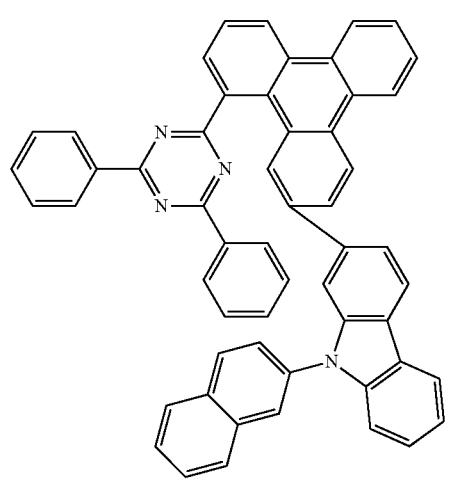
1-79
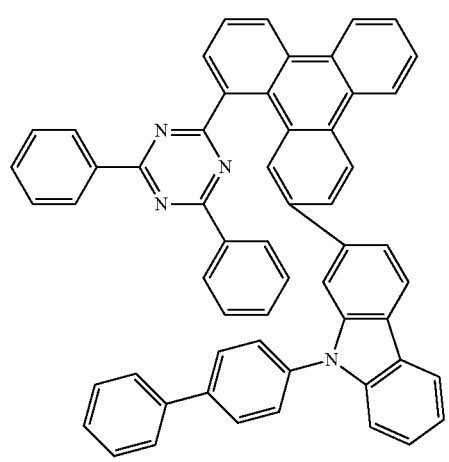
1-80
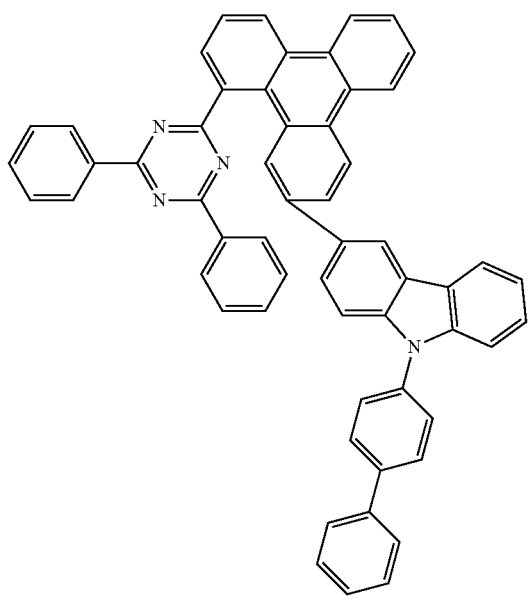
1-81
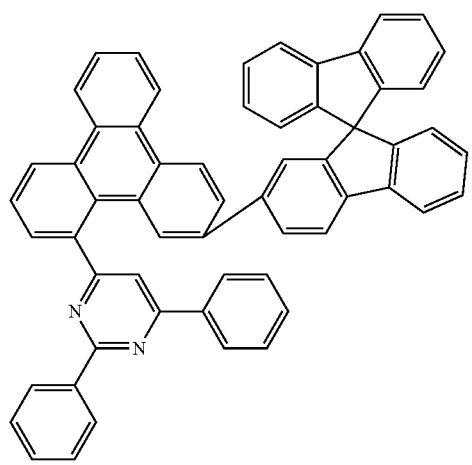
1-82
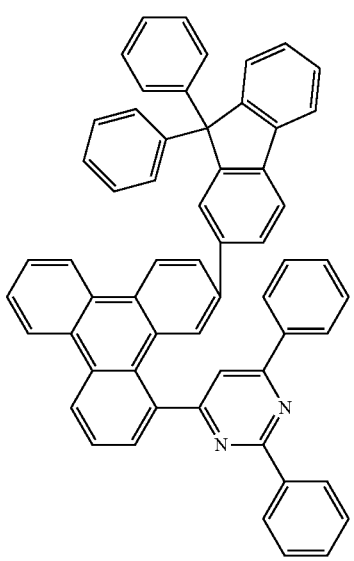

1-83
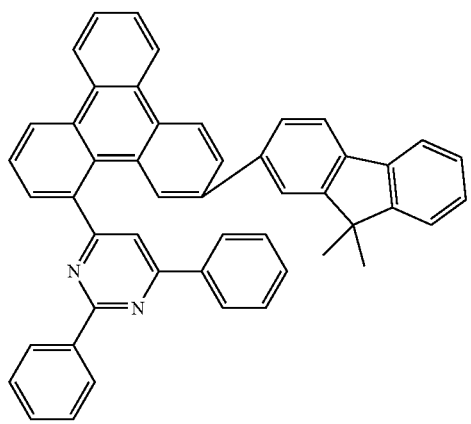
1-86
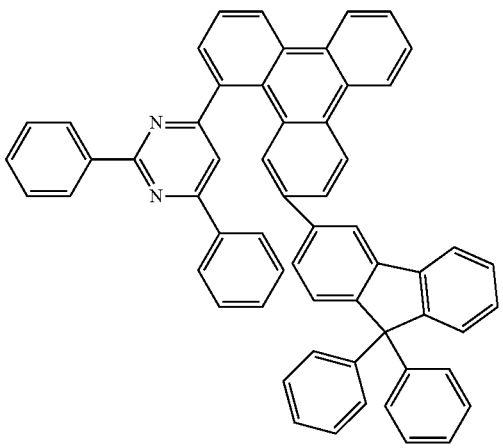
1-84
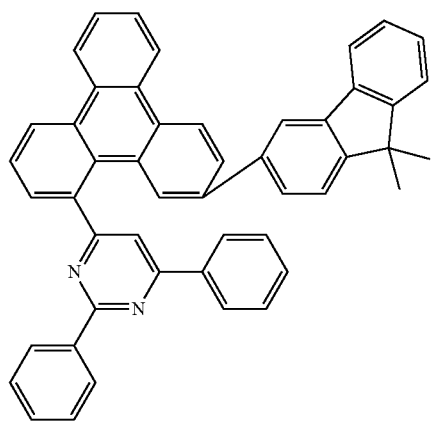
1-87
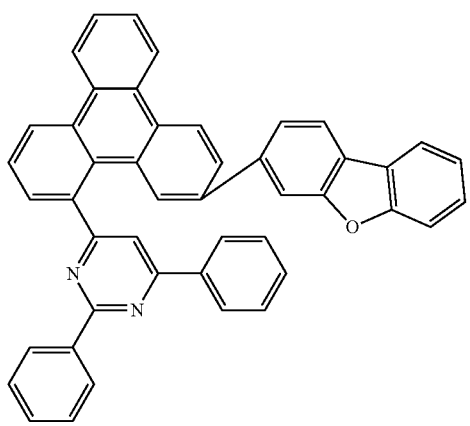
1-85
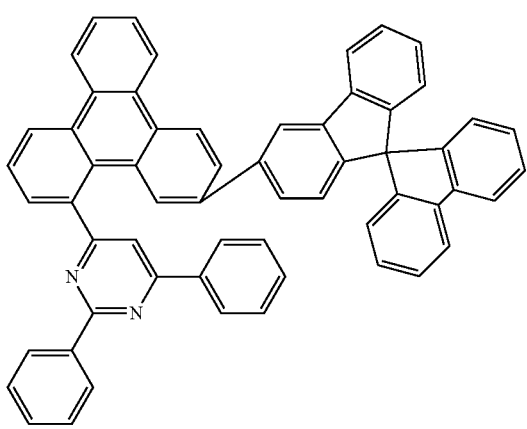
1-88
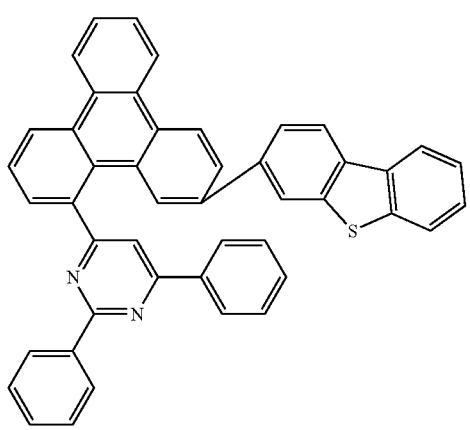

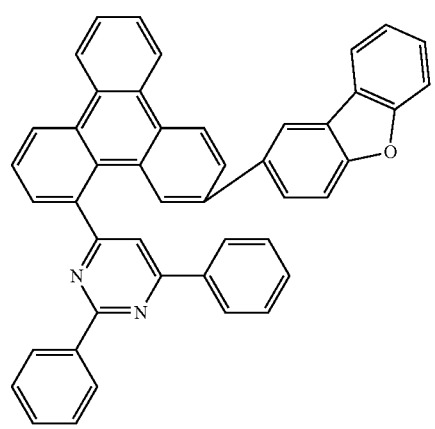
1-89
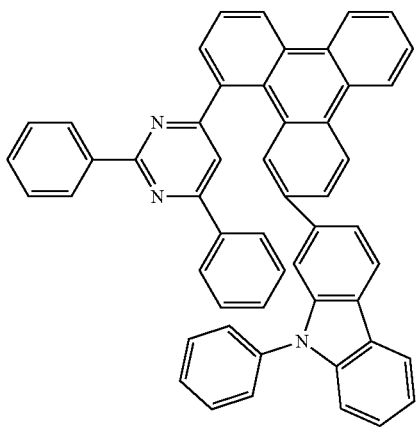
1-92
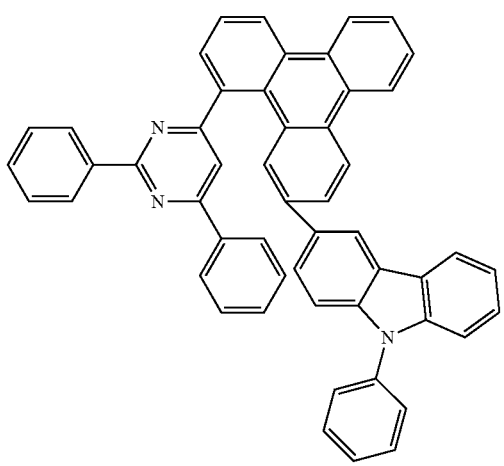
1-90
1-91
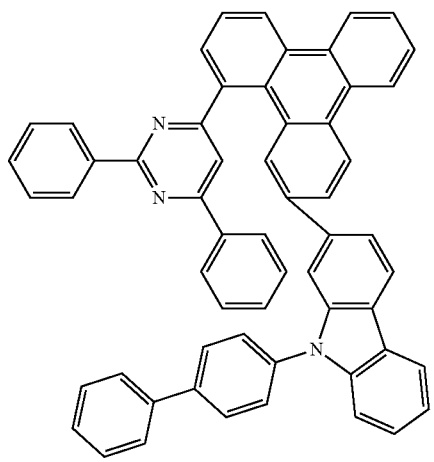
1-93
1-94

1-95
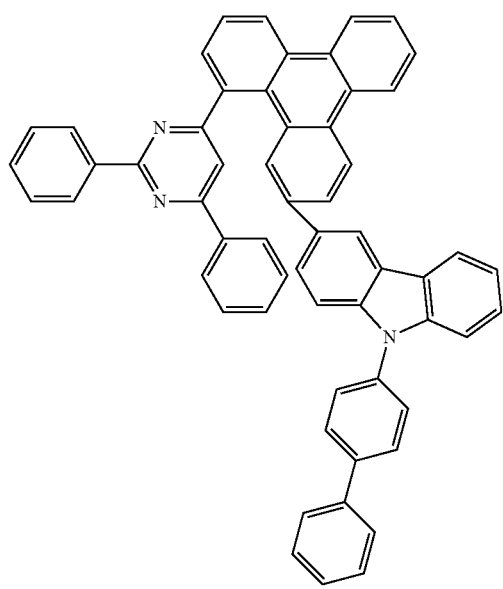
1-98
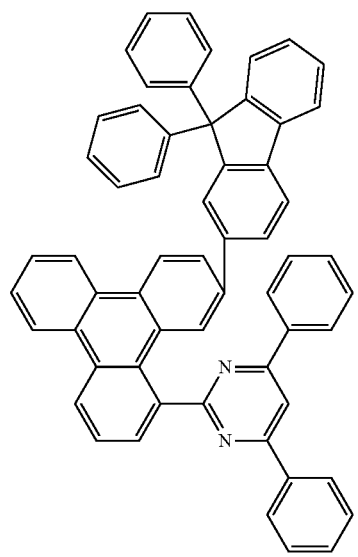
1-96
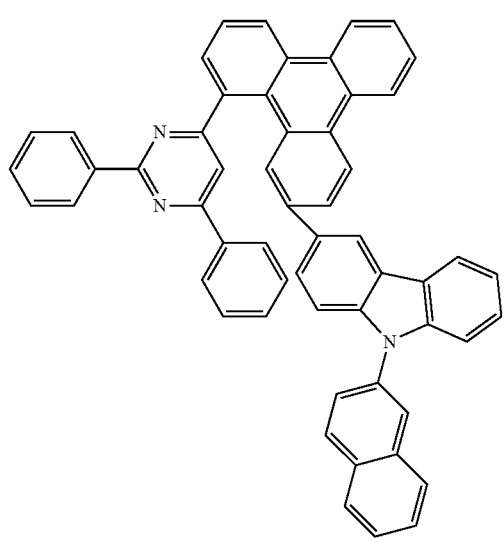
1-99
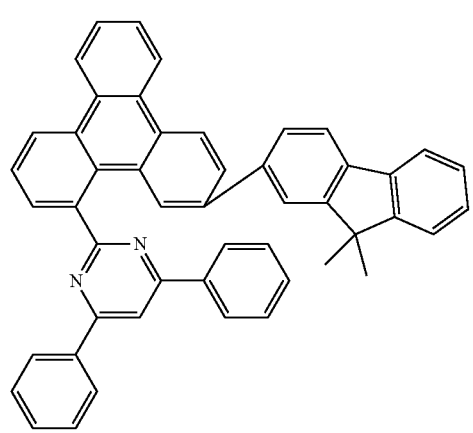
1-97
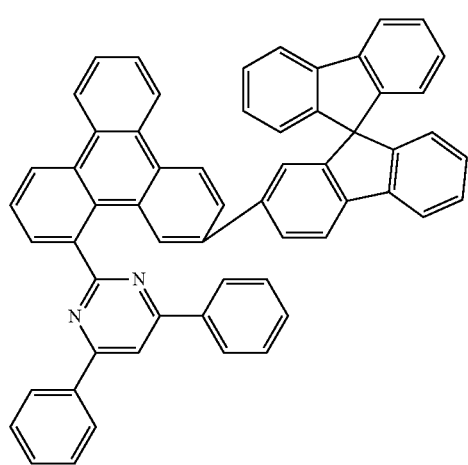
1-100
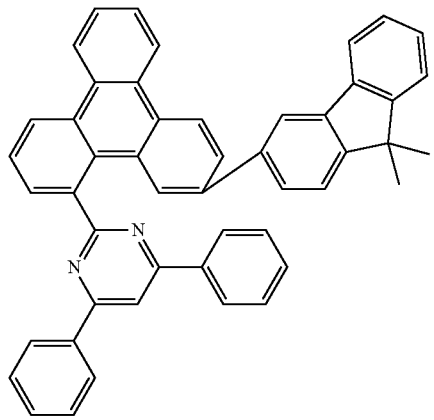

1-101
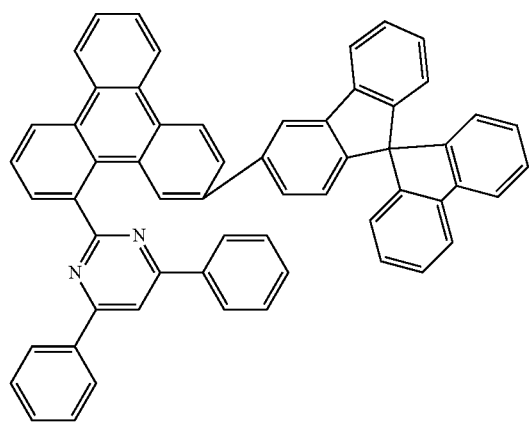
1-102
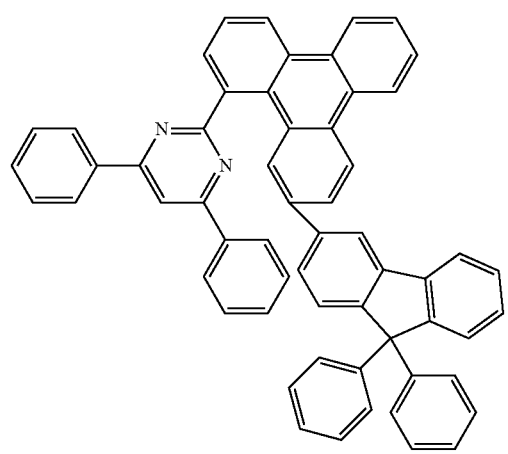
1-103
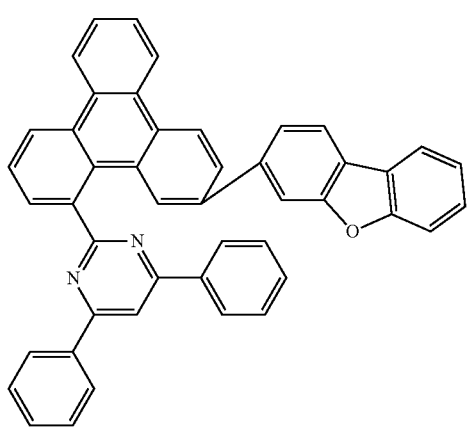
1-104
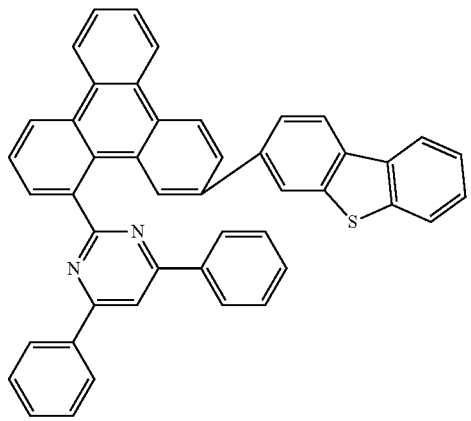
1-105
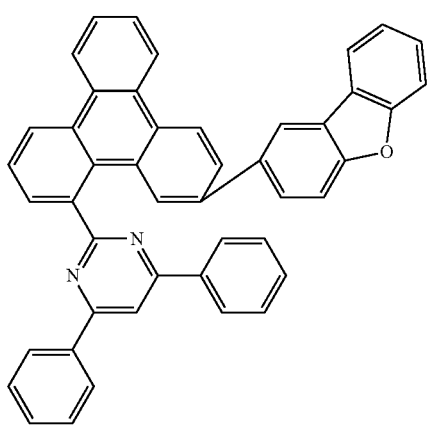
1-106
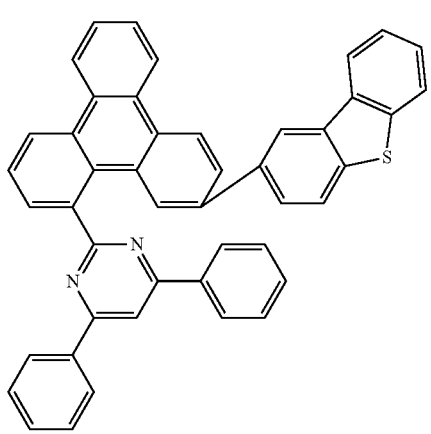

1-107
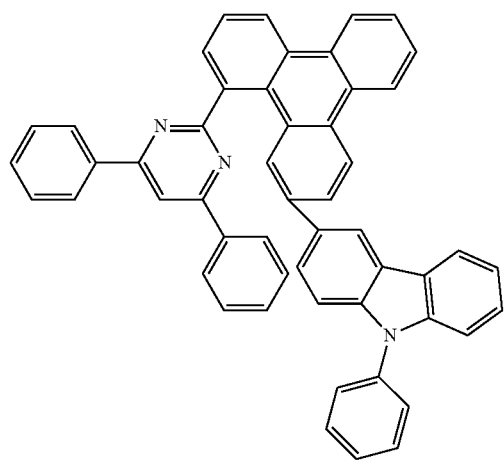
1-108
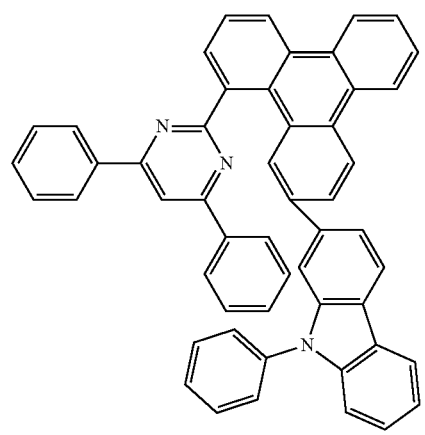
1-109
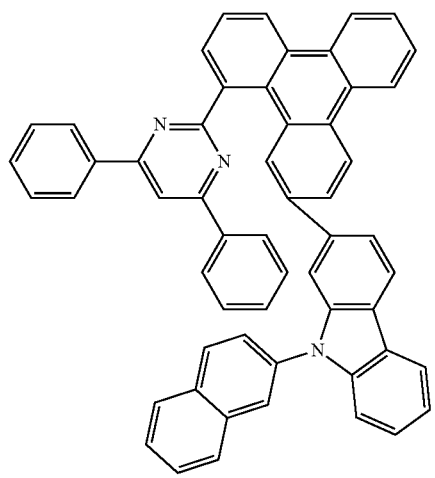
1-110
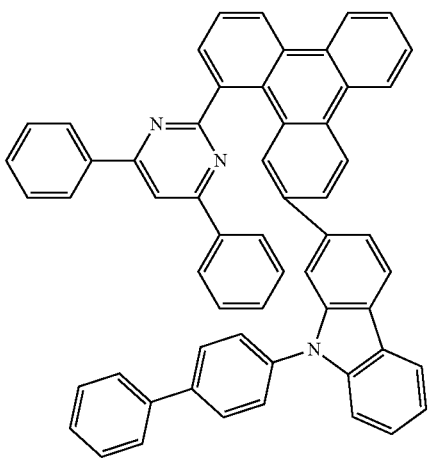
1-111
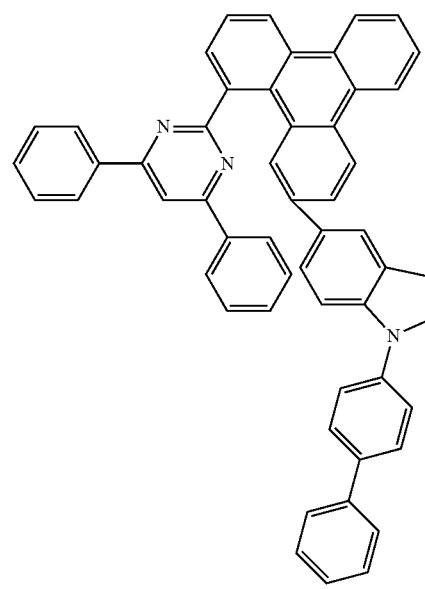
1-112
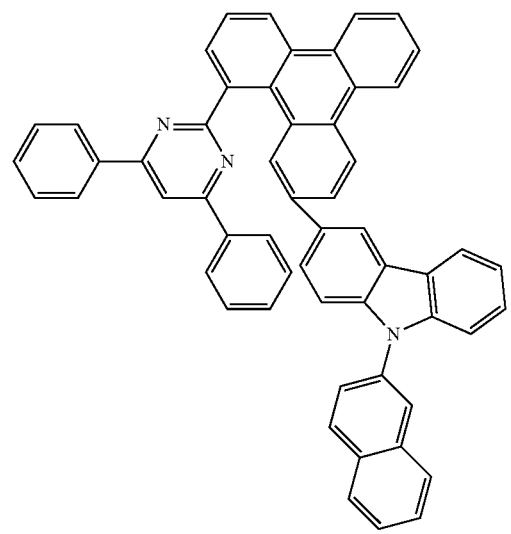

1-113
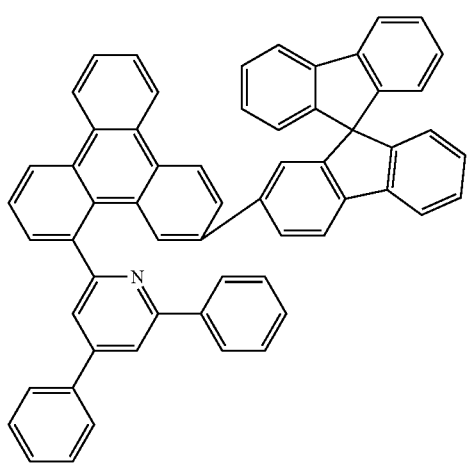
1-114
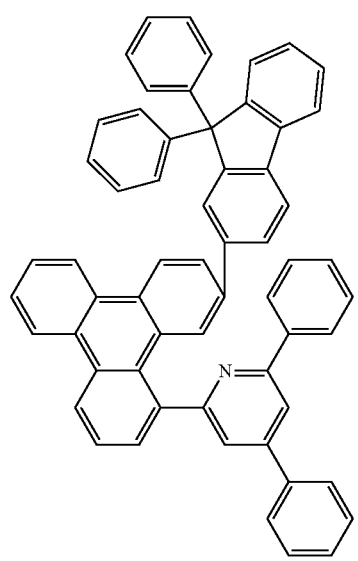
1-115
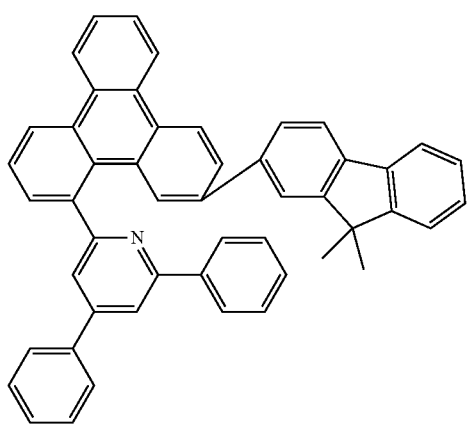
1-116
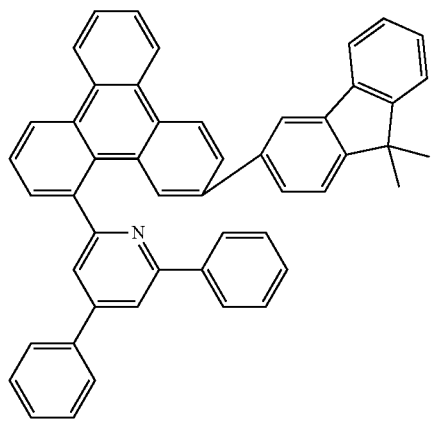
1-117
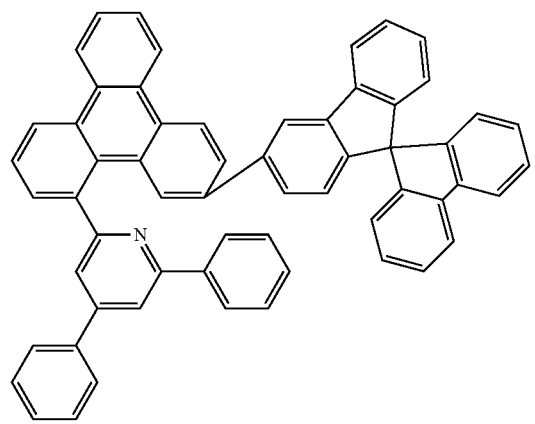
1-118
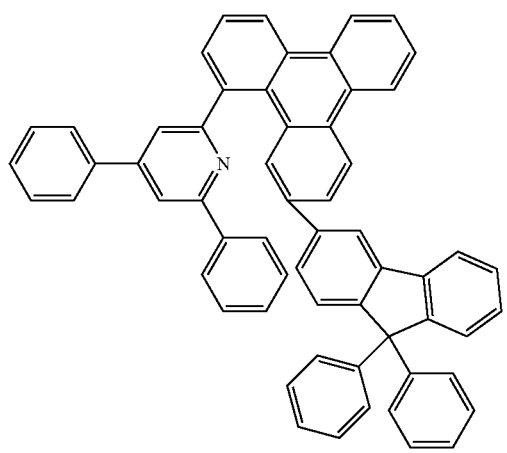

1-119
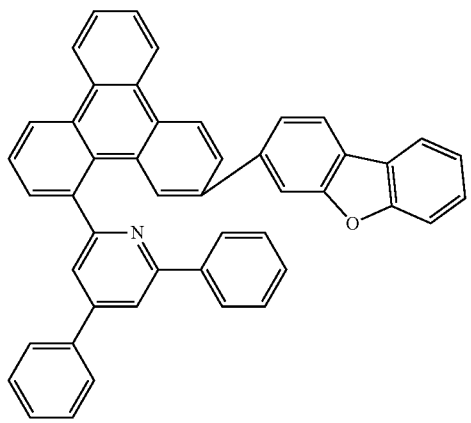
1-122
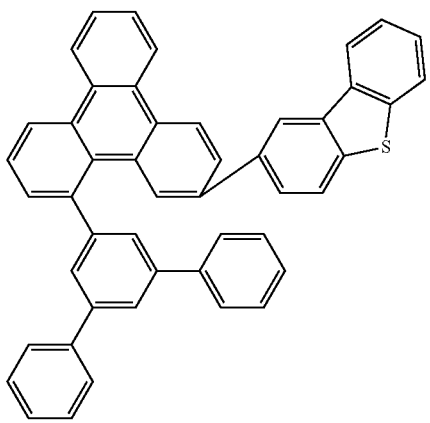
1-120
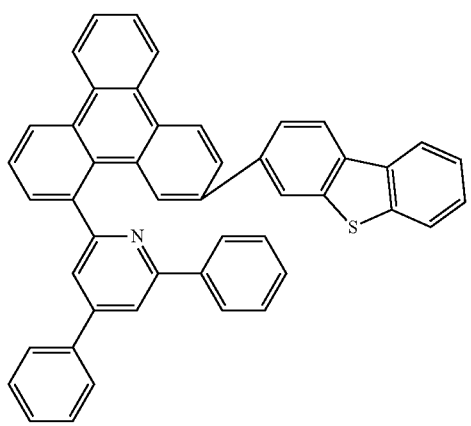
1-123
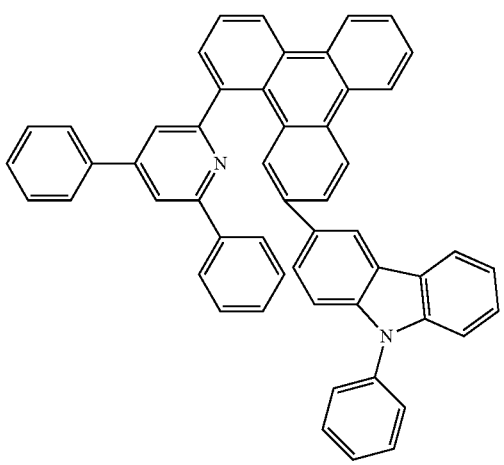
1-121
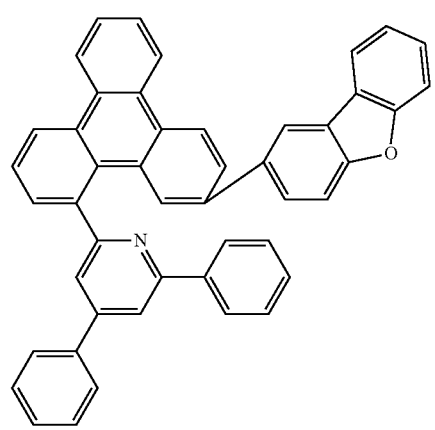
1-124
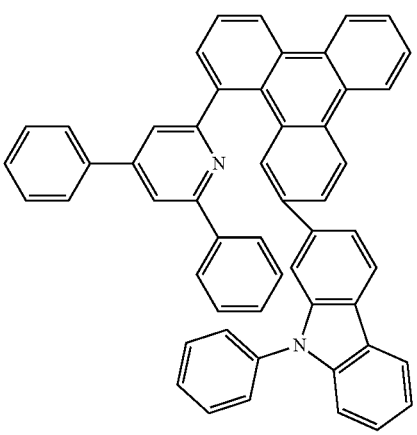

1-125
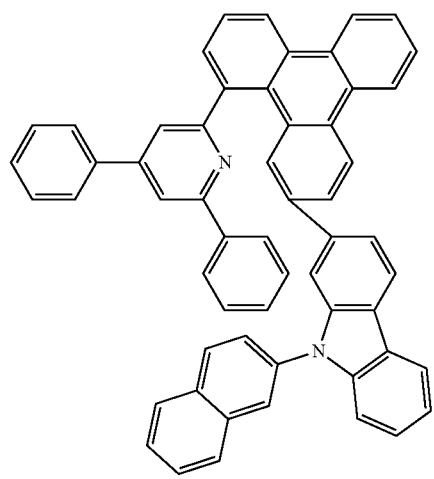
1-126
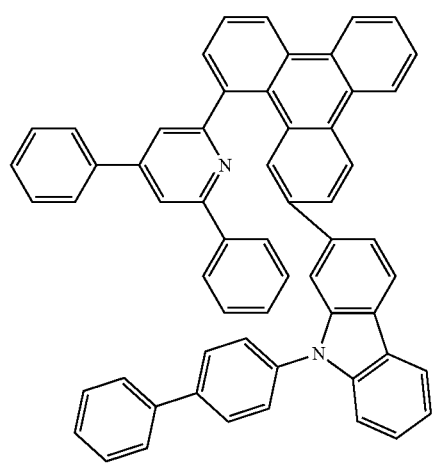
1-127
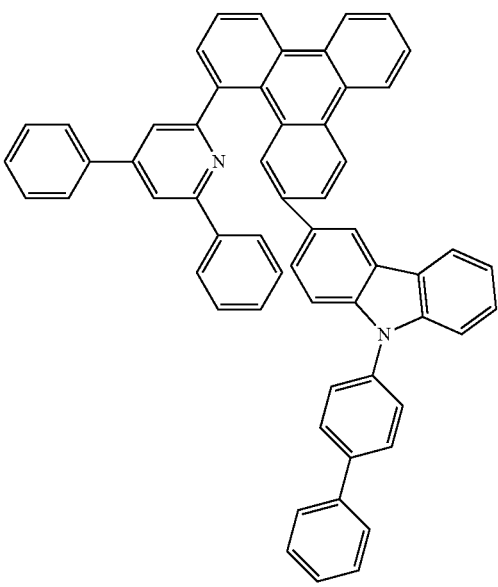
1-128
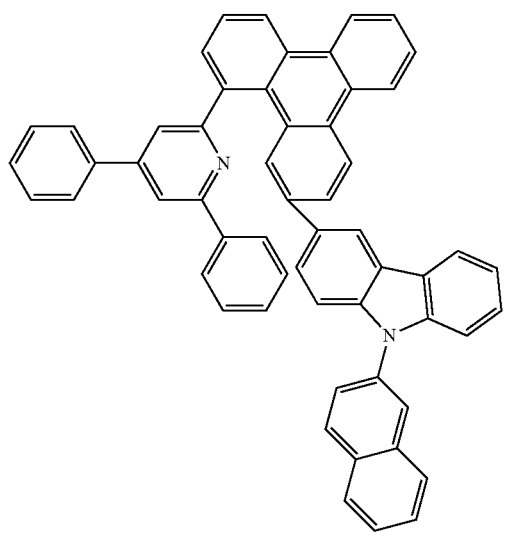
1-129
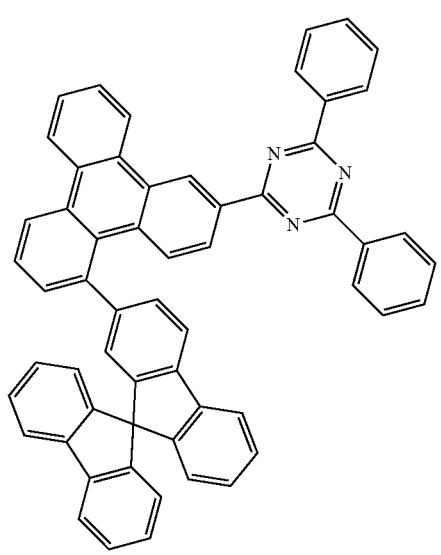
1-130
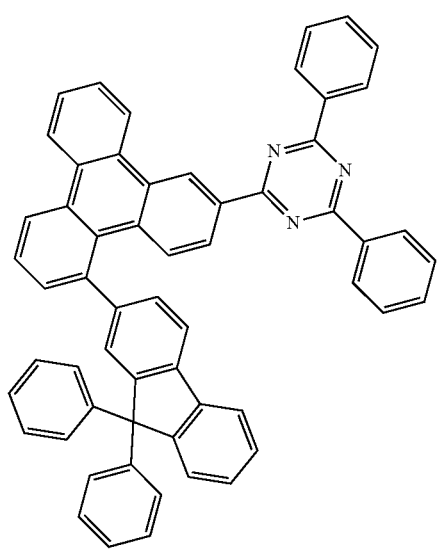

1-131
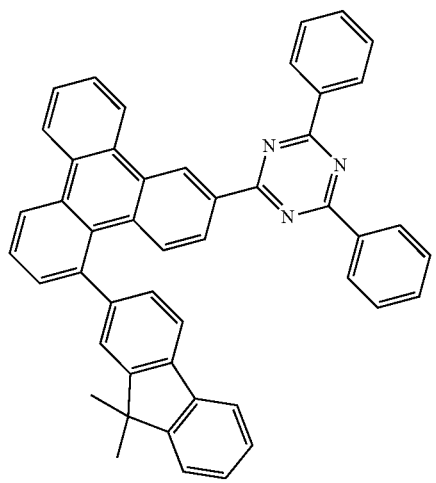
1-132
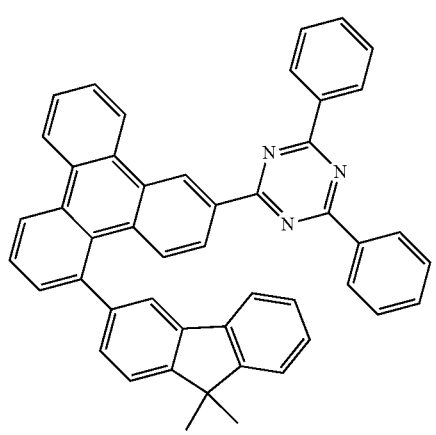
1-133
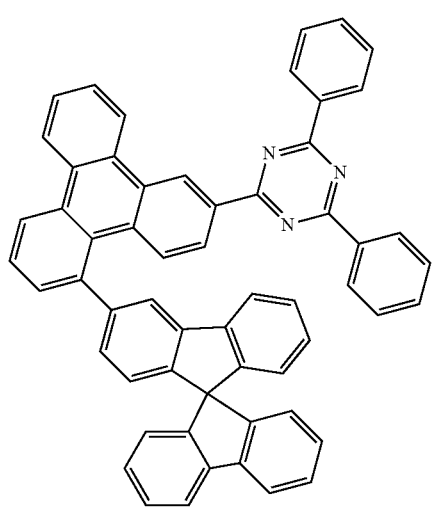
1-134
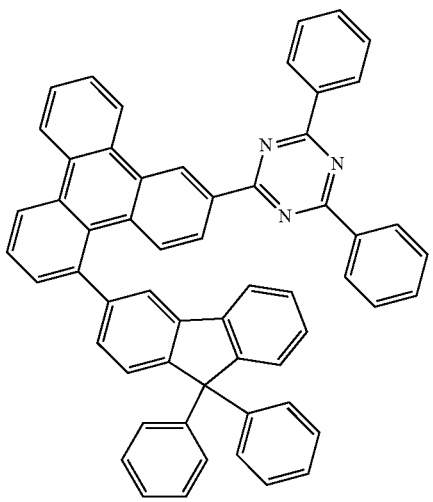
1-135
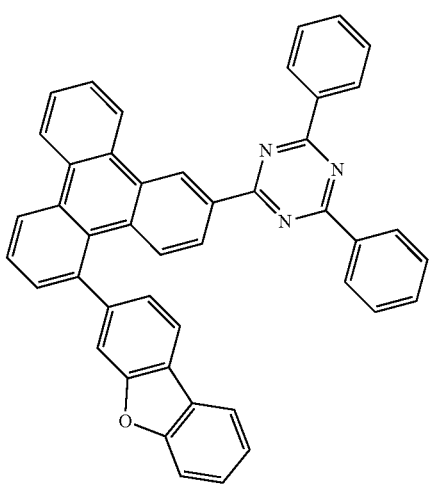
1-136
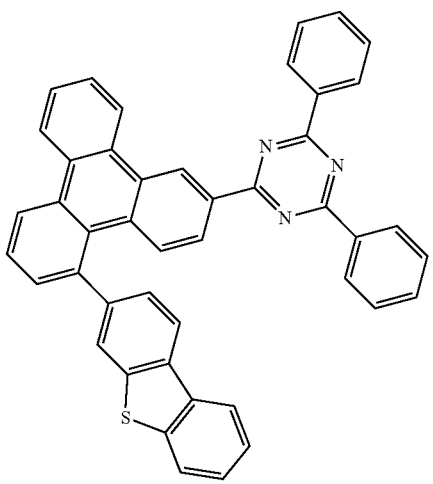

1-137
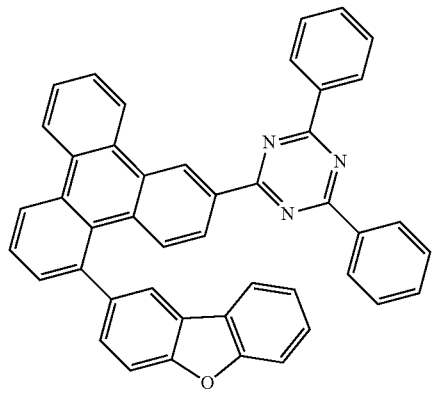
1-140
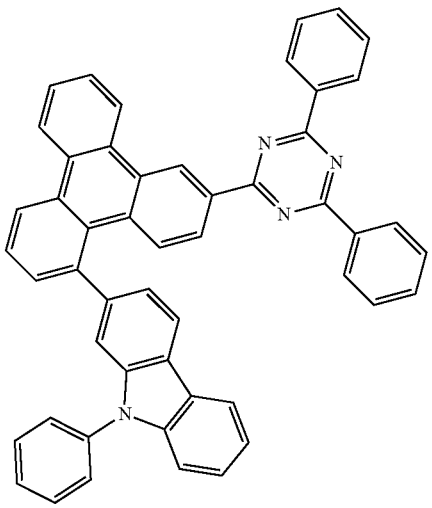
1-138
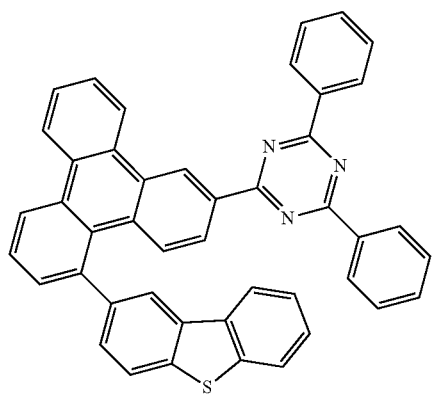
1-139
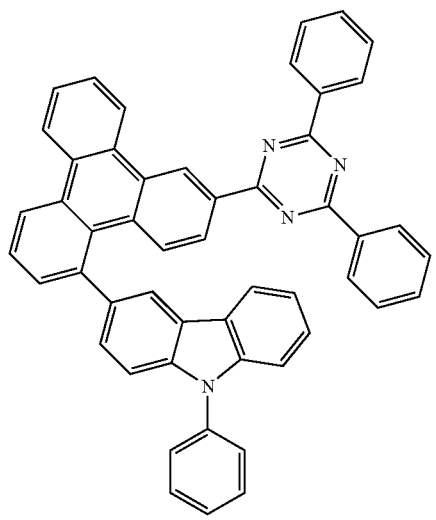
1-141
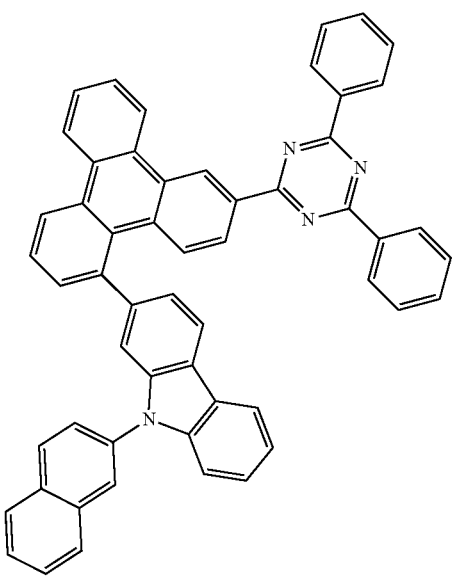

1-142
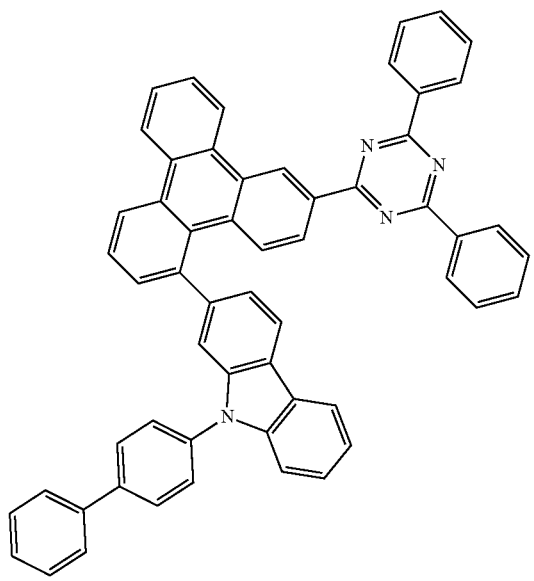
1-143
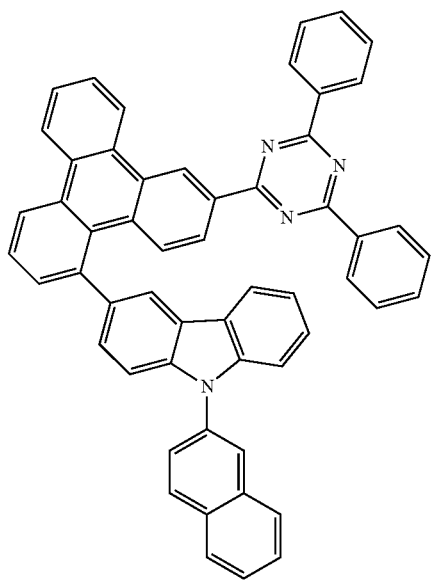
1-144
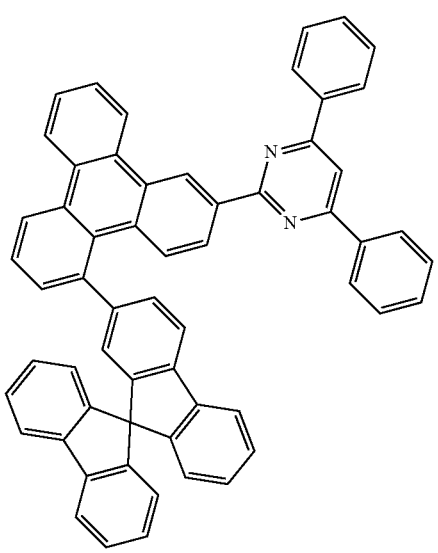
1-145
1-146
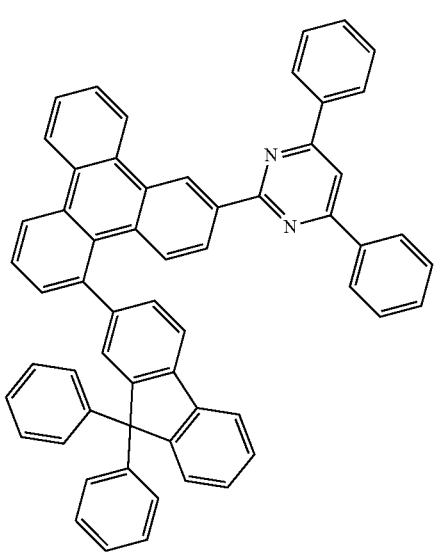

1-147
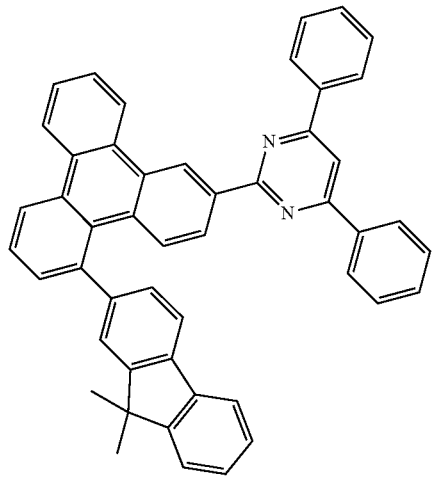
1-148
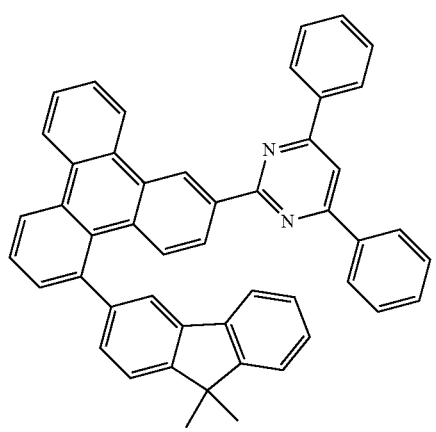
1-149
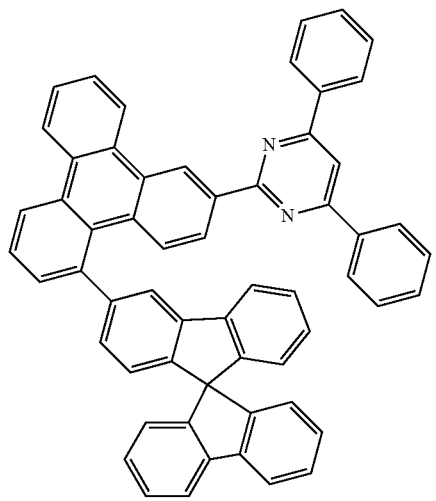
1-150
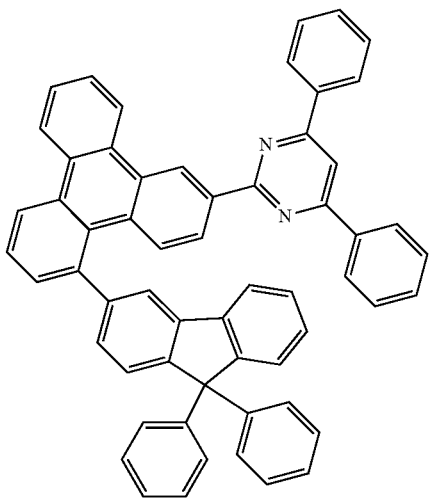
1-151
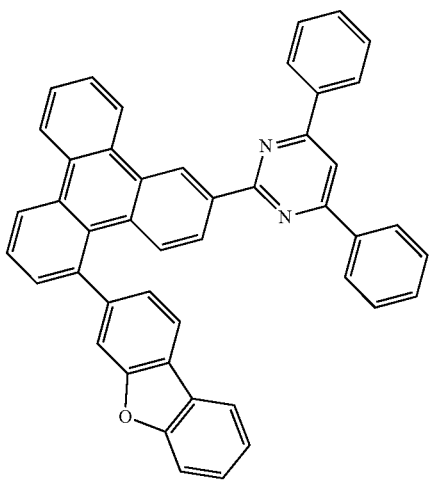
1-152
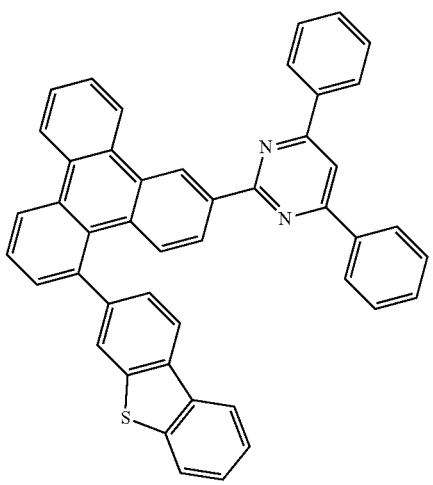

-continued
1-153
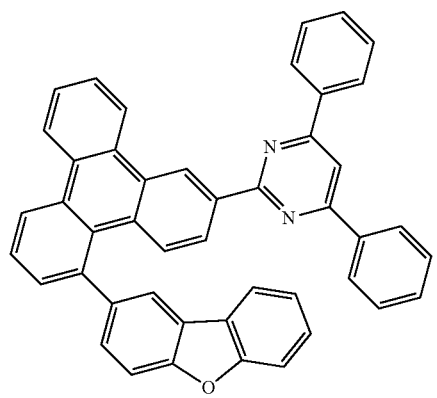
1-154
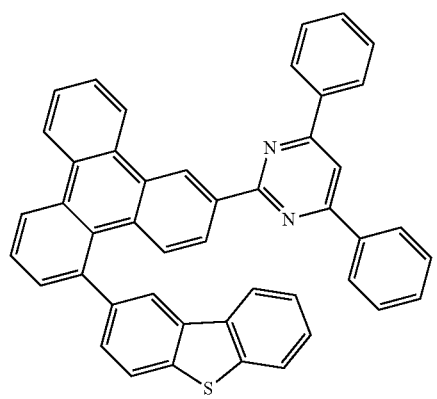
1-155
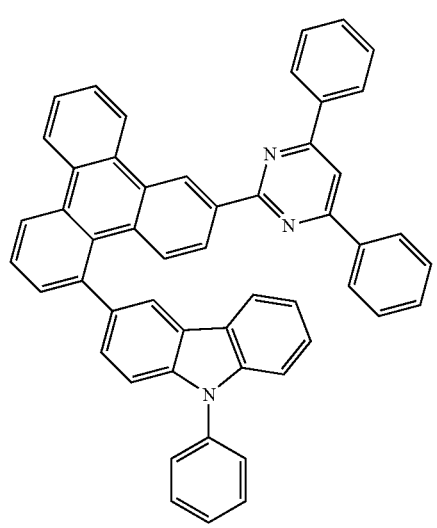
-continued
1-156
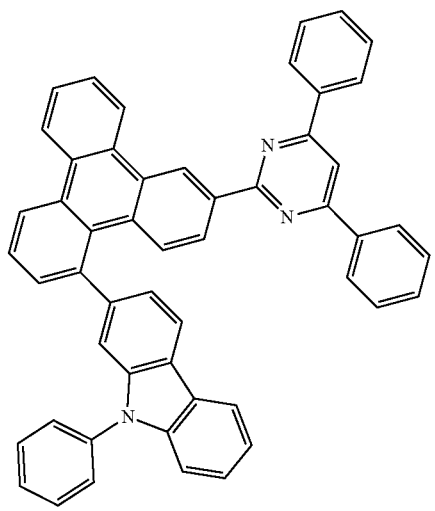
1-157
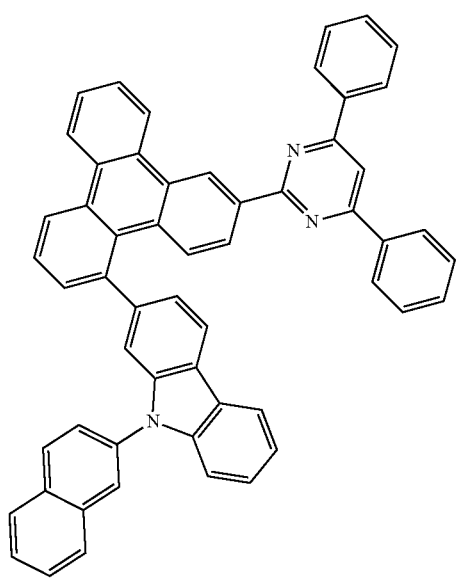

1-158
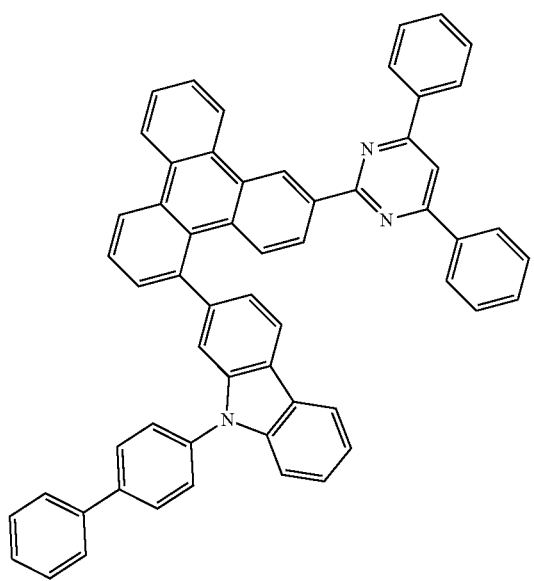
1-159
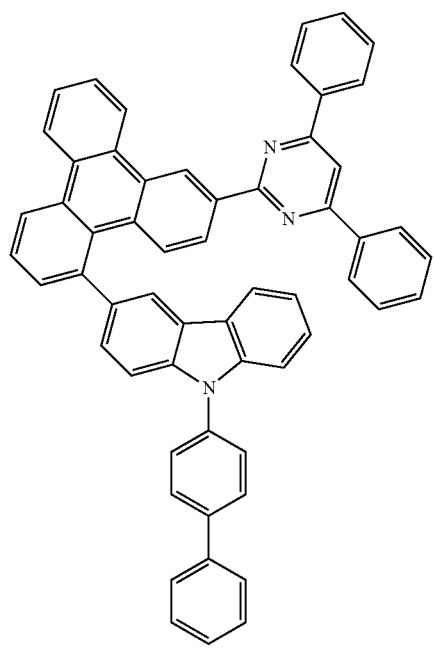
1-160
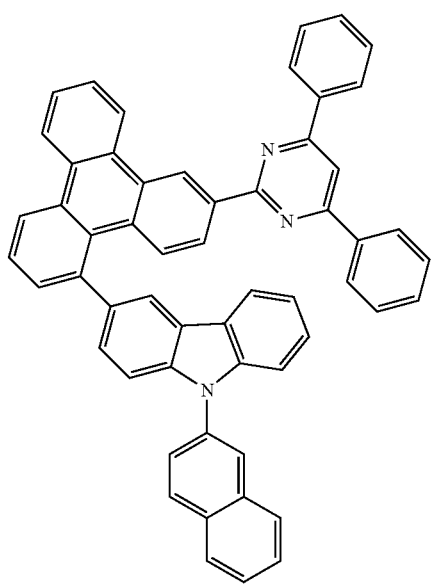
1-161
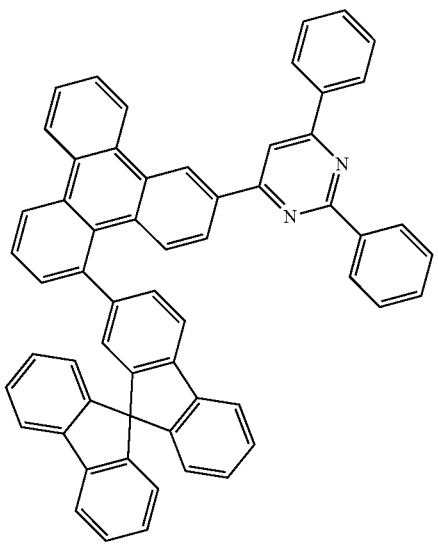

-continued
1-162
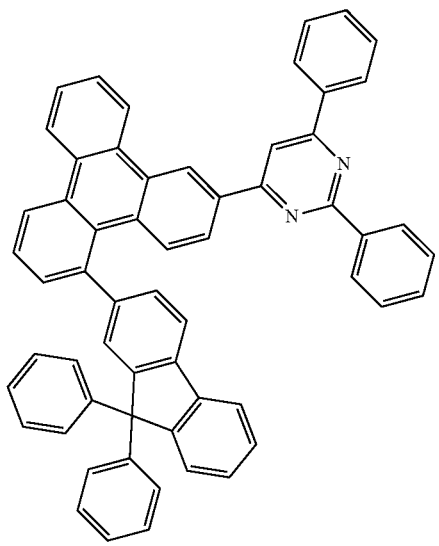
1-163
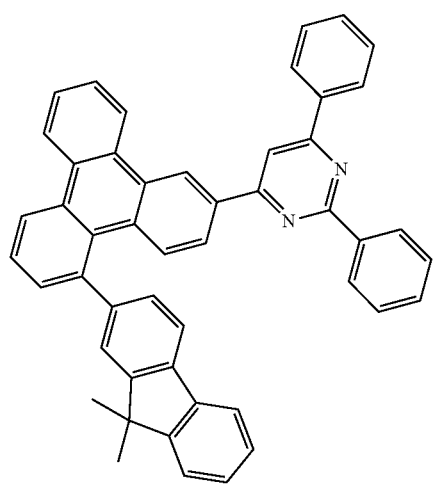
1-164
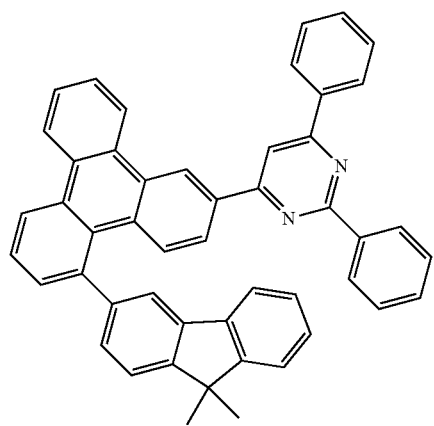
-continued
1-165
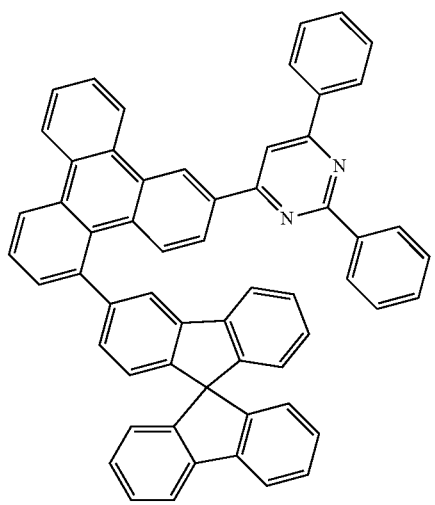
1-166
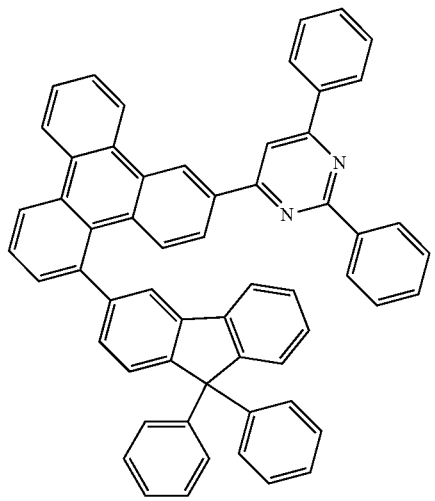
1-167
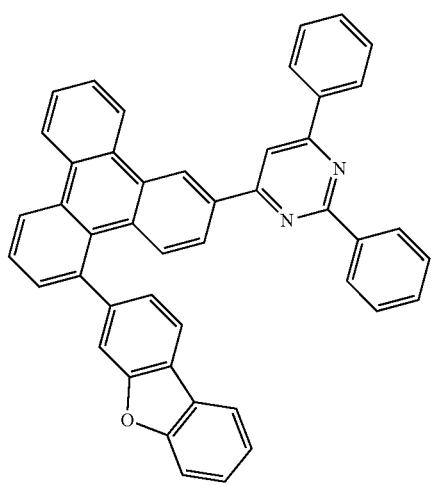

1-168
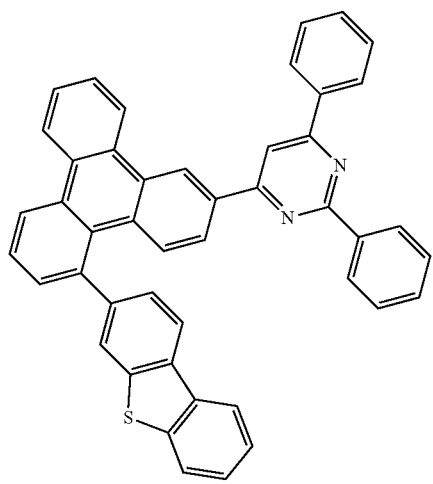
1-169
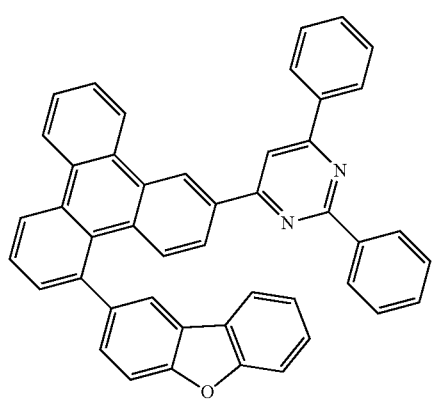
1-170
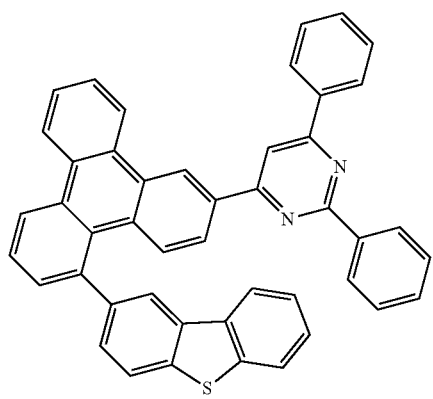
1-171
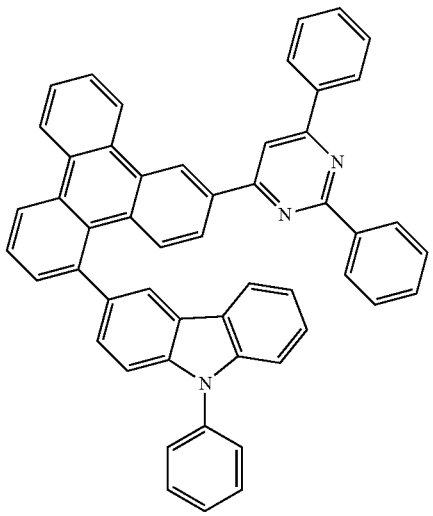
1-172
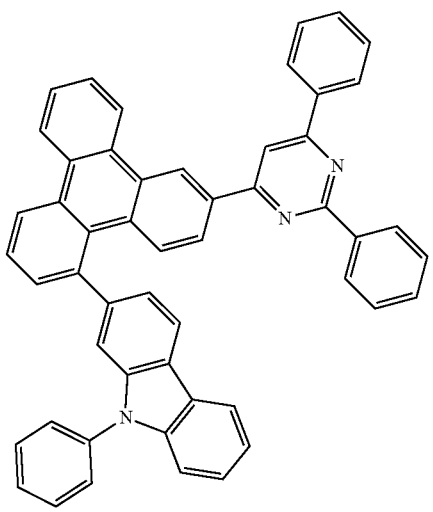
1-173
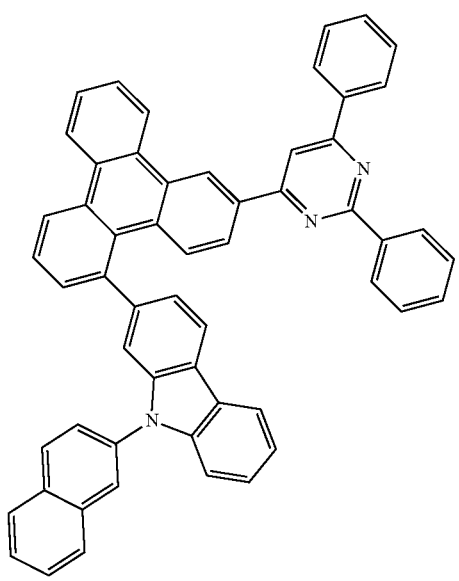

1-174
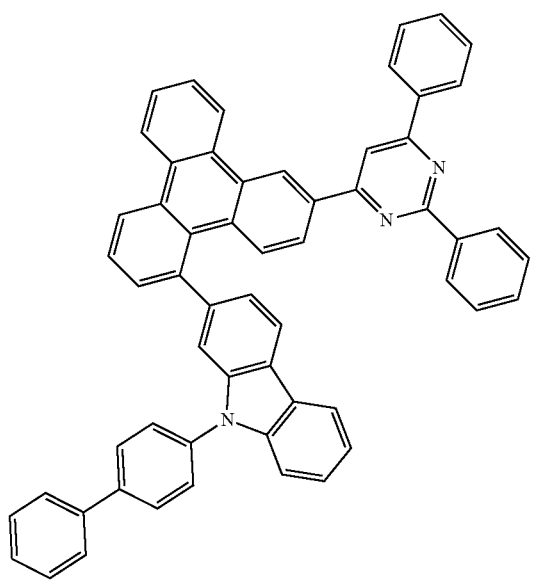
1-175
1-176
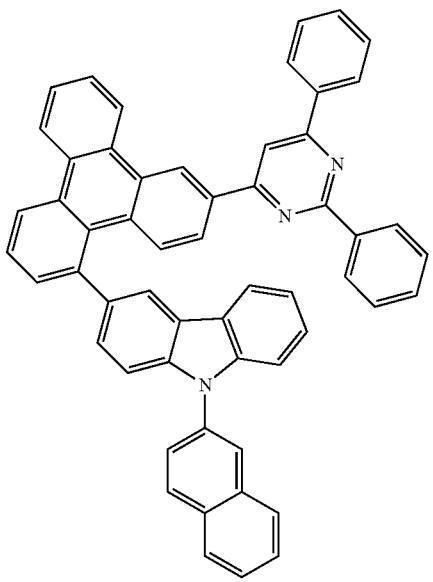
1-177
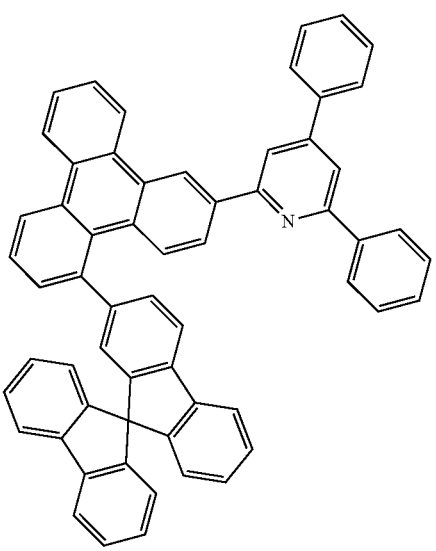
1-178
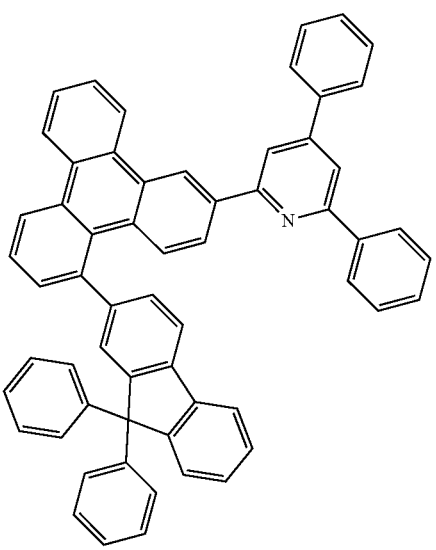

1-179
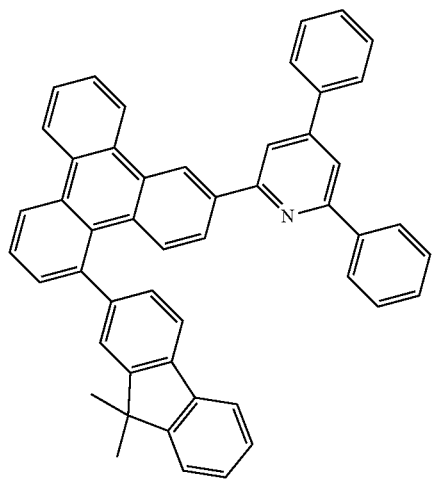
1-180
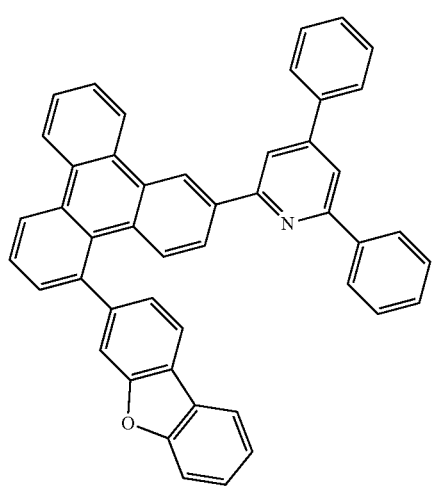
1-181
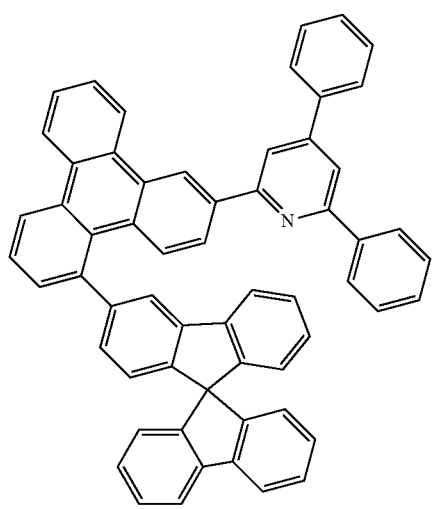
1-182
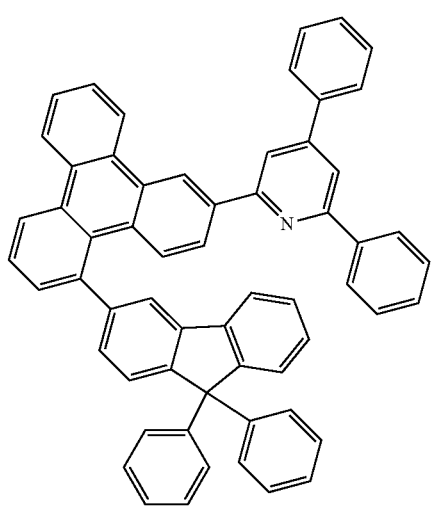
1-183
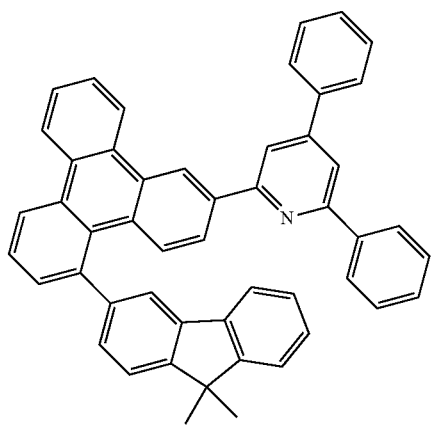
1-184
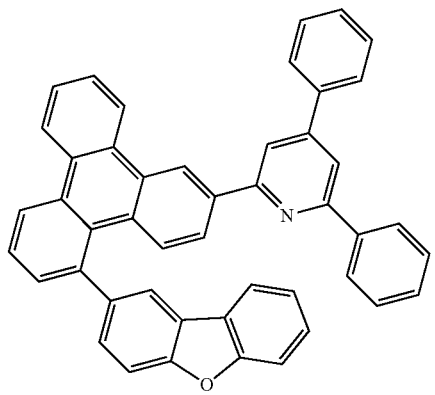

-continued
1-185
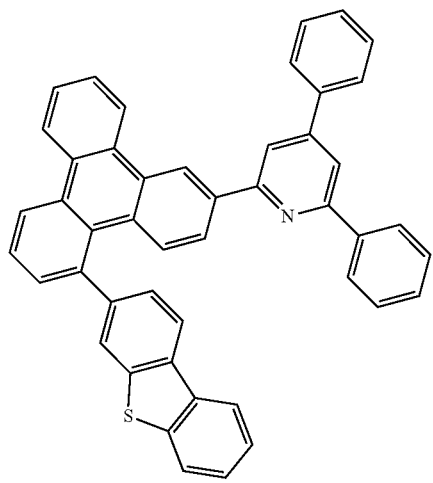
1-186
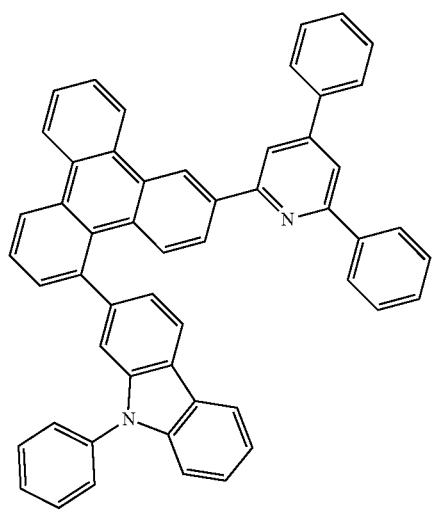
1-187
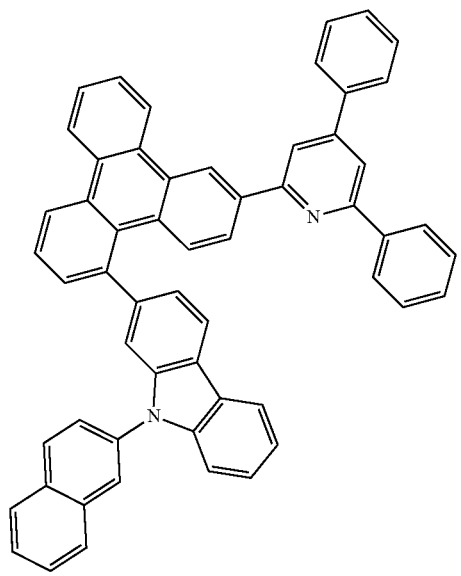
-continued
1-188
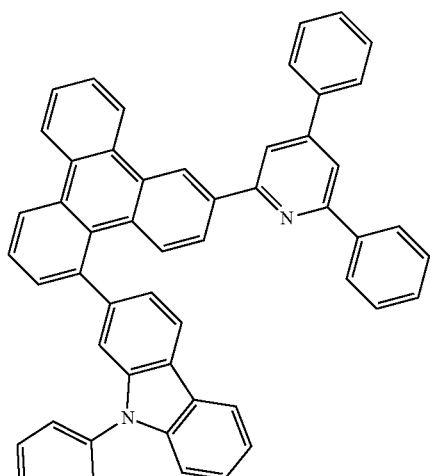
1-189
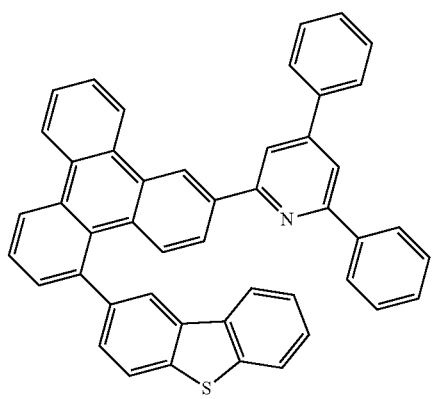
1-190
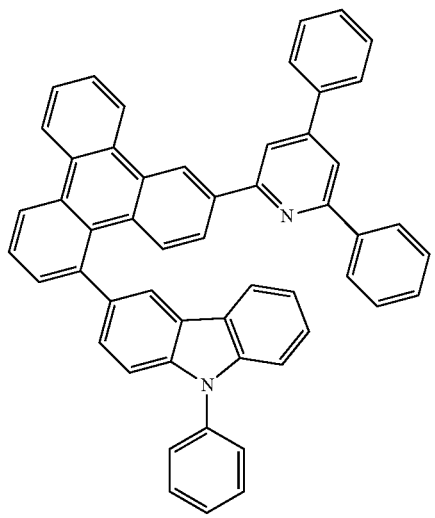

1-191
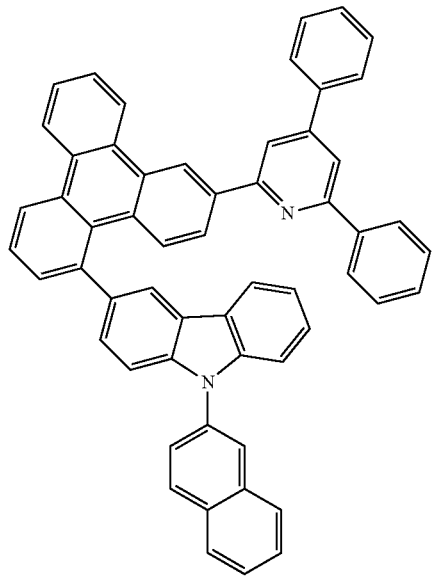
1-192
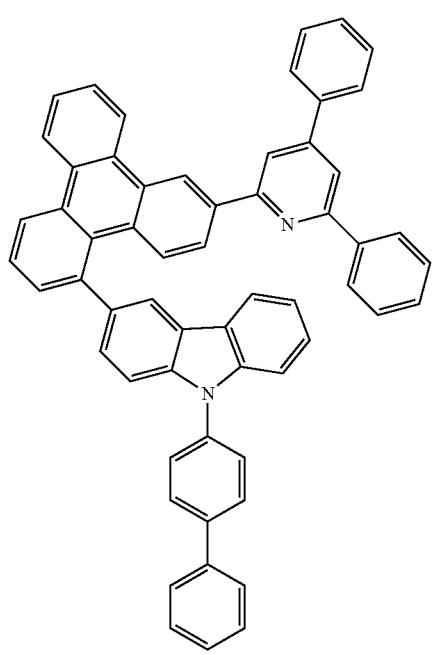
1-193
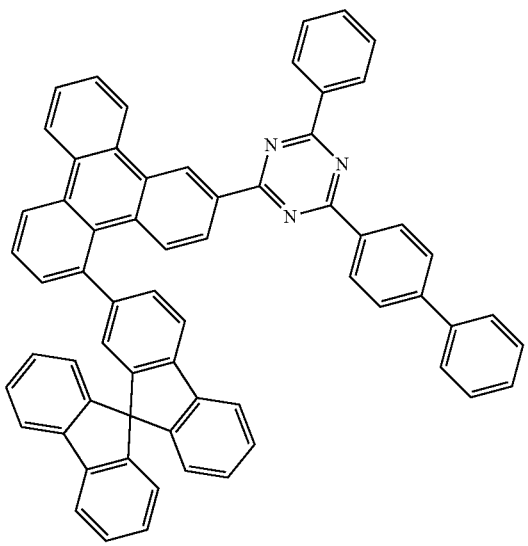
1-194
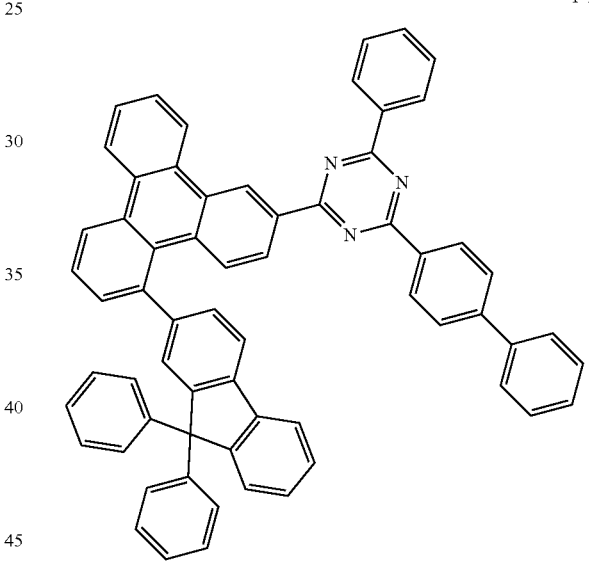
1-195
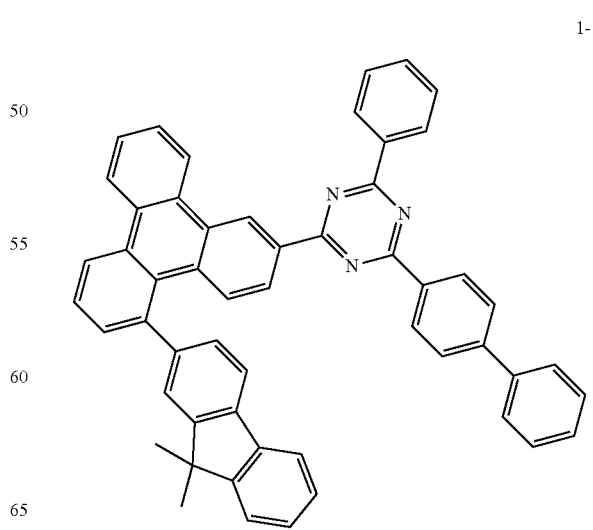

1-196
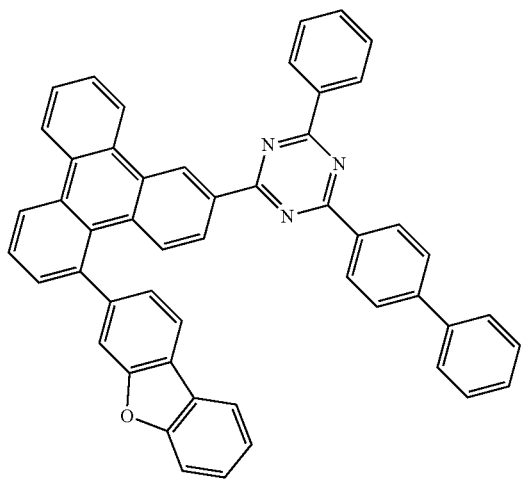
1-197
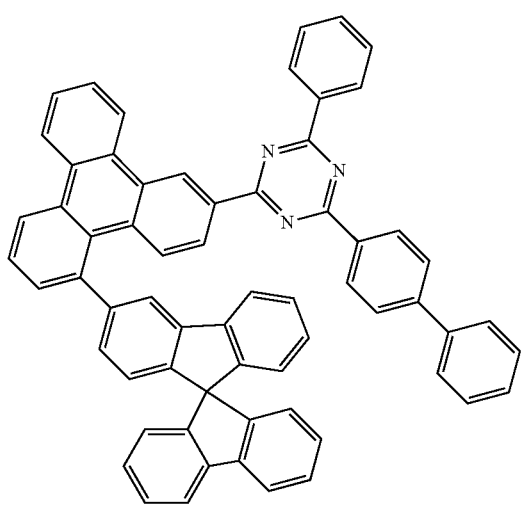
1-198
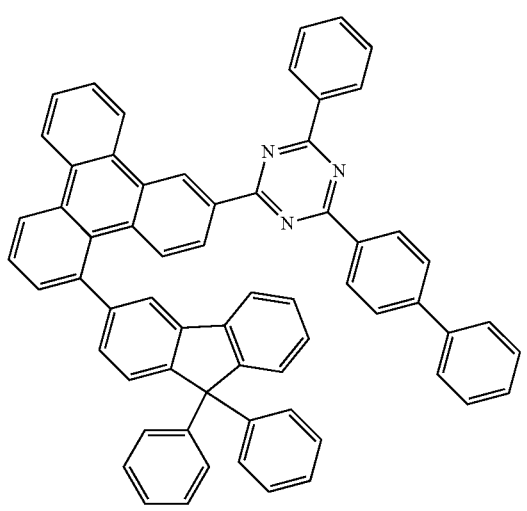
1-199
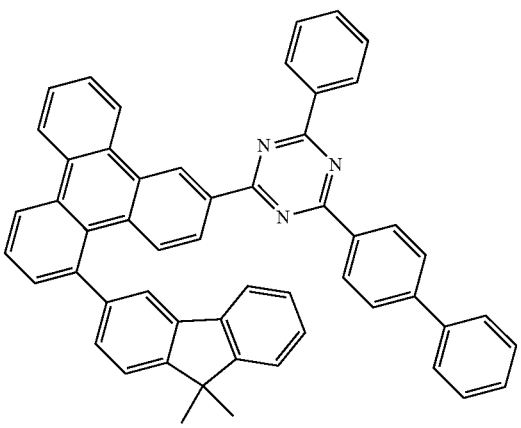
1-200
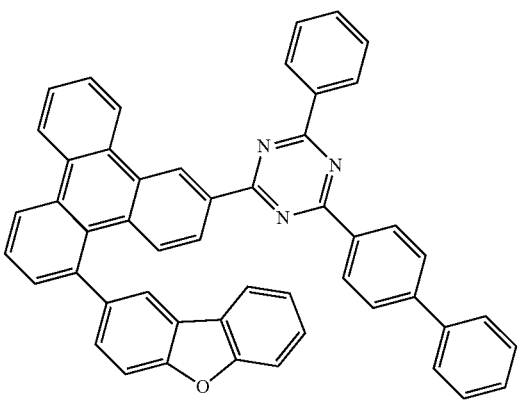
1-201
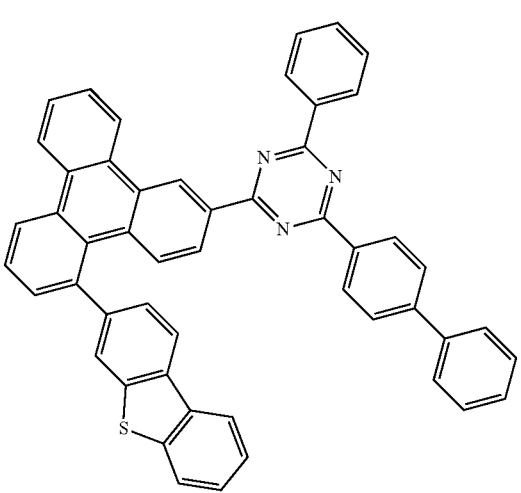

1-202

1-203

1-204

1-205

1-206

1-207

1-208
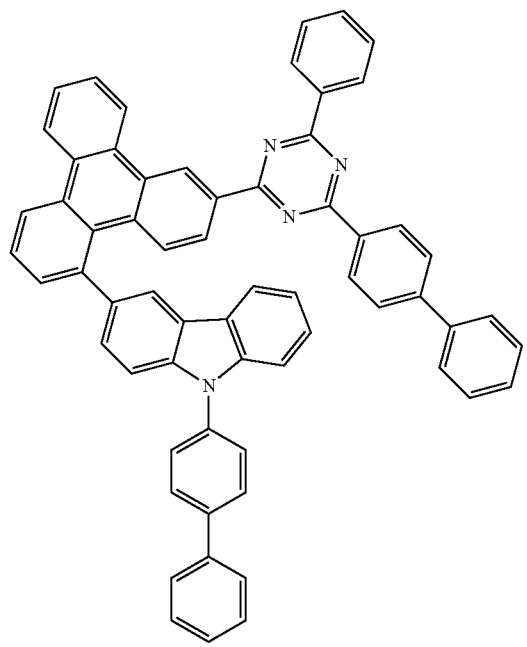
1-210
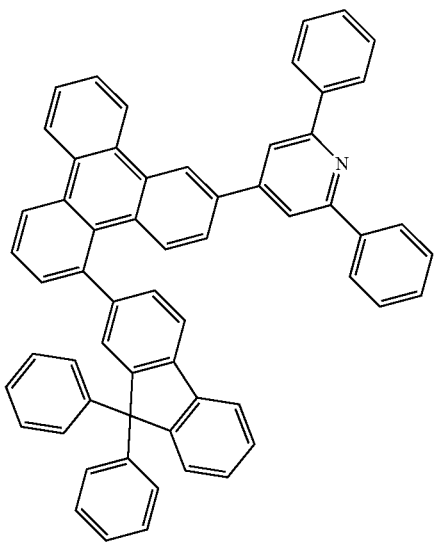
1-211
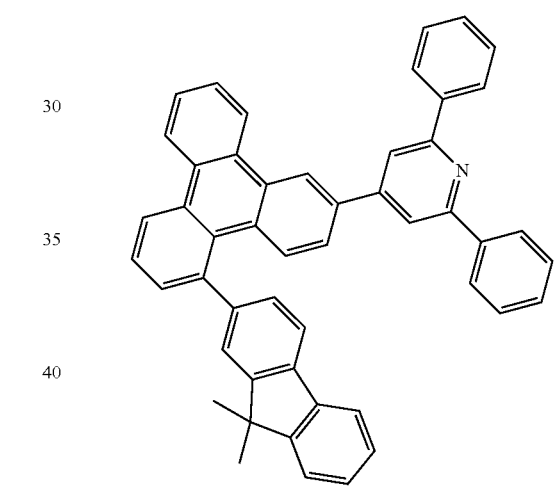
1-209
1-212
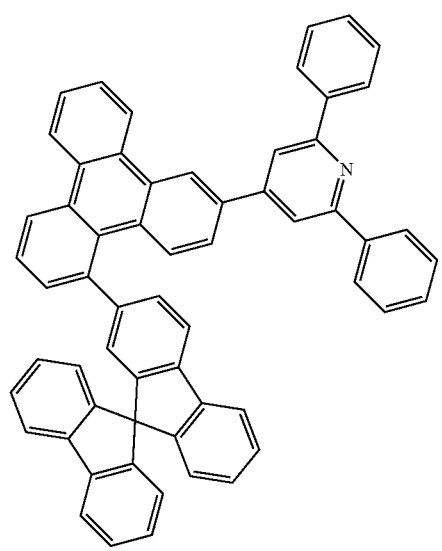

1-213
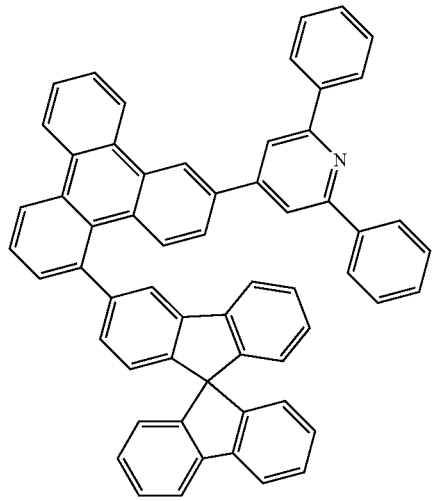
1-214
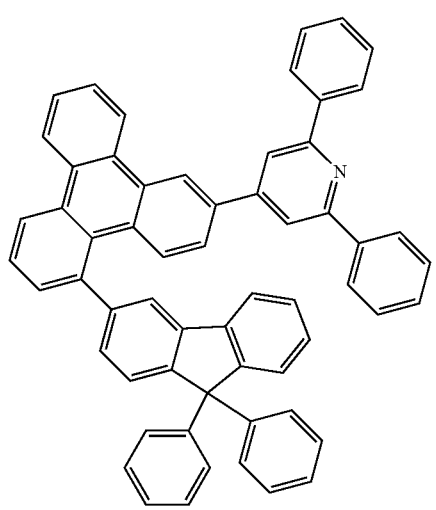
1-215
1-216
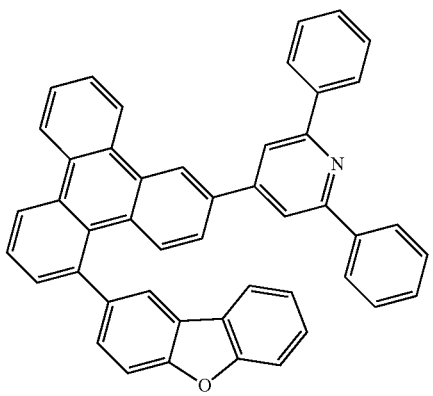
1-217
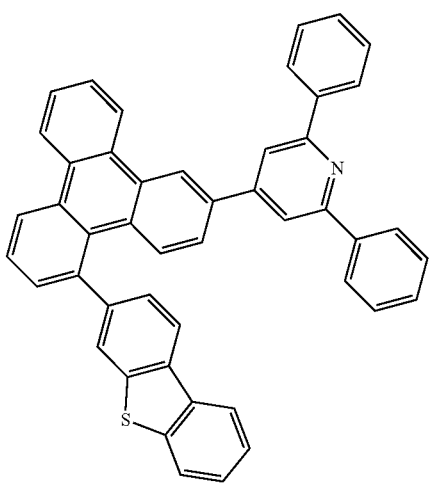
1-218
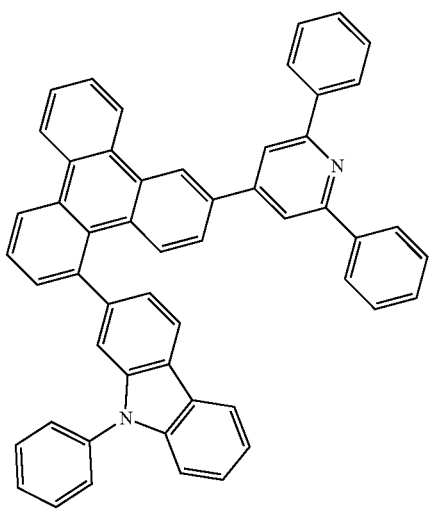

-continued
1-219
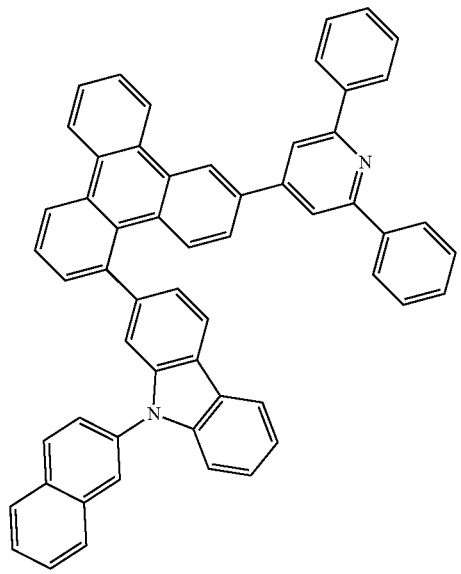
1-220
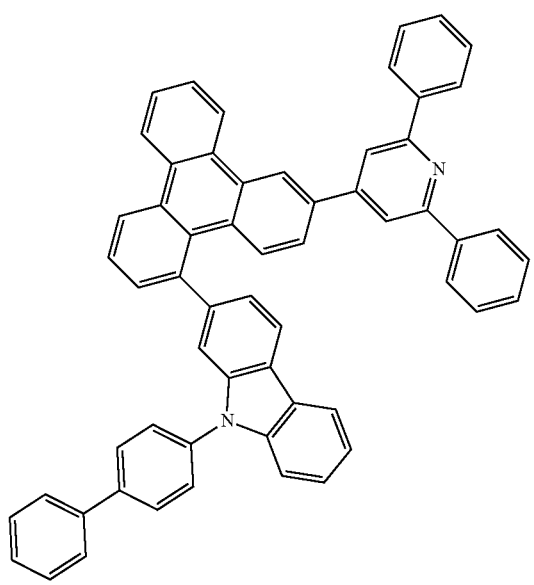
1-221
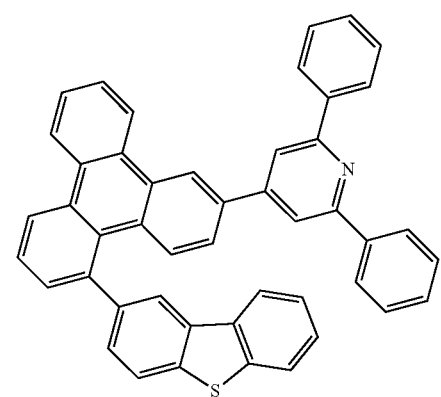
-continued
1-222
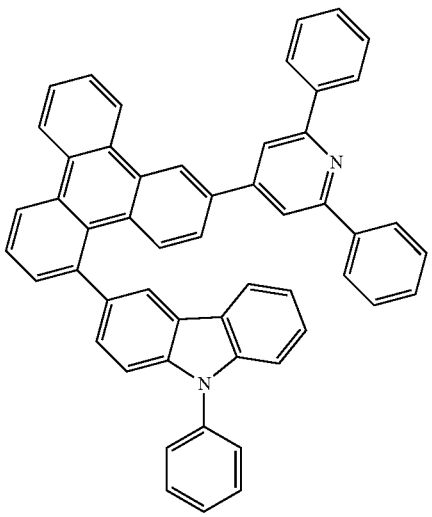
1-223
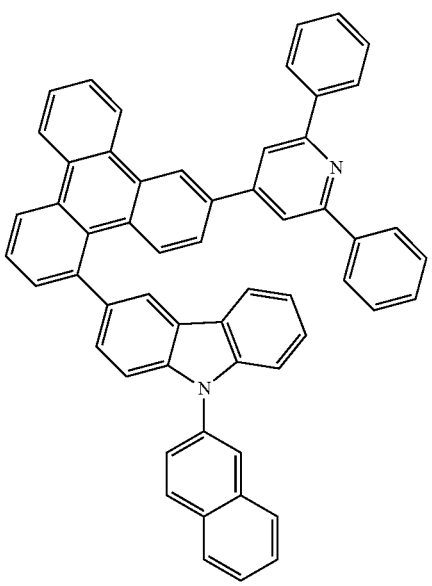

1-224
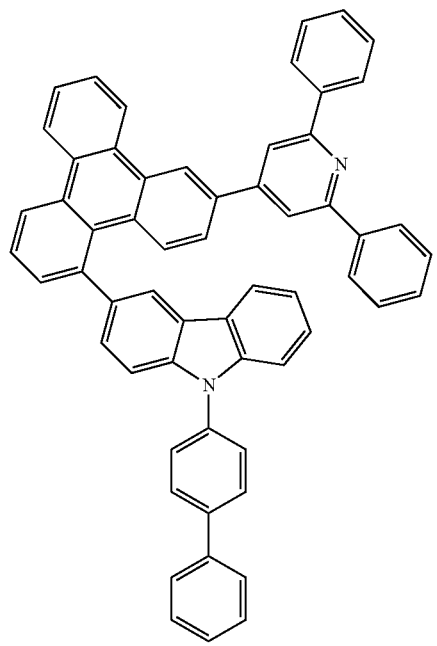
1-225
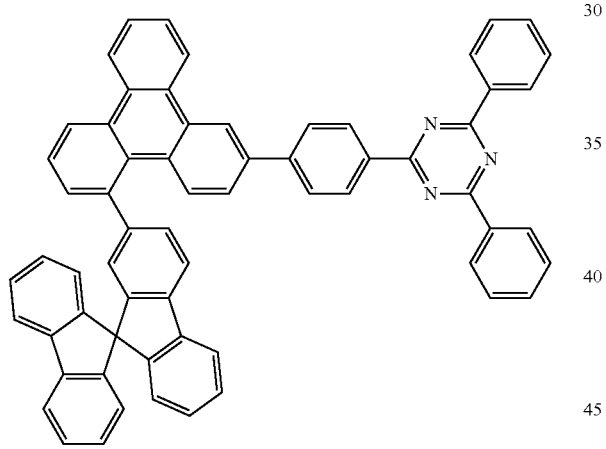
1-226
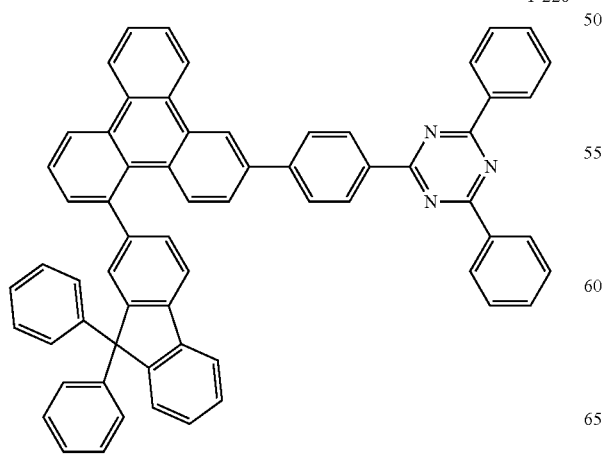
1-227
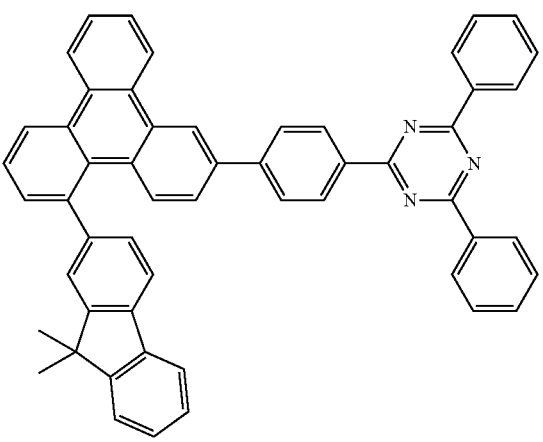
1-228
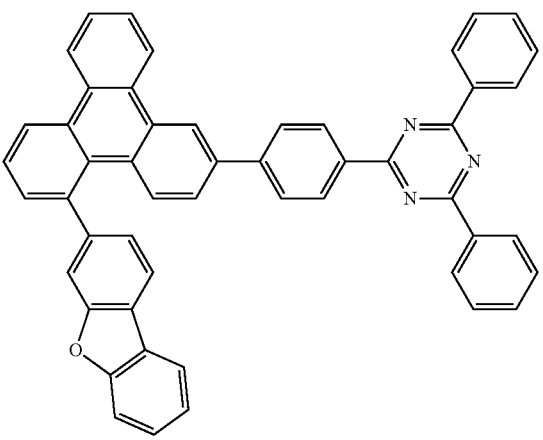
1-229
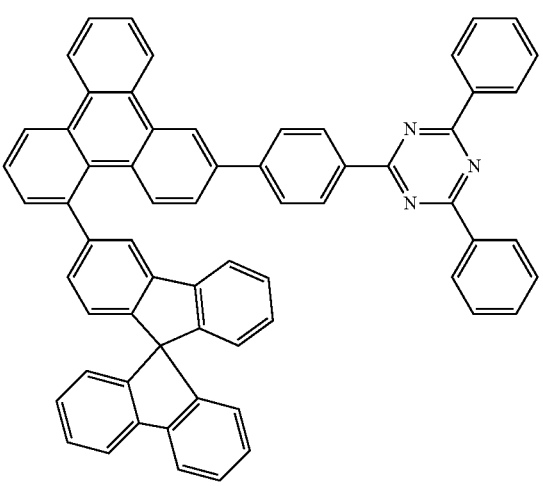

-continued
1-230
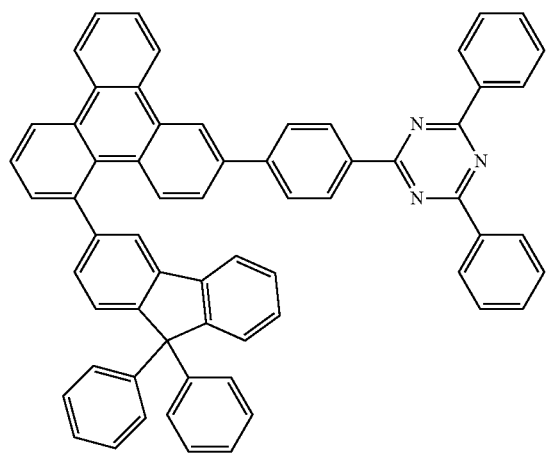
1-233
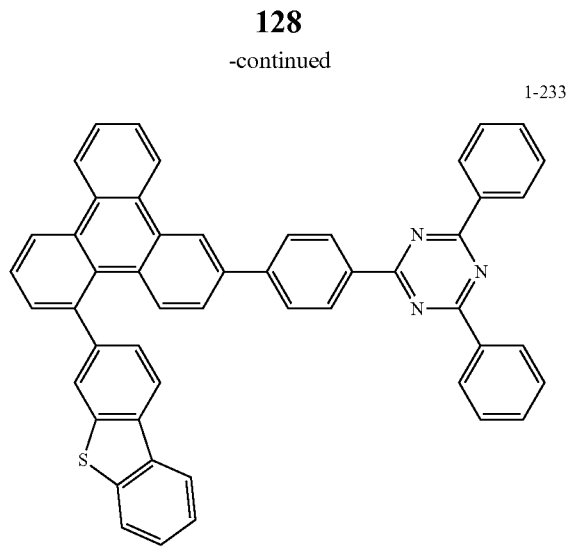
1-231
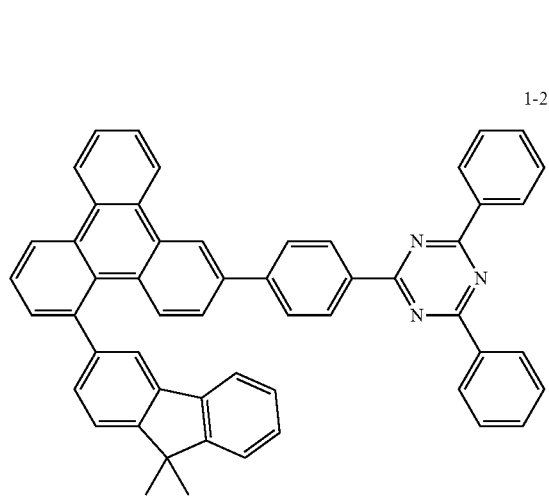
1-234
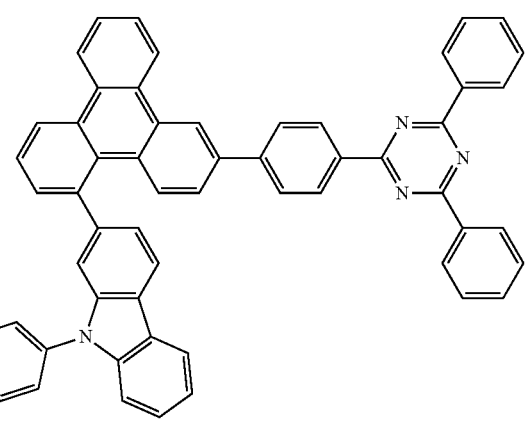
1-232
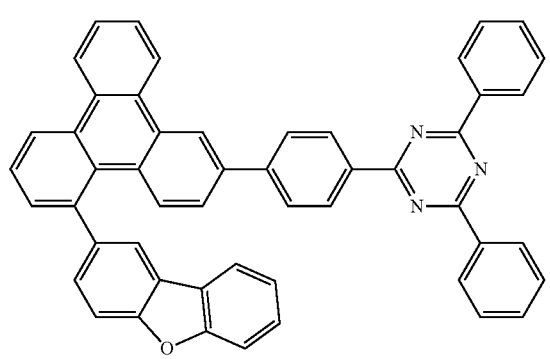
1-235
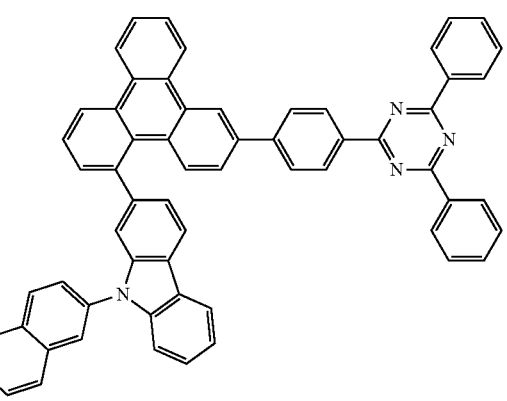

1-236
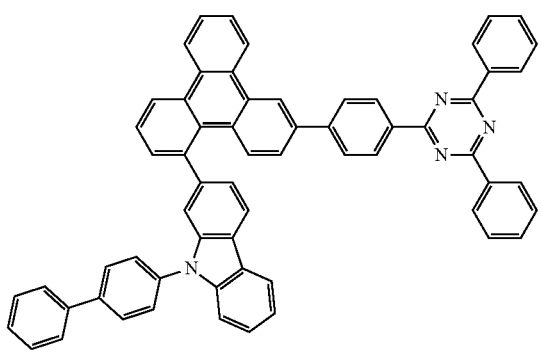
1-239
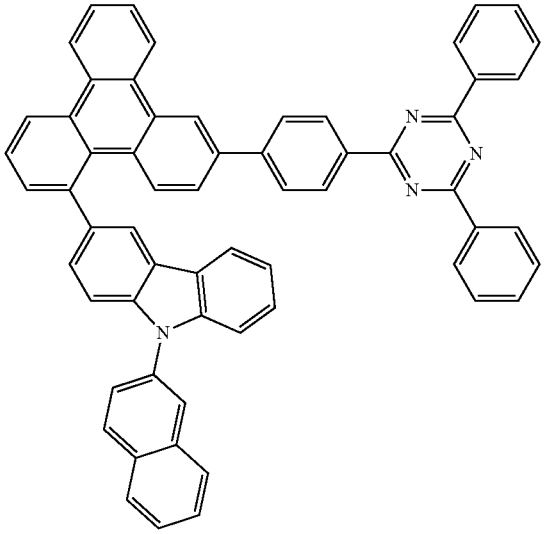
1-237
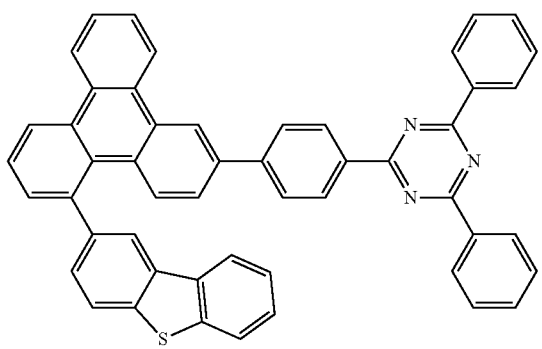
1-238
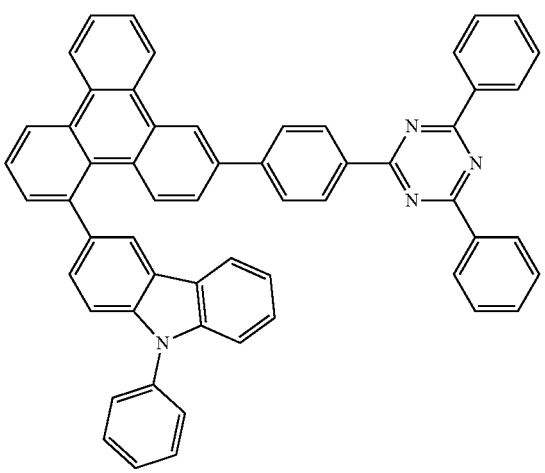
1-240
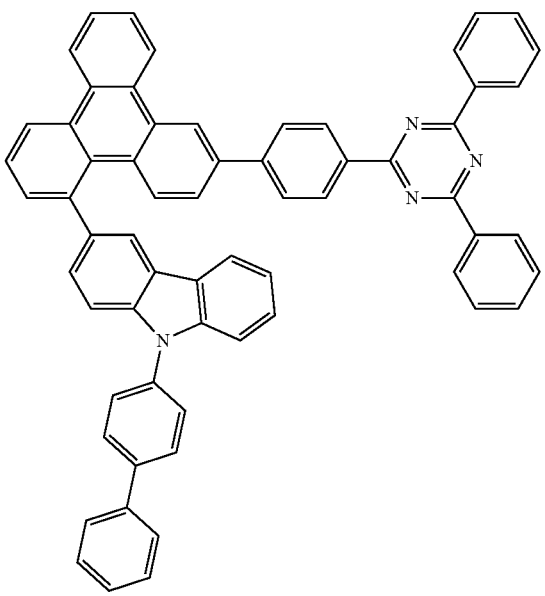

1-241
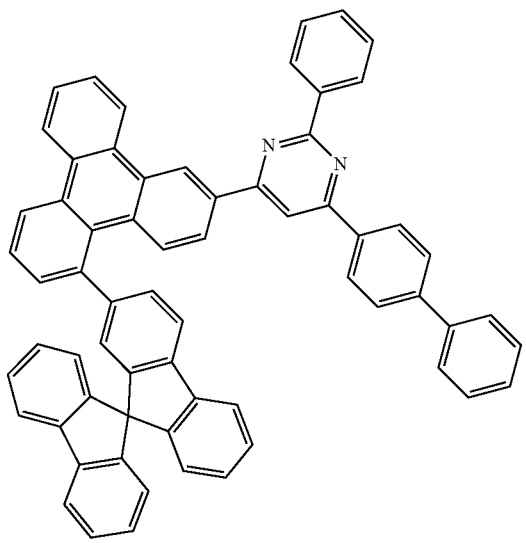
1-242
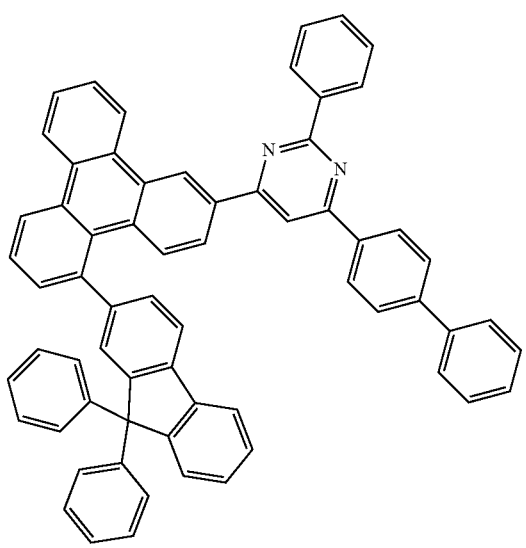
1-243
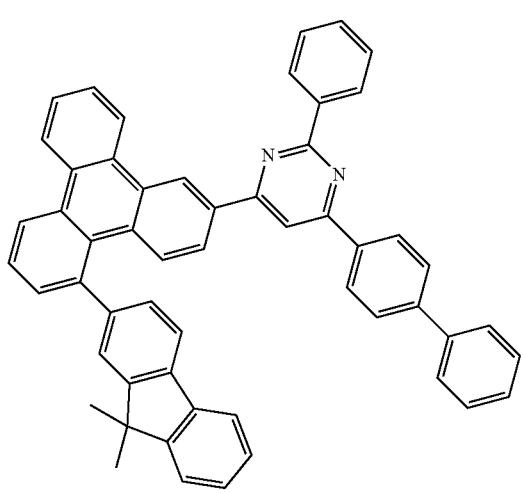
1-244
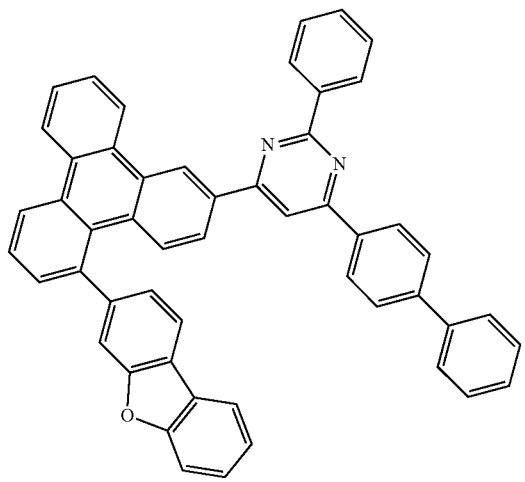
1-245
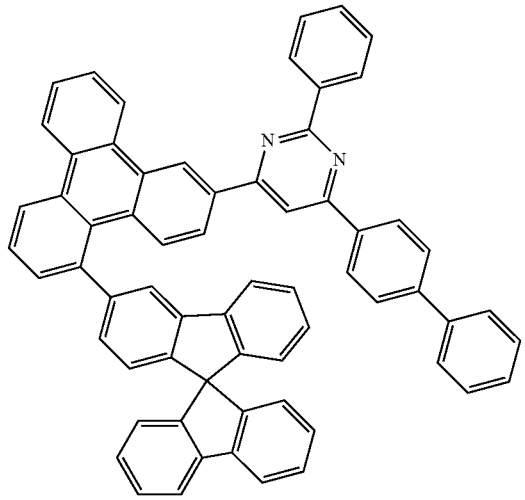
1-246
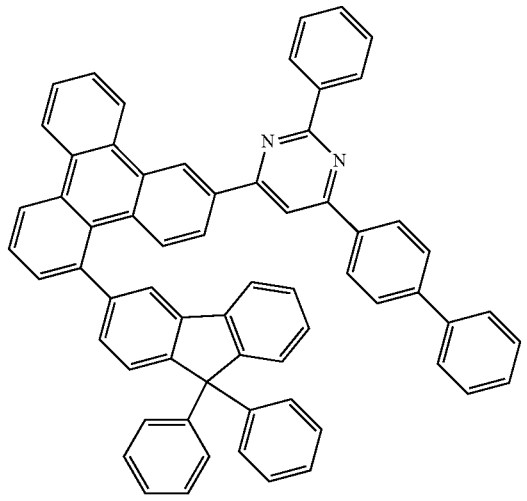

1-247
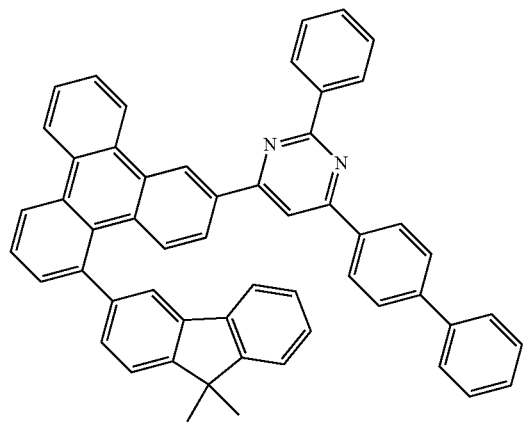
1-248
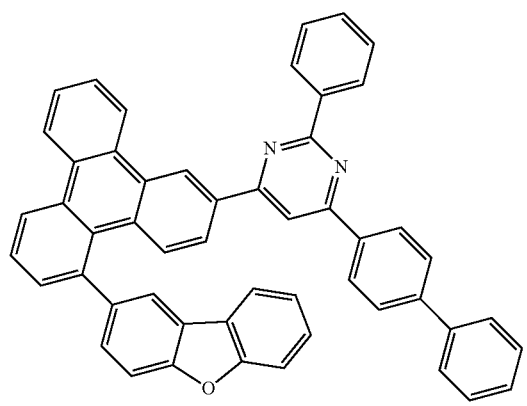
1-249
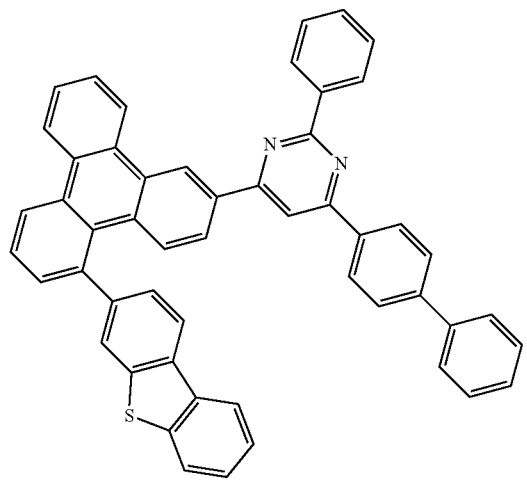
1-250
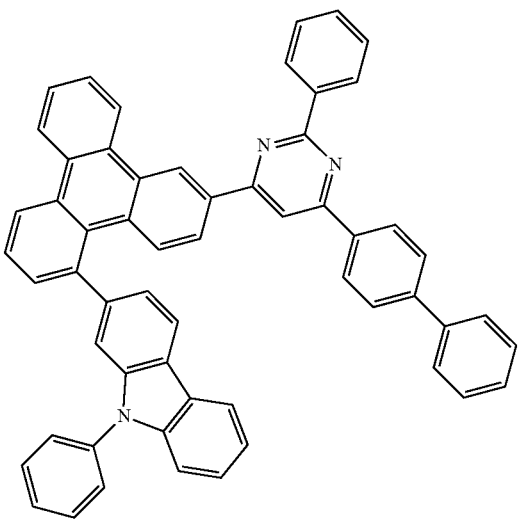
1-251
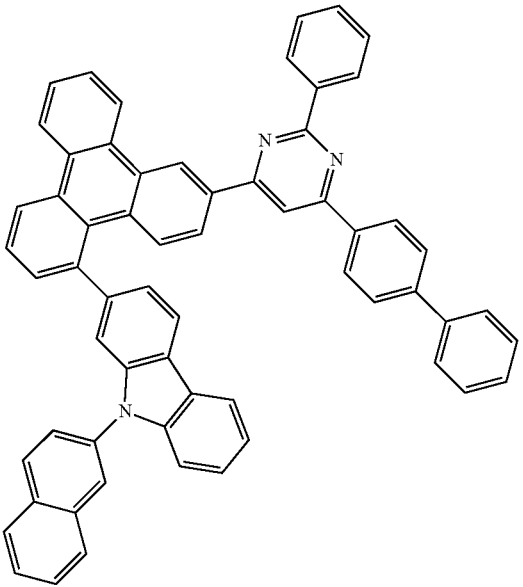

1-252
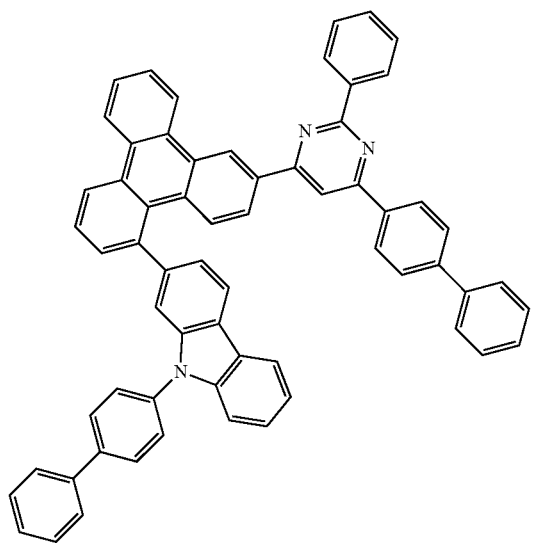
1-253
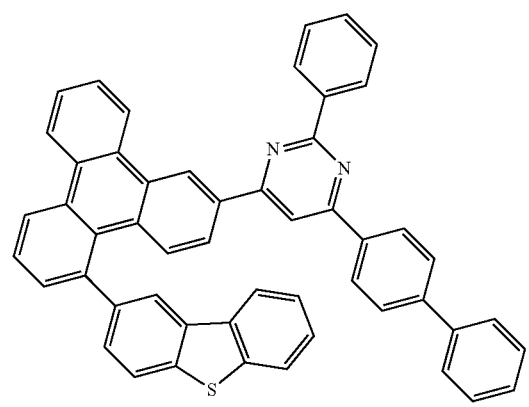
1-255
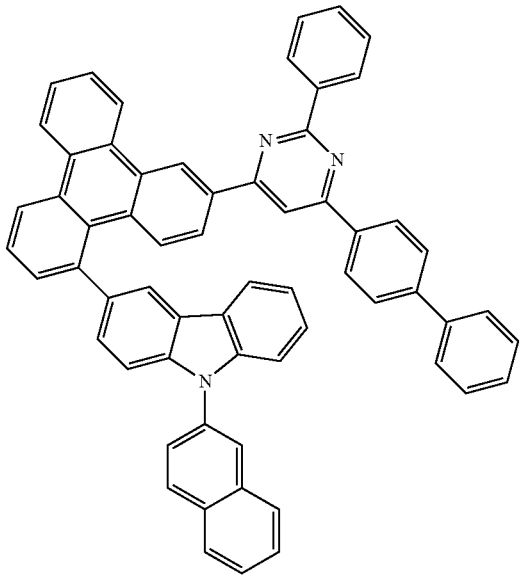
1-256
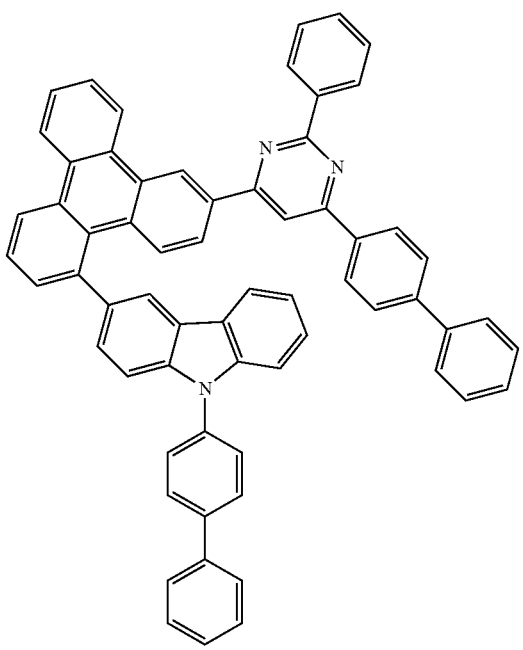

1-257
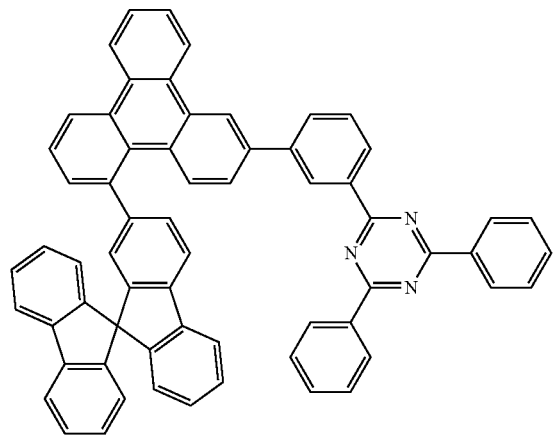
1-258
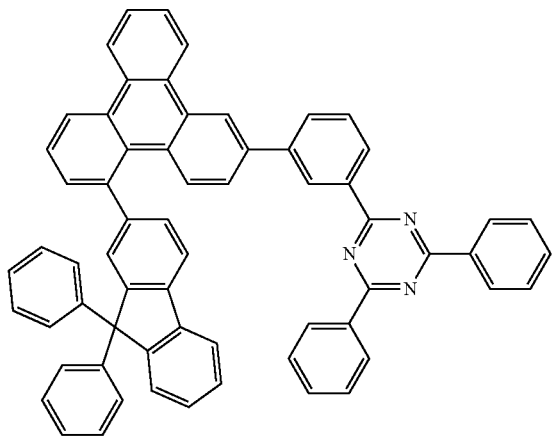
1-259
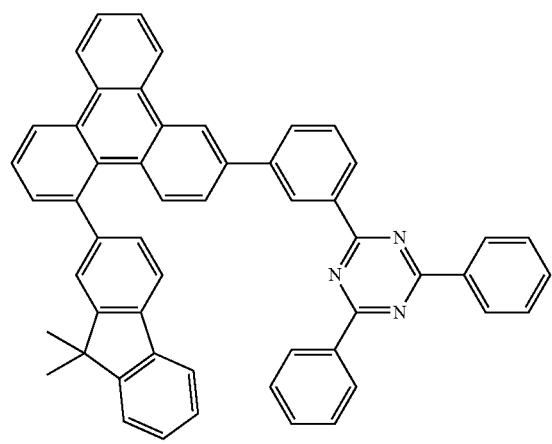
1-260
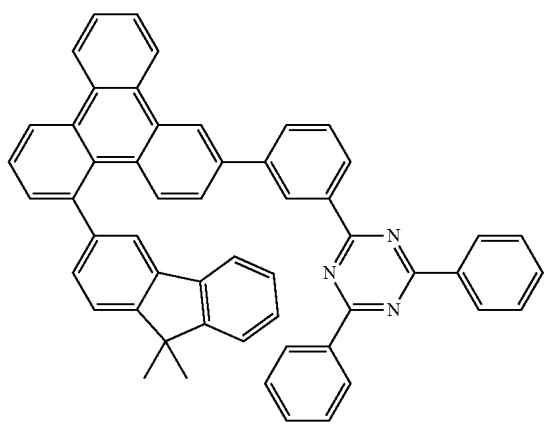
1-261
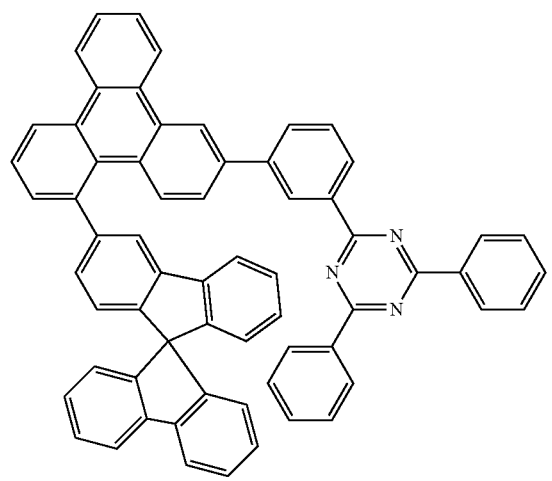
1-262
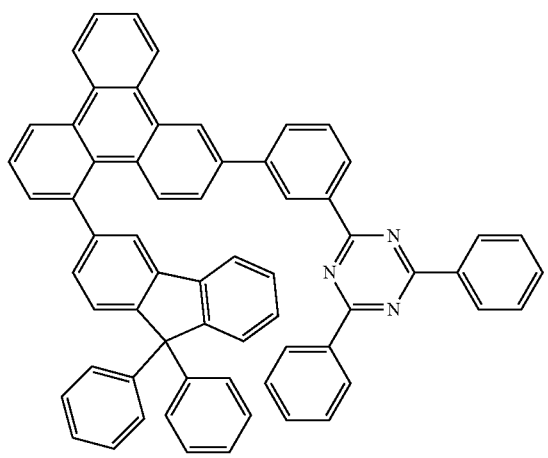

1-263
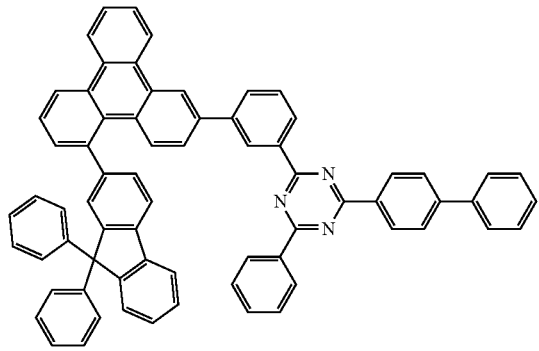
1-264
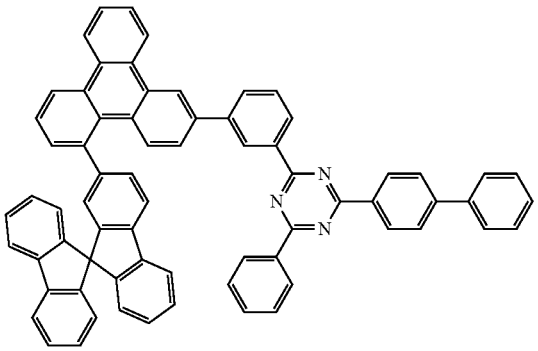
1-265
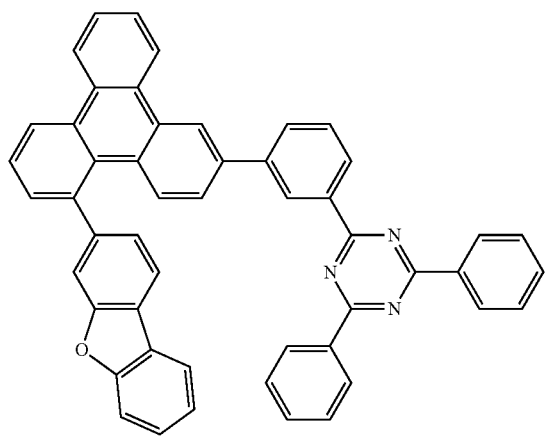
1-266
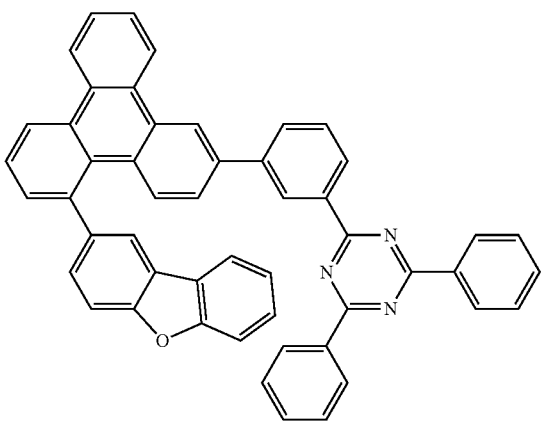
1-267
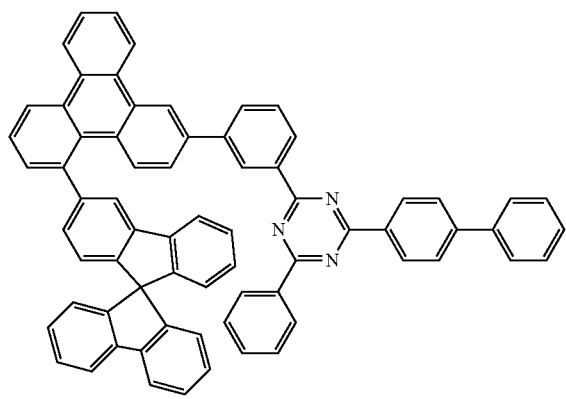
1-268
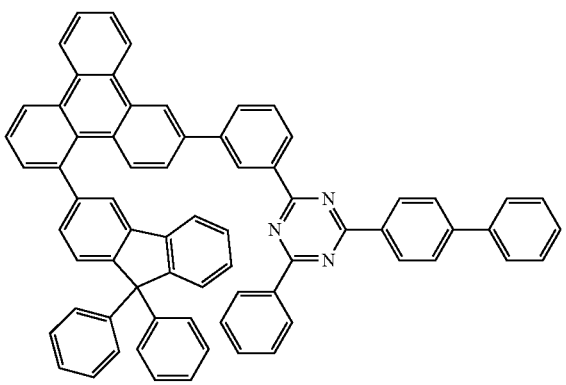
1-269
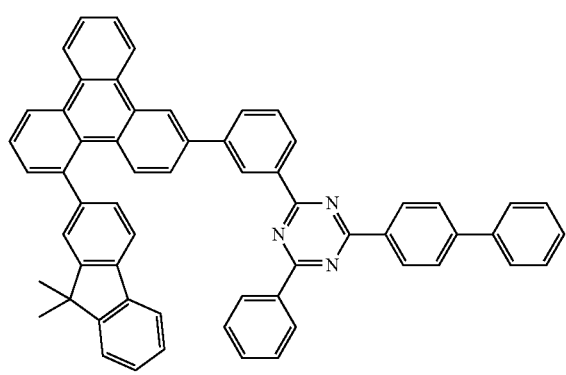
1-270
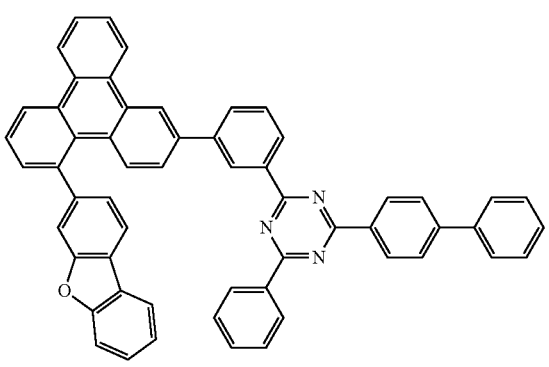

-continued
1-271
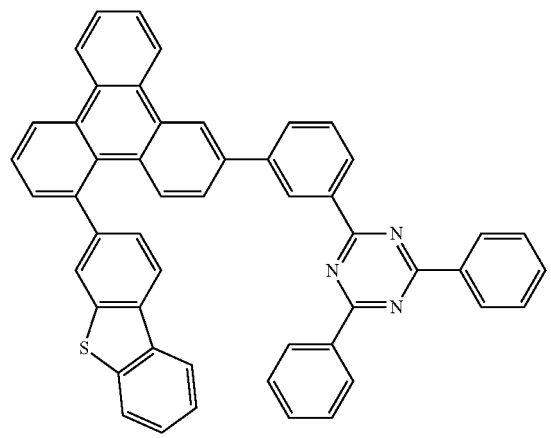
1-272
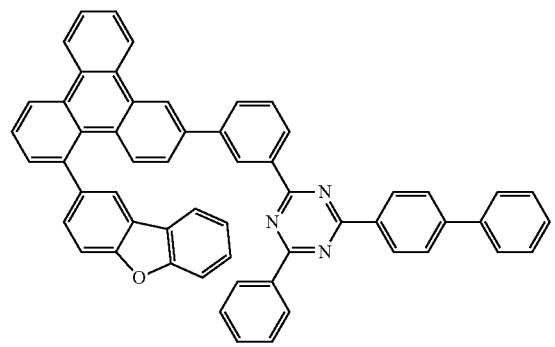
1-273
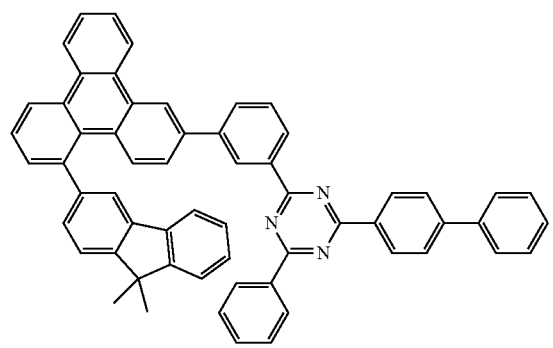
1-274
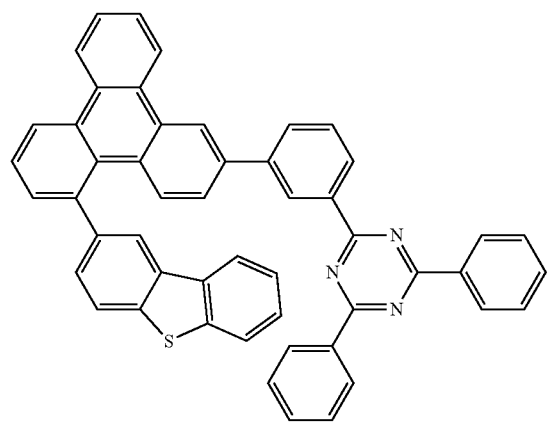
1-275
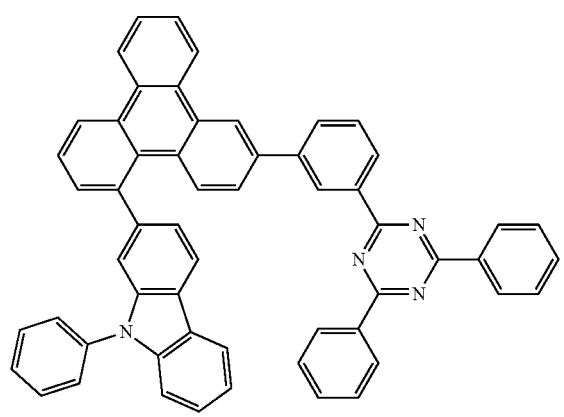
1-276
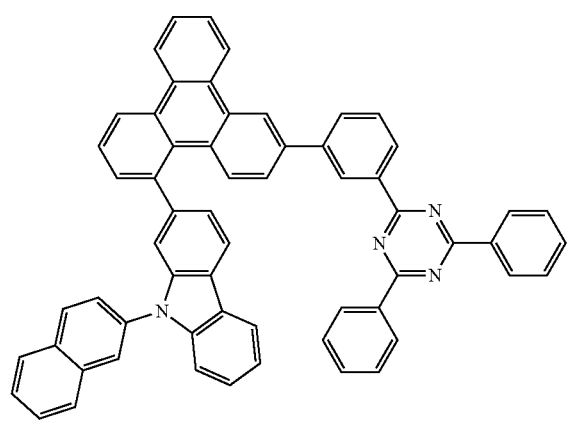

-continued
1-277
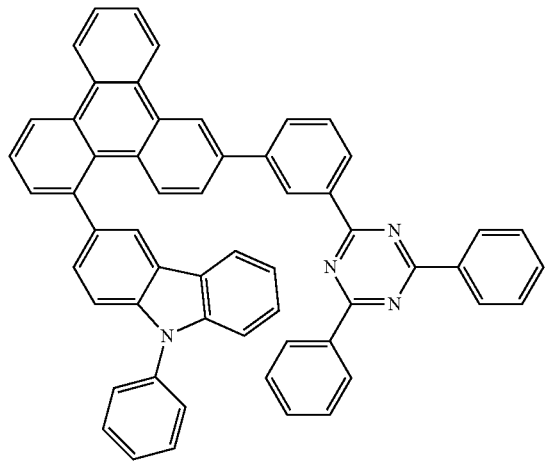
1-278
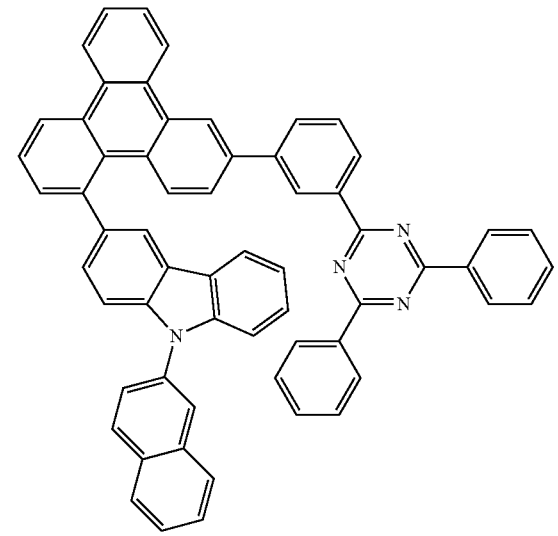
1-279
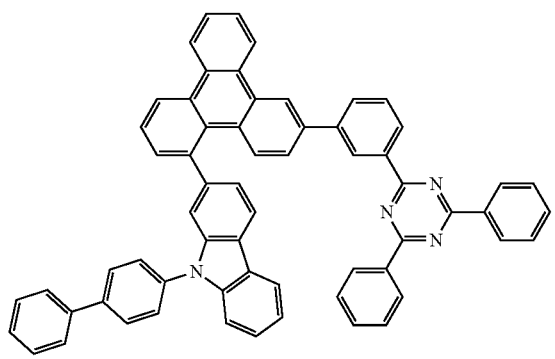
1-280
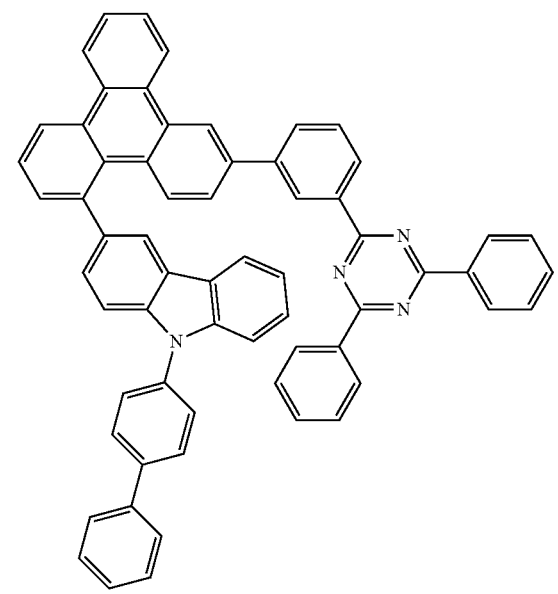
1-281
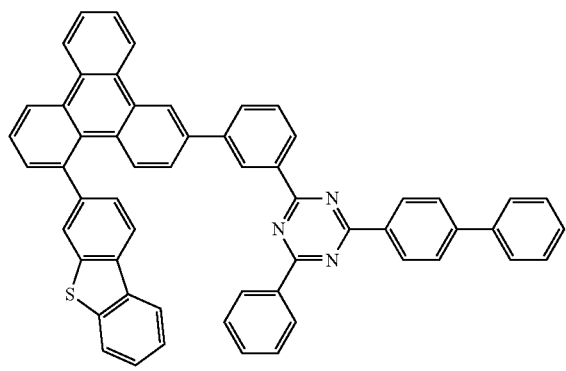
1-282
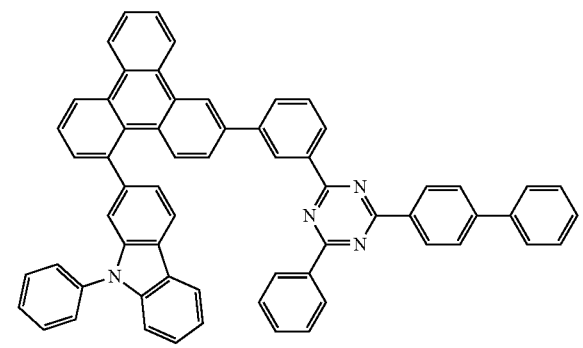

1-283
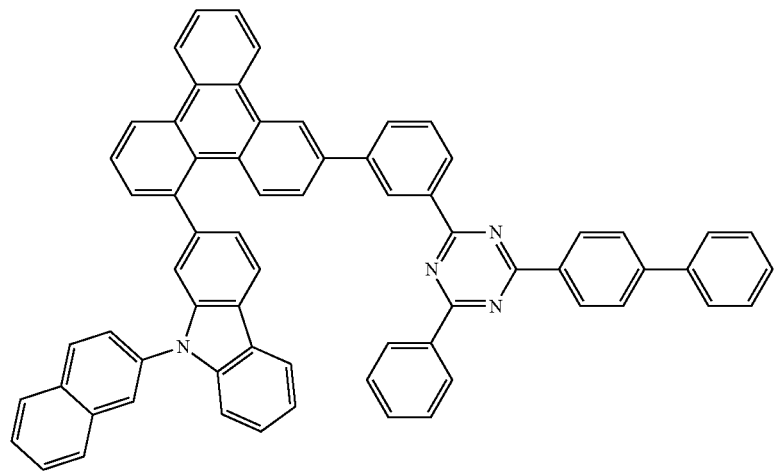
1-284
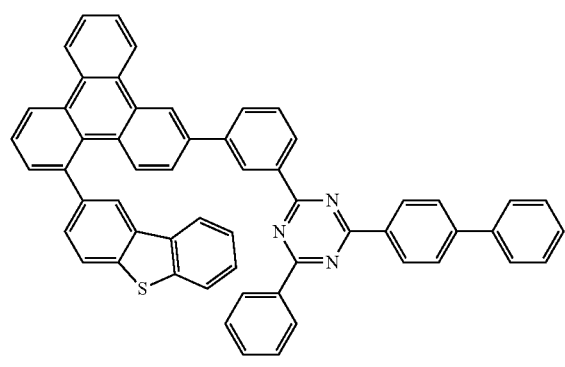
1-285
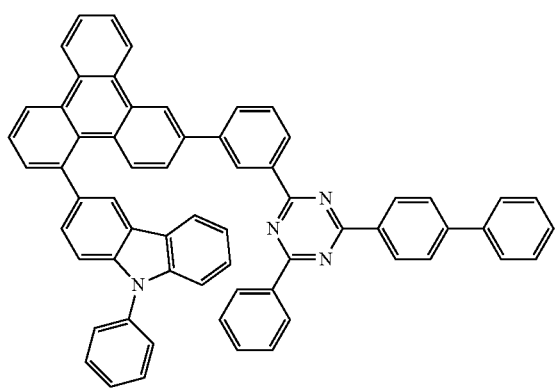
1-286
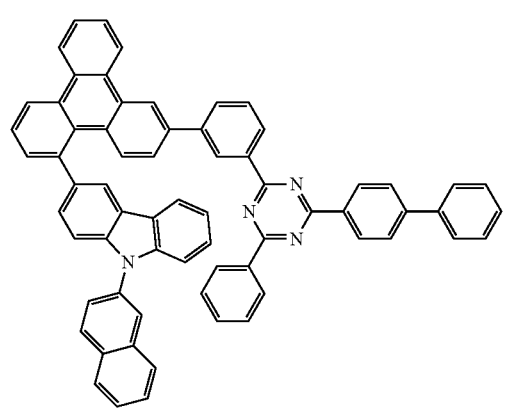

-continued
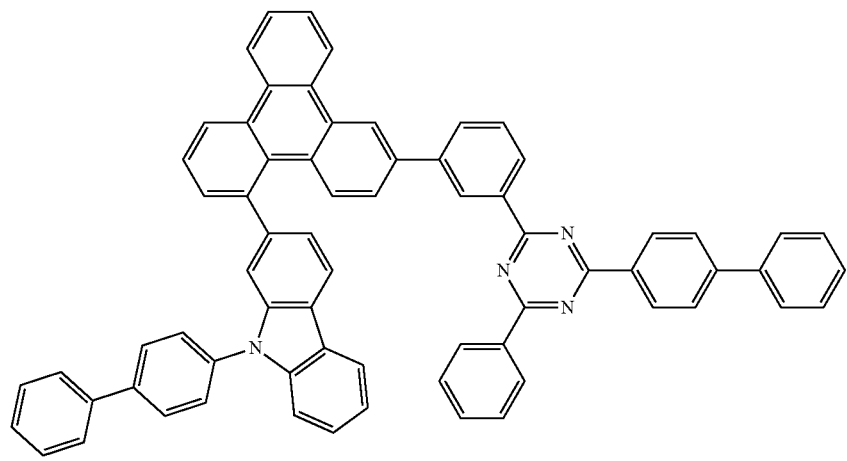
1-287
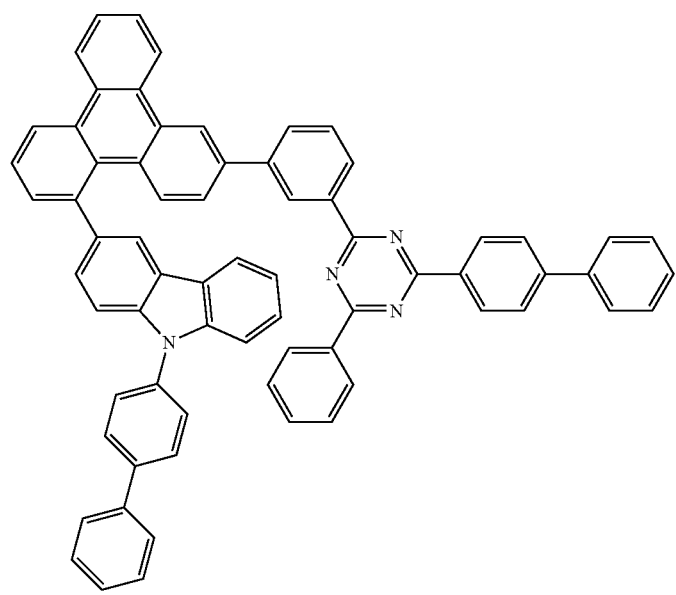
1-288
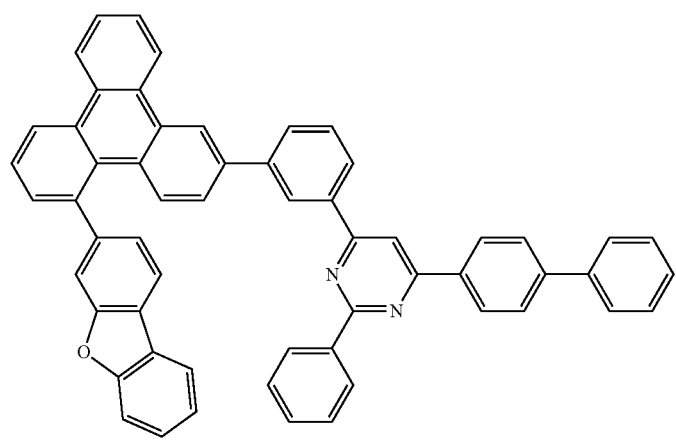
1-289

-continued
1-290
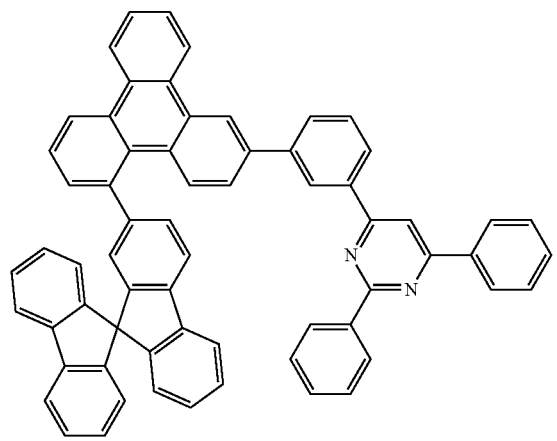
1-291
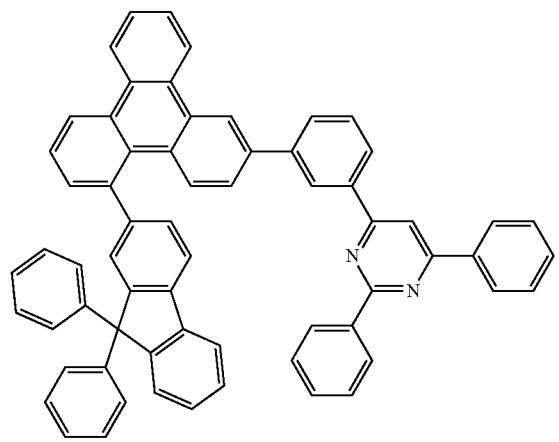
1-292
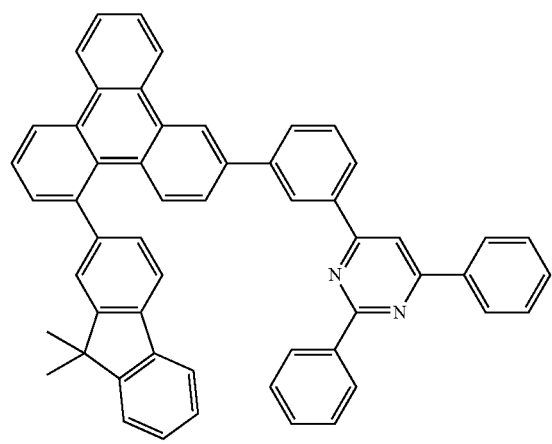
1-293
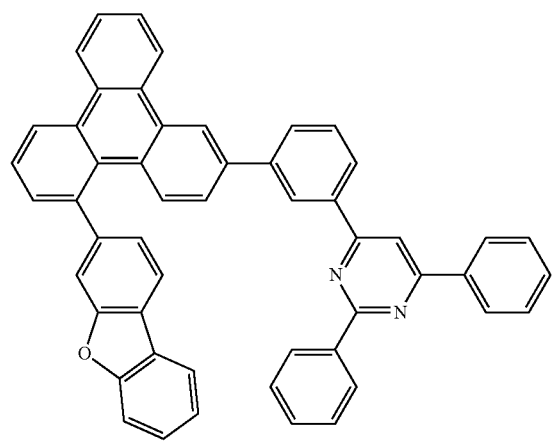
1-294
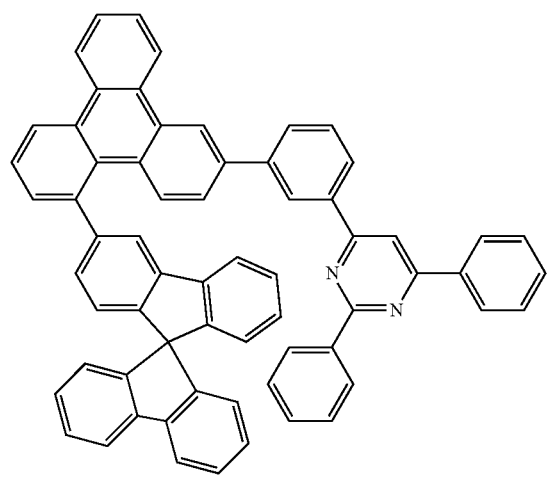
1-295
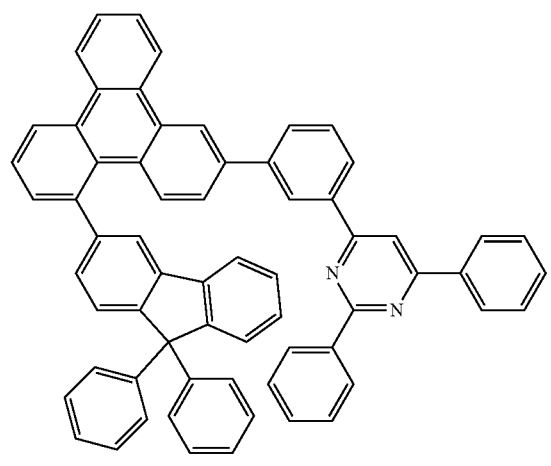

-continued
1-296
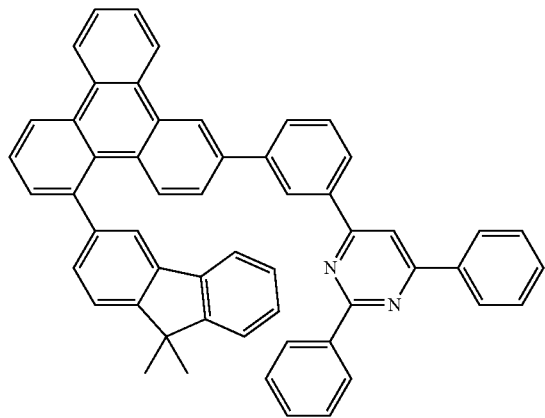
1-297
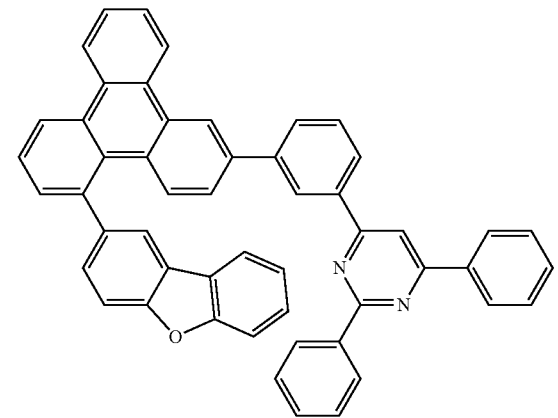
1-298
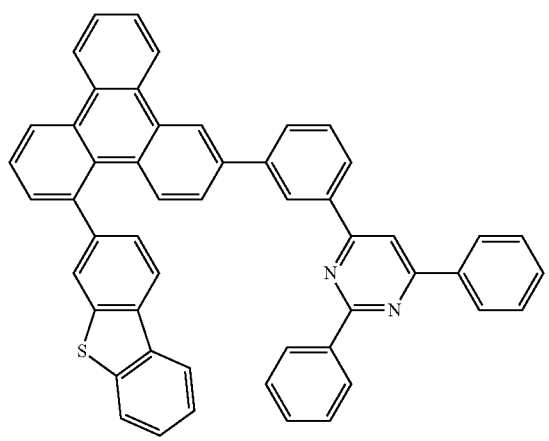
1-299
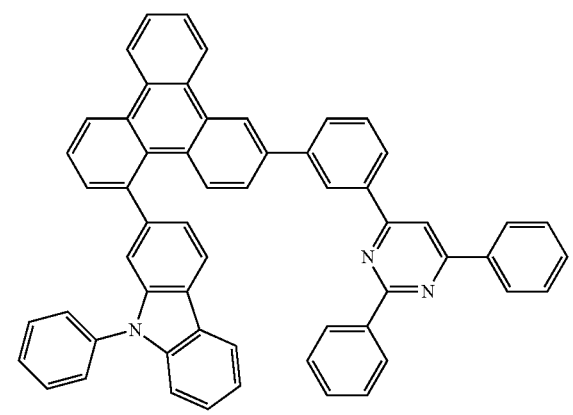
1-300
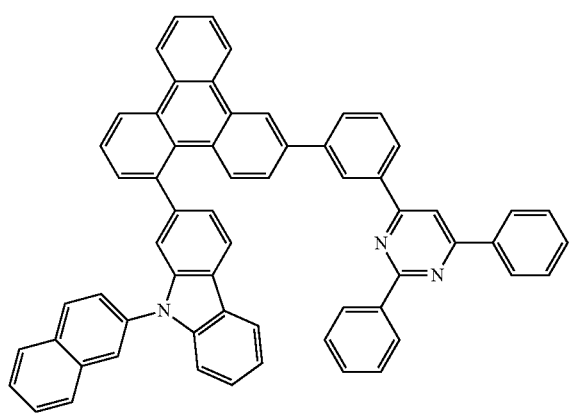
1-301
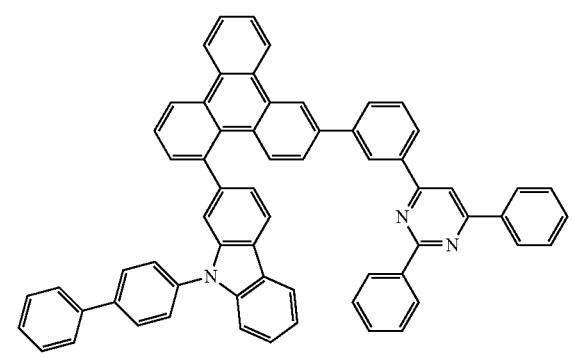

-continued
1-302
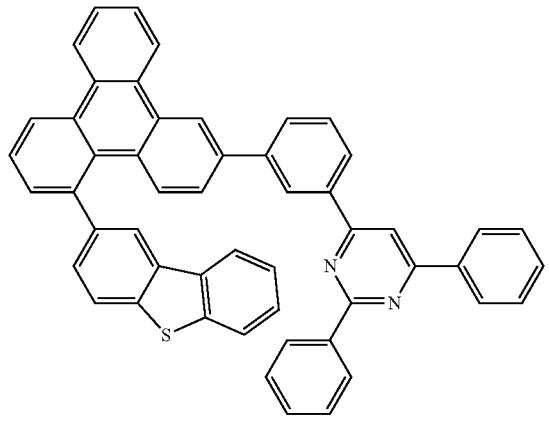
1-303
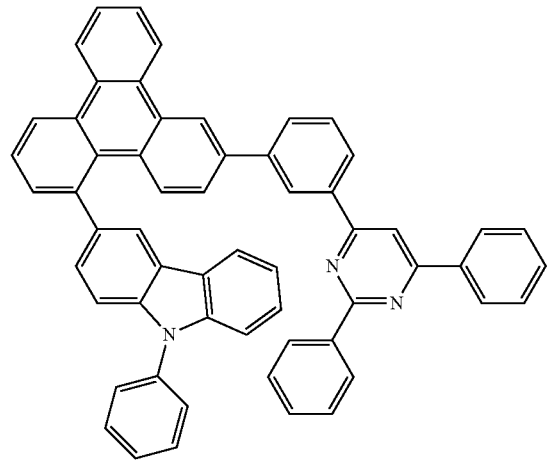
1-304
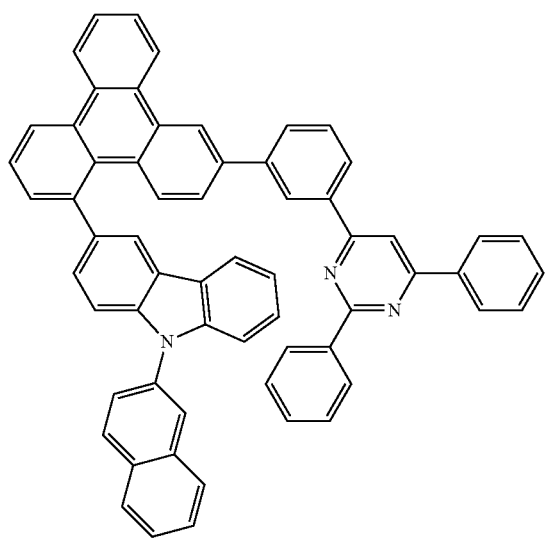
1-305
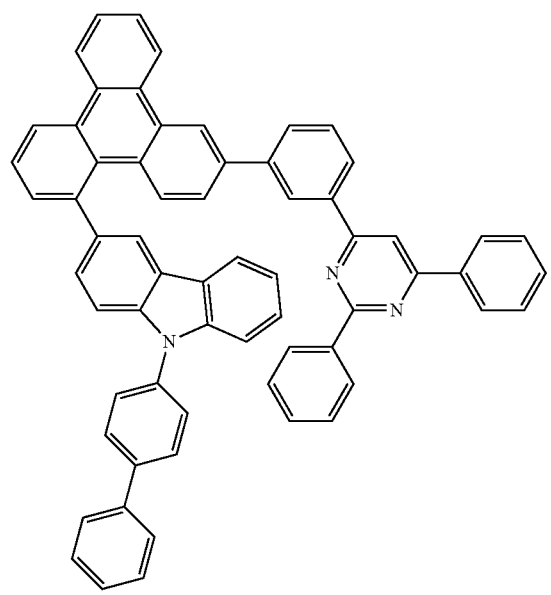
1-306
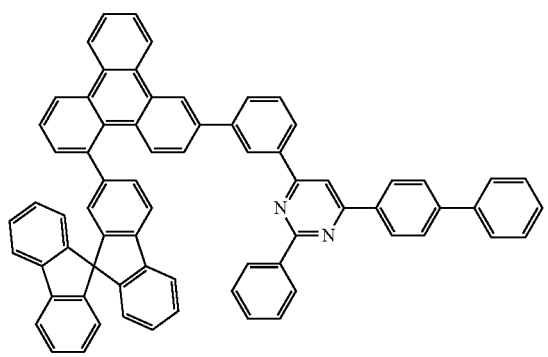
1-307
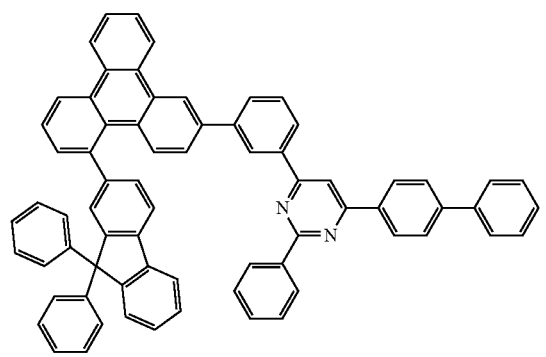

-continued
1-308
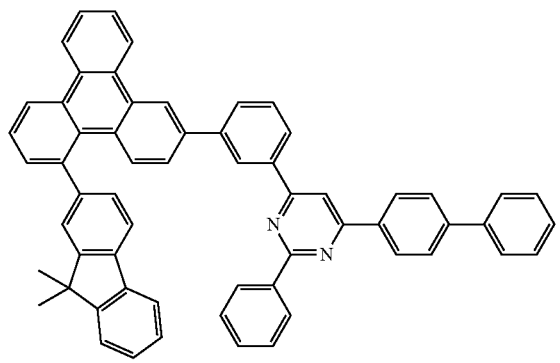
1-309
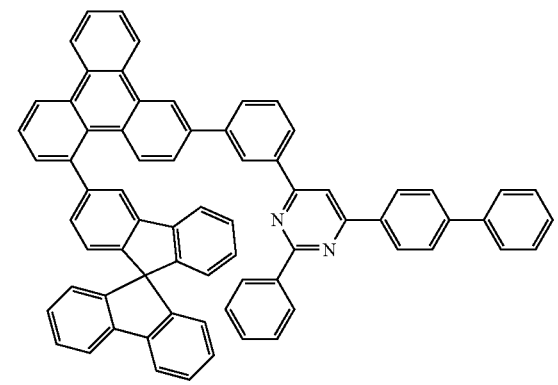
1-310
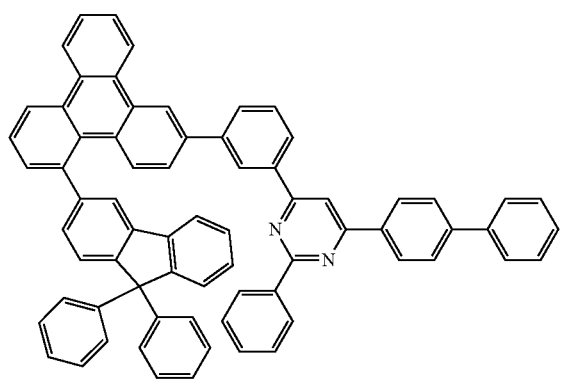
1-311
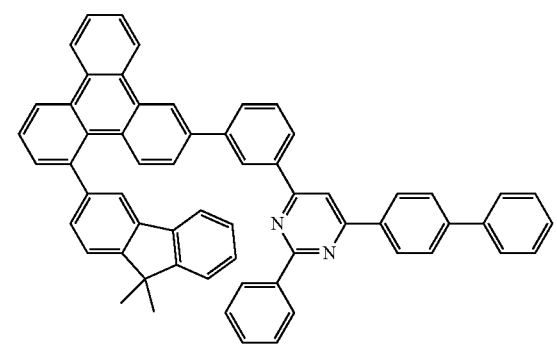
1-312
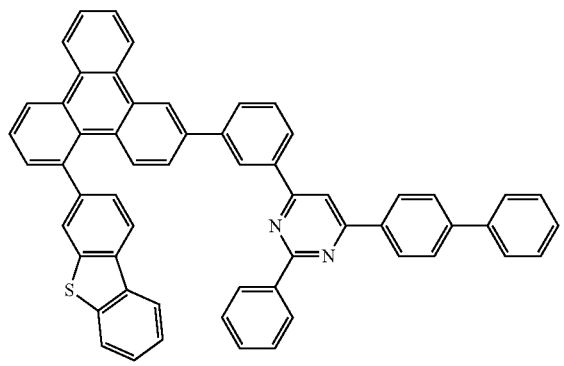
1-313
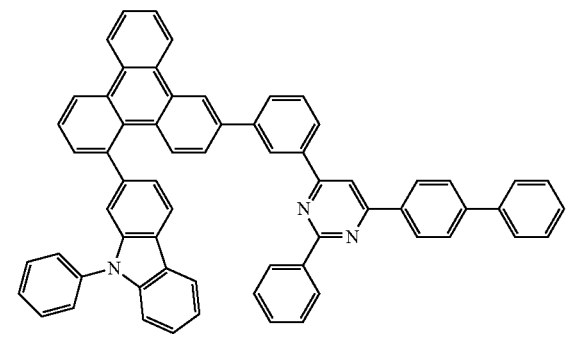
1-134
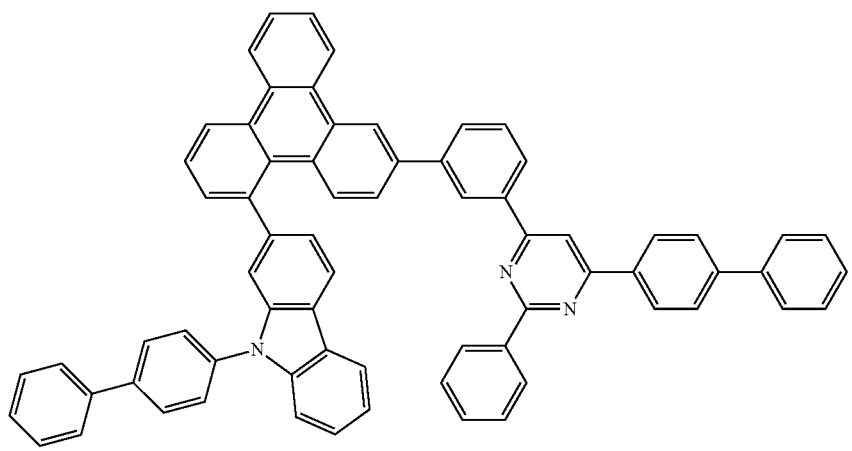

1-315
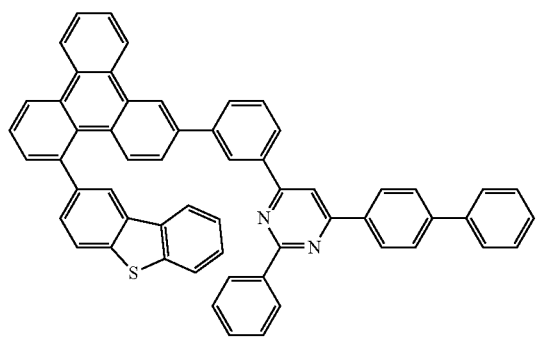
1-316
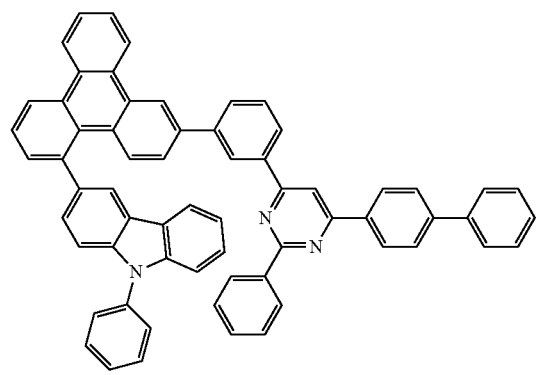
1-317
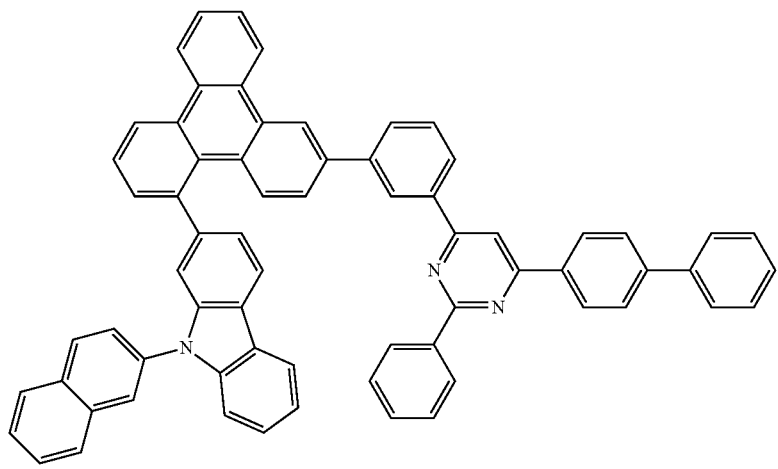
1-318
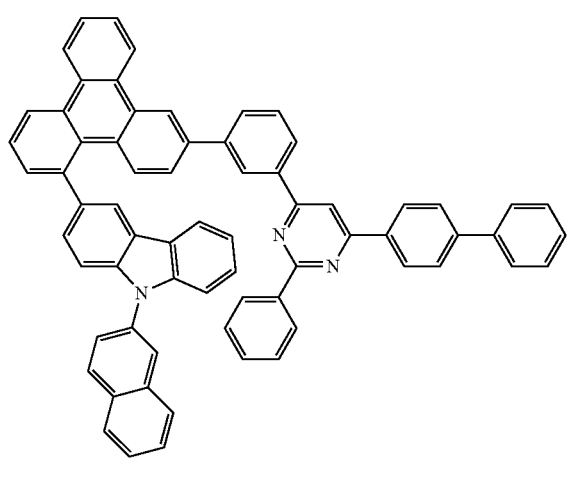
1-319
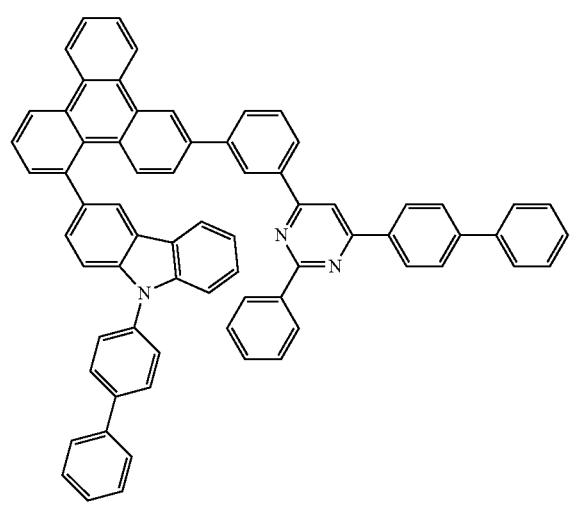

-continued
1-320
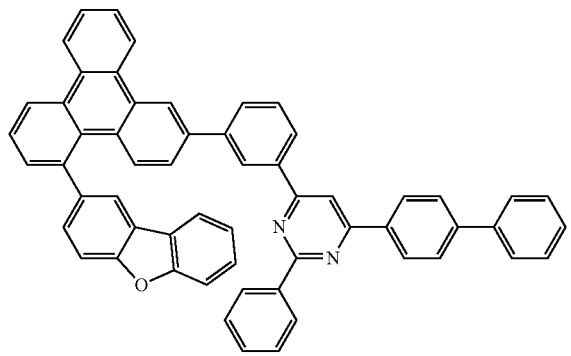
1-321
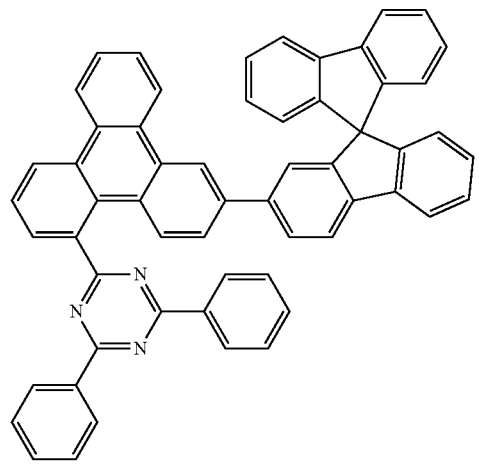
1-322
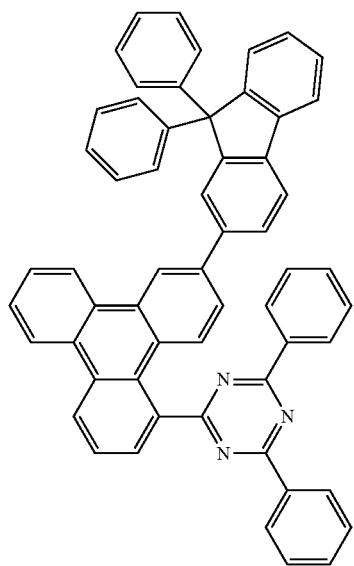
1-323
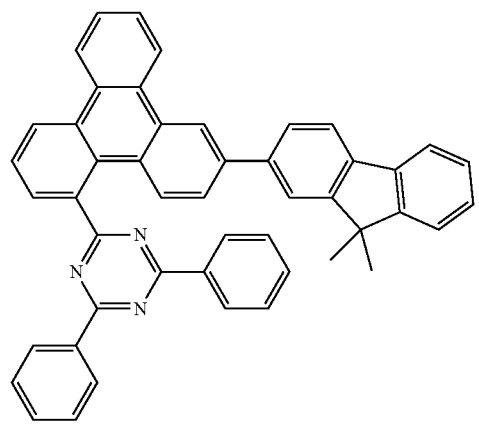
1-324
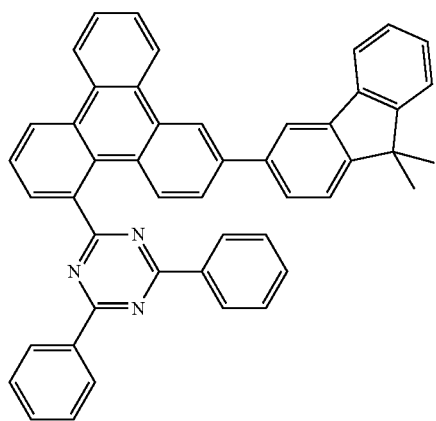
1-325
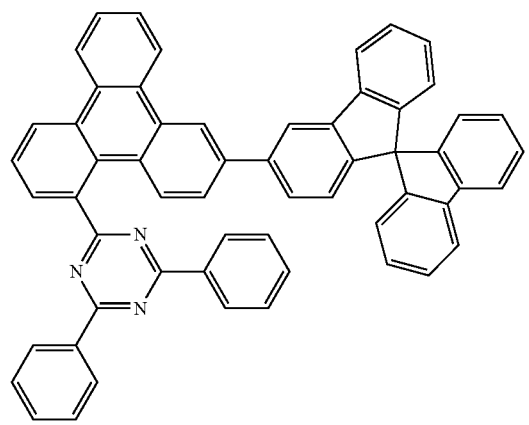

-continued
1-326
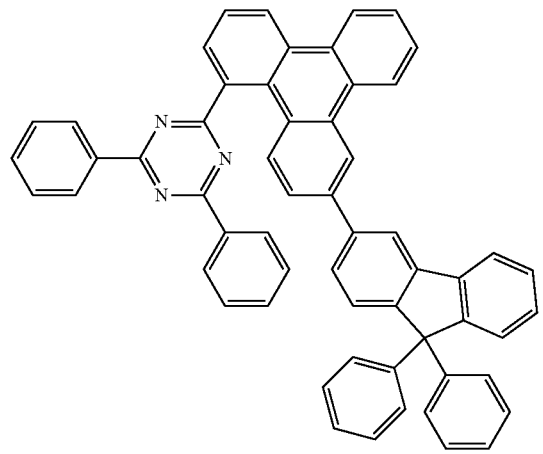
1-327
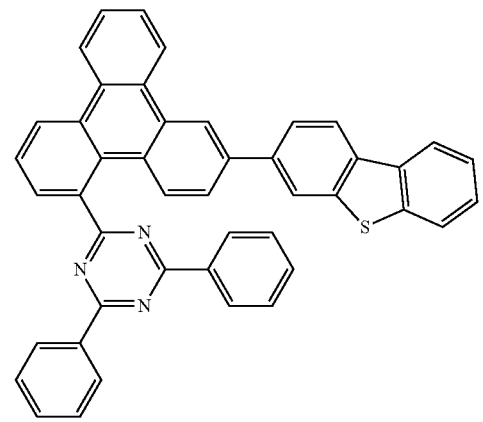
1-328
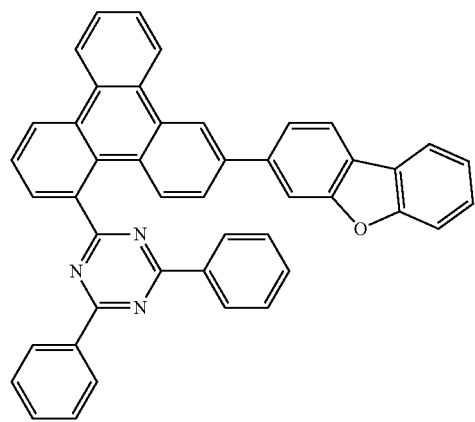
1-329
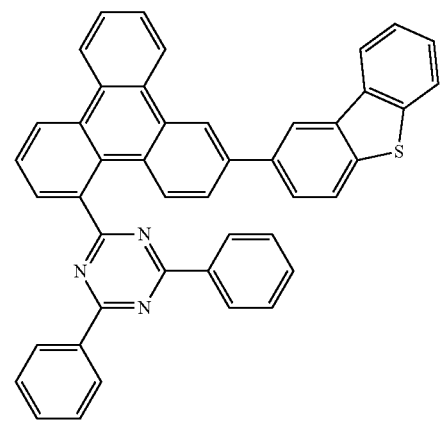
1-330
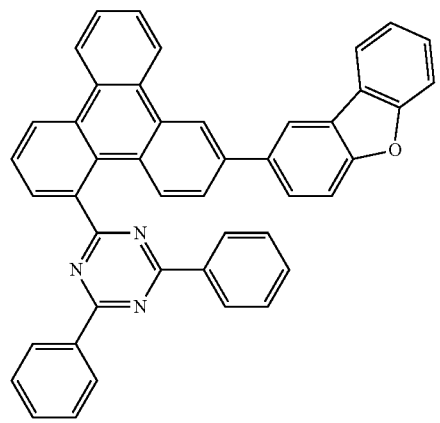
1-331
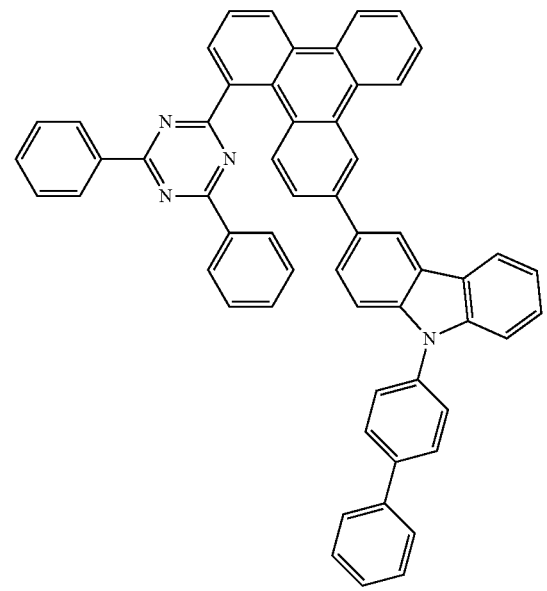

-continued
1-332
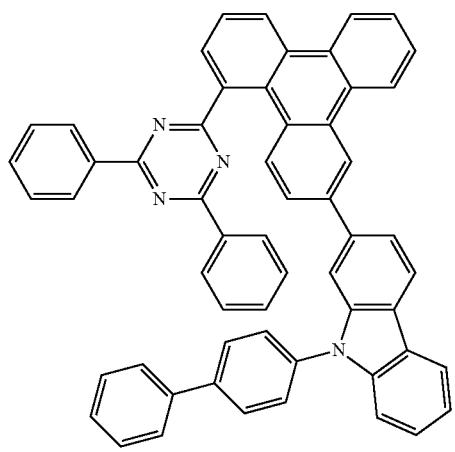
1-333
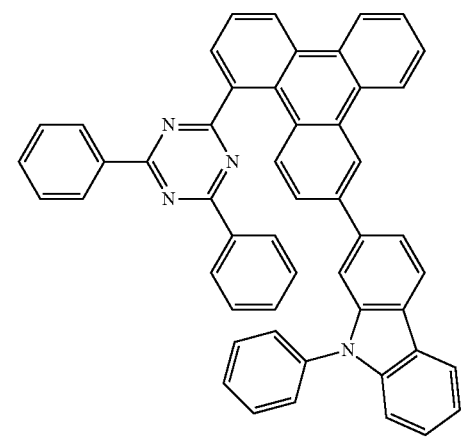
1-334
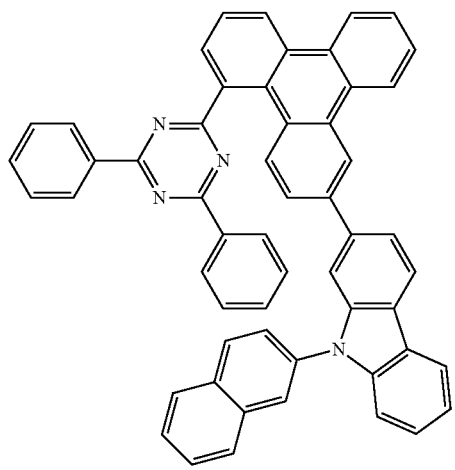
1-335
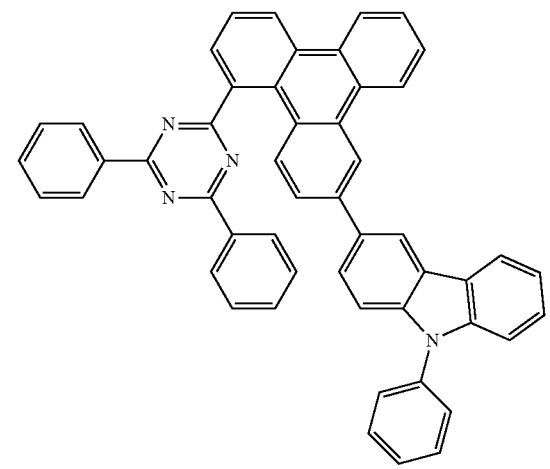
1-336
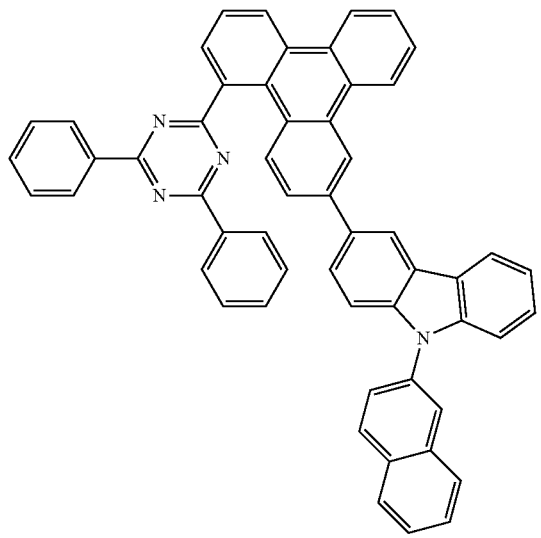
1-337
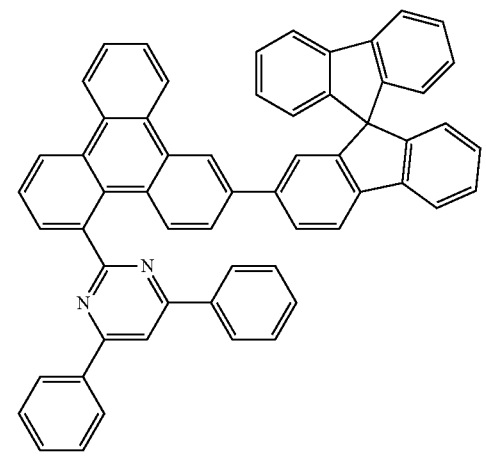

1-338
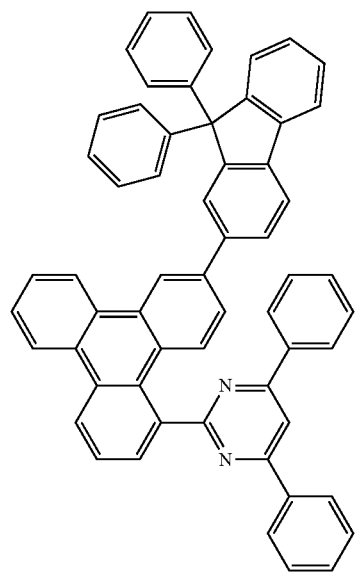
1-339
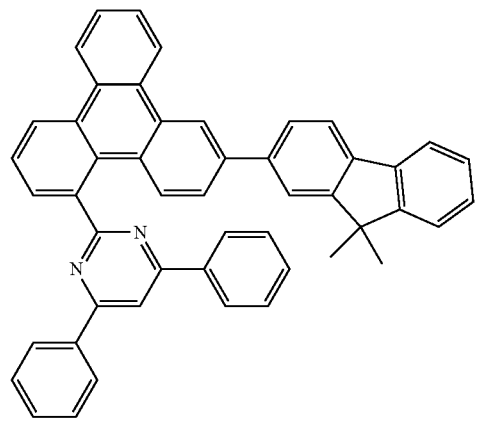
1-340
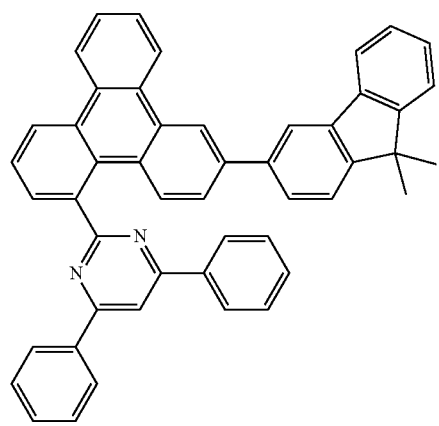
1-341
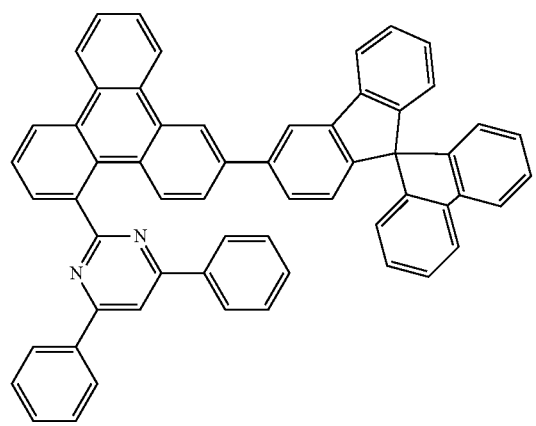
1-342
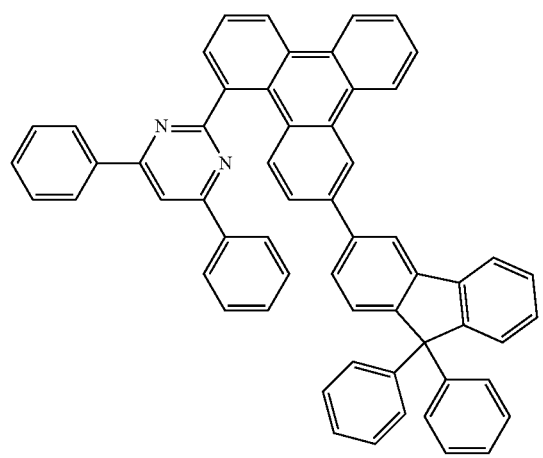
1-343
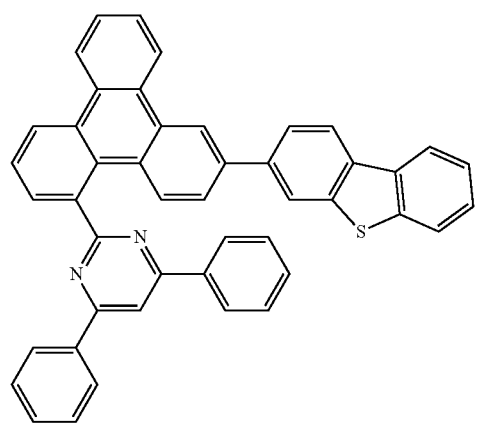

-continued
1-344
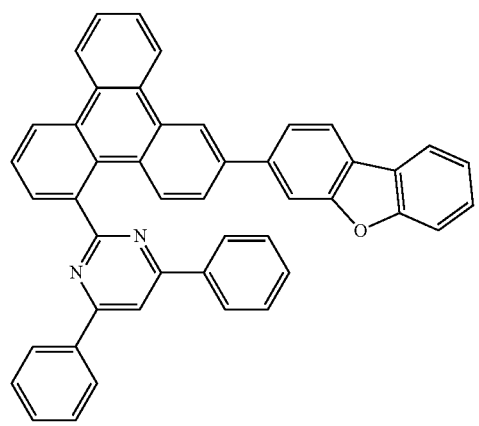
1-345
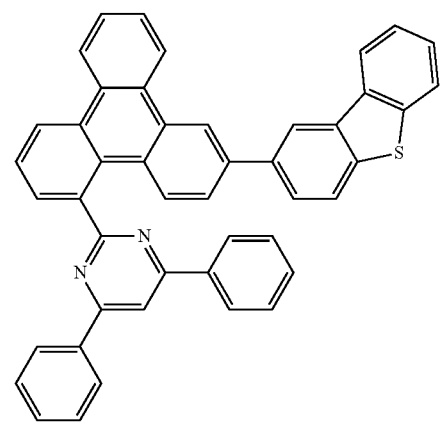
1-346
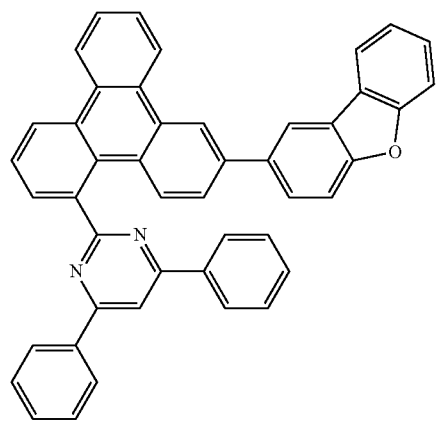
1-347
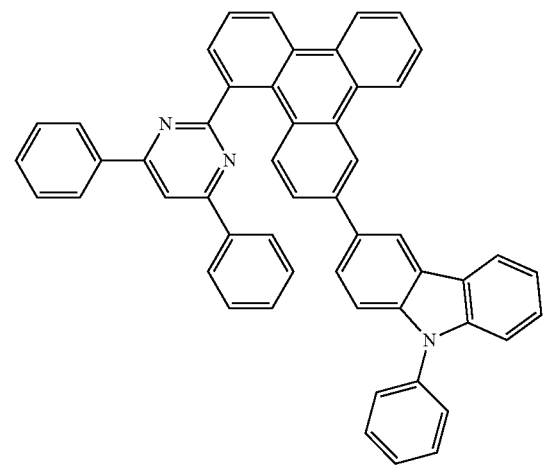
1-348
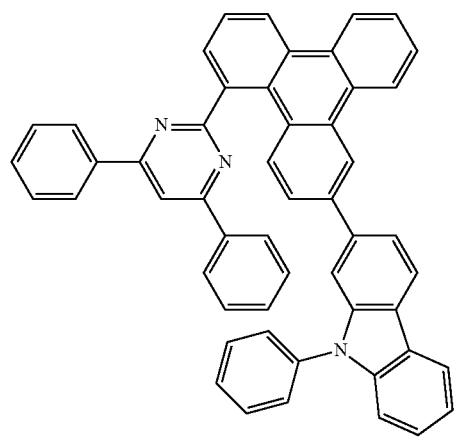
1-349
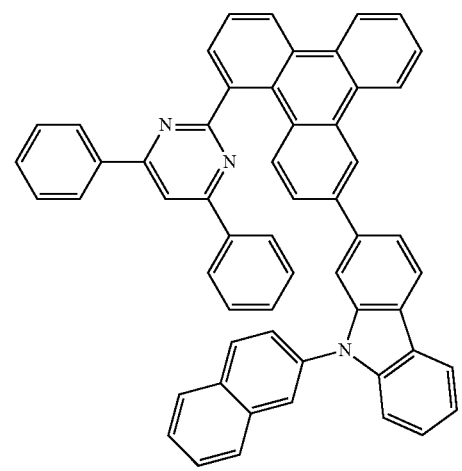

169                                                                 170
-continued
1-350                                                               1-351
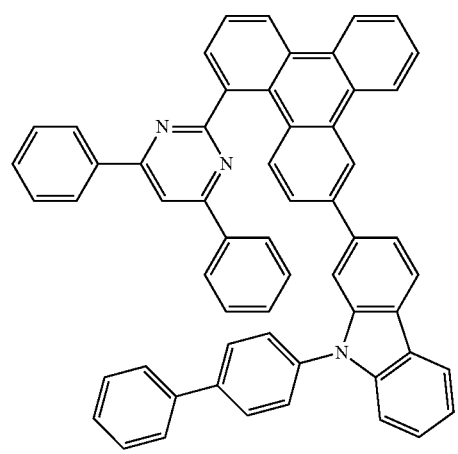
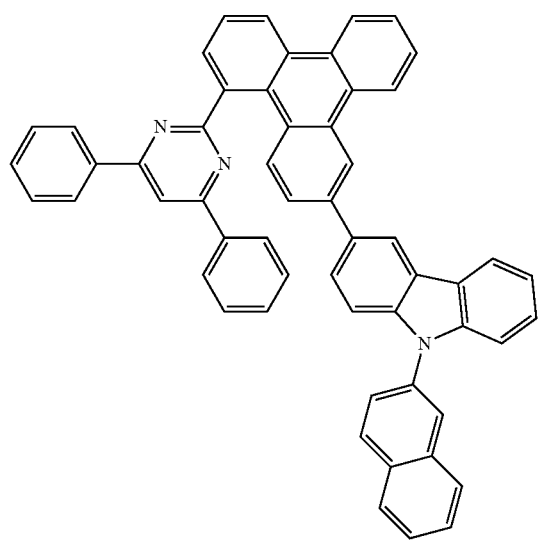
1-352                                                               1-353
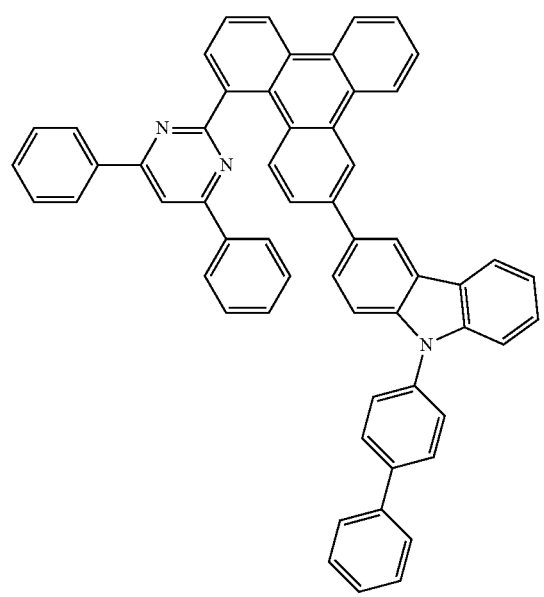
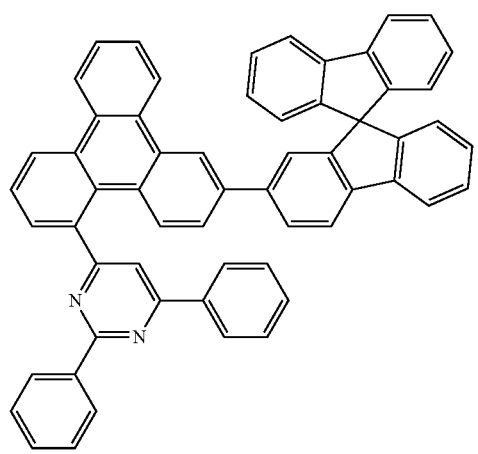

1-354

1-355

1-356

1-357

1-358

1-359

-continued
1-360
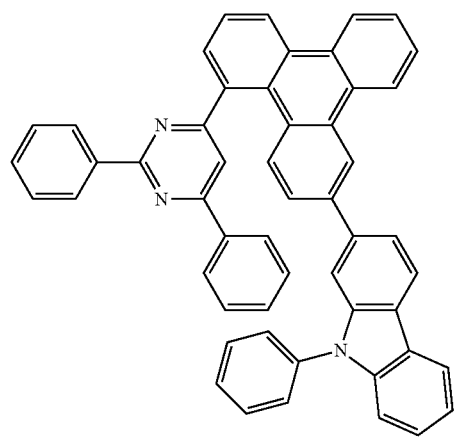
1-361
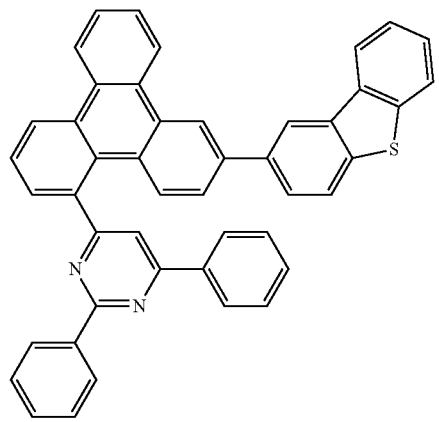
1-362
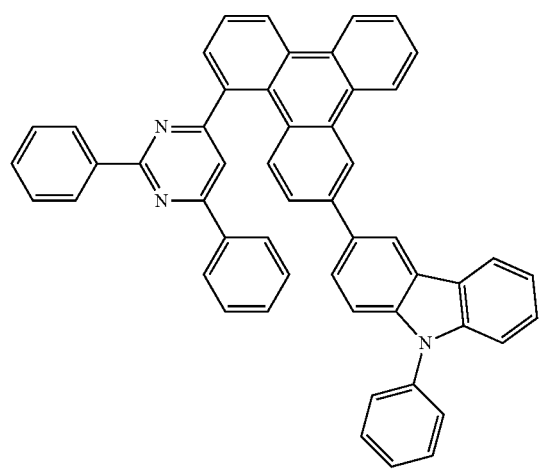
1-363
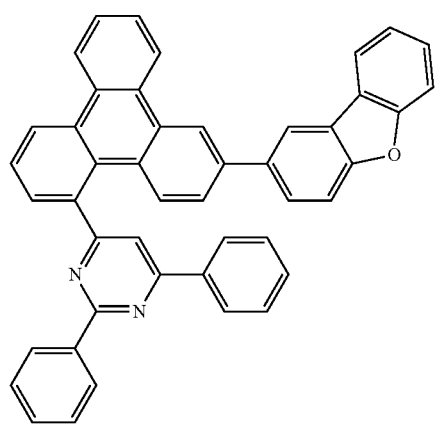
1-364
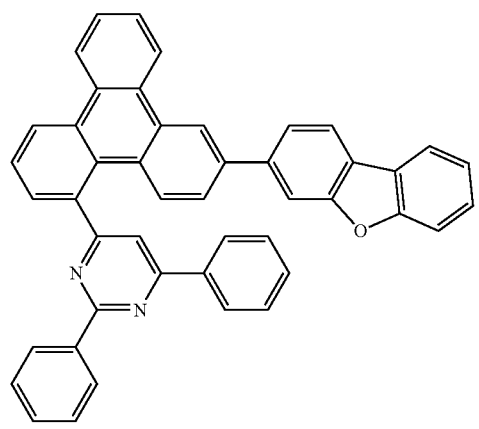
1-365
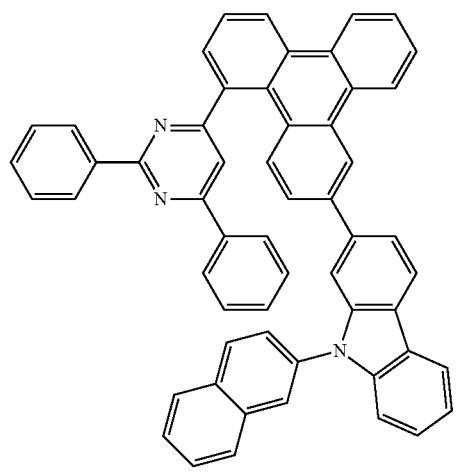

-continued
1-366
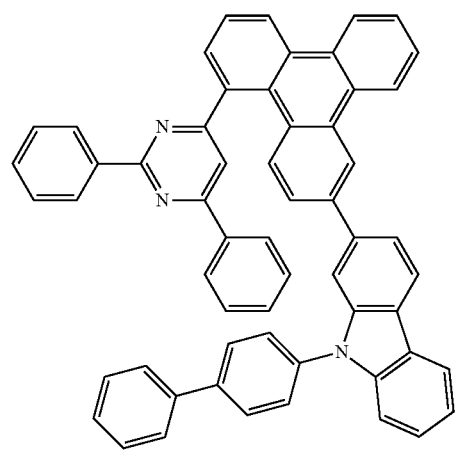
1-367
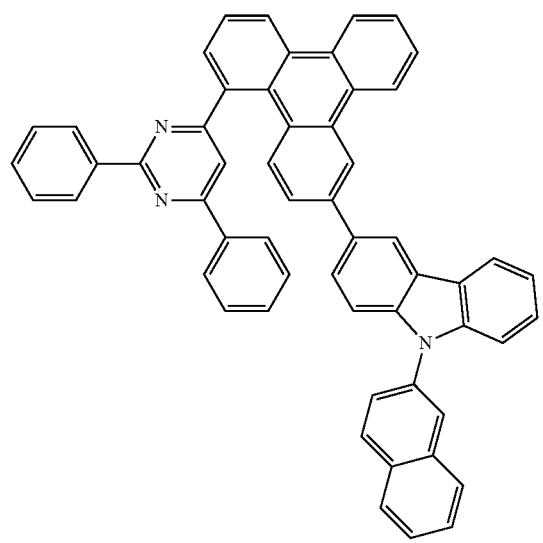
1-368
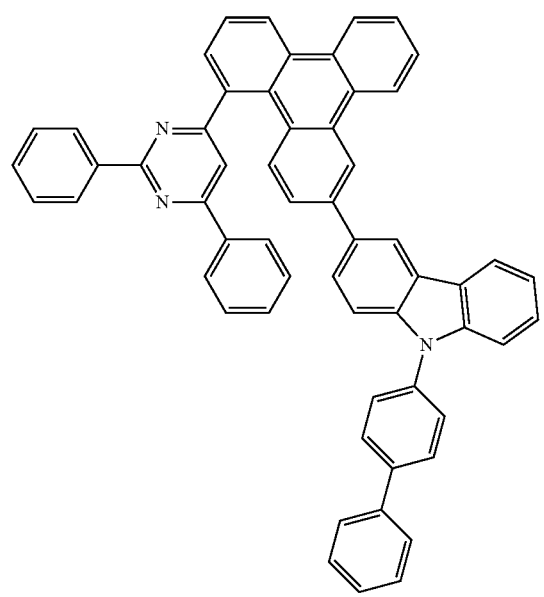
1-369
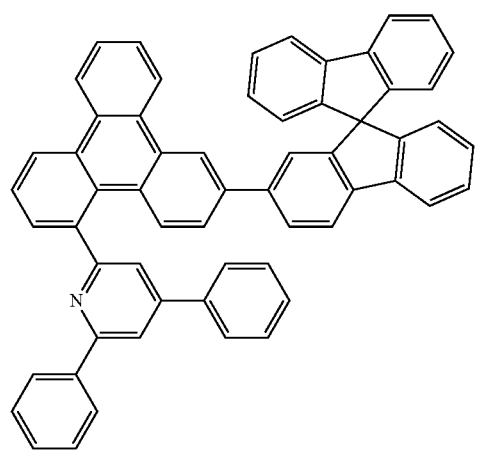

-continued
1-370
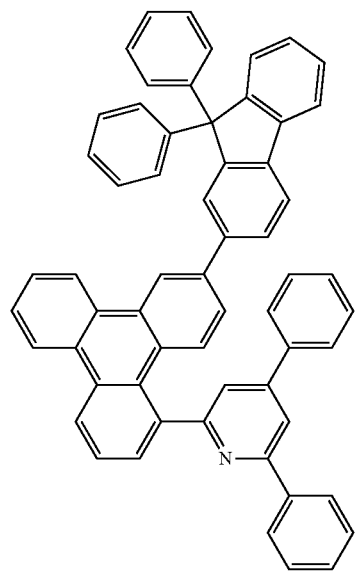
1-371
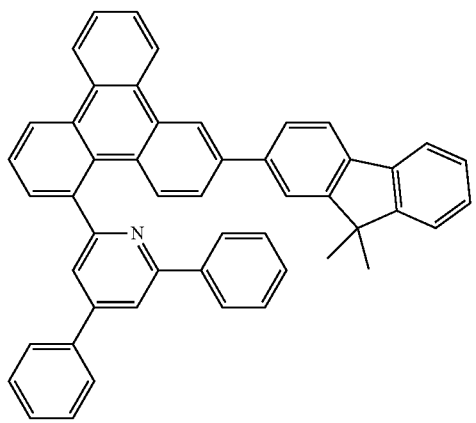
1-372
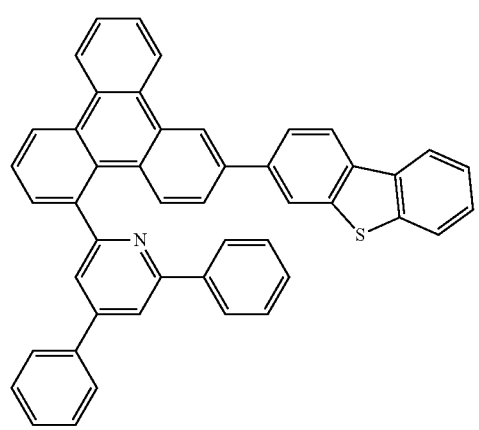
1-373
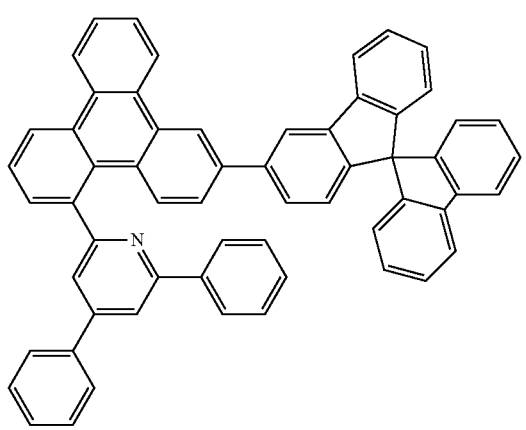
1-374
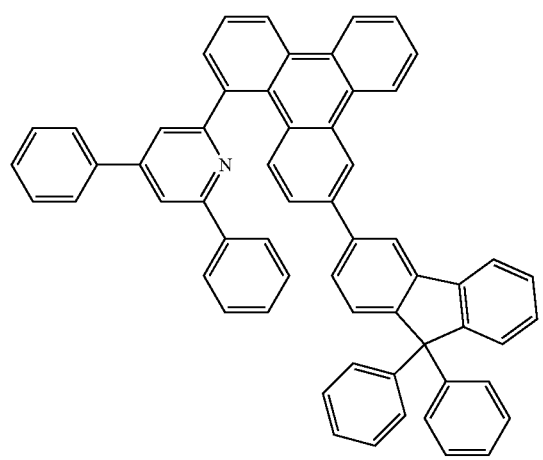
1-375
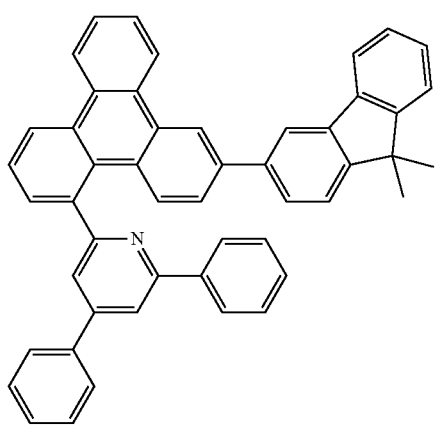

-continued
1-376
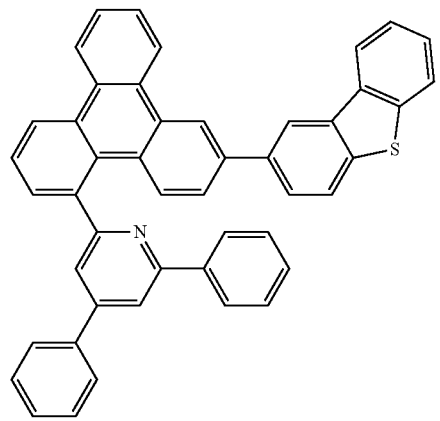
1-377
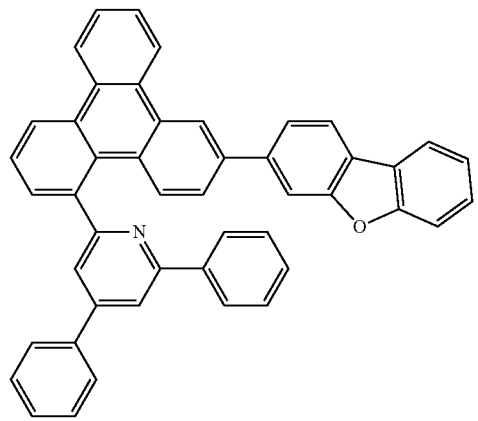
1-378
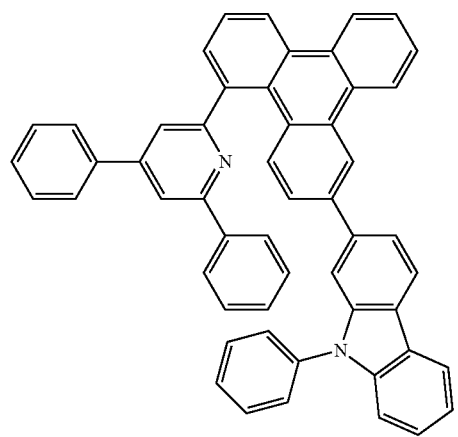
1-379
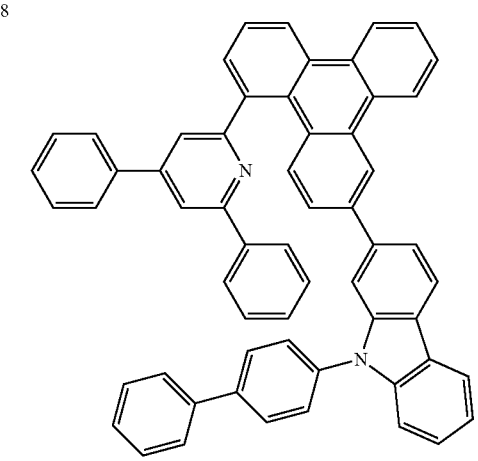
1-380
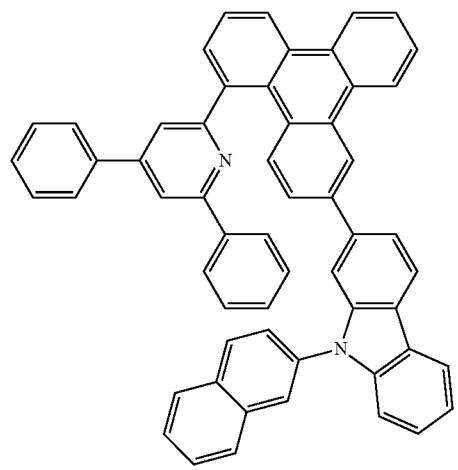
1-381
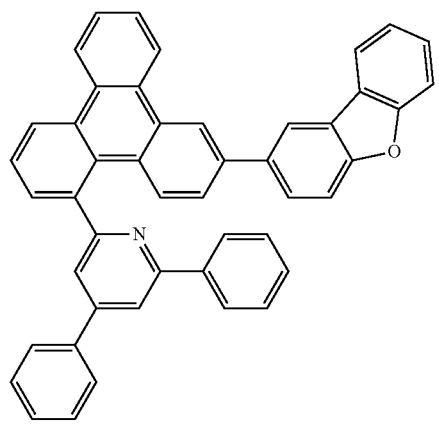

1-382
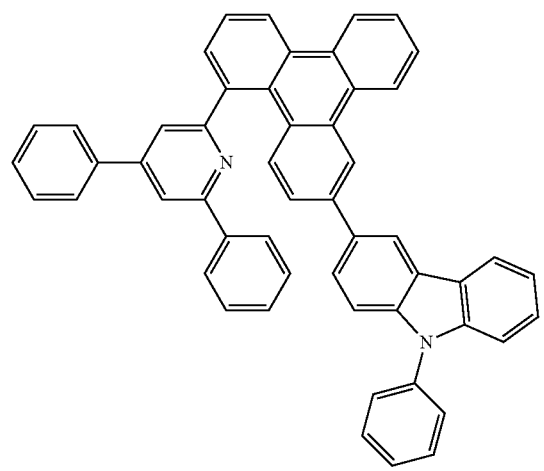
1-383
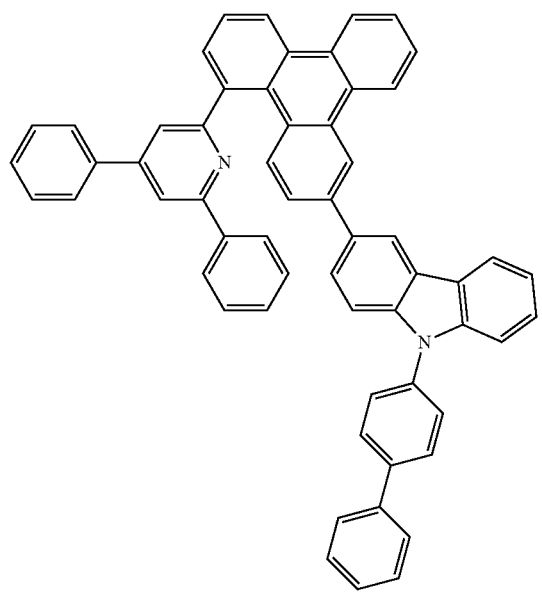
1-384
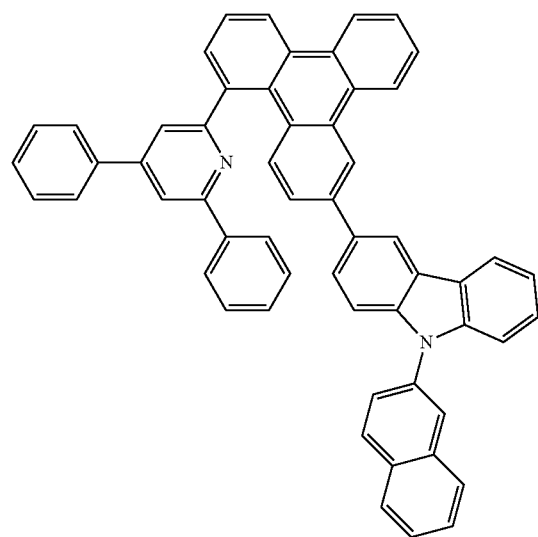
1-385
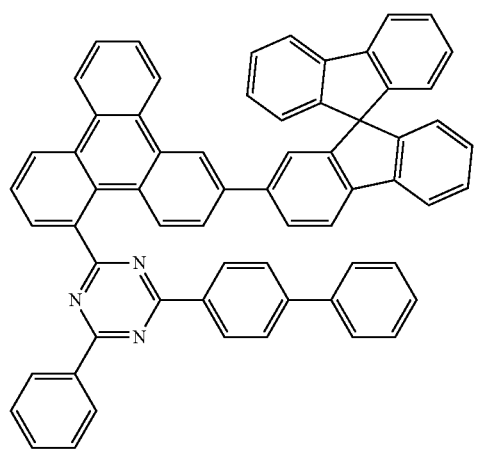

1-386
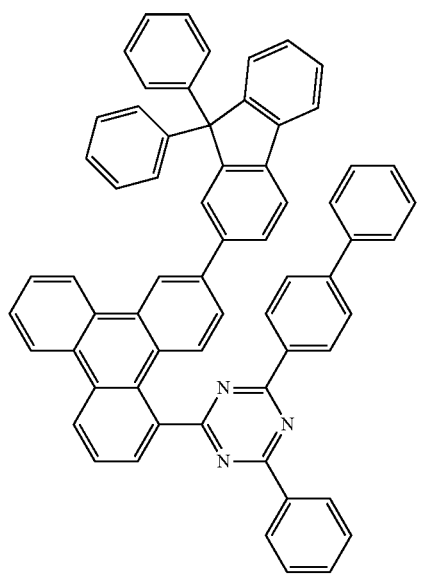
1-387
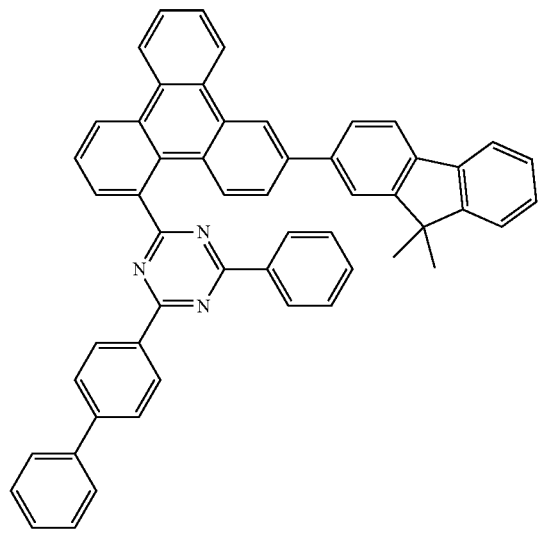
1-388
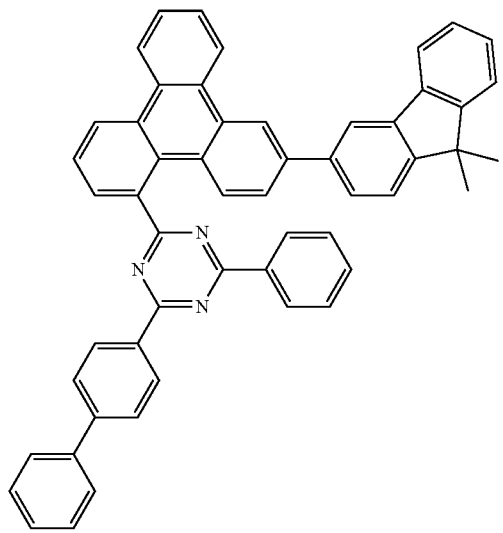
1-389
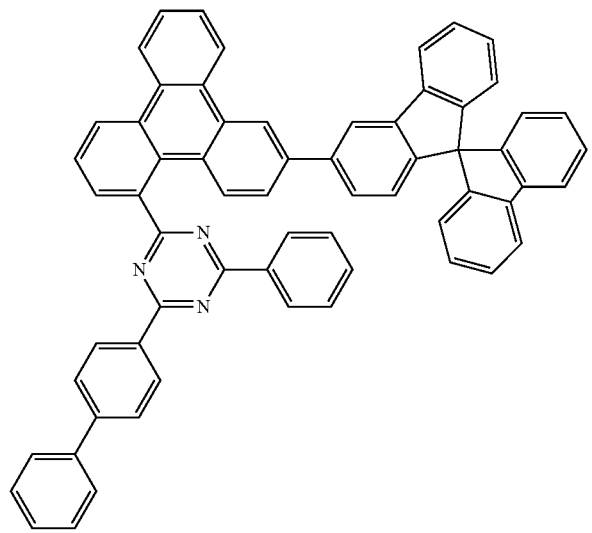

1-390
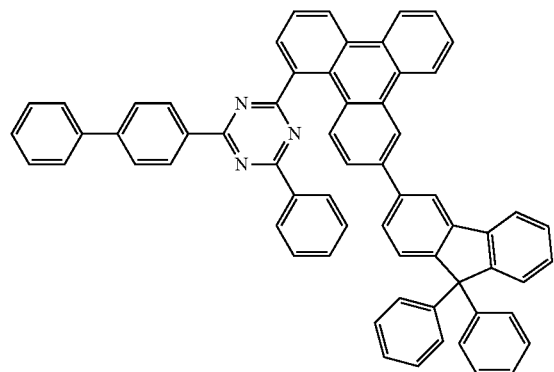
1-391
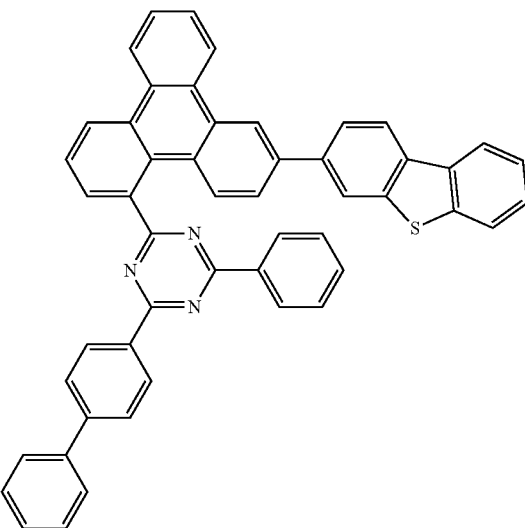
1-392
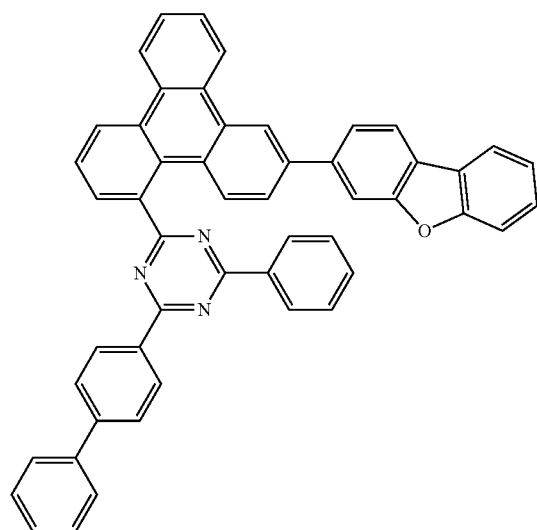
1-393
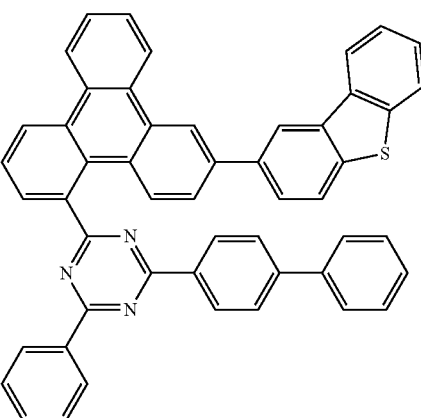
1-394
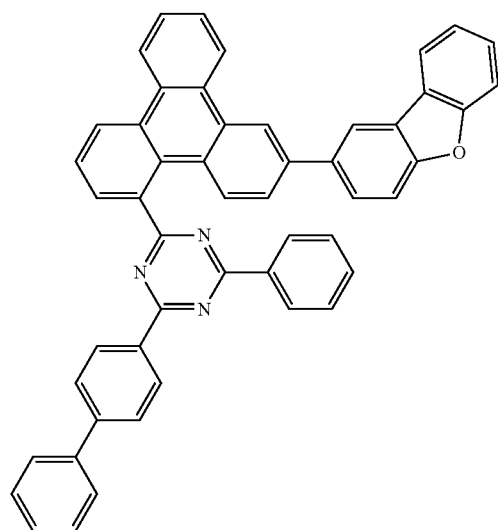
1-395
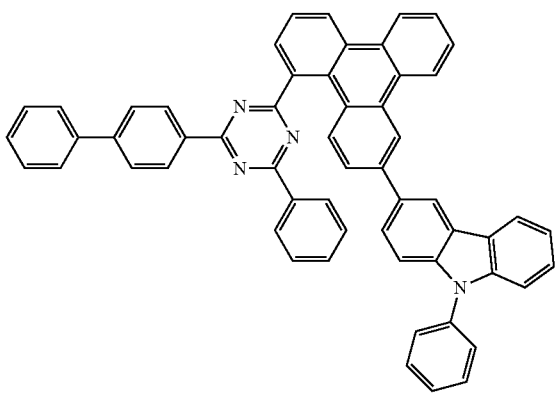

1--396
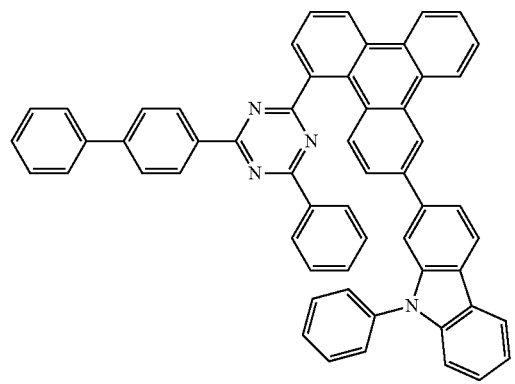
1-397
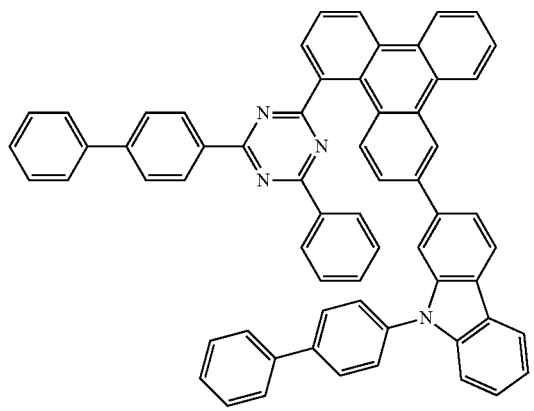
1-398
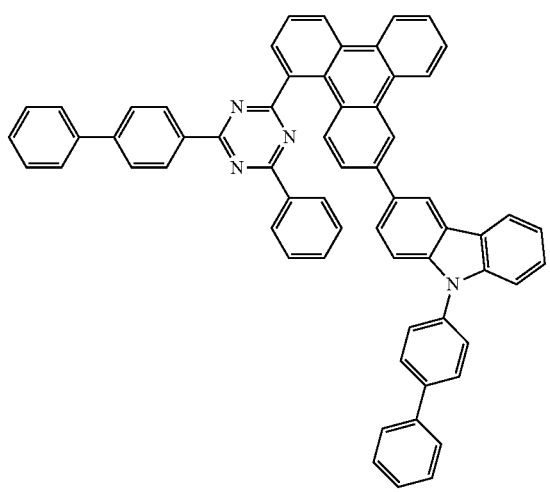
1-399
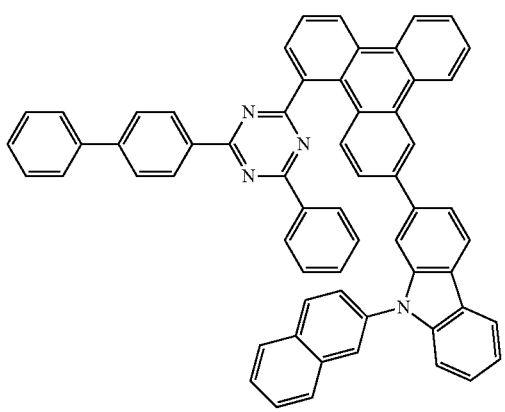
1-400
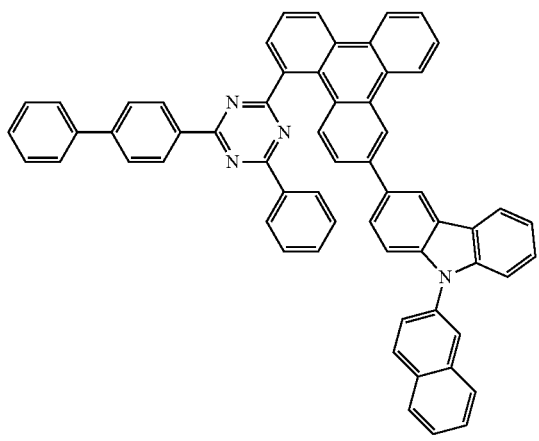
1-401
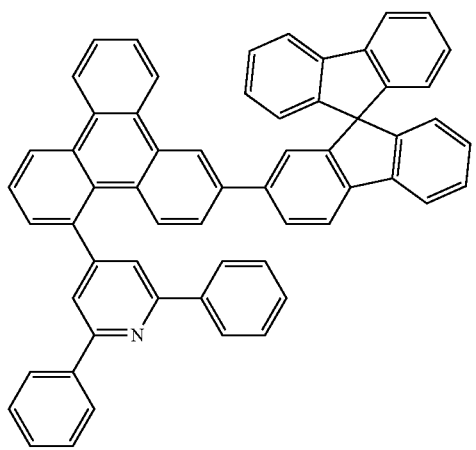

-continued
1-402
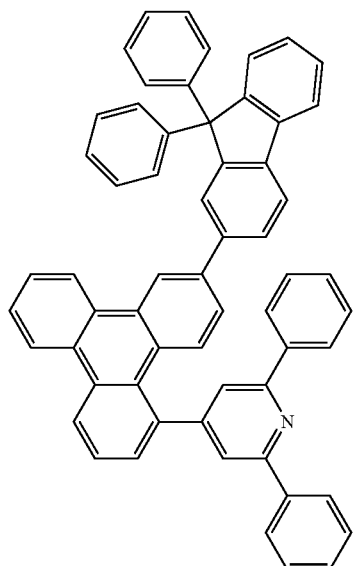
1-403
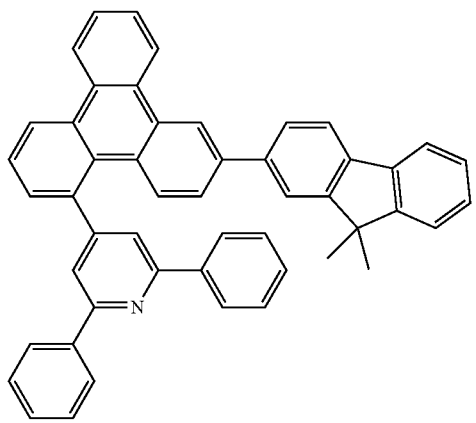
1-404
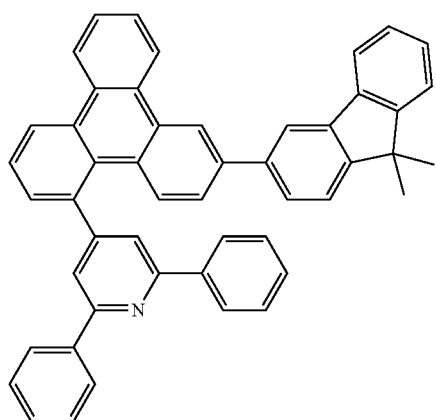
1-405
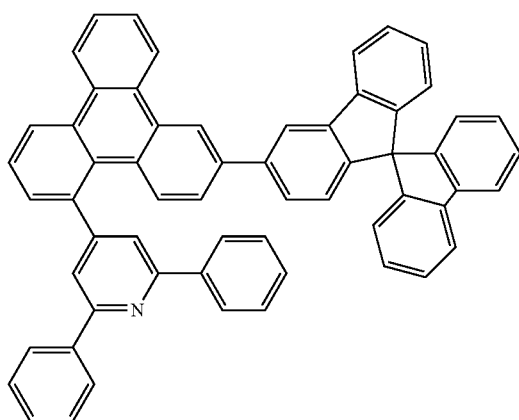
1-406
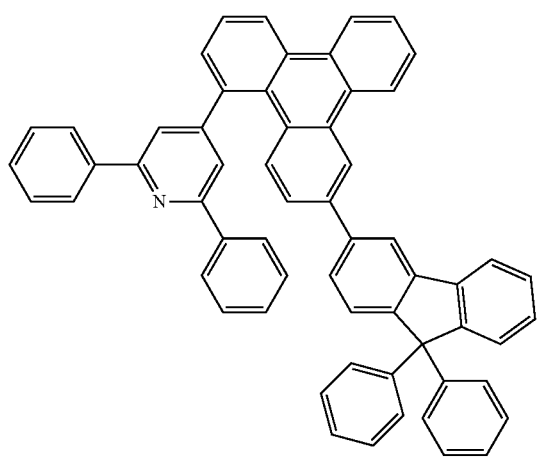
1-407
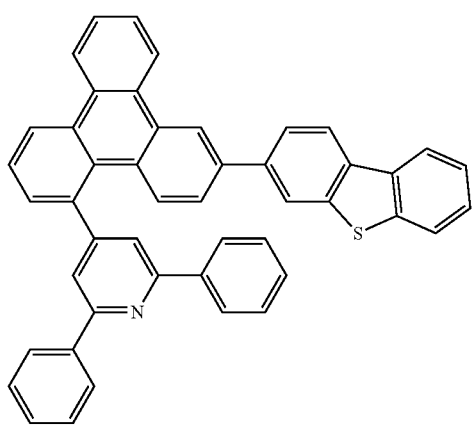

-continued
1-408
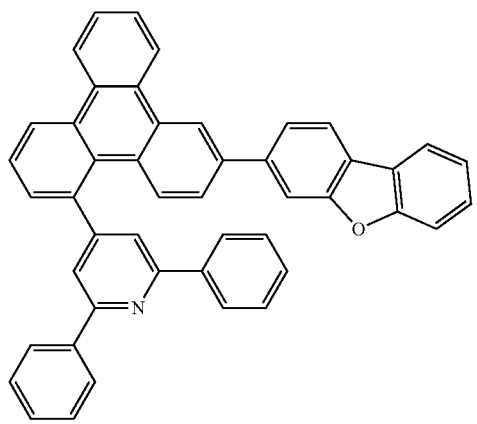
1-409
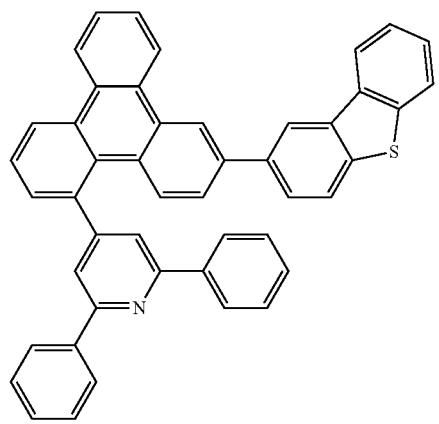
1-410
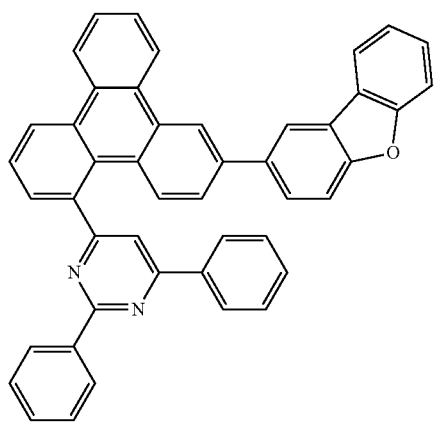
1-411
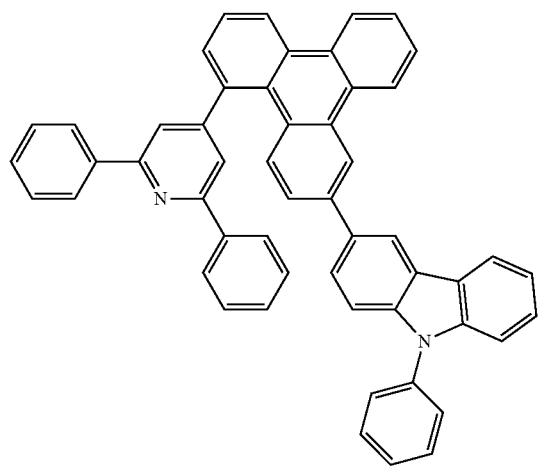
1-412
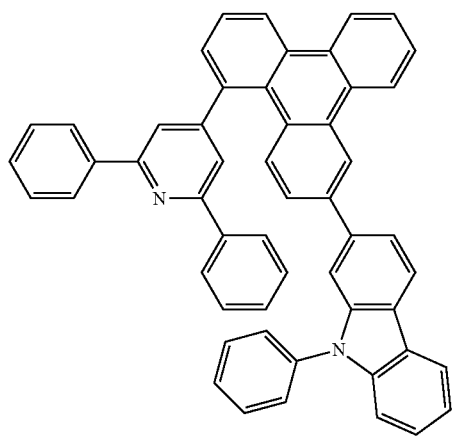
1-413
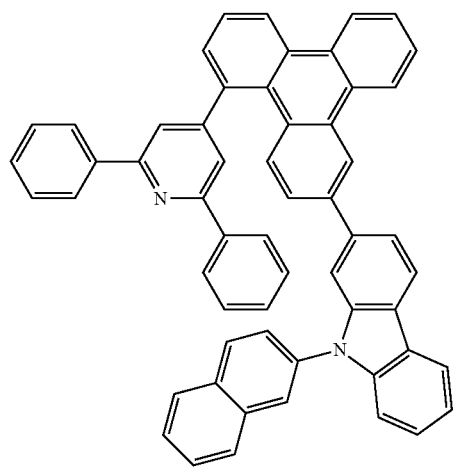

1-414
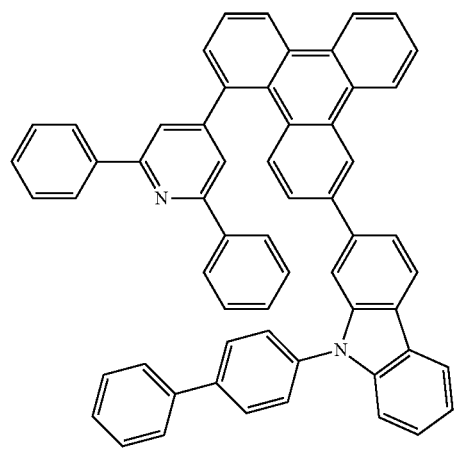
1-415
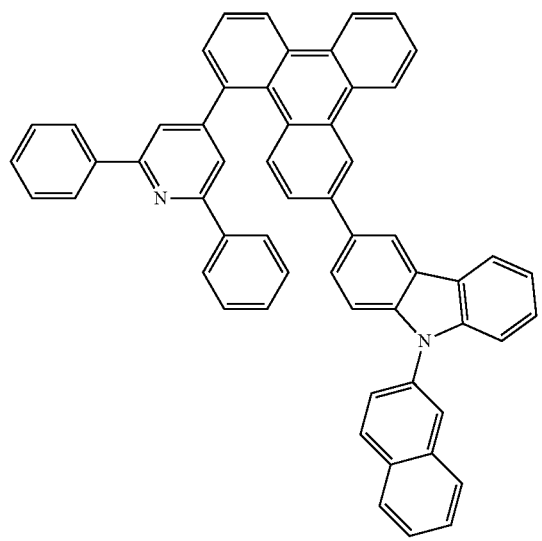
1-416
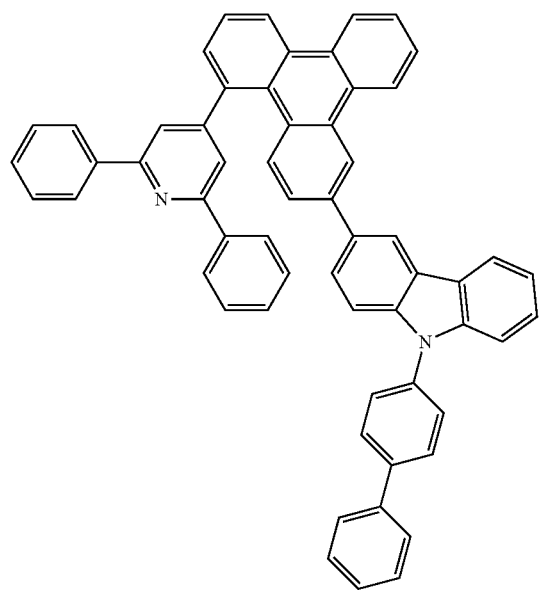
1-417
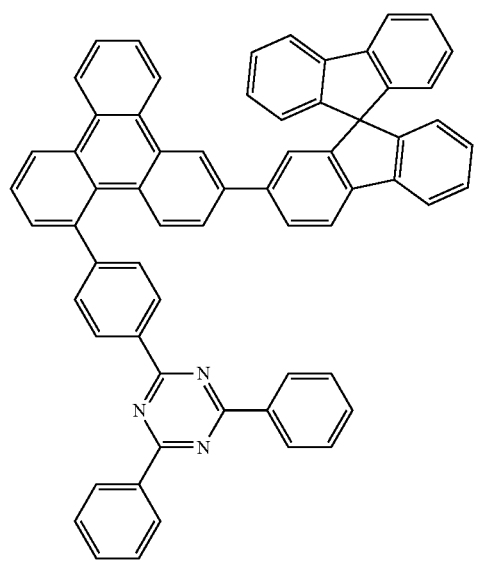

1-418
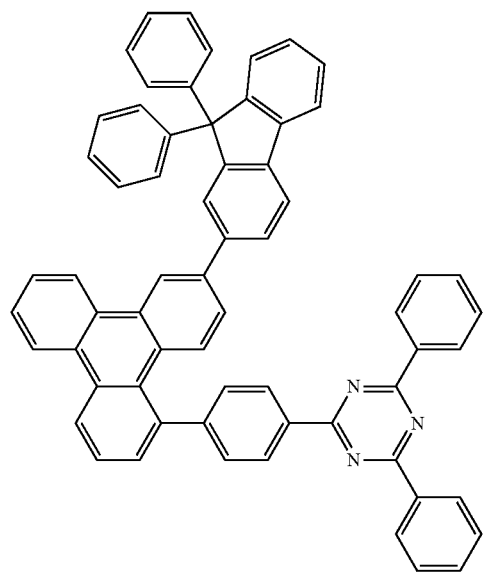
1-419
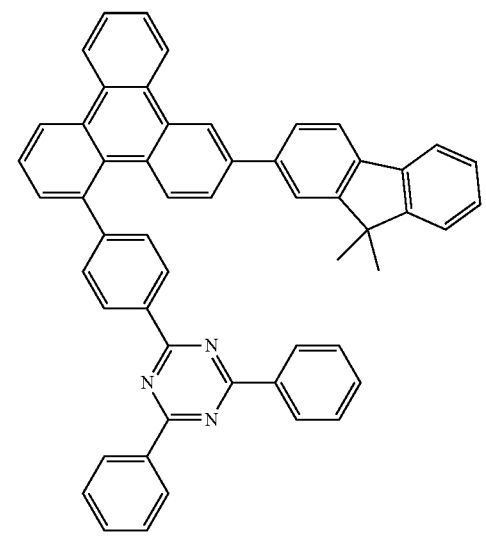
1-420
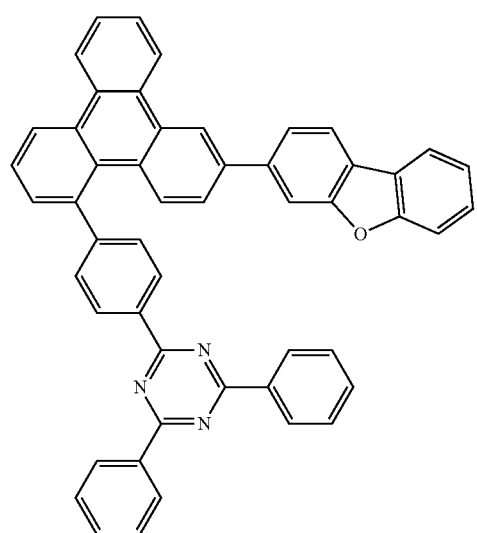
1-421
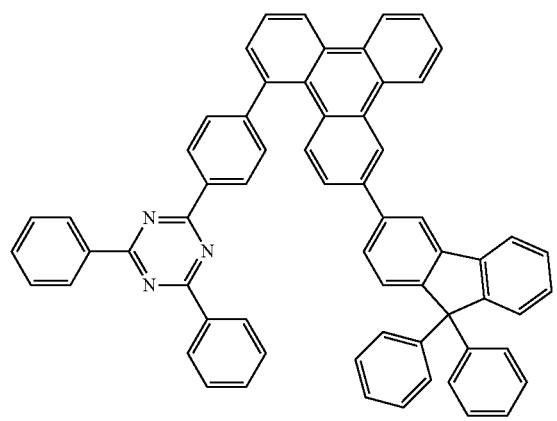
1-422
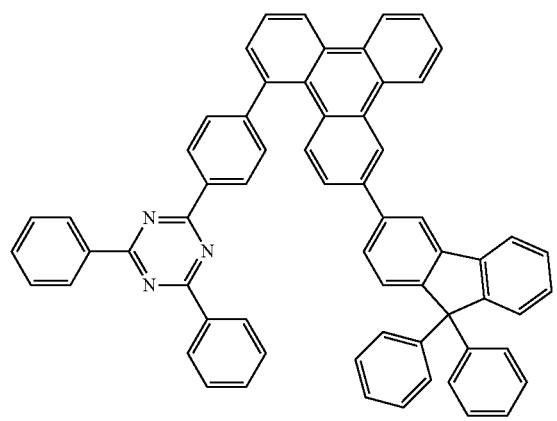
1-423
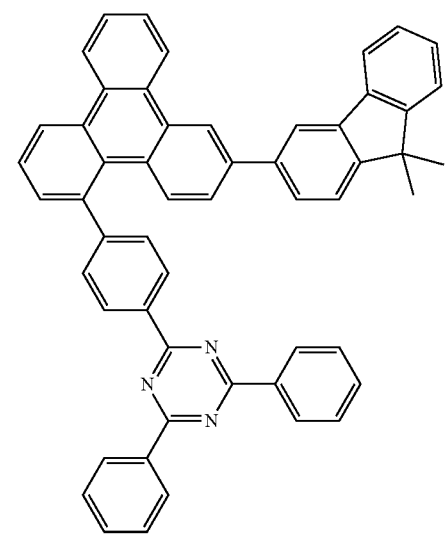

1-424
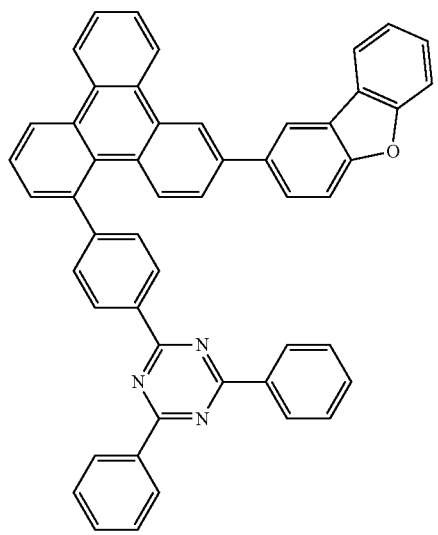
1-425
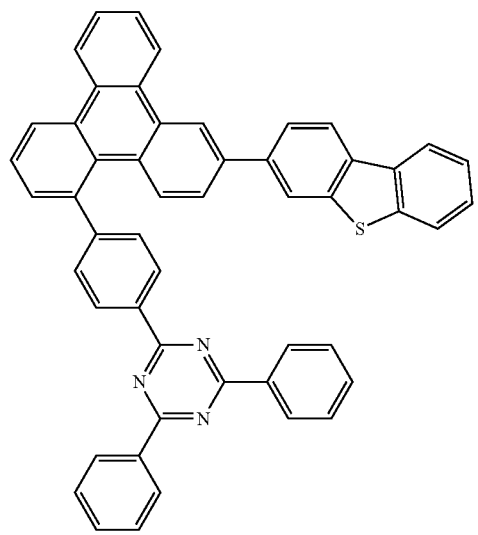
1-426
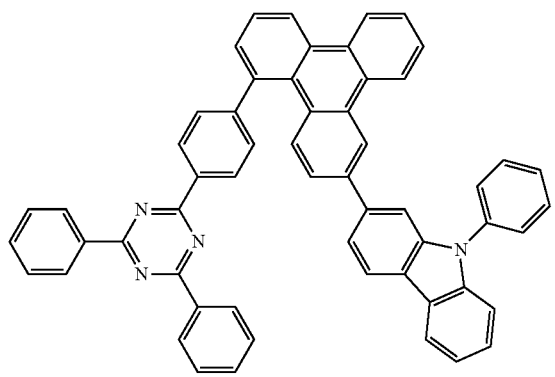
1-427
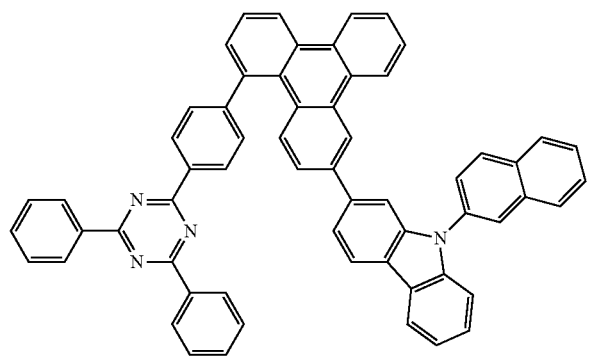
1-428
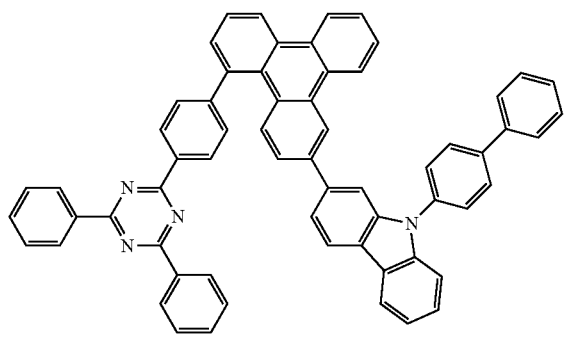
1-429
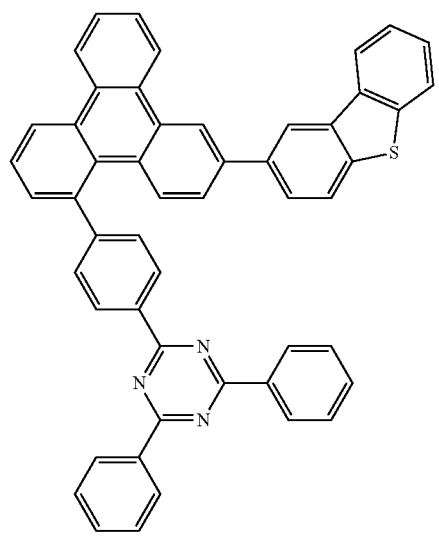

1-430
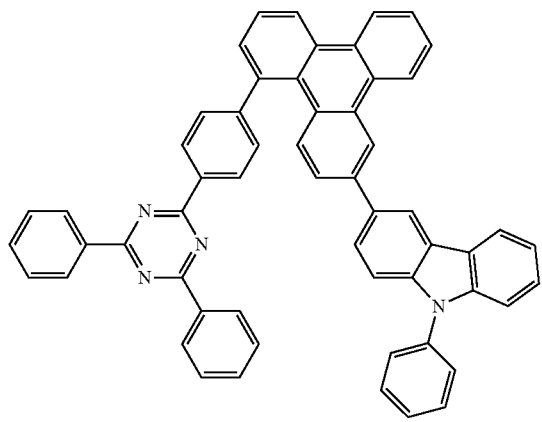
1-431
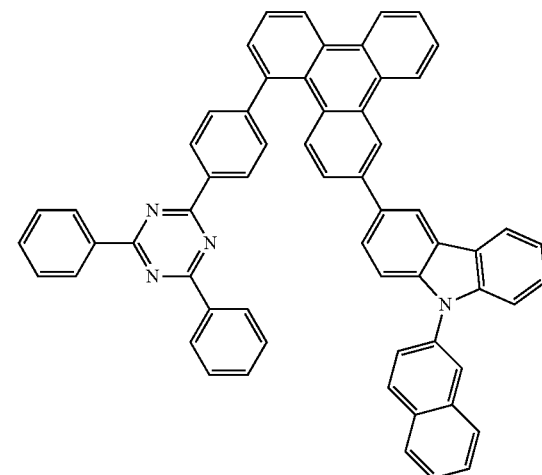
1-432
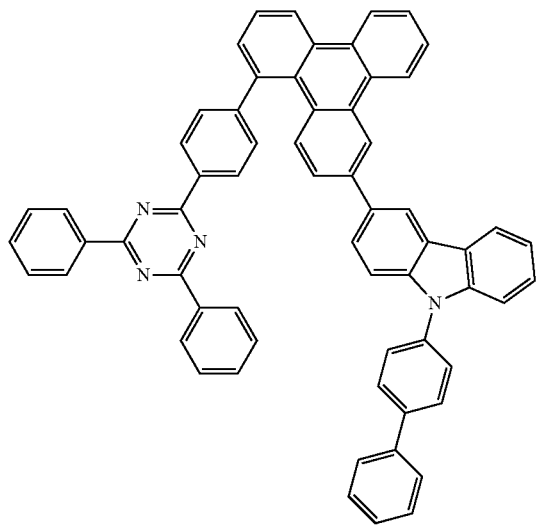
1-433
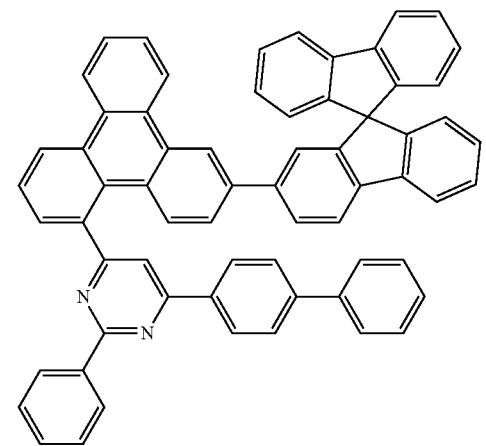
1-434
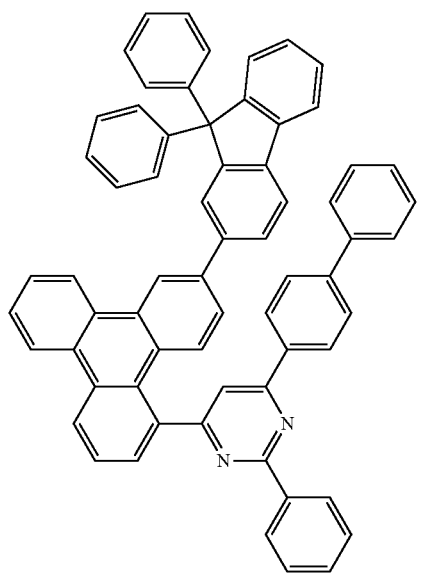
1-435
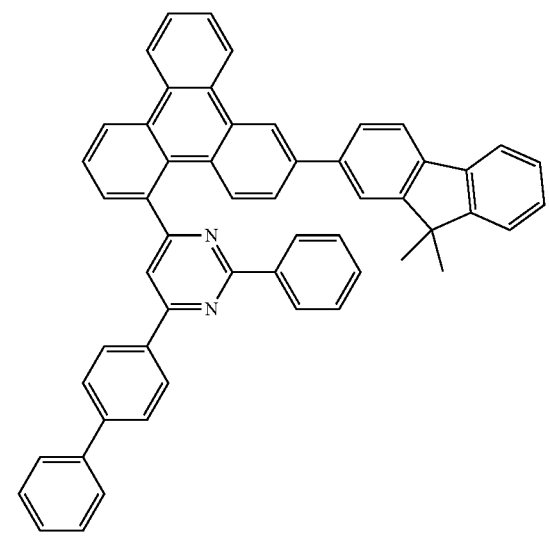

-continued
1-436
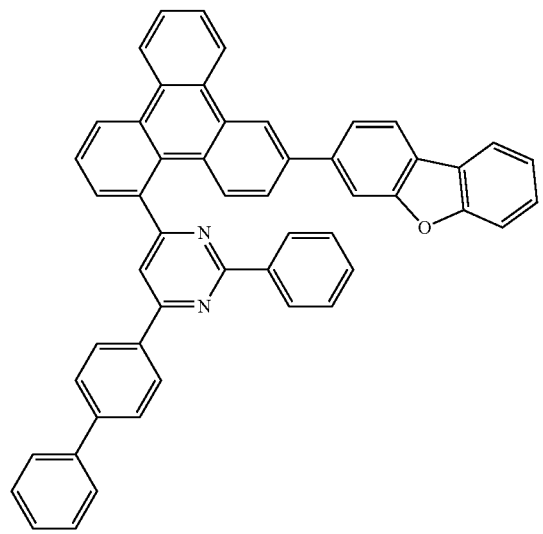
1-437
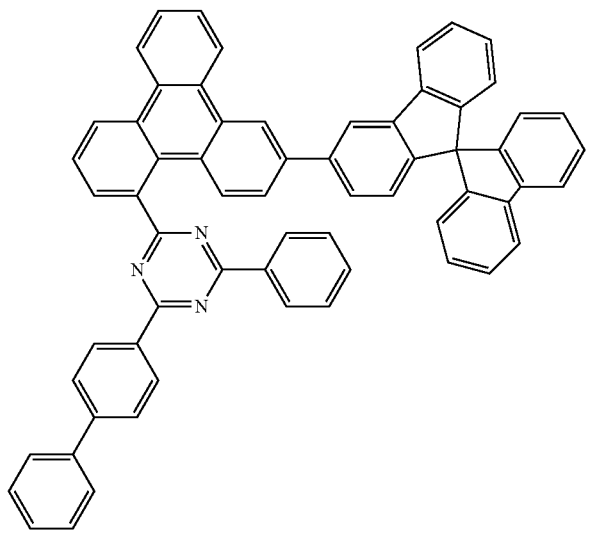
1-438
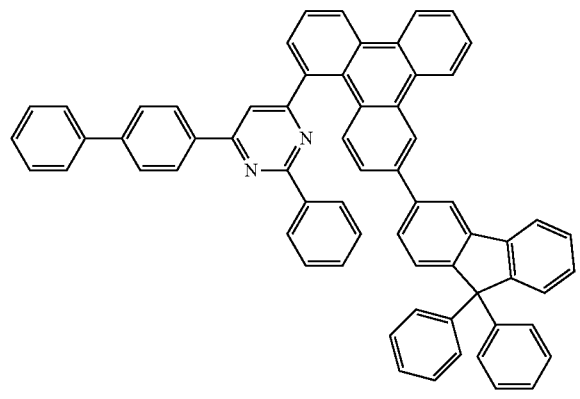
1-439
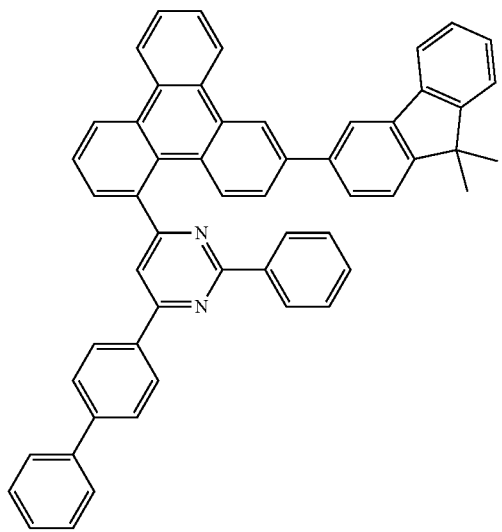
1-440
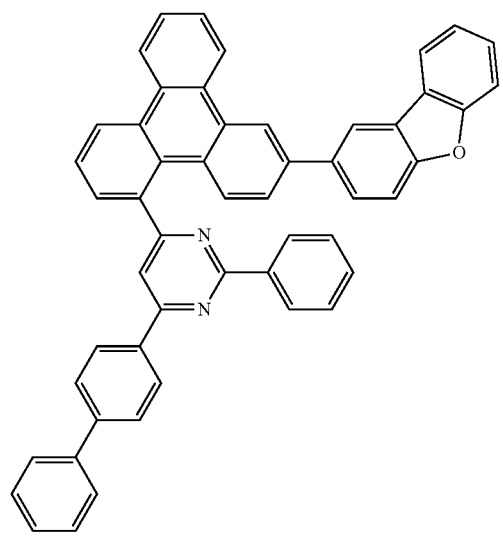
1-441
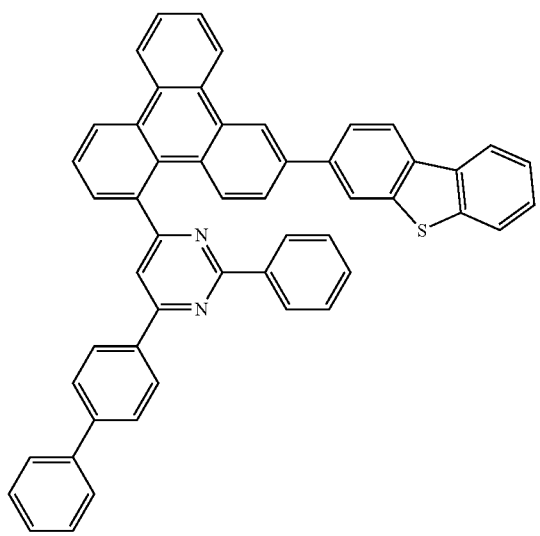

1-442
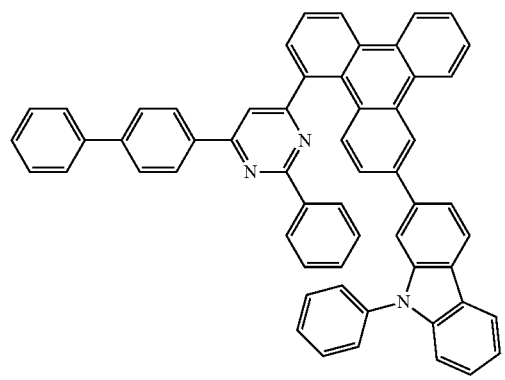
1-443
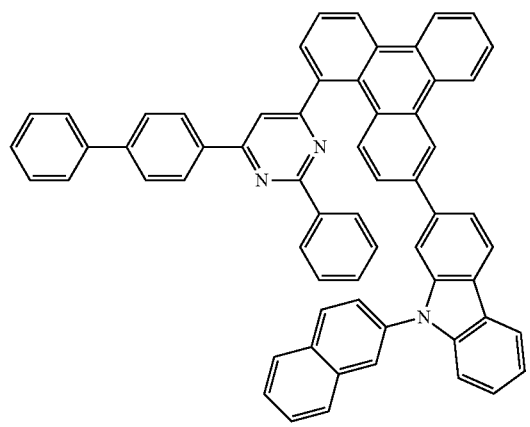
1-444
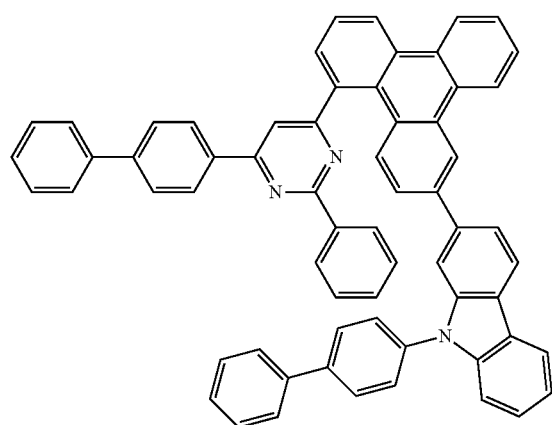
1-445
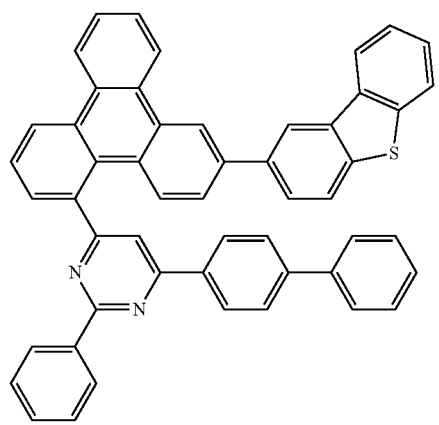
1-446
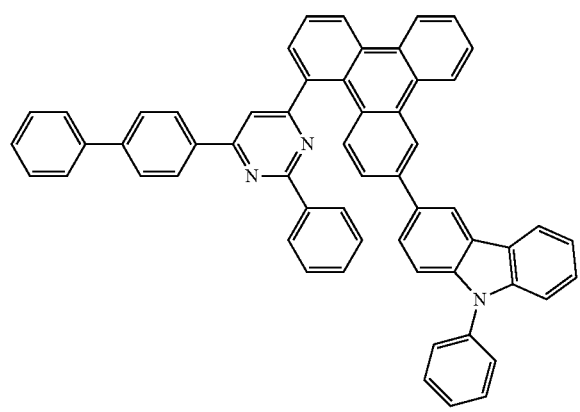
1-447
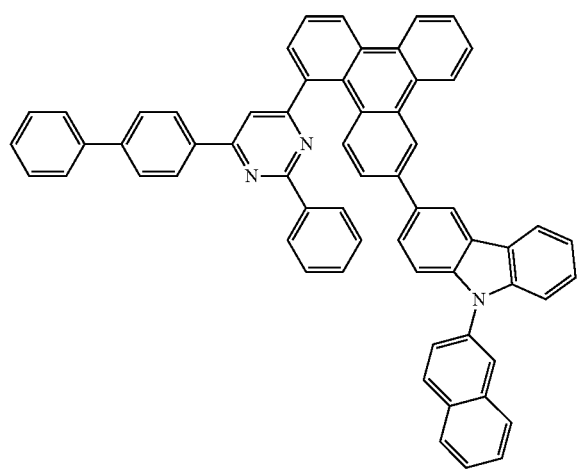

-continued
1-448
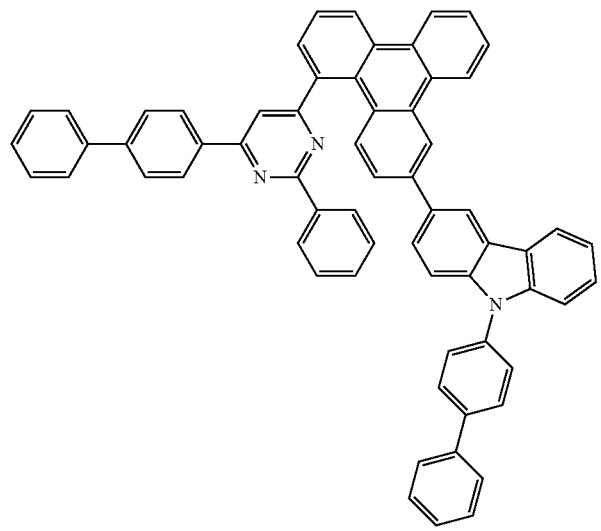
1-449
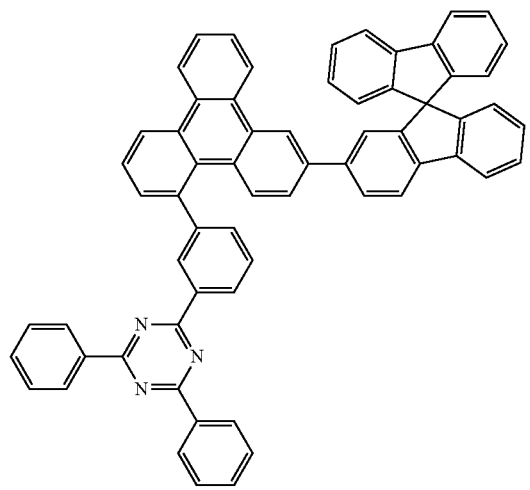
1-450
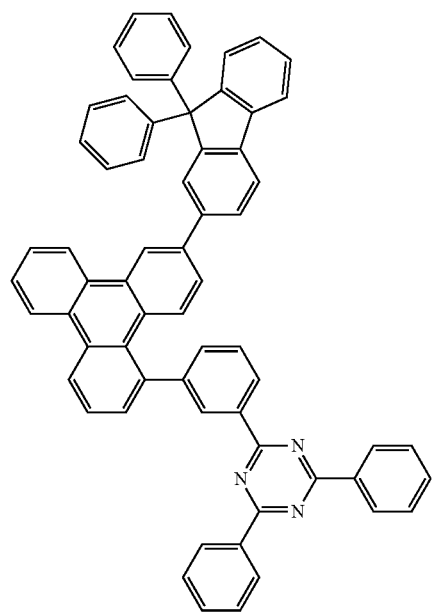
1-451
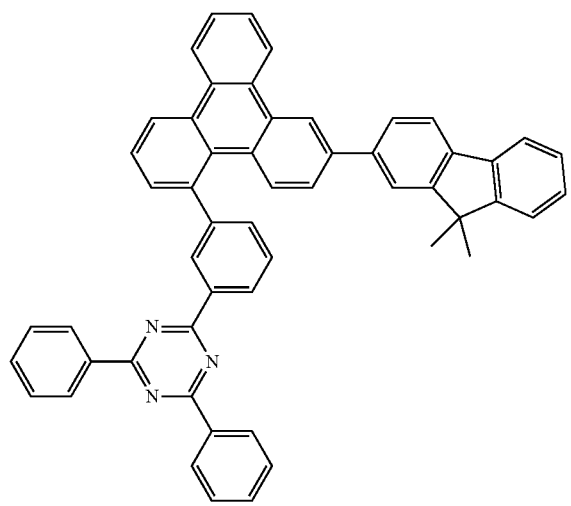

-continued
1-452
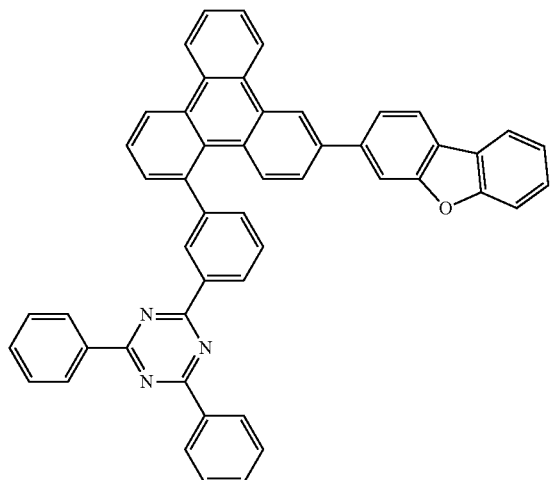
1-453
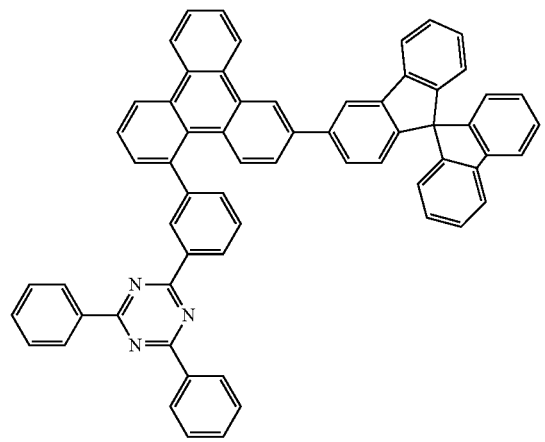
1-454
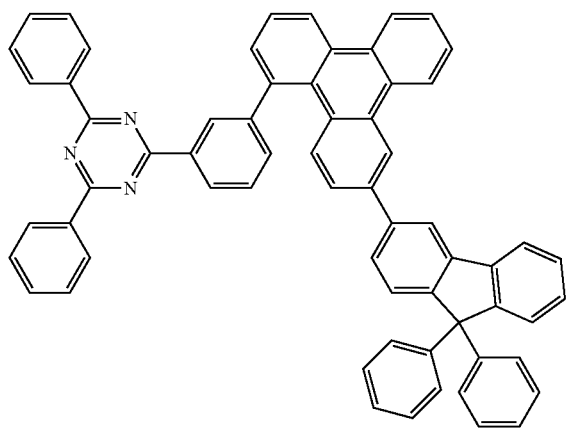
1-455
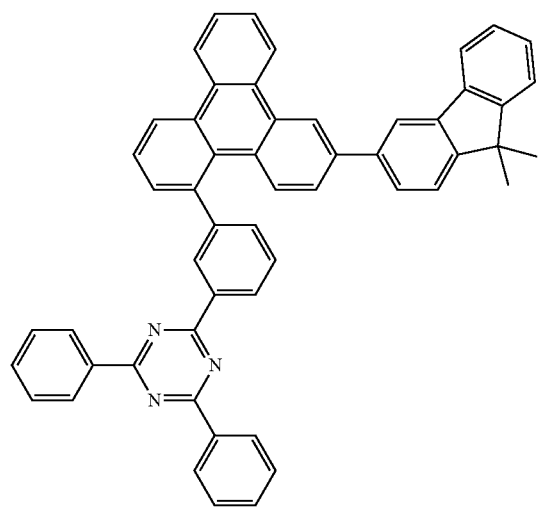
1-456
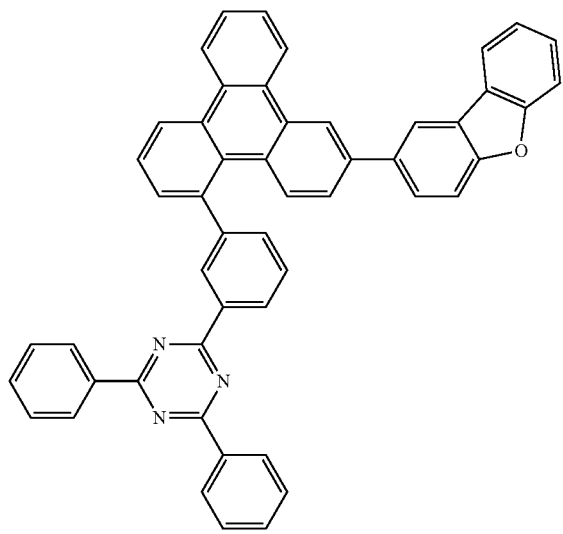
1-457
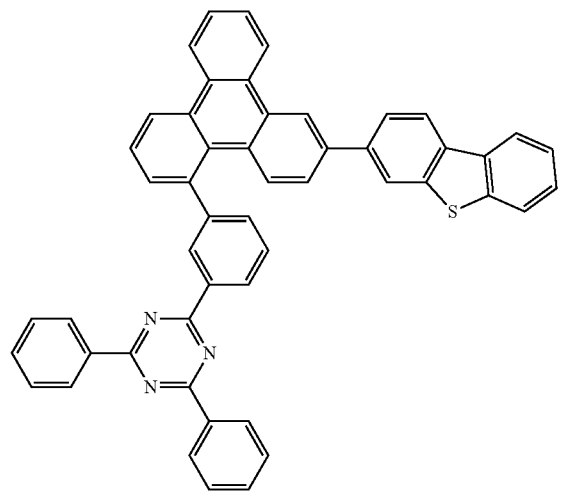

1-458
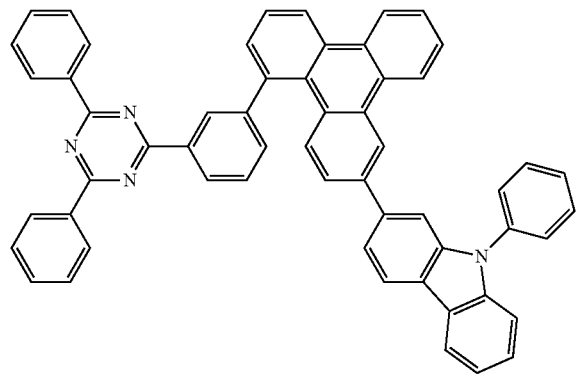
1-459
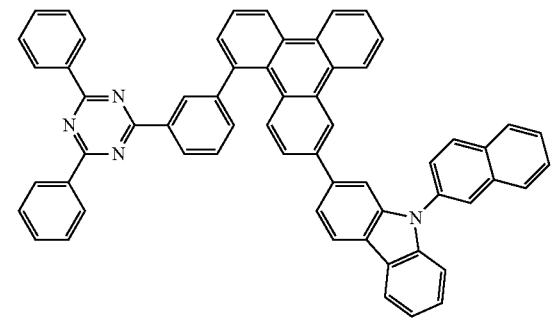
1-460
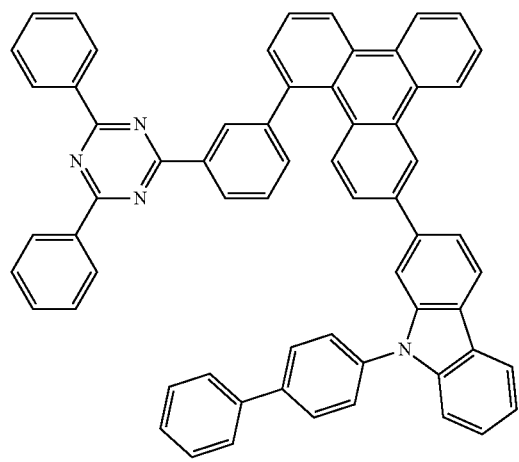
1-461
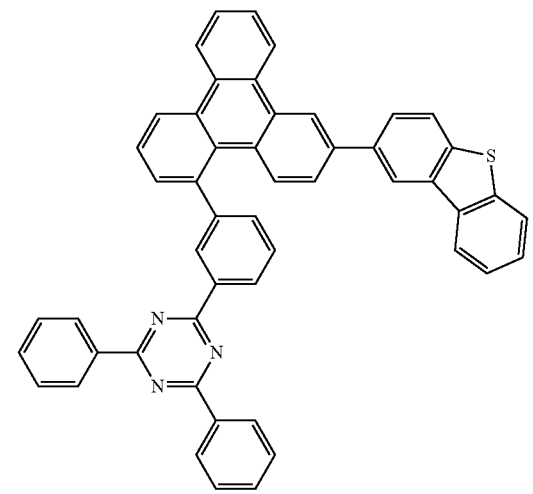
1-462
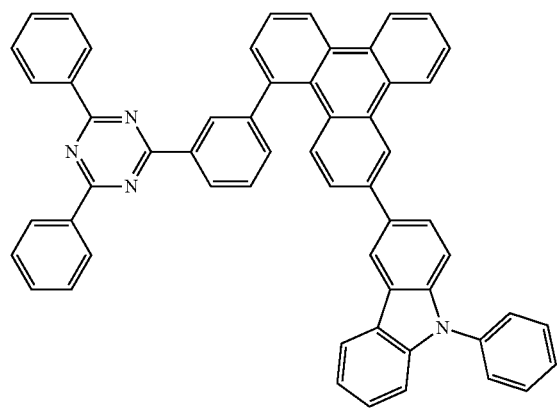
1-463
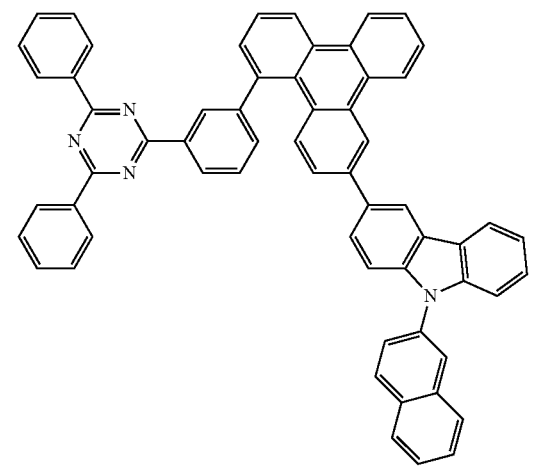

1-464
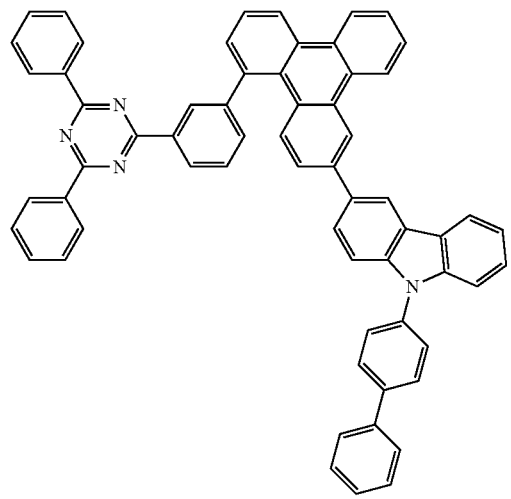
1-465
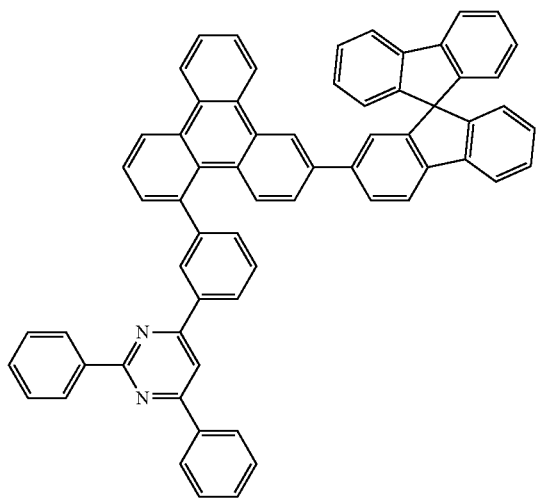
1-466
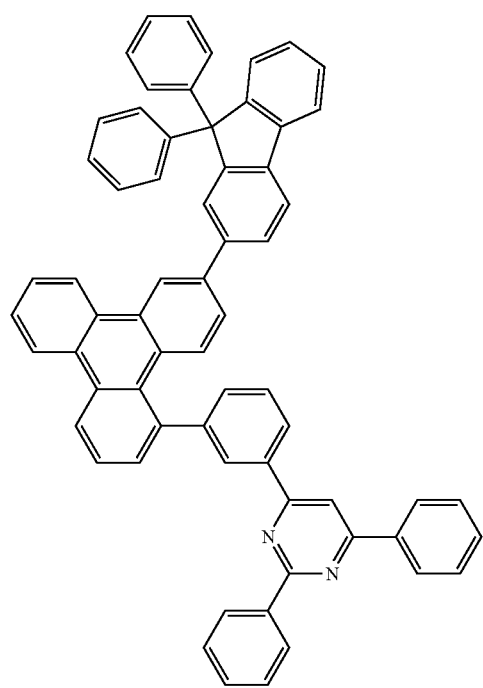
1-467
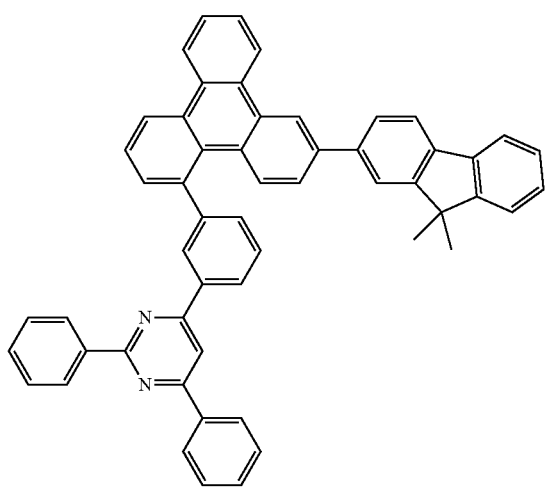

-continued
1-468
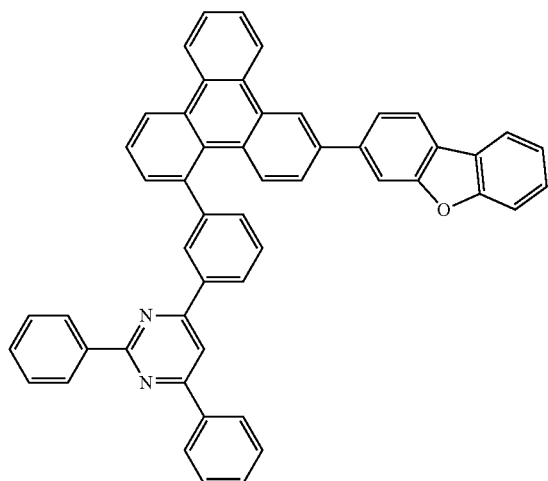
1-469
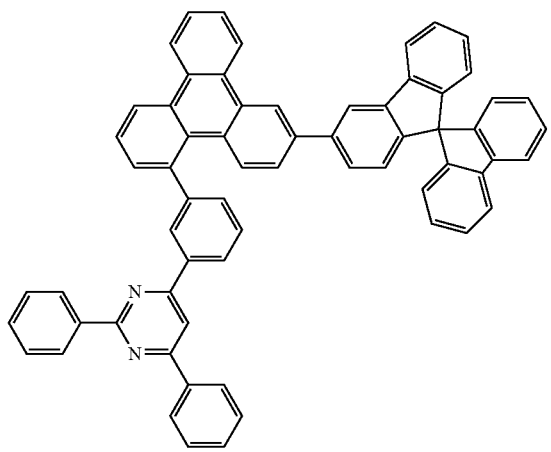
1-470
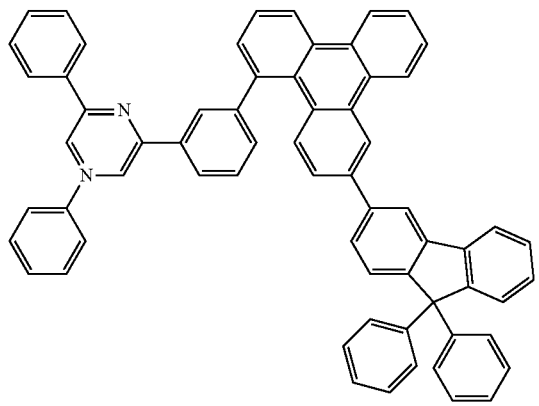
1-471
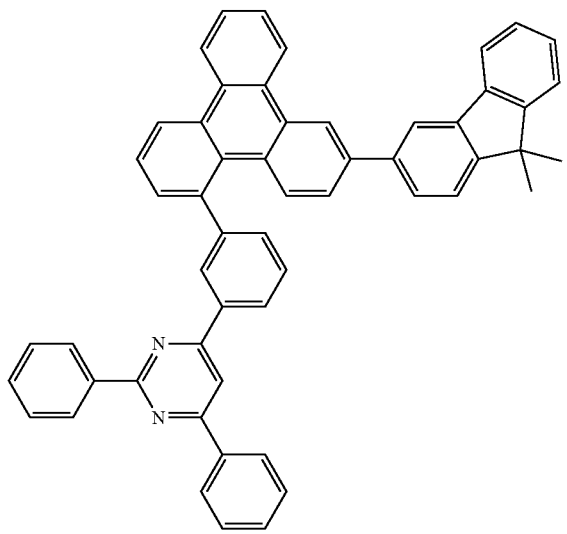
1-472
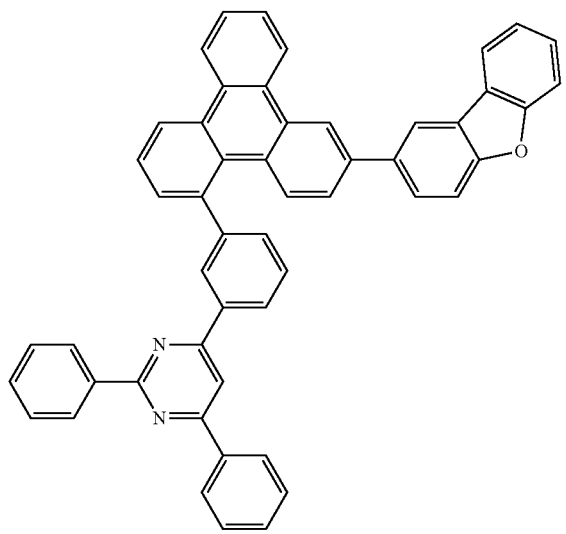
1-473
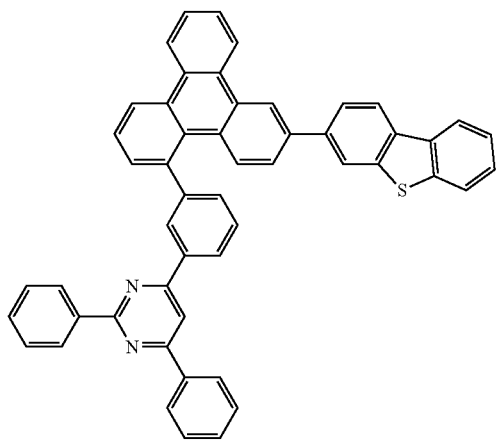

1-474
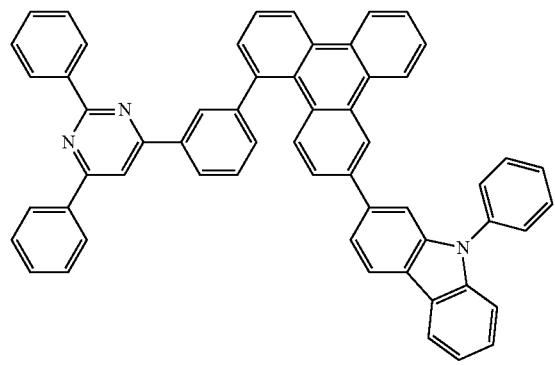
1-475
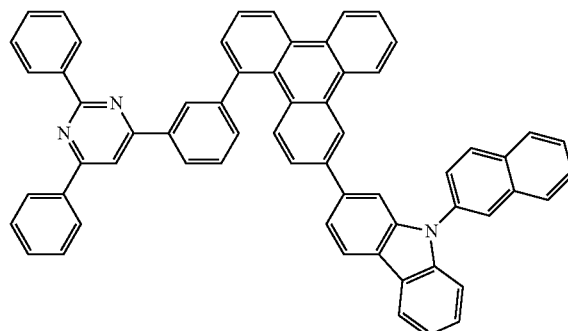
1-476
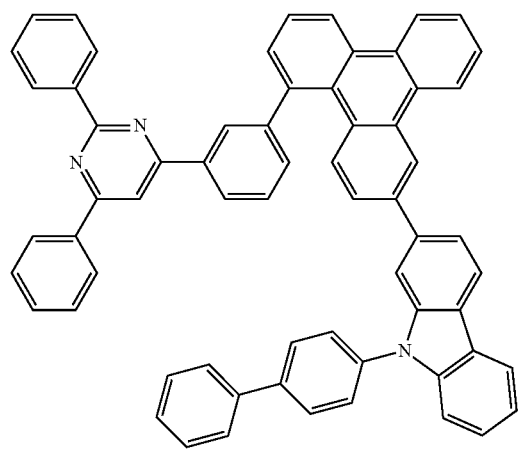
1-477
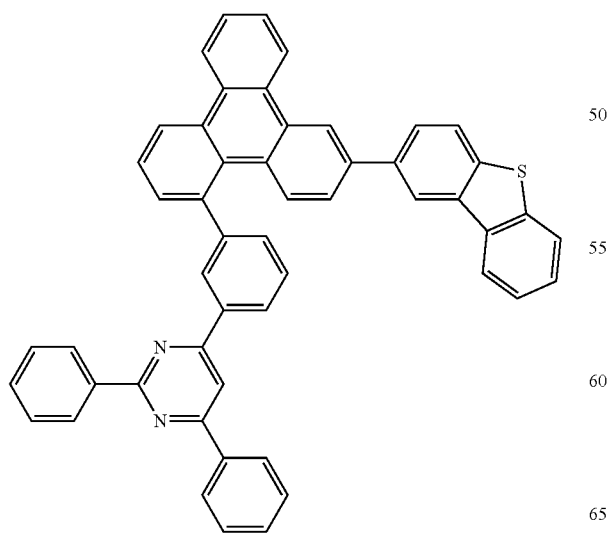

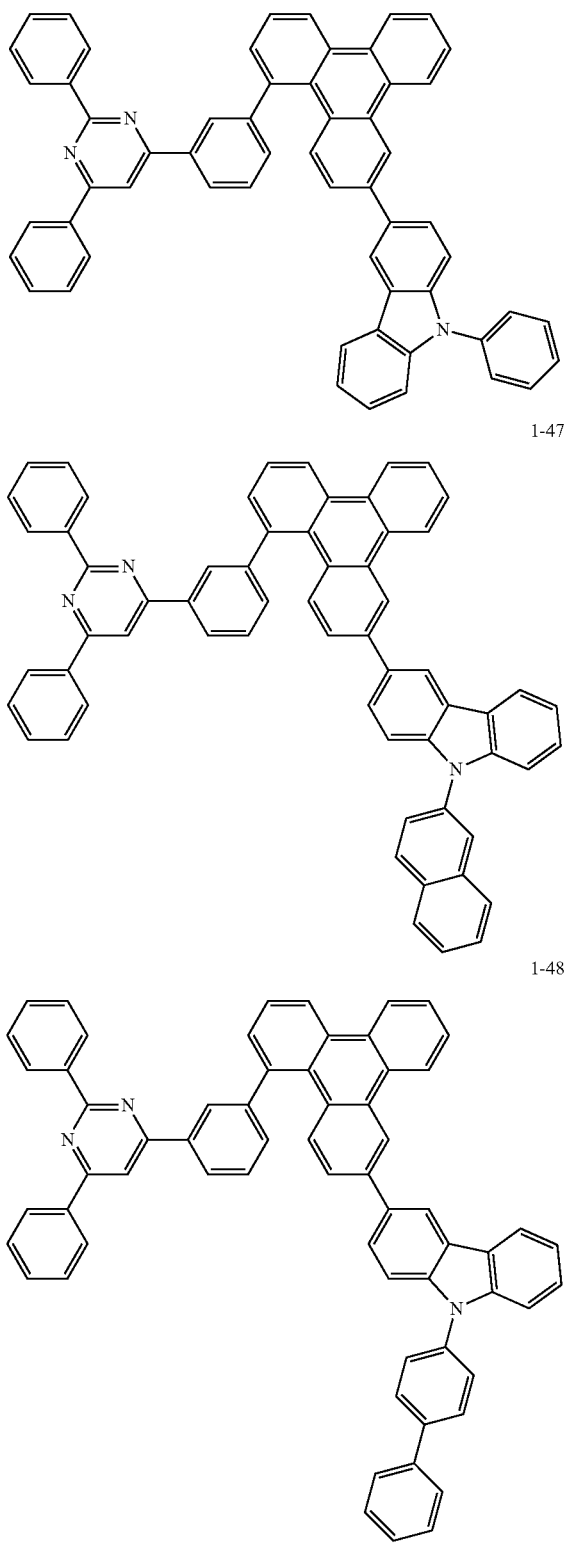

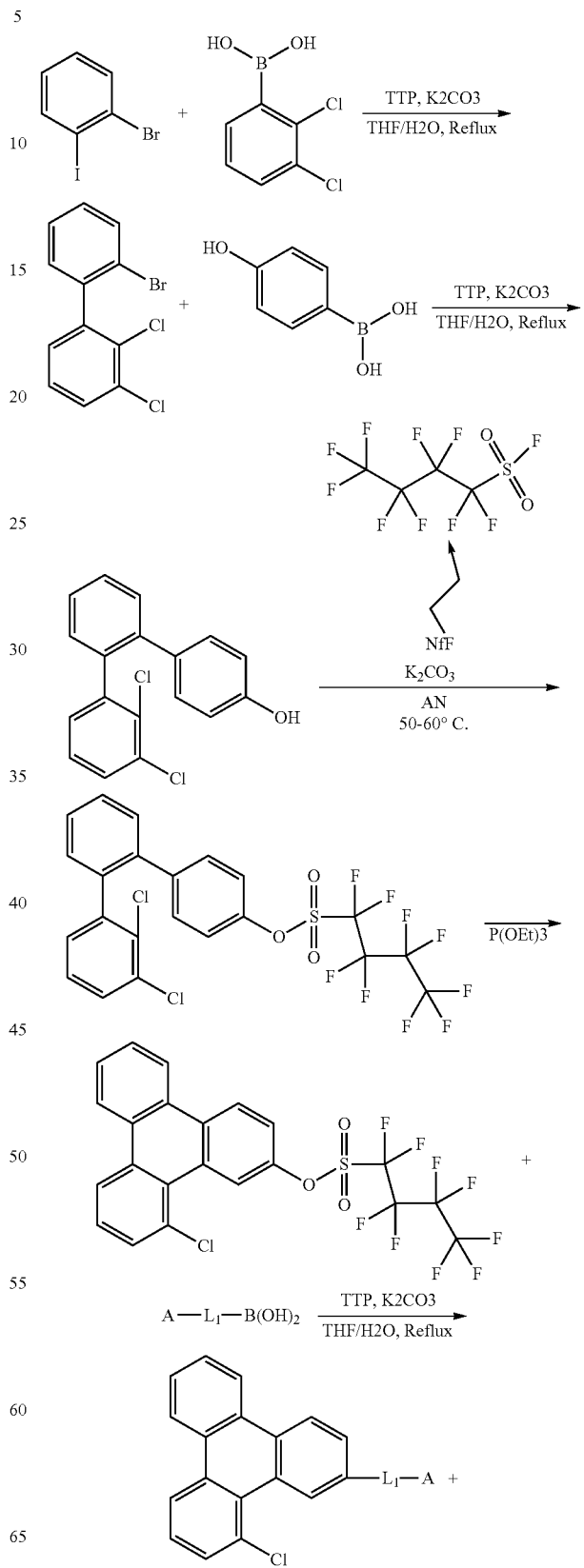

be determined by those skilled in the art from properly selecting known starting materials. As for reaction types and reaction conditions, those known in the art may be used.

According to one embodiment of the present specification, the compounds of Chemical Formulae 1 or 4 to 6 may be prepared according to the following reaction formulae, however, the method is not limited thereto. In the following reaction formulae, types and the number of substituents may

219
220
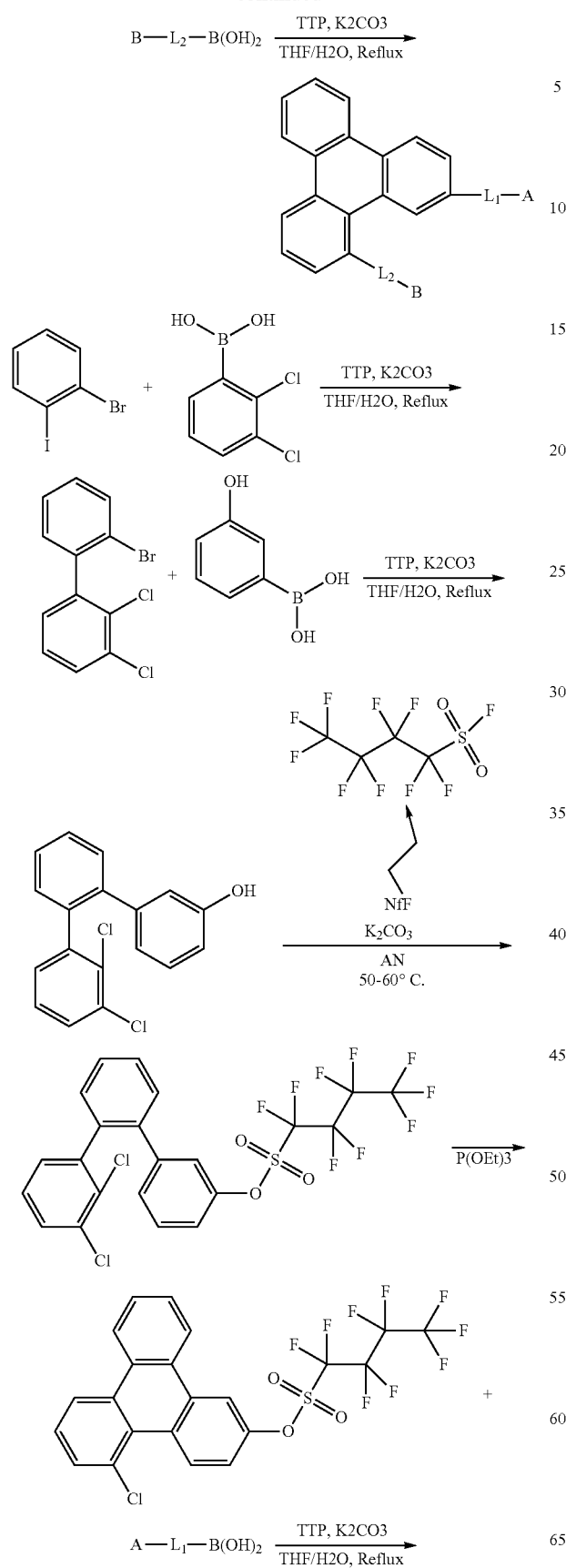
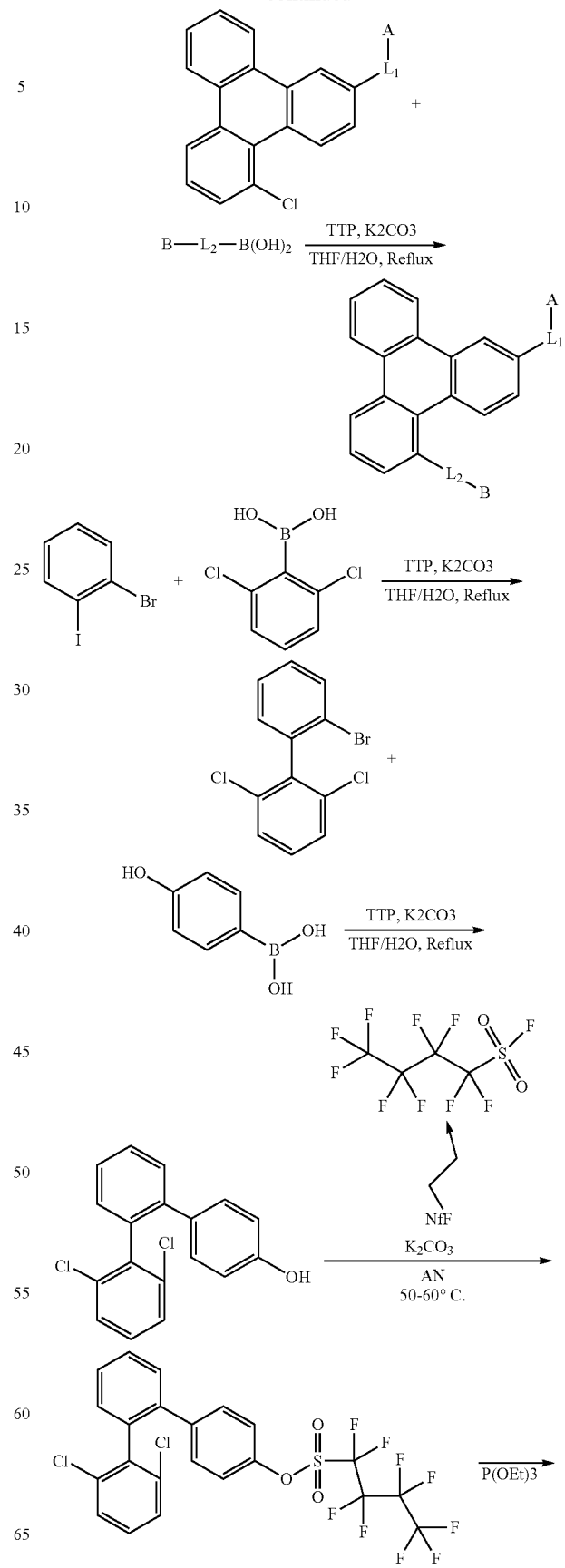

221
-continued

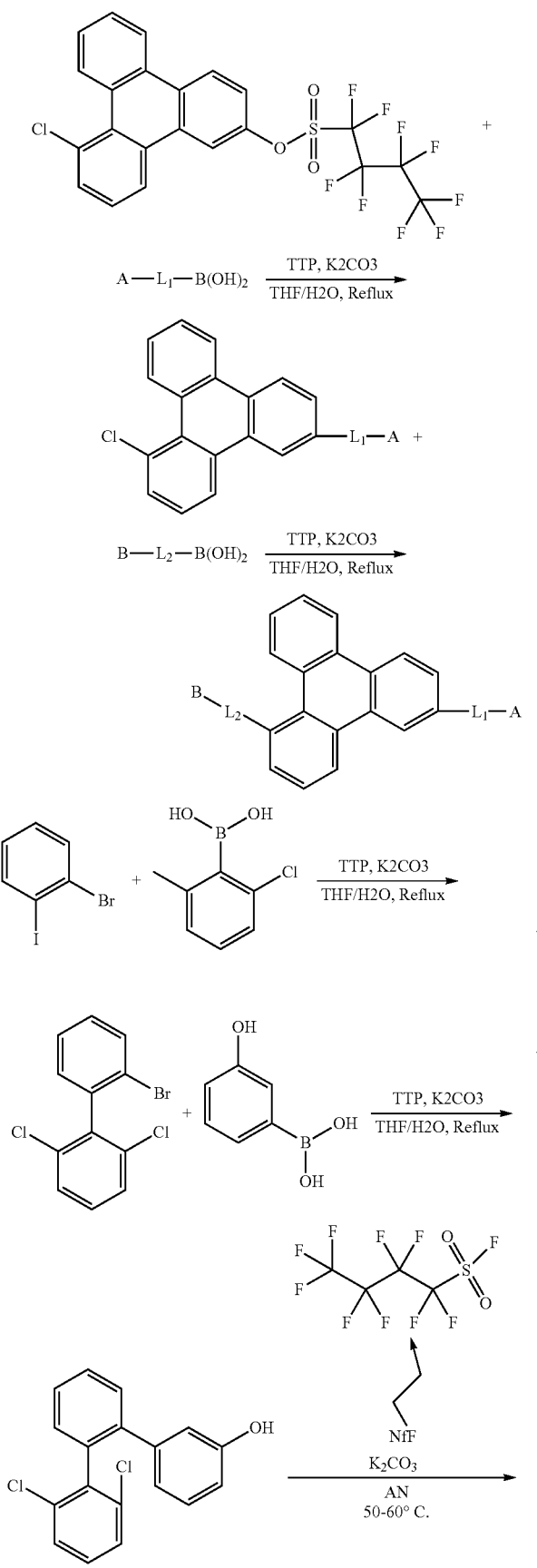

222
-continued

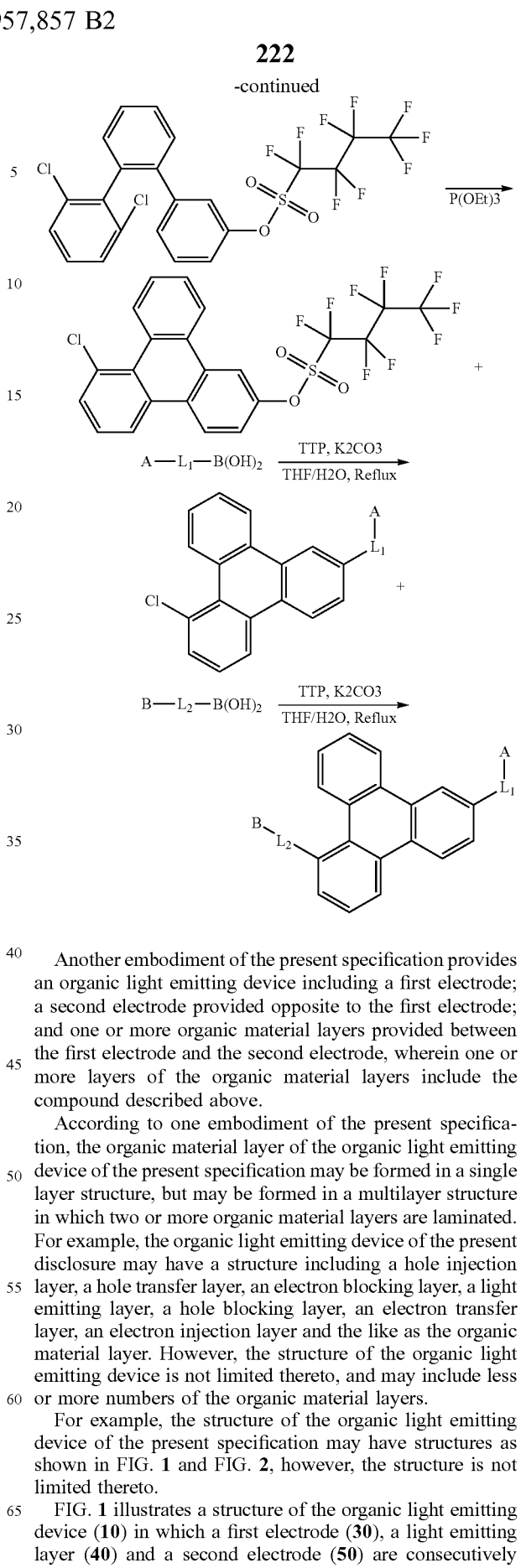

Another embodiment of the present specification provides an organic light emitting device including a first electrode; a second electrode provided opposite to the first electrode; and one or more organic material layers provided between the first electrode and the second electrode, wherein one or more layers of the organic material layers include the compound described above.

According to one embodiment of the present specification, the organic material layer of the organic light emitting device of the present specification may be formed in a single layer structure, but may be formed in a multilayer structure in which two or more organic material layers are laminated. For example, the organic light emitting device of the present disclosure may have a structure including a hole injection layer, a hole transfer layer, an electron blocking layer, a light emitting layer, a hole blocking layer, an electron transfer layer, an electron injection layer and the like as the organic material layer. However, the structure of the organic light emitting device is not limited thereto, and may include less or more numbers of the organic material layers.

For example, the structure of the organic light emitting device of the present specification may have structures as shown in FIG. 1 and FIG. 2, however, the structure is not limited thereto.

FIG. 1 illustrates a structure of the organic light emitting device (10) in which a first electrode (30), a light emitting layer (40) and a second electrode (50) are consecutively laminated on a substrate (20). FIG. 1 is an illustrative structure of the organic light emitting device according to one embodiment of the present specification, and other organic material layers may be further included.

FIG. 2 illustrates a structure of the organic light emitting device in which a first electrode (30), a hole injection layer (60), a hole transfer layer (70), a light emitting layer (40), an electron transfer layer (80), an electron injection layer (90) and a second electrode (50) are consecutively laminated on a substrate (20). FIG. 2 is an illustrative structure of the organic light emitting device according to one embodiment of the present specification, and other organic material layers may be further included.

According to one embodiment of the present specification, the organic material layer includes a hole injection layer, a hole transfer layer or an electron blocking layer, and the hole injection layer, the hole transfer layer or the electron blocking layer includes the compound according to one embodiment of the present specification.

According to one embodiment of the present specification, the organic material layer includes a light emitting layer, and the light emitting layer includes the compound according to one embodiment of the present specification.

According to one embodiment of the present specification, the organic material layer includes a light emitting layer, and the light emitting layer includes the compound according to one embodiment of the present specification as a host of the light emitting layer.

According to one embodiment of the present specification, the organic material layer includes a hole blocking layer, an electron transfer layer or an electron injection layer, and the hole blocking layer, the electron transfer layer or the electron injection layer includes the compound according to one embodiment of the present specification.

According to one embodiment of the present specification, the organic material layer may further include one or more layers selected from the group consisting of a hole injection layer, a hole transfer layer, a light emitting layer, an electron transfer layer and an electron injection layer.

The organic light emitting device of the present specification may be manufactured using materials and methods known in the art, except that one or more layers of the organic material layers include the compound of the present specification, that is, the compound according to one embodiment of the present specification.

When the organic light emitting device includes a plurality of organic material layers, the organic material layers may be formed with materials the same as or different from each other.

For example, the organic light emitting device of the present specification may be manufactured by consecutively laminating a first electrode, an organic material layer and a second electrode on a substrate. Herein, the organic light emitting device may be manufactured by forming a first electrode on a substrate by depositing a metal, a metal oxide having conductivity, or an alloy thereof using a physical vapor deposition (PVD) method such as sputtering or e-beam evaporation, and forming an organic material layer including a hole injection layer, a hole transfer layer, a light emitting layer and an electron transfer layer thereon, and then depositing a material capable of being used as a second electrode thereon. In addition to such a method, the organic light emitting device may also be manufactured by consecutively depositing a second electrode material, an organic material layer and a first electrode material on a substrate. In addition, the compound according to one embodiment of the present specification may be formed into an organic material layer using a solution coating method as well as a vacuum deposition method when manufacturing the organic light emitting device. Herein, the solution coating method means spin coating, dip coating, doctor blading, inkjet printing, screen printing, a spray method, roll coating and the like, but is not limited thereto.

According to one embodiment of the present specification, the first electrode is an anode, and the second electrode is a cathode.

According to another embodiment of the present specification, the first electrode is a cathode, and the second electrode is an anode.

As the anode material, materials having large work function are normally preferred so that hole injection to an organic material layer is smooth. Specific examples of the anode material capable of being used in the present disclosure include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylthiophene), poly[3,4-(ethylene-1,2-dioxy)thiophene] (PEDOT), polypyrrole and polyaniline, but are not limited thereto.

As the cathode material, materials having small work function are normally preferred so that electron injection to an organic material layer is smooth. Specific examples of the cathode material include metals such as magnesium, calcium, sodium, potassium, titanium, indium, yttrium, lithium, gadolinium, aluminum, silver, tin and lead, or alloys thereof; multilayer structure materials such as LiF/Al, $LiO_2$/Al or Mg/Ag, and the like, but are not limited thereto.

The hole injection layer is a layer that injects holes from an electrode, and the hole injection material is preferably a compound that has an ability to transfer holes, therefore, has a hole injection effect in an anode, has an excellent hole injection effect for a light emitting layer or a light emitting material, prevents excitons generated in the light emitting layer from moving to an electron injection layer or an electron injection material, and in addition, has an excellent thin film forming ability. The highest occupied molecular orbital (HOMO) of the hole injection material is preferably in between the work function of an anode material and the HOMO of surrounding organic material layers. Specific examples of the hole injection material include metal porphyrins, oligothiophene, arylamine-based organic materials, hexanitrile hexaazatriphenylene-based organic materials, quinacridone-based organic materials, perylene-based organic materials, anthraquinone, and polyaniline- and polythiophene-based conductive polymers, and the like, but are not limited thereto.

The hole transfer layer is a layer that receives holes from a hole injection layer and transfers the holes to a light emitting layer, and as the hole transfer material, materials capable of receiving holes from an anode or a hole injection layer, moving the holes to a light emitting layer, and having high mobility for the holes are suitable. Specific examples thereof include arylamine-based organic materials, conductive polymers, block copolymers having conjugated parts and non-conjugated parts together, and the like, but are not limited thereto.

The light emitting material of the light emitting layer is a material capable of emitting light in a visible light region by receiving holes and electrons from a hole transfer layer and an electron transfer layer, respectively, and binding the holes and the electrons, and is preferably a material having favorable quantum efficiency for fluorescence or phosphorescence. Specific examples thereof include 8-hydroxyquinoline aluminum complexes (Alq₃); carbazole-based compounds; dimerized styryl compounds; BAlq; 10-hydroxybenzo quinoline-metal compounds; benzoxazole-, benzthiazole- and benzimidazole-based compounds; poly(p-phenylenevinylene) (PPV)-based polymers; spiro compounds; polyfluorene, rubrene, and the like, but are not limited thereto.

The light emitting layer may include a host material and a dopant material. The host material includes fused aromatic ring derivatives, heteroring-containing compounds or the like. Specifically, the fused aromatic ring derivative includes anthracene derivatives, pyrene derivatives, naphthalene derivatives, pentacene derivatives, phenanthrene compounds, fluoranthene compounds and the like, and the heteroring-containing compound includes carbazole derivatives, dibenzofuran derivatives, ladder-type furan compounds, pyrimidine derivatives and the like, but the material is not limited thereto.

The dopant material includes aromatic amine derivatives, styrylamine compounds, boron complexes, fluoranthene compounds, metal complexes and the like. Specifically, the aromatic amine derivative is a fused aromatic ring derivative having a substituted or unsubstituted arylamine group and includes arylamine group-including pyrene, anthracene, chrysene, peryflanthene and the like, and the styrylamine compound is a compound in which substituted or unsubstituted arylamine is substituted with at least one arylvinyl group, and one, two or more substituents selected from the group consisting of an aryl group, a silyl group, an alkyl group, a cycloalkyl group and an arylamino group are substituted or unsubstituted. Specifically, styrylamine, styryldiamine, styryltriamine, styryltetramine or the like is included, but the styrylamine compound is not limited thereto. In addition, the metal complex includes iridium complexes, platinum complexes or the like, but is not limited thereto.

The electron transfer layer is a layer that receives electrons from an electron injection layer and transfers the electrons to a light emitting layer, and as the electron transfer material, materials capable of favorably receiving electrons from a cathode, moving the electrons to a light emitting layer, and having high mobility for the electrons are suitable. Specific examples thereof include Al complexes of 8-hydroxyquinoline; complexes including Alq₃; organic radical compounds; hydroxyflavon-metal complexes, and the like, but are not limited thereto. The electron transfer layer may be used together with any desired cathode material as used in the art. Particularly, examples of the suitable cathode material include common materials that have small work function, and in which an aluminum layer or a silver layer follows. Specifically, the cathode material includes cesium, barium, calcium, ytterbium and samarium, and in each case, an aluminum layer or a silver layer follows.

The electron injection layer is a layer that injects electrons from an electrode, and the electron injection material is preferably a compound that has an ability to transfer electrons, has an electron injection effect from a cathode, has an excellent electron injection effect for a light emitting layer or a light emitting material, prevents excitons generated in the light emitting layer from moving to a hole injection layer, and in addition, has an excellent thin film forming ability. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone or the like, and derivatives thereof, metal complex compounds, nitrogen-containing 5-membered ring derivatives, and the like, but are not limited thereto.

The metal complex compound includes 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato) gallium, bis(10-hydroxybenzo[h]quinolinato)berylium, bis (10-hydroxybenzo[h]quinolinato)zinc, bis(2-methyl-8-quinolinato)chlorogallium, bis(2-methyl-8-quinolinato) (o-cresolato)gallium, bis(2-methyl-8-quinolinato) (1-naphtholato)aluminum, bis(2-methyl-8-quinolinato) (2-naphtholato)gallium and the like, but is not limited thereto.

The organic light emitting device according to the present specification may be a top-emission type, a bottom-emission type or a dual-emission type depending on the materials used.

Hereinafter, the present specification will be described in detail with reference to examples in order to specifically describe the present specification. However, the examples according to the present specification may be modified to various other forms, and the scope of the present specification is not to be construed as being limited to the examples described below. Examples of the present specification are provided in order to more fully describe the present specification to those having average knowledge in the art.

Preparation Example 1

1) Preparation of Compound 1-A

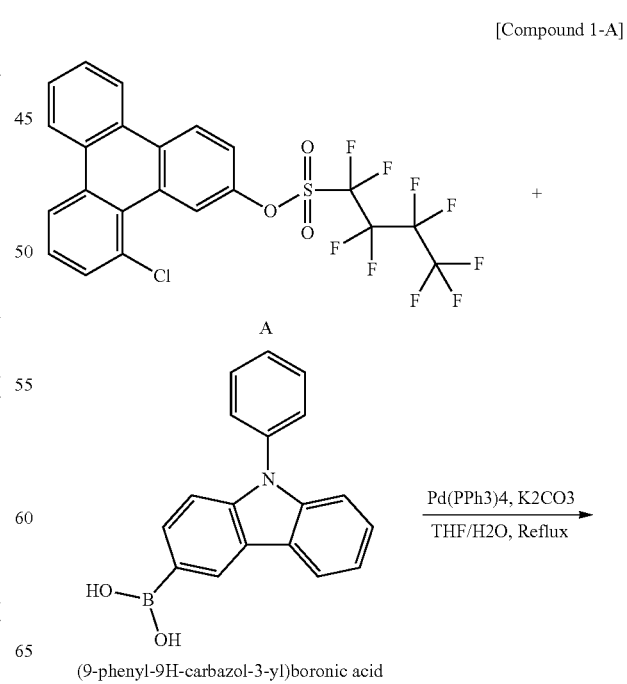

(9-phenyl-9H-carbazol-3-yl)boronic acid

227
-continued

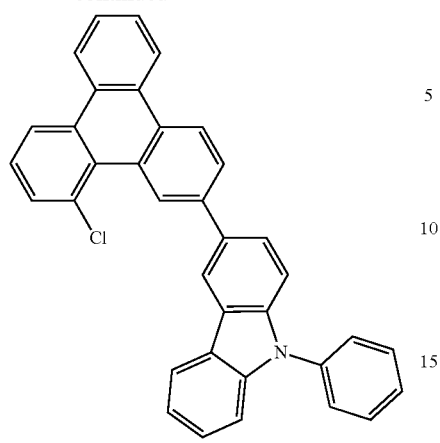

After completely dissolving Compound A (23.45 g, 41.88 mmol) and (9-phenyl-9H-carbazol-3-yl)boronic acid (13.82 g, 48.16 mmol) in 360 ml of tetrahydrofuran in a 500 ml round bottom flask under nitrogen atmosphere, a 2 M aqueous potassium carbonate solution (180 ml) and then tetrakis-(triphenylphosphine)palladium (1.45 g, 1.26 mmol) were added thereto, and the result was heated and stirred for 6 hours. After lowering the temperature to room temperature, the water layer was removed, and the result was dried using anhydrous magnesium sulfate, vacuum concentrated, and recrystallized with 260 ml of ethyl acetate to prepare Compound 1-A (18.26 g, 87%).

MS[M+H]$^+$=504

2) Preparation of Compound 1-B

228
-continued

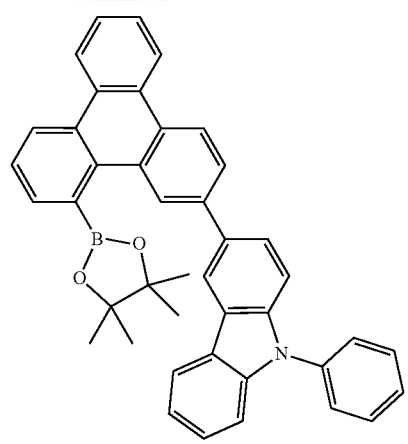

After completely dissolving Compound 1-A (18.26 g, 41.88 mmol) and 4,4,4',4',5,5,5',5'-octamethyl-2,2'-bi(1,3,2-dioxaborolane) (6.24 g, 23.37 mmol) in 400 ml of 1,4-dioxane in a 500 ml round bottom flask under nitrogen atmosphere, KOAc (6.16 g, 62.81 mmol), Pd(dba)$_2$ (0.72 g, 1.26 mmol) and P(Cy)$_3$ (0.69 g, 2.51 mmol) were added thereto, and the result was heated and stirred for 8 hours. After lowering the temperature to room temperature, the organic layer was removed, and the result was dried using anhydrous magnesium sulfate, vacuum concentrated, and recrystallized with 600 ml of ethanol to prepare Compound 1-B (17.15 g, 88%).

MS[M+H]$^+$=596

3) Preparation of Compound 1

[Compound 1]

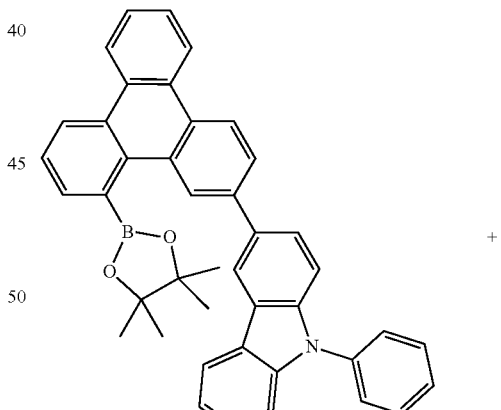

+

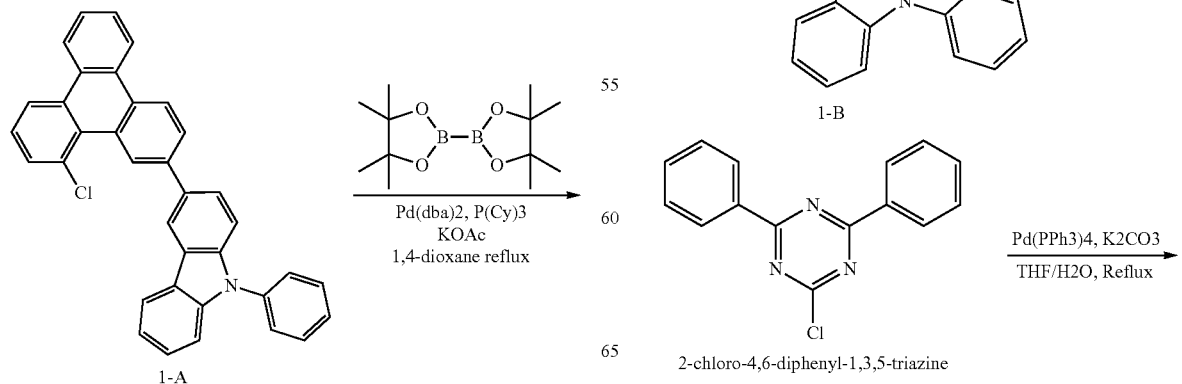

229
-continued

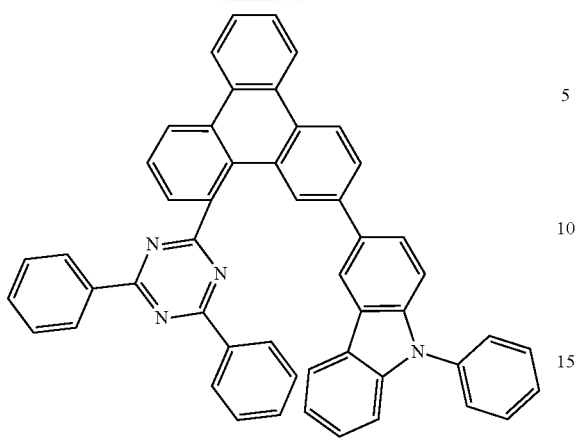

After completely dissolving Compound 1-B (8.45 g, 14.18 mmol) and 2-chloro-4,6-diphenyl-1,3,5-triazine (3.60 g, 13.47 mmol) in 180 ml of tetrahydrofuran in a 500 ml round bottom flask under nitrogen atmosphere, a 2 M aqueous potassium carbonate solution (90 ml) and then tetrakis-(triphenylphosphine)palladium (0.49 g, 0.43 mmol) were added thereto, and the result was heated and stirred for 3 hours. After lowering the temperature to room temperature, the water layer was removed, and the result was dried using anhydrous magnesium sulfate, vacuum concentrated, and recrystallized with 190 ml of tetrahydrofuran to prepare Compound 1 (8.06 g, 81%).

MS[M+H]$^+$=701

Preparation Example 2

[Compound 2]

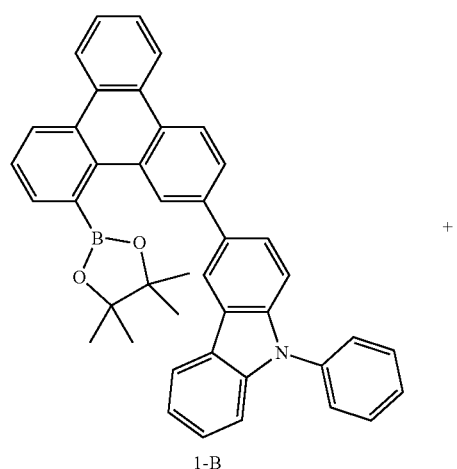

1-B

+

230
-continued

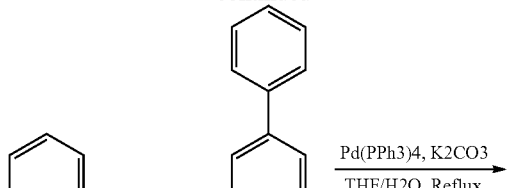

2-([1,1'-biphenyl]-3-yl)-4-
chloro-6-phenyl-1,3,5-triazine

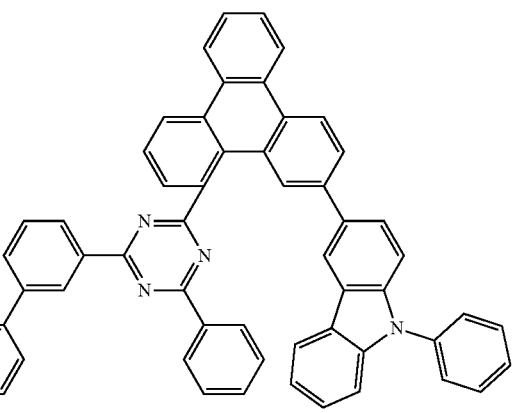

After completely dissolving Compound 1-B (8.70 g, 14.60 mmol) and 2-([1,1'-biphenyl]-3-yl)-4-chloro-6-phenyl-1,3,5-triazine (4.76 g, 13.87 mmol) in 220 ml of tetrahydrofuran in a 500 ml round bottom flask under nitrogen atmosphere, a 2 M aqueous potassium carbonate solution (110 ml) and then tetrakis-(triphenylphosphine)palladium (0.51 g, 0.44 mmol) were added thereto, and the result was heated and stirred for 3 hours. After lowering the temperature to room temperature, the water layer was removed, and the result was dried using anhydrous magnesium sulfate, vacuum concentrated, and recrystallized with 310 ml of tetrahydrofuran to prepare Compound 2 (9.44 g, 83%).

MS[M+H]$^+$=777

Preparation Example 3

1) Preparation of Compound 1-C

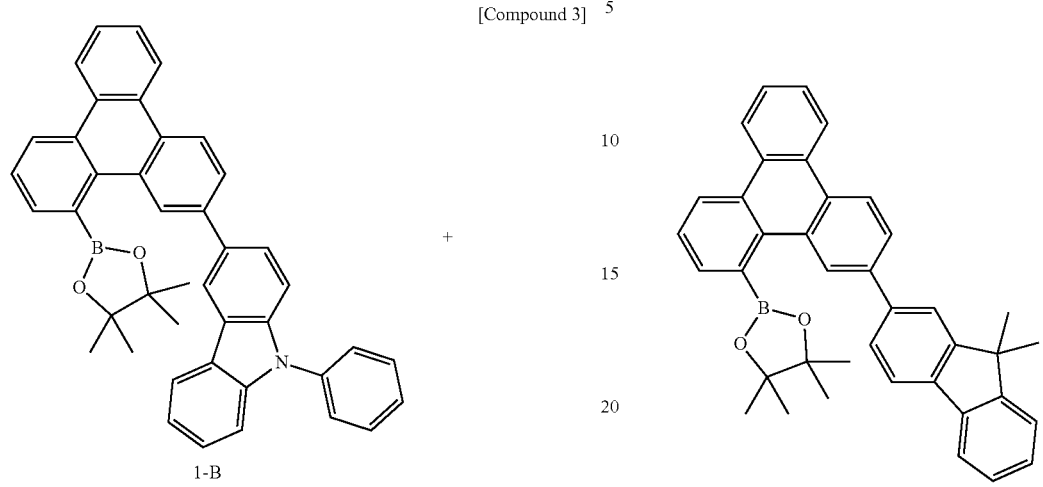

Compound 1-C was prepared through the preparation processes of Preparation Examples 1-A and 1-B except that, in the preparation of Compound 1-A in Preparation Example 1, (9,9-dimethyl-9H-fluoren-2-yl)boronic acid was used instead of (9-phenyl-9H-carbazol-3-yl)boronic acid.

MS[M+H]$^+$=547

2) Preparation of Compound 4

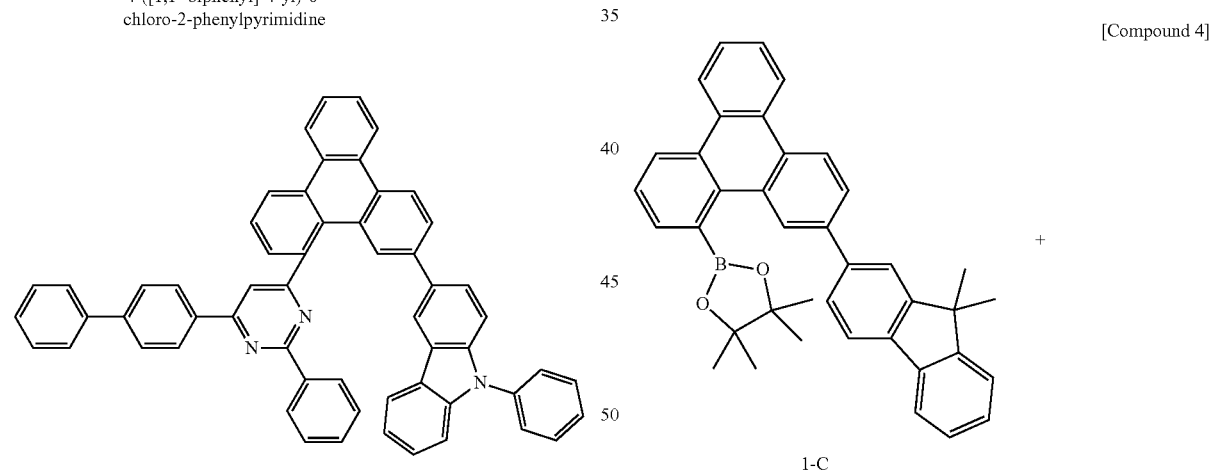

After completely dissolving Compound 1-B (7.15 g, 14.60 mmol) and 4-([1,1'-biphenyl]-4-yl)-6-chloro-2-phenylpyrimidine (4.76 g, 13.87 mmol) in 220 ml of tetrahydrofuran in a 500 ml round bottom flask under nitrogen atmosphere, a 2 M aqueous potassium carbonate solution (110 ml) and then tetrakis-(triphenylphosphine)palladium (0.51 g, 0.44 mmol) were added thereto, and the result was heated and stirred for 3 hours. After lowering the temperature to room temperature, the water layer was removed, and the result was dried using anhydrous magnesium sulfate, vacuum concentrated, and recrystallized with 310 ml of tetrahydrofuran to prepare Compound 3 (9.44 g, 83%).

MS[M+H]$^+$=776

Preparation Example 4

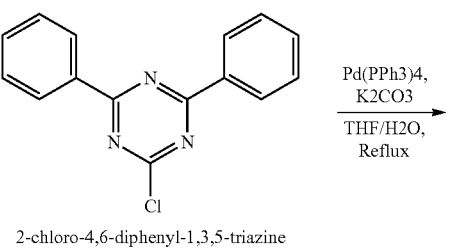

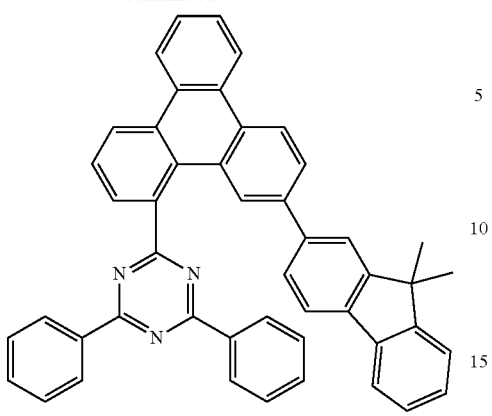

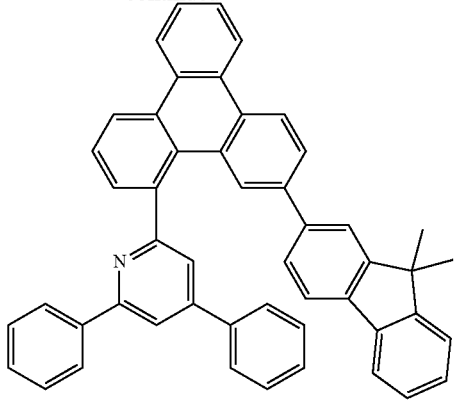

After completely dissolving Compound 1-C (9.62 g, 17.62 mmol) and 2-chloro-4,6-diphenyl-1,3,5-triazine (4.47 g, 16.74 mmol) in 220 ml of tetrahydrofuran in a 500 ml round bottom flask under nitrogen atmosphere, a 2 M aqueous potassium carbonate solution (110 ml) and then tetrakis-(triphenylphosphine)palladium (0.61 g, 0.53 mmol) were added thereto, and the result was heated and stirred for 4 hours. After lowering the temperature to room temperature, the water layer was removed, and the result was dried using anhydrous magnesium sulfate, vacuum concentrated, and recrystallized with 230 ml of ethyl acetate to prepare Compound 4 (7.25 g, 63%).

MS[M+H]$^+$=652

Preparation Example 5

After completely dissolving Compound 1-C (8.73 g, 15.99 mmol) and 2-chloro-4,6-diphenylpyridine (4.03 g, 15.19 mmol) in 190 ml of tetrahydrofuran in a 500 ml round bottom flask under nitrogen atmosphere, a 2 M aqueous potassium carbonate solution (95 ml) and then tetrakis-(triphenylphosphine)palladium (0.55 g, 0.48 mmol) were added thereto, and the result was heated and stirred for 3 hours. After lowering the temperature to room temperature, the water layer was removed, and the result was dried using anhydrous magnesium sulfate, vacuum concentrated, and recrystallized with 180 ml of ethyl acetate to prepare Compound 5 (6.98 g, 67%).

MS[M+H]$^+$=650

Preparation Example 6

1) Preparation of Compound 1-D

[Compound 1-D]

[Compound 5]

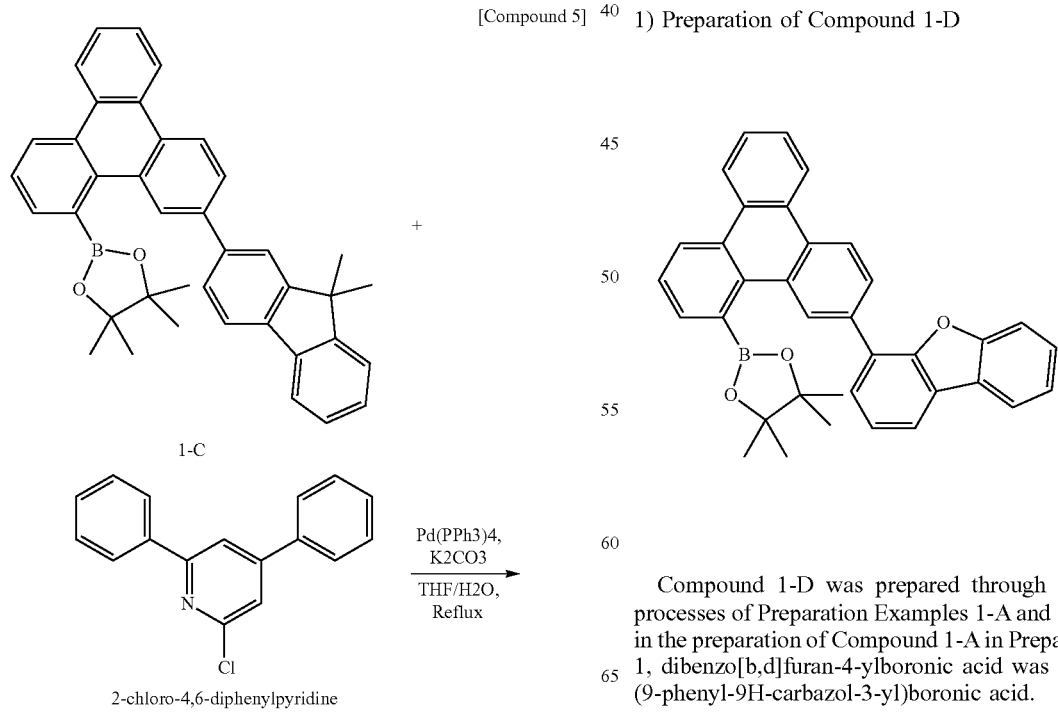

Compound 1-D was prepared through the preparation processes of Preparation Examples 1-A and 1-B except that, in the preparation of Compound 1-A in Preparation Example 1, dibenzo[b,d]furan-4-ylboronic acid was used instead of (9-phenyl-9H-carbazol-3-yl)boronic acid.

MS[M+H]$^+$=521

2) Preparation of Compound 6

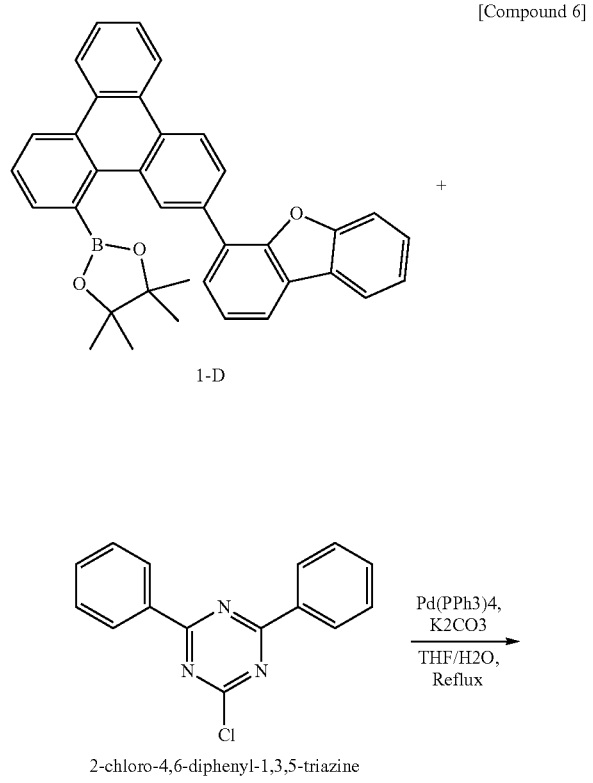

After completely dissolving Compound 1-D (10.46 g, 20.12 mmol) and 2-chloro-4,6-diphenyl-1,3,5-triazine (5.06 g, 19.11 mmol) in 240 ml of tetrahydrofuran in a 500 ml round bottom flask under nitrogen atmosphere, a 2 M aqueous potassium carbonate solution (120 ml) and then tetrakis-(triphenylphosphine)palladium (0.70 g, 0.60 mmol) were added thereto, and the result was heated and stirred for 7 hours. After lowering the temperature to room temperature, the water layer was removed, and the result was dried using anhydrous magnesium sulfate, vacuum concentrated, and recrystallized with 260 ml of ethyl acetate to prepare Compound 6 (10.06 g, 80%).

MS[M+H]$^+$=626

Preparation Example 7

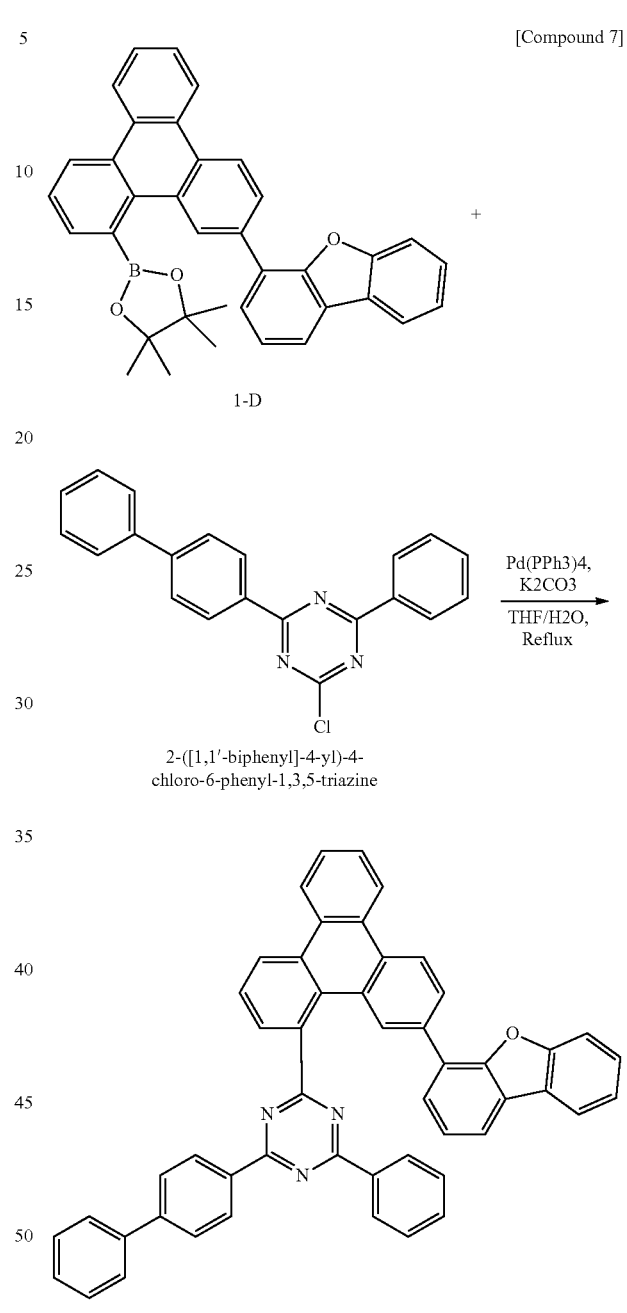

After completely dissolving Compound 1-D (7.69 g, 14.79 mmol) and 2-([1,1'-biphenyl]-4-yl)-4-chloro-6-phenyl-1,3,5-triazine (4.82 g, 14.05 mmol) in 200 ml of tetrahydrofuran in a 500 ml round bottom flask under nitrogen atmosphere, a 2 M aqueous potassium carbonate solution (100 ml) and then tetrakis-(triphenylphosphine)palladium (0.51 g, 0.44 mmol) were added thereto, and the result was heated and stirred for 8 hours. After lowering the temperature to room temperature, the water layer was removed, and the result was dried using anhydrous magnesium sulfate, vacuum concentrated, and recrystallized with 310 ml of ethyl acetate to prepare Compound 7 (8.94 g, 86%).

MS[M+H]$^+$=702

Preparation Example 8

1) Preparation of Compound 1-E

[Compound 1-E]

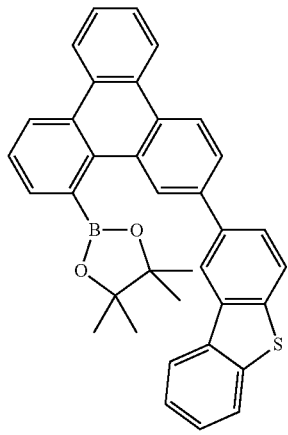

Compound 1-E was prepared through the preparation processes of Preparation Examples 1-A and 1-B except that, in the preparation of Compound 1-A in Preparation Example 1, dibenzo[b,d]thiophen-2-ylboronic acid was used instead of (9-phenyl-9H-carbazol-3-yl)boronic acid.

MS [M+H]$^+$=537

2) Preparation of Compound 8

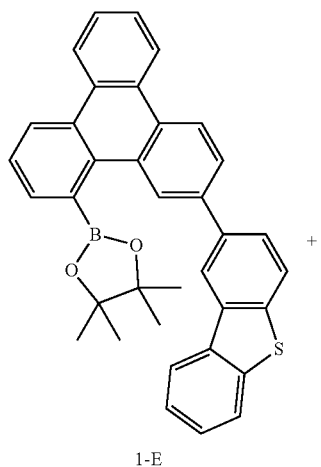

[Compound 8]

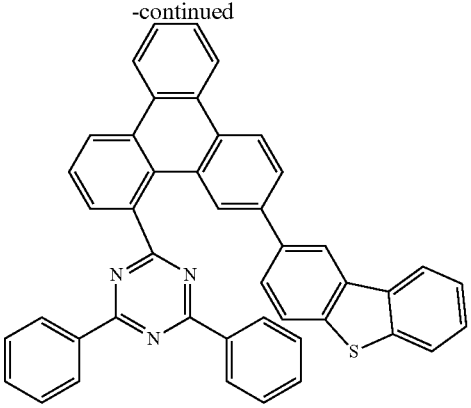

After completely dissolving Compound 1-E (6.55 g, 12.22 mmol) and 2-chloro-4,6-diphenyl-1,3,5-triazine (3.10 g, 11.61 mmol) in 200 ml of tetrahydrofuran in a 500 ml round bottom flask under nitrogen atmosphere, a 2 M aqueous potassium carbonate solution (100 ml) and then tetrakis-(triphenylphosphine)palladium (0.42 g, 0.37 mmol) were added thereto, and the result was heated and stirred for 3 hours. After lowering the temperature to room temperature, the water layer was removed, and the result was dried using anhydrous magnesium sulfate, vacuum concentrated, and recrystallized with 230 ml of ethyl acetate to prepare Compound 8 (4.68 g, 60%).

MS[M+H]$^+$=642

Preparation Example 9

[Compound 9]

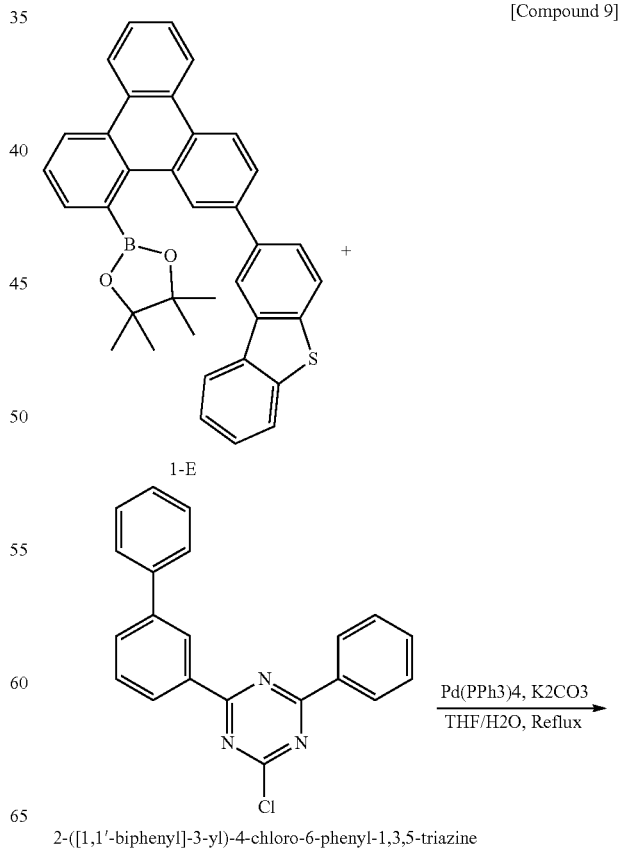

-continued

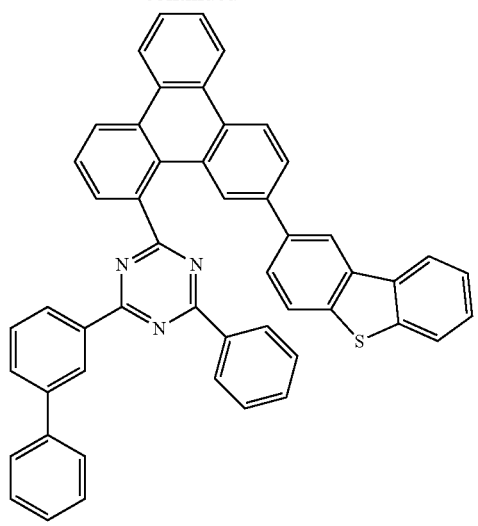

After completely dissolving Compound 1-E (7.69 g, 14.79 mmol) and 2-([1,1'-biphenyl]-3-yl)-4-chloro-6-phenyl-1,3,5-triazine (4.82 g, 14.05 mmol) in 200 ml of tetrahydrofuran in a 500 ml round bottom flask under nitrogen atmosphere, a 2 M aqueous potassium carbonate solution (100 ml) and then tetrakis-(triphenylphosphine)palladium (0.51 g, 0.44 mmol) were added thereto, and the result was heated and stirred for 8 hours. After lowering the temperature to room temperature, the water layer was removed, and the result was dried using anhydrous magnesium sulfate, vacuum concentrated, and recrystallized with 310 ml of ethyl acetate to prepare Compound 9 (8.94 g, 86%).

MS[M+H]$^+$=718

Preparation Example 10

1) Preparation of Compound 2-A

[Compound 2-A]

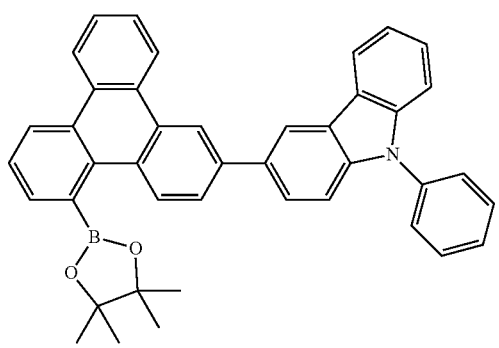

Compound 2-A was prepared through the preparation processes of Preparation Examples 1-A and 1-B except that, in the preparation of Compound 1-A in Preparation Example 1, Intermediate B was used instead of Intermediate A.

MS[M+H]$^+$=596

2) Preparation of Compound 10

[Compound 10]

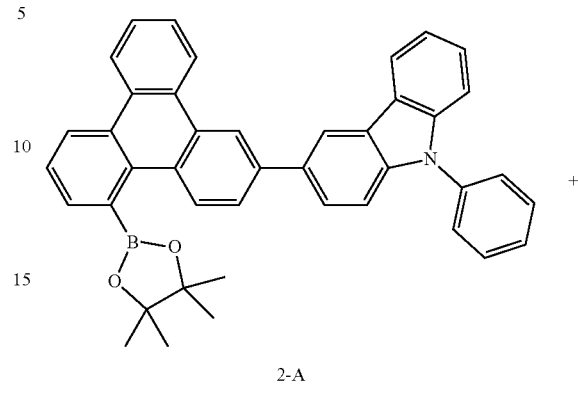

2-A

+

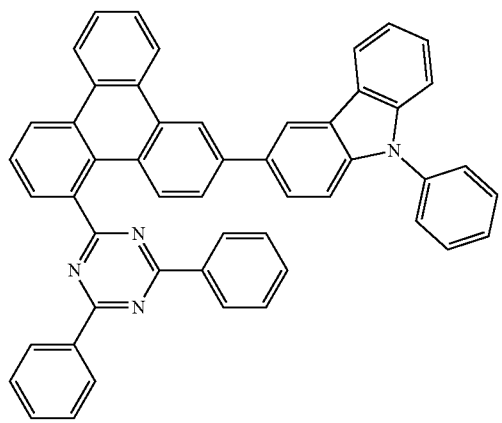

2-chloro-4,6-diphenyl-1,3,5-triazine

Pd(PPh3)4, K2CO3
THF/H2O, Reflux

After completely dissolving Compound 2-A (7.48 g, 12.55 mmol) and 2-chloro-4,6-diphenyl-1,3,5-triazine (3.18 g, 11.92 mmol) in 200 ml of tetrahydrofuran in a 500 ml round bottom flask under nitrogen atmosphere, a 2 M aqueous potassium carbonate solution (100 ml) and then tetrakis-(triphenylphosphine)palladium (0.44 g, 0.38 mmol) were added thereto, and the result was heated and stirred for 2 hours. After lowering the temperature to room temperature, the water layer was removed, and the result was dried using anhydrous magnesium sulfate, vacuum concentrated, and recrystallized with 210 ml of ethyl acetate to prepare Compound 10 (7.25 g, 82%).

MS[M+H]$^+$=701

Preparation Example 11

[Compound 11]

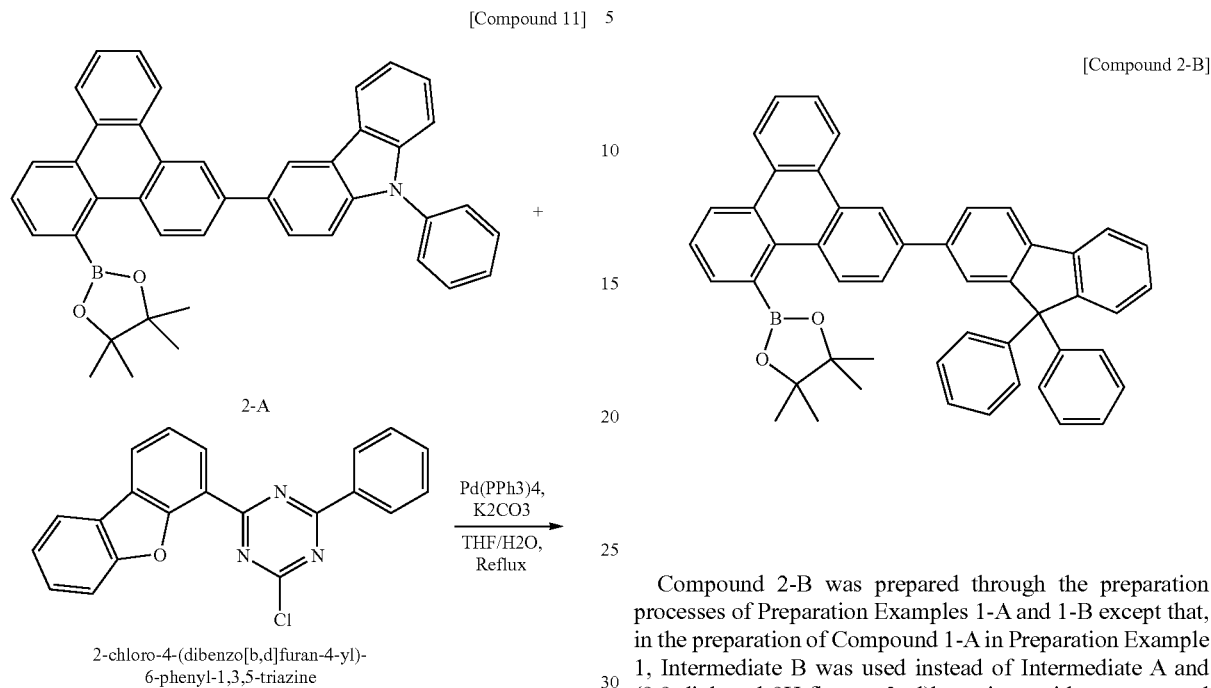

After completely dissolving Compound 2-A (6.39, 10.72 mmol) and 2-chloro-4-(dibenzo[b,d]furan-4-yl)-6-phenyl-1,3,5-triazine (3.64 g, 10.19 mmol) in 180 ml of tetrahydrofuran in a 500 ml round bottom flask under nitrogen atmosphere, a 2 M aqueous potassium carbonate solution (90 ml) and then tetrakis-(triphenylphosphine)palladium (0.37 g, 0.32 mmol) were added thereto, and the result was heated and stirred for 3 hours. After lowering the temperature to room temperature, the water layer was removed, and the result was dried using anhydrous magnesium sulfate, vacuum concentrated, and recrystallized with 310 ml of ethyl acetate to prepare Compound 11 (7.25 g, 82%).

MS[M+H]$^+$=791

Preparation Example 12

1) Preparation of Compound 2-B

[Compound 2-B]

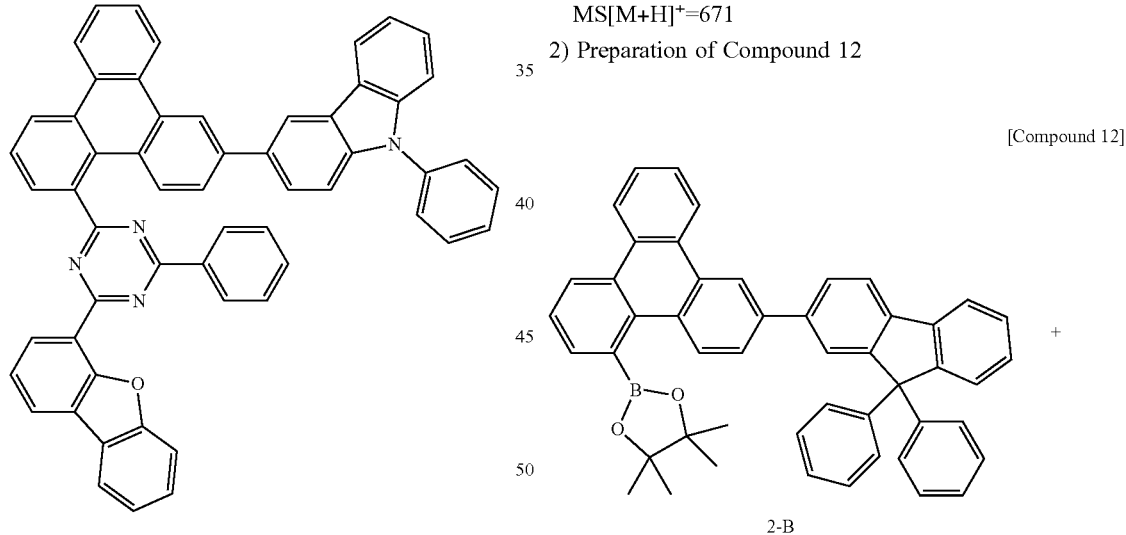

Compound 2-B was prepared through the preparation processes of Preparation Examples 1-A and 1-B except that, in the preparation of Compound 1-A in Preparation Example 1, Intermediate B was used instead of Intermediate A and (9,9-diphenyl-9H-fluoren-2-yl)boronic acid was used instead of (9-phenyl-9H-carbazol-3-yl)boronic acid.

MS[M+H]$^+$=671

2) Preparation of Compound 12

[Compound 12]

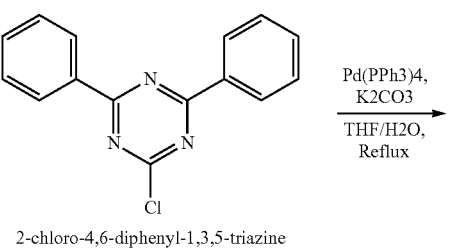

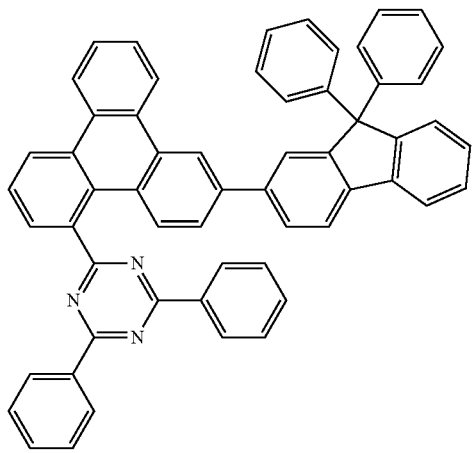

After completely dissolving Compound 2-B (8.36 g, 12.46 mmol) and 2-chloro-4,6-diphenyl-1,3,5-triazine (3.27 g, 11.84 mmol) in 160 ml of tetrahydrofuran in a 500 ml round bottom flask under nitrogen atmosphere, a 2 M aqueous potassium carbonate solution (80 ml) and then tetrakis-(triphenylphosphine)palladium (0.43 g, 0.37 mmol) were added thereto, and the result was heated and stirred for 4 hours. After lowering the temperature to room temperature, the water layer was removed, and the result was dried using anhydrous magnesium sulfate, vacuum concentrated, and recrystallized with 250 ml of ethyl acetate to prepare Compound 12 (6.85 g, 70%).

MS[M+H]$^+$=776

Preparation Example 13

1) Preparation of Compound 2-C

[Compound 2-C]

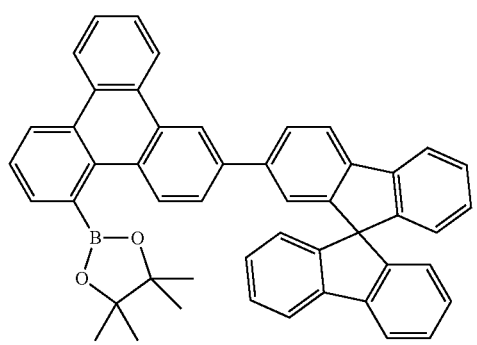

Compound 2-C was prepared through the preparation processes of Preparation Examples 1-A and 1-B except that, in the preparation of Compound 1-A in Preparation Example 1, Intermediate C was used instead of Intermediate A and 9,9'-spirobi[fluoren]-2-ylboronic acid was used instead of (9-phenyl-9H-carbazol-3-yl)boronic acid.

MS[M+H]$^+$=669

2) Preparation of Compound 13

[Compound 13]

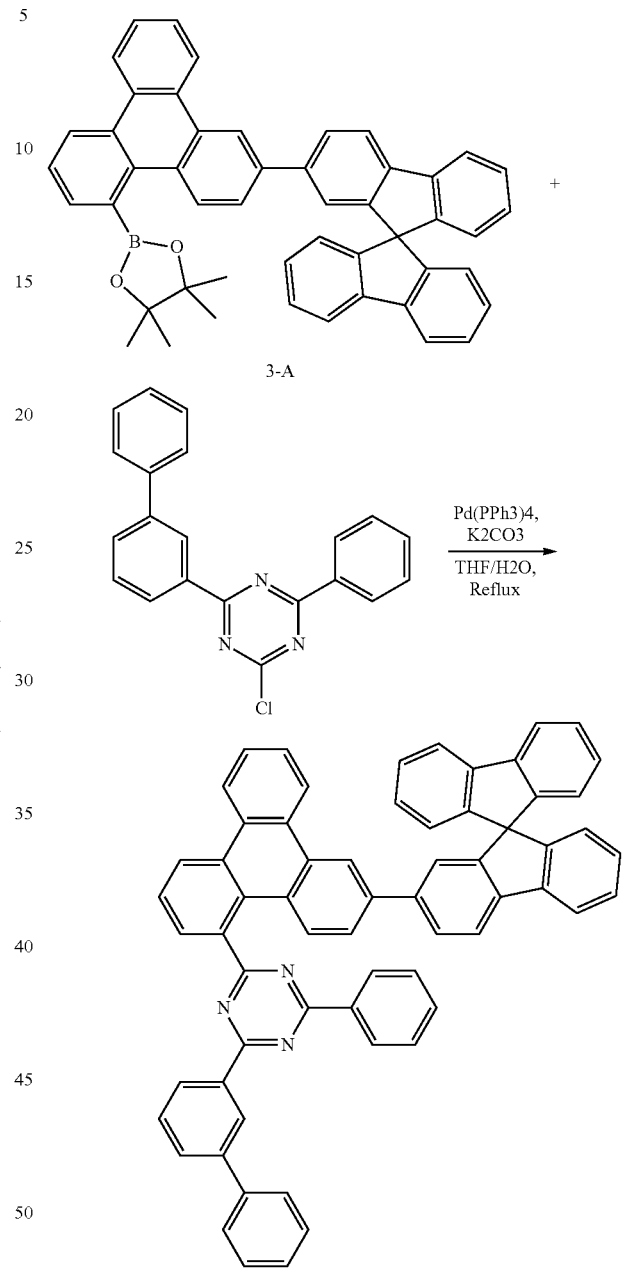

After completely dissolving Compound 2-C (6.98 g, 12.12 mmol) and 2-([1,1'-biphenyl]-3-yl)-4-chloro-6-phenyl-1,3,5-triazine (3.07 g, 11.51 mol) in 160 ml of tetrahydrofuran in a 500 ml round bottom flask under nitrogen atmosphere, a 2 M aqueous potassium carbonate solution (80 ml) and then tetrakis-(triphenylphosphine)palladium (0.42 g, 0.36 mmol) were added thereto, and the result was heated and stirred for 6 hours. After lowering the temperature to room temperature, the water layer was removed, and the result was dried using anhydrous magnesium sulfate, vacuum concentrated, and recrystallized with 350 ml of ethyl acetate to prepare Compound 13 (6.85 g, 60%).

MS[M+H]$^+$=850

Preparation Example 14

1) Preparation of Compound 3-A

[Compound 3-A]

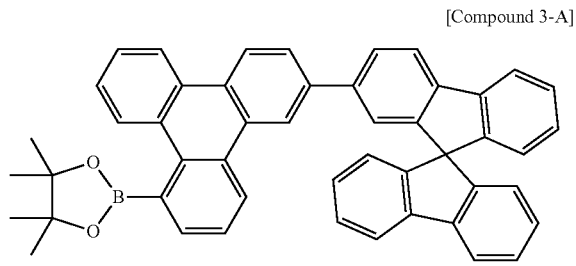 [SMILES: CC1(C)OB(c2cccc3c4cc(-c5ccc6c(c5)C5(c7ccccc7-c7ccccc75)c5ccccc5-6)ccc4c4ccccc4c23)OC1(C)C]

Compound 3-A was prepared through the preparation processes of Preparation Examples 1-A and 1-B except that, in the preparation of Compound 1-A in Preparation Example 1, Intermediate C was used instead of Intermediate A and (9,9-dimethyl-9H-fluoren-2-yl)boronic acid was used instead of (9-phenyl-9H-carbazol-3-yl)boronic acid.

MS[M+H]$^+$=669

2) Preparation of Compound 14

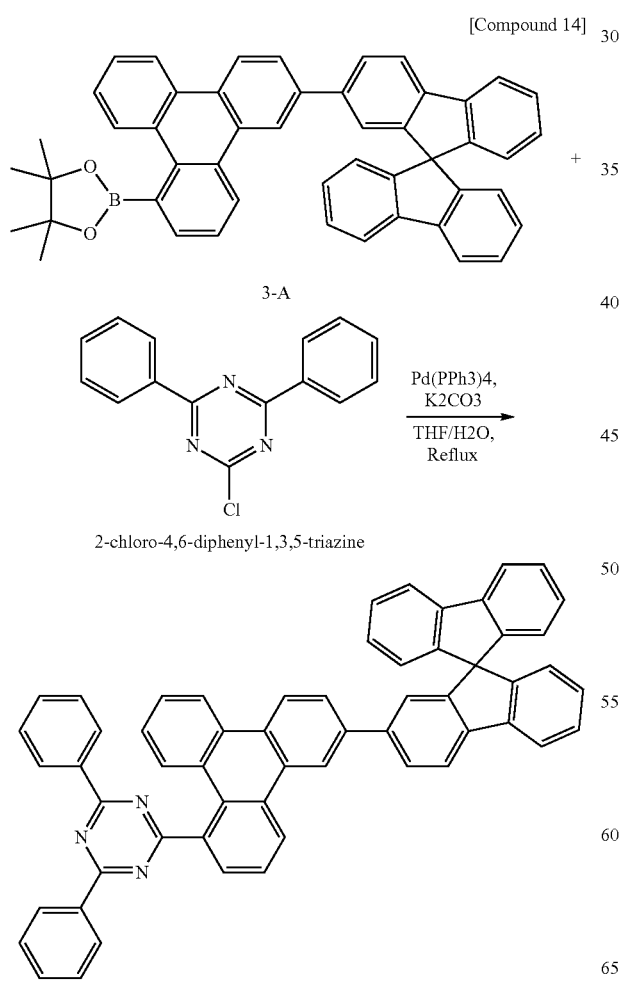

Preparation Example 15

After completely dissolving Compound 3-A (7.66 g, 11.47 mmol) and 2-chloro-4,6-diphenyl-1,3,5-triazine (2.91 g, 10.89 mol) in 160 ml of tetrahydrofuran in a 500 ml round bottom flask under nitrogen atmosphere, a 2 M aqueous potassium carbonate solution (80 ml) and then tetrakis-(triphenylphosphine)palladium (0.40 g, 0.34 mmol) were added thereto, and the result was heated and stirred for 4 hours. After lowering the temperature to room temperature, the water layer was removed, and the result was dried using anhydrous magnesium sulfate, vacuum concentrated, and recrystallized with 290 ml of ethyl acetate to prepare Compound 14 (8.02 g, 90%).

MS[M+H]$^+$=774

Preparation Example 15

1) Preparation of Compound 3-B

[Compound 3-B]

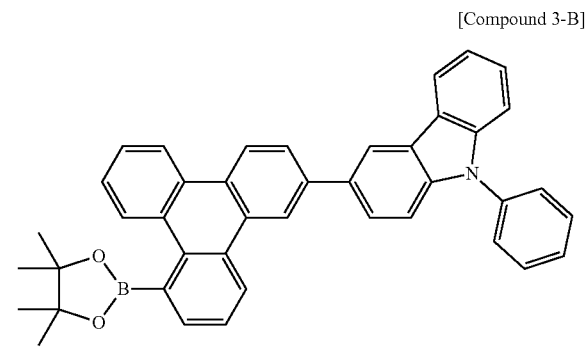 [SMILES: CC1(C)OB(c2cccc3c4cc(-c5ccc6c(c5)c5ccccc5n6-c5ccccc5)ccc4c4ccccc4c23)OC1(C)C]

Compound 3-B was prepared through the preparation processes of Preparation Examples 1-A and 1-B except that, in the preparation of Compound 1-A in Preparation Example 1, Intermediate C was used instead of Intermediate A.

MS[M+H]$^+$=596

2) Preparation of Compound 15

[Compound 15]

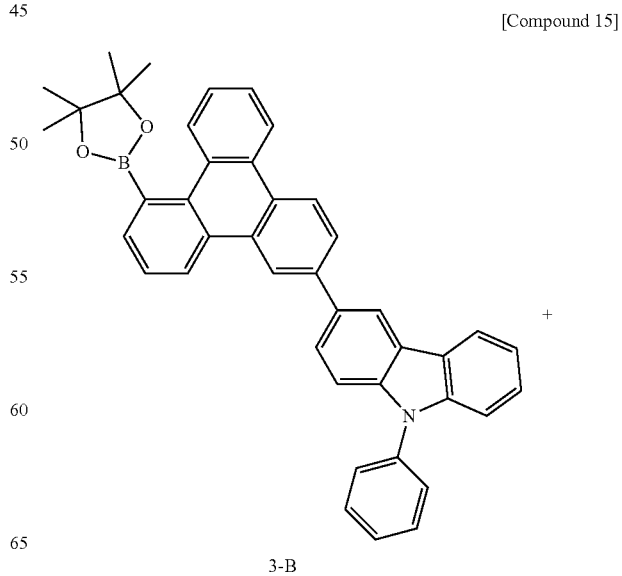

-continued

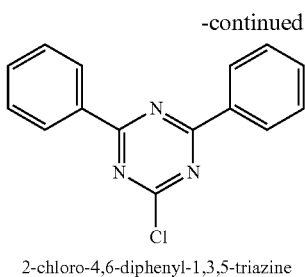

2-chloro-4,6-diphenyl-1,3,5-triazine

Pd(PPh3)4, K2CO3
THF/H2O, Reflux

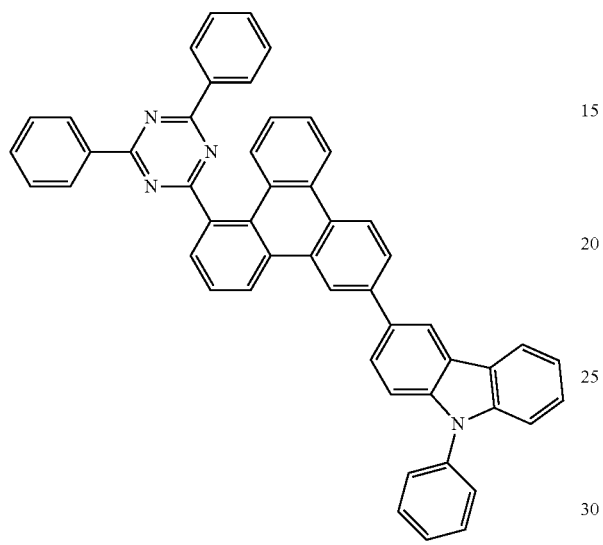

After completely dissolving Compound 3-B (5.86 g, 9.85 mmol) and 2-chloro-4,6-diphenyl-1,3,5-triazine (2.50 g, 9.36 mol) in 120 ml of tetrahydrofuran in a 500 ml round bottom flask under nitrogen atmosphere, a 2 M aqueous potassium carbonate solution (60 ml) and then tetrakis-(triphenylphosphine)palladium (0.34 g, 0.30 mmol) were added thereto, and the result was heated and stirred for 2 hours. After lowering the temperature to room temperature, the water layer was removed, and the result was dried using anhydrous magnesium sulfate, vacuum concentrated, and recrystallized with 230 ml of ethyl acetate to prepare Compound 15 (5.55 g, 80%).

MS[M+H]$^+$=701

Preparation Example 16

1) Preparation of Compound 4-A

[Compound 4-A]

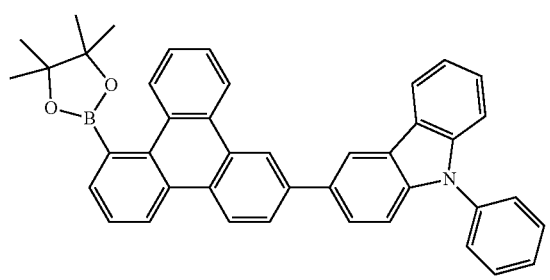

Compound 4-A was prepared through the preparation processes of Preparation Examples 1-A and 1-B except that, in the preparation of Compound 1-A in Preparation Example 1, Intermediate D was used instead of Intermediate A.

MS[M+H]$^+$=596

2) Preparation of Compound 16

[Compound 16]

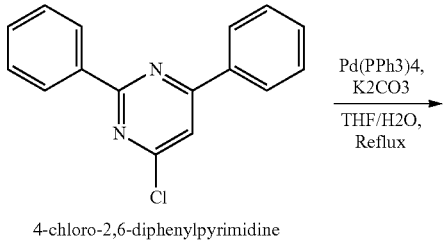

4-A

+

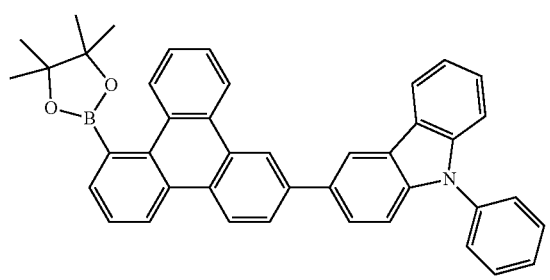

4-chloro-2,6-diphenylpyrimidine

Pd(PPh3)4, K2CO3
THF/H2O, Reflux

After completely dissolving Compound 4-A (5.86 g, 9.85 mmol) and 4-chloro-2,6-diphenylpyrimidine (2.50 g, 9.36 mol) in 120 ml of tetrahydrofuran in a 500 ml round bottom flask under nitrogen atmosphere, a 2 M aqueous potassium carbonate solution (60 ml) and then tetrakis-(triphenylphosphine)palladium (0.34 g, 0.30 mmol) were added thereto, and the result was heated and stirred for 2 hours. After lowering the temperature to room temperature, the water layer was removed, and the result was dried using anhydrous magnesium sulfate, vacuum concentrated, and recrystallized with 230 ml of ethyl acetate to prepare Compound 16 (5.55 g, 80%).

MS[M+H]$^+$=700

Preparation Example 17

1) Preparation of Compound 4-B

[Compound 4-B]

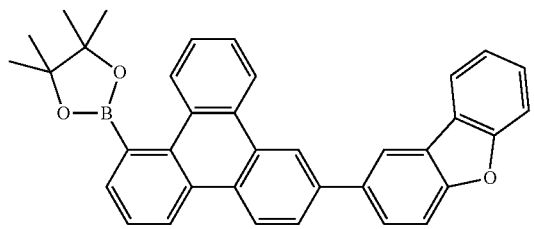

Compound 4-B was prepared through the preparation processes of Preparation Examples 1-A and 1-B except that, in the preparation of Compound 1-A in Preparation Example 1, Intermediate D was used instead of Intermediate A and dibenzo[b,d]furan-4-ylboronic acid was used instead of (9-phenyl-9H-carbazol-3-yl)boronic acid.

MS[M+H]$^+$=521

2) Preparation of Compound 17

[Compound 17]

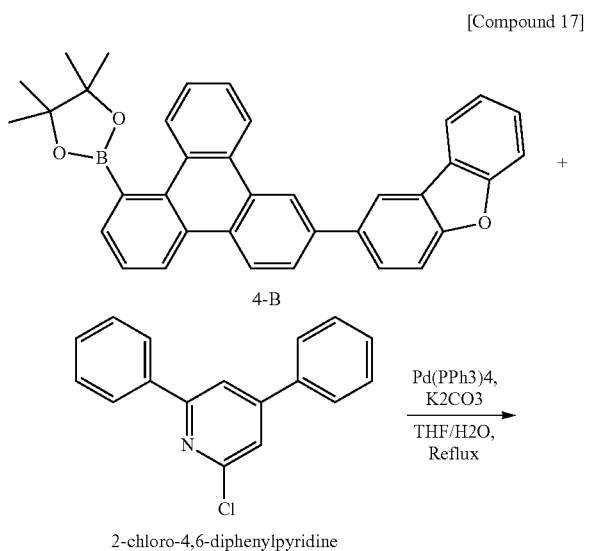

After completely dissolving Compound 4-B (10.06 g, 19.31 mmol) and 2-chloro-4,6-diphenylpyridine (4.90 g, 18.34 mol) in 160 ml tetrahydrofuran in a 500 ml round bottom flask under nitrogen atmosphere, a 2 M aqueous potassium carbonate solution (80 ml) and then tetrakis-(triphenylphosphine)palladium (0.67 g, 0.58 mmol) were added thereto, and the result was heated and stirred for 3 hours. After lowering the temperature to room temperature, the water layer was removed, and the result was dried using anhydrous magnesium sulfate, vacuum concentrated, and recrystallized with 230 ml of ethyl acetate to prepare Compound 17 (8.86 g, 65%).

MS[M+H]$^+$=624

Example 1

A glass substrate on which indium tin oxide (ITO) was coated as a thin film to a thickness of 1,000 Å was placed in detergent-dissolved distilled water and ultrasonic cleaned. Herein, a product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonic cleaned with solvents of isopropyl alcohol, acetone and methanol, then dried, and then transferred to a plasma cleaner. In addition, the substrate was cleaned for 5 minutes using oxygen plasma, and then transferred to a vacuum depositor.

On the transparent ITO electrode prepared as above, a hole injection layer was formed by thermal vacuum depositing hexanitrile hexaazatriphenylene (HAT) of the following chemical formula to a thickness of 150 Å.

[HAT]

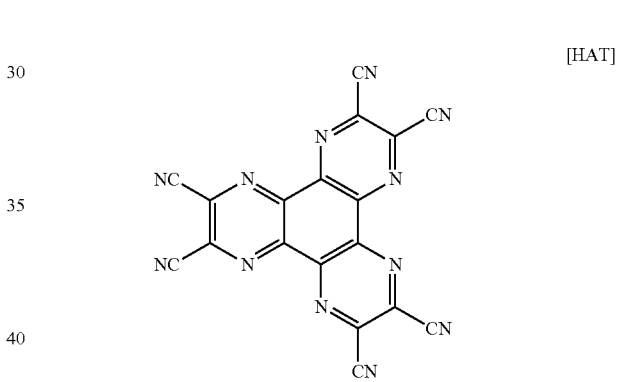

A hole transfer layer was formed on the hole injection layer by vacuum depositing the following compound 4,4'-(9-phenyl-9H-carbazole-3,6-diyl)bis(N,N-diphenylaniline) [HT 1] (1150 Å), a material transferring holes.

[HT 1]

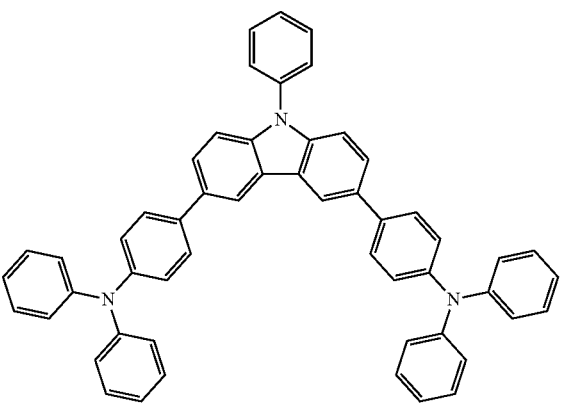

Subsequently, an electron blocking layer was formed on the hole transfer layer to a film thickness of 100 Å by vacuum depositing the following Compound [EB 1].
[EB 1]
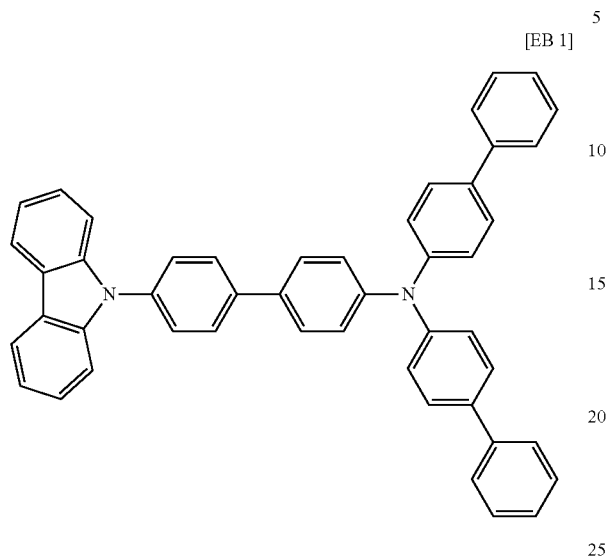
Subsequently, a light emitting layer was formed on the electron blocking layer to a film thickness of 200 Å by vacuum depositing the following Compounds BH and BD in a weight ratio of 25:1.
BH
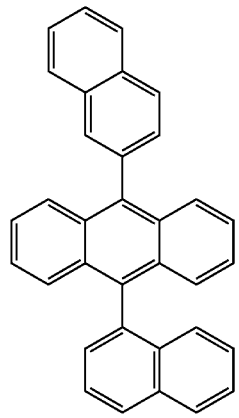
[BD]
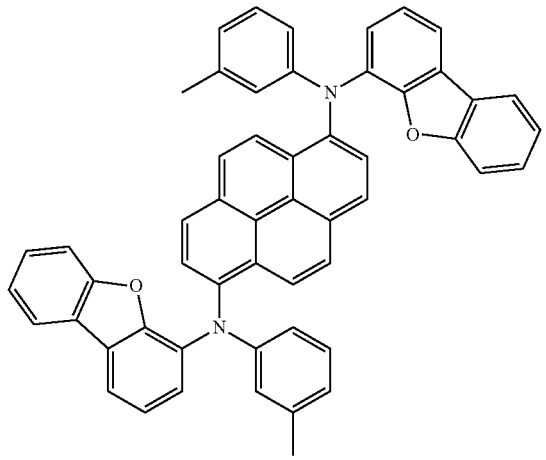
[HB 1]
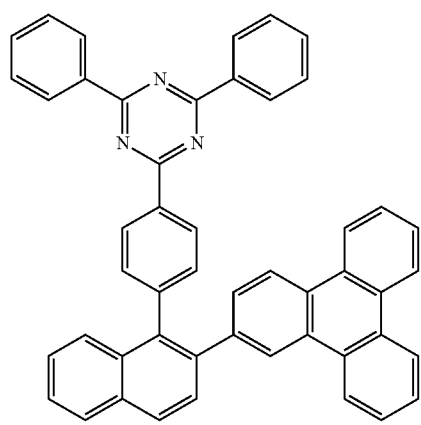

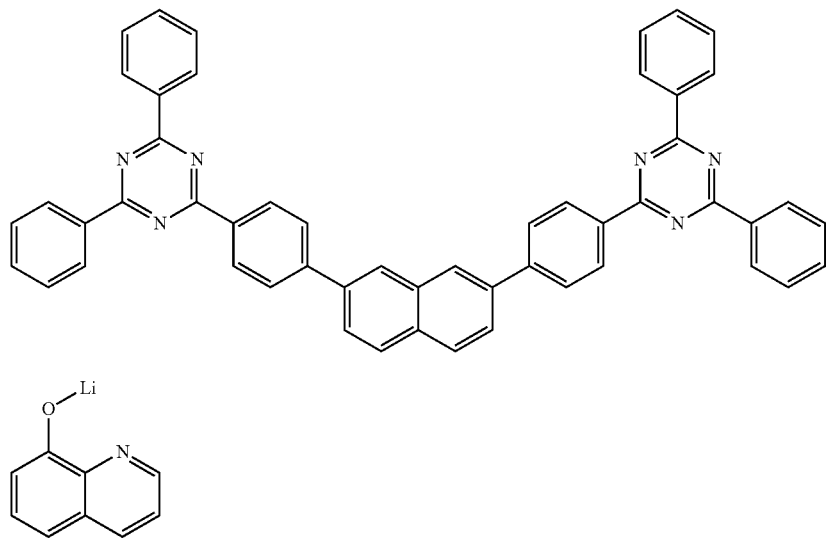

[ET 1]

[LiQ]

A hole blocking layer was formed on the light emitting layer to a film thickness of 50 Å by vacuum depositing Compound [HB 1].

Next, on the hole blocking layer, an electron injection and transfer layer was formed to a thickness of 310 Å by vacuum depositing Compound ET 1 and a lithium quinolate (LiQ) compound in a weight ratio of 1:1. A cathode was formed on the electron injection and transfer layer by depositing lithium fluoride (LiF) to a thickness of 12 Å and aluminum to a thickness of 1,000 Å in consecutive order.

An organic light emitting device was manufactured by maintaining, in the above-mentioned processes, the deposition rates of the organic materials at 0.4 Å/sec to 0.7 Å/sec, the deposition rates of the lithium fluoride and the aluminum of the cathode at 0.3 Å/sec and 2 Å/sec, respectively, and the degree of vacuum during the deposition at $2 \times 10^{-7}$ torr to $5 \times 10^{-6}$ torr.

Example 1-1

An organic light emitting device was manufactured in the same manner as in Example 1 except that Compound 1 was used instead of ET 1.

Example 1-2

An organic light emitting device was manufactured in the same manner as in Example 1 except that Compound 2 was used instead of ET 1.

Example 1-3

An organic light emitting device was manufactured in the same manner as in Example 1 except that Compound 3 was used instead of ET 1.

Example 1-4

An organic light emitting device was manufactured in the same manner as in Example 1 except that Compound 4 was used instead of ET 1.

Example 1-5

An organic light emitting device was manufactured in the same manner as in Example 1 except that Compound 5 was used instead of ET 1.

Example 1-6

An organic light emitting device was manufactured in the same manner as in Example 1 except that Compound 6 was used instead of ET 1.

Example 1-7

An organic light emitting device was manufactured in the same manner as in Example 1 except that Compound 7 was used instead of ET 1.

Example 1-8

An organic light emitting device was manufactured in the same manner as in Example 1 except that Compound 8 was used instead of ET 1.

Example 1-9

An organic light emitting device was manufactured in the same manner as in Example 1 except that Compound 9 was used instead of ET 1.

Example 1-10

An organic light emitting device was manufactured in the same manner as in Example 1 except that Compound 10 was used instead of ET 1.

Example 1-11

An organic light emitting device was manufactured in the same manner as in Example 1 except that Compound 11 was used instead of ET 1.

Example 1-12

An organic light emitting device was manufactured in the same manner as in Example 1 except that Compound 12 was used instead of ET 1.

Example 1-13

An organic light emitting device was manufactured in the same manner as in Example 1 except that Compound 13 was used instead of ET 1.

Example 1-14

An organic light emitting device was manufactured in the same manner as in Example 1 except that Compound 14 was used instead of ET 1.

Example 1-15

An organic light emitting device was manufactured in the same manner as in Example 1 except that Compound 15 was used instead of ET 1.

Example 1-16

An organic light emitting device was manufactured in the same manner as in Example 1 except that Compound 16 was used instead of ET 1.

Example 1-17

An organic light emitting device was manufactured in the same manner as in Example 1 except that Compound 17 was used instead of ET 1.

Comparative Example 1

An organic light emitting device was manufactured in the same manner as in Example 1 except that the following Compound ET 2 was used instead of ET 1.

[ET 2]

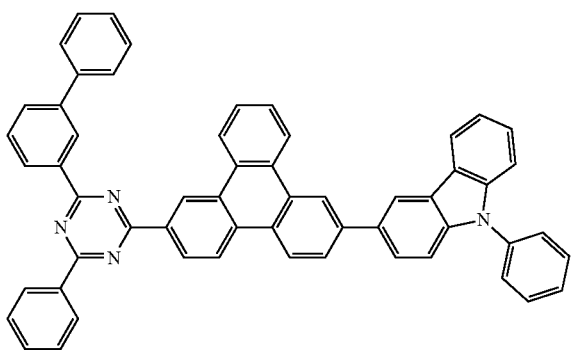

Comparative Example 2

An organic light emitting device was manufactured in the same manner as in Example 1 except that the following Compound ET 3 was used instead of ET 1.

[ET 3]

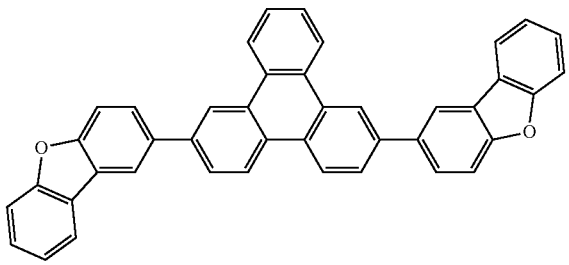

Comparative Example 3

An organic light emitting device was manufactured in the same manner as in Example 1 except that the following Compound ET 4 was used instead of ET 1.

[ET 4]

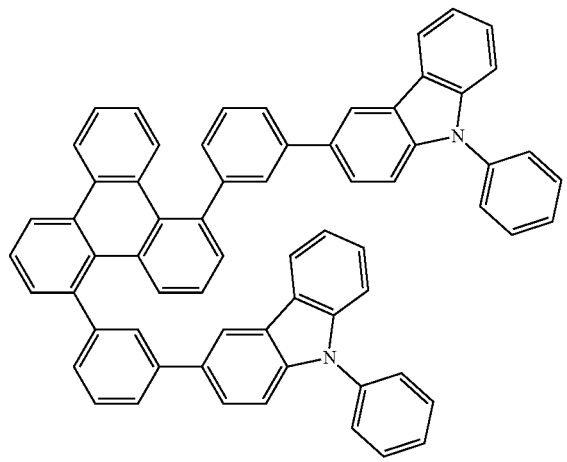

When a current was applied to the organic light emitting devices manufactured in Example 1, Examples 1-1 to 1-17, and Comparative Examples 1 to 3, a voltage, efficiency, a color coordinate and a lifespan were measured, and the results are shown in the following [Table 1]. T95 means time taken for the luminance decreasing to 95% of its initial luminance (1600 nit).

TABLE 1

| | Compound (Electron Transfer Layer) | Voltage (V@10 mA/cm$^2$) | Efficiency (cd/A@10 mA/cm$^2$) | Color Coordinate (x, y) | T95 (hr) |
|---|---|---|---|---|---|
| Example 1 | ET 1 | 5.06 | 5.09 | (0.141, 0.045) | 190 |
| Example 1-1 | Compound 1 | 4.42 | 5.81 | (0.140, 0.049) | 290 |
| Example 1-2 | Compound 2 | 4.46 | 5.76 | (0.141, 0.045) | 285 |
| Example 1-3 | Compound 3 | 4.75 | 5.42 | (0.141, 0.045) | 255 |
| Example 1-4 | Compound 4 | 4.45 | 5.72 | (0.142, 0.046) | 280 |
| Example 1-5 | Compound 5 | 4.71 | 5.46 | (0.141, 0.045) | 250 |

TABLE 1-continued

| | Compound (Electron Transfer Layer) | Voltage (V@10 mA/cm$^2$) | Efficiency (cd/A@10 mA/cm$^2$) | Color Coordinate (x, y) | T95 (hr) |
|---|---|---|---|---|---|
| Example 1-6 | Compound 6 | 4.41 | 5.79 | (0.141, 0.045) | 285 |
| Example 1-7 | Compound 7 | 4.47 | 5.75 | (0.142, 0.046) | 280 |
| Example 1-8 | Compound 8 | 4.48 | 5.73 | (0.141, 0.045) | 290 |
| Example 1-9 | Compound 9 | 4.43 | 5.70 | (0.141, 0.045) | 295 |
| Example 1-10 | Compound 10 | 4.62 | 5.51 | (0.141, 0.045) | 275 |
| Example 1-11 | Compound 11 | 4.66 | 5.64 | (0.141, 0.045) | 280 |
| Example 1-12 | Compound 12 | 4.55 | 5.56 | (0.141, 0.045) | 275 |
| Example 1-13 | Compound 13 | 4.69 | 5.69 | (0.141, 0.045) | 280 |
| Example 1-14 | Compound 14 | 4.64 | 5.65 | (0.141, 0.045) | 285 |
| Example 1-15 | Compound 15 | 4.50 | 5.61 | (0.141, 0.045) | 270 |
| Example 1-16 | Compound 16 | 4.71 | 5.46 | (0.141, 0.045) | 230 |
| Example 1-17 | Compound 17 | 4.75 | 5.41 | (0.141, 0.045) | 235 |
| Comparative Example 1 | ET 2 | 4.95 | 5.16 | (0.141, 0.045) | 205 |
| Comparative Example 2 | ET 3 | 5.32 | 4.74 | (0.141, 0.045) | 225 |
| Comparative Example 3 | ET 4 | 5.28 | 4.95 | (0.141, 0.045) | 210 |

As shown in Table 1, the organic light emitting device manufactured using the compound of the present disclosure as an electron transfer layer exhibited excellent properties in terms of efficiency, driving voltage and/or stability of the organic light emitting device. Particularly, the organic light emitting device using the compound according to one embodiment of the present specification exhibited properties of low voltage, high efficiency and long lifespan compared to the organic light emitting devices manufactured using the compound of Comparative Example 1 having the substituents of Chemical Formulae 2 and 3 symmetrically linked to both sides of triphenylene and the compounds of Comparative Examples 2 and 3 substituted only with Chemical Formula 2 as an electron transfer layer. It was seen that Comparative Examples 2 and 3 not substituted with Chemical Formula 3 having a favorable electron injection property had a greatly increased voltage and decreased efficiency.

Particularly, among the unsymmetrically bent compounds of the present disclosure, the compounds of Examples 1-1,2,4,6,7,8 and 9 with a form of Chemical Formula 4 having steric hindrance had most favorable properties.

As shown in the results of Table 1, it was identified that the compounds according to the present disclosure had an excellent electron transfer ability, and were capable of being used in an organic light emitting device.

Example 2

A light emitting layer was formed to a film thickness of 350 Å by vacuum depositing the following Compounds GH and GD in a weight ratio of 20:1 instead of using BH and BD as the light emitting layer in Example 1.

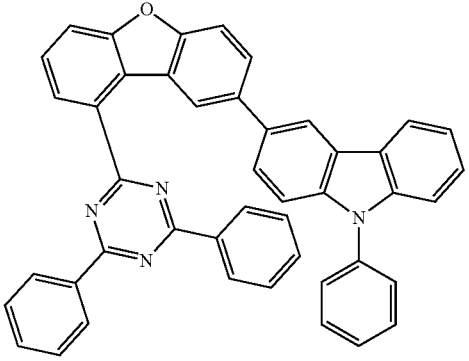

[GH]

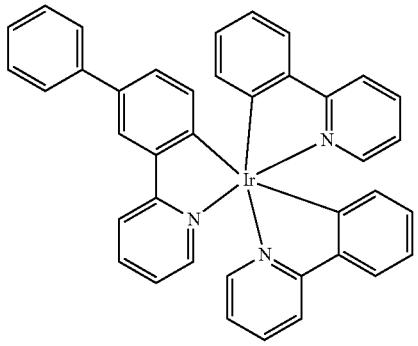

[GD]

Example 2-1

An organic light emitting device was manufactured in the same manner as in Example 2 except that Compound 1 was used instead of GH.

Example 2-2

An organic light emitting device was manufactured in the same manner as in Example 2 except that Compound 2 was used instead of GH.

Example 2-3

An organic light emitting device was manufactured in the same manner as in Example 2 except that Compound 4 was used instead of GH.

Example 2-4

An organic light emitting device was manufactured in the same manner as in Example 2 except that Compound 6 was used instead of GH.

Example 2-5

An organic light emitting device was manufactured in the same manner as in Example 2 except that Compound 7 was used instead of GH.

Example 2-6

An organic light emitting device was manufactured in the same manner as in Example 2 except that Compound 8 was used instead of GH.

Example 2-7

An organic light emitting device was manufactured in the same manner as in Example 2 except that Compound 9 was used instead of GH.

Example 2-8

An organic light emitting device was manufactured in the same manner as in Example 2 except that Compound 10 was used instead of GH.

Example 2-9

An organic light emitting device was manufactured in the same manner as in Example 2 except that Compound 11 was used instead of GH.

Example 2-10

An organic light emitting device was manufactured in the same manner as in Example 2 except that Compound 12 was used instead of GH.

Example 2-11

An organic light emitting device was manufactured in the same manner as in Example 2 except that Compound 13 was used instead of GH.

Example 2-12

An organic light emitting device was manufactured in the same manner as in Example 2 except that Compound 14 was used instead of GH.

Example 2-13

An organic light emitting device was manufactured in the same manner as in Example 2 except that Compound 15 was used instead of GH.

Comparative Example 4

An experiment was carried out in the same manner as in Example 2 except that the following Compound GH 2 was used as the green light emitting layer.

[GH 2]

Comparative Example 5

An experiment was carried out in the same manner as in Example 2 except that the following Compound GH 3 was used as the green light emitting layer.

[GH 3]

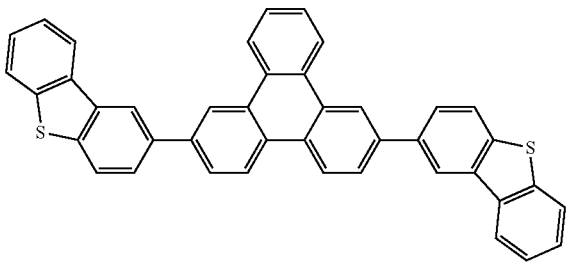

When a current was applied to the organic light emitting devices in manufactured Example 2, Examples 2-1 to 2-13, and Comparative Examples 4 and 5, a voltage, efficiency, a color coordinate and a lifespan were measured, and the results are shown in the following [Table 2]. T95 means time taken for the luminance decreasing to 95% of its initial luminance (1600 nit).

TABLE 2

|  | Compound (Green Light Emitting Layer) | Voltage (V@10 mA/cm$^2$) | Efficiency (cd/A@10 mA/cm$^2$) | Color Coordinate (x, y) | T95 (hr) |
| --- | --- | --- | --- | --- | --- |
| Example 2 | GH 1 | 4.23 | 102.46 | (0.257, 0.713) | 260 |
| Example 2-1 | Compound 1 | 3.79 | 117.21 | (0.256, 0.710) | 380 |
| Example 2-2 | Compound 2 | 3.82 | 116.81 | (0.256, 0.712) | 375 |
| Example 2-3 | Compound 4 | 3.81 | 116.23 | (0.254, 0.713) | 365 |
| Example 2-4 | Compound 6 | 3.85 | 116.17 | (0.254, 0.715) | 360 |
| Example 2-5 | Compound 7 | 3.87 | 116.65 | (0.254, 0.716) | 365 |
| Example 2-6 | Compound 8 | 3.89 | 115.92 | (0.255, 0.711) | 355 |
| Example 2-7 | Compound 9 | 3.88 | 115.81 | (0.255, 0.708) | 360 |
| Example 2-8 | Compound 10 | 3.93 | 113.45 | (0.255, 0.707) | 350 |
| Example 2-9 | Compound 11 | 3.93 | 113.81 | (0.254, 0.706) | 365 |
| Example 2-10 | Compound 12 | 3.96 | 111.15 | (0.253, 0.702) | 345 |
| Example 2-11 | Compound 13 | 3.95 | 110.95 | (0.250, 0.699) | 325 |
| Example 2-12 | Compound 14 | 3.91 | 112.26 | (0.251, 0.697) | 335 |
| Example 2-13 | Compound 15 | 3.94 | 111.13 | (0.250, 0.698) | 320 |
| Comparative Example 4 | GH 2 | 4.51 | 96.05 | (0.257, 0.713) | 230 |
| Comparative Example 5 | GH 3 | 5.13 | 72.44 | (0.244, 0.694) | 165 |

As shown in Table 2, the organic light emitting device manufactured using the compound of the present disclosure as a green light emitting layer exhibited excellent properties in terms of efficiency, driving voltage and/or stability of the organic light emitting device. Particularly, the organic light emitting device using the compound according to one embodiment of the present specification exhibited properties of low voltage, high efficiency and long lifespan compared to the organic light emitting device manufactured using the compound of Comparative Example 4 having the substituents of Chemical Formulae 2 and 3 symmetrically linked to both sides of triphenylene. It was seen that Comparative Example 5 not substituted with Chemical Formula 3 having a favorable electron injection property had a greatly increased voltage and decreased efficiency.

In addition, among the unsymmetrically bent compounds of the present disclosure, the compounds of Examples 1-1,2,4,6,7,8 and 9 with a form of Chemical Formula 4 having steric hindrance had most favorable properties.

As shown in the results of Table 2, it was identified that the compounds according to the present disclosure had an excellent light emitting ability, and were capable of being used in an organic light emitting device.

REFERENCE NUMERAL

1: Substrate
2: Anode
3: Light Emitting Layer
4: Cathode
5: Hole Injection Layer
6: Hole Transfer Layer
7: Electron Transfer Layer

The invention claimed is:

1. A compound represented by the following Chemical Formula 4, Chemical Formula 5, or Chemical Formula 6:

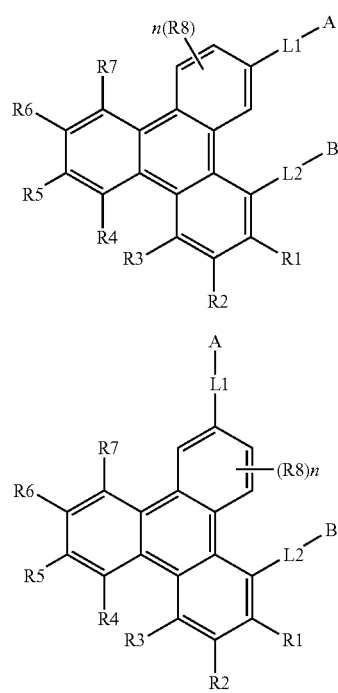

wherein, in Chemical Formulas 4 to 6,

A is represented by the following Chemical Formula 2 and B is represented by the following Chemical Formula 3, or B is represented by the following Chemical Formula 2 and A is represented by the following Chemical Formula 3, L1 and L2 are the same as or different from each other, and each independently a direct bond; a substituted or unsubstituted arylene group; or a substituted or unsubstituted heteroarylene group, R1 to R8 are the same as or different from each other, and each independently hydrogen or deuterium, n is an integer of 0 to 3, and when n is 2 or greater, each R8 is the same as or different from each other,

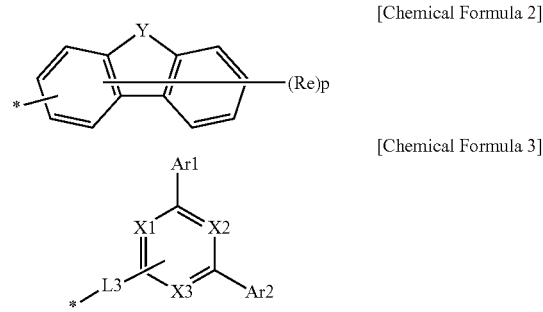

wherein in Chemical Formulae 2 and 3,

Y is S, O, NRa, or CRbRc,

Ar1 and Ar2 are the same as or different from each other, and each independently a substituted or unsubstituted aryl group; or a substituted or unsubstituted heteroaryl group, X1 to X3 are the same as or different from each other, and each independently N or CRd, L3 is a direct bond; a substituted or unsubstituted arylene group; or a substituted or unsubstituted heteroarylene group, Ra to Re are the same as or different from each other, and each independently hydrogen; deuterium; a nitrile group; a substituted or unsubstituted alkyl group; a substituted or unsubstituted aryl group; or a substituted or unsubstituted heteroaryl group, Rb and Rc bond to each other to form a ring structure, two or more adjacent groups of Re optionally bond to each other to form a ring, p is an integer of 0 to 7, and when p is 2 or greater, each Re is the same as or different from each other, and

*is a site bonding to L1 or L2.

2. The compound of claim 1, wherein Chemical Formula 3 is any one selected from the following substituents:

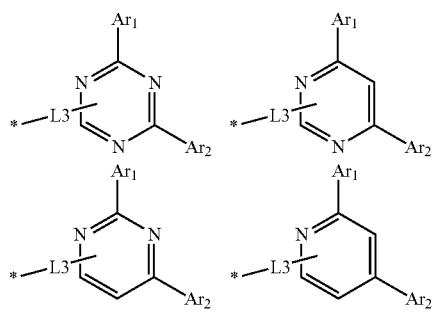

-continued

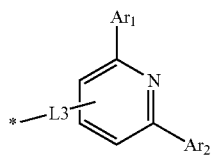

Ar1 and Ar2 are the same as or different from each other, and each independently a substituted or unsubstituted aryl group, or a substituted or unsubstituted heteroaryl group, and each L3 is the same as or different from each other, and each independently a direct bond, a phenyl group, a biphenyl group, a fluorene group, a naphthalene group or a carbazole group.

3. The compound of claim 2, wherein Ar1 and Ar2 are any one selected from the following substituents:

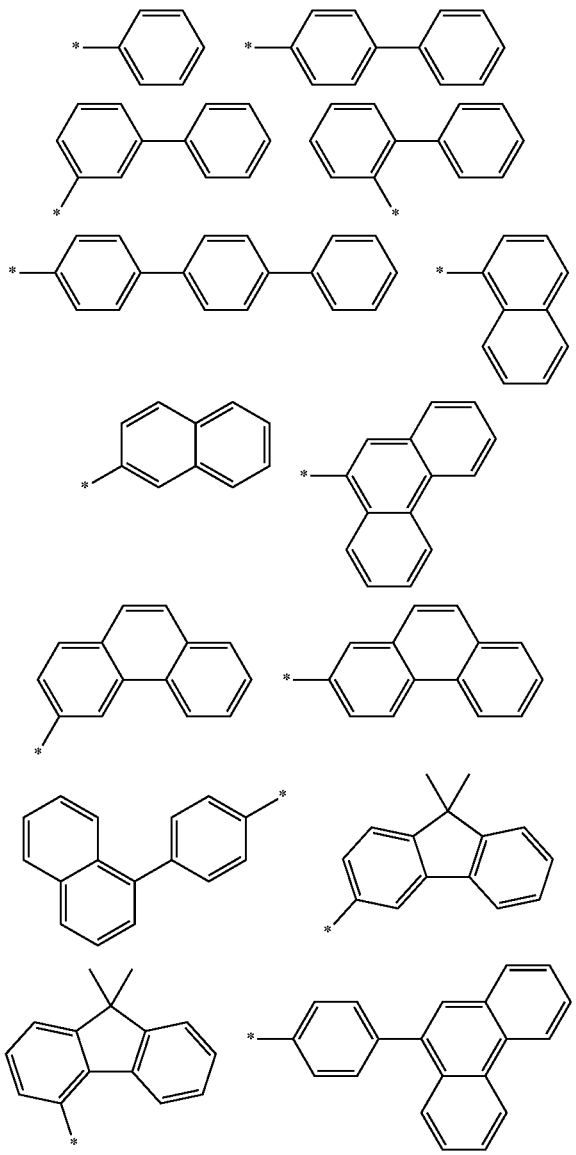

-continued

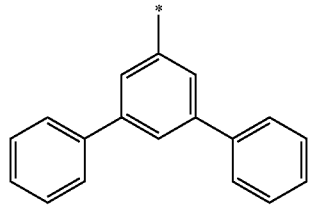

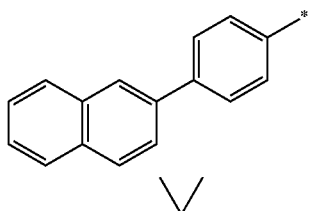

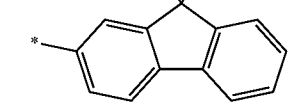

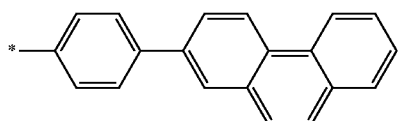

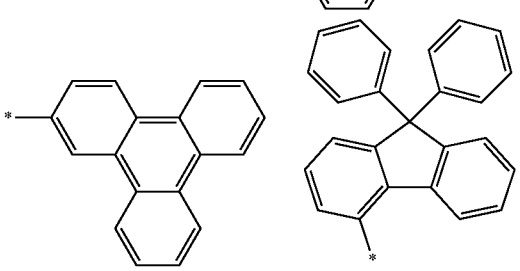

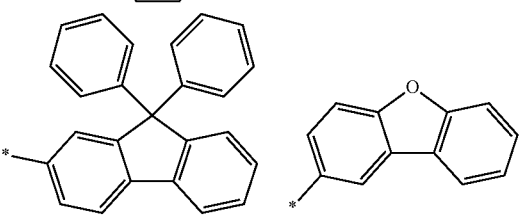

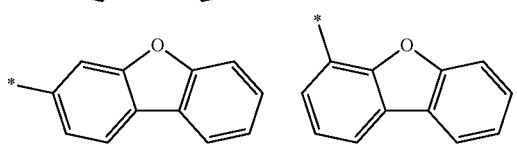

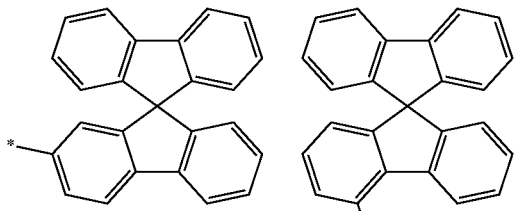

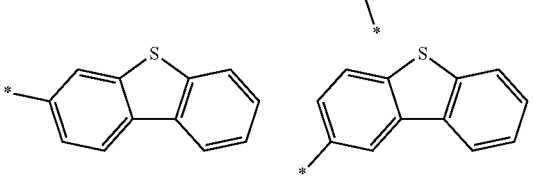

-continued

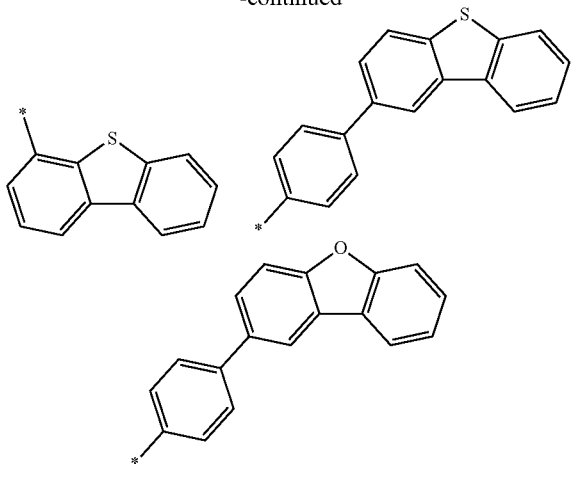

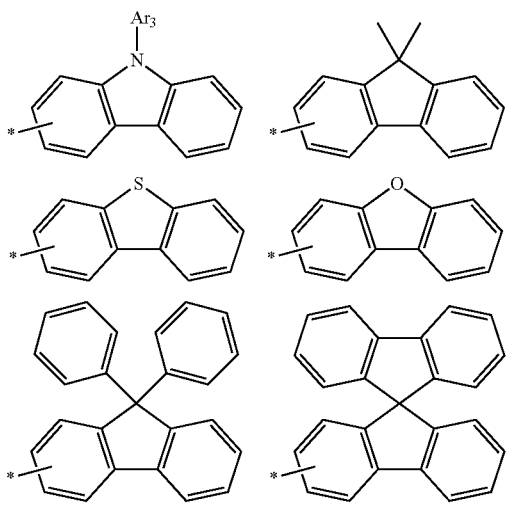

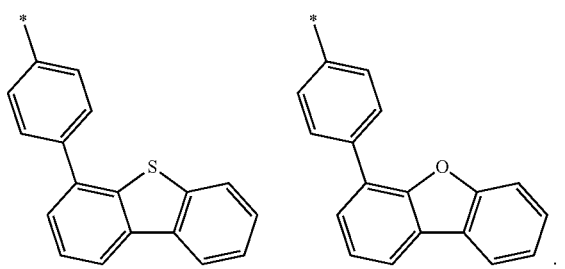 [SMILES: *c1ccc(-c2cccc3c2sc2ccccc23)cc1 ; *c1ccc(-c2cccc3c2oc2ccccc23)cc1 ; "."]

Ar3 is a methyl group, a phenyl group, a biphenyl group or a naphthalene group.

11. The compound of claim 1, wherein Chemical Formula 2 is any one selected from the following substituents:

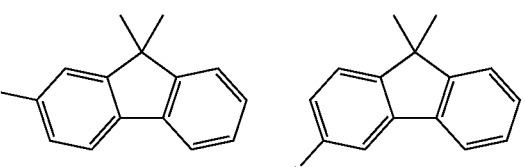

4. An organic light emitting device comprising:
   a first electrode,
   a second electrode provided opposite to the first electrode, and
   one or more organic material layers provided between the first electrode and the second electrode,
   wherein one or more layers of the one or more organic material layers include the compound of any one of claim 1.

5. The organic light emitting device of claim 4, wherein the one or more organic material layer includes a light emitting layer, and the light emitting layer includes the compound.

6. The organic light emitting device of claim 4, wherein the one or more organic material layer includes a hole injection layer, a hole transfer layer or an electron blocking layer, and the hole injection layer, the hole transfer layer or the electron blocking layer includes the compound as a host of the light emitting layer.

7. The organic light emitting device of claim 4, wherein the one or more organic material layer includes a hole blocking layer, an electron transfer layer or an electron injection layer, and the hole blocking layer, the electron transfer layer or the electron injection layer includes the compound.

8. The compound of claim 1, wherein Y is S, O or NRa.

9. The compound of claim 1, wherein the compound is represented by Chemical Formula 4, and at least one of L1 and L2 is a direct bond.

10. The compound of claim 1, wherein Chemical Formula 2 is any one selected from the following substituents:

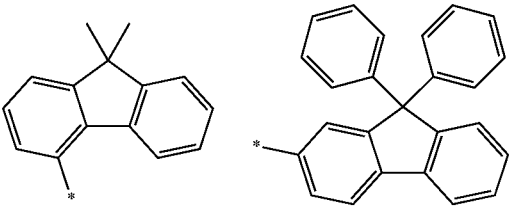

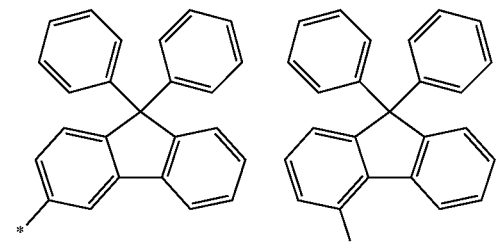

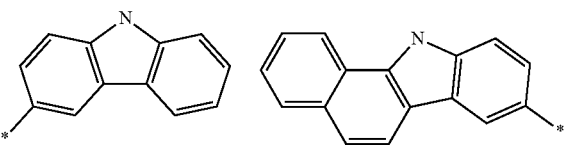

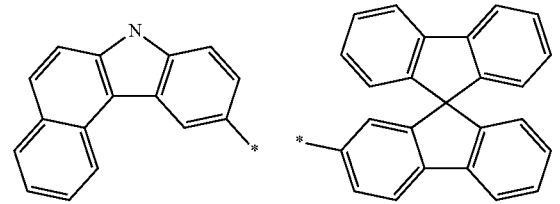

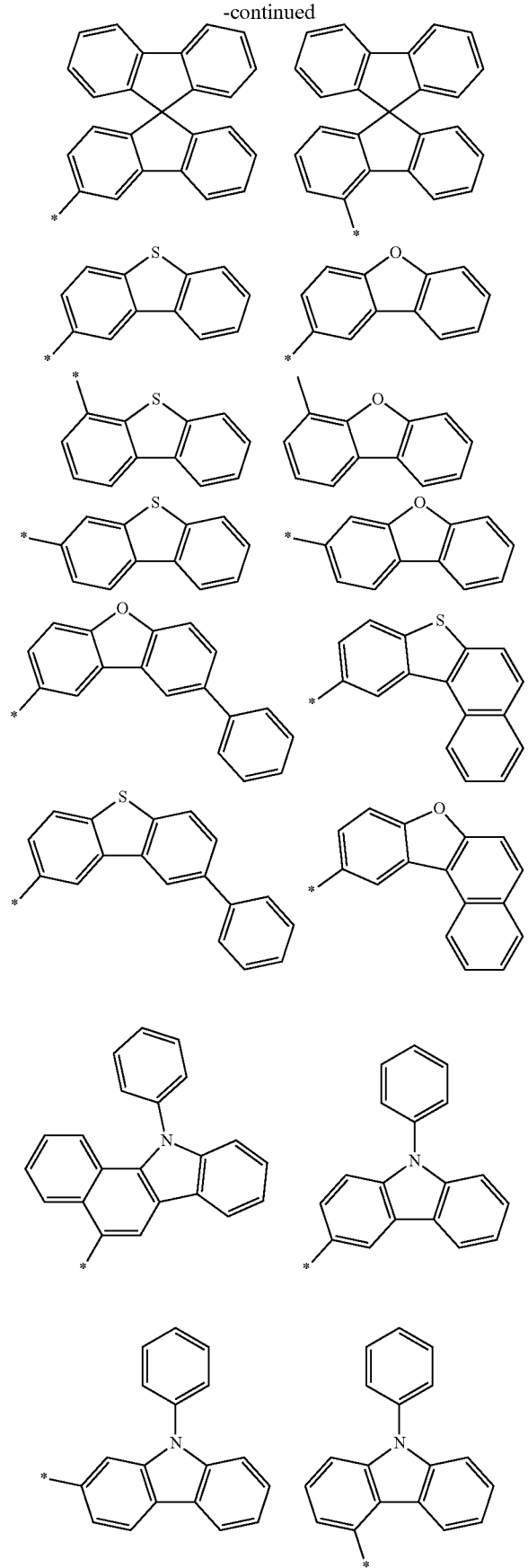
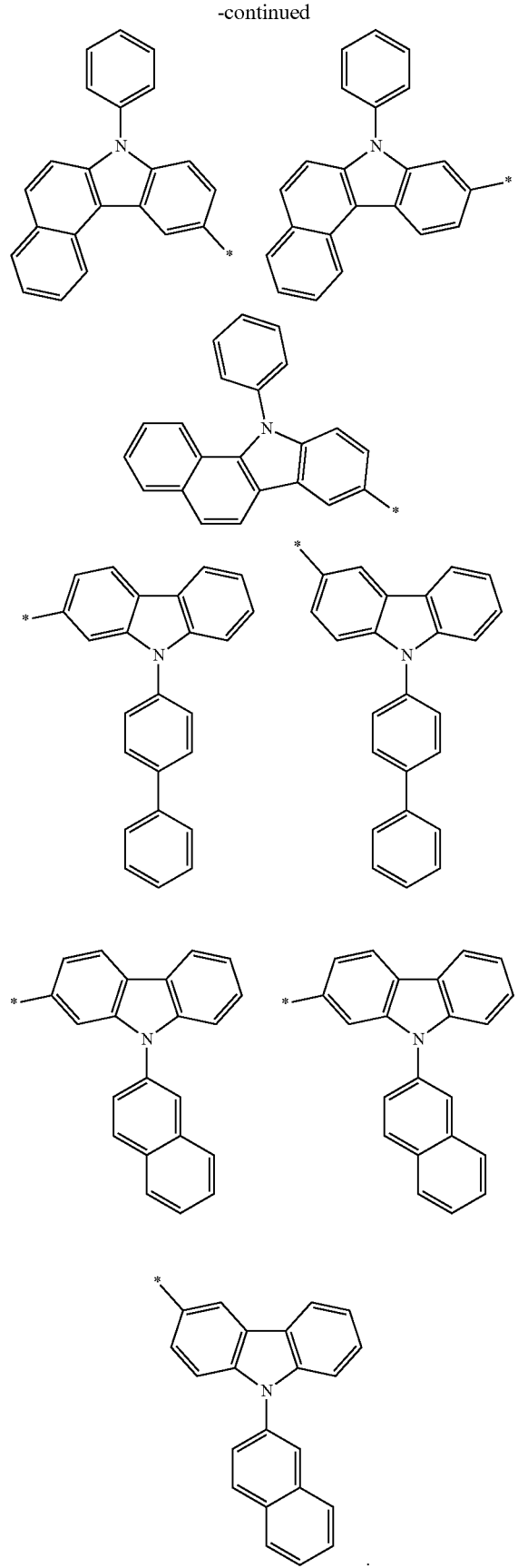

12. The compound of claim 1, wherein Chemical Formula 3 is any one selected from the following substituents:
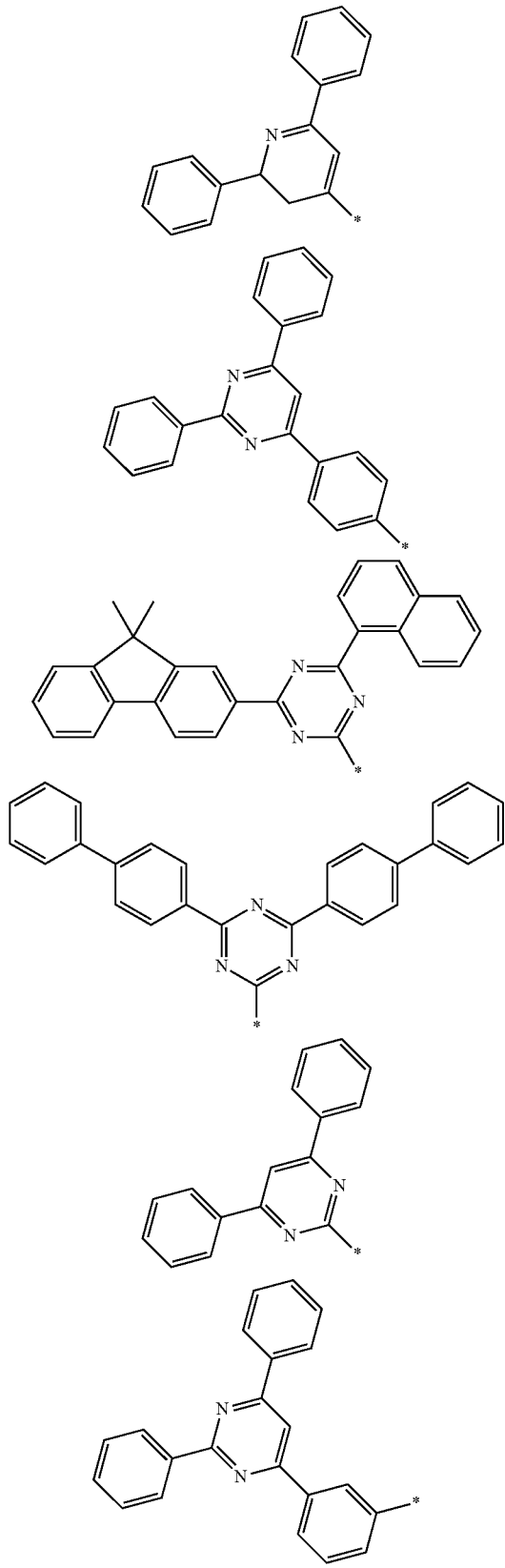
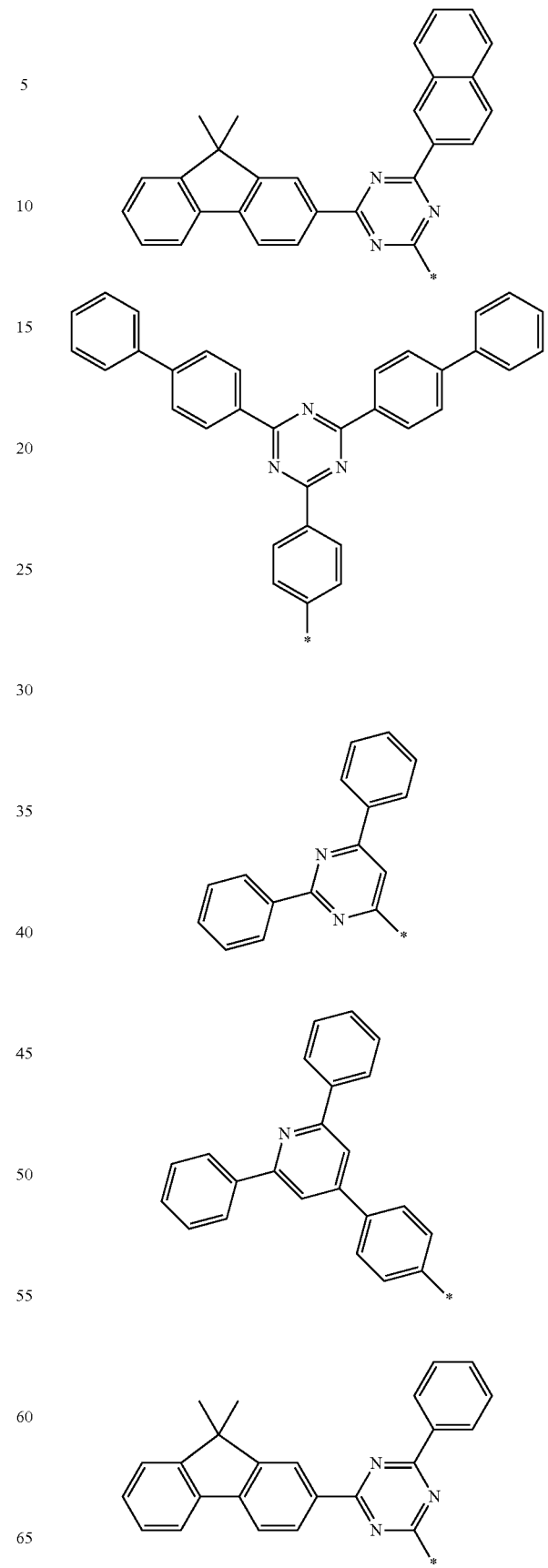

271
-continued
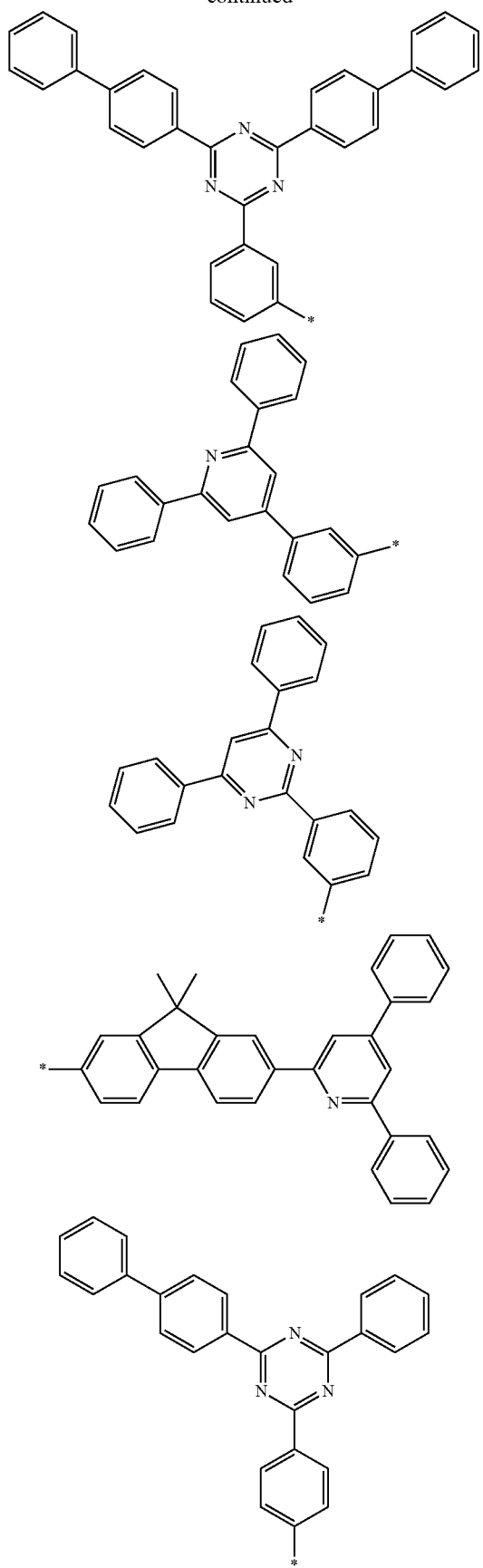
272
-continued
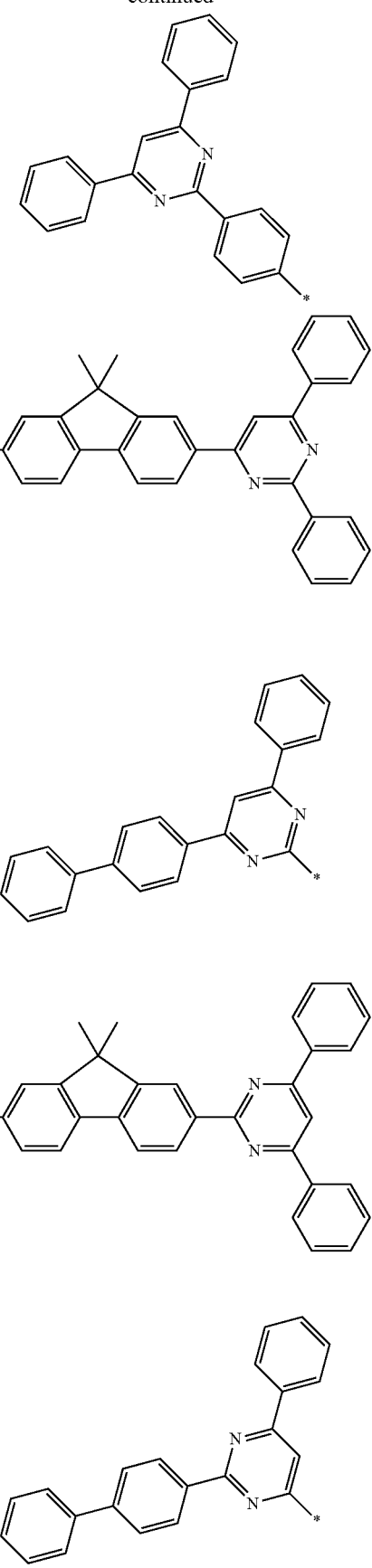

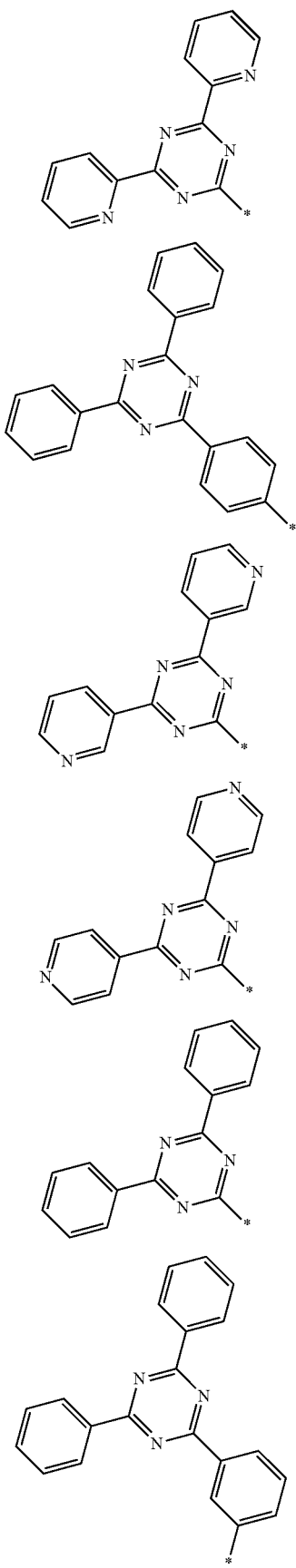
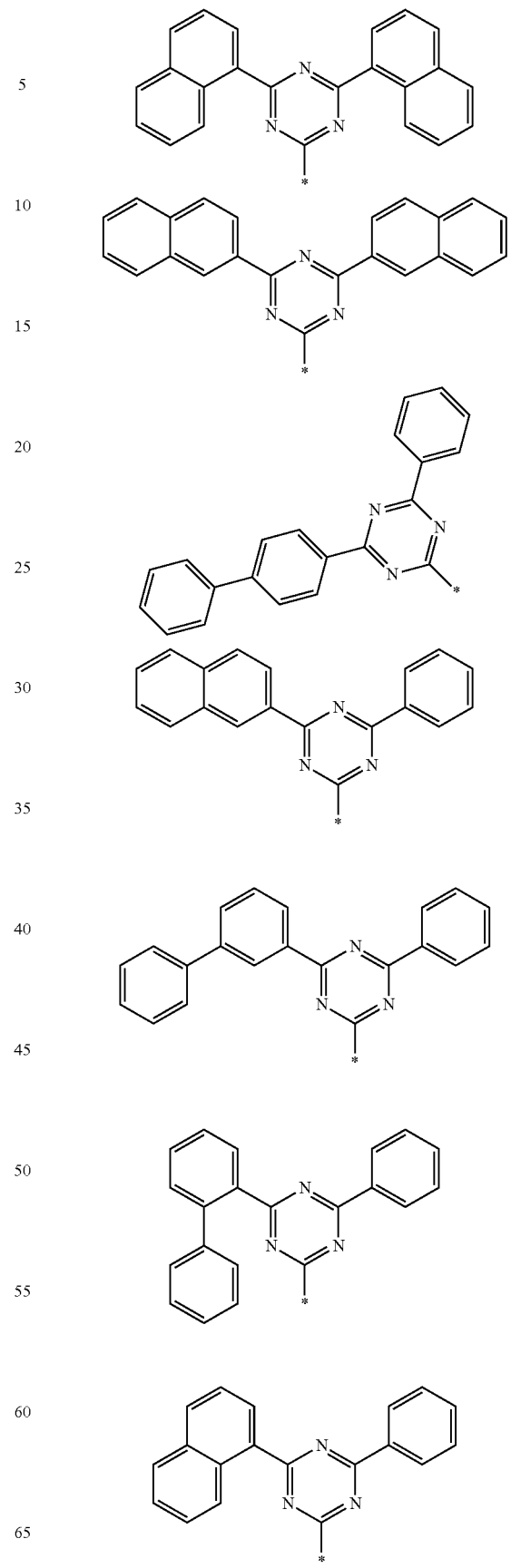

275
-continued
276
-continued
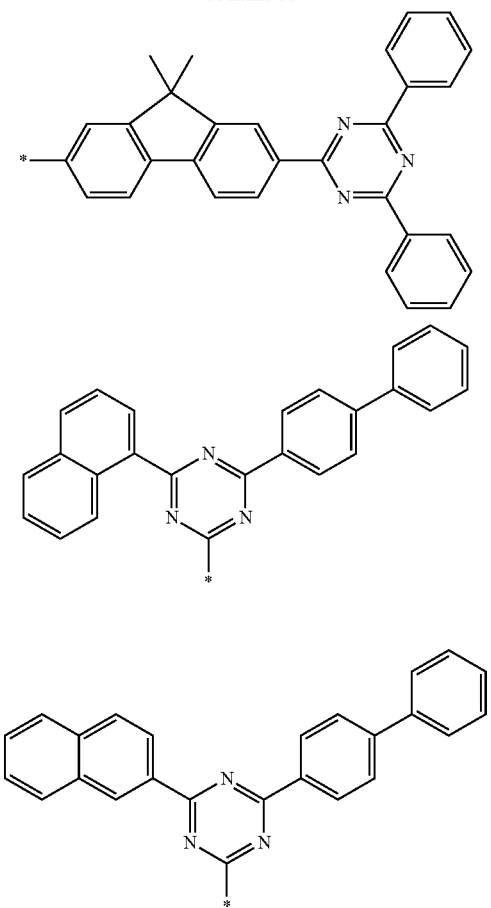
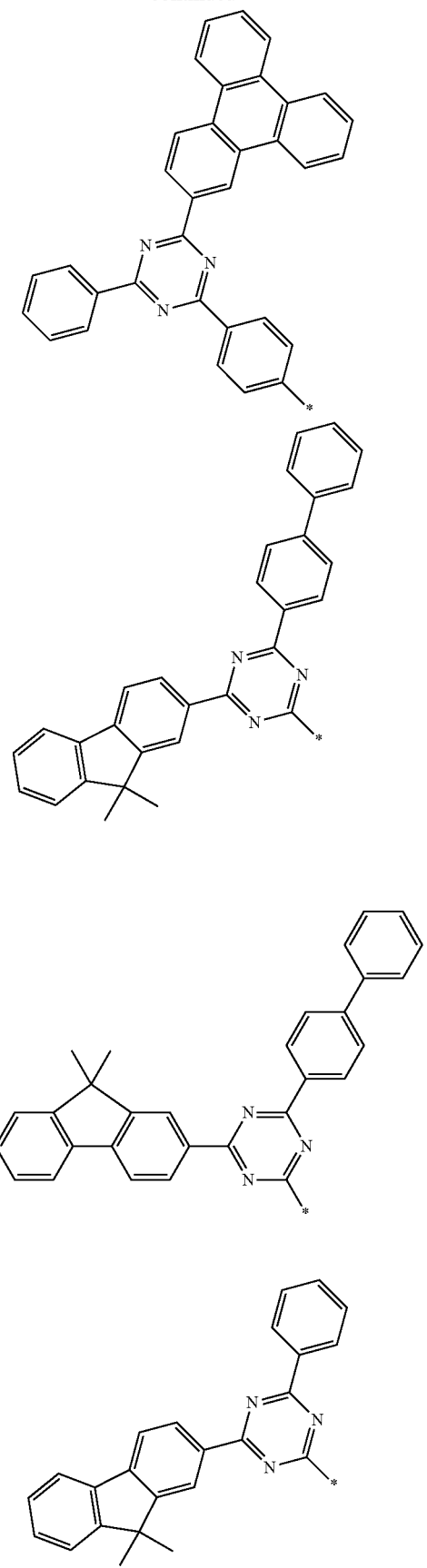

277
-continued
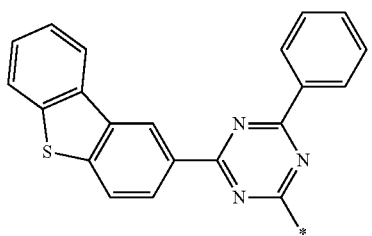
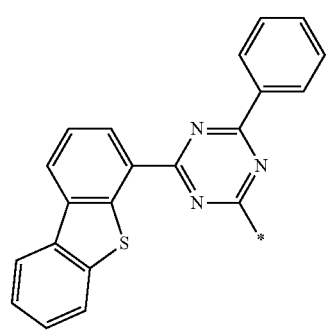
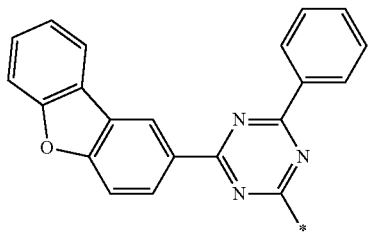
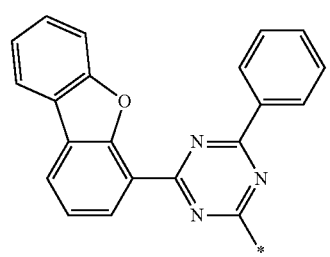
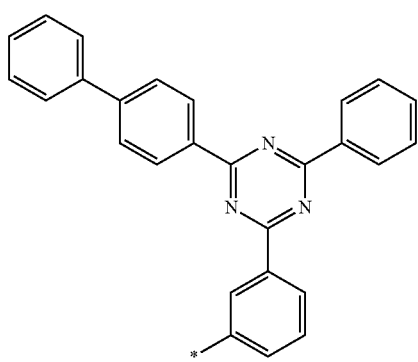
278
-continued
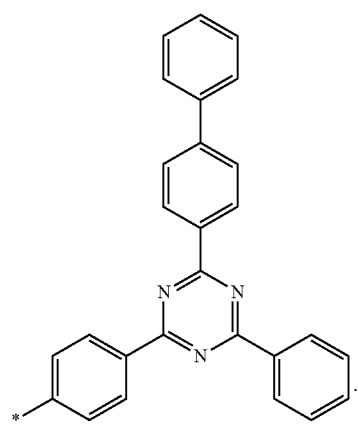
13. The compound of claim 1, wherein the compound is any one selected from the following compounds:
1-1
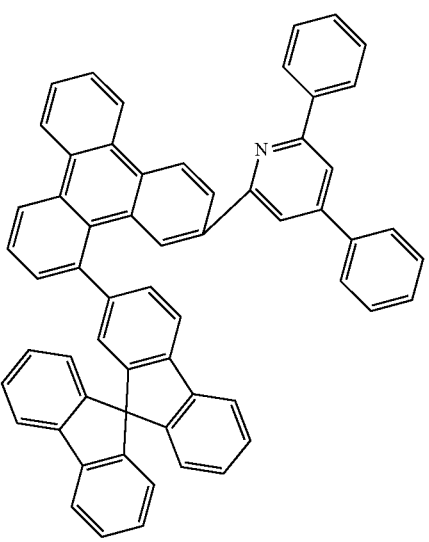
1-2
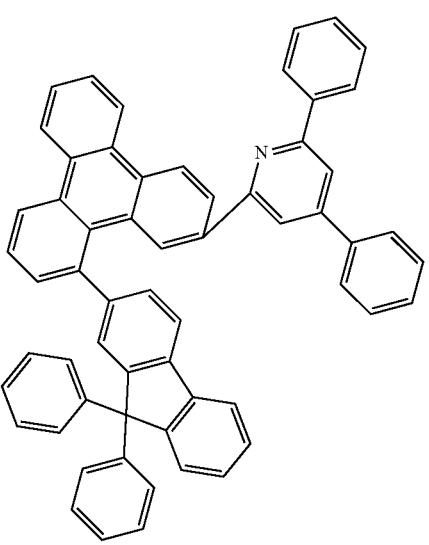

1-3
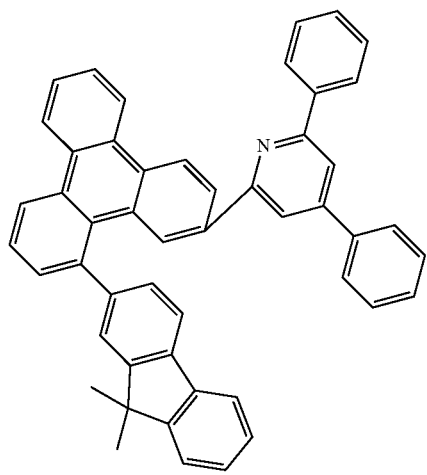
1-6
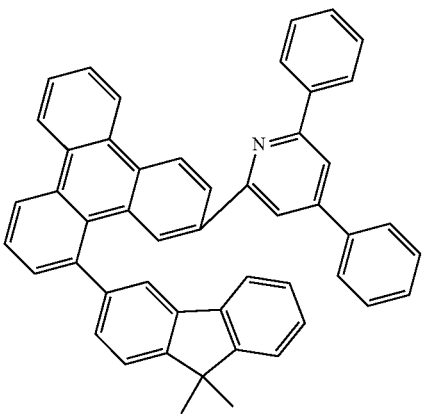
1-4
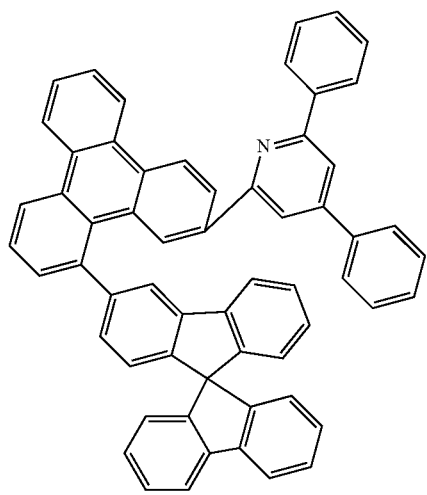
1-7
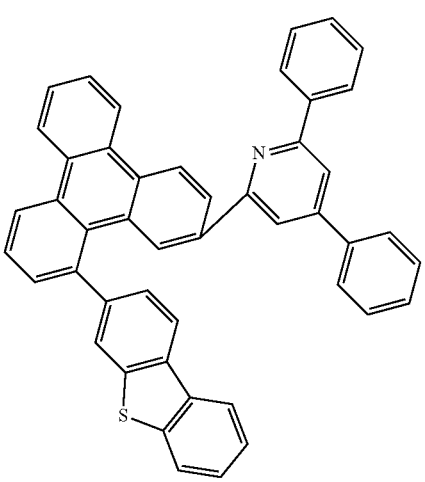
1-5
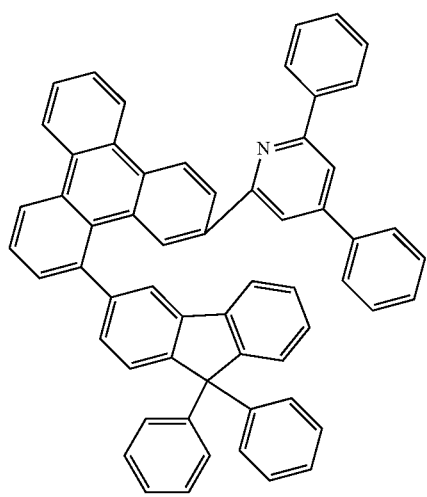
1-8
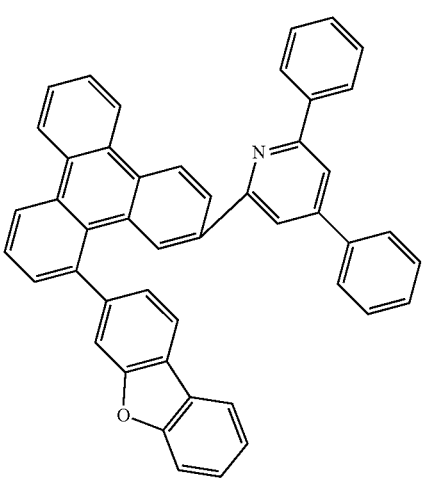

1-9
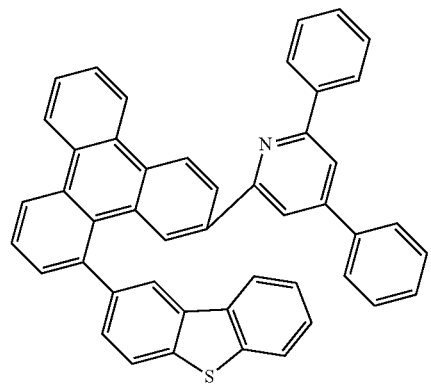
1-10
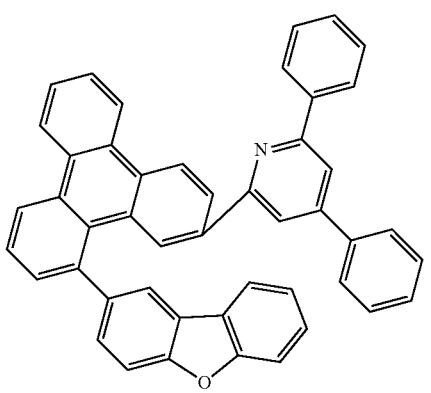
1-11
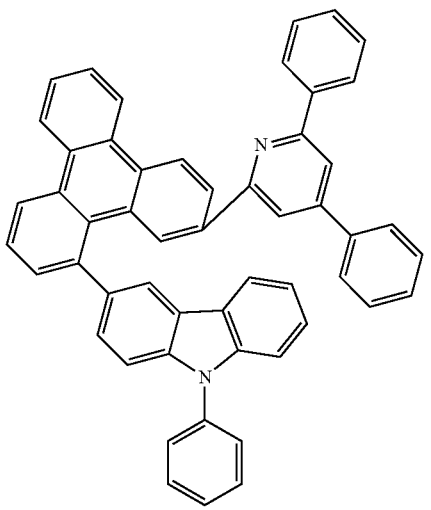
1-12
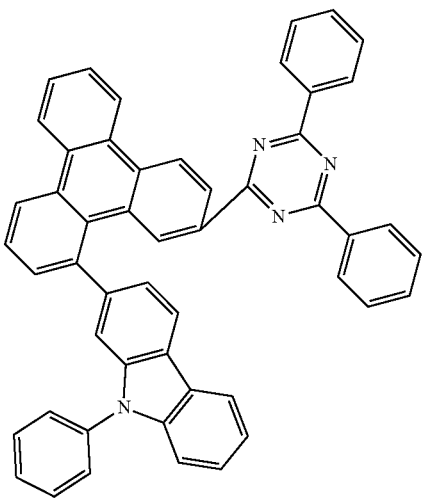
1-13
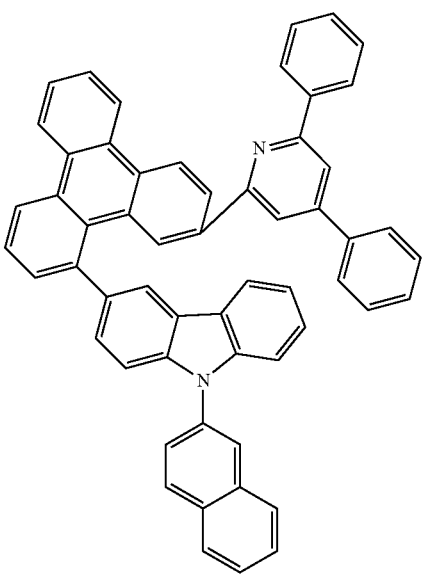
1-14
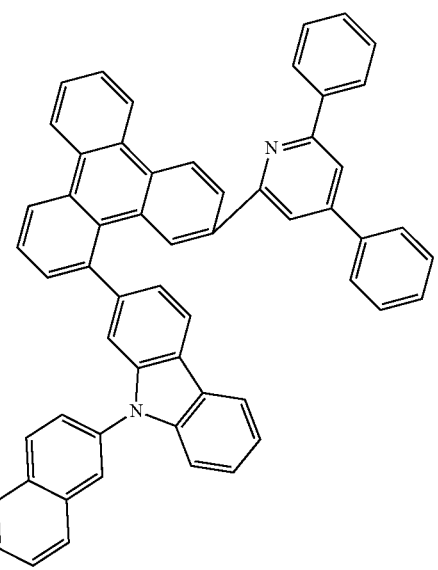

1-15
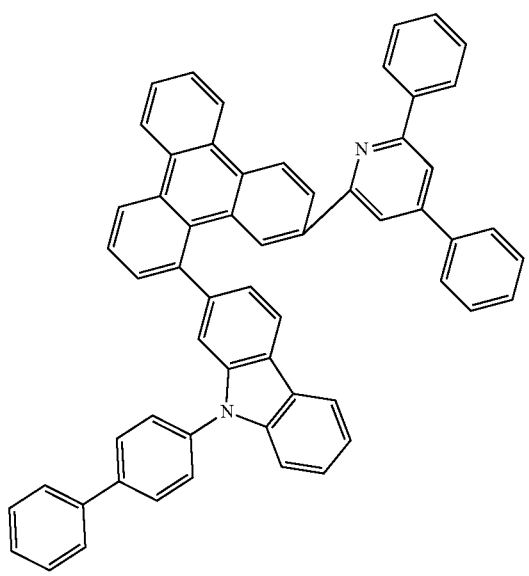
1-16
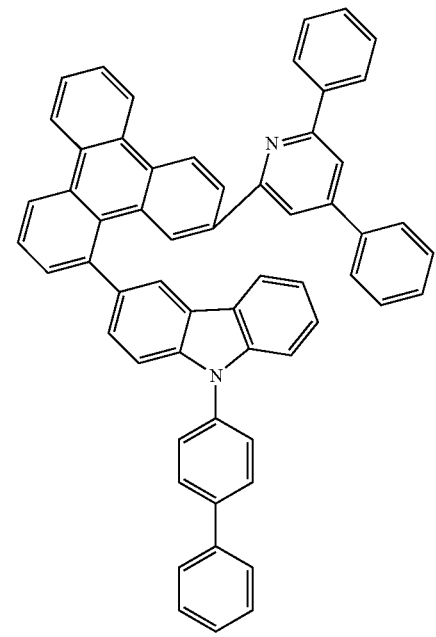
1-17
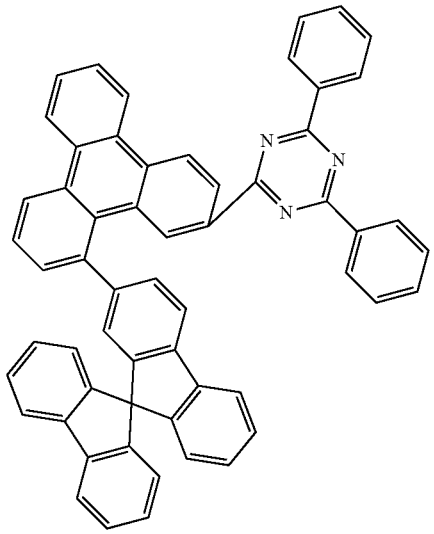
1-18
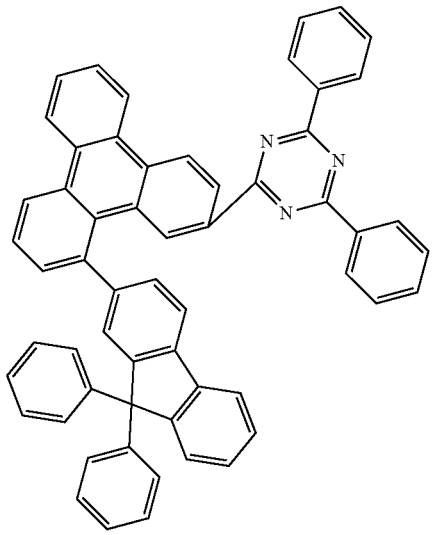
1-19
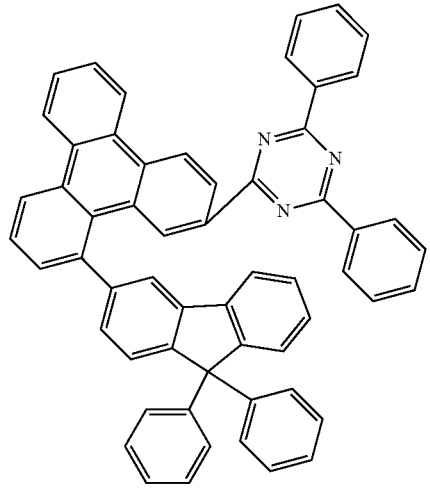

1-20
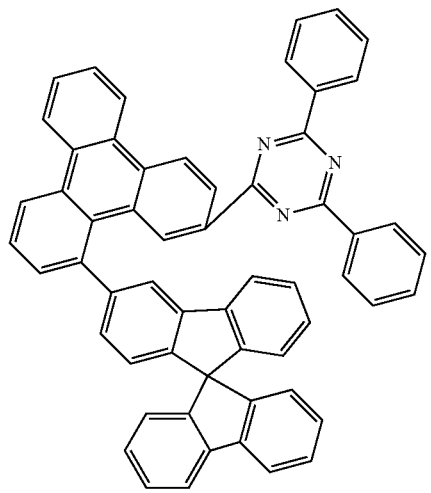
1-21
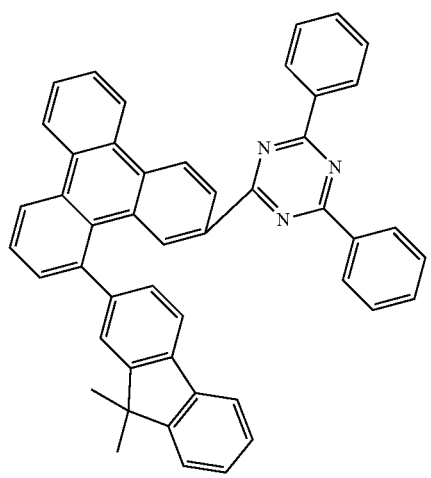
1-22
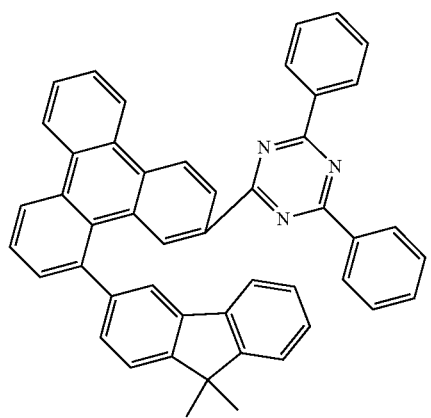
1-23
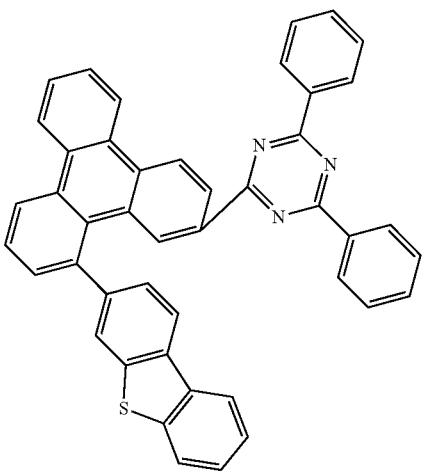
1-24
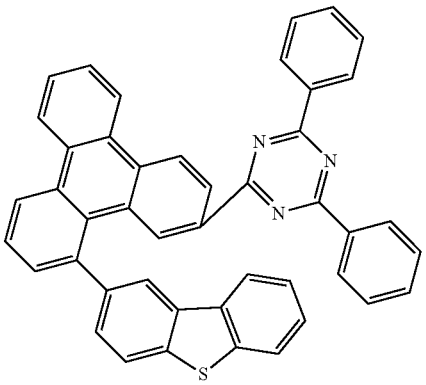
1-25
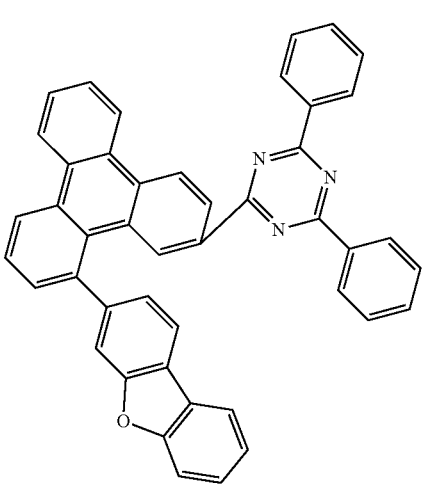

1-26
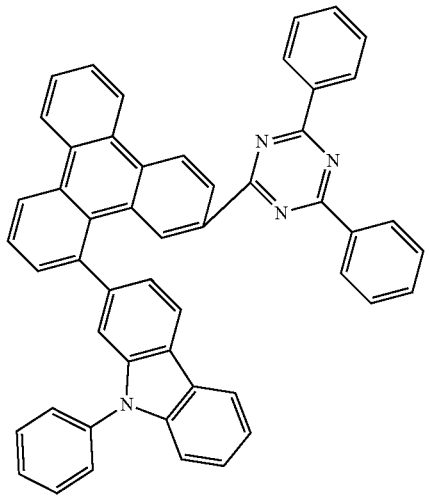
1-27
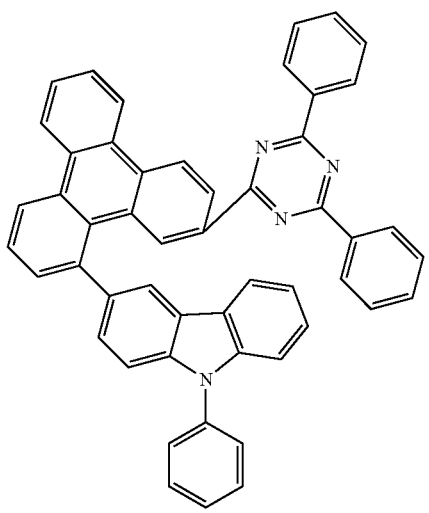
1-28
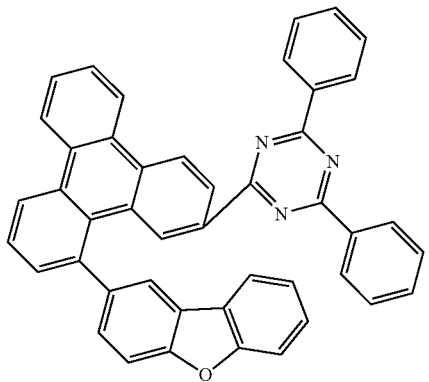
1-29
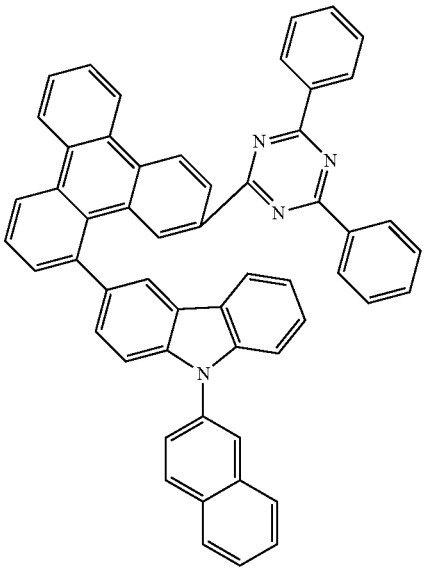
1-30
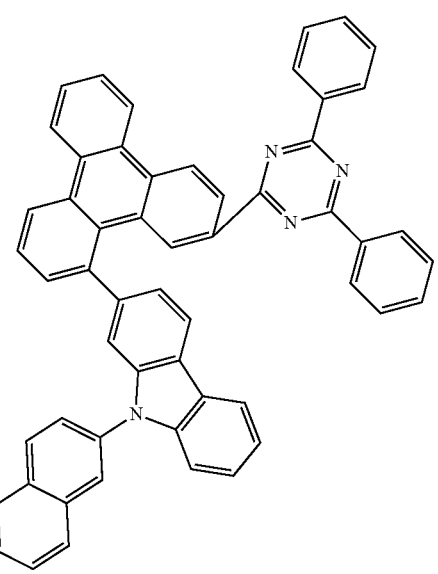

1-31
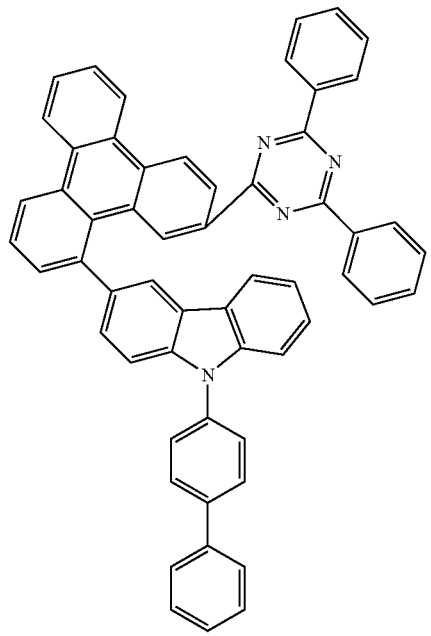
1-32
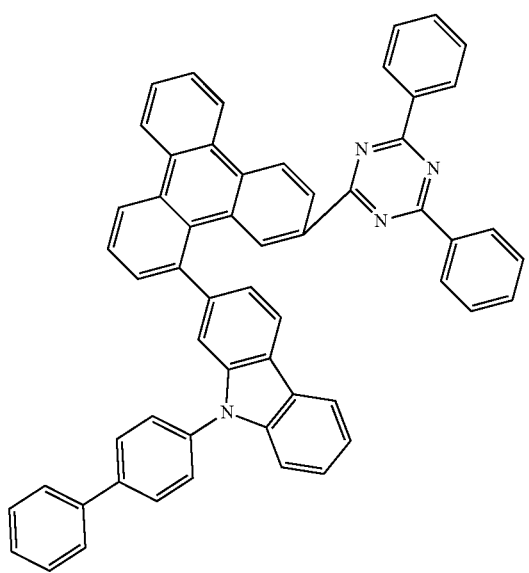
1-33
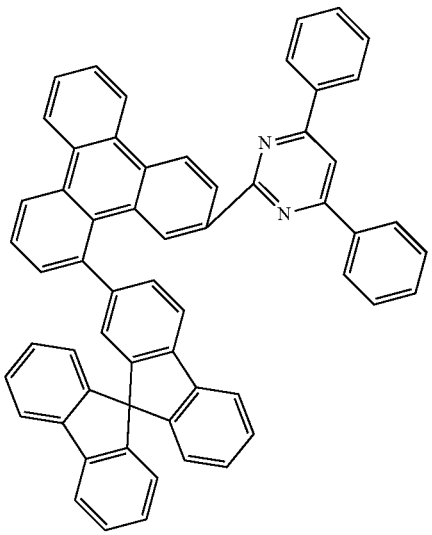
1-34
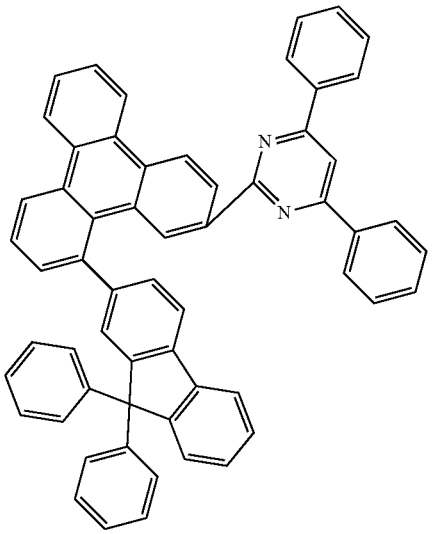
1-35
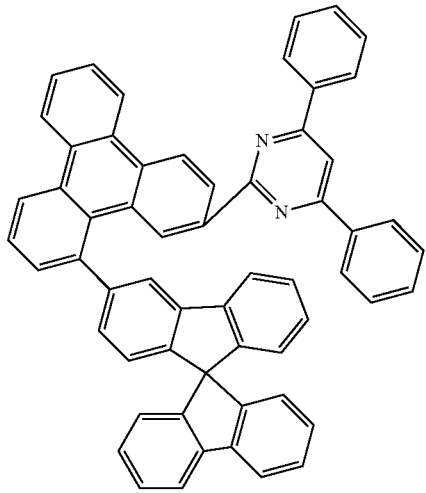

-continued 1-36

1-37

1-38

-continued 1-39

1-40

1-41

1-42
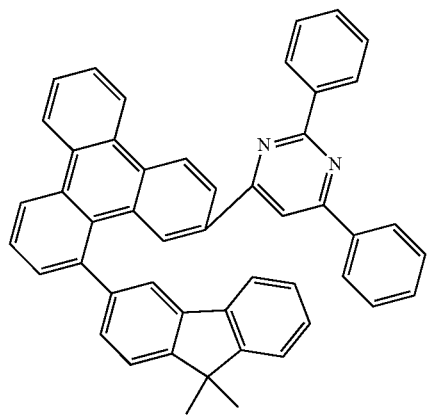
1-43
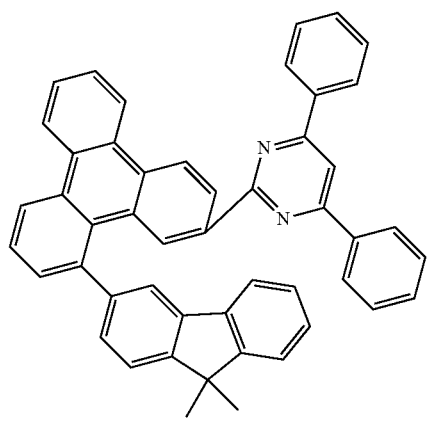
1-44
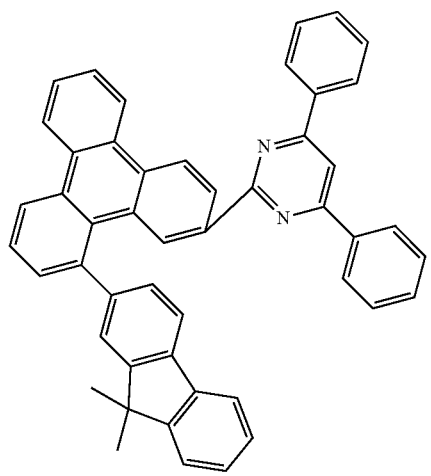
1-45
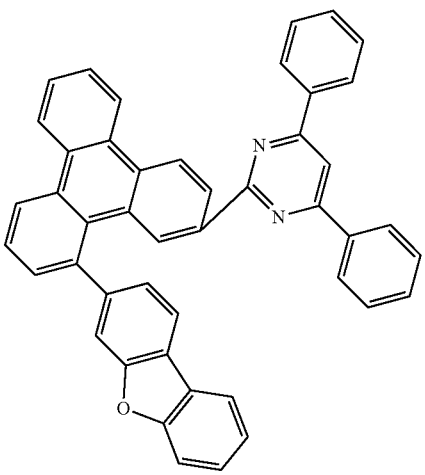
1-46
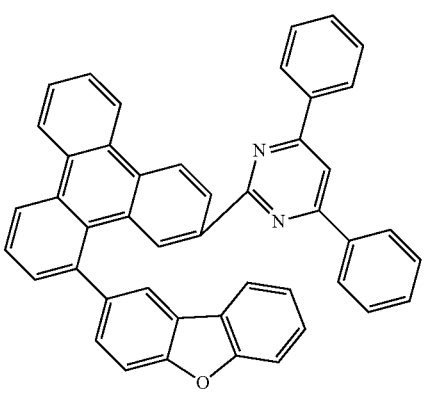
1-47
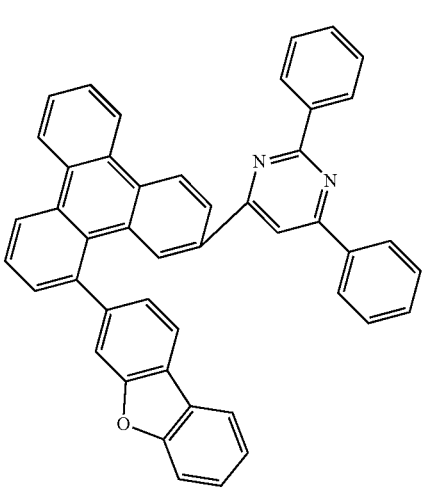

1-48
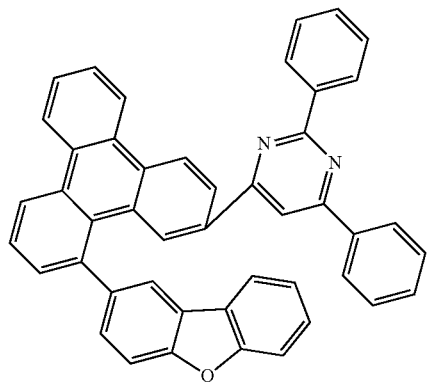
1-49
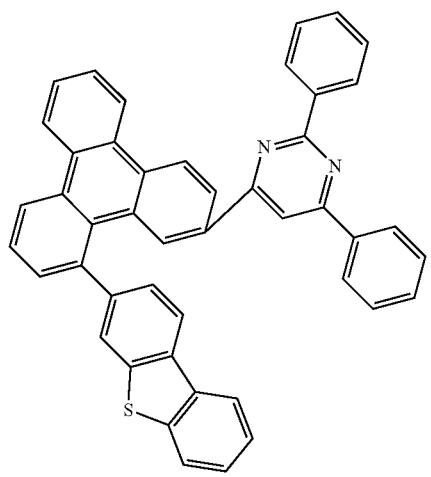
1-50
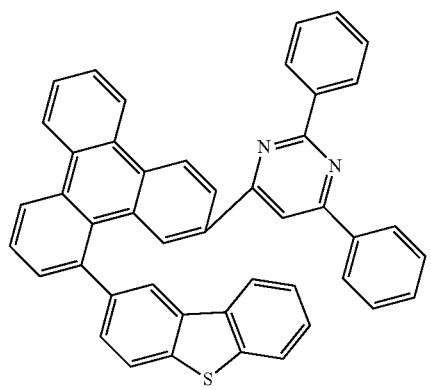
1-51
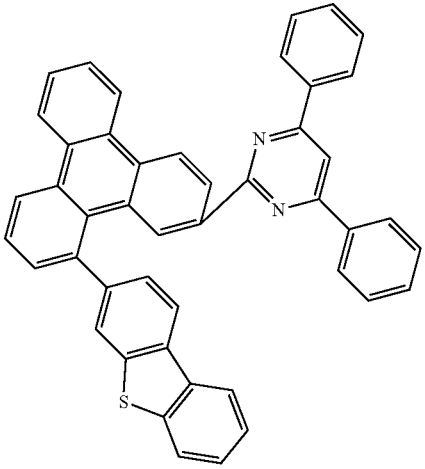
1-52
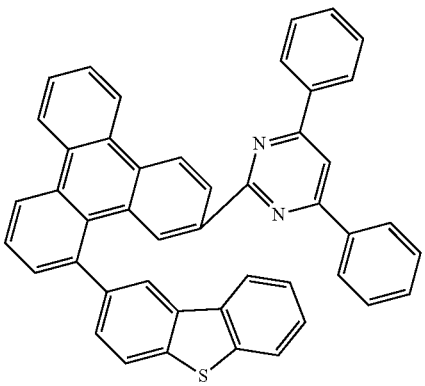
1-53
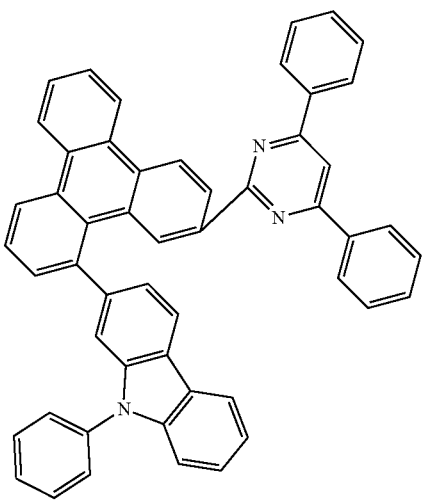

1-54
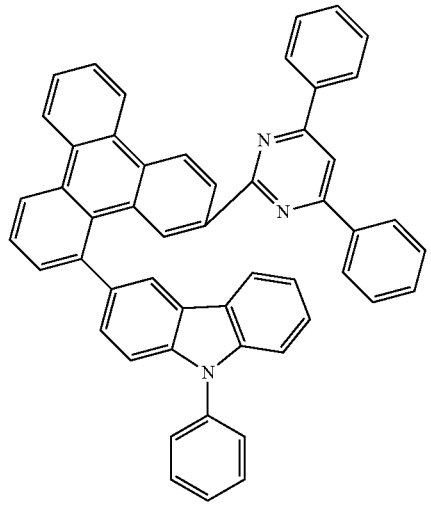
1-55
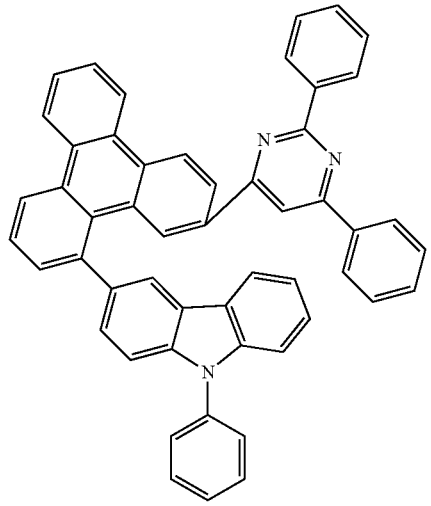
1-57
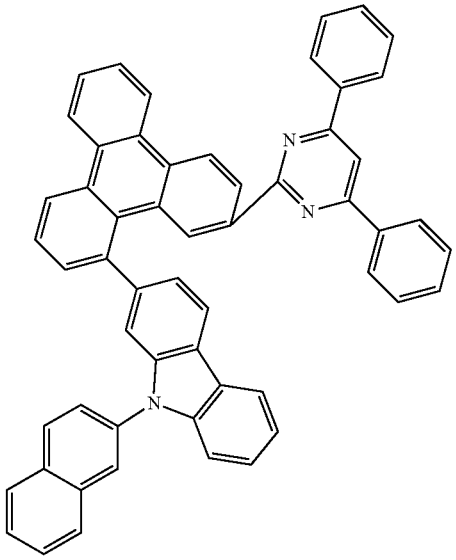
1-58
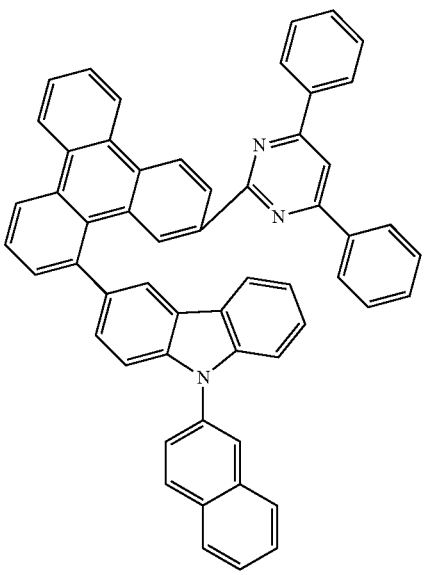
1-56

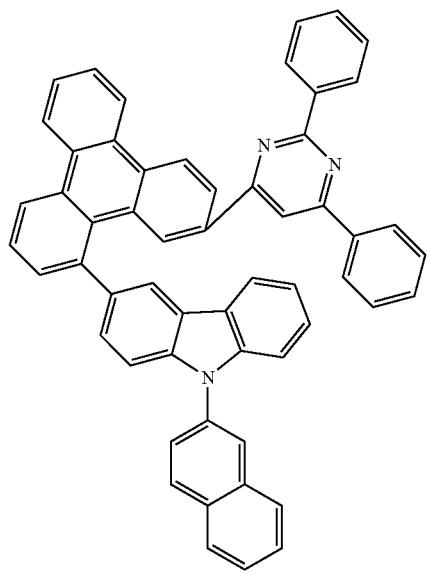
1-59
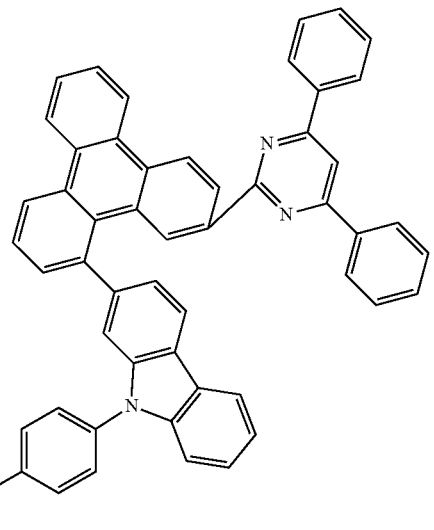
1-61
1-60
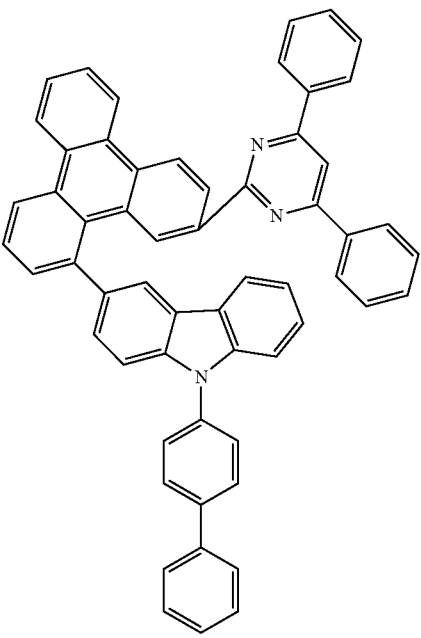
1-62

301
-continued
1-63
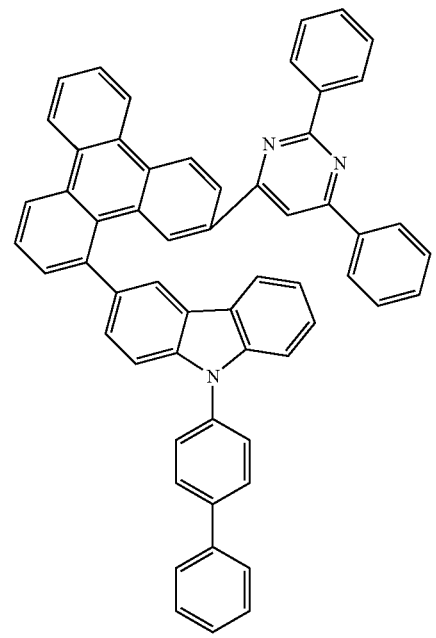
1-64
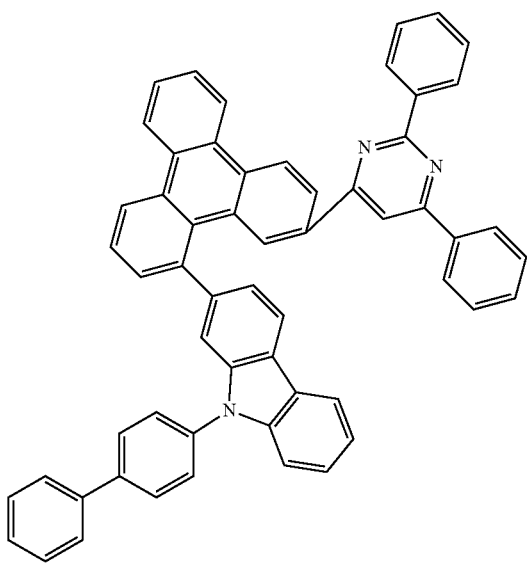
302
-continued
1-65
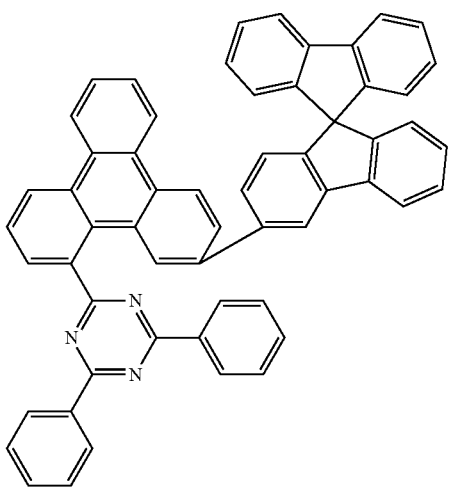
1-66
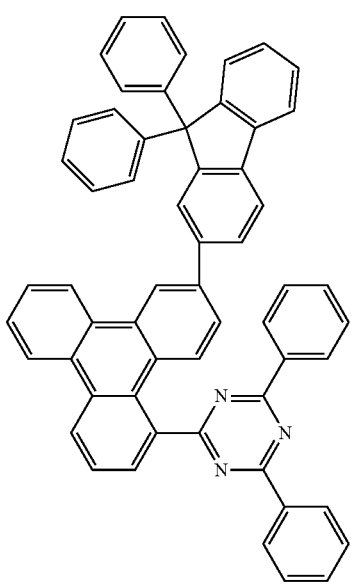
1-67
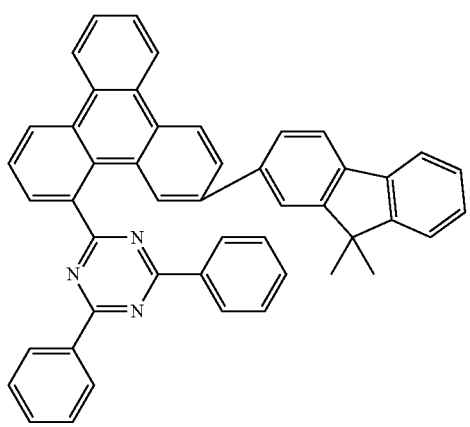

1-68
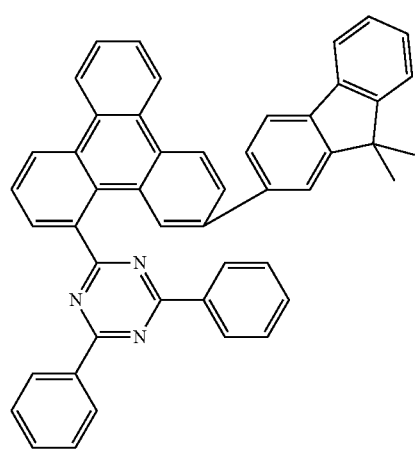
1-69
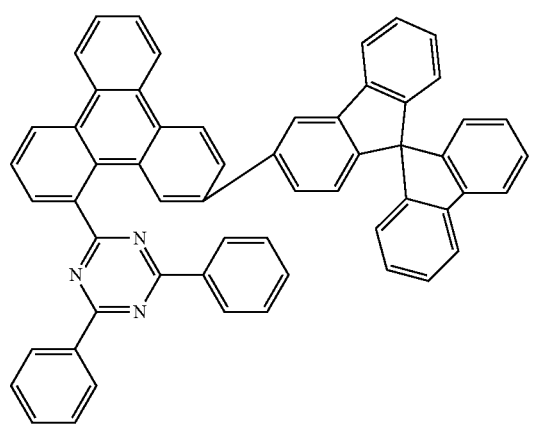
1-70
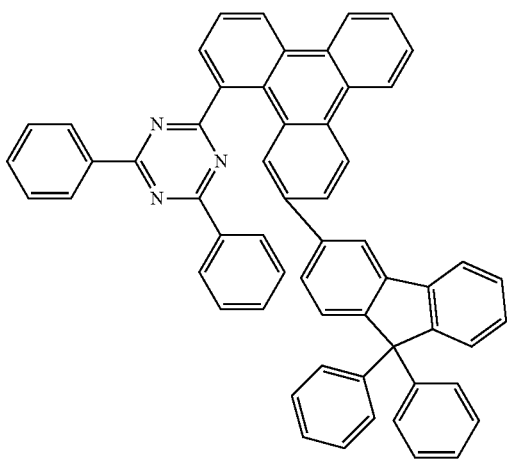
1-71
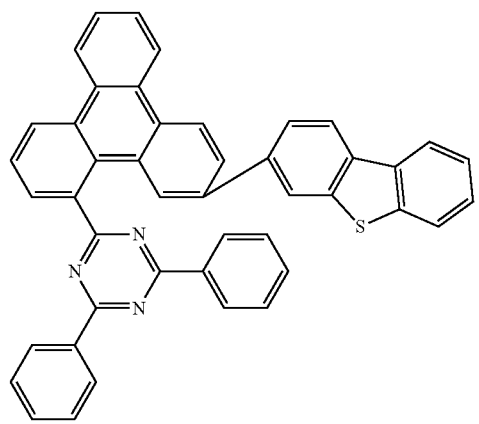
1-72
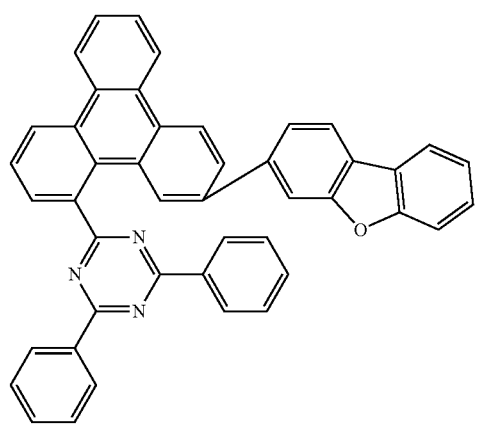
1-73
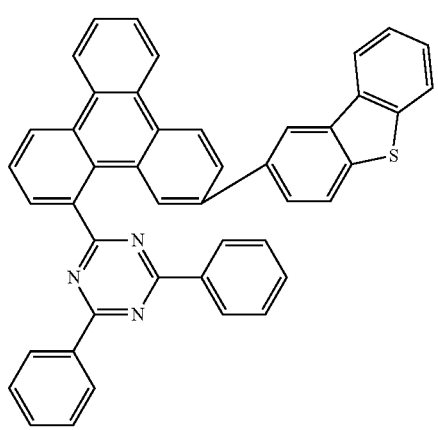

1-74
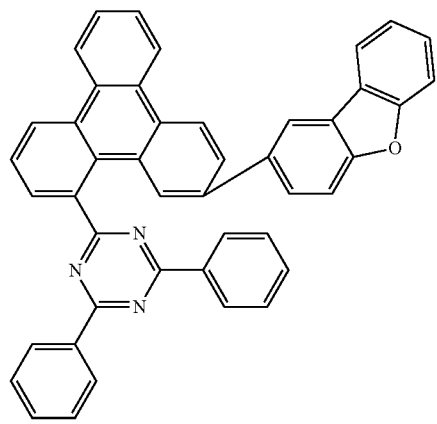
1-75
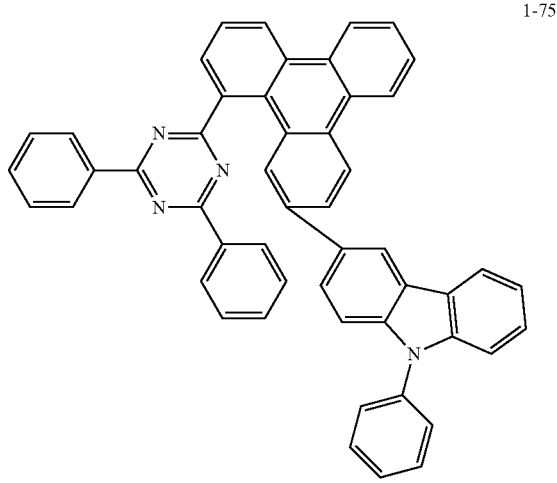
1-76
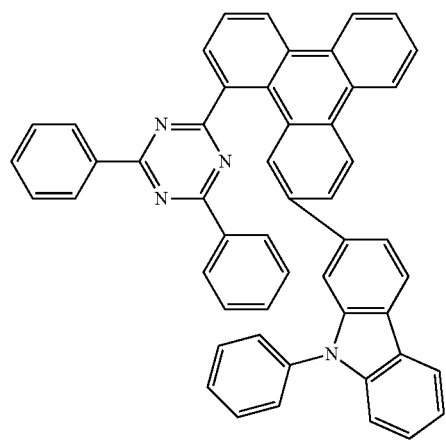
1-77
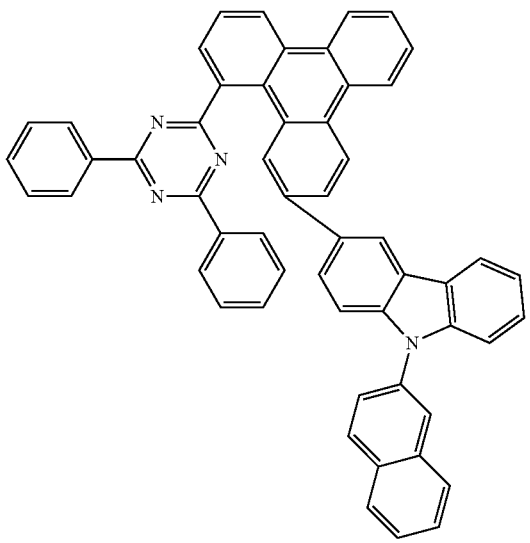
1-78
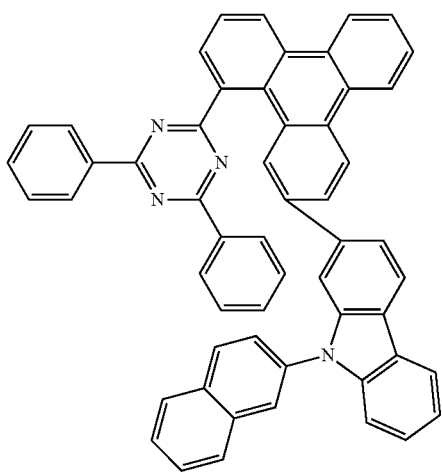
1-79
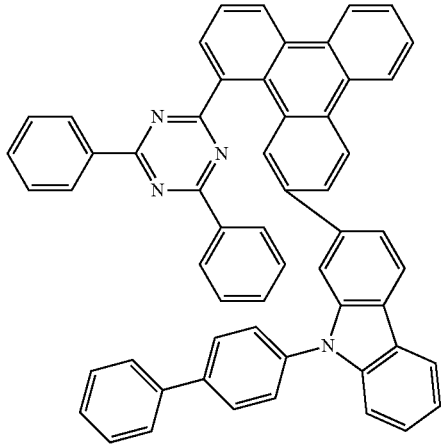

1-80
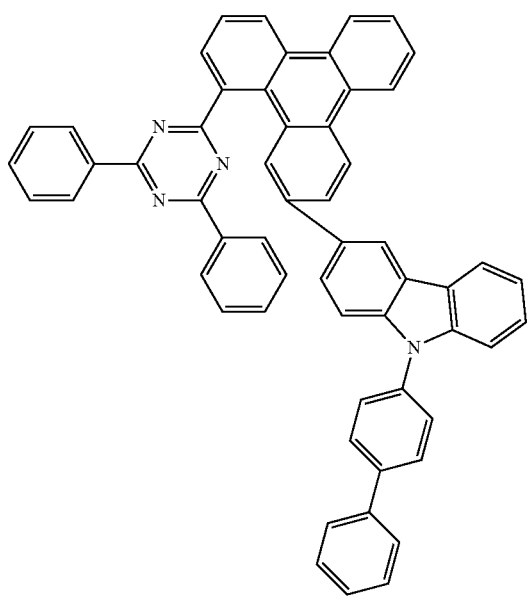
1-81
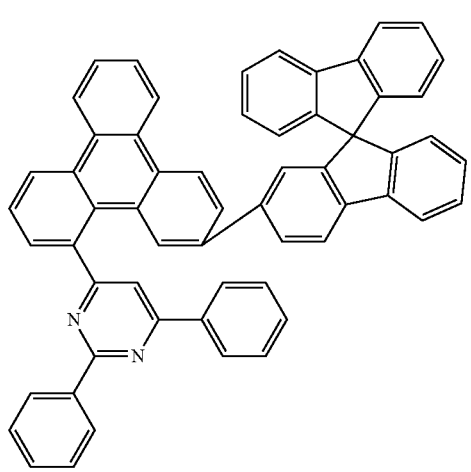
1-82
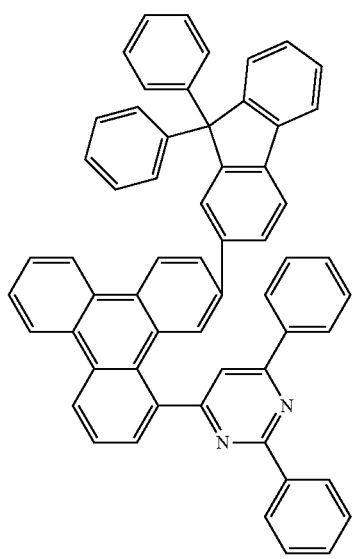
1-83
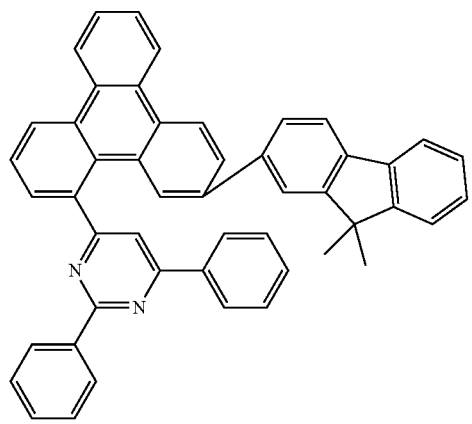
1-84
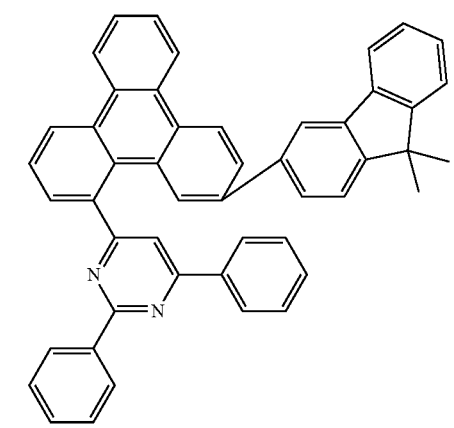
1-85
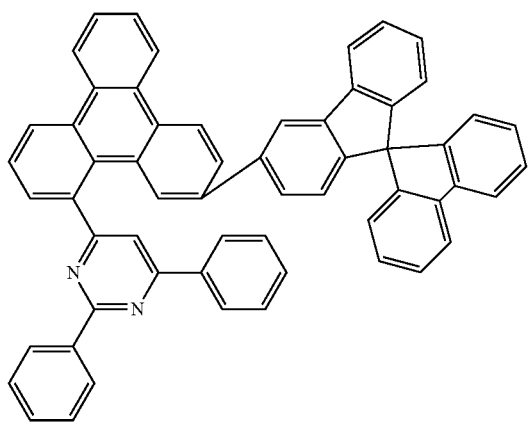

1-86
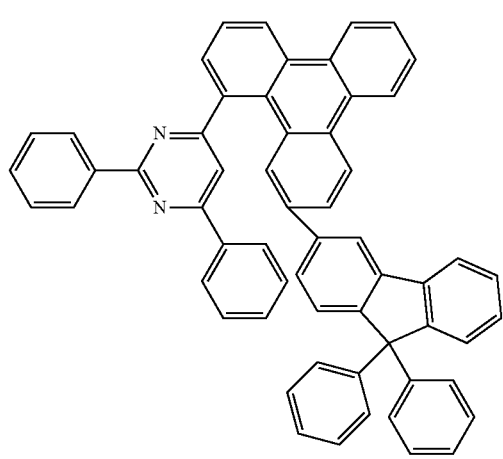
1-87
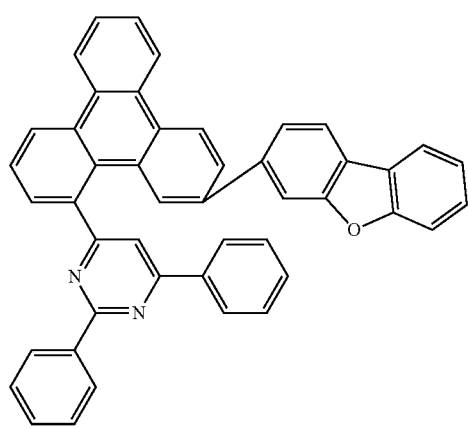
1-88
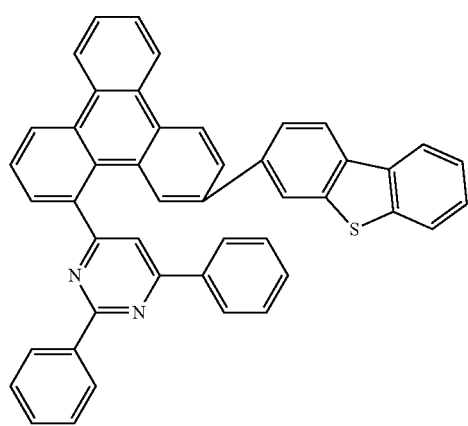
1-89
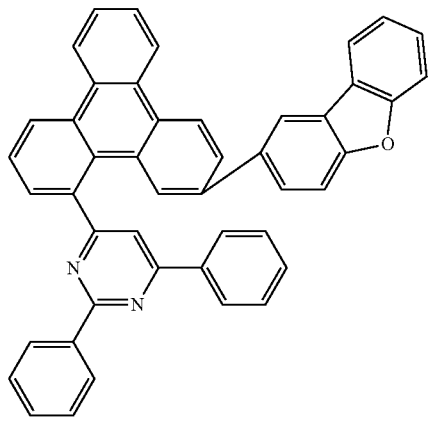
1-90
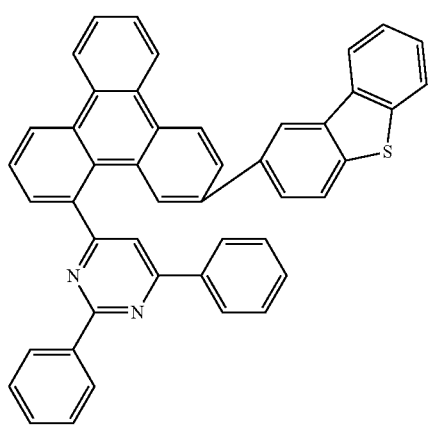
1-91
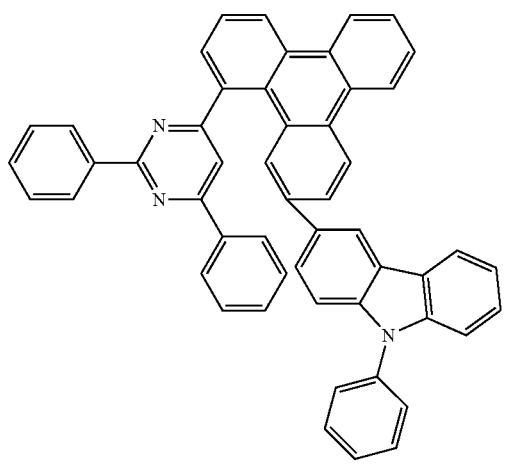

-continued
1-92
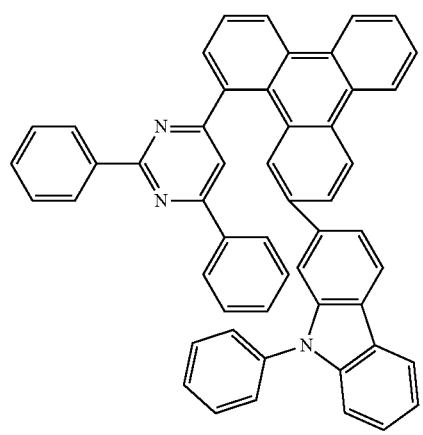
1-93
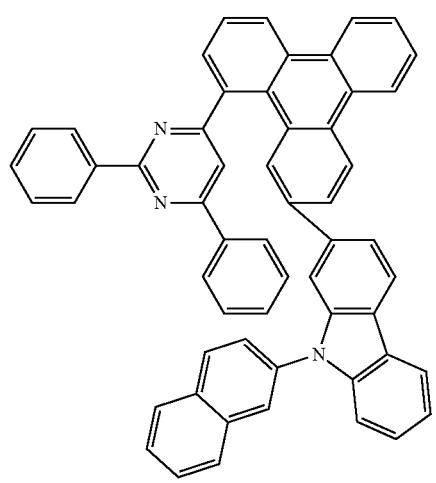
1-94
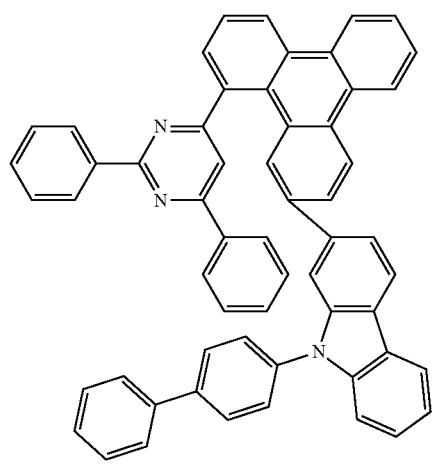
-continued
1-95
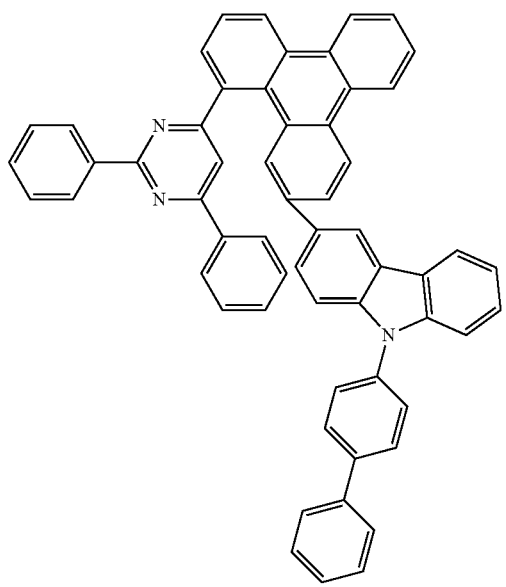
1-96
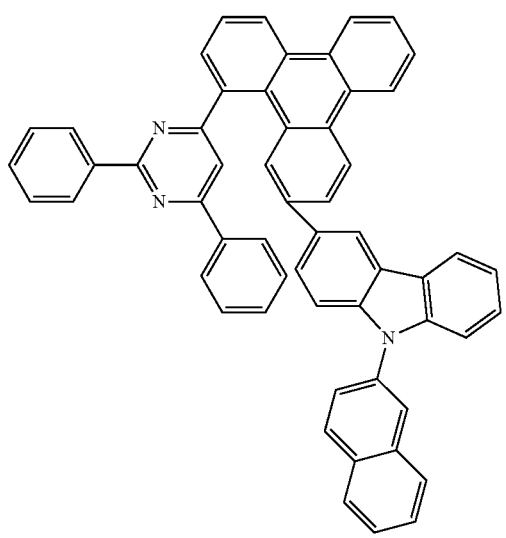
1-97
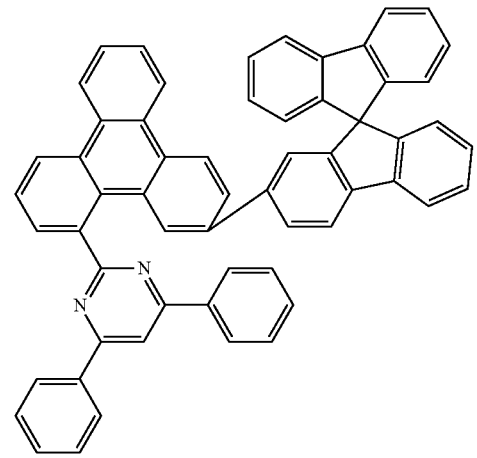

1-98
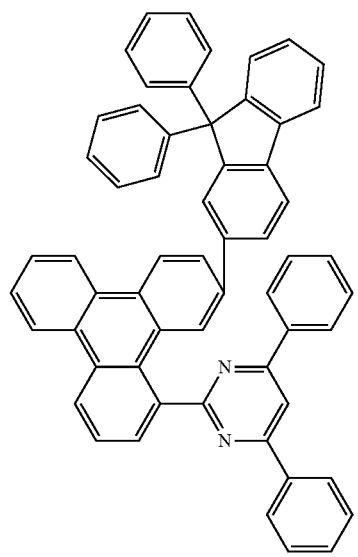
1-99
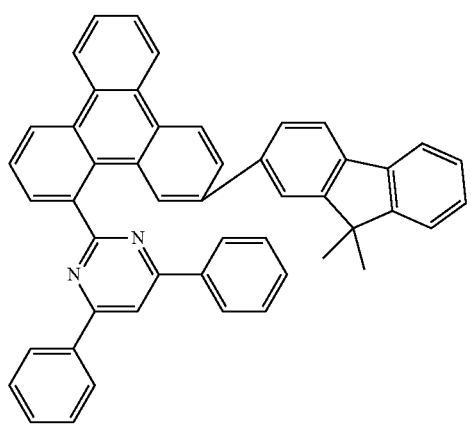
1-100
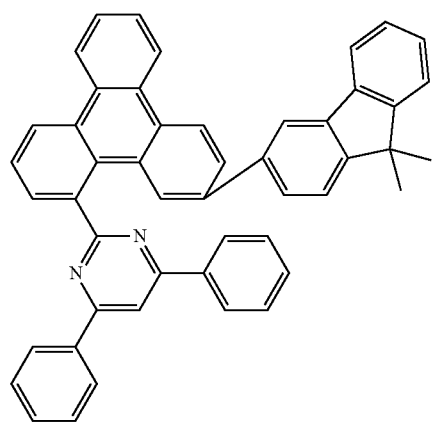
1-101
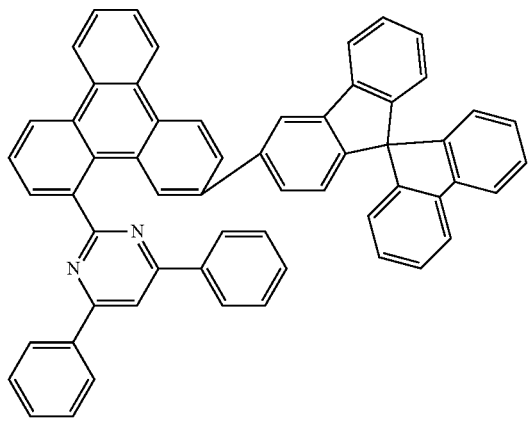
1-102
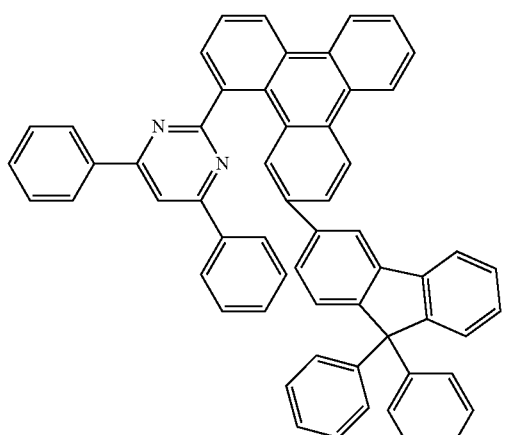
1-103
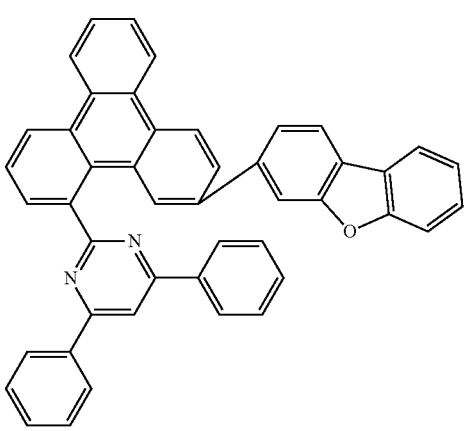

1-104
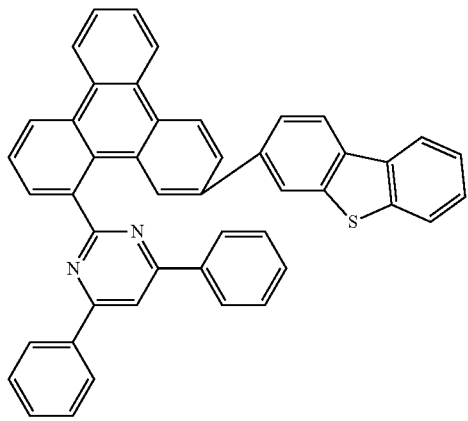
1-105
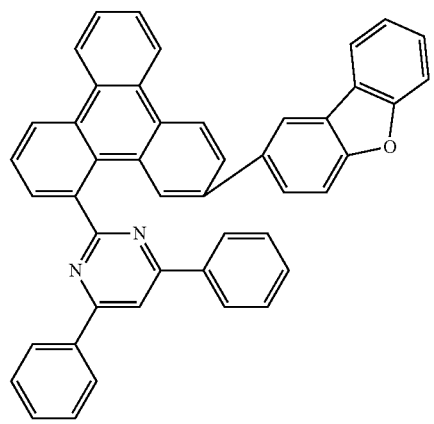
1-107
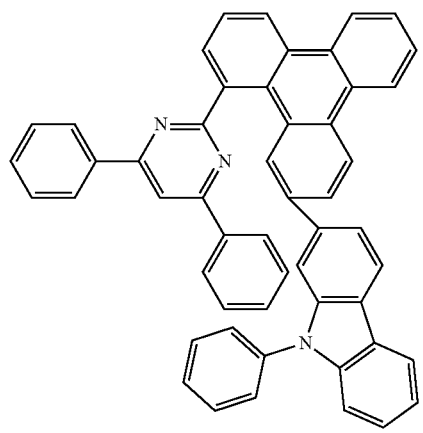
1-106
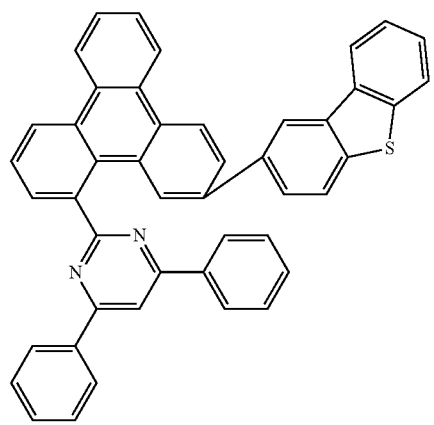
1-108
1-109
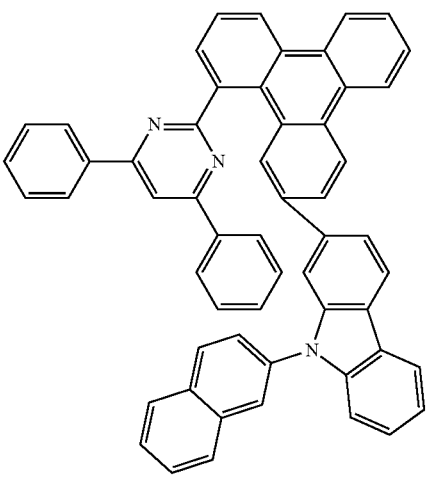

1-110
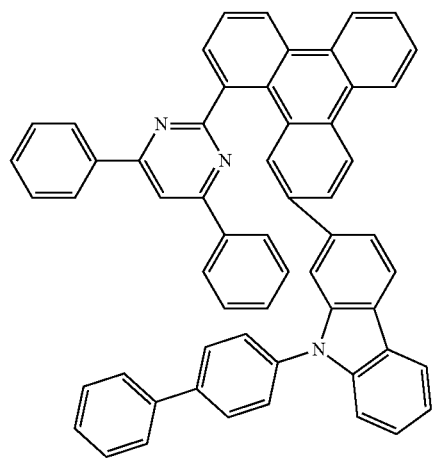
1-111
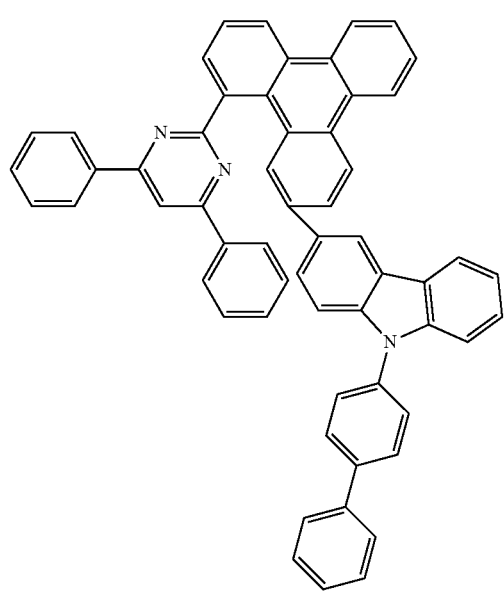
1-112
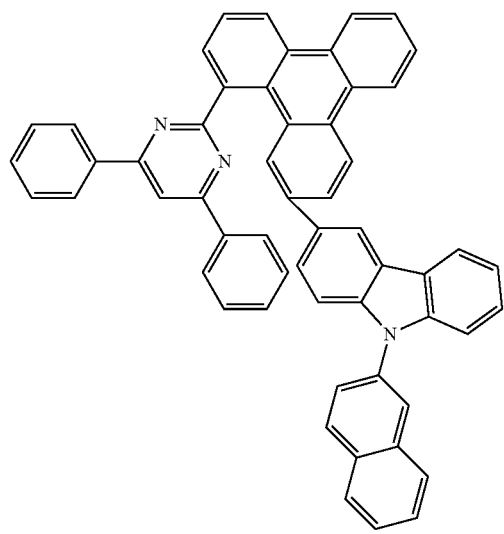
1-113
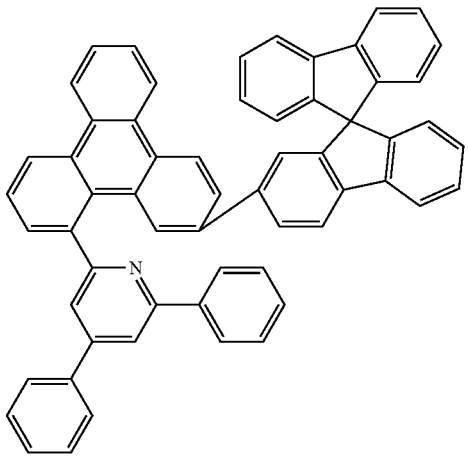
1-114
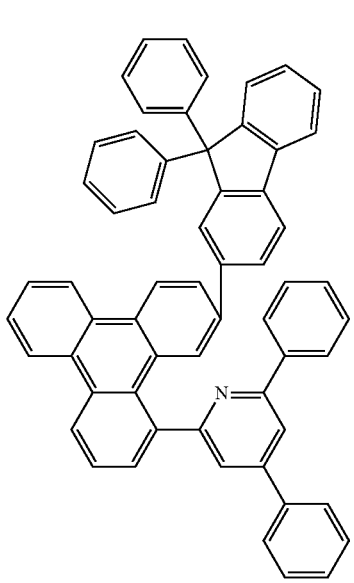
1-115
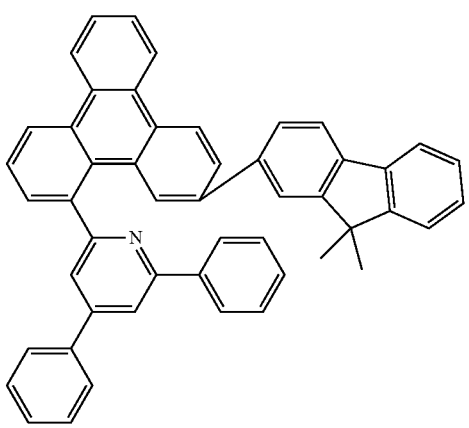

1-116
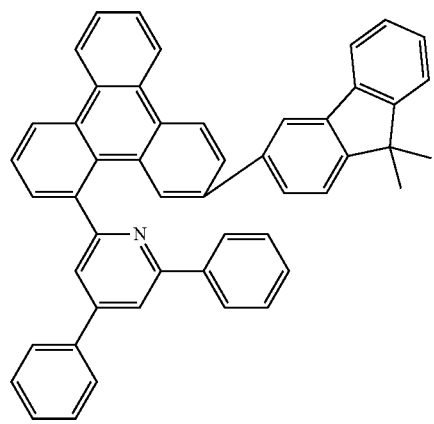
1-117
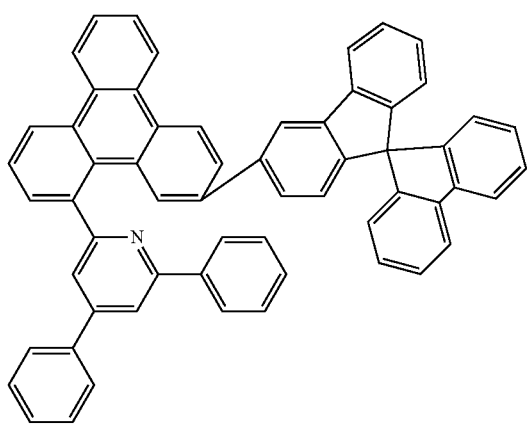
1-118
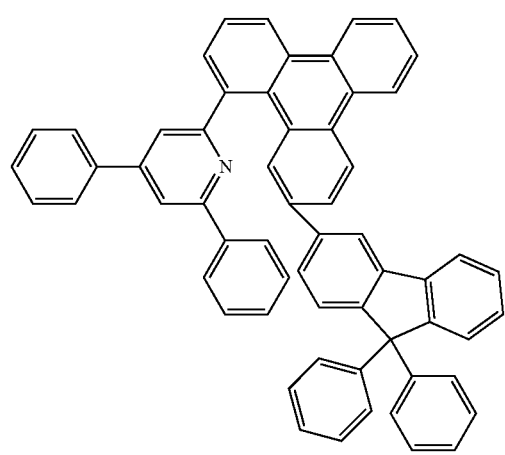
1-119
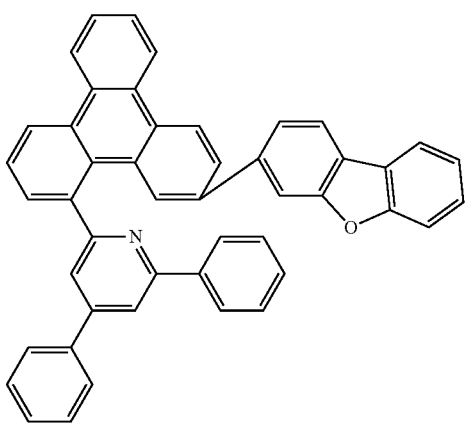
1-120
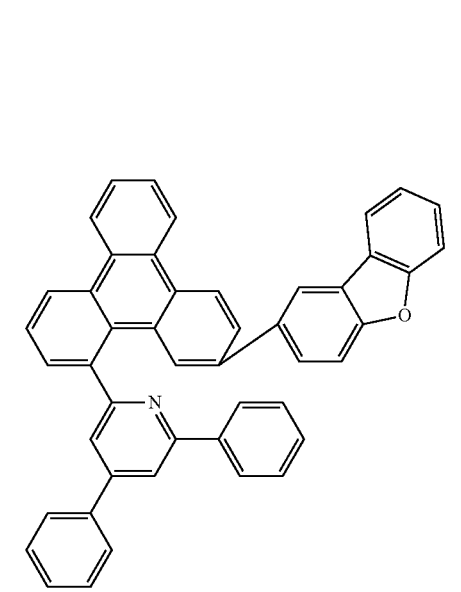
1-121

1-122
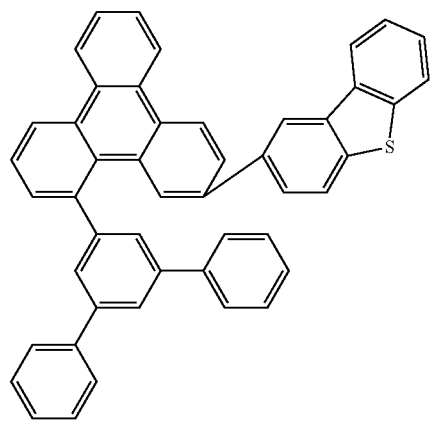
1-123
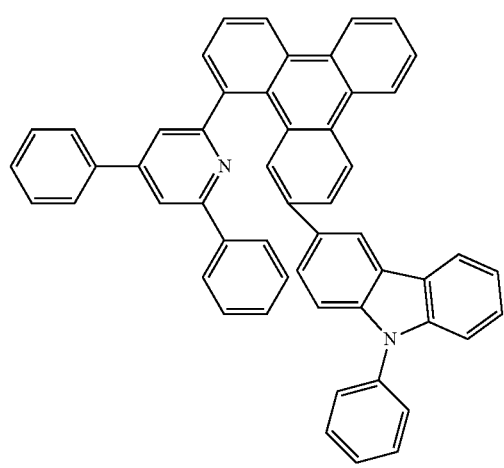
1-124
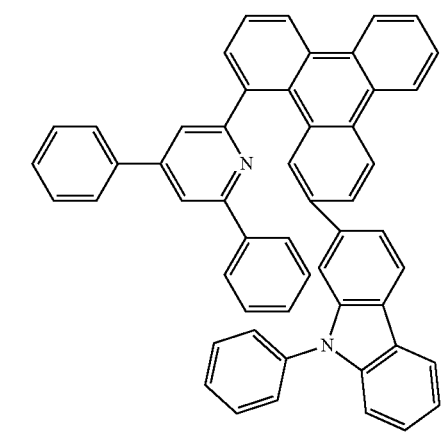
1-125
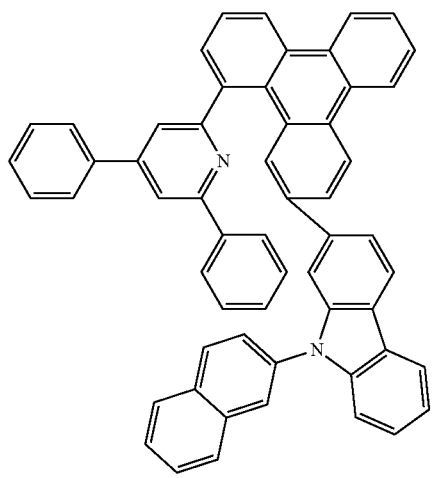
1-126
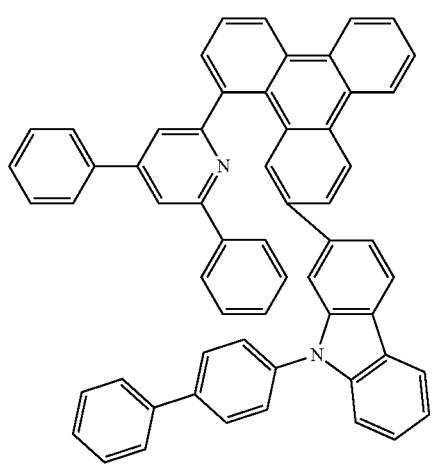
1-127
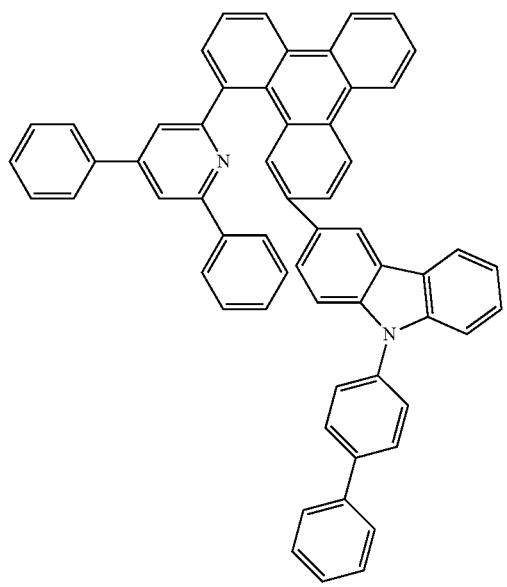

323
-continued
1-128
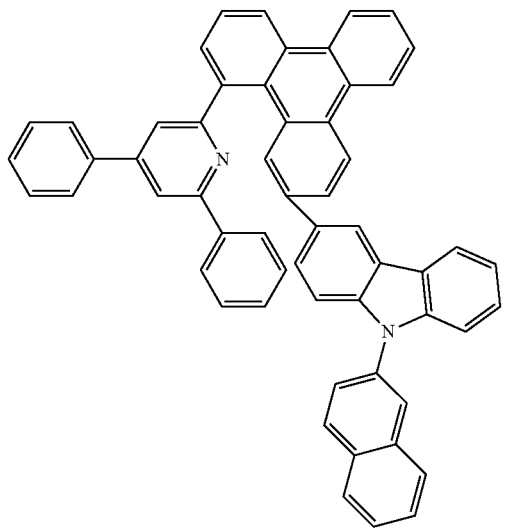
1-129
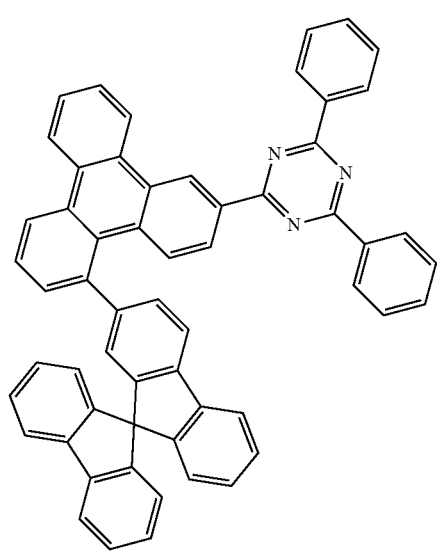
1-130
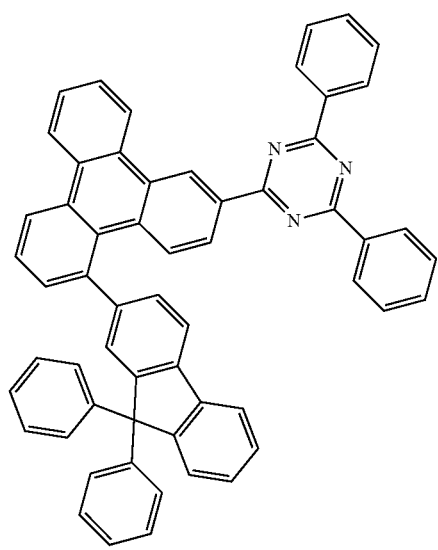
324
-continued
1-131
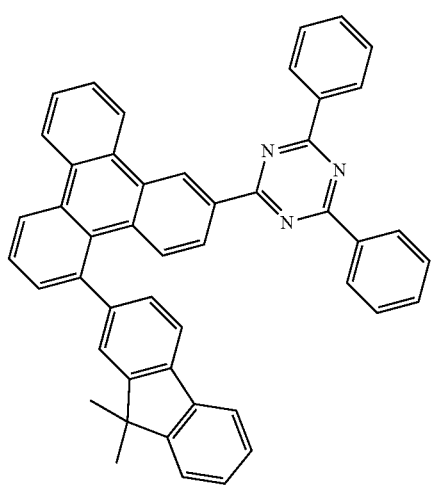
1-132
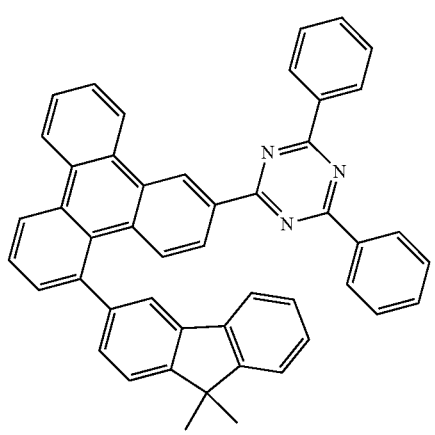
1-133
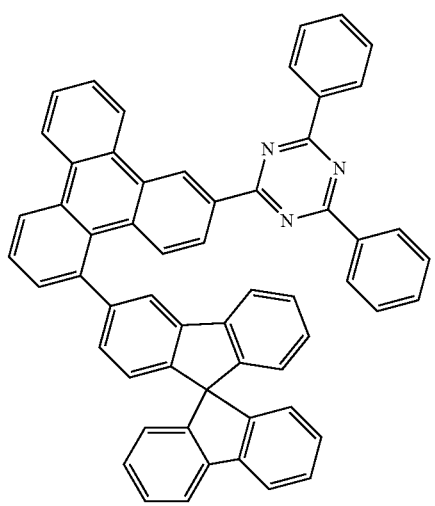

325
-continued
1-134
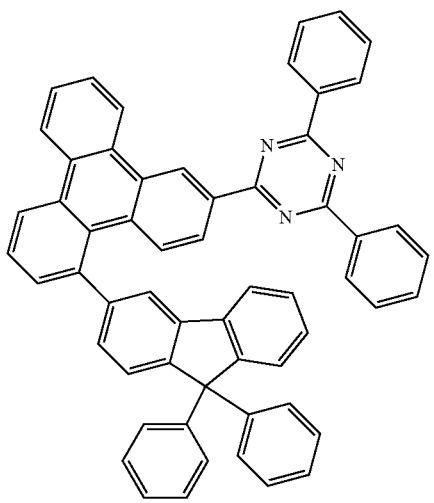
1-135
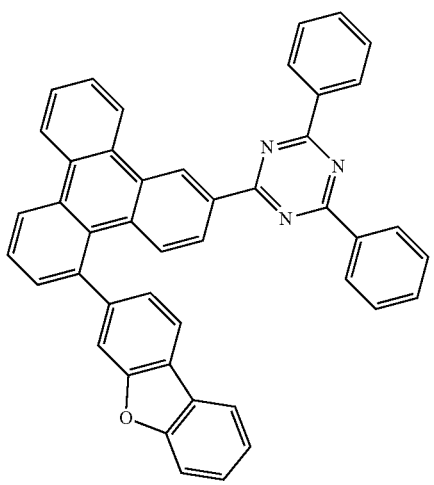
1-136
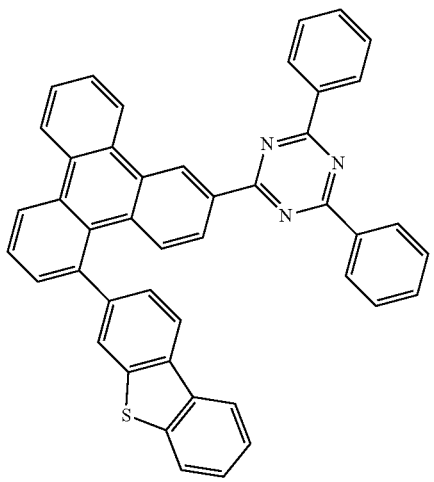
326
-continued
1-137
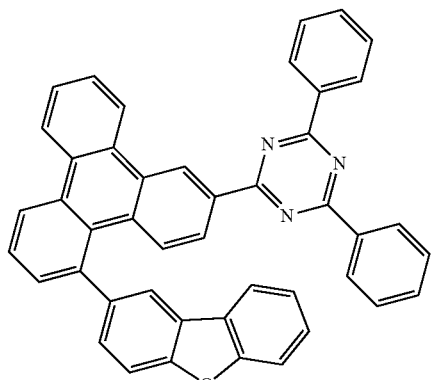
1-138
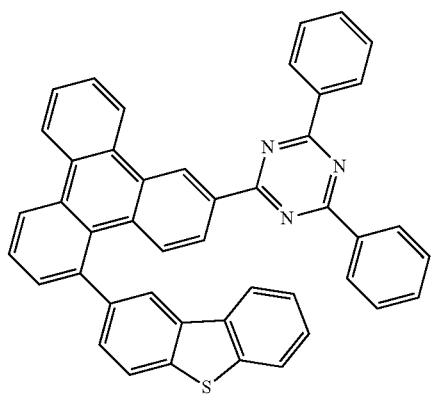
1-139
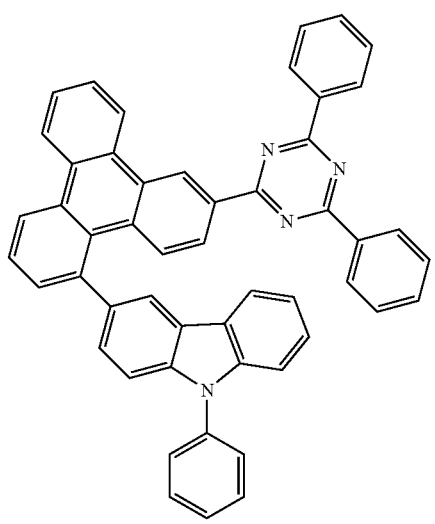

327
-continued
1-140
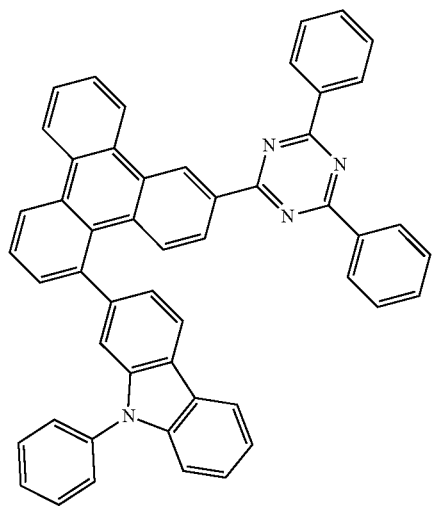
328
-continued
1-142
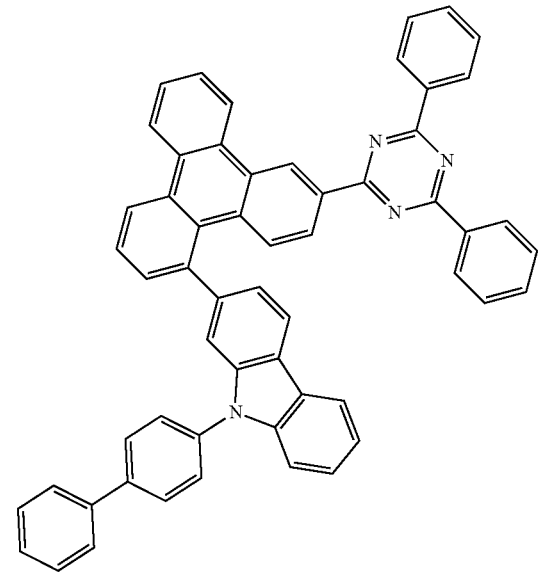
1-141
1-143
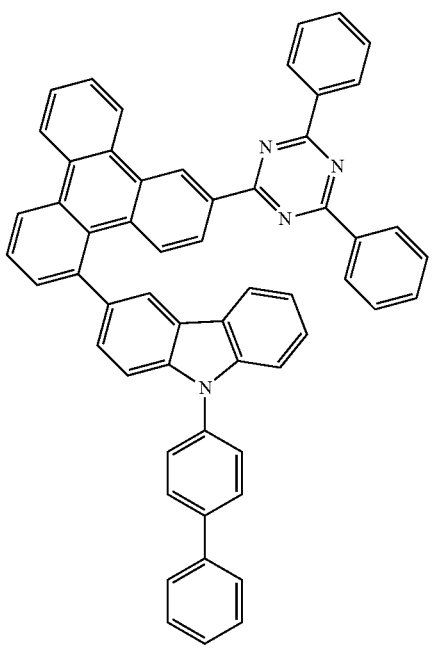

1-144
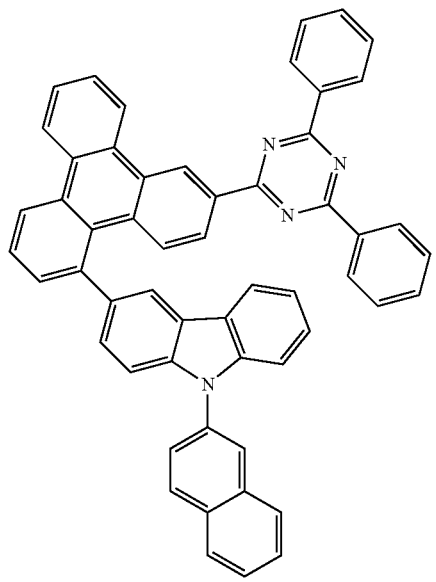
1-145
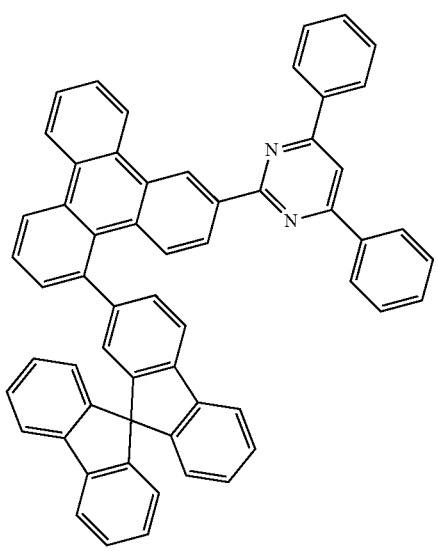
1-146
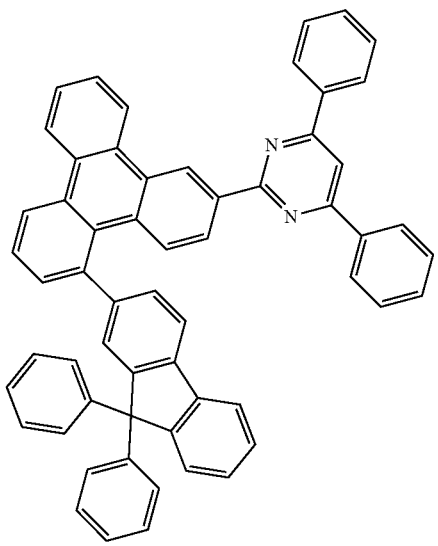
1-147
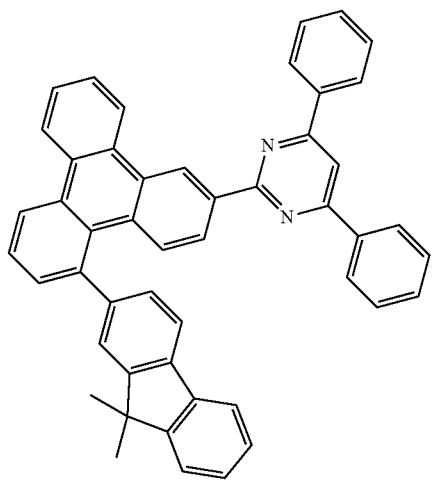
1-148
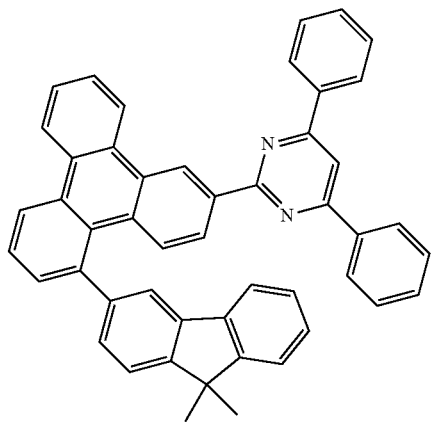
1-149
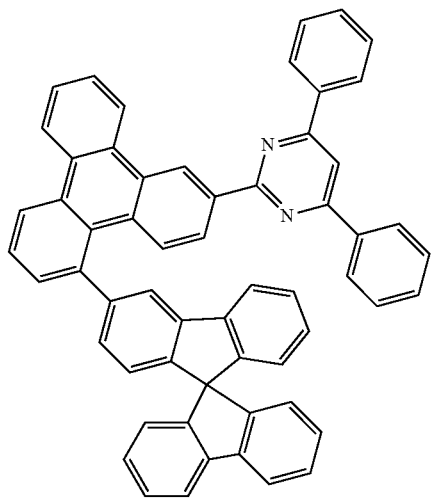

1-150
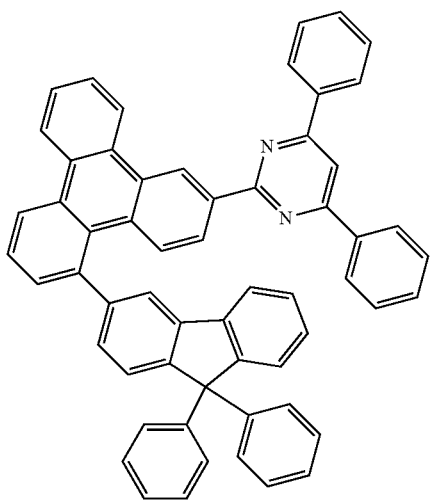
1-151
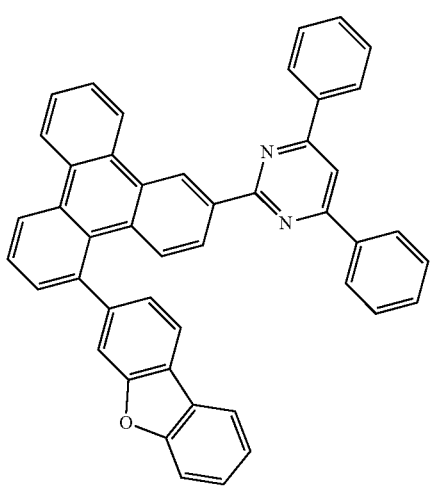
1-152
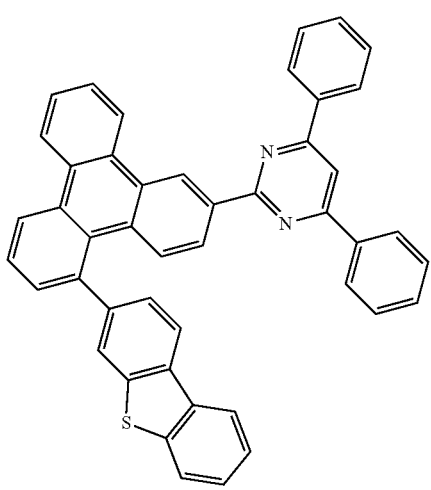
1-153
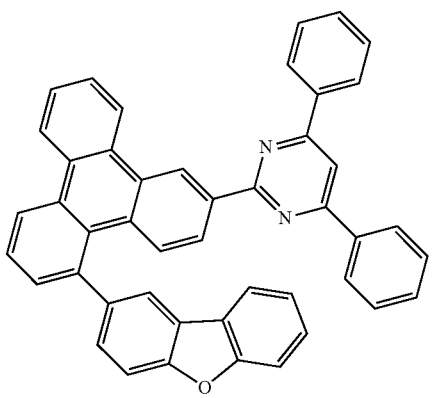
1-154
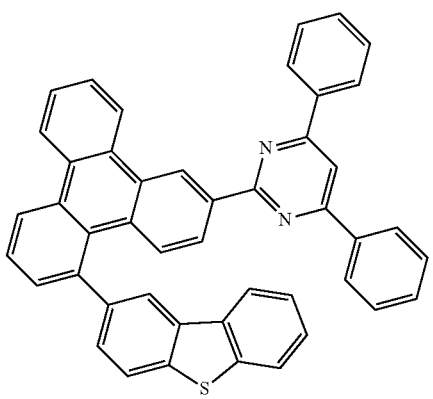
1-155
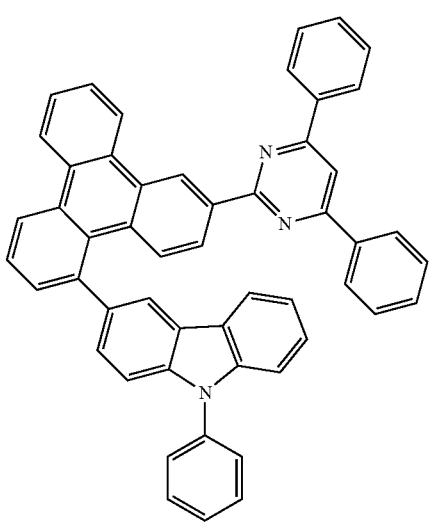

1-156
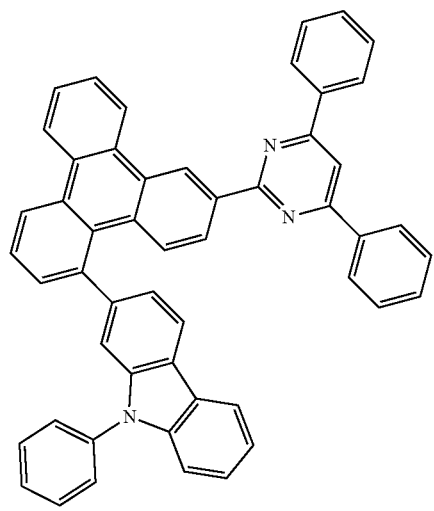
1-158
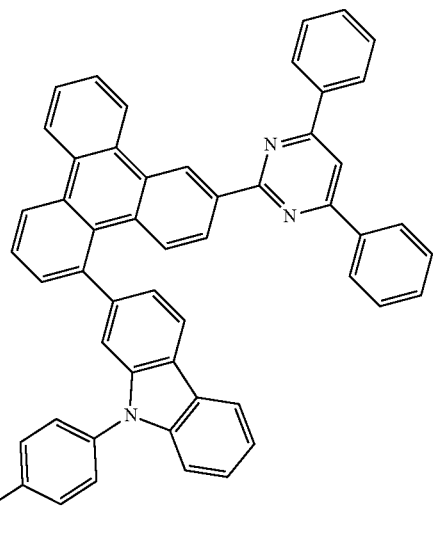
1-157
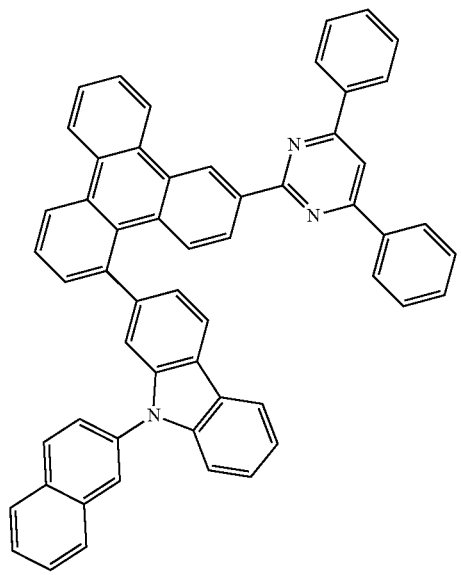
1-159
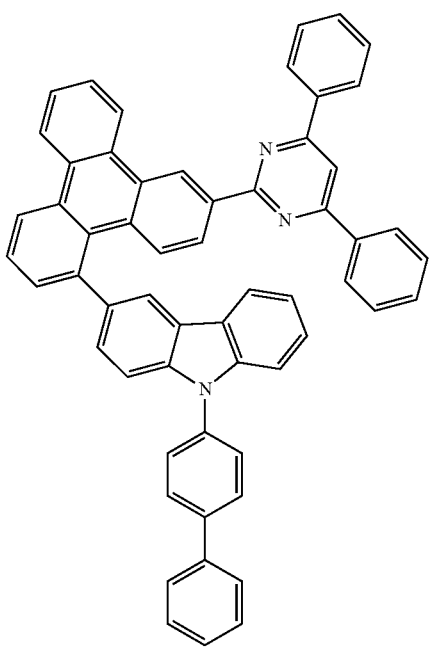

1-160
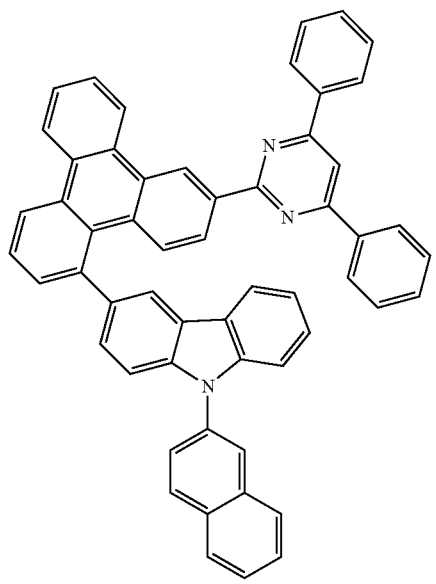
1-161
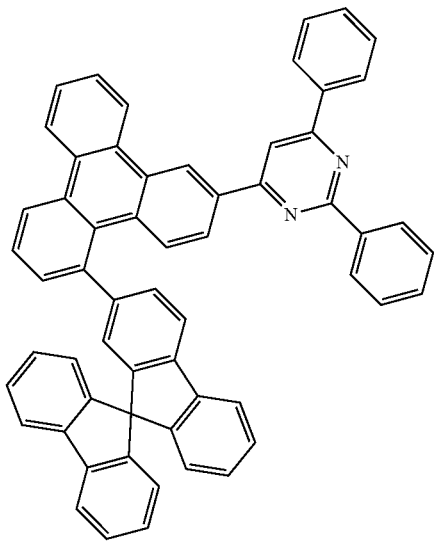
1-162
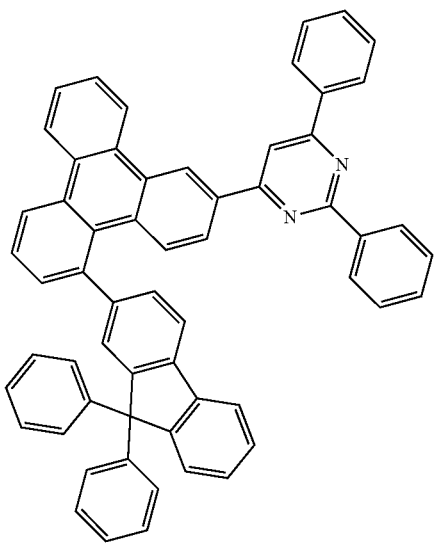
1-163
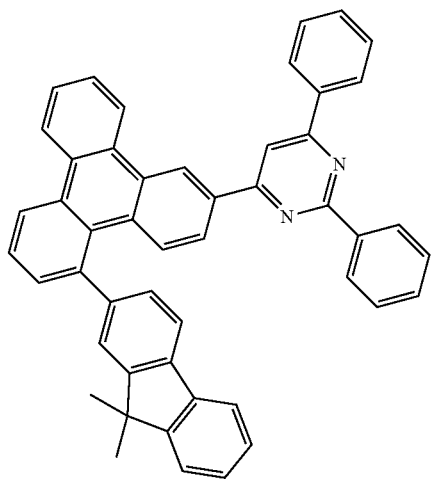
1-164
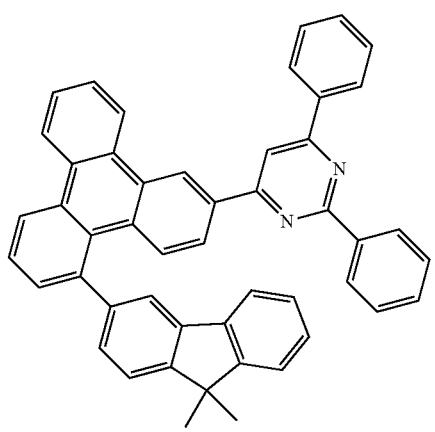

1-165
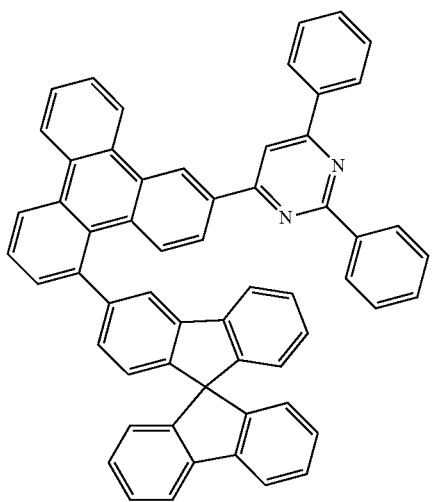
1-166
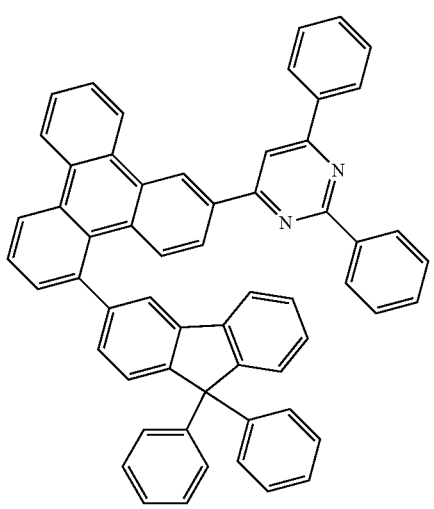
1-167
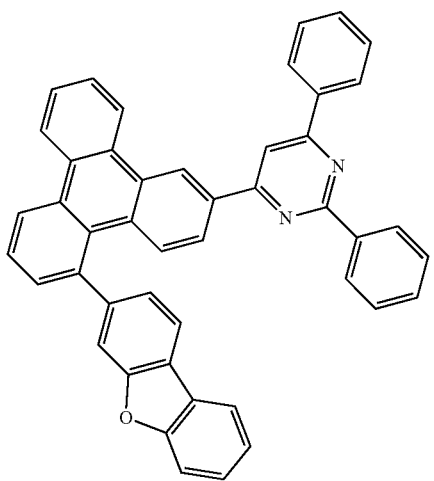
1-168
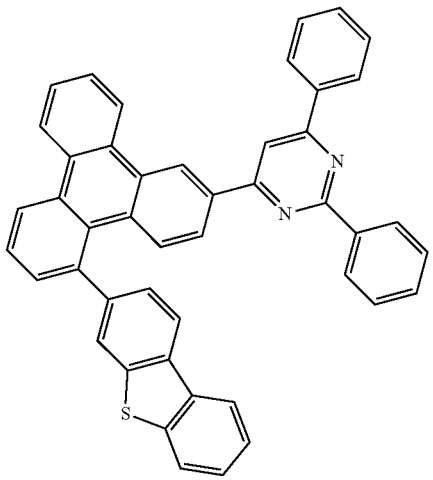
1-169
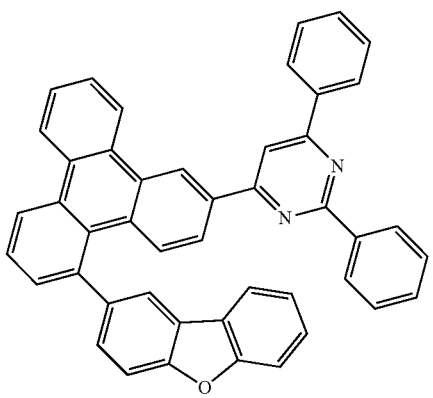
1-170
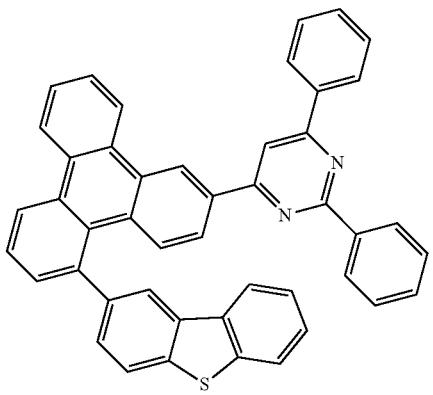

339
-continued
1-171
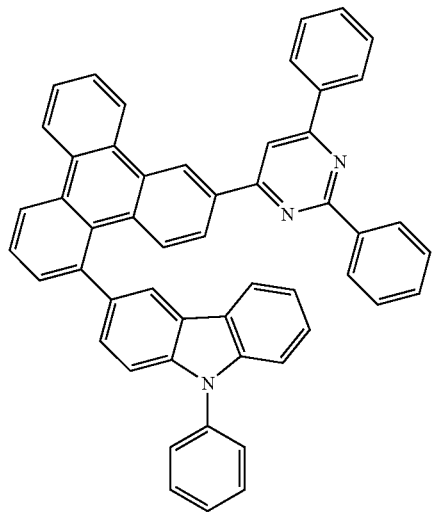
1-172
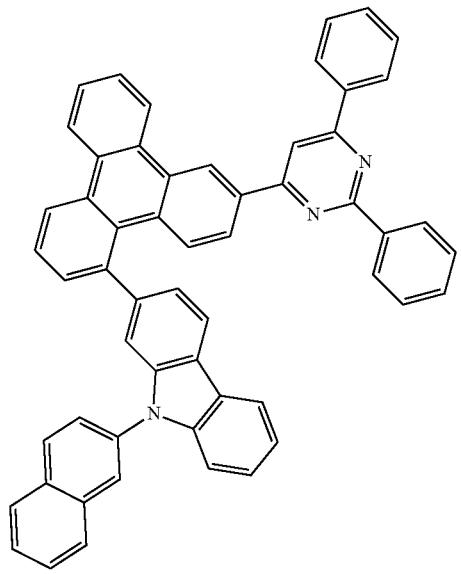
1-173
340
-continued
1-174
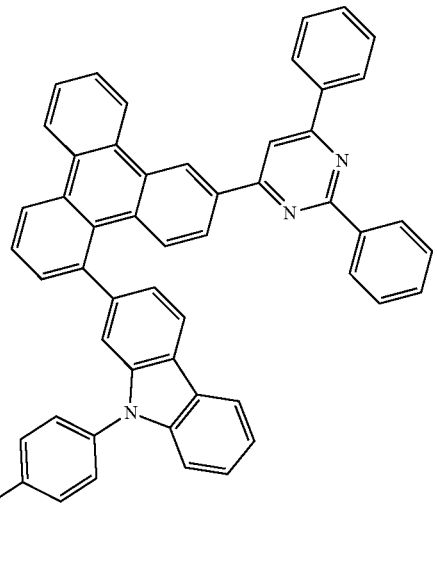
1-175
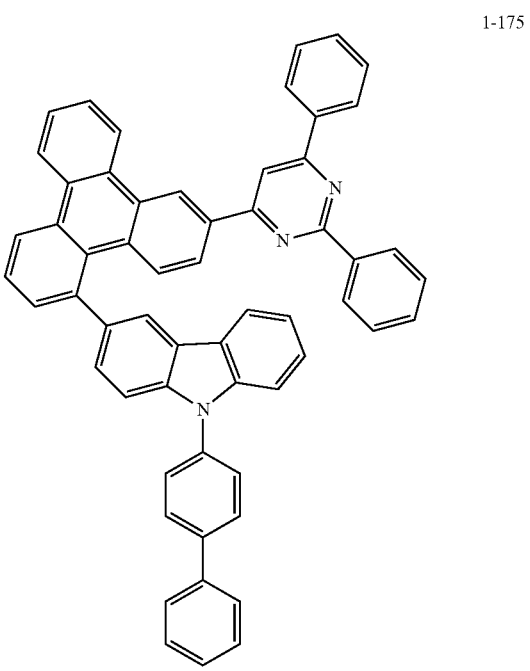

-continued
1-176
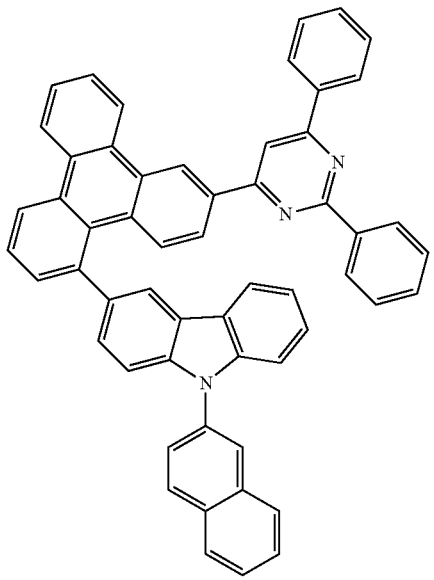
1-177
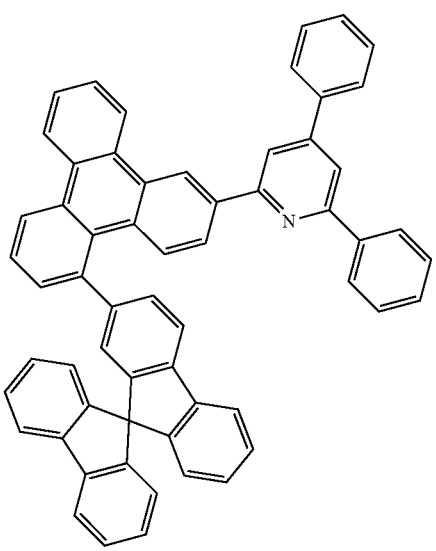
1-178
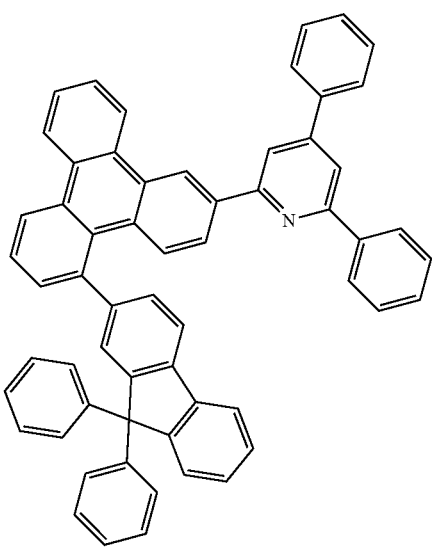
-continued
1-179
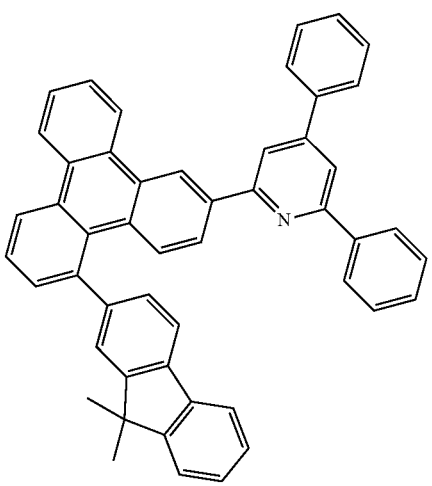
1-180
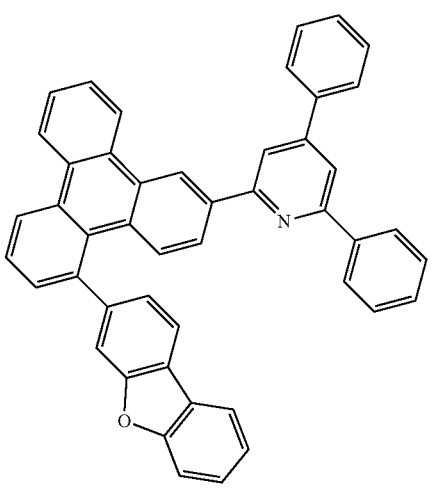
1-181
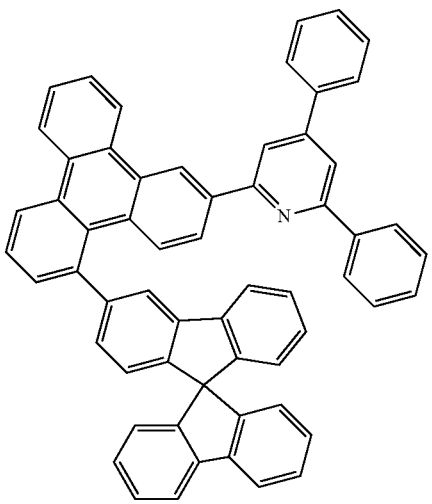

-continued
1-182
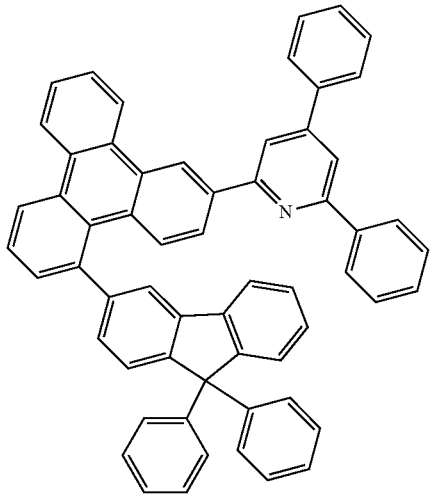
1-183
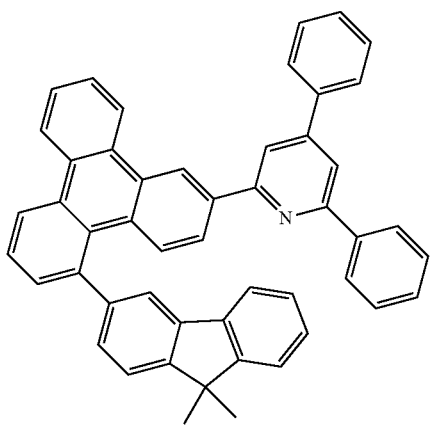
1-184
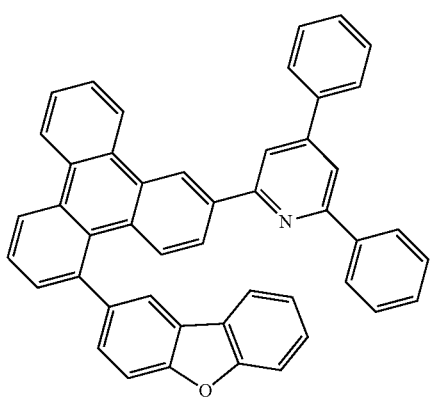
-continued
1-185
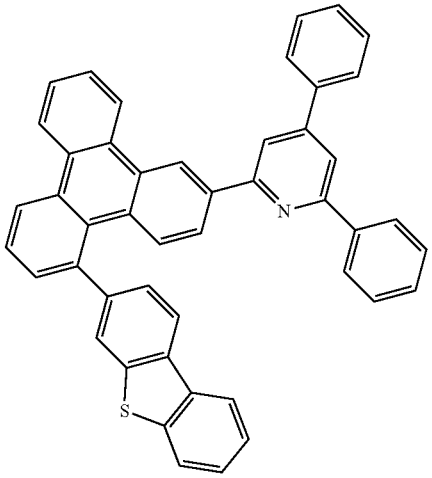
1-186
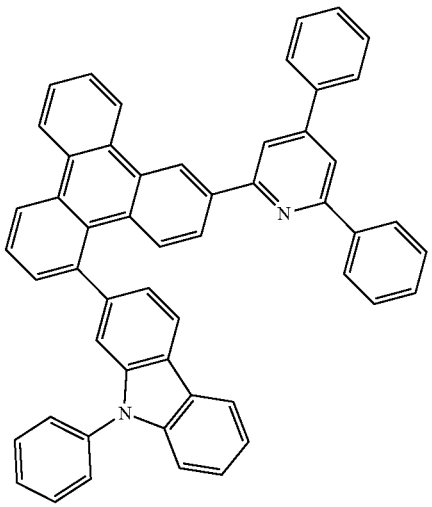
1-187
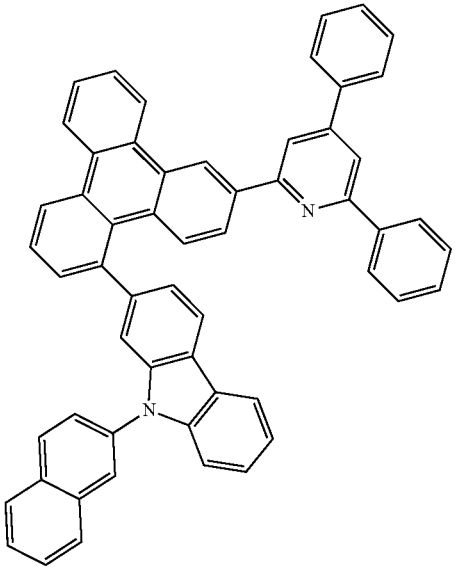

1-188
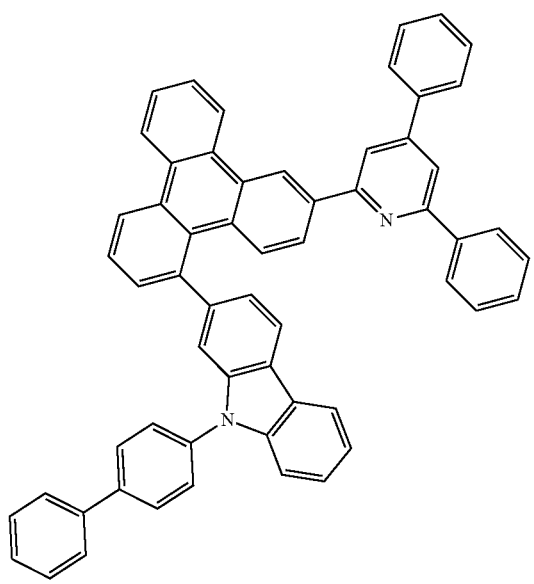
1-189
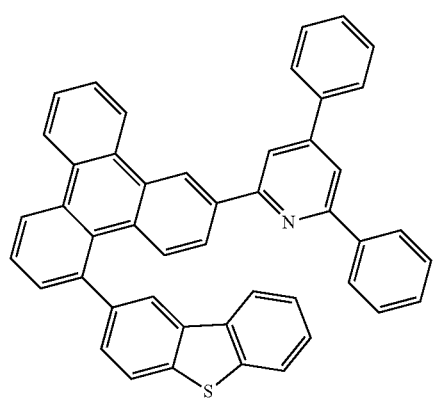
1-190
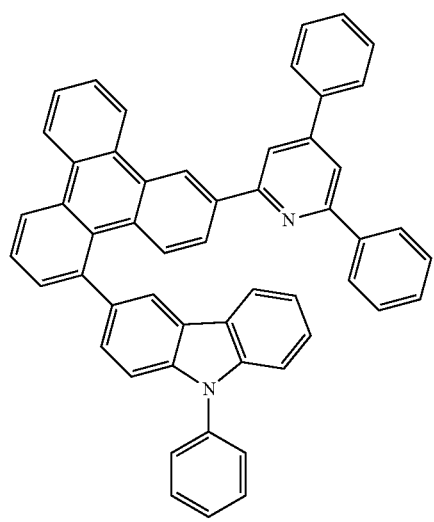
1-191
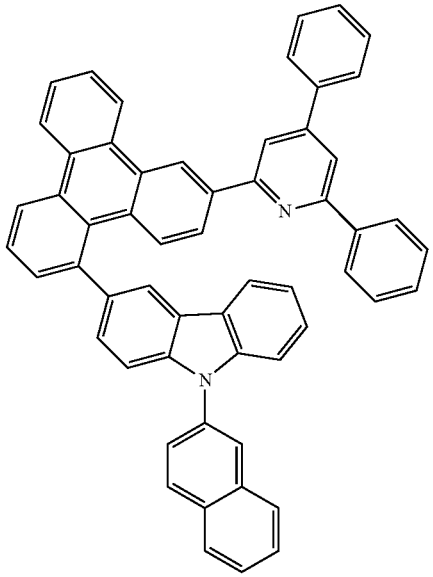
1-192
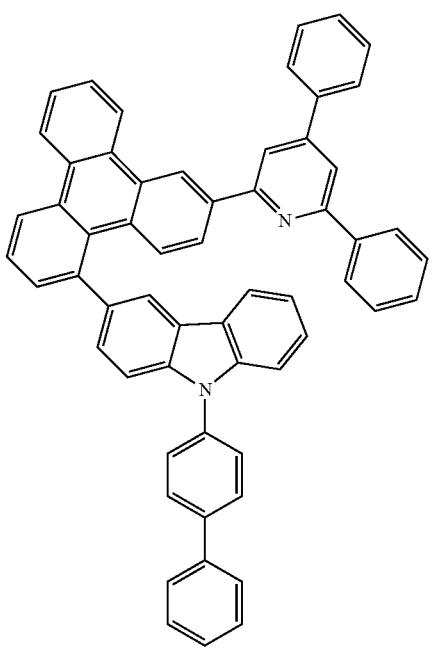

-continued
1-193
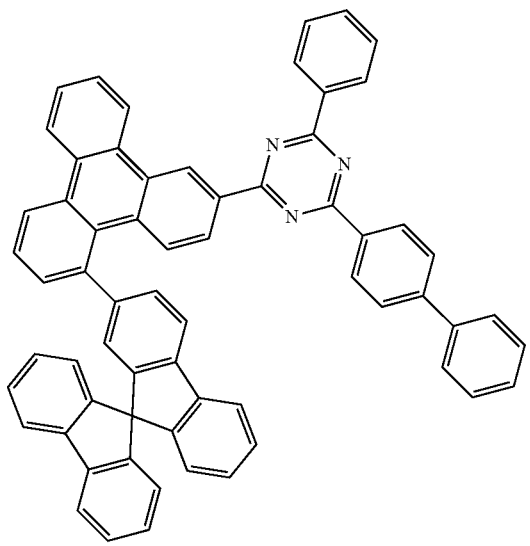
1-194
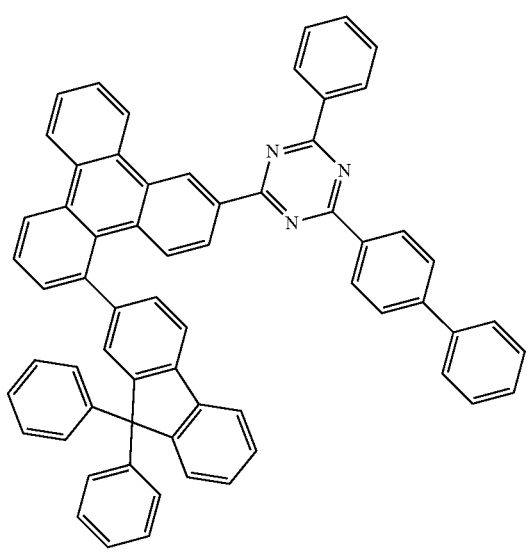
1-195
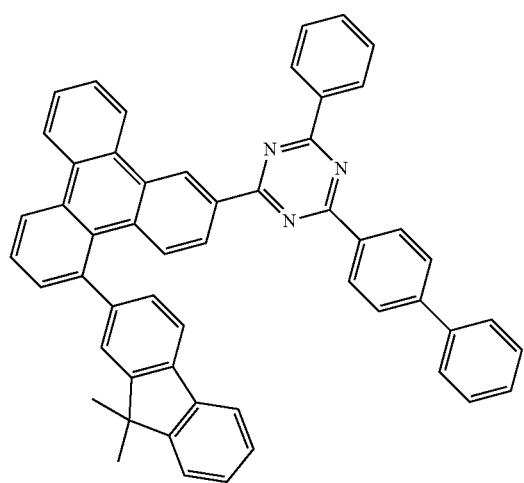
-continued
1-196
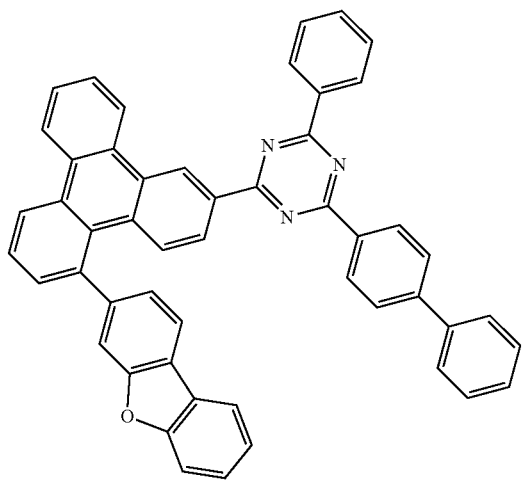
1-197
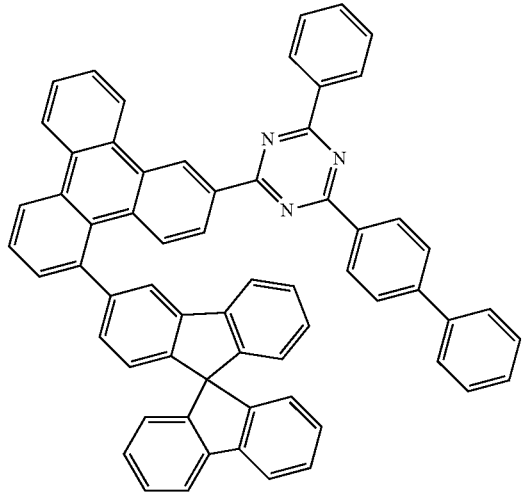
1-198
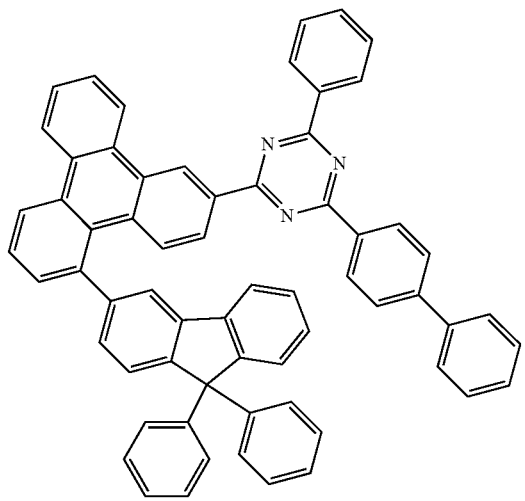

1-199
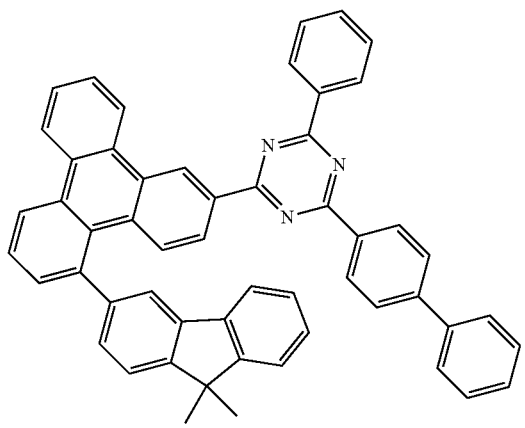
1-202
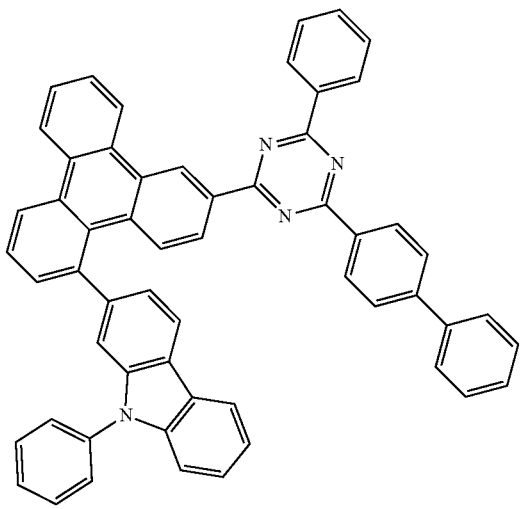
1-200
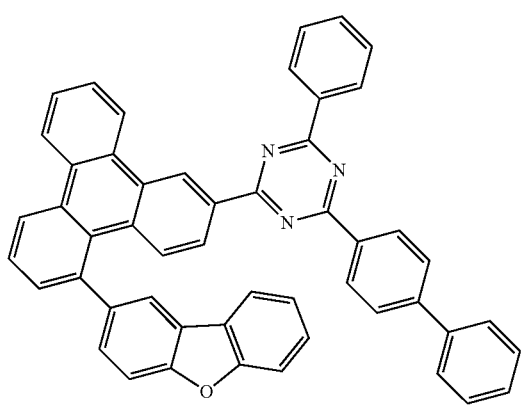
1-203
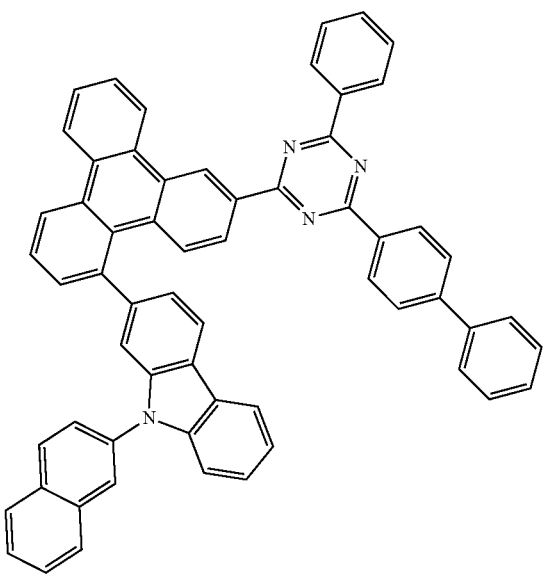
1-201
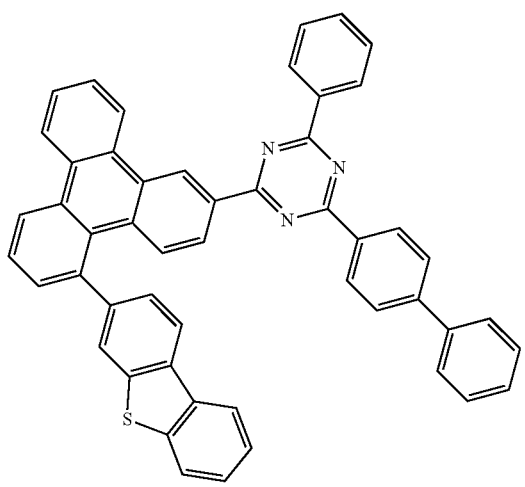
1-204
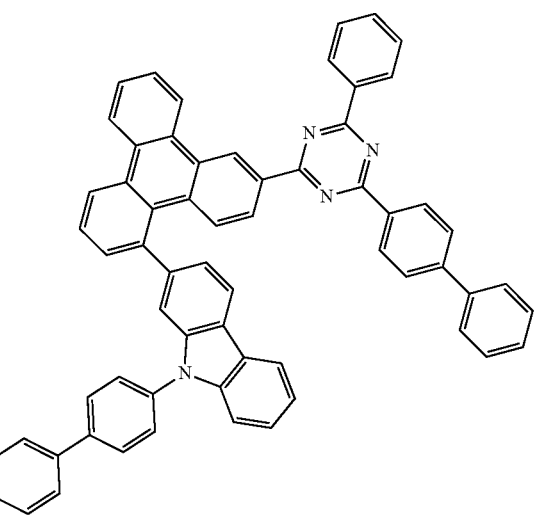

-continued
1-205
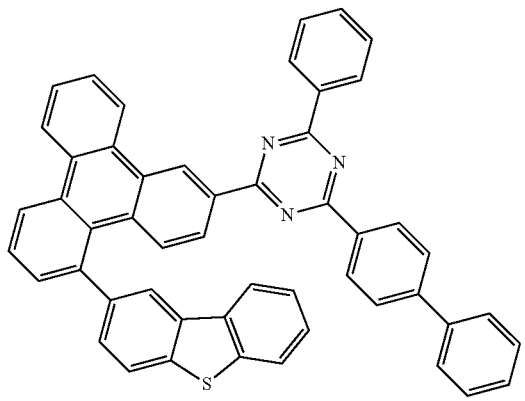
1-206
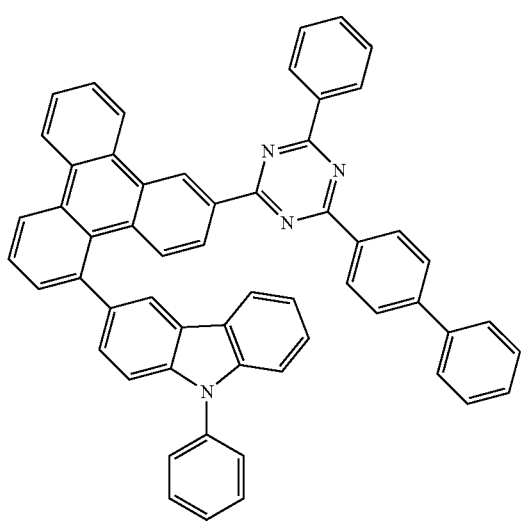
1-207
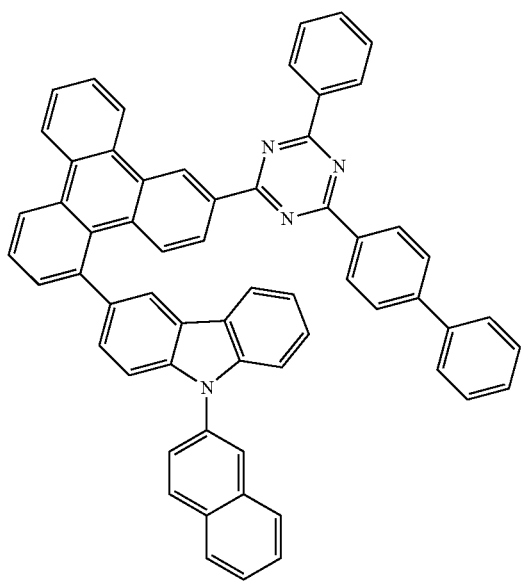
-continued
1-208
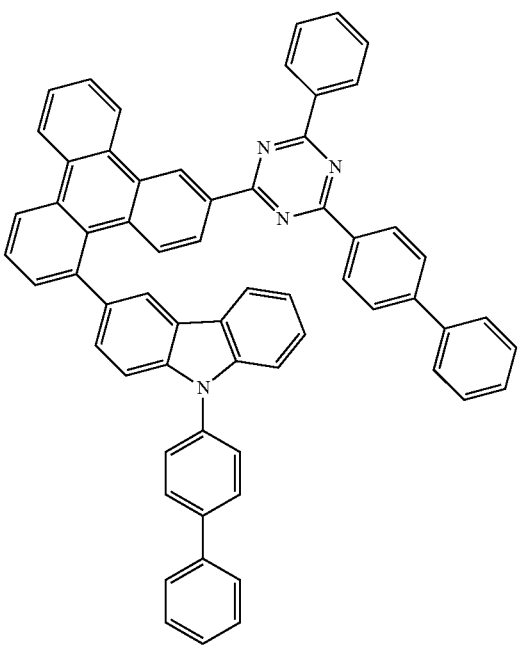
1-209
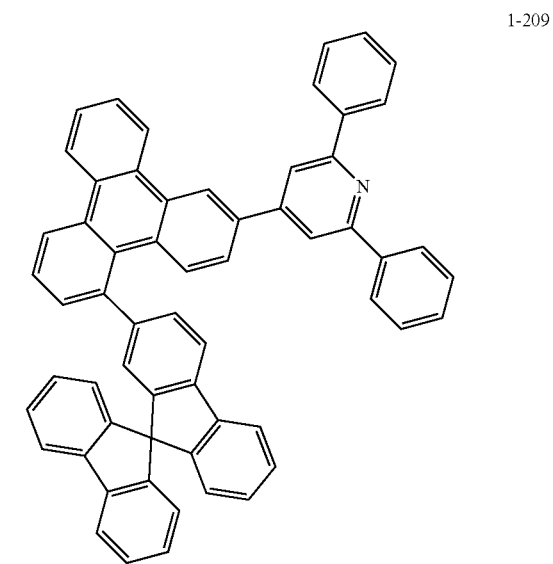

1-210
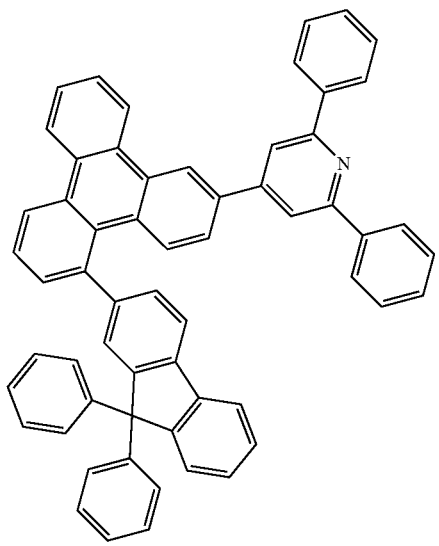
1-211
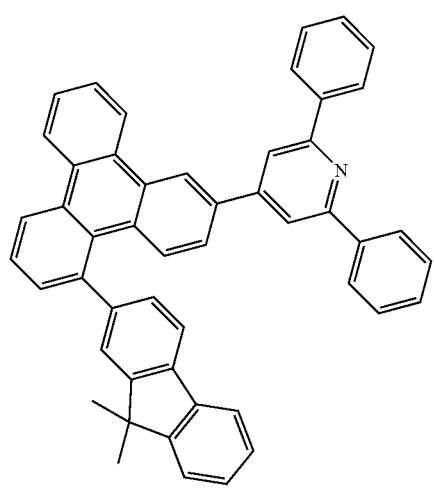
1-212
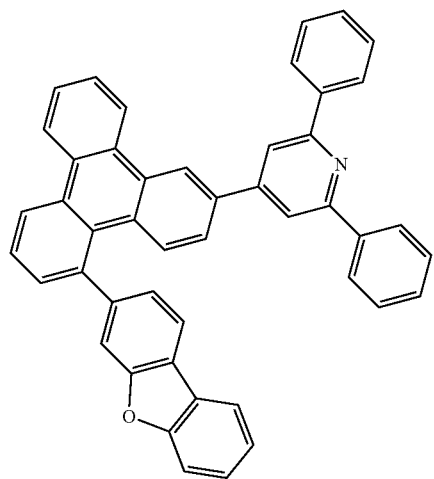
1-213
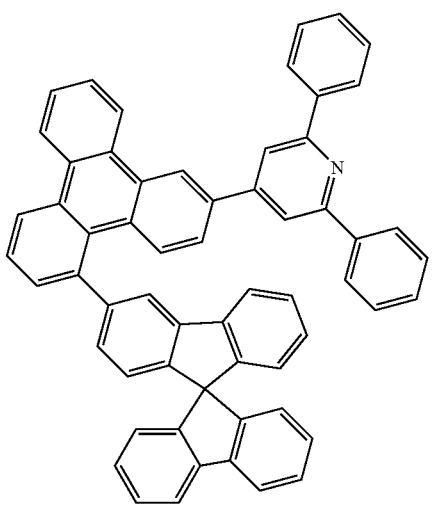
1-214
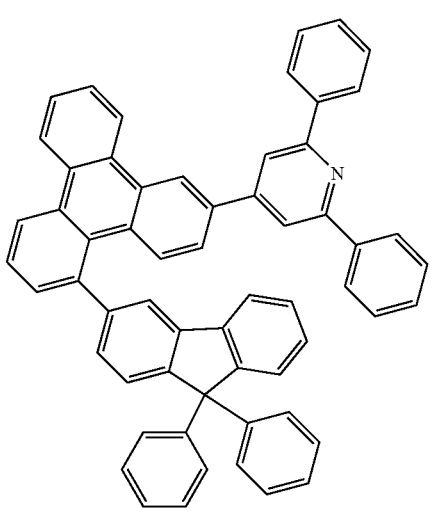
1-215
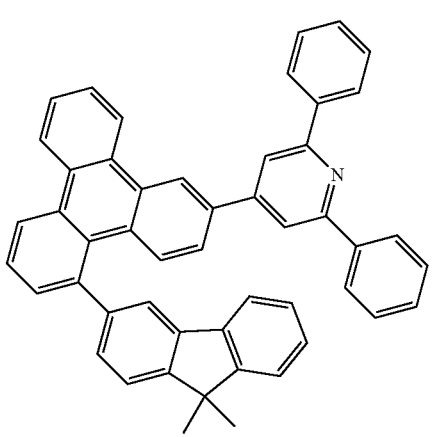

1-216
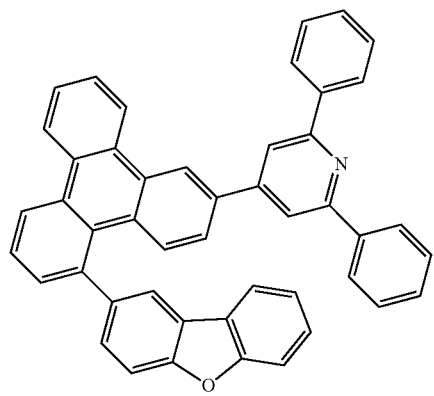
1-217
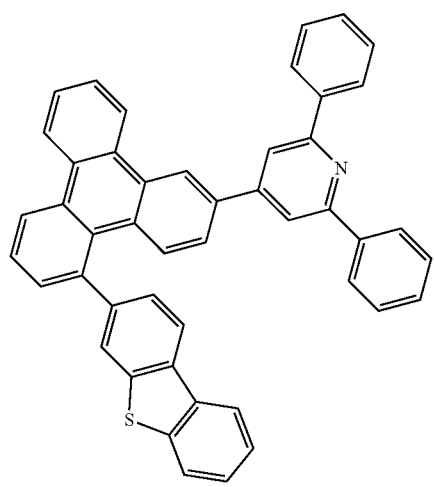
1-218
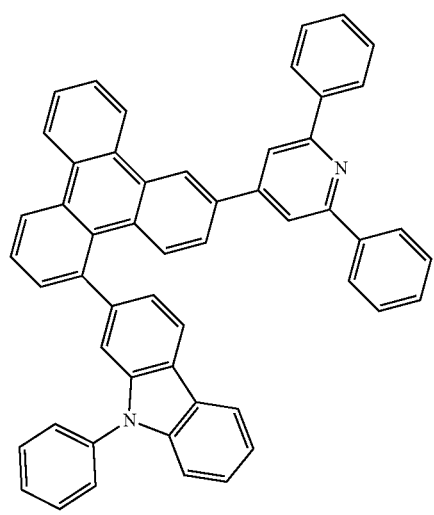
1-219
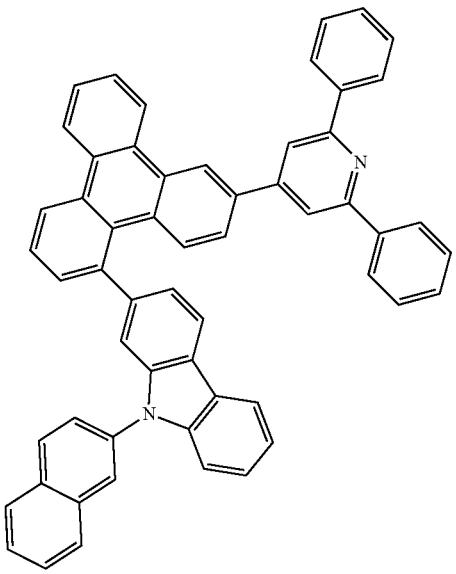
1-220
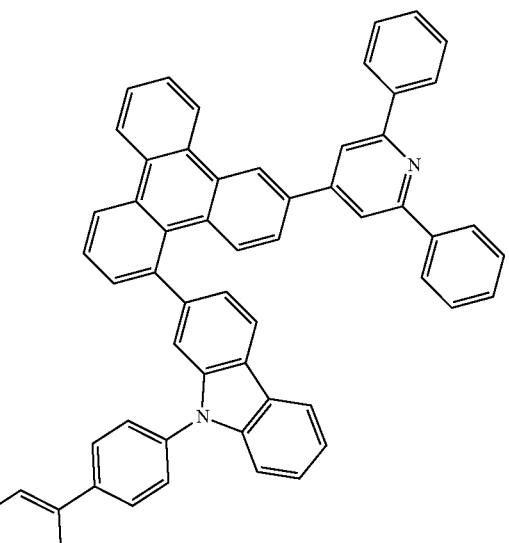
1-221
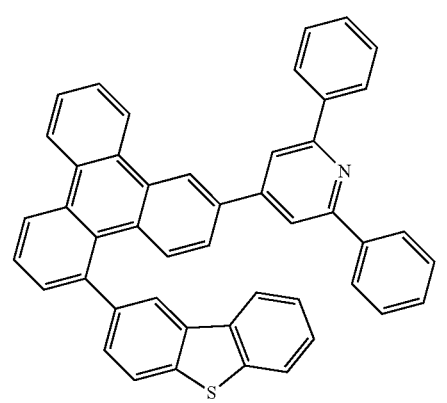

1-222
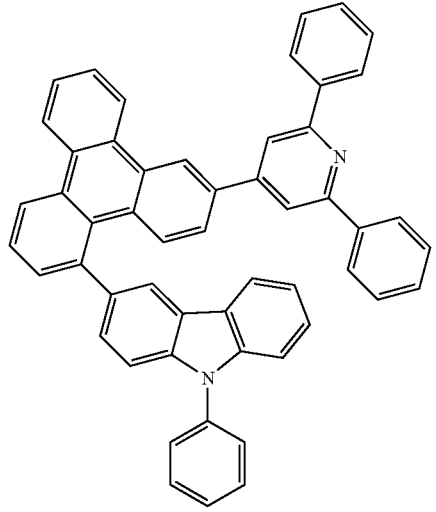
1-223
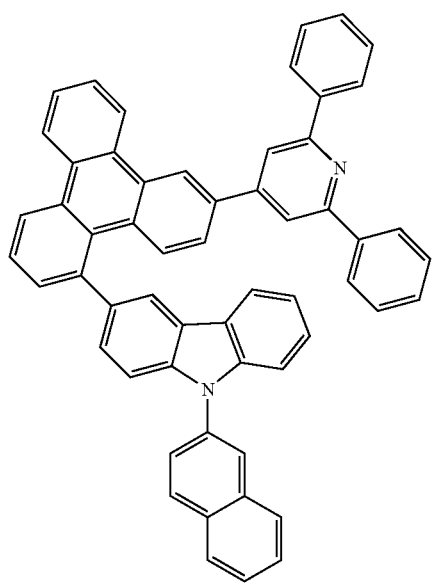
1-224
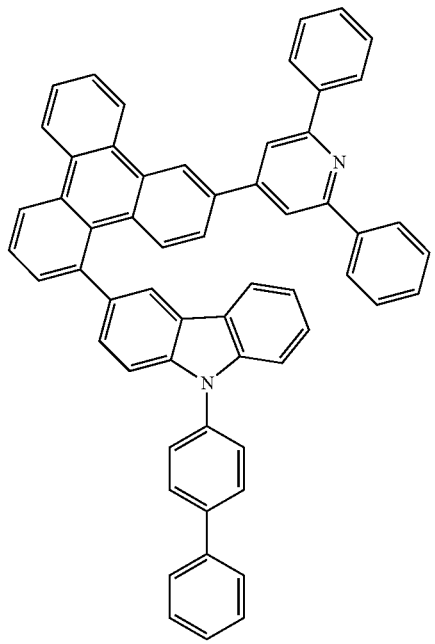
1-225
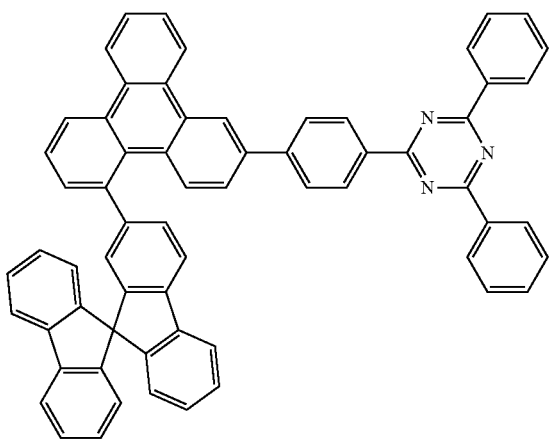
1-226
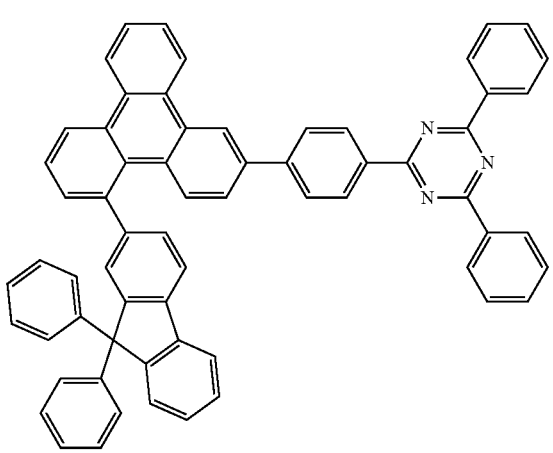

1-227
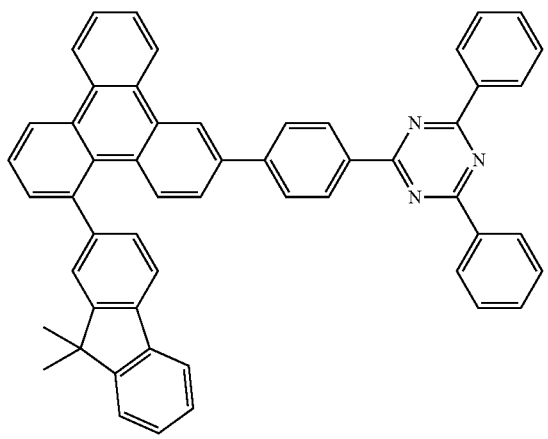
1-230
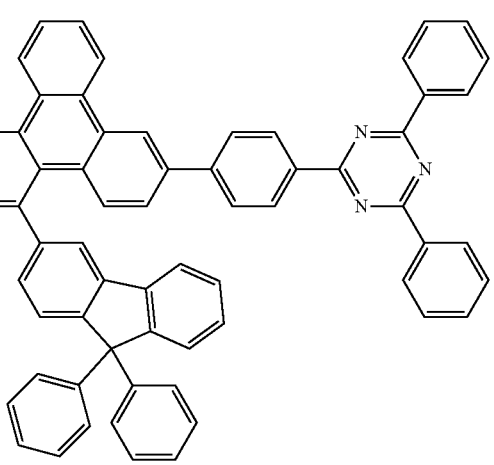
1-228
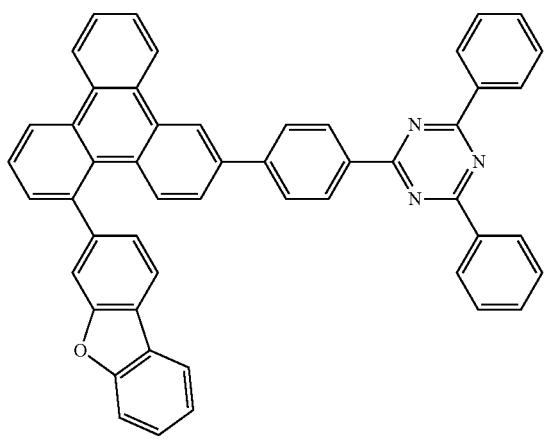
1-231
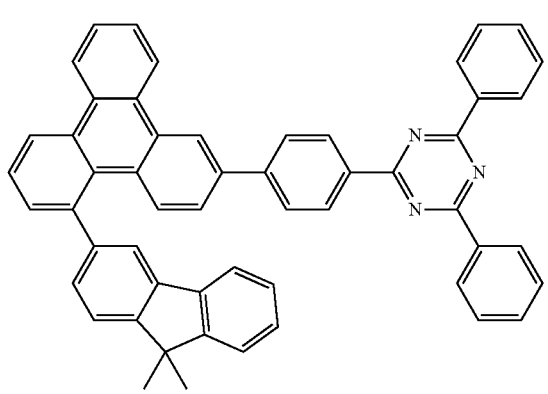
1-229
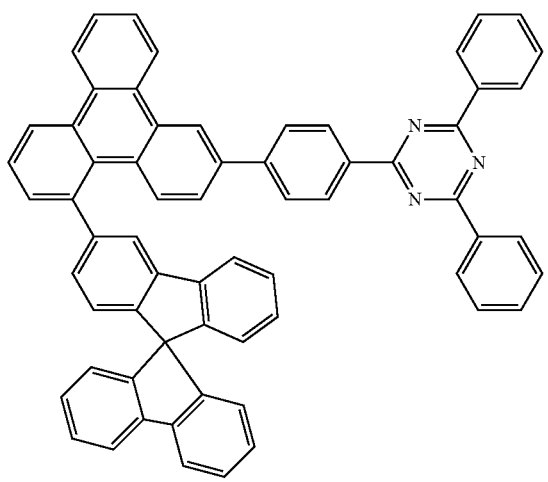
1-232
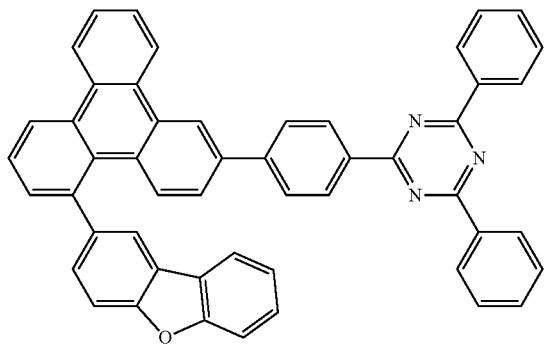

-continued
1-233
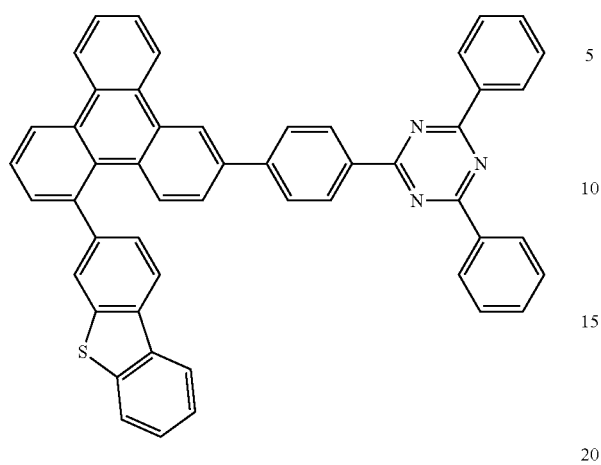
1-234
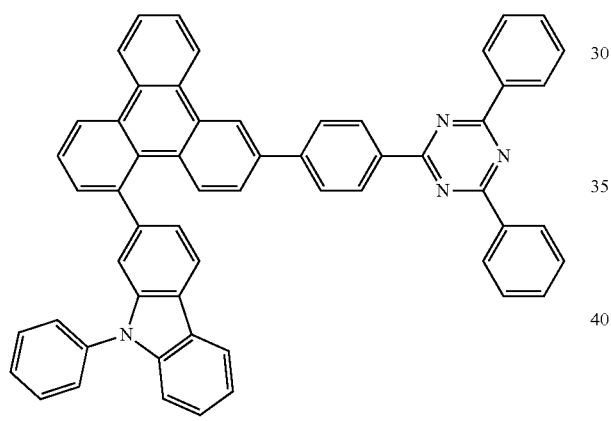
1-235
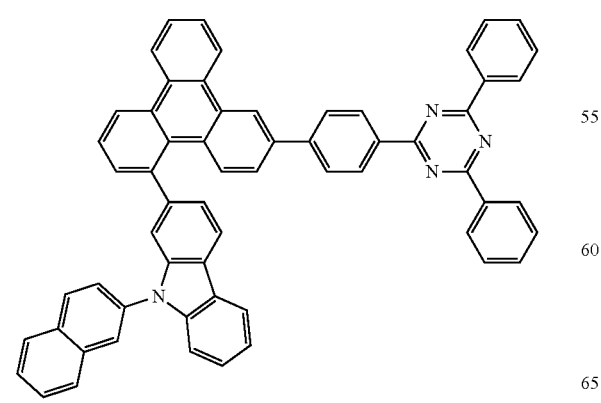
-continued
1-236
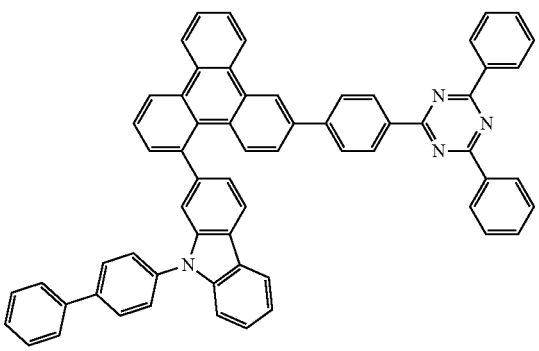
1-237
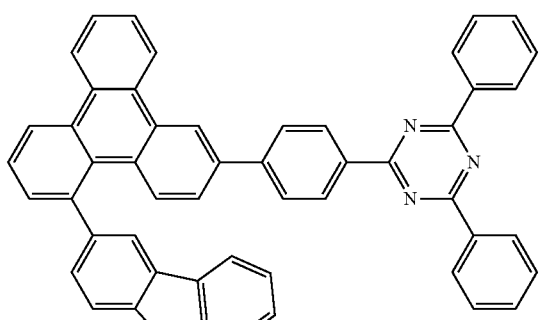
1-238
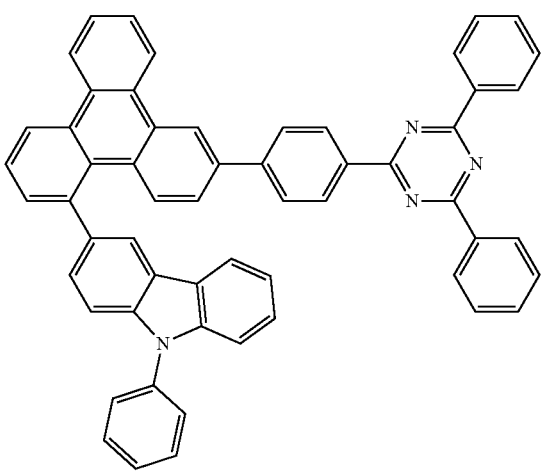

1-239
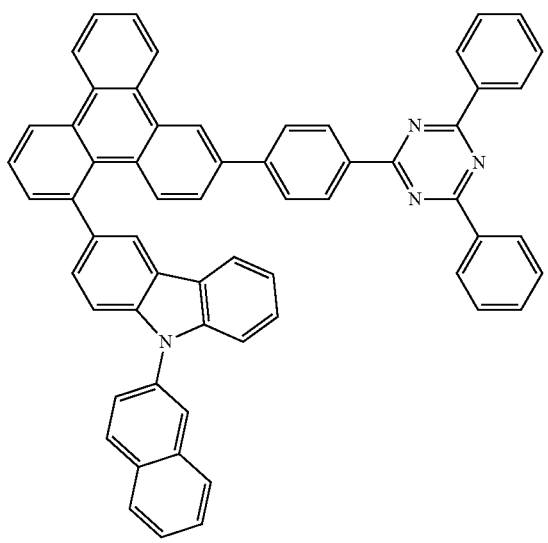
1-240
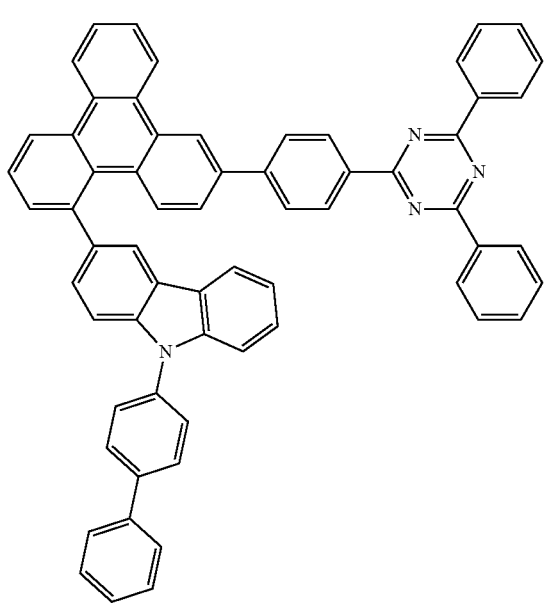
1-241
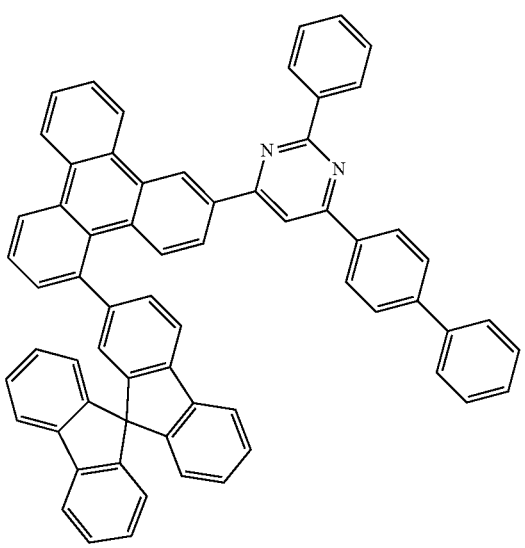
1-242
1-243
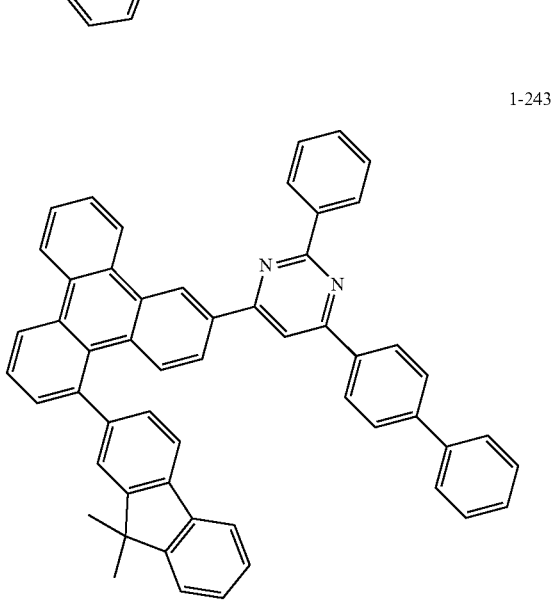

-continued
1-244
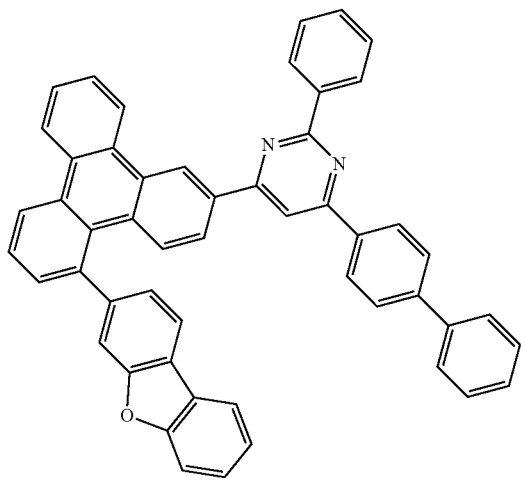
1-245
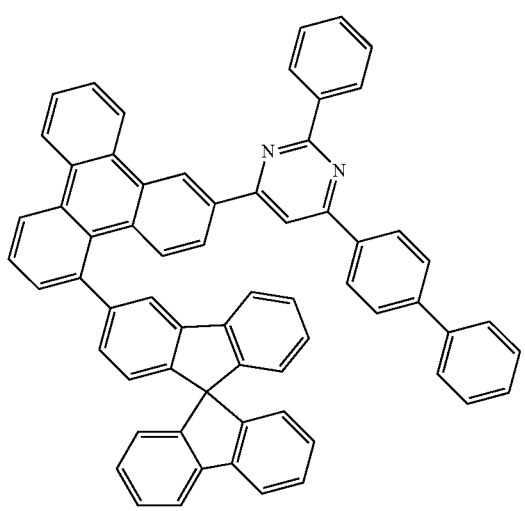
1-246
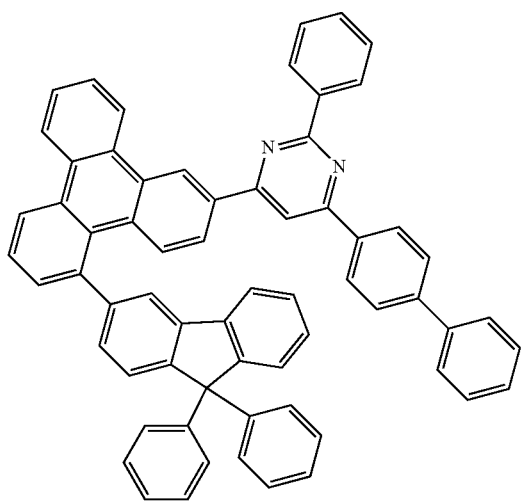
-continued
1-247
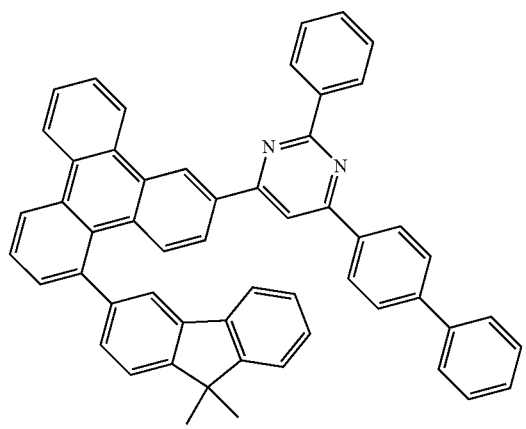
1-248
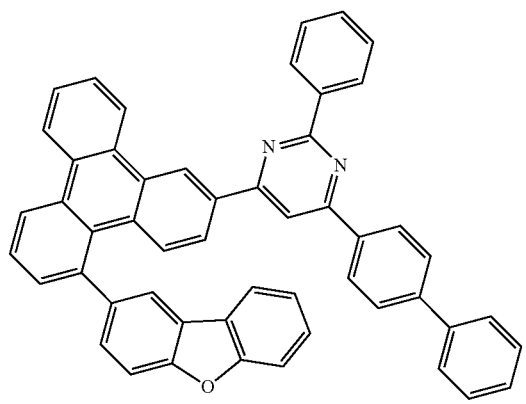
1-249
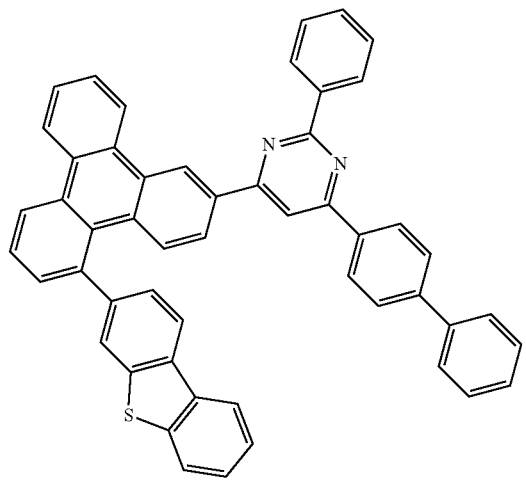

1-250
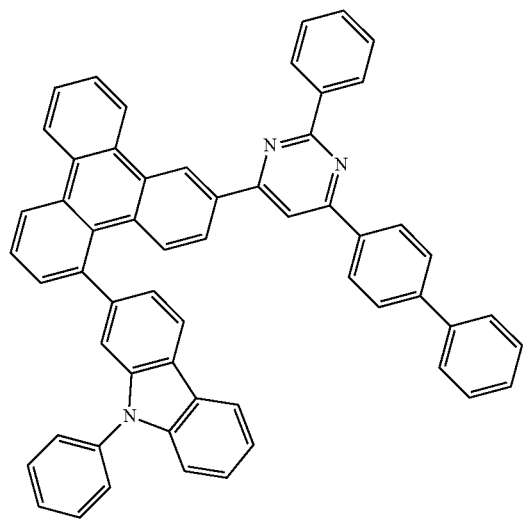
1-252
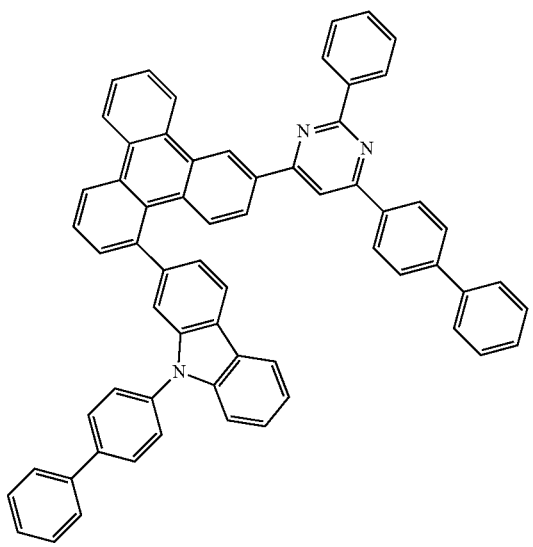
1-253
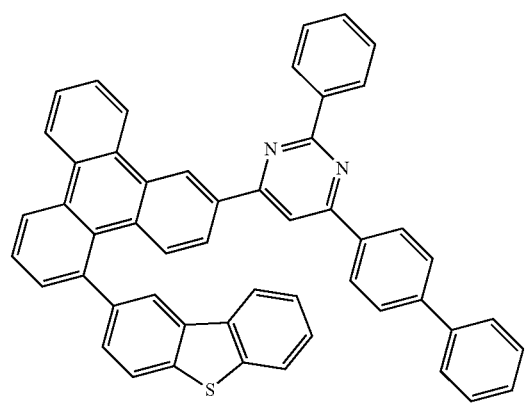
1-251
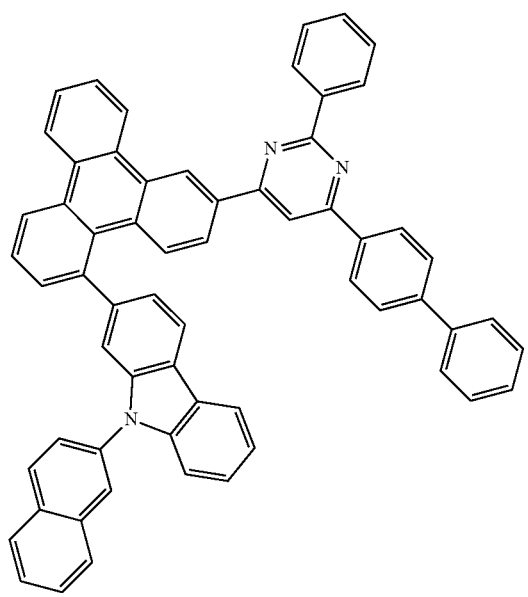
1-254
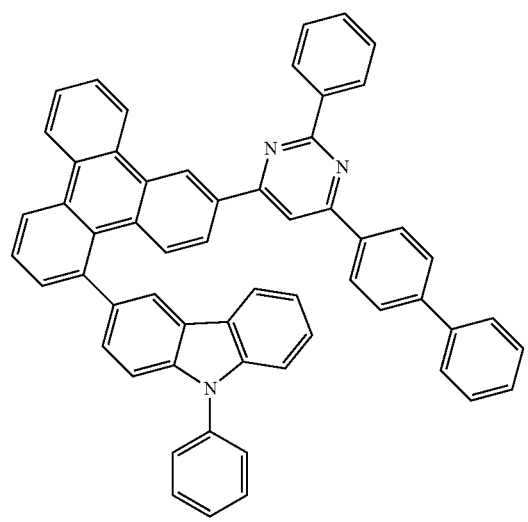

1-255
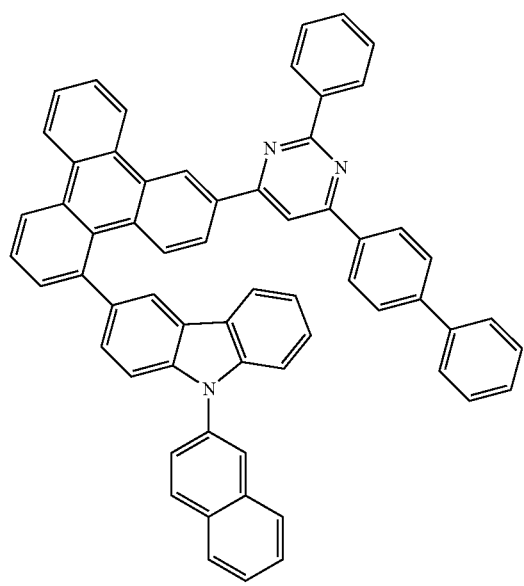
1-256
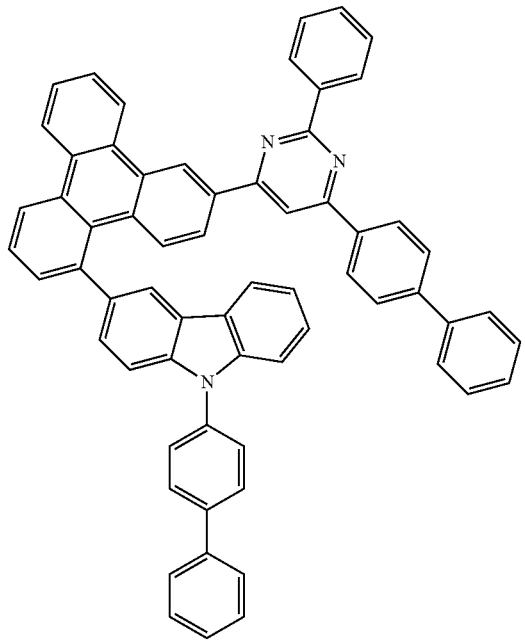
1-257
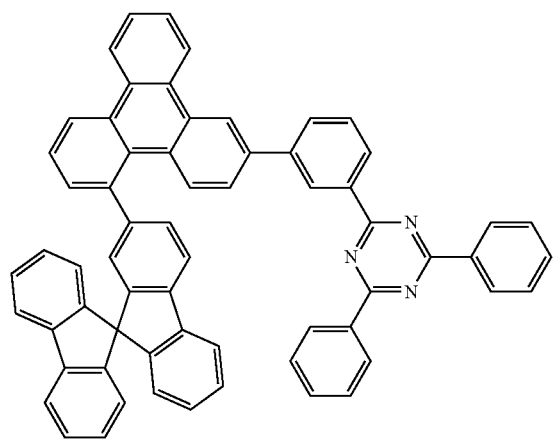
1-258
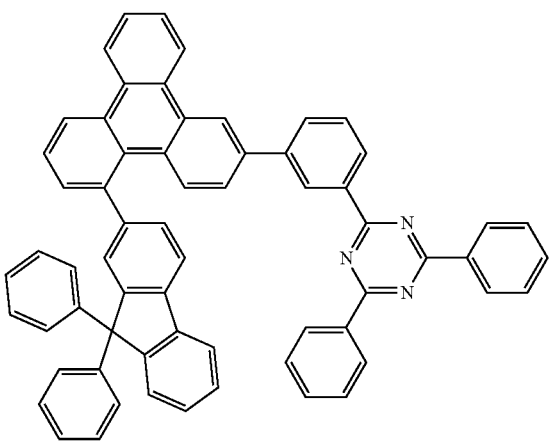
1-259
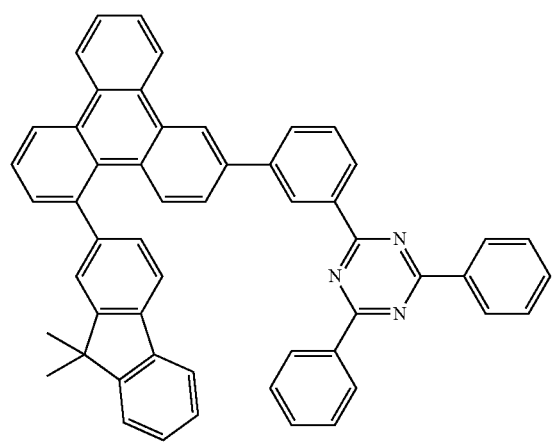
1-260
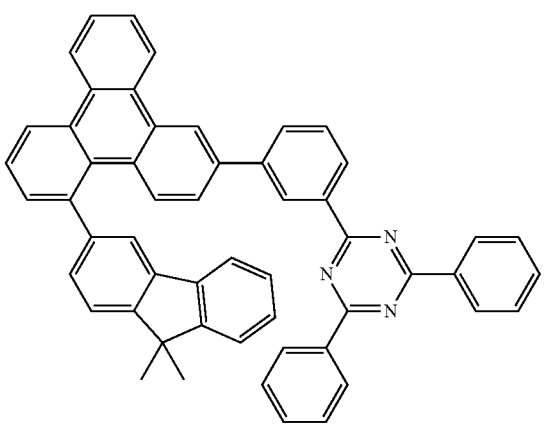

-continued
1-261
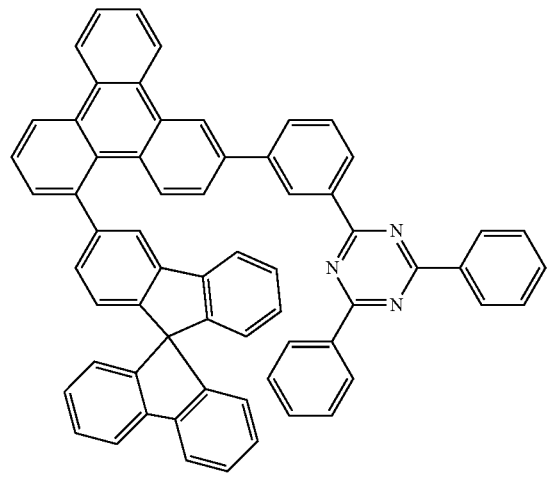
1-262
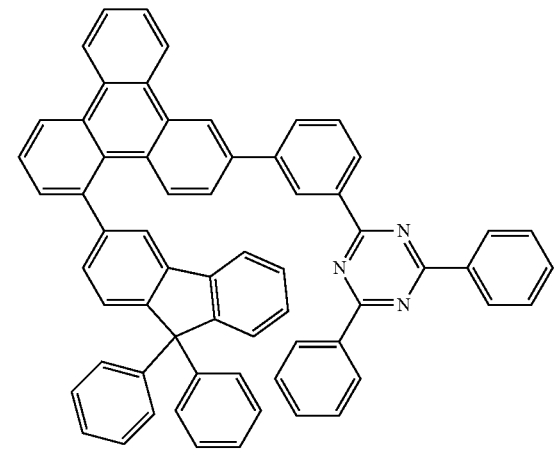
1-263
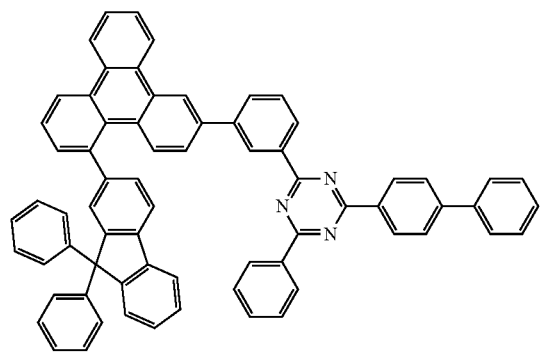
1-264
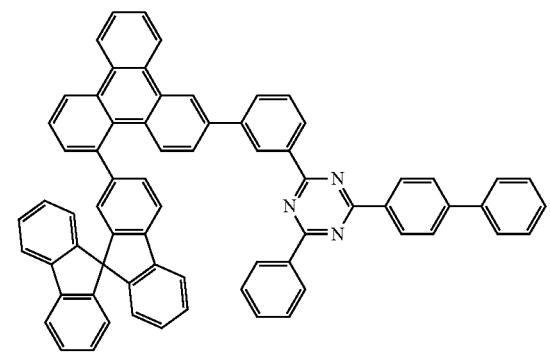
1-265
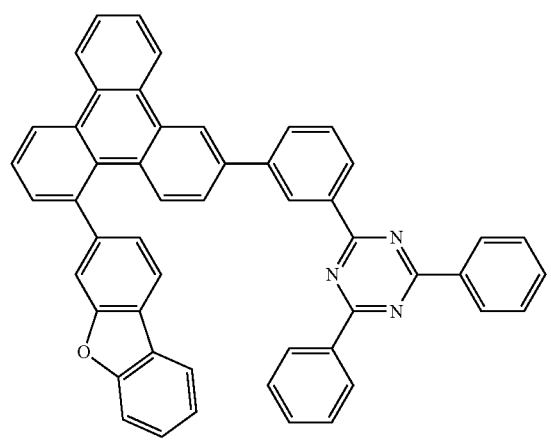
1-266
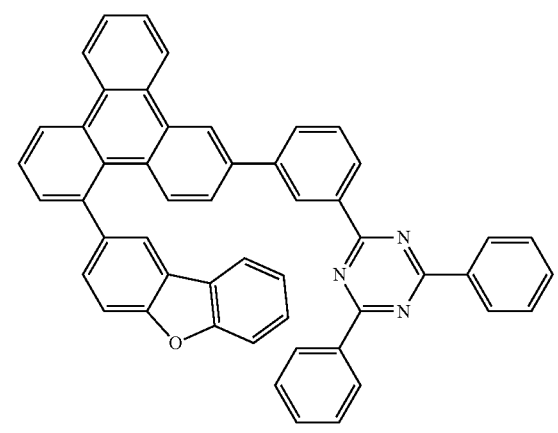

-continued
1-267
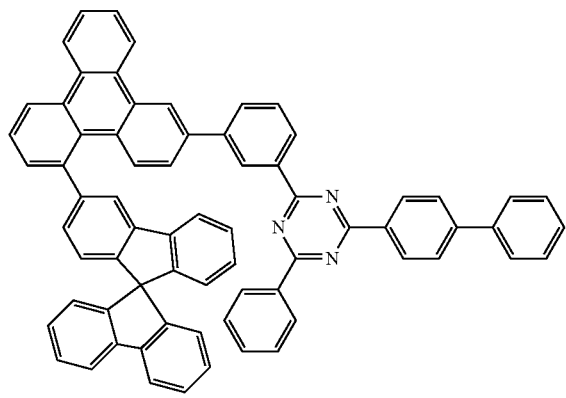
1-268
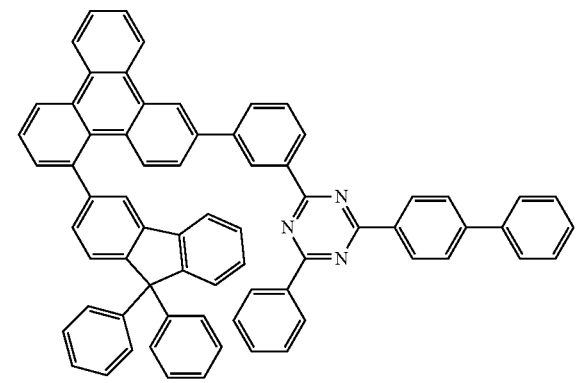
1-269
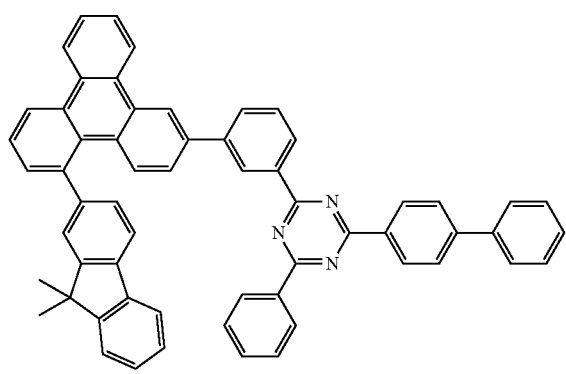
1-270
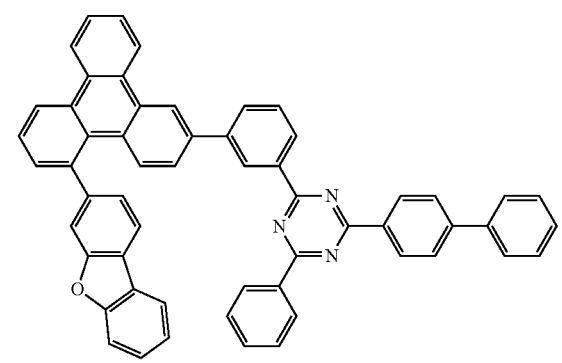
1-271
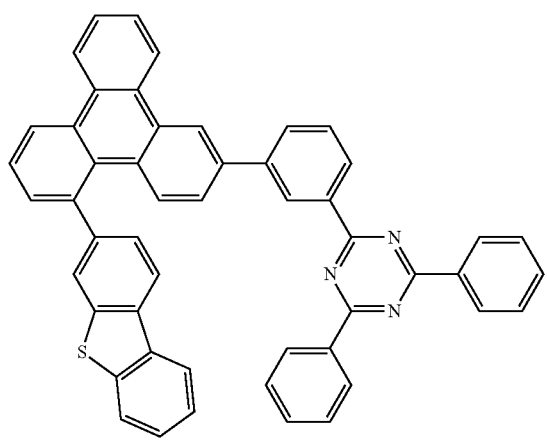
1-272
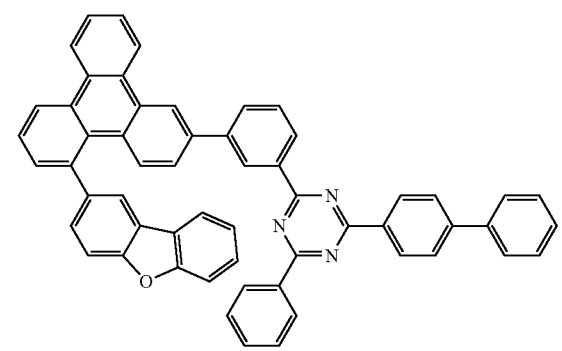

-continued
1-273
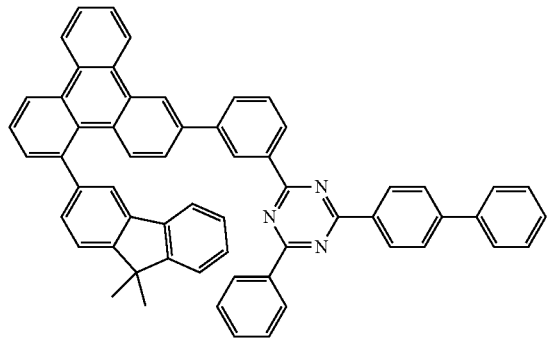
1-274
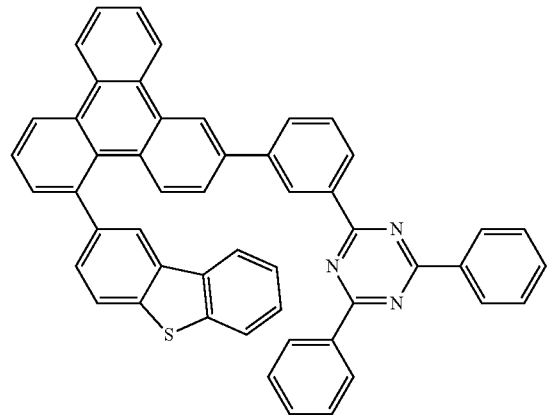
1-275
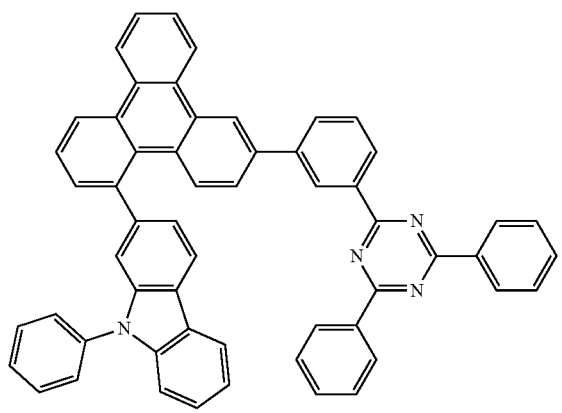
1-276
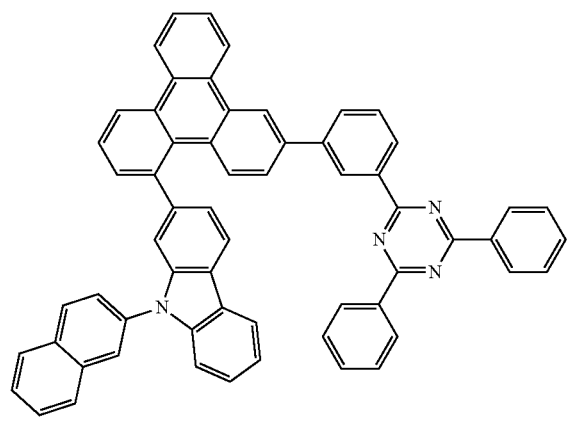
1-277
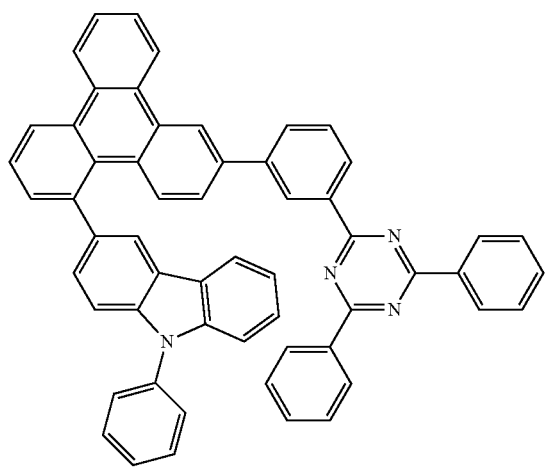
1-278
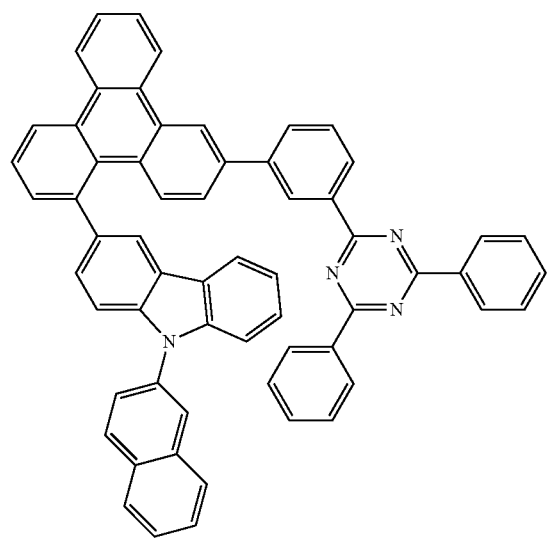

1-279
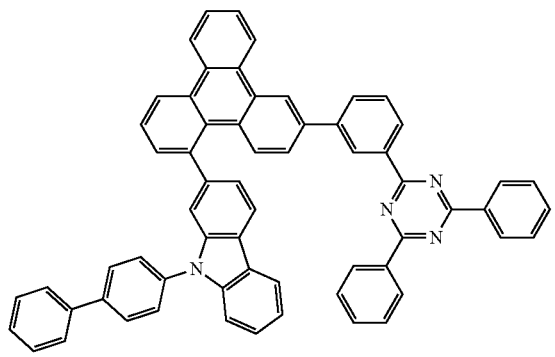
1-280
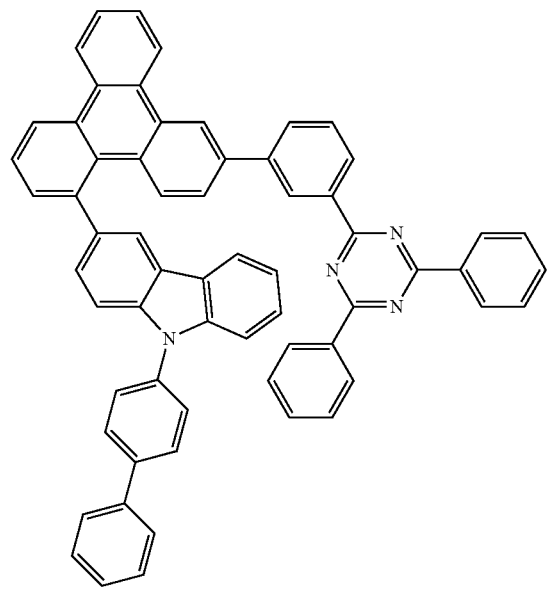
1-281
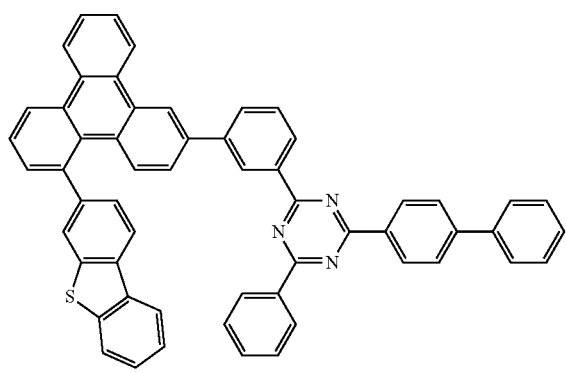
1-282
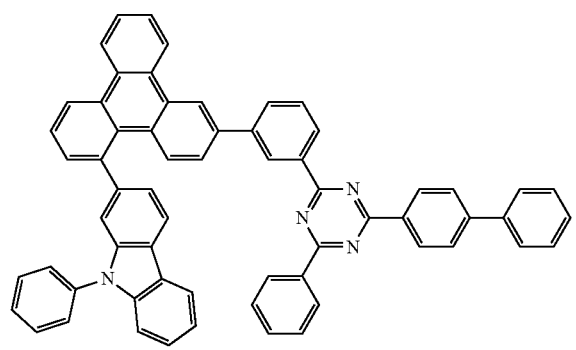
1-283
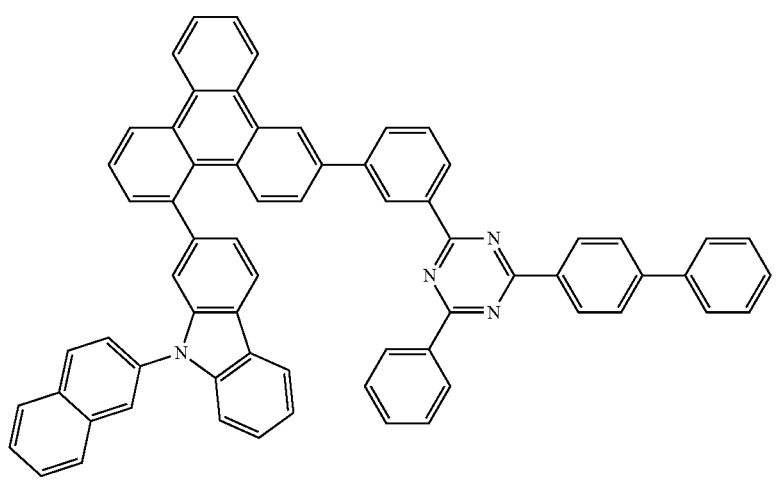

-continued
1-284
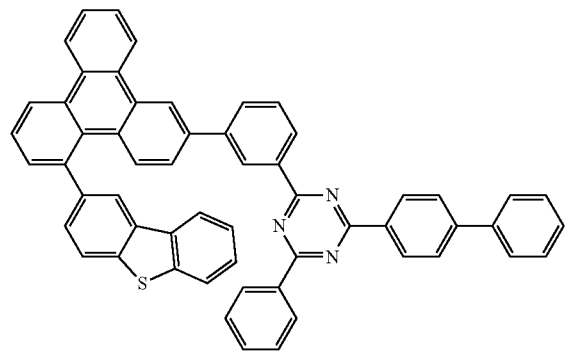
1-285
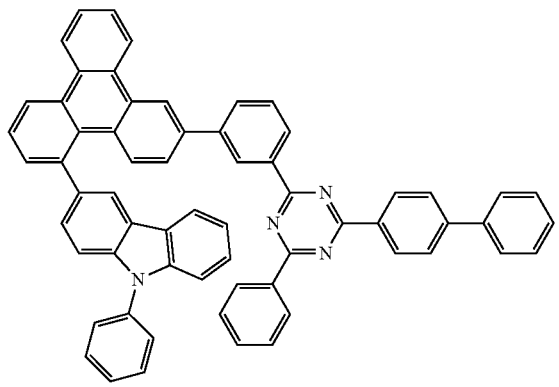
1-286
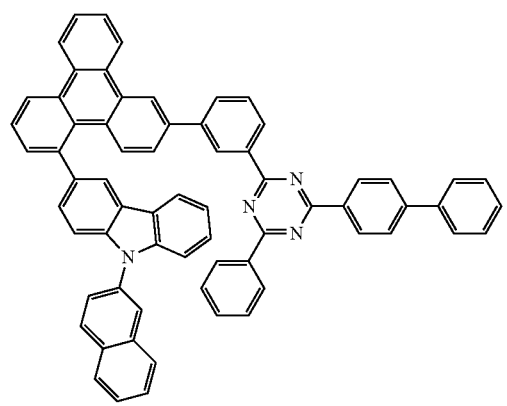
1-287
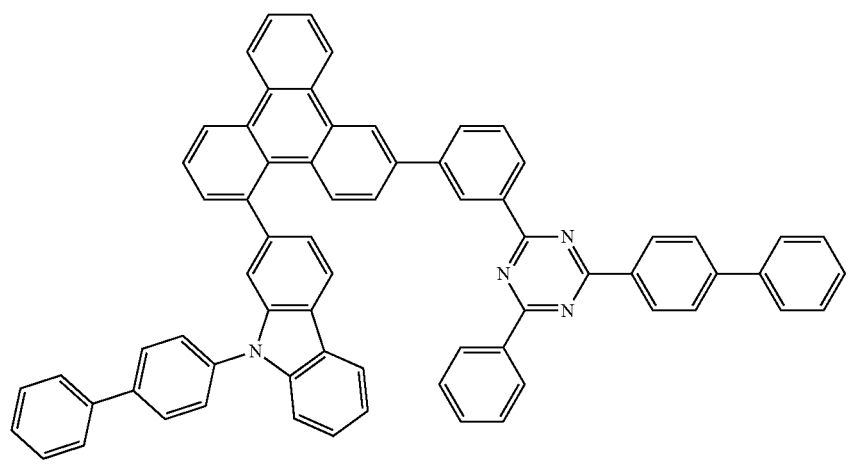

1-288
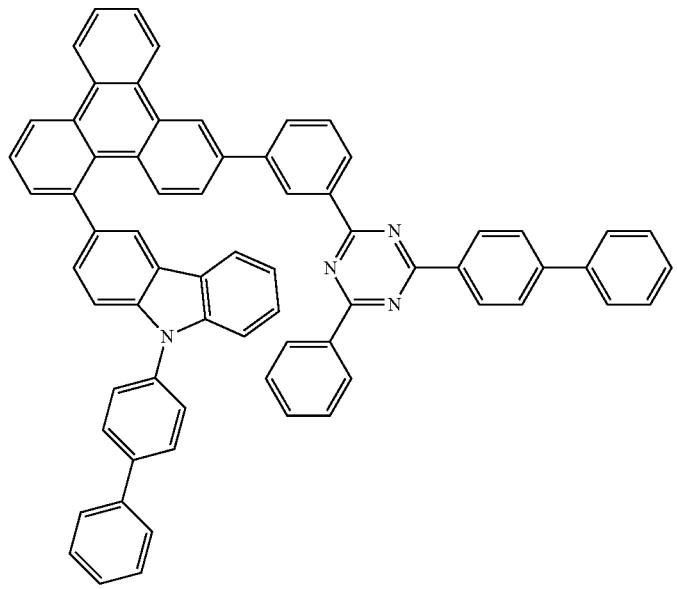
1-289
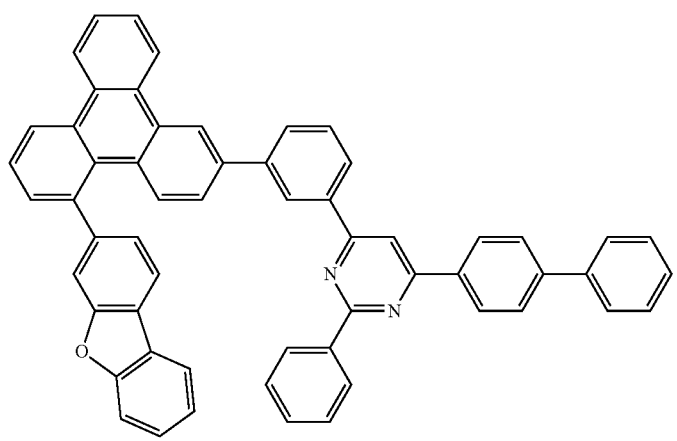
1-290
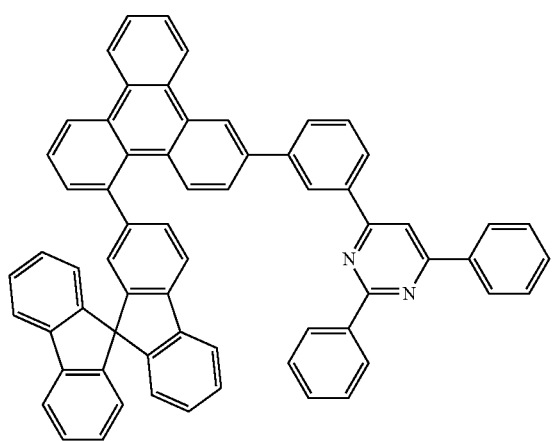
1-291
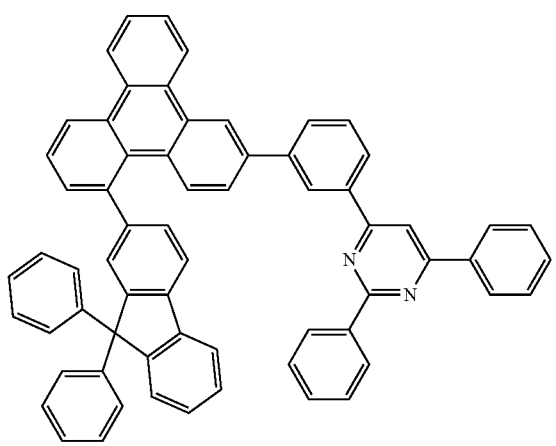

-continued
1-292
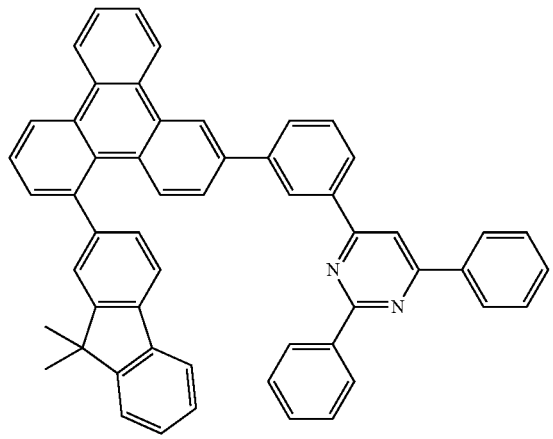
1-293
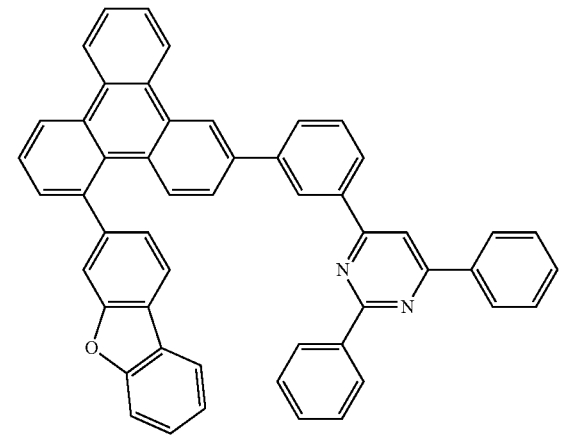
1-294
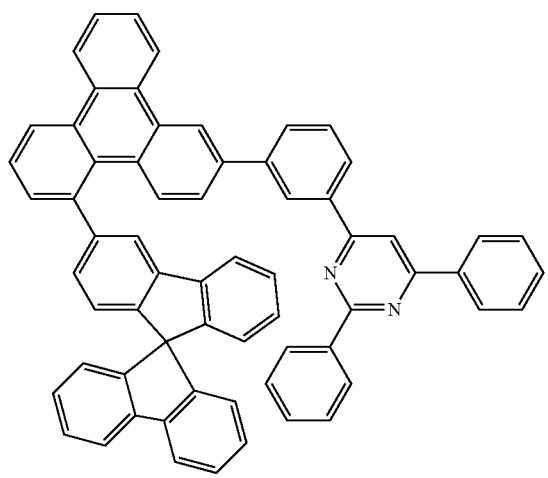
1-295
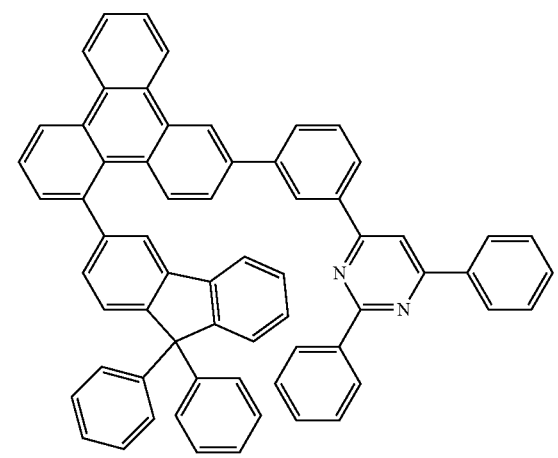
1-296
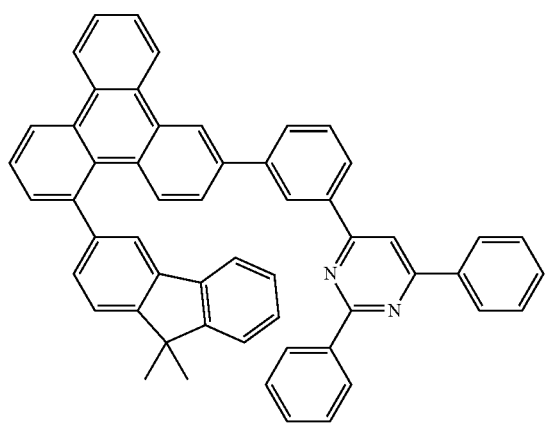
1-297
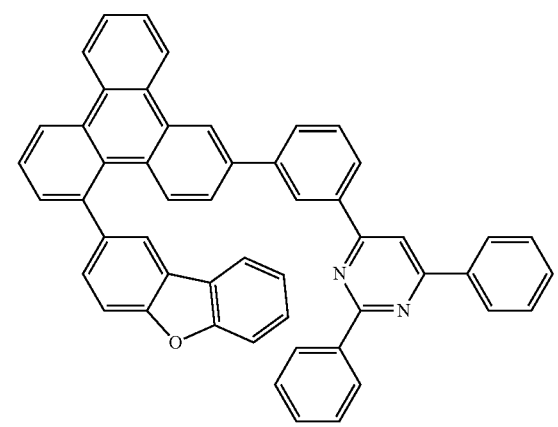

-continued
1-298
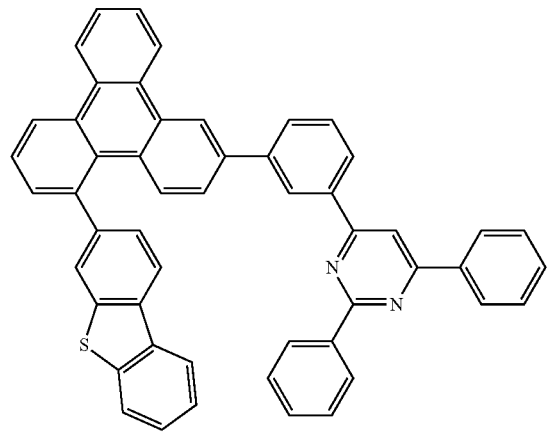
1-299
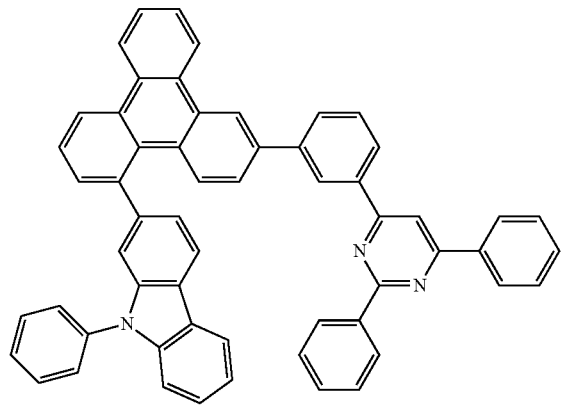
1-300
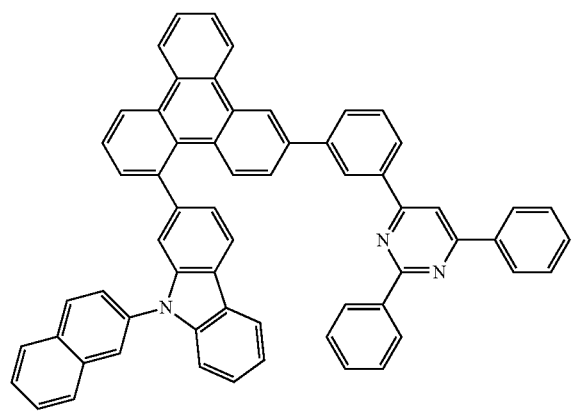
1-301
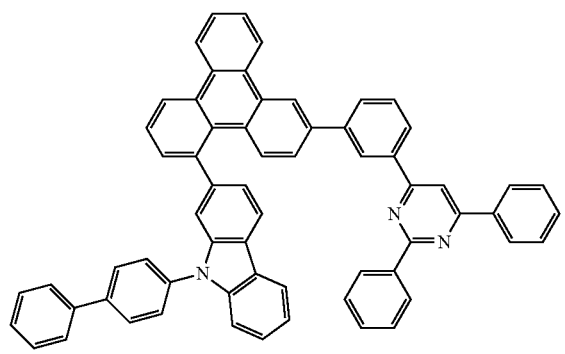
1-302
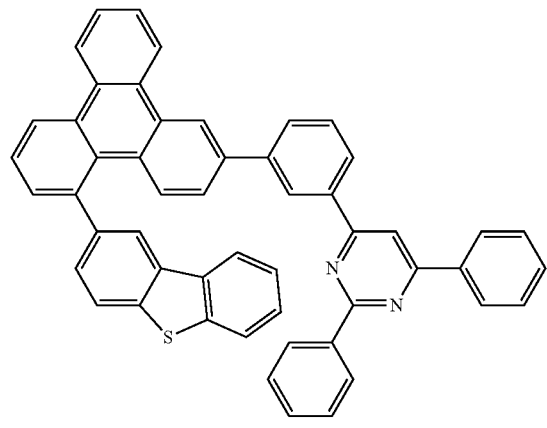
1-303
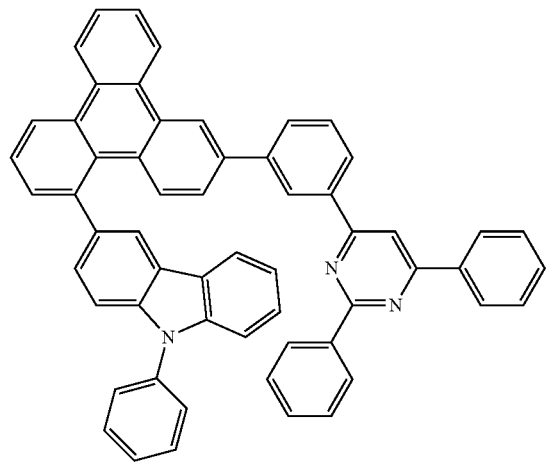

1-304
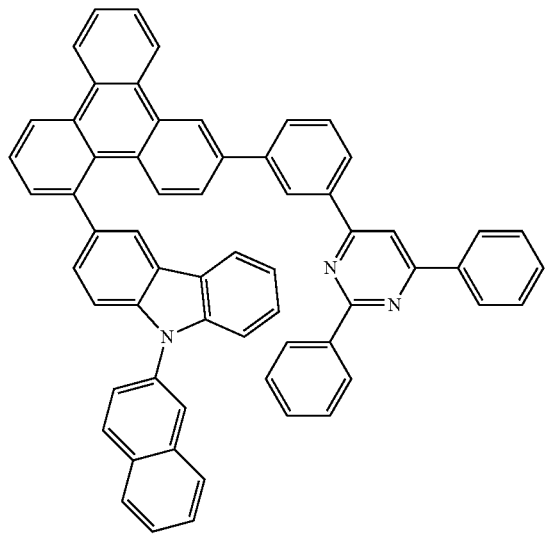
1-305
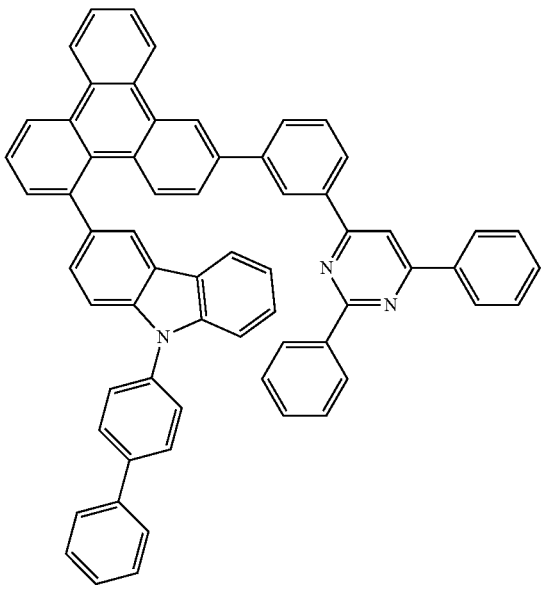
1-306
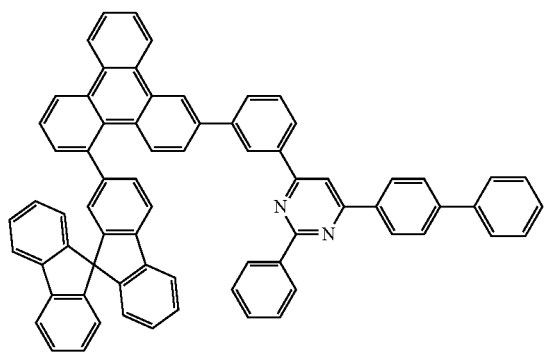
1-307
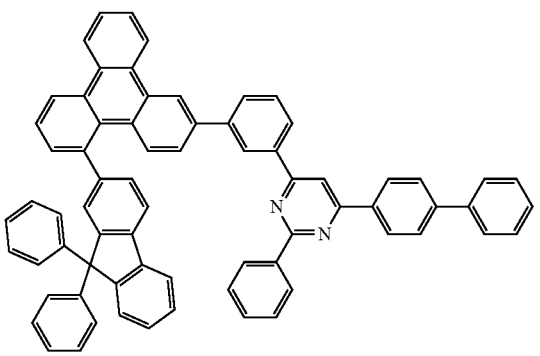
1-308
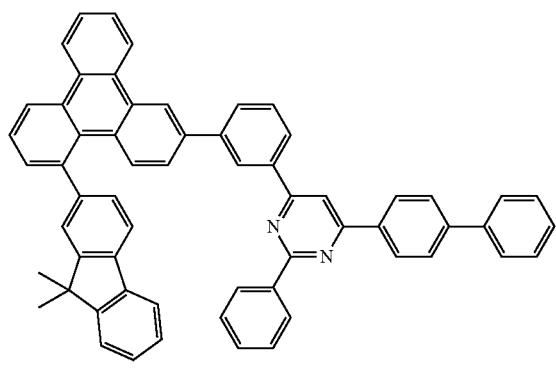
1-309
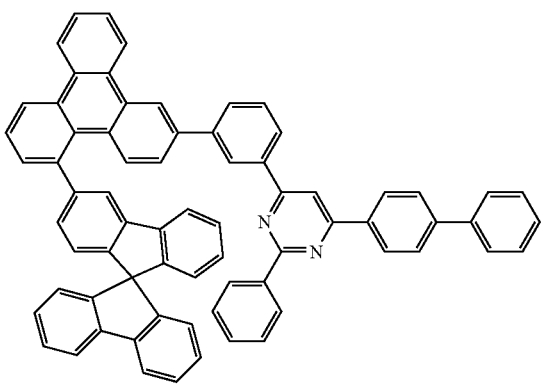

-continued
1-310
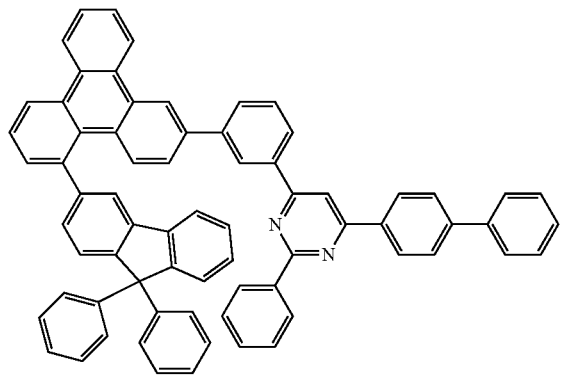
1-311
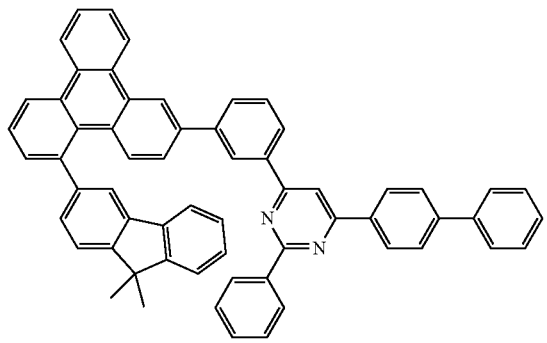
1-312
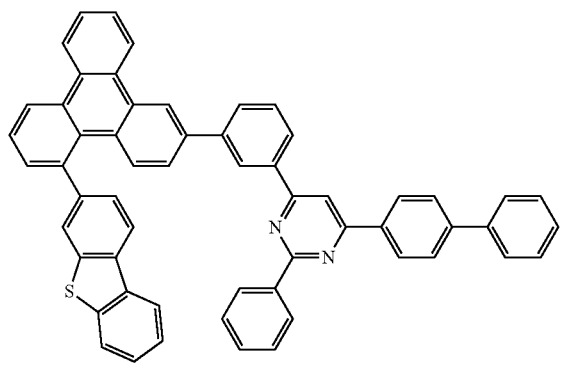
1-313
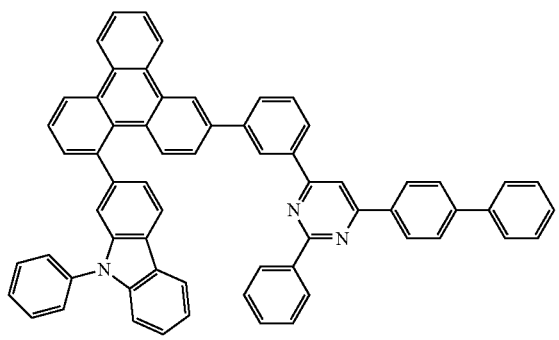
1-134
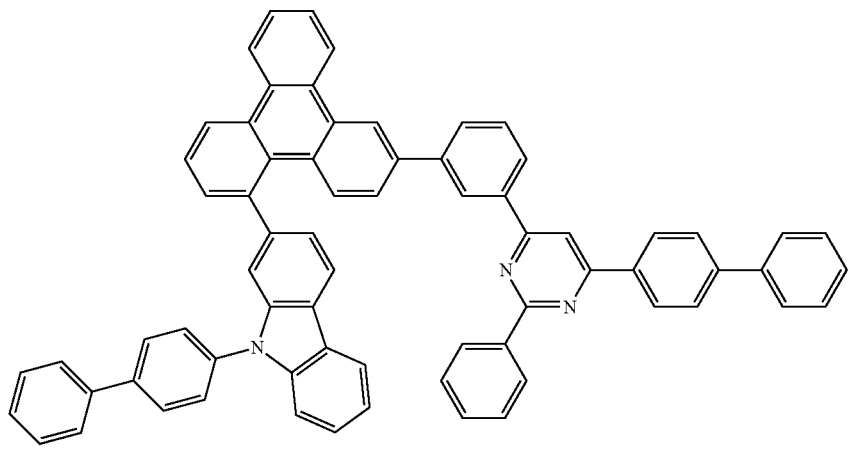
1-315
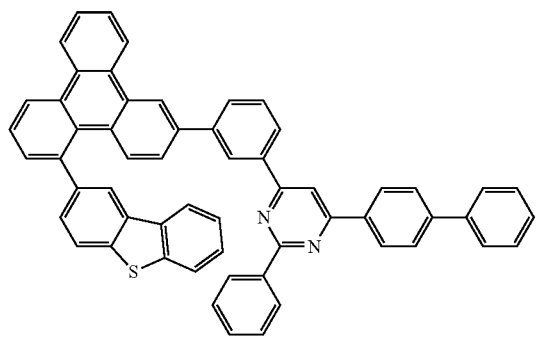
1-316
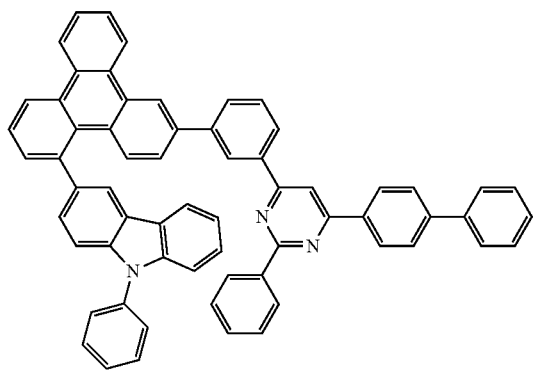

1-317
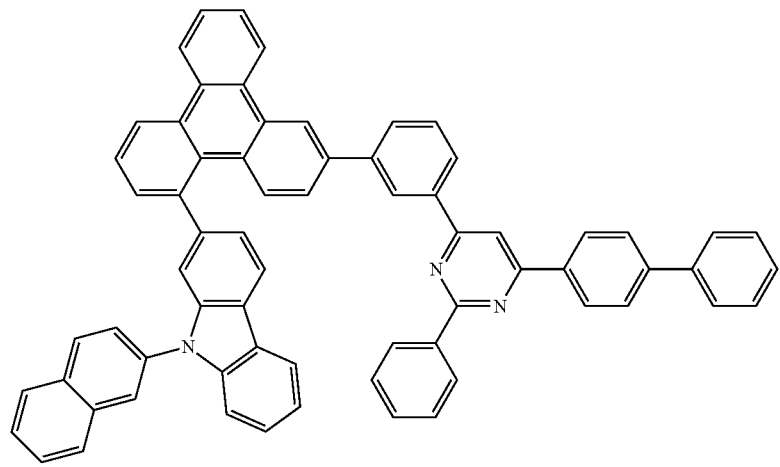
1-318
1-319
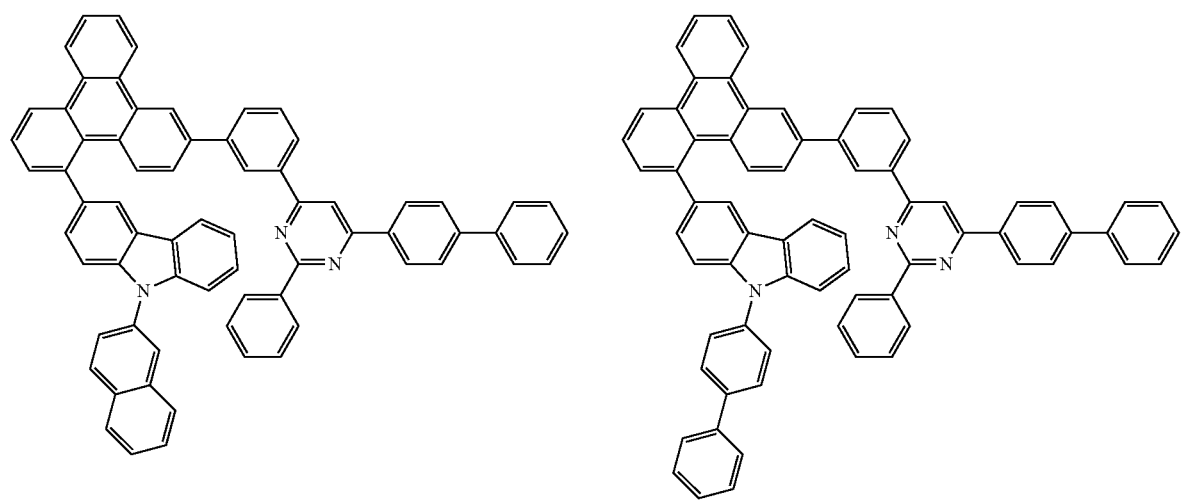
1-320
1-321
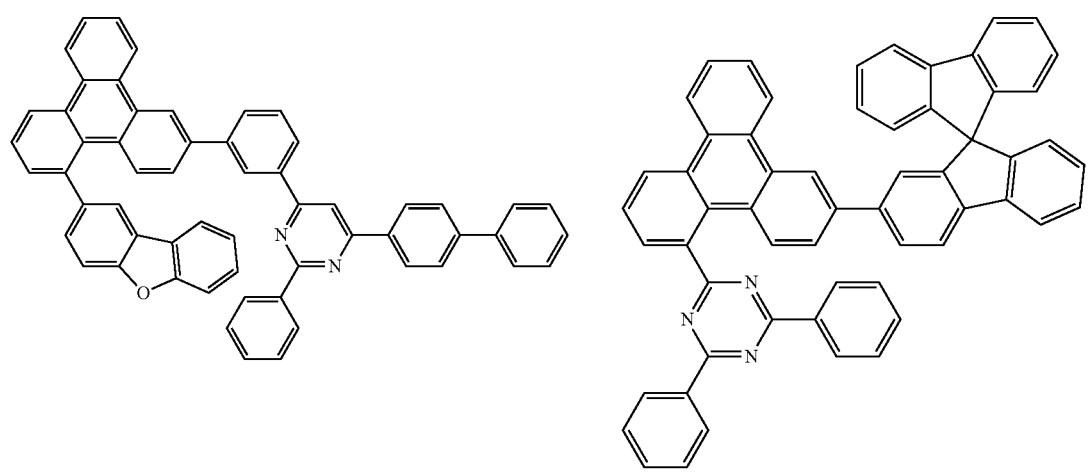

-continued
1-322
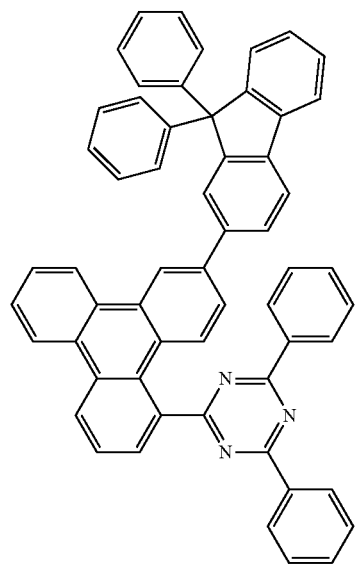
1-323
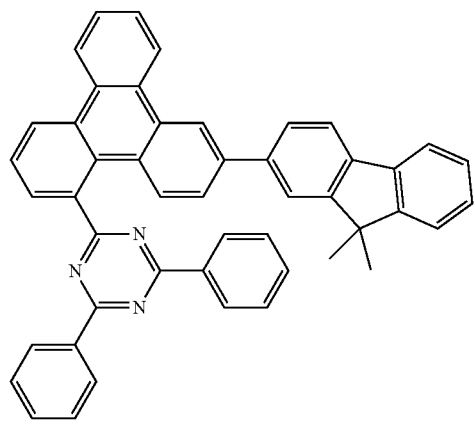
1-324
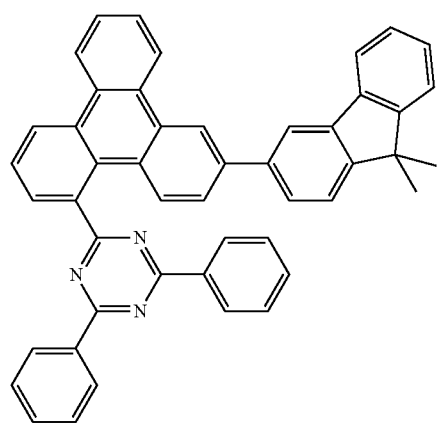
1-325
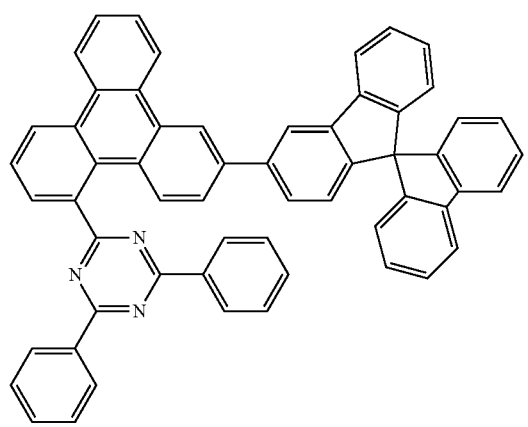
1-326
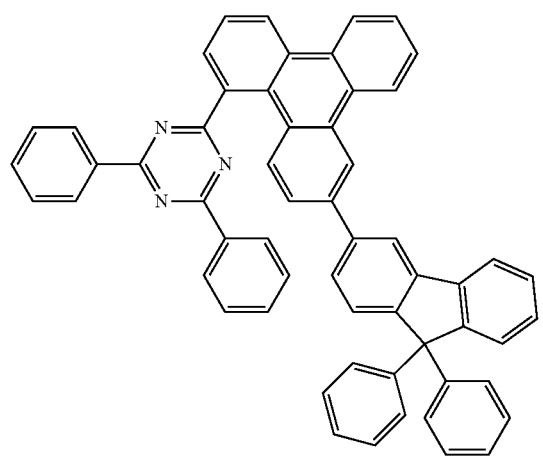
1-327
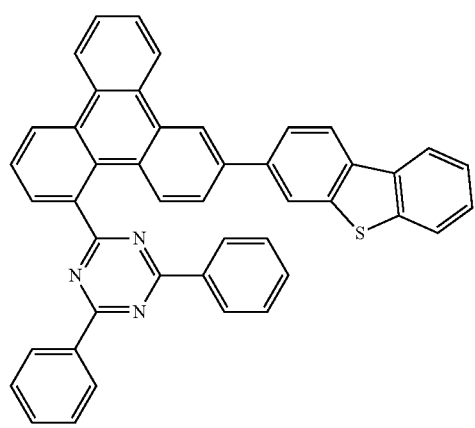

1-328
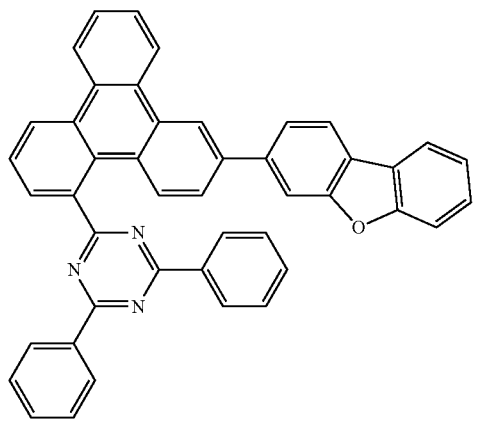
1-329
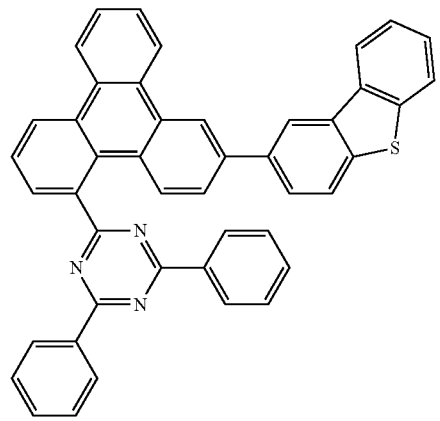
1-330
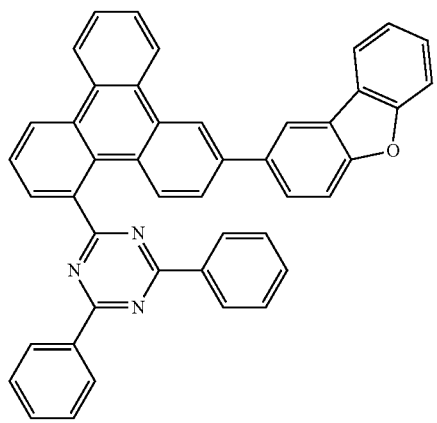
1-331
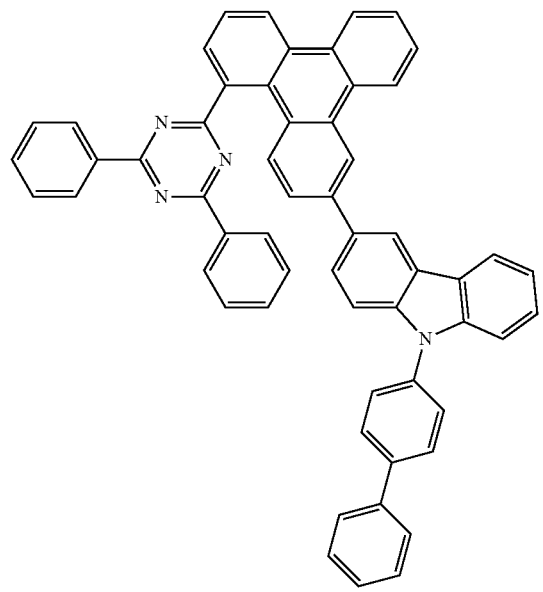
1-332
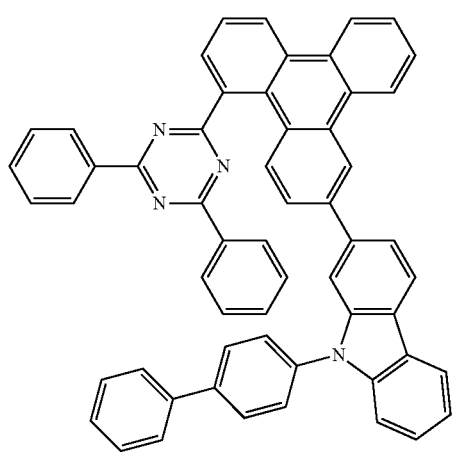
1-333
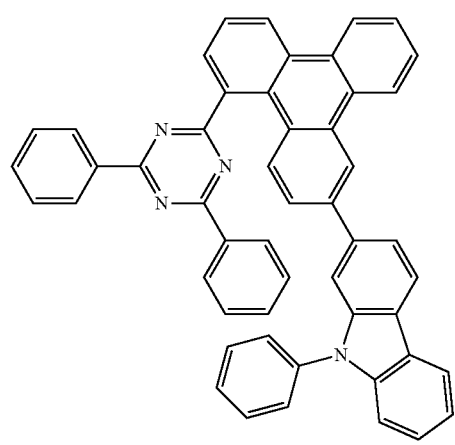

-continued
1-334
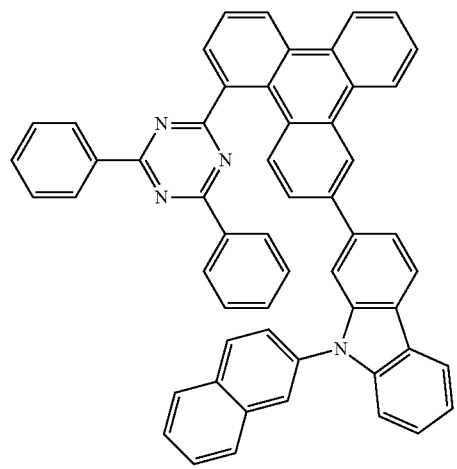
1-335
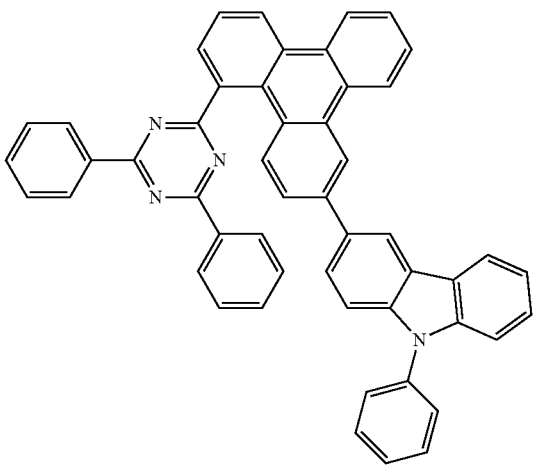
1-336
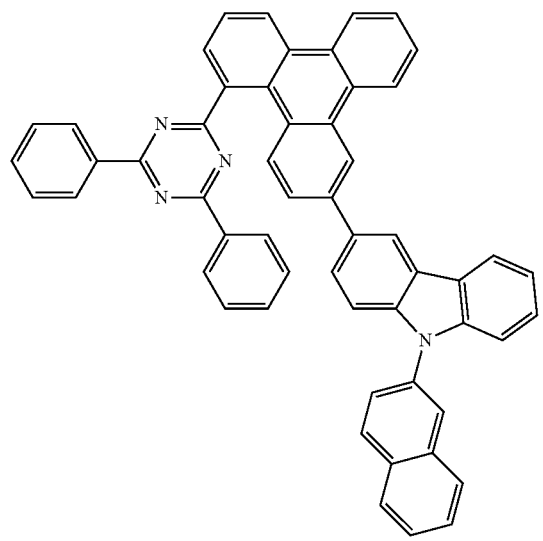
1-337
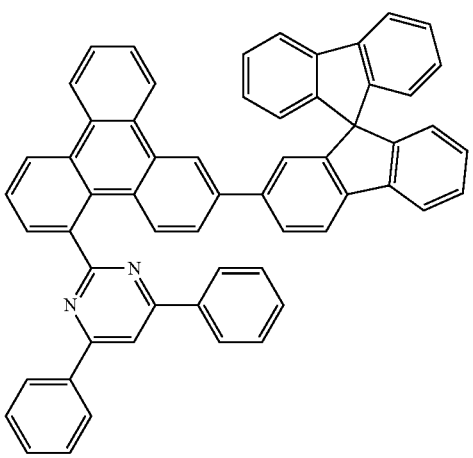
1-338
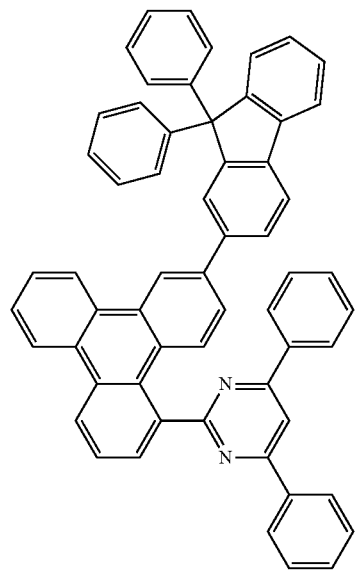
1-339
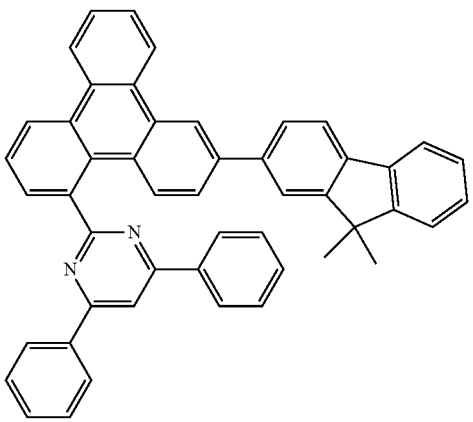

-continued
1-340
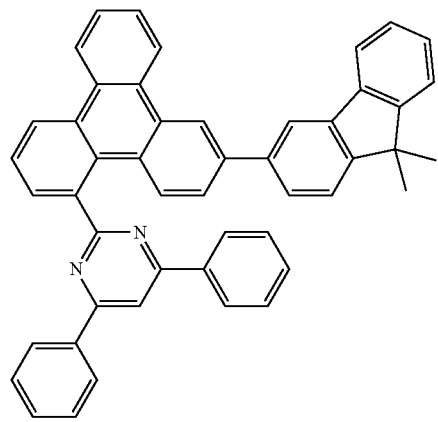
1-341
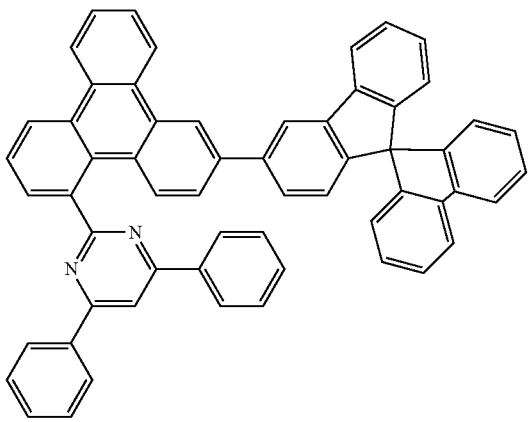
1-342
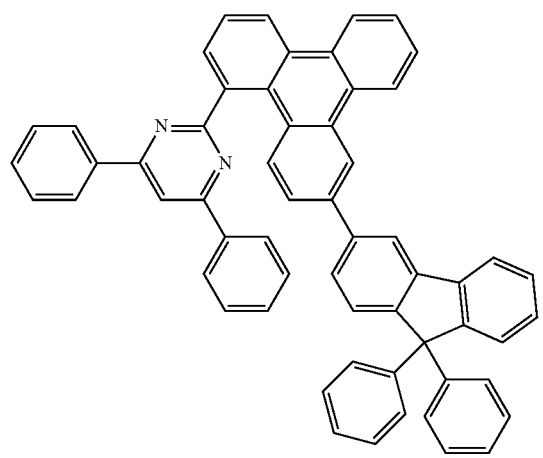
1-343
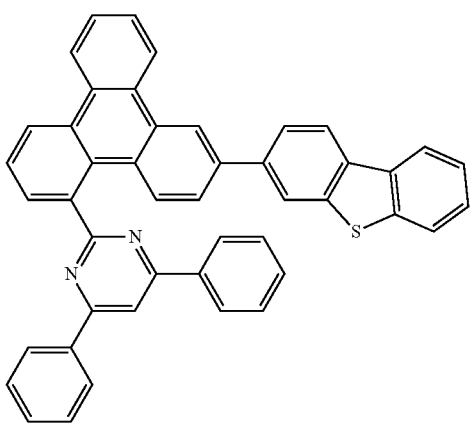
1-344
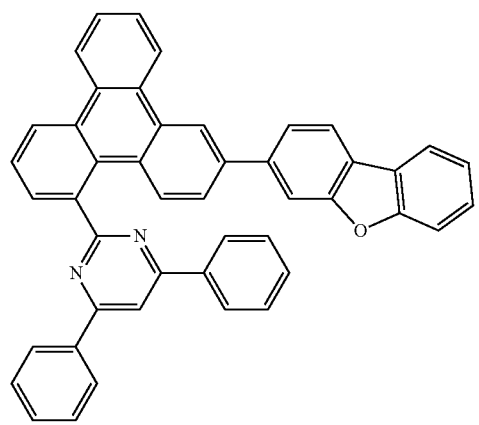
1-345
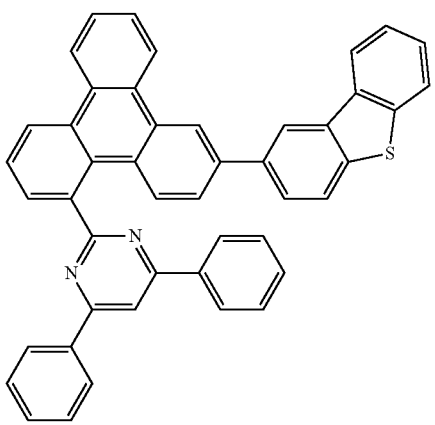

-continued
1-346
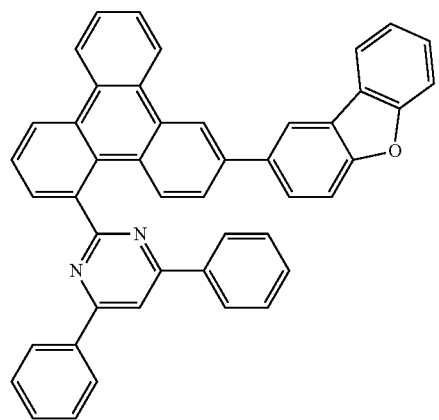
1-347
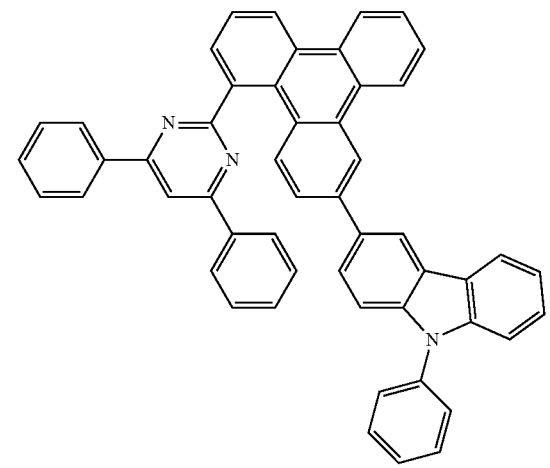
1-348
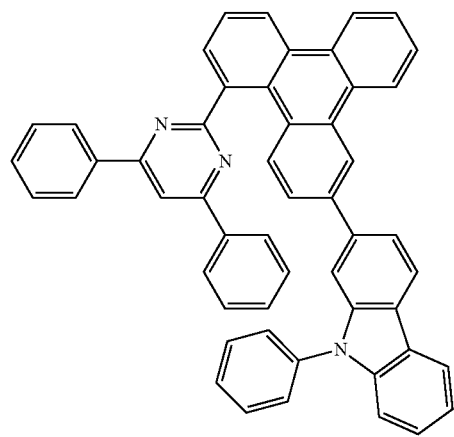
1-349
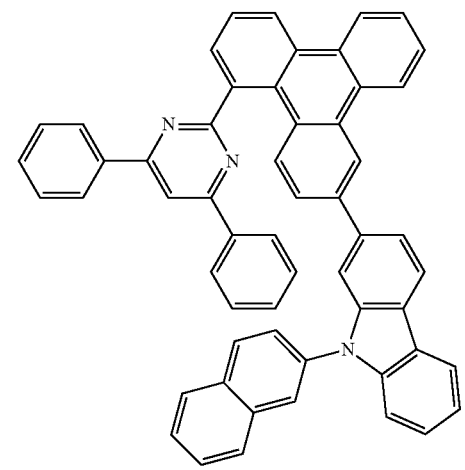
1-350
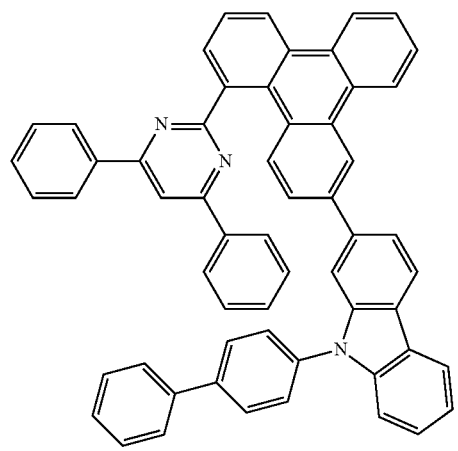
1-351
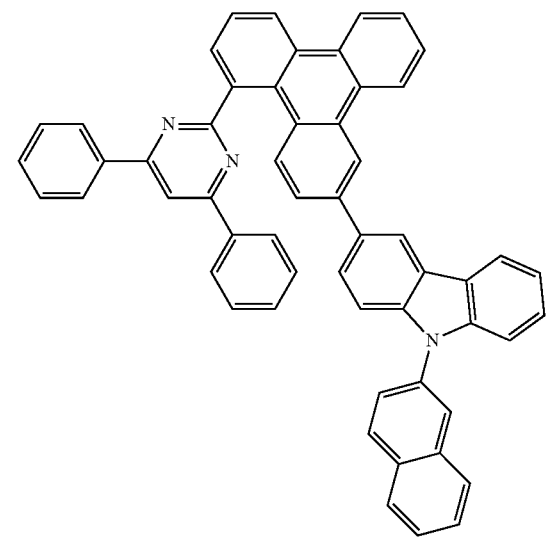

-continued
1-352
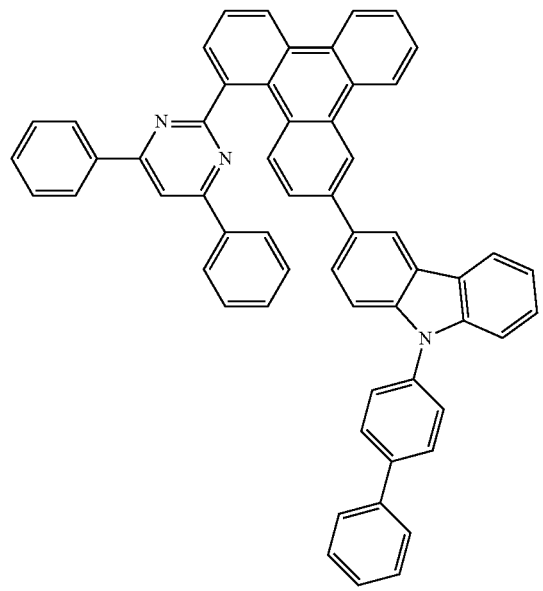
1-353
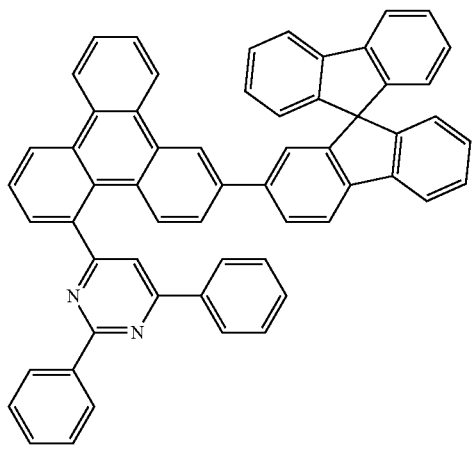
1-354
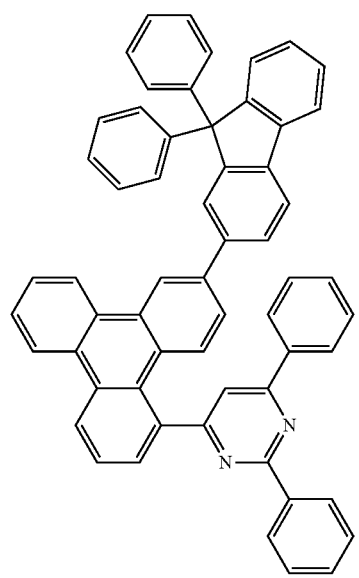
1-355
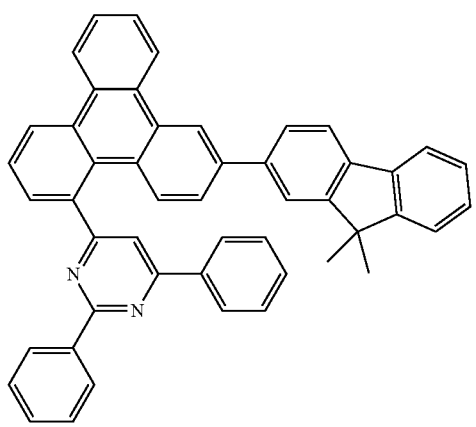
1-356
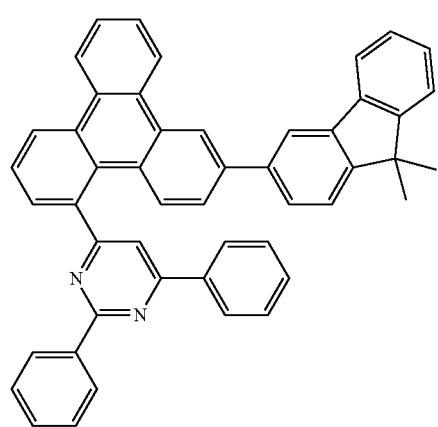
1-357
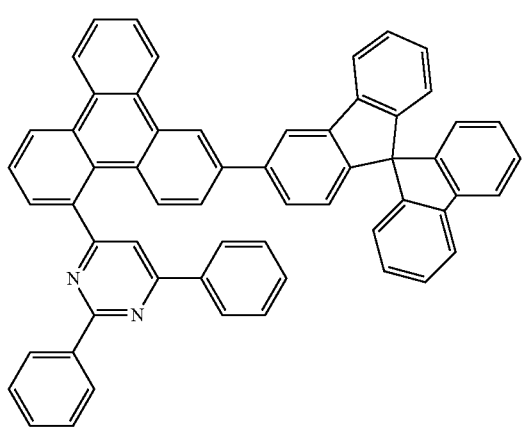

-continued
1-358
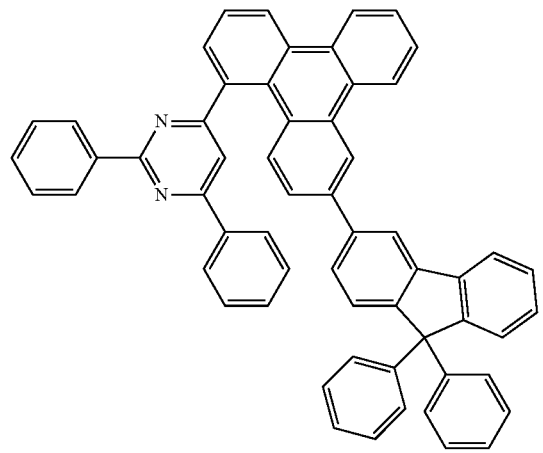
1-359
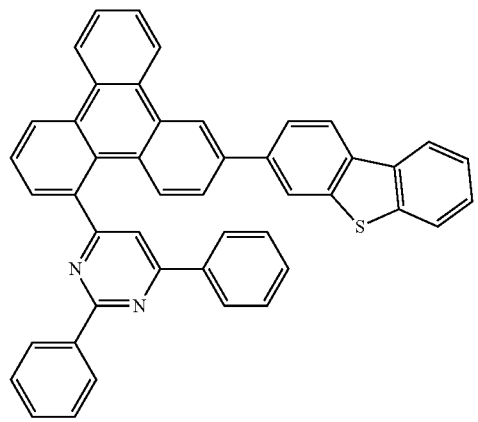
1-360
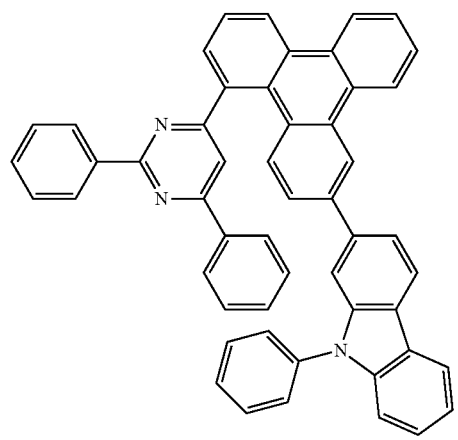
1-361
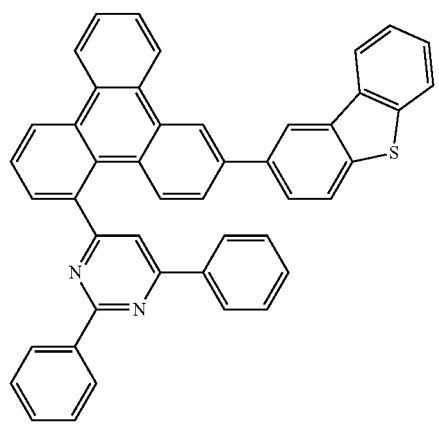
1-362
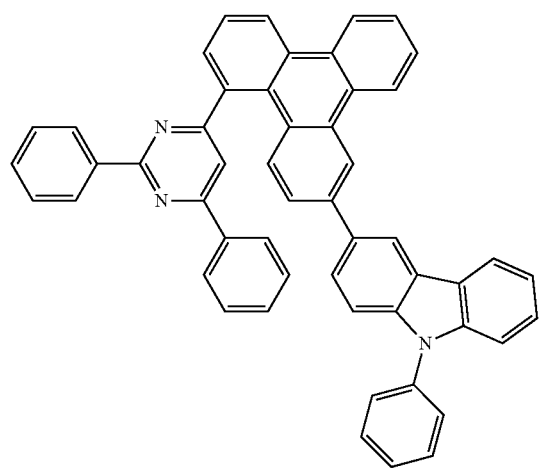
1-363
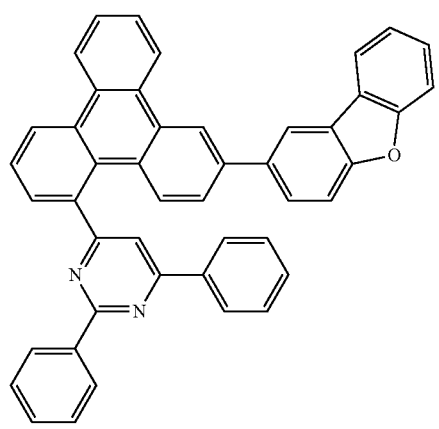

1-364
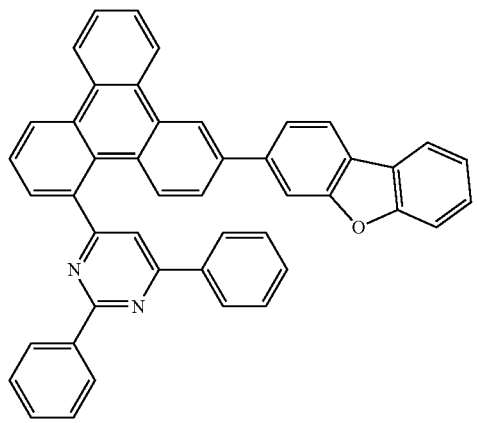
1-365
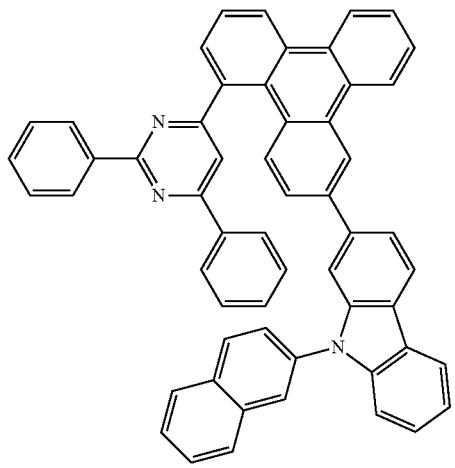
1-366
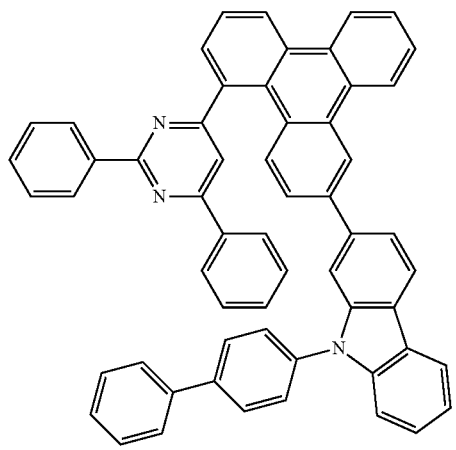
1-367
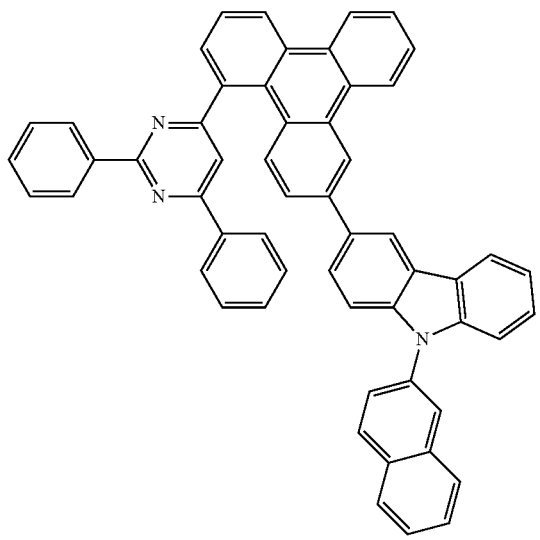
1-368
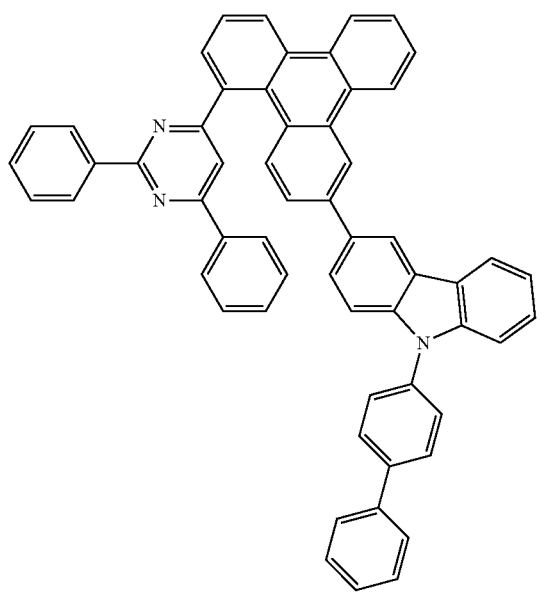
1-369
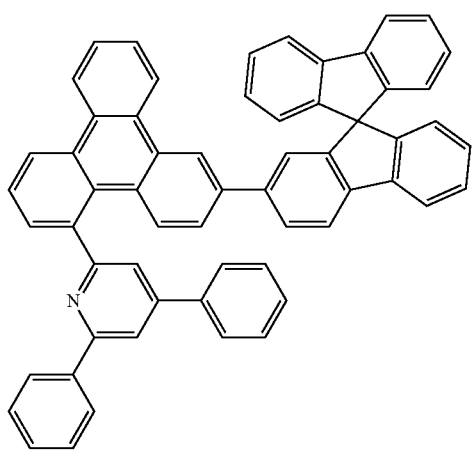

1-370
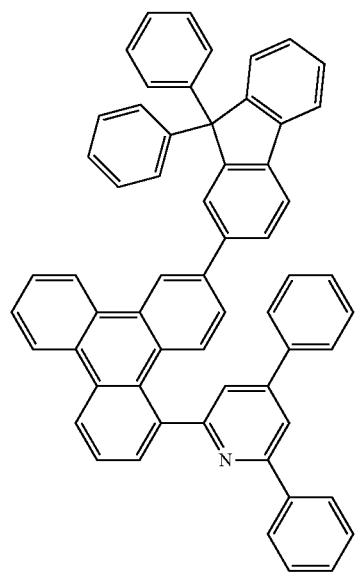
1-371
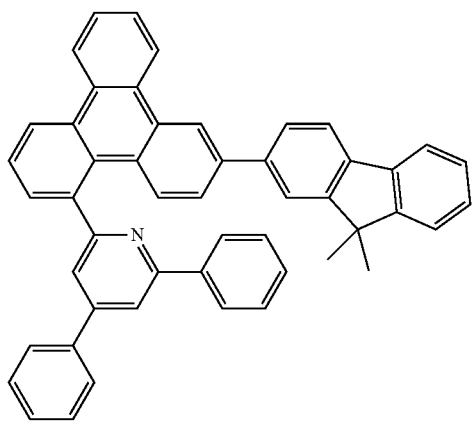
1-372
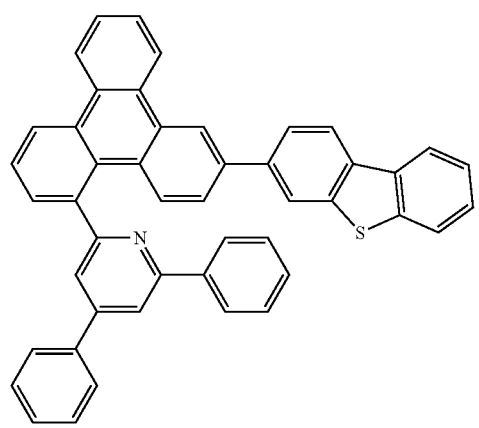
1-373
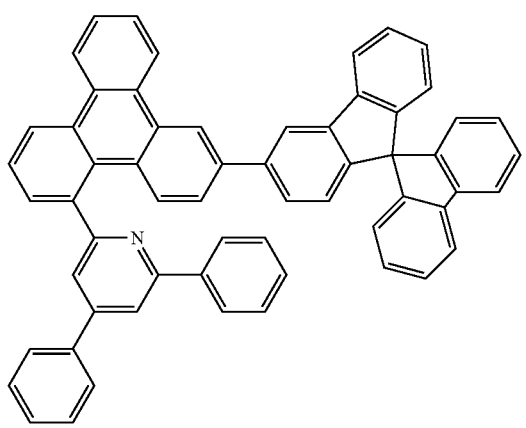
1-374
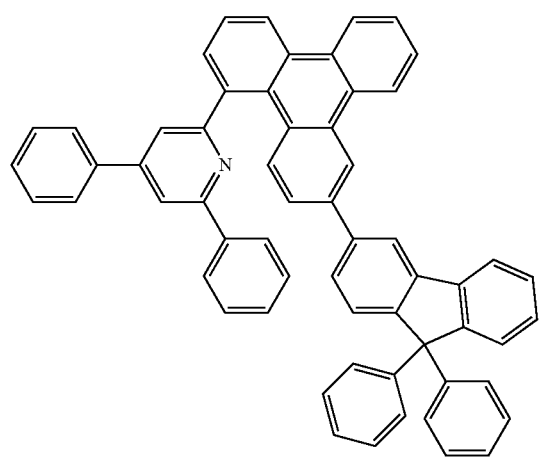
1-375
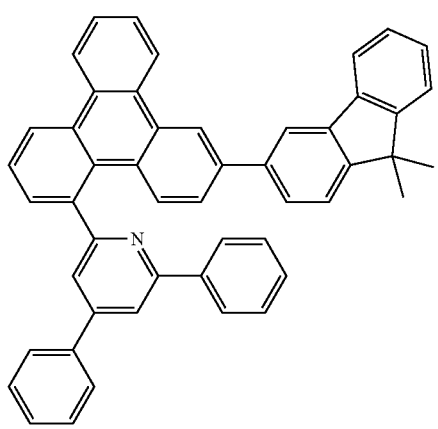

-continued
1-376
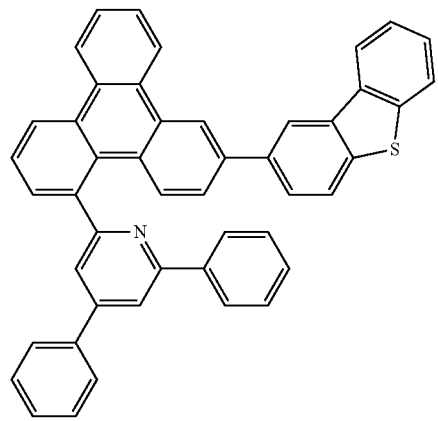
1-377
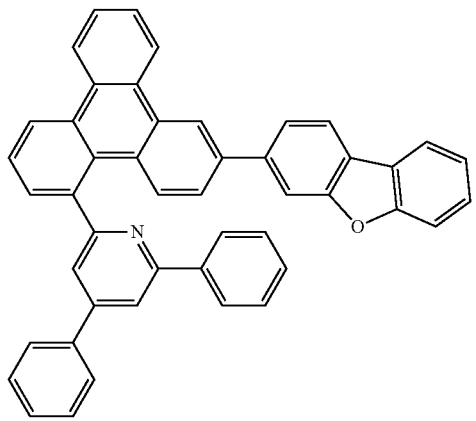
1-378
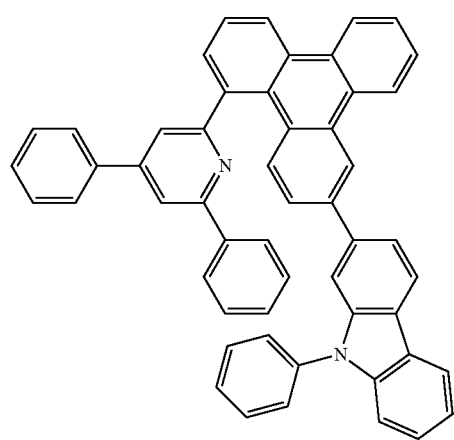
1-379
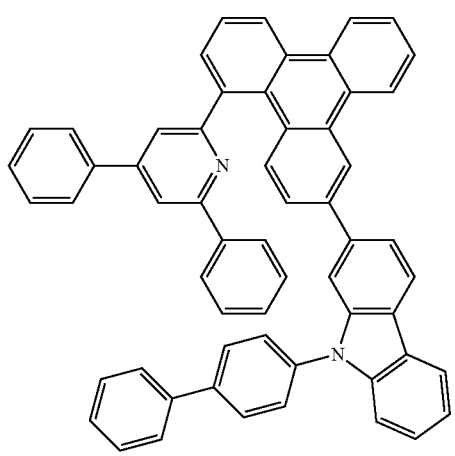
1-380
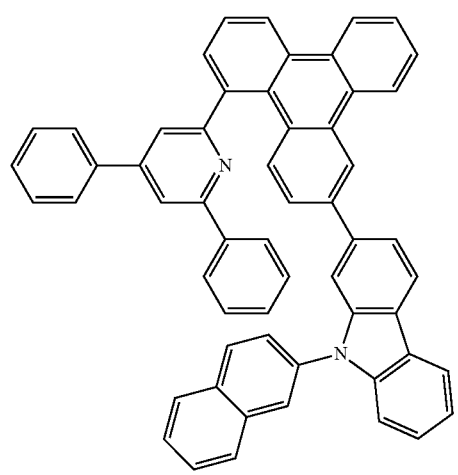
1-381
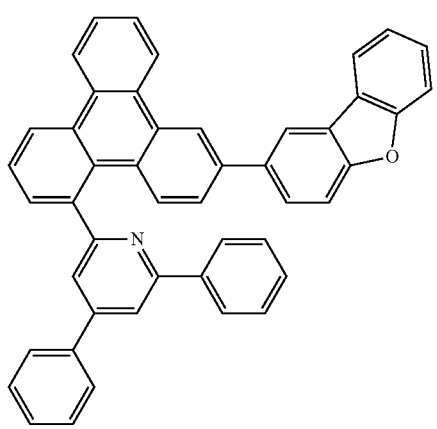

413
1-382
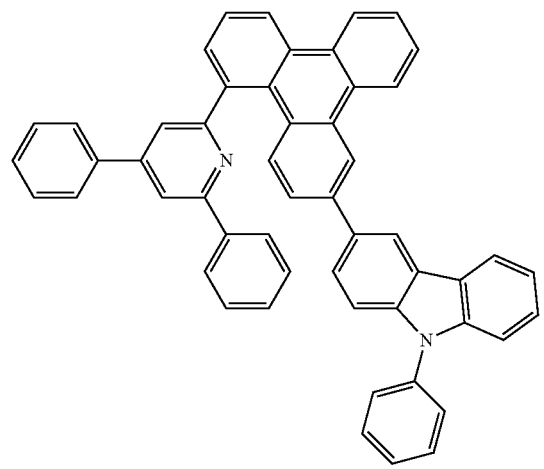
414
-continued
1-383
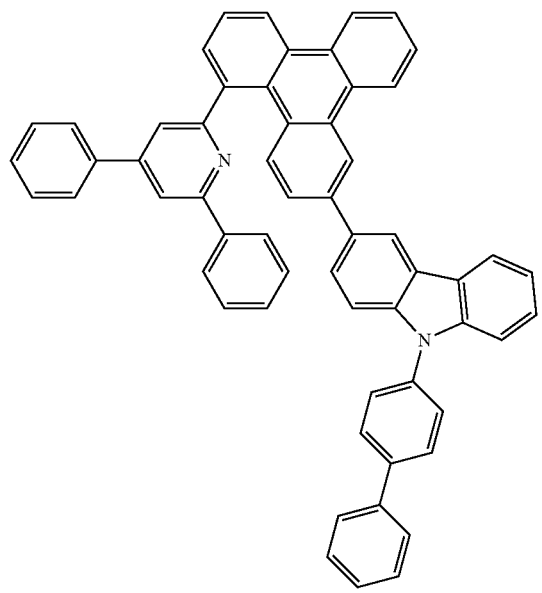
1-384
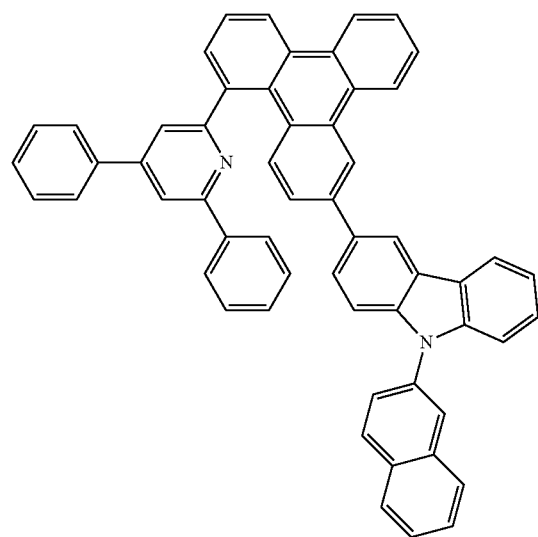
1-385
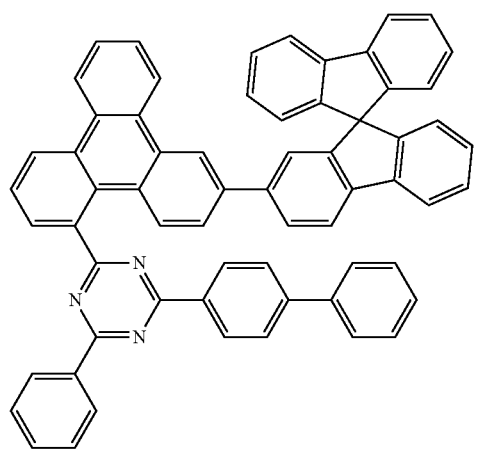

-continued
1-386
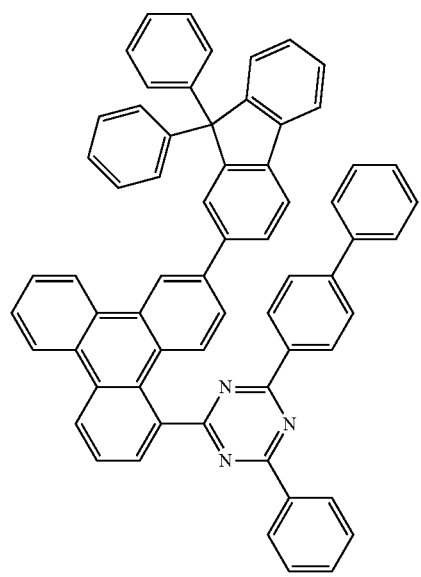
1-387
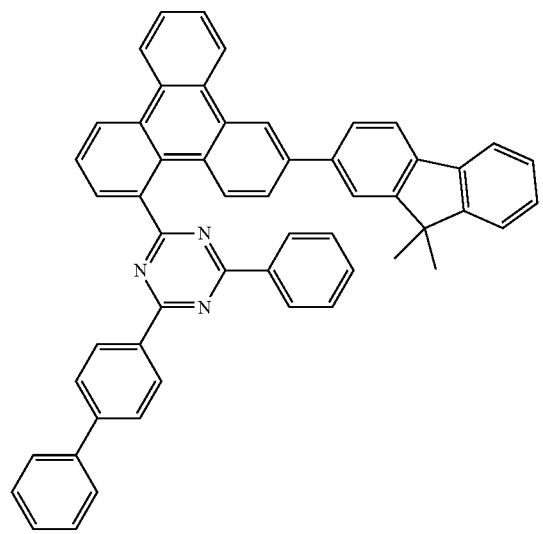
1-388
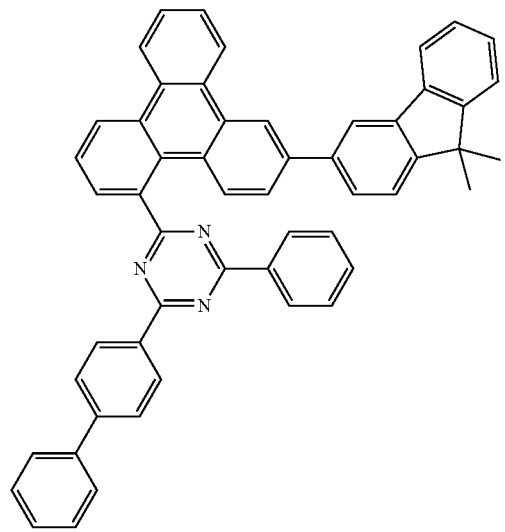
1-389
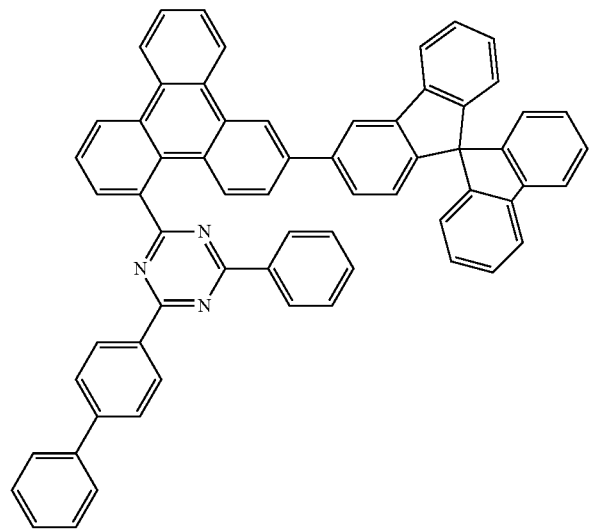

-continued
1-390
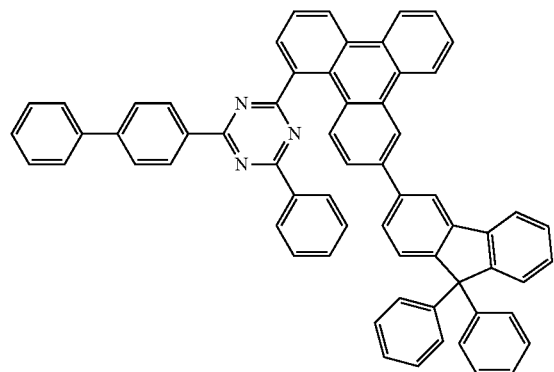
1-391
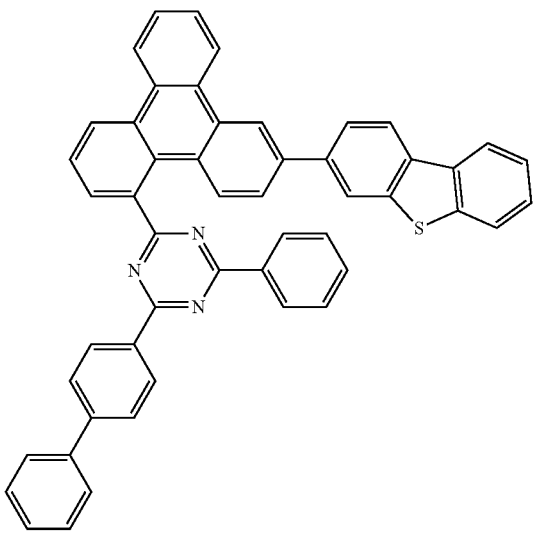
1-392
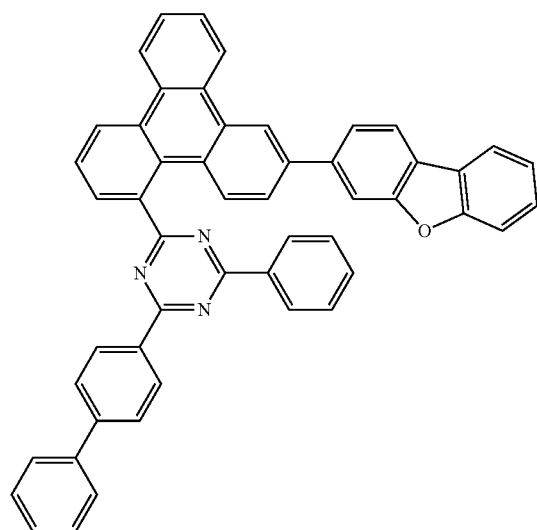
1-393
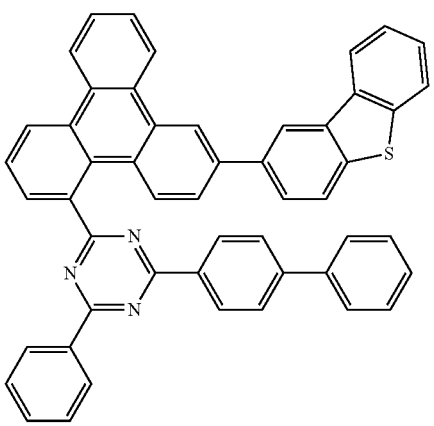
1-394
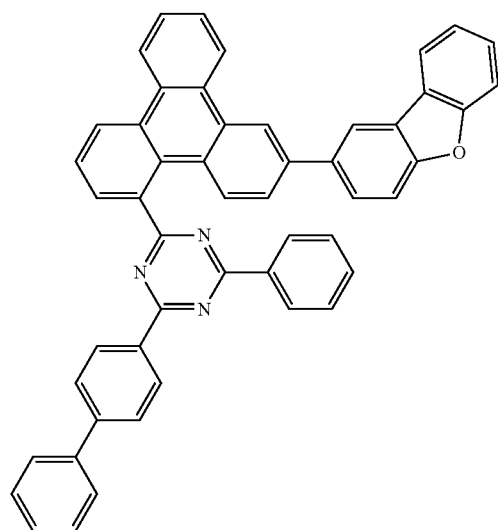
1-395
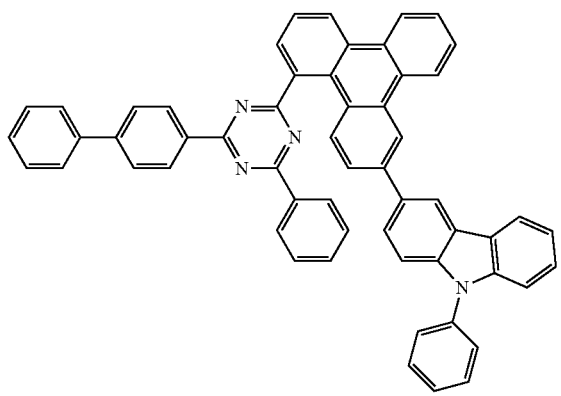

-continued
1-396
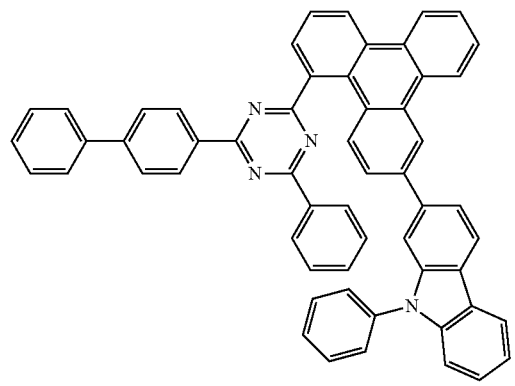
1-397
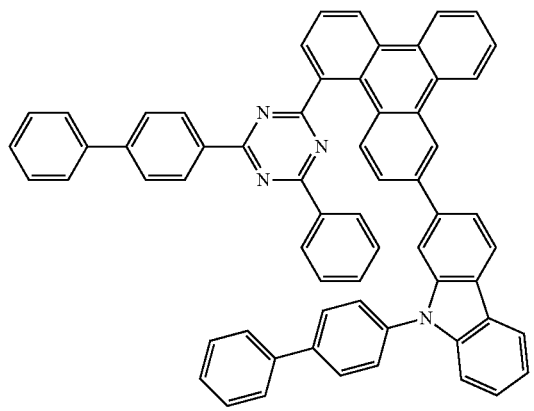
1-398
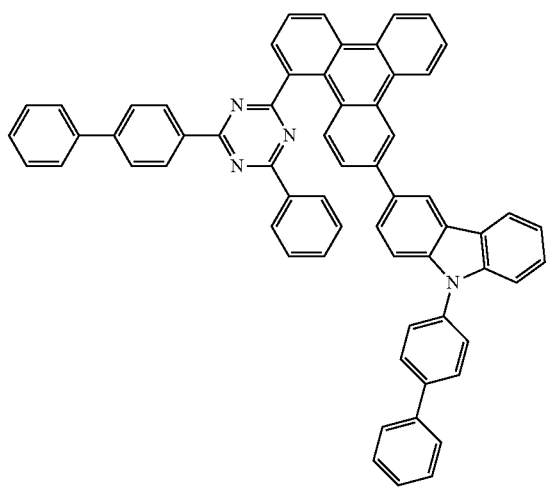
1-399
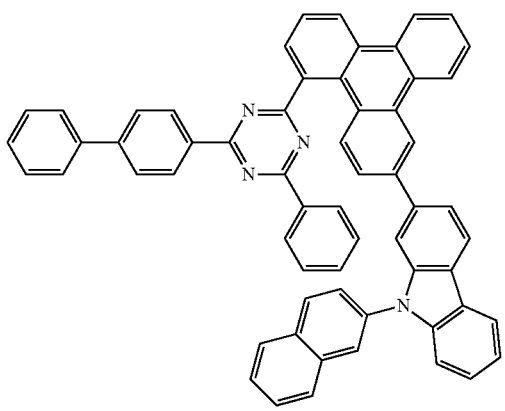
1-400
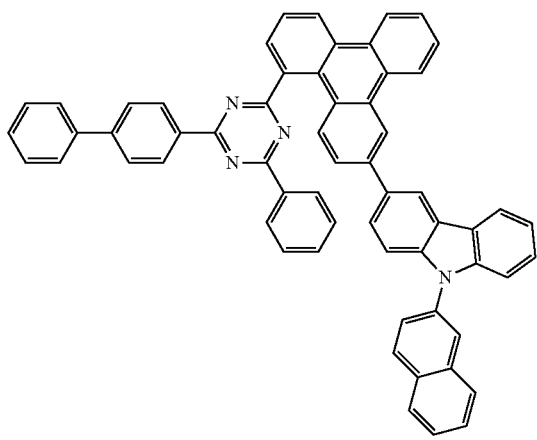
1-401
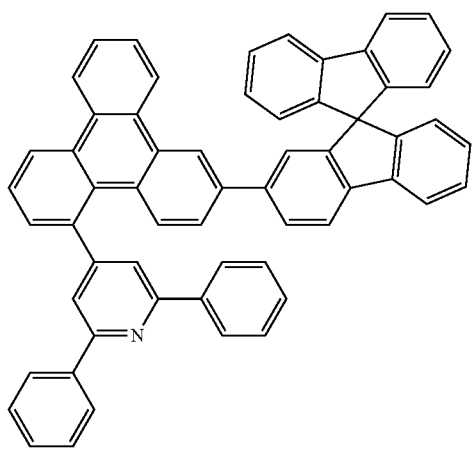

-continued
1-402
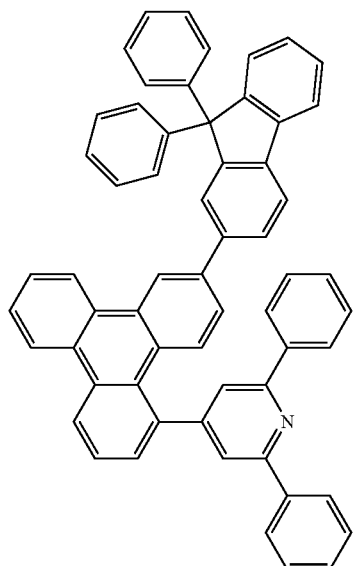
1-403
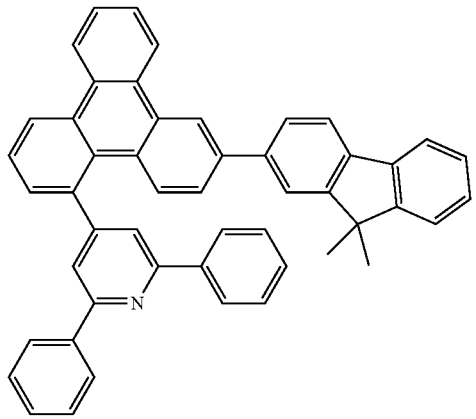
1-404
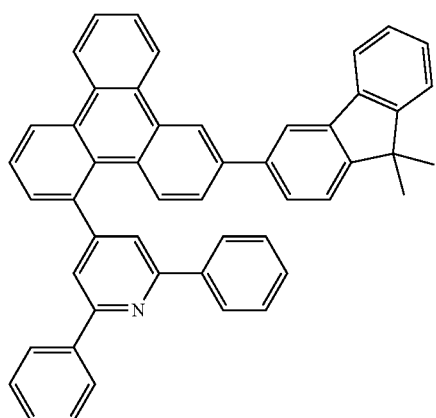
1-405
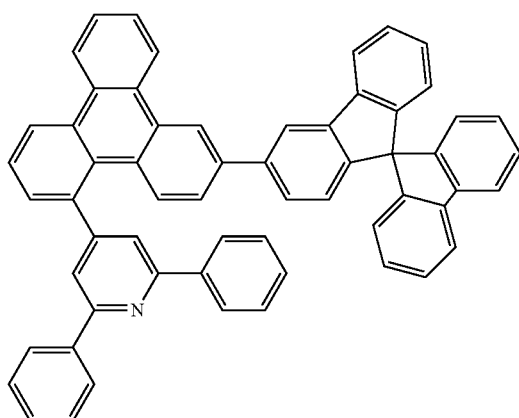
1-406
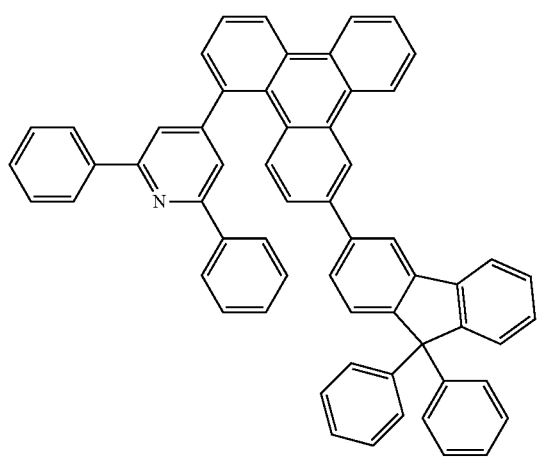
1-407
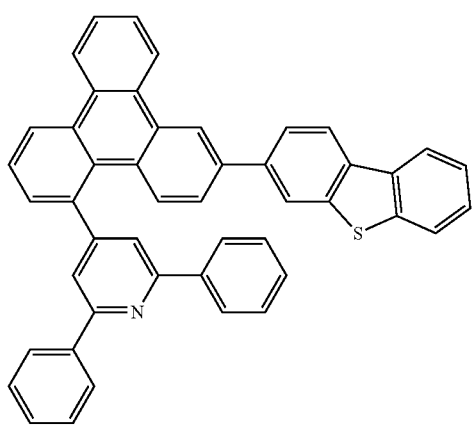

-continued
| 1-408 | 1-409 |
|---|---|
| 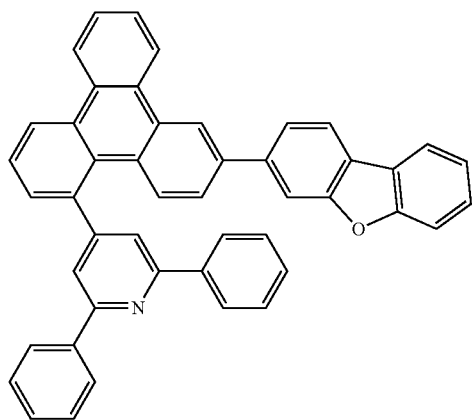 | 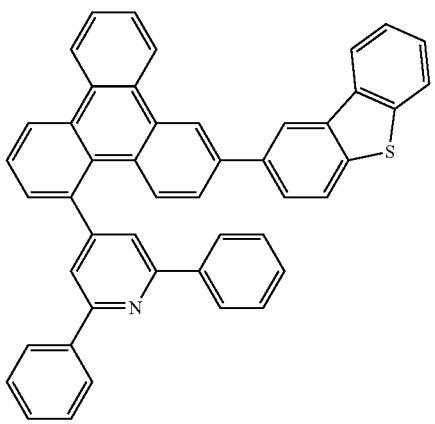 |
| 1-410 | 1-411 |
|---|---|
| 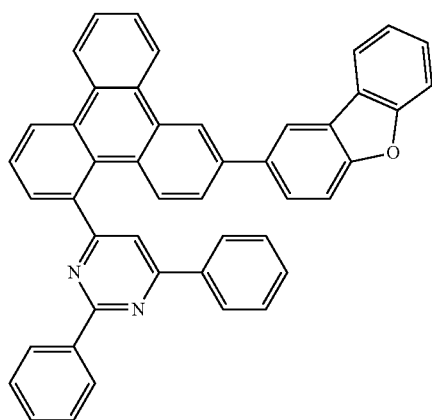 | 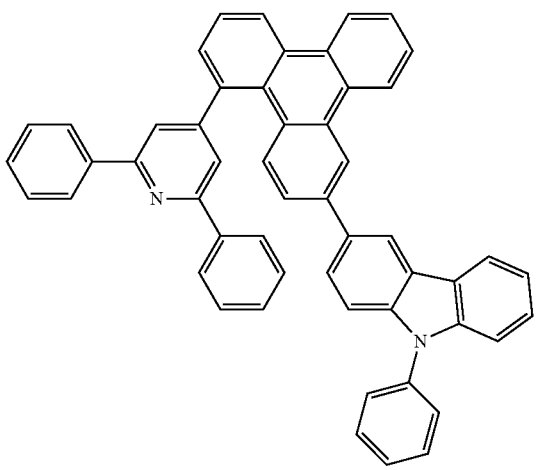 |
| 1-412 | 1-413 |
|---|---|
| 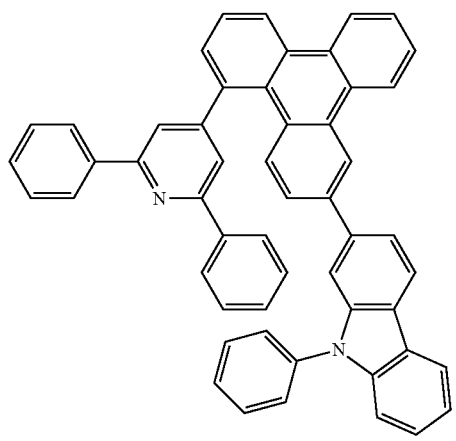 | 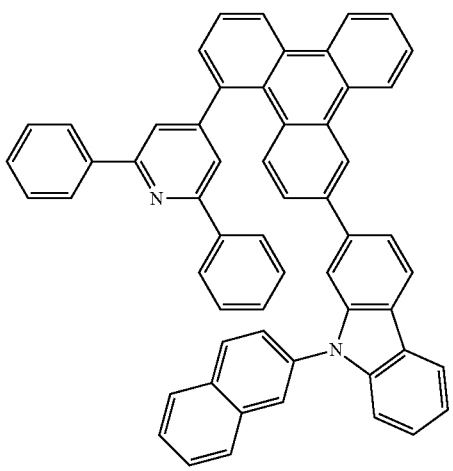 |

1-414
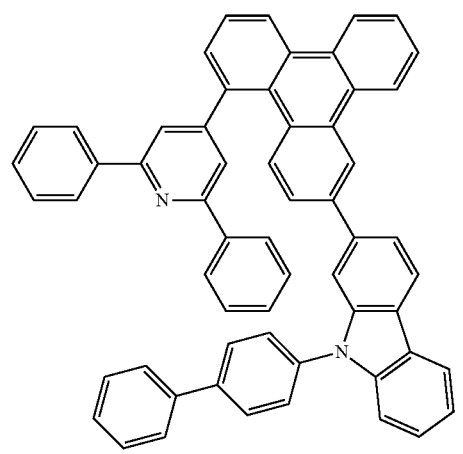
1-415
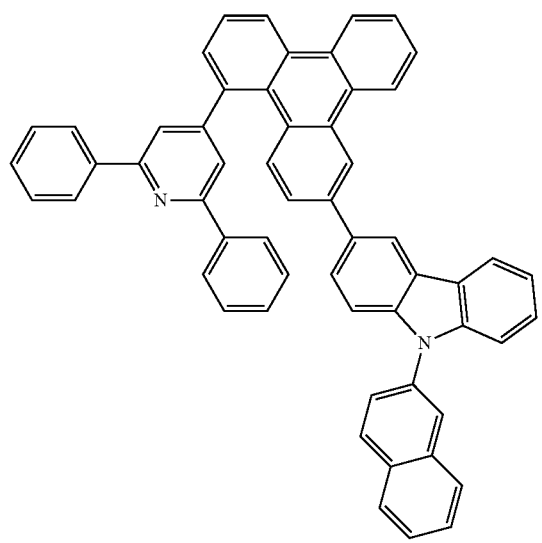
1-416
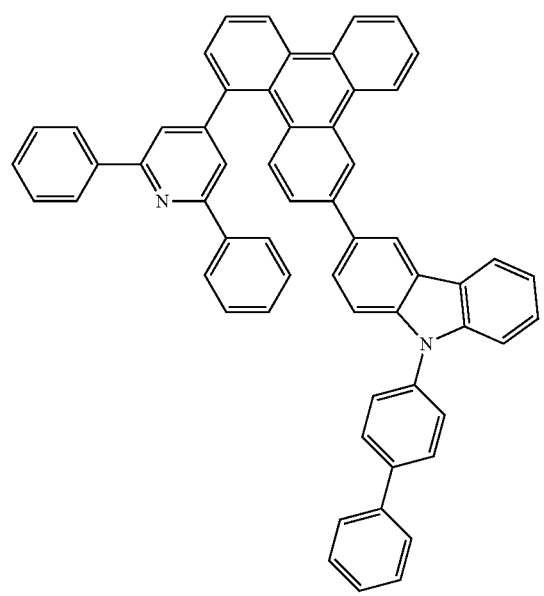
1-417
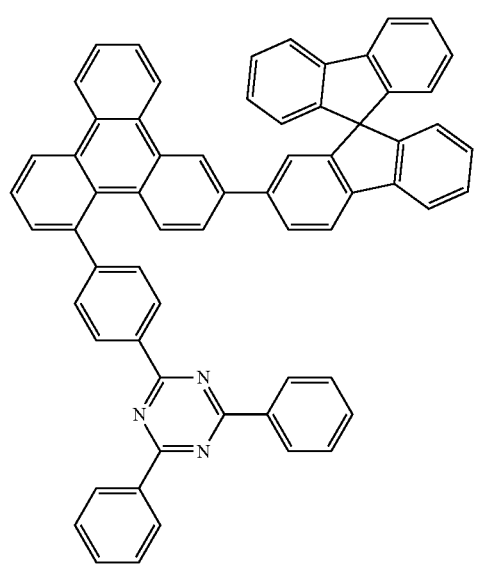

-continued
1-418
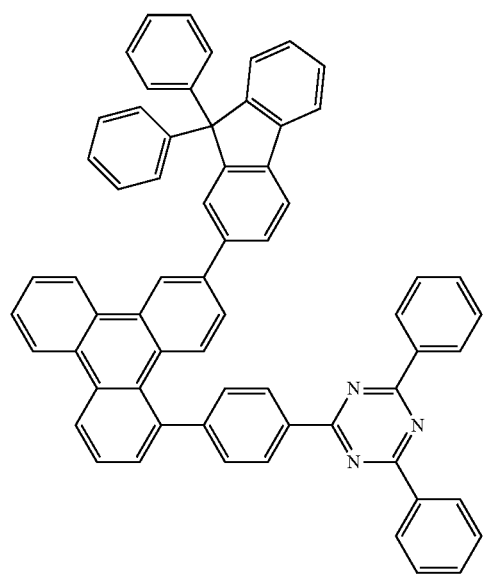
1-419
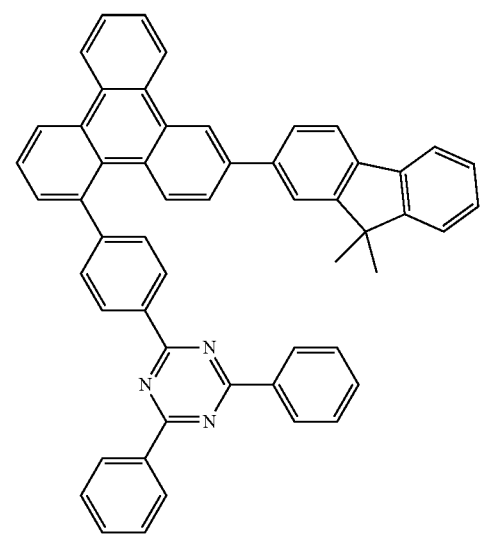
1-420
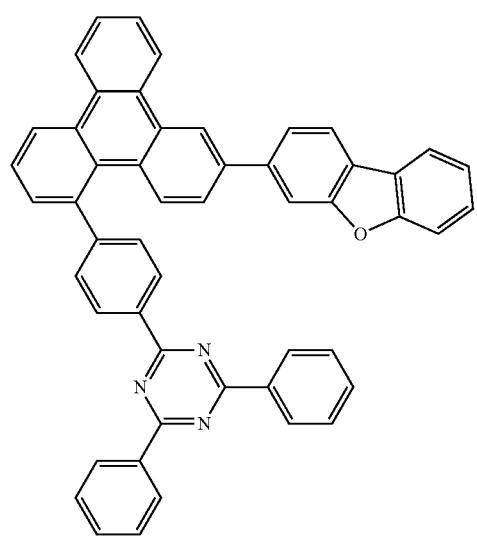
1-421
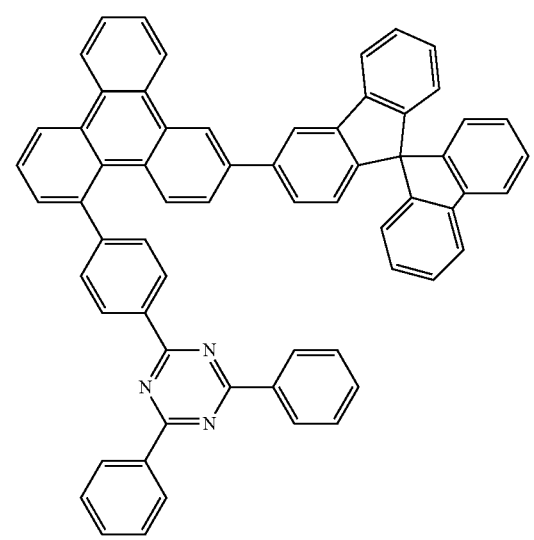
1-422
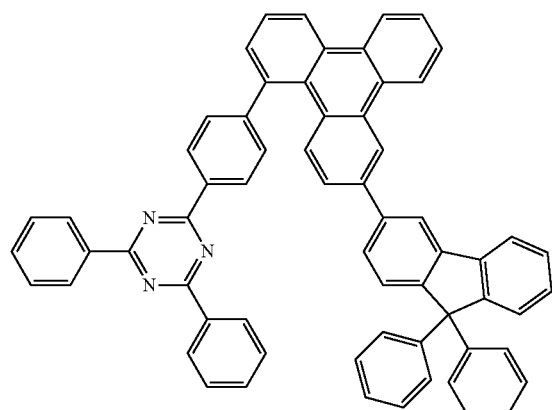
1-423
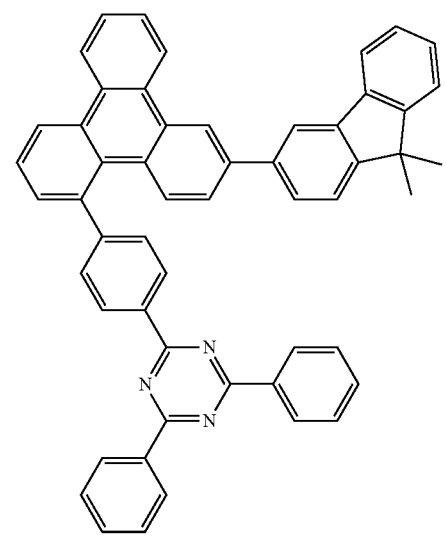

1-424
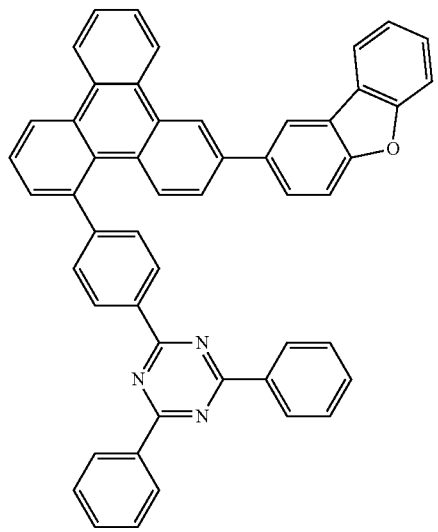
1-425
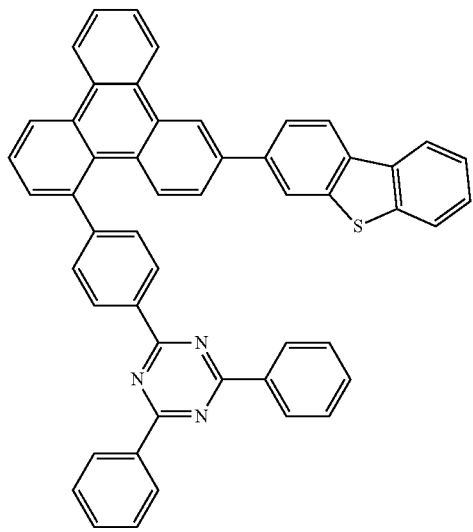
1-426
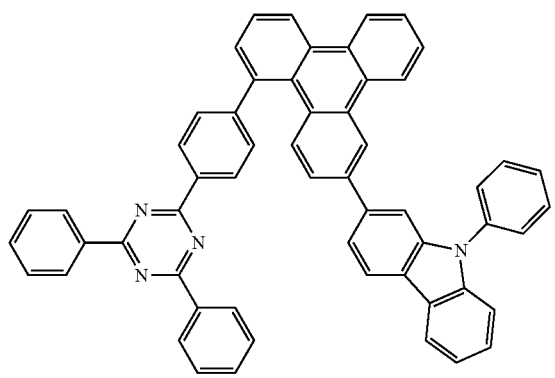
1-427
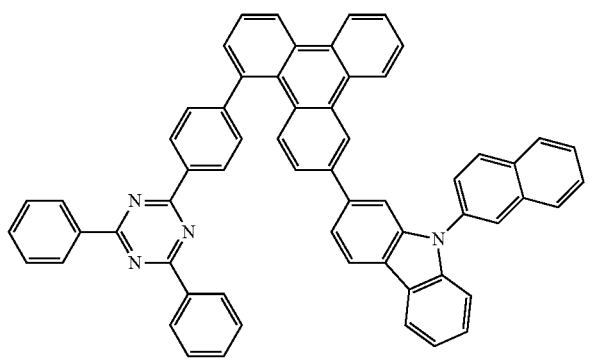
1-428
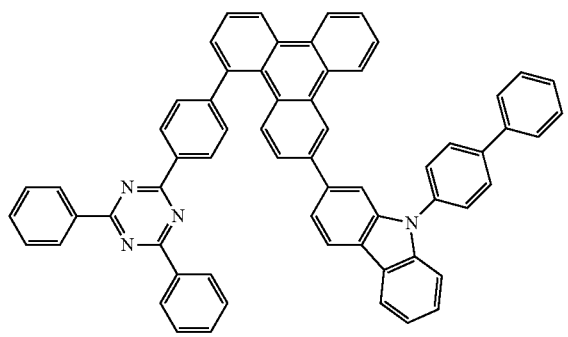
1-429
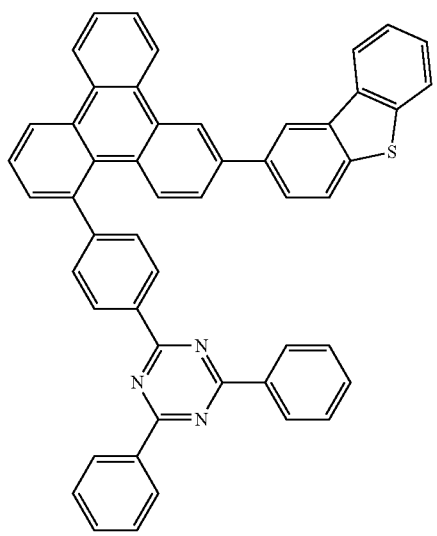

-continued
1-430
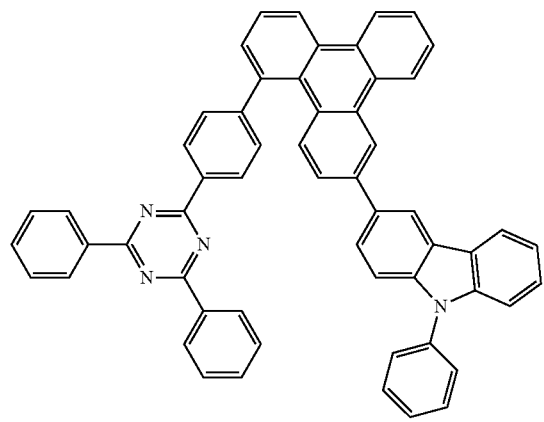
1-431
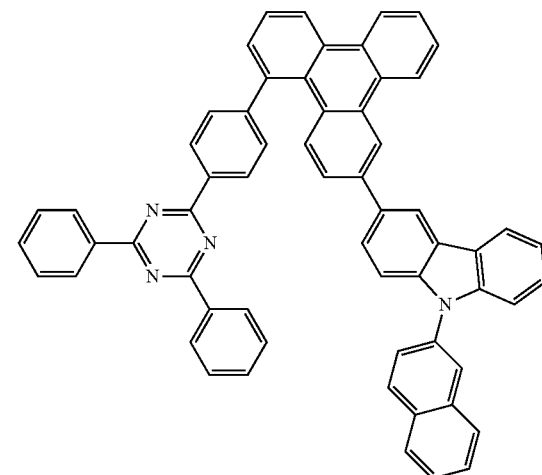
1-432
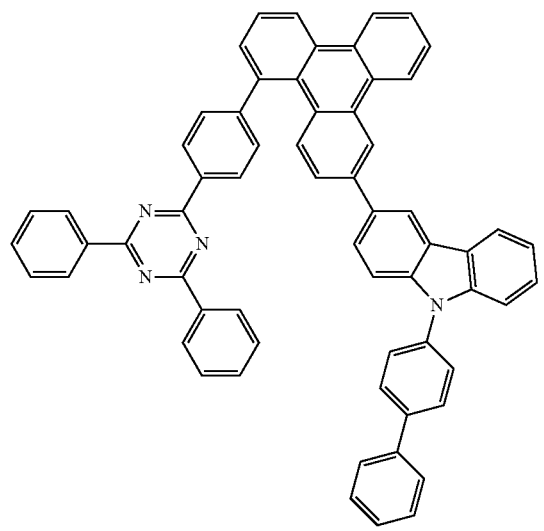
1-433
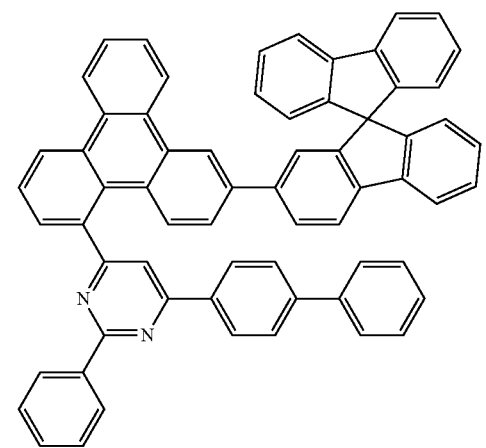
1-434
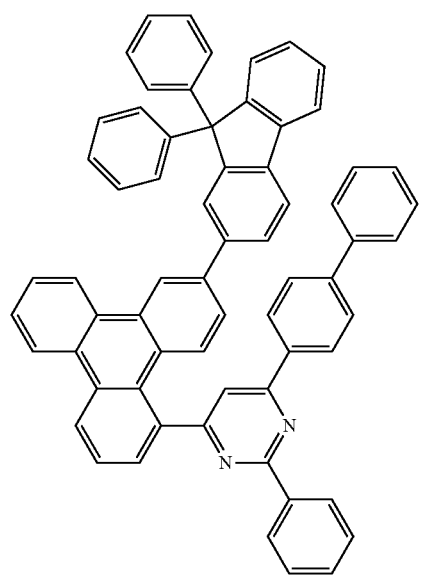
1-435
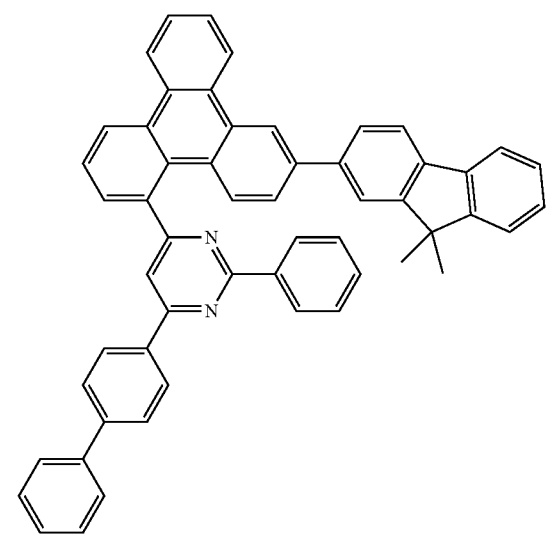

-continued
1-436
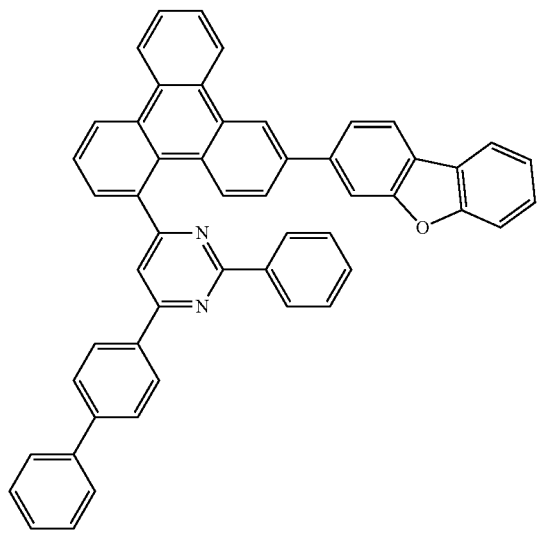
1-437
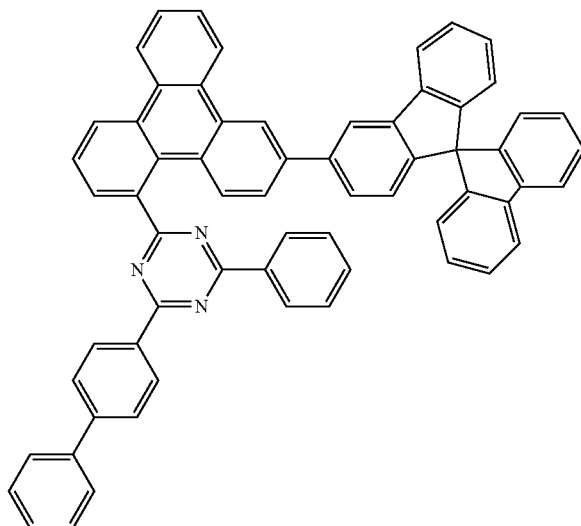
1-438
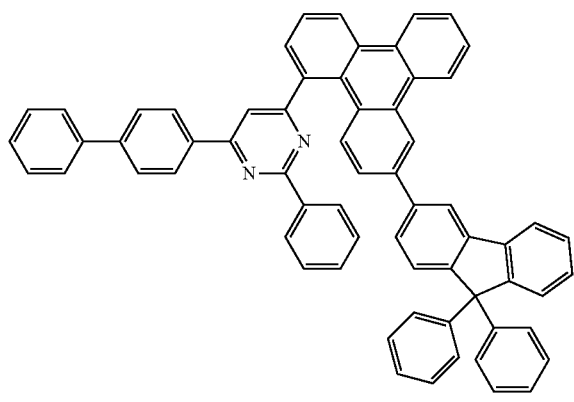
1-439
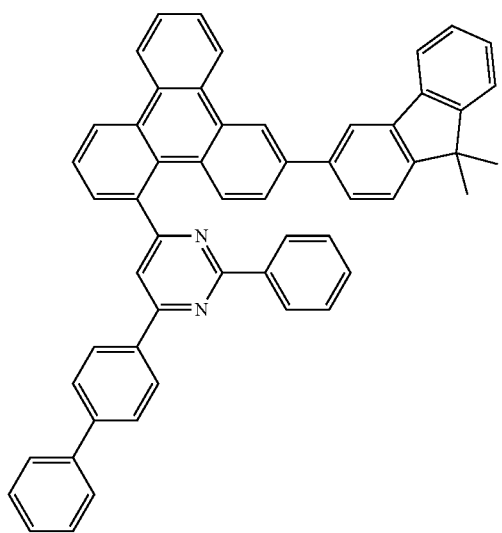
1-440
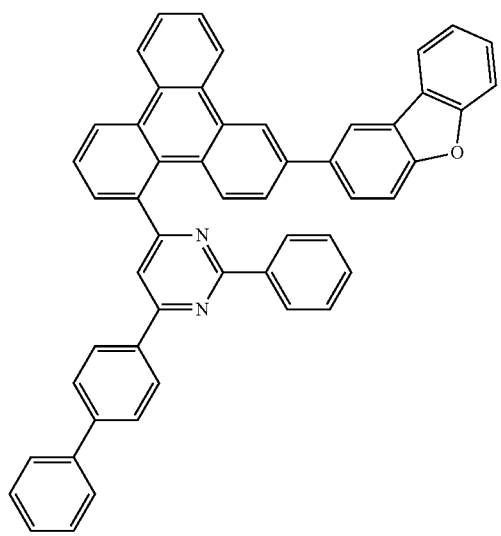
1-441
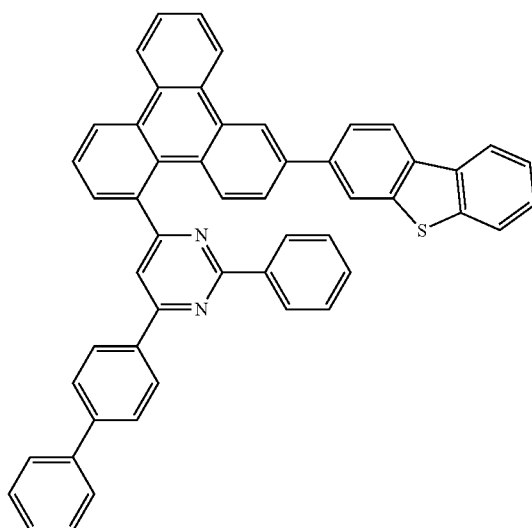

-continued
1-442
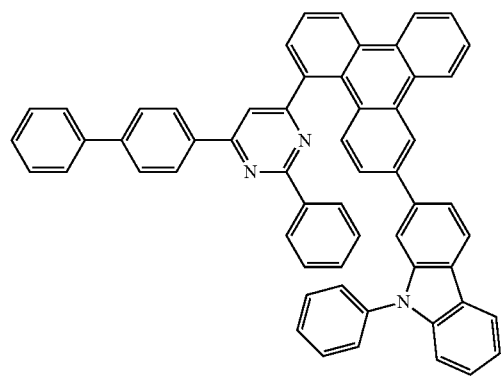
1-443
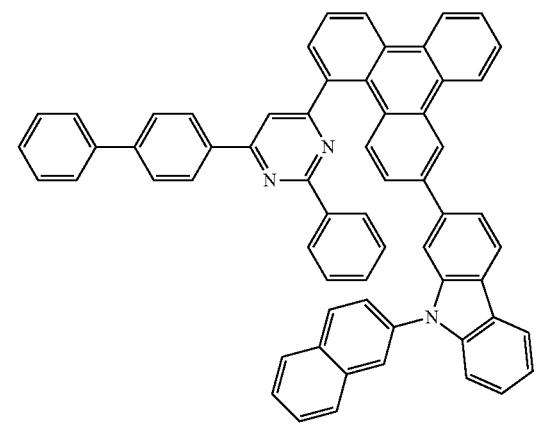
1-444
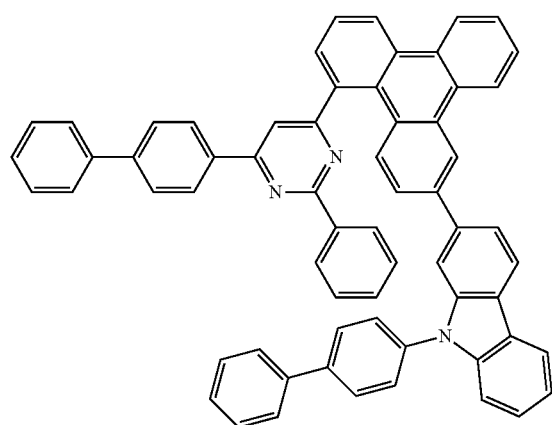
1-445
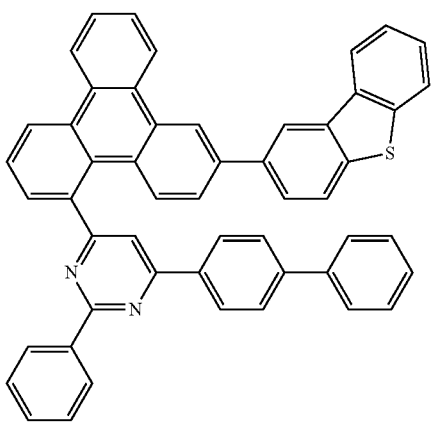
1-446
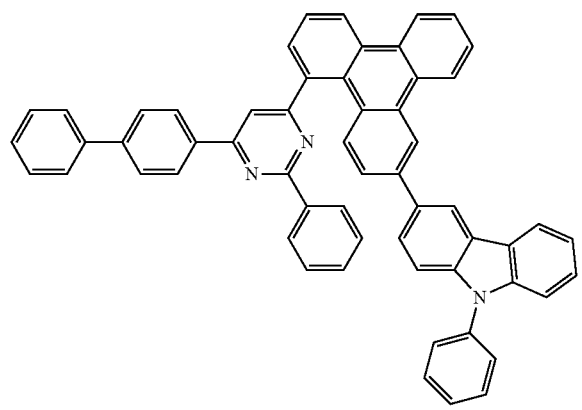
1-447
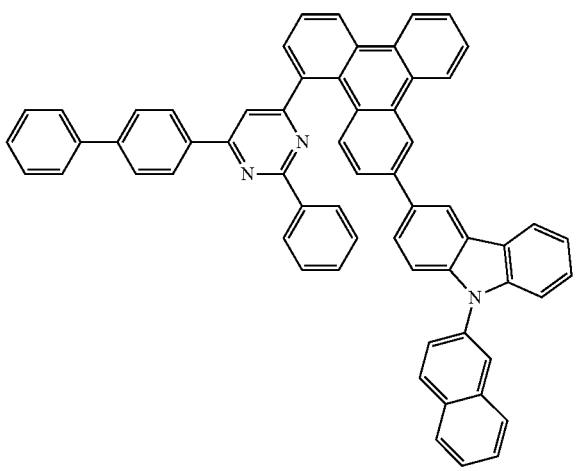

1-448
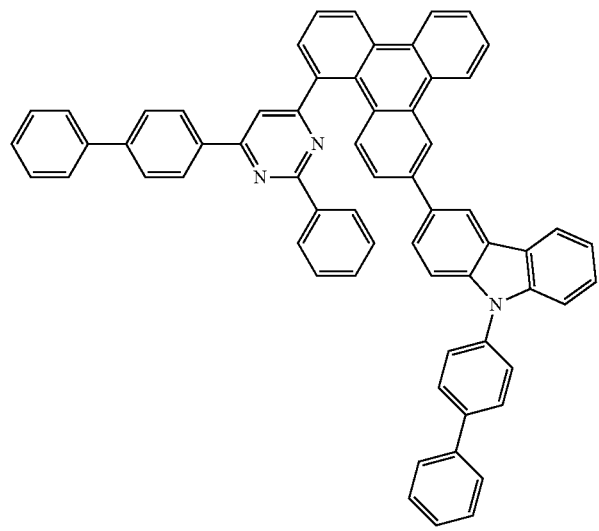
1-449
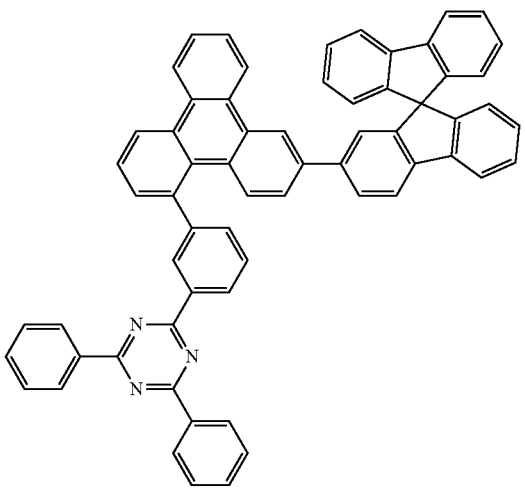
1-450
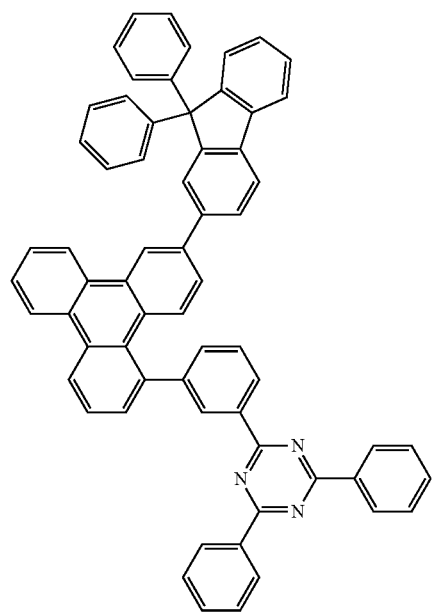
1-451
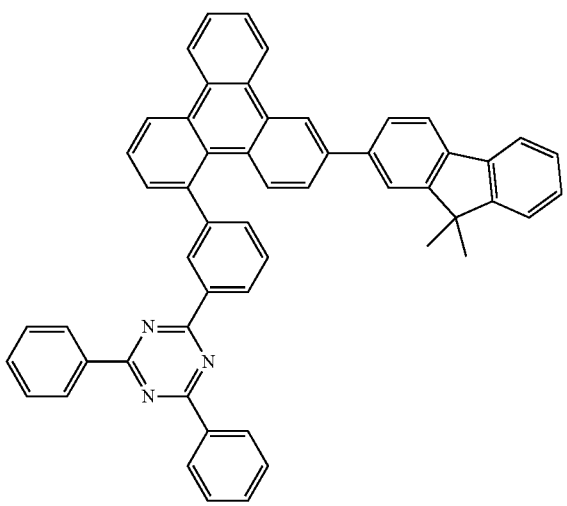

-continued
1-452
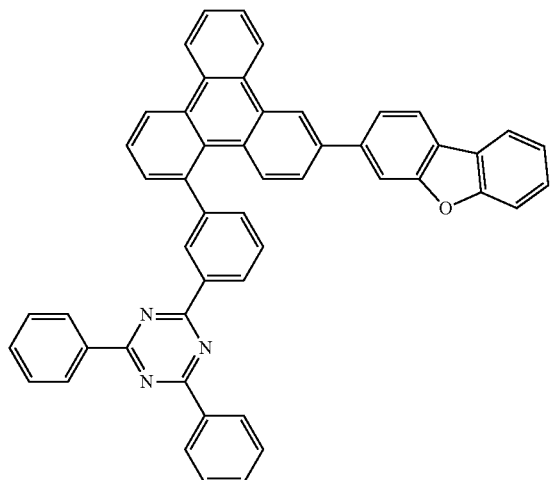
1-453
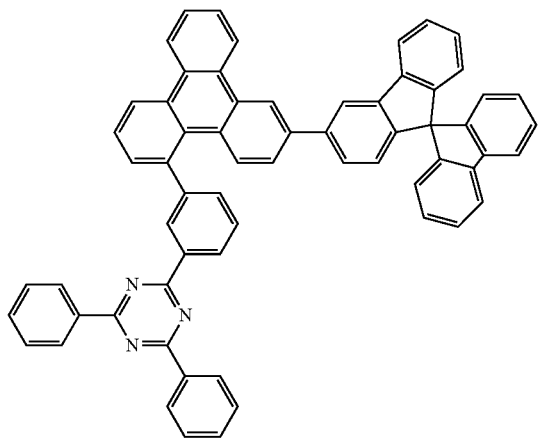
1-454
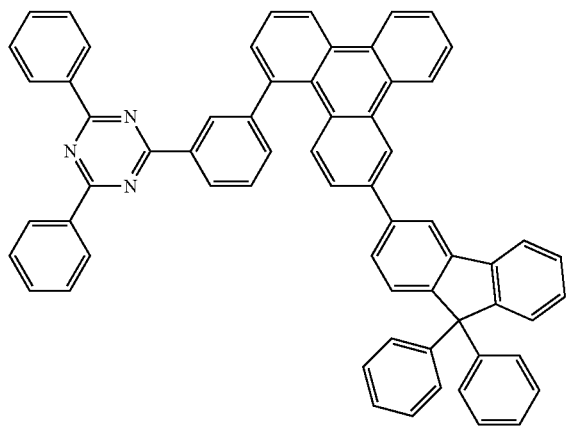
1-455
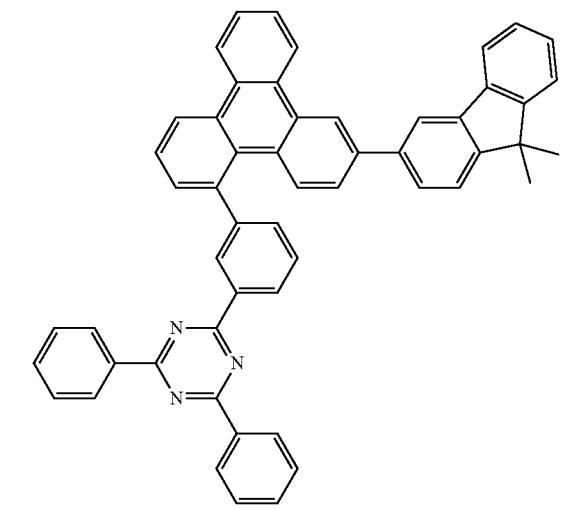
1-456
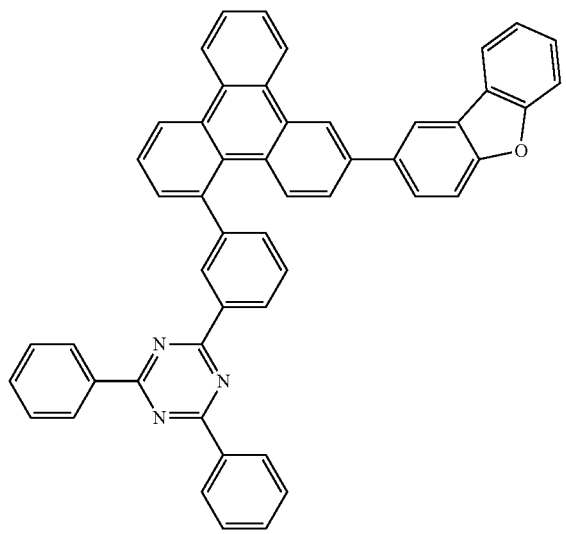
1-457
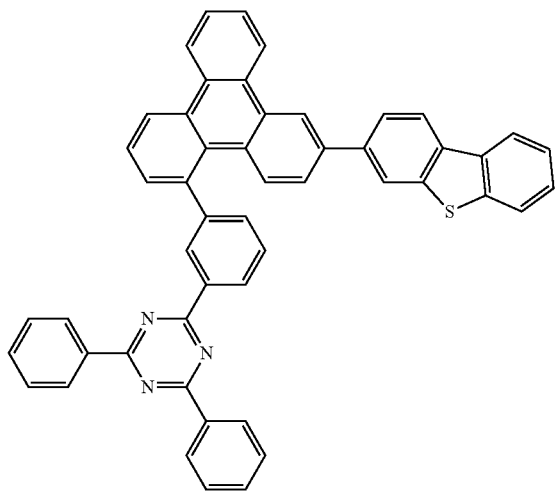

-continued
1-458
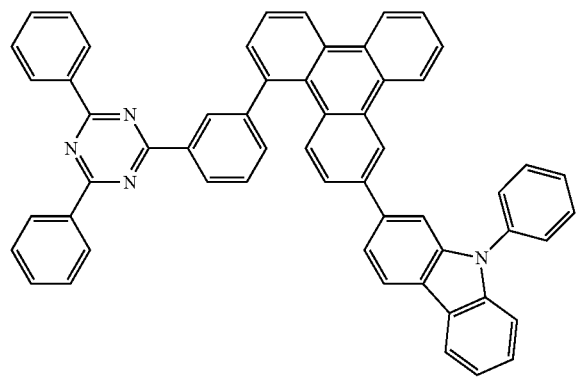
1-459
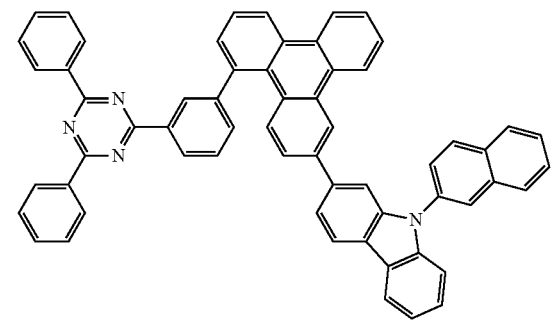
1-460
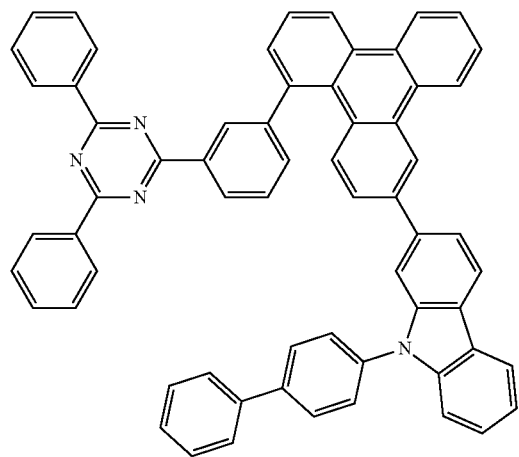
1-461
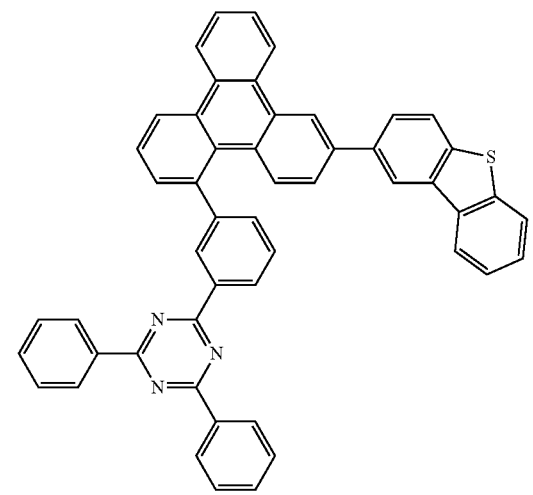
1-462
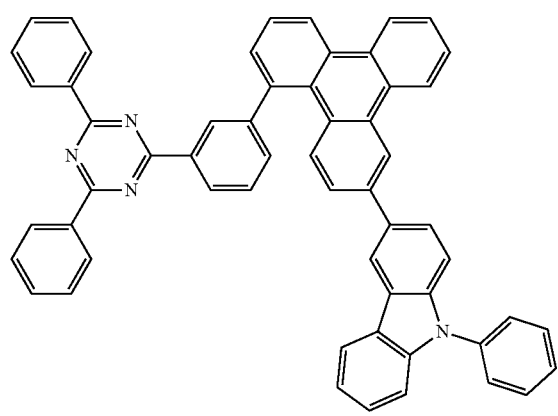
1-463
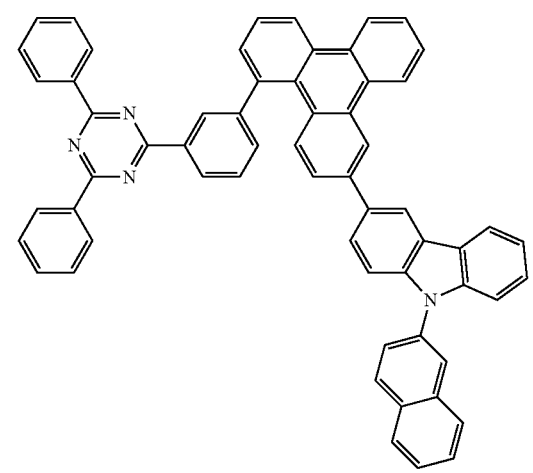

1-464
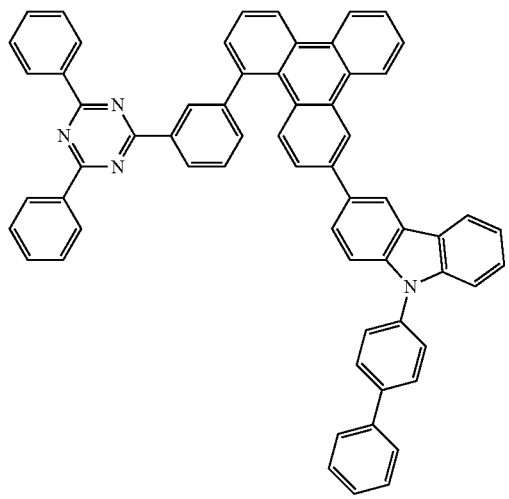
1-465
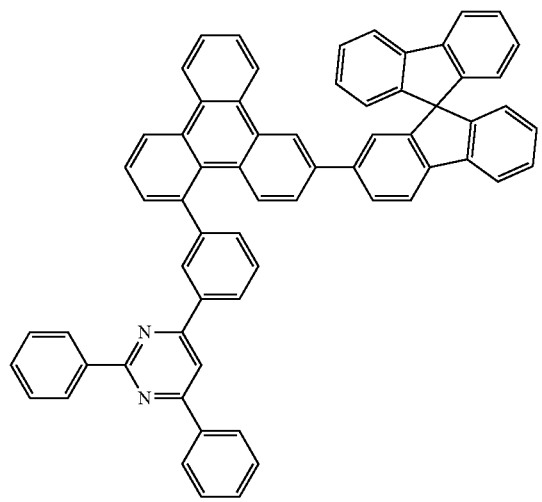
1-466
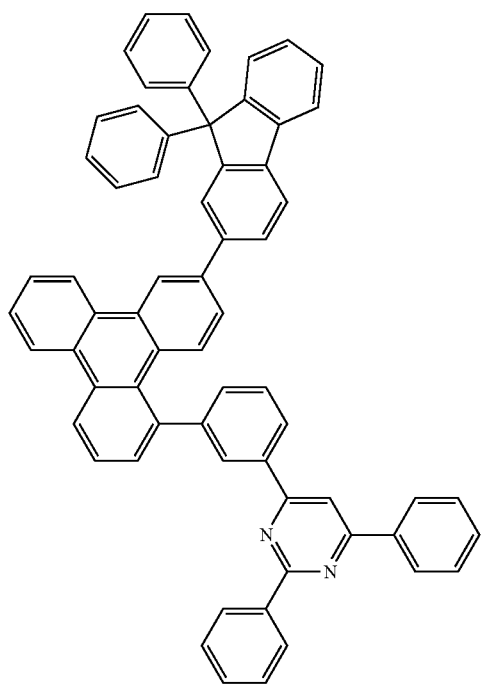
1-467
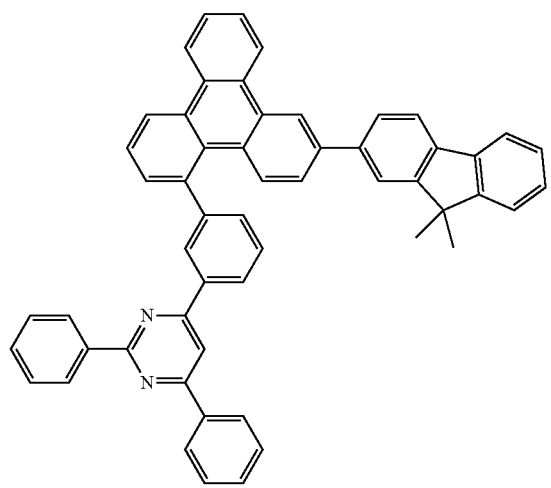

1-468
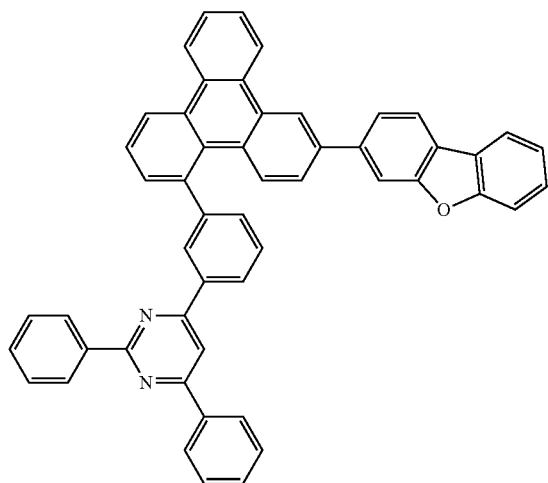
1-469
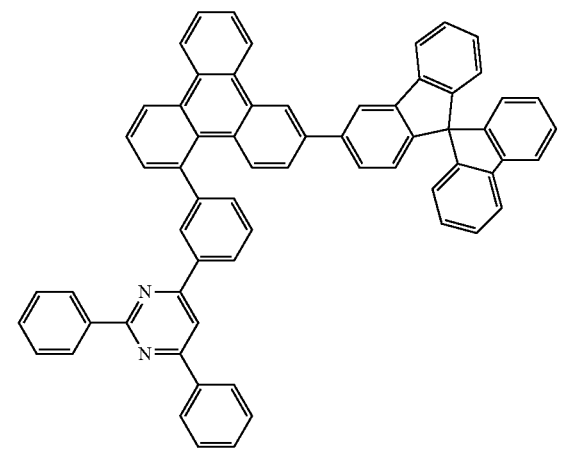
1-470
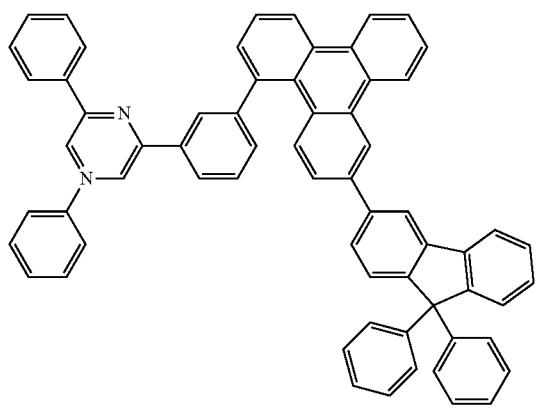
1-471
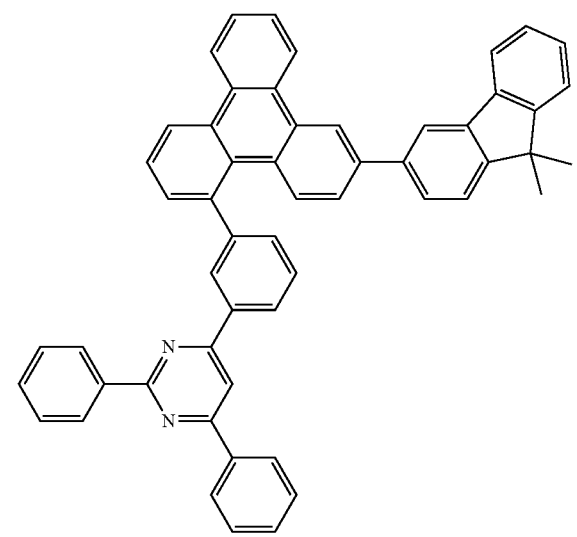
1-472
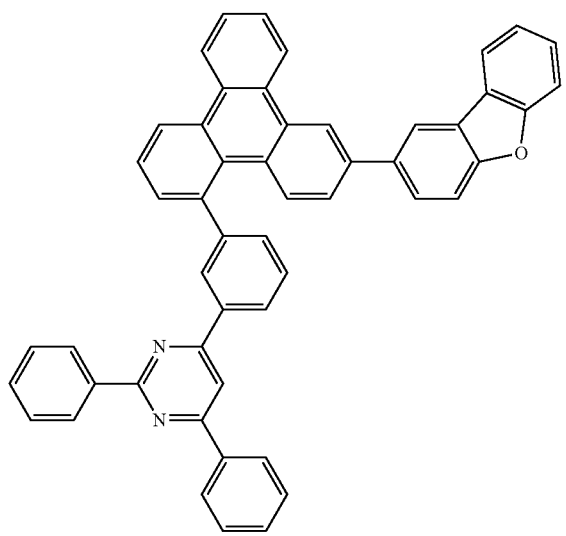
1-473
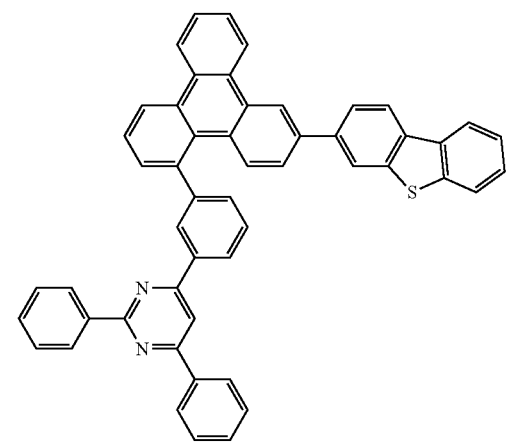

447
1-474
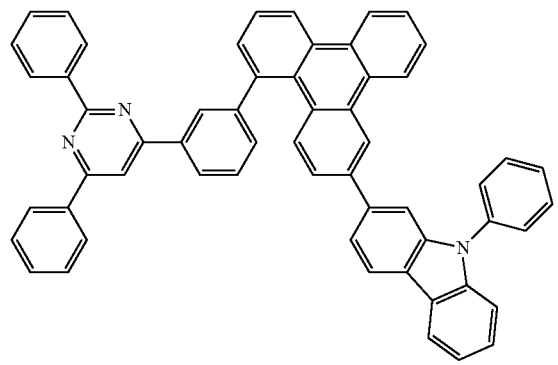
448
1-475
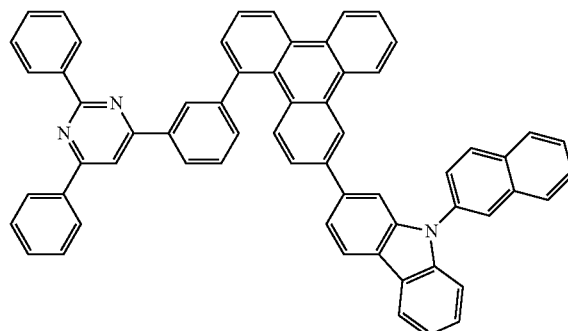
1-476
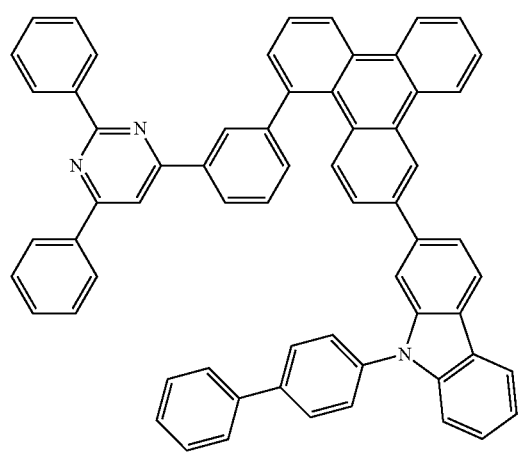

1-477
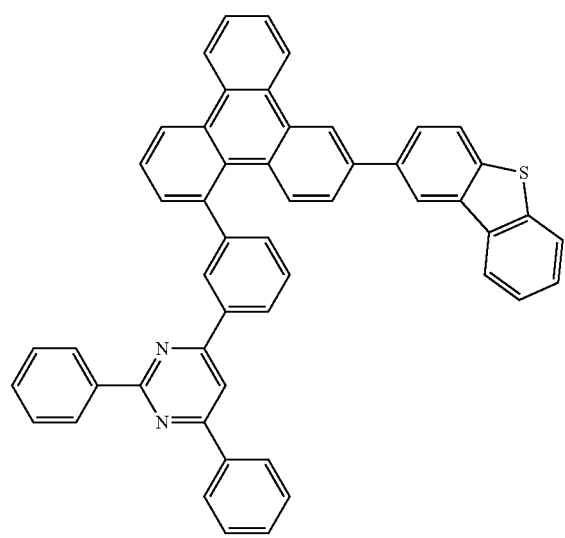
1-479
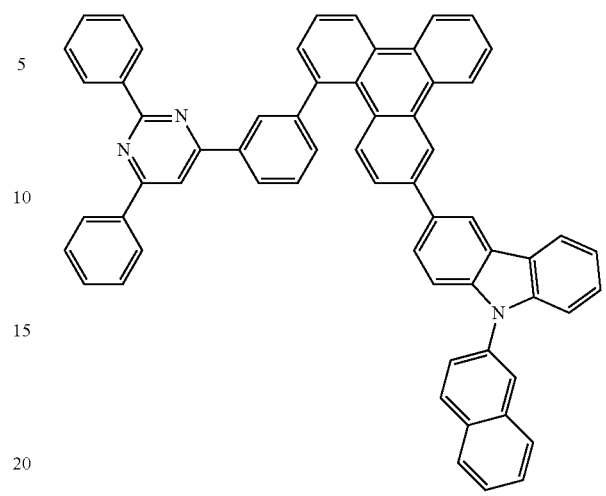
1-478
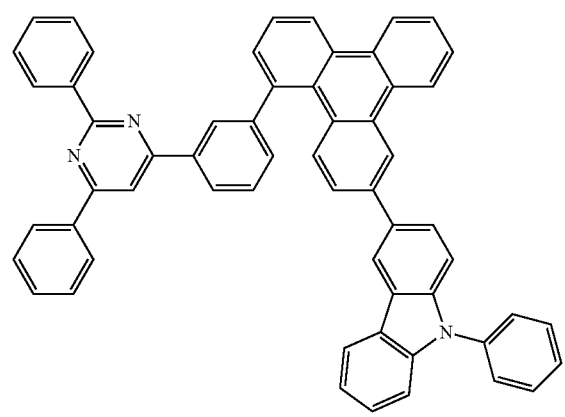
1-480
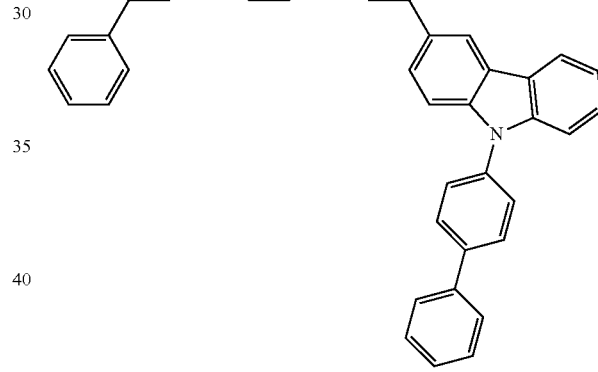
* * * * *